US012365722B2

(12) United States Patent
Li et al.

(10) Patent No.: US 12,365,722 B2
(45) Date of Patent: Jul. 22, 2025

(54) MULTISPECIFIC ANTIBODIES TARGETING MULTIPLE EPITOPES ON THE HIV-1 ENVELOPE

(71) Applicants: University of Maryland, College Park, College Park, MD (US); University of Maryland, Baltimore, Baltimore, MD (US); The United States of America, as Represented by the Secretary, Department of Health and Human Services, Bethesda, MD (US); International AIDS Vaccine Initiative, New York, NY (US)

(72) Inventors: Yuxing Li, Boyds, MD (US); James Steinhardt, Westminster, MD (US); Javier Guenaga, San Diego, CA (US); John R. Mascola, Rockville, MD (US); Tae-Wook Chun, North Bethesda, MD (US); Susan Moir, Washington, DC (US); Chi-I Chiang, Rockville, MD (US)

(73) Assignees: University of Maryland, College Park, College Park, MD (US); University of Maryland, Baltimore, Baltimore, MD (US); The United States of America, as Represented by the Secretary, Department of Health and Human Servives, Bethesda, MD (US); International AIDS Vaccine Initiative, New York, NY (US)

( * ) Notice: Subject to any disclaimer, the term of this patent is extended or adjusted under 35 U.S.C. 154(b) by 925 days.

(21) Appl. No.: 17/285,956

(22) PCT Filed: Oct. 18, 2019

(86) PCT No.: PCT/US2019/057089

§ 371 (c)(1),
(2) Date: Apr. 16, 2021

(87) PCT Pub. No.: WO2020/082045

PCT Pub. Date: Apr. 23, 2020

(65) Prior Publication Data

US 2022/0227845 A1 Jul. 21, 2022

Related U.S. Application Data

(60) Provisional application No. 62/749,510, filed on Oct. 23, 2018, provisional application No. 62/748,228, filed on Oct. 19, 2018.

(51) Int. Cl.
*C07K 16/10* (2006.01)
*A61K 39/42* (2006.01)
(Continued)

(52) U.S. Cl.
CPC .......... *C07K 16/1063* (2013.01); *A61K 39/42* (2013.01); *A61K 45/06* (2013.01);
(Continued)

(58) Field of Classification Search
CPC .................................................. C07K 16/1063
See application file for complete search history.

(56) References Cited

U.S. PATENT DOCUMENTS

| | | | |
|---|---|---|---|
| 3,720,760 | A | 3/1973 | Bennich |
| 4,235,871 | A | 11/1980 | Papahadjopoulos et al. |

(Continued)

FOREIGN PATENT DOCUMENTS

| | | | |
|---|---|---|---|
| WO | 9005144 | A1 | 5/1990 |
| WO | 2017093985 | A1 | 6/2017 |

(Continued)

OTHER PUBLICATIONS

International Search Report and Written Opinion issued by the Internatoinal Searching Authority on Jan. 29, 2020, corresponding to counterpart International Applicatoin No. PCT/US2019/057089; 8 total pages.

(Continued)

*Primary Examiner* — Jeffrey S Parkin
(74) *Attorney, Agent, or Firm* — Carter, DeLuca & Farrell LLP; George Likourezos

(57) ABSTRACT

The present invention provides a multispecific anti-HIV antibody that binds to multiple epitopes on HIV envelope
(Continued)

protein, wherein the antibody comprises: i. an amino acid sequence that binds to a V1/V2 apex glycan epitope; ii. an amino acid sequence that binds to a V3-base glycan region epitope; iii. an amino acid sequence that binds to a CD4 binding site (CD4bs) epitope; iv. an amino acid sequence that binds to a gp120/gp41 interface epitope; and v. an amino acid sequence that binds to a membrane proximal external region (MPER) epitope.

30 Claims, 30 Drawing Sheets

Specification includes a Sequence Listing.

(51) Int. Cl.
*A61K 45/06* (2006.01)
*A61P 31/18* (2006.01)
*A61K 39/00* (2006.01)

(52) U.S. Cl.
CPC .......... *A61P 31/18* (2018.01); *C07K 16/1045* (2013.01); *A61K 2039/505* (2013.01); *C07K 2317/31* (2013.01); *C07K 2317/52* (2013.01); *C07K 2317/565* (2013.01); *C07K 2317/622* (2013.01); *C07K 2317/76* (2013.01); *C07K 2317/92* (2013.01)

(56) References Cited

U.S. PATENT DOCUMENTS

| | | | |
|---|---|---|---|
| 4,501,728 | A | 2/1985 | Geho et al. |
| 4,722,848 | A | 2/1988 | Paoletti et al. |
| 4,816,567 | A | 3/1989 | Cabilly et al. |
| 4,837,028 | A | 6/1989 | Allen |
| 4,902,505 | A | 2/1990 | Pardridge et al. |
| 4,957,735 | A | 9/1990 | Huang |
| 5,004,697 | A | 4/1991 | Pardridge |
| 5,019,369 | A | 5/1991 | Presant et al. |
| 5,055,303 | A | 10/1991 | Riley, Jr. |
| 5,188,837 | A | 2/1993 | Domb |
| 5,254,342 | A | 10/1993 | Shen et al. |
| 5,268,164 | A | 12/1993 | Kozarich et al. |
| 5,271,961 | A | 12/1993 | Mathiowitz et al. |
| 5,413,797 | A | 5/1995 | Khan et al. |
| 5,506,206 | A | 4/1996 | Kozarich et al. |
| 5,514,670 | A | 5/1996 | Friedman et al. |
| 5,534,496 | A | 7/1996 | Lee et al. |
| 7,501,049 | B2 | 3/2009 | Schmidt |
| 2015/0218257 | A1 | 8/2015 | Chan-Hui et al. |
| 2018/0118816 | A1 | 5/2018 | Keyt et al. |

FOREIGN PATENT DOCUMENTS

| | | | |
|---|---|---|---|
| WO | 2017133640 A1 | | 8/2017 |
| WO | WO 2018/075564 A1 | * | 4/2018 |

OTHER PUBLICATIONS

International Preliminary Report on Patentability issued by The International Bureau of WIPO corresponding to counterpart International Application No. PCT/US2019/057089 dated Apr. 14, 2021; 1 page.
Asokan M, et al., Bispecific Antibodies Targeting Different Epitopes on the HIV-1 Envelope Exhibit Broad and Potent Neutralization. J Virol 89, 12501-12512 (2015).
Bar KJ, et al. Effect of HIV Antibody VRC01 on Viral Rebound after Treatment Interruption. N Engl J Med 375, 2037-2050 (2016).
Barre-Sinoussi F, et al., Isolation of a T-lymphotropic retrovirus from a patient at risk for acquired immune deficiency syndrome (AIDS). Science 220:868-871 (1983).
Buchacher A, et al. Generation of human monoclonal antibodies against HIV-1 proteins; electrofusion and Epstein-Barr virus transformation for peripheral blood lymphocyte immortalization. AIDS Res Hum Retroviruses 10, 359-369 (1994).
Burton DR, et al., A large array of human monoclonal antibodies to type 1 human immunodeficiency ; virus from combinatorial libraries of asymptomatic seropositive individuals. Proc Natl Acad Sci U S A 88, 10134-10137 (1991).
Burton DR, Mascola JR. Antibody responses to envelope glycoproteins in HIV-1 infection. Nat Immunol 16, 571-576 (2015).
Caskey M, et al. Antibody 10-1074 suppresses viremia in HIV-1-infected individuals. Nat Med 23, 185-191 (2017).
Caskey M, et al. Viraemia suppressed in HIV-1-infected humans by broadly neutralizing antibody 3BNC117. Nature 522, 487-491 (2015).
Doria-Rose NA, et al., HIV-1 neutralization coverage is improved by combining monoclonal antibodies that target independent epitopes. J Virol 86, 3393-3397 (2012).
Galimidi RP, et al. Intra-spike crosslinking overcomes antibody evasion by HIV-1. Cell 160, 433-446 (2015).
Gallo RC, et al., Frequent detection and isolation of cytopathic retroviruses (HTLV-111) from patients with AIDS and at risk for AIDS. Science 224:500-503 (1984).
Hu Q, et al., Recent advances of cocktail chemotherapy by combination drug delivery systems. Adv Drug Deliv Rev 98, 19-34 (2016).
Huang J, et al. Broad and potent neutralization of HIV-1 by a gp41-specific human antibody. Nature 491, 406-412 (2012).
Huang Y, et al, Engineered Sispecific Antobidies with Exquisite HIV-1- Neutralizing Activity. Cell 165, 1621-1631 (2016).
Klein F, et al., HIV therapy by a combination of broadly neutralizing antibodies in humanized mice. Nature 192:118-122 (2012).
Kong R, et al. Improving neutralization potency and breadth by combining broadly reactive HIV-1 antibodies targeting major neutralization epitopes. J Virol 89, 2659-2671 (2015).
Kowalski M, et al., Functional regions of the envelope glycoprotein of human immunodeficiency virus type 1. Science 237:1351-1355 (1987).
Kwong PD, et al., Broadly neutralizing antibodies and the search for an HIV-1 vaccine: the end of the beginning. Nat Rev Immunol 13:693-701 (2013).
Ledgerwood JE, et al. Safety, pharmacokinetics and neutralization of the broadly neutralizing HIV-1 human monoclonal antibody VRC01 in healthy adults. ; Clin Exp Immunol 182, 289-301 (2015).
Lu M, et al., A trimeric structural domain of the HIV-1 transmembrane glycoprotein. Nat Struct Biol 2:1075-1082 (1995).
Lynch RM, et al. HIV-1 fitness cost associated with escape from the VRC01 class of CD4 binding site neutralizing antibodies. J Virol 89, 4201-4213 (2015).
Lynch RM, et al. Virologic effects of broadly neutralizing antibody VRC01 administration during chronic HIV-1 infection. Sci Transl Med 7, 319ra206 (2015).
Pietzsch J, et al. Human anti-HIV-neutralizing antibodies frequently target a conserved epitope essential for viral fitness. J Exp Med 207, 1995-2002 (2010).
Sather DN, et al., Broadly neutralizing antibodies developed by an HIV-positive elite neutralizer exact a replication fitness cost on the contemporaneous virus. J Virol 86, 12676-12685 (2012).
Scheid JF, et al. Sequence and structural convergence of broad and potent HIV antibodies that mimic CD4 binding. Science 333, 1633-1637 (2011).
Shingai M, et al., Antibody-mediated immunotherapy of macaques chronically infected with SHIV suppresses viraemia. Nature 503:277-280 (2013).
Tebit DM, et al., HIV diversity, recombination and disease progression: how does fitness "fit" into the puzzle? AIDS Rev 9, 75-87 (2007).
Walker LM, et al., Broad neutralization coverage of HIV by multiple highly potent antibodies. Nature 477, 466-470 (2011).
Wu X, et al. Rational design of envelope identifies broadly neutralizing human monoclonal antibodies to HIV-1. Science 329, 856-861 (2010).
Wyatt R, et al., The HIV-I envelope glycoproteins: fusogens, antigens, and immunogens. Science 280:1884-1888 (1998).

(56) References Cited

OTHER PUBLICATIONS

Kobayashi et al., "Tryptophan H33 plays an important role in pyrimidine (6-4) pyrimidone photoproduct binding by a high-affinity antibody," Protein Engineering, 1999, vol. 12, No. 10; pp. 879-884.
Burks et al., "In Vitro Scanning Saturation Mutagenesis of an Antibody Binding Pocket," Proc. Natl. Acad. Sci. USA, Jan. 1997, vol. 94; pp. 412-417.
Huston et al., "Protein Engineering of Antibody Binding Sites: Recovery of Specific Activity in an Anti-Digoxin Single Chain Fv Analogue Produced in *Escherichia coli*,", Proc. Natl. Acad. Sci. USA, vol. 85, Aug. 1988; pp. 5879-5883.
Holliger et al., ""Diabodies": Small Bivalent and Bispecific Antibody Fragments," Proc. Natl. Acad. Sci., USA, Jul. 1993, vol. 90; pp. 6444-6448.
Poljak, "Production and Structure of diabodies," Structure, Dec. 15, 1994, vol. 2; pp. 1121-1123.
Shankarappa et al., "Consistent Viral Evolutionary Changes Associated with the Progression of Human Immunodeficiency Virus Type 1 Infection," Journal of Virology, vol. 73, No. 12, Dec. 1999; pp. 10489-10502.

* cited by examiner

208 Virus Panel

| | PentaNAb$_{2.0}$* | PentaScFv$_{2.0}$ | TetraNAb1 | TetraNAb2 | TriNAb | BiNAb | BiScFv* | 10E8 | VRC01 | 35O22 | PGT121 |
|---|---|---|---|---|---|---|---|---|---|---|---|
| # Viruses | 208 | 208 | 208 | 208 | 208 | 208 | 208 | 208 | 208 | 208 | 208 |
| Total VS Neutralized $IC_{50}<50\mu g/mL$ | 207 | 207 | 205 | 205 | 207 | 198 | 197 | 203 | 188 | 94 | 133 |
| % VS Neutralized $IC_{50}<50\mu g/mL$ | 99.5 | 99.5 | 98.6 | 98.6 | 99.5 | 95.2 | 94.7 | 97.6 | 90.4 | 45.2 | 63.9 |
| Median IC50 (μg/mL) | 0.0695 | 0.0050 | 0.0790 | 0.0630 | 0.0630 | 0.1975 | 0.2100 | 0.3920 | 0.2865 | 0.0100 | 0.0190 |
| GMT (μg/mL) | 0.0716 | 0.0056 | 0.1014 | 0.0765 | 0.0692 | 0.2971 | 0.3057 | 0.2993 | 0.3014 | 0.0251 | 0.0453 |

| Virus ID | Clade | PentaNAb2.0 | PentaScFv2.0 | VRC01 | PGT121 | 10E8 | 35022 |
|---|---|---|---|---|---|---|---|
| 0260.v5.c36 | A | 0.099 | 0.006 | 0.523 | 0.039 | 9.87 | 0.070 |
| 0330.v4.c3 | A | 0.030 | 0.002 | 0.066 | 0.041 | 1.12 | >50 |
| 0439.v5.c1 | A | 0.665 | 0.076 | 0.228 | >50 | 1.23 | 0.010 |
| 3365.v2.c20 | A | 0.073 | 0.006 | 0.060 | 0.059 | 1.60 | >50 |
| 3415.v1.c1 | A | 0.108 | 0.010 | 0.087 | >50 | 4.69 | >50 |
| 3718.v3.c11 | A | 0.039 | 0.004 | 0.411 | 1.40 | 0.838 | >50 |
| 398-F1_F6_20 | A | 0.022 | 0.001 | 0.102 | 0.002 | 0.704 | >50 |
| BB201.B42 | A | 0.019 | 0.002 | 0.262 | 0.003 | 0.613 | >50 |
| BB539.2B13 | A | 0.057 | 0.005 | 0.105 | >50 | 0.591 | >50 |
| BG505.W6M.C2 | A | 0.042 | 0.005 | 0.037 | 0.032 | 0.689 | >50 |
| B1369.9A | A | 0.150 | 0.105 | 0.047 | 0.008 | 0.356 | 0.007 |
| BS208.B1 | A | 0.024 | 0.003 | 0.027 | >50 | 0.319 | >50 |
| KER2018.12 | A | 0.036 | 0.002 | 0.487 | 2.22 | >50 | 0.0003 |
| KER2018.11 | A | 0.034 | 0.004 | 0.348 | >50 | 1.89 | 0.005 |
| KNH1209.18 | A | 0.038 | 0.002 | 0.119 | 0.002 | 0.406 | 0.040 |
| MB201.A1 | A | 0.081 | 0.006 | 0.241 | 0.005 | 0.411 | >50 |
| MB539.2B7 | A | 0.148 | 0.016 | 0.512 | >50 | >50 | 1.49 |
| M1369.A5 | A | 0.079 | 0.007 | 0.236 | 0.022 | 0.671 | 0.004 |
| MS208.A1 | A | 0.056 | 0.007 | 0.174 | >50 | 0.187 | >50 |
| Q23.17 | A | 0.012 | 0.001 | 0.099 | 0.004 | 0.461 | 0.003 |
| Q259.17 | A | 0.042 | 0.003 | 0.085 | >50 | 4.76 | >50 |
| Q769.d22 | A | 0.110 | 0.006 | 0.036 | >50 | 1.91 | 0.053 |
| Q769.h5 | A | 0.131 | 0.005 | 0.072 | >50 | 2.89 | 0.635 |
| Q842.d12 | A | 0.037 | 0.002 | 0.034 | 0.016 | 2.82 | 0.006 |
| QH209.14M.A2 | A | 0.185 | 0.009 | 0.026 | >50 | 1.30 | >50 |
| RW020.2 | A | 0.048 | 0.004 | 0.217 | 0.002 | 0.902 | 0.009 |
| UG037.8 | A | 0.119 | 0.015 | 0.073 | 0.065 | 0.048 | 0.063 |
| 246-F3.C10.2 | AC | 0.018 | 0.003 | 0.254 | >50 | 0.210 | 0.021 |
| 3301.V1.C24 | AC | 0.069 | 0.006 | 0.095 | 0.009 | 2.97 | 0.057 |
| 3589.V1.C4 | AC | 0.059 | 0.005 | 0.081 | >50 | 5.77 | 0.004 |
| 6540.v4.c1 | AC | 0.114 | 0.006 | >50 | >50 | 2.24 | >50 |
| 6545.V4.C1 | AC | 0.069 | 0.005 | >50 | >50 | 2.54 | >50 |
| 0815.V3.C3 | ACD | 0.055 | 0.005 | 0.029 | 0.020 | 0.491 | 0.002 |
| 6095.V1.C10 | ACD | 0.023 | 0.006 | 0.631 | 37.3 | 0.0005 | >50 |
| 3468.V1.C12 | AD | 0.108 | 0.008 | 0.058 | 0.042 | 0.381 | 0.005 |
| Q168.a2 | AD | 0.061 | 0.009 | 0.101 | >50 | 0.463 | 0.051 |
| Q461.e2 | AD | 0.435 | 0.043 | 0.420 | >50 | 2.29 | 0.001 |
| 620345.c1 | AE | 0.125 | 0.011 | >50 | >50 | 0.989 | >50 |
| BJOX009000.02.4 | AE | 0.109 | 0.011 | 1.74 | 14.7 | 0.251 | >50 |
| BJOX010000.06.2 | AE | 0.282 | 0.027 | 8.40 | >50 | 0.060 | 3.00 |
| BJOX025000.01.1 | AE | 0.008 | 0.001 | 20.2 | >50 | 0.228 | 3.00 |
| BJOX028000.10.3 | AE | 0.014 | 0.001 | 0.118 | >50 | 0.167 | 0.004 |
| C1080.c3 | AE | 0.020 | 0.001 | 2.63 | >50 | 0.108 | 0.005 |
| C2101.c1 | AE | 0.128 | 0.007 | 0.269 | >50 | 1.20 | 0.007 |
| C3347.c11 | AE | 0.078 | 0.005 | 0.213 | >50 | 0.019 | 0.004 |
| C4118.09 | AE | 0.044 | 0.003 | 0.285 | >50 | 0.421 | 0.0003 |
| CM244.ec1 | AE | 0.100 | 0.006 | 0.116 | >50 | 0.365 | 0.023 |

FIG. 4A

| Virus ID | Clade | PentaNAb2.0 | PentaScFv2.0 | VRC01 | PGT121 | 10E8 | 35022 |
|---|---|---|---|---|---|---|---|
| CN3 | AE | 0.125 | 0.011 | 1.79 | >50 | 1.37 | 0.020 |
| CNE5 | AE | 0.031 | 0.002 | 0.398 | >50 | 1.17 | >50 |
| CNE55 | AE | 0.044 | 0.004 | 0.358 | >50 | 0.038 | >50 |
| CNE56 | AE | 0.580 | 0.024 | 0.525 | >50 | 0.060 | >50 |
| CNE59 | AE | 0.056 | 0.007 | 0.368 | >50 | 0.0010 | >50 |
| CNE8 | AE | 0.021 | 0.0007 | 0.299 | >50 | 0.140 | >50 |
| M02138 | AE | 0.093 | 0.007 | 0.898 | >50 | 0.014 | >50 |
| R1166.c1 | AE | 0.600 | 0.020 | 2.09 | >50 | 0.488 | >50 |
| R2184.c4 | AE | 0.070 | 0.007 | 0.106 | >50 | 0.576 | 0.052 |
| R3264.c6 | AE | 0.486 | 0.023 | 0.382 | >50 | 1.58 | >50 |
| TH023.6 | AE | 0.018 | 0.002 | 0.546 | >50 | 0.0003 | 0.086 |
| TH966.8 | AE | 0.037 | 0.002 | 0.390 | >50 | 0.039 | >50 |
| TH976.17 | AE | 0.036 | 0.003 | 0.299 | >50 | 0.392 | 1.00 |
| 235-47 | AG | 0.029 | 0.004 | 0.043 | 0.110 | 0.244 | >50 |
| 242-14 | AG | 0.026 | 0.002 | >50 | >50 | 0.568 | >50 |
| 263-8 | AG | 0.049 | 0.005 | 0.176 | 1.23 | 0.229 | >50 |
| 269.12 | AG | 0.096 | 0.005 | 0.313 | 0.164 | 0.124 | >50 |
| 271-11 | AG | 0.020 | 0.002 | 0.059 | 11.7 | 0.891 | 0.080 |
| 928-28 | AG | 0.125 | 0.005 | 0.394 | 31.0 | 0.079 | >50 |
| DJ263.8 | AG | 0.028 | 0.0010 | 0.047 | 0.064 | 0.009 | 0.030 |
| T250-4 | AG | 0.014 | 0.0010 | >50 | 0.0010 | 1.07 | >50 |
| T251-18 | AG | 1.59 | 0.094 | 4.21 | 10.8 | 0.666 | >50 |
| T253-11 | AG | 0.045 | 0.011 | 0.397 | >50 | 1.21 | 2.89 |
| T255-34 | AG | 0.037 | 0.003 | 0.500 | >50 | 0.228 | 0.005 |
| T257-31 | AG | 0.039 | 0.003 | 1.72 | >50 | 0.336 | >50 |
| T266-60 | AG | 0.100 | 0.012 | 1.81 | 0.160 | >50 | >50 |
| T278-50 | AG | 0.241 | 0.019 | >50 | >50 | 0.357 | 2.27 |
| T280-5 | AG | 0.078 | 0.012 | 0.032 | 0.002 | 0.715 | >50 |
| T33-7 | AG | 0.038 | 0.004 | 0.018 | >50 | 0.818 | 1.00 |
| 3988.25 | B | 0.072 | 0.005 | 0.494 | 0.002 | 0.070 | 0.609 |
| 5768.04 | B | 0.307 | 0.028 | 0.365 | 0.039 | 1.63 | 0.074 |
| 6101.10 | B | 0.076 | 0.006 | 0.035 | 0.002 | 0.0010 | >50 |
| 6535.3 | B | 0.051 | 0.004 | 1.93 | 0.003 | 0.190 | >50 |
| 7165.18 | B | 0.090 | 0.004 | 28.2 | 0.019 | 0.659 | >50 |
| 45_01dG5 | B | 0.126 | 0.013 | 0.018 | 0.002 | 0.106 | >50 |
| 89.6.DG | B | 0.016 | 0.0010 | 0.762 | 0.016 | 0.318 | >50 |
| AC10.29 | B | 0.229 | 0.011 | 1.81 | 0.028 | 0.102 | >50 |
| ADA.DG | B | 0.052 | 0.005 | 0.470 | 0.002 | 0.055 | >50 |
| Bal.01 | B | 0.066 | 0.003 | 0.095 | 0.011 | 0.421 | 0.002 |
| Bal.26 | B | 0.137 | 0.010 | 0.042 | 0.010 | 0.518 | 0.0010 |
| BG1168.01 | B | 1.52 | 0.079 | 0.869 | >50 | 0.396 | >50 |
| BL01.DG | B | 0.467 | 0.039 | >50 | >50 | 0.362 | 0.009 |
| BR07.DG | B | 0.128 | 0.003 | 1.57 | 0.064 | 0.118 | 0.002 |
| BX08.16 | B | 0.031 | 0.002 | 0.274 | 0.002 | 0.213 | 0.040 |
| CAAN.A2 | B | 0.256 | 0.014 | 1.03 | 0.005 | 1.45 | 0.0010 |
| CNE10 | B | 0.099 | 0.005 | 0.565 | 0.005 | 0.014 | >50 |
| CNE12 | B | 0.166 | 0.010 | 0.866 | 0.002 | 0.301 | 0.010 |

FIG. 4A (Countinued)

| Virus ID | Clade | PentaNAb2.0 | PentaScFv2.0 | VRC01 | PGT121 | 10E8 | 35022 |
|---|---|---|---|---|---|---|---|
| CNE14 | B | 0.106 | 0.008 | 0.275 | 0.002 | 0.151 | 0.004 |
| CNE4 | B | 0.249 | 0.014 | 0.910 | 11.5 | 0.059 | 0.010 |
| CNE57 | B | 0.068 | 0.005 | 0.563 | 0.008 | 0.059 | >50 |
| H086.8 | B | 0.605 | 0.024 | >50 | >50 | 0.326 | >50 |
| HT593.1 | B | 0.365 | 0.030 | 0.476 | >50 | 0.049 | >50 |
| HXB2.DG | B | 0.105 | 0.002 | 0.034 | >50 | 0.003 | 17.3 |
| JRCSF.JB | B | 0.235 | 0.017 | 0.362 | 0.061 | 0.429 | 0.070 |
| JRFL.JB | B | 0.279 | 0.017 | 0.028 | 0.017 | 0.174 | 0.020 |
| MN.3 | B | 0.070 | 0.008 | 0.020 | >50 | 0.0003 | 0.009 |
| PVO.04 | B | 0.228 | 0.029 | 0.511 | 0.132 | 1.60 | 45.0 |
| QH0515.01 | B | 1.56 | 0.093 | 1.01 | 8.70 | 2.25 | >50 |
| QH0692.42 | B | 0.530 | 0.020 | 1.54 | 0.940 | 0.531 | 0.100 |
| REJO.67 | B | 0.204 | 0.011 | 0.075 | 8.87 | 0.302 | 0.003 |
| RHPA.7 | B | 0.168 | 0.010 | 0.034 | 0.014 | 1.01 | >50 |
| SC422.8 | B | 0.115 | 0.006 | 0.127 | 0.098 | 0.343 | >50 |
| SF162.LS | B | 0.010 | 0.0009 | 0.207 | 0.004 | 0.245 | >50 |
| SS1196.01 | B | 0.034 | 0.0010 | 0.304 | 0.002 | 0.244 | 0.068 |
| THRO.18 | B | 0.113 | 0.006 | 3.16 | >50 | 0.092 | >50 |
| TRJO.58 | B | 0.675 | 0.034 | 0.101 | 4.31 | 1.13 | 0.0010 |
| TRO.11 | B | 0.109 | 0.006 | 0.469 | 0.006 | 0.028 | >50 |
| WITO.33 | B | 0.111 | 0.008 | 0.102 | 0.787 | 0.031 | 7.24 |
| X2278.C2.B6 | B | 0.029 | 0.004 | 0.151 | 0.007 | 0.442 | 0.0003 |
| YU2.DG | B | 0.170 | 0.013 | 0.076 | 0.068 | 1.17 | >50 |
| BJOX00200.03.2 | BC | 0.042 | 0.005 | >50 | 0.018 | 0.384 | 45.0 |
| CH038.12 | BC | 0.039 | 0.002 | 0.447 | 0.004 | 0.271 | >50 |
| CH070.1 | BC | 0.018 | 0.0010 | 14.0 | 0.003 | 6.65 | >50 |
| CH117.4 | BC | 0.009 | 0.0008 | 0.105 | >50 | 0.270 | >50 |
| CH119.10 | BC | 0.081 | 0.006 | 0.833 | 0.029 | 0.591 | 38.2 |
| CH181.12 | BC | 0.014 | 0.002 | 0.487 | 0.007 | 0.754 | 10.6 |
| CNE15 | BC | 0.094 | 0.006 | 0.141 | 19.0 | 0.844 | >50 |
| CNE19 | BC | 0.020 | 0.0010 | 0.247 | 0.007 | 0.251 | 0.0010 |
| CNE20 | BC | 0.026 | 0.002 | 7.39 | 0.002 | 0.131 | >50 |
| CNE21 | BC | 0.042 | 0.004 | 0.274 | 0.004 | 0.979 | 0.062 |
| CNE40 | BC | 0.038 | 0.004 | 0.433 | 0.224 | 0.0010 | 0.006 |
| CNE7 | BC | 0.075 | 0.006 | 0.187 | 0.032 | 0.130 | 0.003 |
| 286.36 | C | 0.057 | 0.003 | 0.223 | 0.002 | 1.19 | 0.009 |
| 288.38 | C | 0.011 | 0.0010 | 1.38 | 0.006 | 0.435 | >50 |
| 0013095-2.11 | C | 0.012 | 0.0010 | 0.086 | >50 | 0.009 | >50 |
| 001428-2.42 | C | 0.045 | 0.003 | 0.014 | 0.023 | 1.71 | >50 |
| 0077_V1.C16 | C | 0.063 | 0.008 | 1.13 | >50 | 1.86 | 0.005 |
| 00836-2.5 | C | 0.071 | 0.004 | 0.122 | 31.8 | 0.666 | >50 |
| 0921.V2.C14 | C | 0.030 | 0.003 | 0.230 | >50 | 0.908 | >50 |
| 16055-2.3 | C | 0.042 | 0.003 | 0.100 | 1.02 | 1.10 | >50 |
| 16845-2.22 | C | 0.260 | 0.016 | 2.95 | 9.41 | 0.020 | >50 |
| 16936-2.21 | C | 0.014 | 0.0007 | 0.154 | 0.003 | 0.264 | 0.0010 |
| 25710-2.43 | C | 0.033 | 0.003 | 0.487 | 0.014 | 0.064 | >50 |
| 25711-2.4 | C | 0.082 | 0.006 | 0.559 | 0.010 | 0.516 | >50 |

FIG. 4A (Countinued)

| Virus ID | Clade | PentaNAb2.0 | PentaScFv2.0 | VRC01 | PGT121 | 10E8 | 35022 |
|---|---|---|---|---|---|---|---|
| 25925-2.22 | C | 0.037 | 0.002 | 0.550 | 0.024 | 0.402 | >50 |
| 26191-2.48 | C | 0.048 | 0.004 | 0.183 | 0.150 | 1.83 | >50 |
| 3168.V4.C10 | C | 0.151 | 0.011 | 0.129 | 0.485 | 2.83 | 0.004 |
| 3637.V5.C3 | C | 13.9 | 1.47 | 1.97 | >50 | 2.12 | >50 |
| 3873.V1.C24 | C | 0.019 | 0.007 | 2.81 | 0.015 | 5.51 | >50 |
| 426c | C | 0.680 | 0.030 | 1.93 | >50 | 0.445 | >50 |
| 6322.V4.C1 | C | 0.103 | 0.015 | >50 | >50 | 0.923 | >50 |
| 6471.V1.C16 | C | >50 | >50 | >50 | >50 | 4.98 | >50 |
| 6631.V3.C10 | C | 3.25 | 0.351 | >50 | >50 | 0.934 | >50 |
| 6644.V2.C33 | C | 0.080 | 0.005 | 0.153 | 0.018 | 0.013 | 0.037 |
| 6785.V5.C14 | C | 0.114 | 0.008 | 0.253 | 0.019 | 0.701 | >50 |
| 6838.V1.C35 | C | 0.046 | 0.003 | 0.288 | 0.019 | 0.292 | >50 |
| 96ZM651.02 | C | 0.075 | 0.005 | 0.807 | 0.009 | 0.033 | >50 |
| BR025.9 | C | 0.032 | 0.002 | 0.528 | 0.002 | 0.307 | 0.005 |
| CAP210.E8 | C | 0.053 | 0.003 | >50 | >50 | 0.474 | 0.019 |
| CAP244.D3 | C | 0.120 | 0.004 | 1.34 | >50 | 0.369 | >50 |
| CAP256.206.C9 | C | 0.043 | 0.003 | 1.07 | 0.010 | 0.713 | 0.033 |
| CAP45.G3 | C | 0.030 | 0.002 | 6.75 | 2.08 | 0.722 | 0.016 |
| Ce1176.A3 | C | 0.040 | 0.003 | 1.85 | 0.016 | 0.252 | 0.005 |
| CE703010217.B6 | C | 0.033 | 0.0010 | 0.195 | 0.002 | 0.096 | >50 |
| CNE30 | C | 0.468 | 0.020 | 0.693 | 0.061 | 0.456 | >50 |
| CNE31 | C | 0.195 | 0.017 | 0.772 | 0.789 | 1.32 | >50 |
| CNE53 | C | 0.137 | 0.008 | 0.112 | 0.022 | 0.213 | >50 |
| CNE58 | C | 0.038 | 0.005 | 0.252 | >50 | 0.229 | 0.070 |
| DU123.06 | C | 0.015 | 0.0002 | 5.70 | 0.033 | 0.132 | >50 |
| DU151.02 | C | 0.034 | 0.002 | 10.5 | 0.005 | 0.461 | 8.00 |
| DU156.12 | C | 0.024 | 0.002 | 0.077 | 0.005 | 0.023 | >50 |
| DU173.17 | C | 0.080 | 0.003 | >50 | 0.104 | 0.057 | >50 |
| DU422.01 | C | 0.081 | 0.004 | >50 | 0.164 | 0.224 | >50 |
| MW965.26 | C | 0.013 | 0.003 | 0.043 | 0.011 | 0.0010 | 5.60 |
| SO18.18 | C | 0.015 | 0.0010 | 0.052 | 0.002 | 1.60 | >50 |
| TV1.29 | C | 0.035 | 0.004 | >50 | 0.118 | 0.248 | >50 |
| TZA125.17 | C | 0.052 | 0.004 | >50 | 9.96 | 0.217 | >50 |
| TZBD.02 | C | 0.251 | 0.140 | 0.043 | 0.005 | 1.41 | >50 |
| ZA012.29 | C | 0.077 | 0.010 | 0.327 | 0.005 | 1.47 | >50 |
| ZM106.9 | C | 0.094 | 0.008 | 0.264 | 0.005 | >50 | >50 |
| ZM109.4 | C | 0.057 | 0.005 | 0.142 | 13.7 | 0.161 | >50 |
| ZM135.10a | C | 0.100 | 0.004 | 1.40 | 1.50 | 0.033 | >50 |
| ZM176.66 | C | 0.033 | 0.002 | 0.045 | 13.8 | 0.267 | >50 |
| ZM197.7 | C | 0.113 | 0.005 | 0.532 | >50 | 0.055 | >50 |
| ZM214.15 | C | 0.090 | 0.007 | 0.957 | 0.682 | 2.22 | >50 |
| ZM215.8 | C | 0.027 | 0.003 | 0.362 | 0.014 | 0.044 | 0.015 |
| ZM233.6 | C | 0.019 | 0.002 | 1.98 | 4.14 | 0.270 | 0.005 |
| ZM249.1 | C | 0.046 | 0.002 | 0.107 | >50 | 0.830 | 0.0010 |
| ZM53.12 | C | 0.028 | 0.002 | 0.702 | 0.002 | 2.62 | >50 |
| ZM55.28a | C | 0.080 | 0.009 | 0.241 | 0.070 | 2.34 | >50 |
| 3326.V4.C3 | C | 0.021 | 0.002 | 0.107 | >50 | 1.40 | >50 |

FIG. 4A (Countinued)

| Virus ID | Clade | PentaNAb2.0 | PentaScFv2.0 | VRC01 | PGT121 | 10E8 | 35022 |
|---|---|---|---|---|---|---|---|
| 3337.V2.C6 | CD | 0.017 | 0.0010 | 0.105 | 21.1 | 1.09 | 0.0009 |
| 3817.v2.c59 | CD | 0.070 | 0.011 | >50 | >50 | 0.229 | >50 |
| 191821.E6.1 | D | 0.115 | 0.014 | 0.438 | >50 | 1.91 | >50 |
| 231965.c1 | D | 0.100 | 0.015 | 0.392 | >50 | 11.0 | >50 |
| 247-23 | D | 0.049 | 0.004 | 1.63 | >50 | 0.344 | 0.0010 |
| 3016.v5.c45 | D | 0.033 | 0.004 | 0.117 | >50 | 0.710 | >50 |
| 57128.vrc15 | D | 0.024 | 0.004 | >50 | 2.16 | 0.212 | 0.043 |
| 6405.v4.c34 | D | 0.344 | 0.015 | 1.69 | 0.019 | 0.461 | 0.004 |
| AO3349M1.vrc4a | D | 0.190 | 0.011 | 4.42 | 0.013 | 0.270 | 0.0009 |
| AO7412M1.vrc12 | D | 0.070 | 0.006 | 0.101 | 0.012 | 0.140 | >50 |
| NKU3006.ec1 | D | 1.11 | 0.157 | 0.460 | >50 | 0.673 | 0.004 |
| UG021.16 | D | 0.234 | 0.027 | 0.451 | 2.41 | 0.046 | >50 |
| UG024.2 | D | 0.105 | 0.016 | 0.219 | >50 | 0.053 | >50 |
| P0402.c2.11 | G | 0.006 | 0.0010 | 0.207 | 0.004 | 0.057 | 0.006 |
| P1981.C5.3 | G | 0.023 | 0.003 | 0.336 | 0.004 | 0.024 | 0.0003 |
| X1193.c1 | G | 0.075 | 0.009 | 0.124 | 0.028 | 0.341 | 0.020 |
| X1254.c3 | G | 0.125 | 0.016 | 0.055 | 0.024 | 3.67 | >50 |
| X1632.S2.B10 | G | 0.050 | 0.003 | 0.131 | >50 | 0.387 | 0.564 |
| X2088.c9 | G | 0.129 | 0.017 | >50 | 0.003 | >50 | >50 |
| C2131.C1.B5 | G | 0.033 | 0.003 | 0.467 | 0.010 | 0.039 | >50 |
| SIVmac251.30.SG3 | NA | >50 | >50 | >50 | >50 | >50 | >50 |
| SVA.MLV | NA | >50 | >50 | >50 | >50 | >50 | >50 |

FIG. 4A (Countinued)

FIG. 4B

| | $PentaNAb_{2.0}$ | $PentaScFv_{2.0}$ | VRC01 | PGT121 | 10E8 | 35O22 |
|---|---|---|---|---|---|---|
| # Viruses | 208 | 208 | 208 | 208 | 208 | 208 |
| **Total VS Neutralized** | | | | | | |
| IC>50 <>50ug/ml | 207 | 207 | 188 | 133 | 203 | 94 |
| IC>50 <10ug/ml | 206 | 207 | 184 | 122 | 202 | 89 |
| IC>50 <1.0ug/ml | 201 | 206 | 152 | 108 | 152 | 79 |
| IC>50 <0.1ug/ml | 135 | 202 | 40 | 93 | 42 | 75 |
| IC>50 <0.01ug/ml | 3 | 149 | 0 | 47 | 10 | 45 |
| **% VS Neutralized** | | | | | | |
| IC>50 <>50ug/ml | 99.5 | 99.5 | 90.4 | 63.9 | 97.6 | 45.2 |
| IC>50 <10ug/ml | 99.0 | 99.5 | 88.5 | 58.7 | 97.1 | 42.8 |
| IC>50 <1.0ug/ml | 96.6 | 99.0 | 73.1 | 51.9 | 73.1 | 38.0 |
| IC>50 <0.1ug/ml | 64.9 | 97.1 | 19.2 | 44.7 | 20.2 | 36.1 |
| IC>50 <0.01ug/ml | 1.4 | 71.6 | 0.0 | 22.6 | 4.8 | 21.6 |
| Median IC>50 | 0.070 | 0.005 | 0.287 | 0.019 | 0.392 | 0.010 |
| Geometric Mean | 0.072 | 0.006 | 0.301 | 0.045 | 0.299 | 0.025 |

| | | Viruses from VRC01 Clinical Trial | | | |
|---|---|---|---|---|---|
| | | $IC_{50,80}$ Titer (μg/ml) | | | |
| | | V07-RD (A) | | V09-JF (B) | |
| | Test Antibody | $IC_{50}$ | $IC_{80}$ | $IC_{50}$ | $IC_{80}$ |
| Parental mAbs | VRC01 | >40 | >40 | >40 | >40 |
| | N6 | 0.096 | 0.34 | 4.68 | 12.95 |
| | 35022 | >40 | >40 | 5.90 | >40 |
| | 10E8v4S100cF | 0.80 | 3.86 | 2.20 | 9.67 |
| | 35022 & 10E8v4S100cF | 0.58 | 3.32 | 0.36 | 1.86 |
| Multi-NAbs | Penta-Nab IgG | <0.04 | <0.16 | 0.052 | 0.13 |
| | Penta-ScFv | <0.04 | <0.04 | <0.04 | <0.04 |

FIG. 5C

| | PentaNAb2.0 | | | | |
|---|---|---|---|---|---|
| | Forward ScFv | Reverse ScFv | Forward IgG1-LS | Reverse IgG1-LS | Forward/ Reverse IgG1-LS |
| # Viruses | 25 | 25 | 25 | 25 | 25 |
| Total VS Neutralized | | | | | |
| IC50<50μg/mL | 25 | 25 | 23 | 23 | 23 |
| IC50<1μg/mL | 23 | 23 | 19 | 21 | 20 |
| % VS Neutralized | | | | | |
| IC50<50μg/mL | 100 | 100 | 92 | 92 | 92 |
| IC50<1μg/mL | 92 | 92 | 76 | 84 | 80 |
| Median IC50 | 0.024 | 0.010 | 0.131 | 0.062 | 0.109 |
| Geometric Mean | 0.055 | 0.024 | 0.221 | 0.074 | 0.146 |

PentaNAb2.0

| Virus | Clade | Forward ScFv | Reverse ScFv | Forward IgG1-LS | Reverse IgG1-LS | Forward/ Reverse IgG1-LS |
|---|---|---|---|---|---|---|
| KER2008.12.SG3 | A | 0.012 | 0.005 | 0.087 | 0.016 | 0.080 |
| Q769.d22.SG3 | A | 0.024 | 0.008 | 0.113 | 0.079 | 0.088 |
| 3589.V1.C4.SG3 | AC | 0.008 | 0.007 | 0.070 | 0.101 | 0.085 |
| 6095.V1.C10.SG3 | ACD | 0.010 | 0.005 | 0.055 | 0.024 | 0.042 |
| Q168.a2.SG3 | AD | 0.024 | 0.010 | 0.130 | 0.033 | 0.186 |
| BJOX009000.02.4.SG3 | AE | 0.006 | 0.004 | 0.083 | 0.062 | 0.041 |
| 242-14.SG3 | AG | 0.014 | 0.010 | 0.131 | 0.022 | 0.109 |
| T251-18.SG3 | AG | 0.291 | 0.062 | 2.36 | 0.813 | 1.18 |
| T266-60.SG3 | AG | 0.130 | 0.022 | 0.717 | 0.095 | 0.258 |
| 7165.18.SG3 | B | 0.008 | 0.007 | 0.079 | 0.083 | 0.040 |
| AC10.29.SG3 | B | 0.053 | 0.039 | 0.309 | 0.077 | 0.235 |
| BG1168.01.SG3 | B | 0.703 | 0.327 | 8.56 | 29.1 | 11.4 |
| JRFL.JB.SG3 | B | 0.152 | 0.084 | 1.18 | 0.589 | 0.646 |
| QH0692.42.SG3 | B | 0.147 | 0.059 | 4.16 | 1.54 | 1.43 |
| 3637.V5.C3.SG3 | C | 20.2 | 43.4 | >50 | >50 | >50 |
| 6471.V1.C16.SG3 | C | 35.8 | 19.0 | >50 | >50 | >50 |
| CAP210.E8.SG3 | C | 0.014 | 0.007 | 0.084 | 0.018 | 0.061 |
| DU172.17.SG3 | C | 0.014 | 0.016 | 0.149 | 0.069 | 0.088 |
| DU422.01.SG3 | C | 0.040 | 0.009 | 0.288 | 0.030 | 0.128 |
| TZA125.17.SG3 | C | 0.016 | 0.003 | 0.078 | 0.008 | 0.037 |
| ZM106.9.SG3 | C | 0.112 | 0.021 | 0.466 | 0.057 | 0.260 |
| ZM214.15.SG3 | C | 0.017 | 0.0006 | 0.020 | 0.007 | 0.017 |
| ZM249.1.SG3 | C | 0.023 | 0.011 | 0.134 | 0.028 | 0.113 |
| 57128.vrc15.SG3 | D | 0.007 | 0.006 | 0.055 | 0.018 | 0.036 |
| X2088.c9.SG3 | G | 0.083 | 0.032 | 0.475 | 0.085 | 0.216 |

FIG. 7C

Distance Between PGT121-VRC01 termini (Using PDB:5FYK)

Intra-Protomer (1↔1)

Orientation

| VRC01 | PGT121 | VRC01 C-terminus | PGT121 N-terminus | Distance (A) |
|---|---|---|---|---|
| VH-VL | VH-VL | VAL 106.V CB | GLN 1.H CB | 106.920 |
| VH-VL | VL-VH | VAL 106.V CB | PRO 7.L CB | 100.662 |
| VL-VH | VL-VH | VAL 111.U CB | ALA 6.L CB | 73.361 |
| VL-VH | VH-VL | VAL 111.U CB | GLN 1.H CB | 78.762 |

Orientation

| PGT121 | VRC01 | PGT121 C-terminus | VRC01 N-terminus | Distance (A) |
|---|---|---|---|---|
| VH-VL | VH-VL | VAL 106.L CB | GLN 1.U CB | 96.925 |
| VH-VL | VL-VH | VAL 106.L CB | VAL 3.V CB | 94.519 |
| VL-VH | VL-VH | SER 111.H CB | VAL 3.V CB | 93.620 |
| VL-VH | VH-VL | SER 111.H CB | GLN 1.U CB | 94.350 |

Intra-Protomer (1↔2)

Orientation

| VRC01 | PGT121 | VRC01 C-terminus | PGT121 N-terminus | Distance (A) |
|---|---|---|---|---|
| VH-VL | VH-VL | VAL 106.V CB | GLN 1.H CB | 106.920 |
| VH-VL | VL-VH | VAL 106.V CB | PRO 7.L CB | 100.662 |
| VL-VH | VL-VH | VAL 111.U CB | ALA 6.L CB | 73.361 |
| VL-VH | VH-VL | VAL 111.U CB | GLN 1.H CB | 78.762 |

Orientation

| PGT121 | VRC01 | PGT121 C-terminus | VRC01 N-terminus | Distance (A) |
|---|---|---|---|---|
| VH-VL | VH-VL | VAL 106.L CB | GLN 1.U CB | 96.925 |
| VH-VL | VL-VH | VAL 106.L CB | VAL 3.V CB | 94.519 |
| VL-VH | VL-VH | SER 111.H CB | VAL 3.V CB | 93.620 |
| VL-VH | VH-VL | SER 111.H CB | GLN 1.U CB | 94.350 |

FIG. 8A

Distance Between VRC01-35O22 termini (Using PDB:5FYK)

Inter-Protomer (1↔1)

| Orientation VRC01 | 35O22 | VRC01 C-terminus | 35O22 N-terminus | Distance (A) |
|---|---|---|---|---|
| VH-VL | VH-VL | VAL 104.V CB | GLN 1.D CB | 46.765 |
| VH-VL | VL-VH | VAL 104.V CB | SER 2.E CB | 76.260 |
| VL-VH | VL-VH | VAL 111.U CB | SER 2.E CB | 92.977 |
| VL-VH | VH-VL | VAL 111.U CB | GLN 1.D CB | 63.737 |

| Orientation 35O22 | VRC01 | 35O22 C-terminus | VRC01 N-terminus | Distance (A) |
|---|---|---|---|---|
| VH-VL | VH-VL | LEU 106A.E CB | GLN 1.U CB | 78.858 |
| VH-VL | VL-VH | LEU 106A.E CB | VAL 3.V CB | 69.351 |
| VL-VH | VL-VH | SER 113.D CB | VAL 3.V CB | 56.967 |
| VL-VH | VH-VL | SER 113.D CB | GLN 1.U CB | 81.817 |

FIG. 8B

Distance Between 35022-10E8 termini (Using PDB:5FYK and 5IQ7)

Intra-Protomer (1↔1)

Orientation

| 35022 | 10E8 | 35022 C-terminus | 10E8 N-terminus | Distance (A) |
|---|---|---|---|---|
| VH-VL | VH-VL | LEU 106.E CB | GLU 1.H CB | 89.563 |
| VH-VL | VL-VH | LEU 106.E CB | TYR 2.L CB | 95.750 |
| VL-VH | VL-VH | SER 113.D CB | TYR 2.L CB | 117.268 |
| VL-VH | VH-VL | SER 113.D CB | GLU 1.H CB | 123.646 |

Orientation

| 10E8 | 35022 | 10E8 C-terminus | 35022 N-terminus | Distance (A) |
|---|---|---|---|---|
| VH-VL | VH-VL | SER 108.L CB | GLN 1.D CB | 115.711 |
| VH-VL | VL-VH | SER 108.L CB | SER 2.E CB | 120.145 |
| VL-VH | VL-VH | SER 103.H CB | SER 2.E CB | 85.261 |
| VL-VH | VH-VL | SER 103.H CB | GLN 1.D CB | 89.240 |

Inter-Protomer (1↔2)

Orientation

| 35022 | 10E8 | 35022 C-terminus | 10E8 N-terminus | Distance (A) |
|---|---|---|---|---|
| VH-VL | VH-VL | LEU 106.E CB | GLU 1.H CB | 91.172 |
| VH-VL | VL-VH | LEU 106.E CB | TYR 2.L CB | 58.521 |
| VL-VH | VL-VH | SER 113.D CB | TYR 2.L CB | 62.283 |
| VL-VH | VH-VL | SER 113.D CB | GLU 1.H CB | 99.062 |

Orientation

| 10E8 | 35022 | 10E8 C-terminus | 35022 N-terminus | Distance (A) |
|---|---|---|---|---|
| VH-VL | VH-VL | SER 108.L CB | GLN 1.D CB | 87.385 |
| VH-VL | VL-VH | SER 108.L CB | SER 2.E CB | 66.283 |
| VL-VH | VL-VH | SER 103.H CB | SER 2.E CB | 48.278 |
| VL-VH | VH-VL | SER 103.H CB | GLN 1.D CB | 66.278 |

Inter-Protomer (1↔3)

Orientation

| 35022 | 10E8 | 35022 C-terminus | 10E8 N-terminus | Distance (A) |
|---|---|---|---|---|
| VH-VL | VH-VL | LEU 106.E CB | GLU 1.H CB | 24.748 |
| VH-VL | VL-VH | LEU 106.E CB | TYR 2.L CB | 45.442 |
| VL-VH | VL-VH | SER 113.D CB | TYR 2.L CB | 60.646 |
| VL-VH | VH-VL | SER 113.D CB | GLU 1.H CB | 85.162 |

Orientation

| 10E8 | 35022 | 10E8 C-terminus | 35022 N-terminus | Distance (A) |
|---|---|---|---|---|
| VH-VL | VH-VL | SER 108.L CB | GLN 1.D CB | 70.113 |
| VH-VL | VL-VH | SER 108.L CB | SER 2.E CB | 64.627 |
| VL-VH | VL-VH | SER 103.H CB | SER 2.E CB | 71.182 |
| VL-VH | VH-VL | SER 103.H CB | GLN 1.D CB | 73.829 |

FIG. 8C

Linker: (G4S)n, where n=3 (3x) or 5 (5x)

FIG. 12
HexaNAb1.0 Reverse ScFv
A
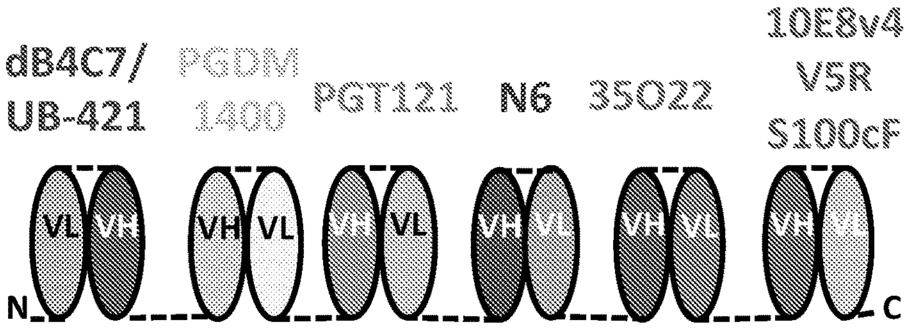
B
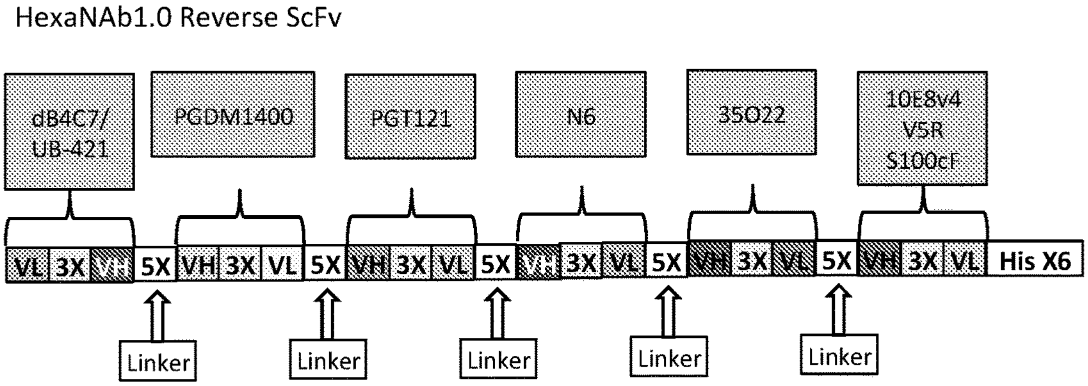
Linker: (G4S)n, where n=3 (3x) or 5 (5x)

A  PentaNAb4.0 Stem HC LSv2 IgG

B  PentaNAb4.0 Stem HC LSv2 – Heavy Chain

C  PentaNAb4.0 Stem HC LSv2 – Light Chain

Linker: (G4S)n, where n=3 (3x) or 5 (5x)

| Virus ID | Clade | Penta-nab 2.0 IgG3C LS | Penta-nab 2.0 ScFv | Penta-nab 2.0 Reverse ScFv | Penta-Nab 4.0 ScFv | Penta-Nab 4.0 Reverse ScFv | Penta-Nab 4.0_Stem_HC-LS_v2 | HexaNab 1.0 Reverse ScFv | VRC01 | PGT121 | 35022 | N6 | 10E8v4 | 10E8v4 x PGDM 1400/ VRC01 | 10E8v4 x PGDM 1400/ N6-LS |
|---|---|---|---|---|---|---|---|---|---|---|---|---|---|---|---|
| 0260.v5.c36 | A | 0.197 | 0.006 | 0.004 | 0.019 | 0.048 | 0.017 | 0.009 | 0.445 | 0.060 | 0.070 | 0.171 | 7.31 | 0.025 | 0.036 |
| 0330.v.c3 | A | 0.060 | 0.002 | 0.002 | 0.011 | 0.019 | 0.005 | 0.003 | 0.083 | 0.066 | >50 | 0.057 | 1.27 | 0.012 | 0.006 |
| 0439.v5.c1 | A | 1.33 | 0.076 | 0.079 | 0.389 | 2.48 | 0.168 | 0.030 | 0.173 | >50 | 0.010 | 0.108 | 1.41 | 0.417 | 0.284 |
| 3365.v2.c20 | A | 0.146 | 0.006 | 0.004 | 0.015 | 0.028 | 0.009 | 0.007 | 0.068 | 0.121 | >50 | 0.032 | 0.792 | 0.017 | 0.011 |
| 3415.v1.c1 | A | 0.215 | 0.010 | 0.008 | 0.014 | 0.107 | 0.035 | 0.019 | 0.096 | >50 | >50 | 0.053 | 2.07 | 0.025 | 0.020 |
| 3718.v3.c11 | A | 0.078 | 0.004 | 0.003 | 0.008 | 0.017 | 0.007 | 0.003 | 0.0381 | 0.603 | >50 | 0.033 | 1.75 | 0.015 | 0.006 |
| 398-F1_F6_20 | A | 0.044 | 0.001 | 0.002 | 0.006 | 0.013 | 0.012 | 0.002 | 0.224 | 0.023 | >50 | 0.029 | 1.71 | 0.021 | 0.039 |
| BB201.B42 | A | 0.037 | 0.002 | 0.0009 | 0.003 | 0.004 | 0.006 | 0.001 | 0.261 | 0.011 | >50 | 0.187 | 0.412 | 0.006 | 0.0010 |
| BB539.2B13 | A | 0.113 | 0.005 | 0.005 | 0.030 | 0.057 | 0.041 | 0.016 | 0.116 | >50 | >50 | 0.025 | 6.77 | 0.009 | 0.011 |
| BG505.W6M.C2 | A | 0.083 | 0.005 | 0.001 | 0.009 | 0.012 | 0.022 | 0.003 | 0.067 | 0.048 | >50 | 0.042 | 0.843 | 0.018 | 0.005 |
| B1369.9A | A | 0.300 | 0.105 | 0.001 | 0.009 | 0.023 | 0.016 | 0.001 | 0.236 | 0.036 | 0.007 | 0.176 | 0.605 | 0.010 | 0.011 |
| BS208.B1 | A | 0.048 | 0.003 | 0.001 | 0.003 | 0.012 | 0.004 | 0.003 | 0.034 | >50 | >50 | 0.019 | 1.30 | 0.008 | 0.002 |
| KER20008.12 | A | 0.071 | 0.002 | 0.002 | 0.003 | 0.005 | 0.003 | 0.002 | 0.595 | 0.578 | 0.0003 | 0.468 | >50 | 0.005 | 0.002 |
| KER20018.11 | A | 0.068 | 0.004 | 0.001 | 0.005 | 0.008 | 0.010 | 0.003 | 0.551 | >50 | 0.005 | 0.279 | 3.17 | 0.007 | 0.002 |
| KNH1209.18 | A | 0.075 | 0.002 | 0.002 | 0.005 | 0.013 | 0.009 | 0.003 | 0.128 | 0.012 | 0.040 | 0.092 | 1.30 | 0.005 | 0.016 |
| MB201.A1 | A | 0.161 | 0.006 | 0.005 | 0.007 | 0.021 | 0.015 | 0.002 | 0.198 | 0.010 | >50 | 0.151 | 0.665 | 0.154 | 0.150 |
| MB539.2B7 | A | 0.296 | 0.016 | 0.056 | 0.023 | 0.063 | 0.037 | 0.021 | 0.470 | >50 | 1.49 | 0.231 | >50 | 0.015 | 0.039 |
| M1369.A5 | A | 0.158 | 0.007 | 0.003 | 0.013 | 0.039 | 0.015 | 0.005 | 0.391 | 0.055 | 0.004 | 0.149 | 0.804 | 0.003 | 0.014 |
| MS208.A1 | A | 0.111 | 0.007 | 0.005 | 0.016 | 0.054 | 0.020 | 0.014 | 0.220 | >50 | >50 | 0.162 | 1.68 | 0.010 | 0.004 |
| Q23.17 | A | 0.024 | 0.001 | 0.001 | 0.003 | 0.005 | 0.002 | 0.001 | 0.085 | 0.011 | 0.003 | 0.055 | 0.541 | 0.002 | 0.0010 |
| Q259.17 | A | 0.084 | 0.003 | 0.003 | 0.006 | 0.050 | 0.019 | 0.009 | 0.086 | >50 | >50 | 0.289 | 3.75 | 0.002 | 0.015 |
| Q769.d22 | A | 0.220 | 0.006 | 0.023 | 0.010 | 0.020 | 0.009 | 0.004 | 0.042 | >50 | 0.053 | 0.021 | 0.512 | 0.0010 | 0.008 |
| Q769.h5 | A | 0.262 | 0.005 | 0.029 | 0.006 | 0.018 | 0.009 | 0.006 | 0.065 | >50 | 0.635 | 0.038 | 3.09 | 0.013 | 0.006 |
| Q842.d12 | A | 0.073 | 0.002 | 0.002 | 0.007 | 0.007 | 0.007 | 0.001 | 0.034 | 0.023 | 0.006 | 0.014 | 1.98 | 0.009 | 0.002 |
| QH209.14M.A2 | A | 0.369 | 0.009 | 0.030 | 0.031 | 0.073 | 0.028 | 0.014 | 0.046 | >50 | >50 | 0.019 | 0.750 | 0.029 | 0.017 |
| RW020.2 | A | 0.095 | 0.004 | 0.002 | 0.008 | 0.015 | 0.017 | 0.003 | 0.276 | 0.010 | 0.009 | 0.069 | 1.56 | 0.007 | 0.023 |
| UG037.8 | A | 0.238 | 0.015 | 0.010 | 0.047 | 0.082 | 0.068 | 0.022 | 0.109 | 0.103 | 0.063 | 0.084 | 0.179 | 0.036 | 0.028 |
| 246-F3.C10.2 | AC | 0.035 | 0.003 | 0.001 | 0.005 | 0.009 | 0.003 | 0.002 | 0.298 | >50 | 0.021 | 0.055 | 0.314 | 0.031 | 0.011 |
| 3301.V1.C24 | AC | 0.138 | 0.006 | 0.003 | 0.015 | 0.030 | 0.014 | 0.010 | 0.121 | 0.021 | 0.057 | 0.021 | 3.58 | 0.049 | 0.016 |
| 3589.V1.C4 | AC | 0.117 | 0.005 | 0.008 | 0.009 | 0.065 | 0.010 | 0.010 | 0.070 | >50 | 0.004 | 0.045 | 0.853 | 0.022 | 0.007 |
| 6540.v4.c1 | AC | 0.228 | 0.006 | 0.004 | 0.010 | 0.022 | 0.012 | 0.010 | >50 | >50 | >50 | 0.070 | 1.57 | 0.020 | 0.007 |
| 6545.V4.C1 | AC | 0.137 | 0.005 | 0.003 | 0.006 | 0.019 | 0.010 | 0.004 | >50 | >50 | >50 | >50 | 1.95 | 0.013 | 0.007 |
| 0815.V3.C3 | ACD | 0.109 | 0.005 | 0.003 | 0.028 | 0.094 | 0.048 | 0.009 | 0.034 | 0.037 | 0.002 | 0.031 | 0.469 | 0.095 | 0.084 |
| 6095.V1.C10 | ACD | 0.045 | 0.006 | 0.002 | 0.010 | 0.019 | 0.014 | 0.004 | 0.783 | >50 | >50 | 0.355 | 0.005 | 0.006 | 0.015 |
| 3468.V1.C12 | AD | 0.215 | 0.008 | 0.007 | 0.013 | 0.024 | 0.021 | 0.005 | 0.059 | 0.086 | 0.005 | 0.029 | 0.629 | 0.250 | 0.061 |
| Q168.a2 | AD | 0.121 | 0.009 | 0.004 | 0.009 | 0.018 | 0.008 | 0.011 | 0.112 | >50 | 0.051 | 0.072 | 0.464 | 0.017 | 0.007 |
| Q461.e2 | AD | 0.869 | 0.043 | 0.011 | 0.078 | 0.239 | 0.079 | 0.056 | 0.766 | >50 | 0.001 | 0.428 | 3.76 | 0.116 | 0.145 |
| 620345.c1 | AE | 0.250 | 0.011 | 0.005 | 0.044 | 0.635 | 0.060 | 0.013 | >50 | >50 | >50 | 3.88 | 0.422 | 2.74 | 0.061 |
| BJOX009000.02.4 | AE | 0.218 | 0.011 | 0.005 | 0.020 | 0.087 | 0.023 | 0.009 | 1.66 | 4.79 | >50 | 0.388 | 0.244 | 0.099 | 0.096 |
| BJOX010000.06.2 | AE | 0.564 | 0.027 | 0.033 | 0.003 | 0.038 | 0.035 | 0.008 | 6.99 | >50 | 3.00 | 0.689 | 0.083 | 0.029 | 0.015 |
| BJOX025000.01.1 | AE | 0.015 | 0.001 | 0.008 | 0.001 | 0.004 | 0.011 | 0.001 | 5.49 | >50 | 3.00 | 0.072 | 0.143 | 0.011 | 0.010 |
| BJOX028000.10.3 | AE | 0.028 | 0.001 | 0.004 | 0.004 | 0.022 | 0.029 | 0.005 | 0.157 | >50 | 0.004 | 0.007 | 0.213 | 0.021 | 0.014 |

FIG. 14A

| Virus ID | Clade | Penta-nab 2.0 IgG3C LS | Penta-nab 2.0 ScFv | Penta-nab 2.0 Reverse ScFv | Penta-Nab 4.0 ScFv | Penta-Nab 4.0 Reverse ScFv | Penta-Nab 4.0_Stem_HC-LS_v2 | HexaNab 1.0 Reverse ScFv | VRC01 | PGT121 | 35022 | N6 | 10E8v4 | 10E8v4 x PGDM 1400/ VRC01 | 10E8v4 x PGDM 1400/ N6-LS |
|---|---|---|---|---|---|---|---|---|---|---|---|---|---|---|---|
| C1080.c3 | AE | 0.039 | 0.001 | 0.0008 | 0.001 | 0.003 | 0.002 | 0.0006 | 1.66 | >50 | 0.005 | 0.257 | 0.073 | 0.005 | 0.002 |
| C2101.c1 | AE | 0.255 | 0.007 | 0.010 | 0.005 | 0.023 | 0.008 | 0.005 | 0.193 | >50 | 0.007 | 0.085 | 1.05 | 0.022 | 0.009 |
| C3347.c11 | AE | 0.156 | 0.005 | 0.002 | 0.002 | 0.014 | 0.014 | 0.003 | 0.101 | >50 | 0.004 | 0.020 | 0.027 | 0.018 | 0.007 |
| C4118.09 | AE | 0.087 | 0.003 | 0.001 | 0.003 | 0.010 | 0.005 | 0.002 | 0.206 | >50 | 0.0003 | 0.073 | 0.599 | 0.009 | 0.003 |
| CM244.ec1 | AE | 0.200 | 0.006 | 0.001 | 0.002 | 0.004 | 0.002 | 0.001 | 0.135 | >50 | 0.023 | 0.025 | 0.904 | 0.0006 | 0.0009 |
| CNE3 | AE | 0.250 | 0.011 | 0.018 | 0.013 | 0.051 | 0.012 | 0.010 | 1.67 | >50 | 0.020 | 0.059 | 1.61 | 0.0010 | 0.007 |
| CNE5 | AE | 0.061 | 0.002 | 0.002 | 0.004 | 0.006 | 0.005 | 0.002 | 0.315 | >50 | >50 | 0.100 | 0.727 | 0.006 | 0.002 |
| CNE55 | AE | 0.088 | 0.004 | 0.003 | 0.007 | 0.018 | 0.011 | 0.005 | 0.355 | >50 | >50 | 0.126 | 0.176 | 0.016 | 0.008 |
| CNE56 | AE | 1.16 | 0.024 | 0.034 | 0.040 | 0.312 | 0.076 | 0.012 | 0.454 | >50 | >50 | 0.133 | 0.169 | 0.365 | 0.209 |
| CNE59 | AE | 0.111 | 0.007 | 0.014 | 0.010 | 0.015 | 0.012 | 0.002 | 0.825 | >50 | >50 | 0.220 | 0.009 | 0.016 | 0.005 |
| CNE8 | AE | 0.041 | 0.0007 | 0.0006 | 0.002 | 0.004 | 0.011 | 0.0007 | 0.490 | >50 | >50 | 0.071 | 0.039 | 0.009 | 0.002 |
| M02138 | AE | 0.186 | 0.007 | 0.015 | 0.022 | 0.022 | 0.050 | 0.019 | 1.06 | >50 | >50 | 0.486 | 0.096 | 0.026 | 0.038 |
| M1166.c1 | AE | 1.20 | 0.020 | 0.052 | 0.044 | 0.161 | 0.188 | 0.026 | 0.917 | >50 | >50 | 0.247 | 0.235 | 0.867 | 0.513 |
| R2184.c4 | AE | 0.139 | 0.007 | 0.006 | 0.008 | 0.033 | 0.021 | 0.007 | 0.106 | >50 | 0.052 | 0.056 | 0.347 | 0.005 | 0.015 |
| R3265.c6 | AE | 0.971 | 0.023 | 0.167 | 0.016 | 0.043 | 0.015 | 0.009 | 0.564 | >50 | >50 | 0.096 | 1.40 | 0.025 | 0.027 |
| TH023.6 | AE | 0.035 | 0.002 | 0.002 | 0.003 | 0.008 | 0.019 | 0.002 | 1.06 | >50 | 0.086 | 0.027 | 0.033 | 0.014 | 0.004 |
| TH966.8 | AE | 0.073 | 0.002 | 0.001 | 0.003 | 0.008 | 0.030 | 0.003 | 0.489 | >50 | >50 | 0.100 | 0.094 | 0.019 | 0.004 |
| TH976.17 | AE | 0.071 | 0.003 | 0.001 | 0.017 | 0.386 | 0.204 | 0.017 | 0.342 | >50 | 1.00 | 0.105 | 0.278 | 0.022 | 0.135 |
| 235-47 | AG | 0.058 | 0.004 | 0.002 | 0.007 | 0.022 | 0.009 | 0.002 | 0.054 | 0.150 | >50 | 0.020 | 0.111 | 0.027 | 0.006 |
| 242-14 | AG | 0.051 | 0.002 | 0.002 | 0.004 | 0.015 | 0.005 | 0.004 | >50 | >50 | >50 | 0.785 | 0.431 | 0.019 | 0.014 |
| 263-8 | AG | 0.098 | 0.005 | 0.003 | 0.010 | 0.028 | 0.009 | 0.003 | 0.196 | 0.447 | >50 | 0.045 | 0.089 | 0.010 | 0.017 |
| 269-12 | AG | 0.192 | 0.005 | 0.003 | 0.016 | 0.028 | 0.023 | 0.006 | 0.296 | 0.142 | >50 | 0.072 | 0.079 | 0.386 | 0.185 |
| 271-11 | AG | 0.039 | 0.002 | 0.001 | 0.004 | 0.012 | 0.006 | 0.002 | 0.077 | >50 | 0.080 | 0.037 | 0.764 | 0.016 | 0.007 |
| 928-28 | AG | 0.250 | 0.005 | 0.002 | 0.016 | 0.069 | 0.042 | 0.012 | 0.578 | 7.34 | >50 | 0.136 | 0.220 | 0.031 | 0.037 |
| DJ263.8 | AG | 0.055 | 0.001 | 0.003 | 0.005 | 0.011 | 0.020 | 0.002 | 0.102 | 0.042 | 0.030 | 0.071 | 0.021 | 0.015 | 0.002 |
| T250-4 | AG | 0.028 | 0.001 | 0.0004 | 0.001 | 0.002 | 0.003 | 0.0006 | >50 | 0.005 | >50 | 0.029 | 1.30 | 0.007 | 0.0010 |
| T251-18 | AG | 3.18 | 0.094 | 0.002 | 0.003 | 0.012 | 0.581 | 0.003 | 3.84 | 2.96 | >50 | 0.640 | 0.596 | 1.33 | 0.903 |
| T253-11 | AG | 0.090 | 0.011 | 0.003 | 0.018 | 0.035 | 0.071 | 0.005 | 0.340 | >50 | 2.89 | 0.171 | 0.700 | 0.0010 | 0.006 |
| T255-34 | AG | 0.073 | 0.003 | 0.003 | 0.009 | 0.027 | 0.014 | 0.002 | 0.458 | 7.62 | 0.005 | 0.097 | 0.360 | 0.002 | 0.009 |
| T257-31 | AG | 0.078 | 0.003 | 0.001 | 0.005 | 0.019 | 0.012 | 0.003 | 1.54 | >50 | >50 | 0.366 | 0.443 | 0.0010 | 0.006 |
| T266-60 | AG | 0.200 | 0.012 | 0.010 | 0.100 | 0.337 | 0.216 | 0.125 | 2.13 | 0.144 | >50 | 0.277 | >50 | 0.648 | 0.223 |
| T278-50 | AG | 0.481 | 0.019 | 0.001 | 0.001 | 0.004 | 0.196 | 0.001 | >50 | >50 | 2.27 | >50 | 2.96 | 0.189 | 1.08 |
| T280-5 | AG | 0.156 | 0.012 | 0.003 | 0.007 | 0.028 | 0.046 | 0.006 | 0.043 | 0.019 | >50 | 0.024 | 4.23 | 0.038 | 0.007 |
| T33-7 | AG | 0.076 | 0.004 | 0.003 | 0.010 | 0.017 | 0.017 | 0.005 | 0.024 | >50 | 1.00 | 0.015 | 0.838 | 0.008 | 0.003 |
| 3988.25 | B | 0.144 | 0.005 | 0.003 | 0.016 | 0.047 | 0.018 | 0.011 | 0.462 | 0.014 | 0.609 | 0.162 | 0.177 | 0.120 | 0.091 |
| 5768.04 | B | 0.613 | 0.028 | 0.021 | 0.040 | 0.090 | 0.043 | 0.018 | 0.424 | 0.121 | 0.074 | 0.121 | 3.00 | 0.063 | 0.069 |
| 6101.10 | B | 0.151 | 0.006 | 0.003 | 0.006 | 0.023 | 0.017 | 0.004 | 0.067 | 0.014 | >50 | 0.016 | 0.031 | 0.040 | 0.087 |
| 6535.3 | B | 0.102 | 0.004 | 0.003 | 0.004 | 0.010 | 0.009 | 0.003 | 2.53 | 0.007 | >50 | 0.225 | 0.150 | 0.027 | 0.006 |
| 7165.18 | B | 0.179 | 0.004 | 0.004 | 0.007 | 0.026 | 0.031 | 0.005 | 31.0 | 0.043 | >50 | 1.71 | 0.332 | 2.22 | 0.210 |
| 45_01dG5 | B | 0.252 | 0.013 | 0.005 | 0.020 | 0.041 | 0.025 | 0.004 | 0.037 | 0.012 | >50 | 0.006 | 0.390 | 0.022 | 0.010 |
| 89.6.DG | B | 0.032 | 0.001 | 0.0009 | 0.003 | 0.007 | 0.021 | 0.001 | 1.31 | 0.036 | >50 | 0.183 | 0.389 | 0.569 | 0.009 |
| AC10.29 | B | 0.458 | 0.011 | 0.004 | 0.012 | 0.065 | 0.051 | 0.010 | 1.80 | 0.074 | >50 | 0.450 | 0.231 | 0.221 | 0.132 |

FIG. 14A (countinued)

| Virus ID | Clade | Penta-nab 2.0 IgG3C LS | Penta-nab 2.0 ScFv | Penta-nab 2.0 Reverse ScFv | Penta-Nab 4.0 ScFv | Penta-Nab 4.0 Reverse ScFv | Penta-Nab 4.0_Stem_HC-LS_v2 | HexaNab 1.0 Reverse ScFv | VRC01 | PGT121 | 35022 | N6 | 10E8v4 | 10E8v4 x PGDM 1400/ VRC01 | 10E8v4 x PGDM 1400/ N6-LS |
|---|---|---|---|---|---|---|---|---|---|---|---|---|---|---|---|
| ADA.DG | B | 0.103 | 0.005 | 0.003 | 0.009 | 0.023 | 0.025 | 0.010 | 0.584 | 0.036 | >50 | 0.275 | 0.051 | 0.125 | 0.036 |
| Bal.01 | B | 0.131 | 0.003 | 0.002 | 0.002 | 0.007 | 0.004 | 0.002 | 0.113 | 0.013 | 0.002 | 0.036 | 0.479 | 0.012 | 0.004 |
| BaL.26 | B | 0.273 | 0.010 | 0.005 | 0.007 | 0.011 | 0.005 | 0.003 | 0.047 | 0.023 | 0.001 | 0.023 | 0.316 | 0.014 | 0.004 |
| BG1168.01 | B | 3.04 | 0.079 | 0.106 | 0.126 | 0.4686 | 0.652 | 0.051 | 0.549 | >50 | >50 | 0.106 | 0.230 | 0.793 | 0.295 |
| BL01.DG | B | 0.933 | 0.039 | 0.031 | 0.093 | 0.216 | 0.176 | 0.014 | >50 | 15.4 | 0.009 | >50 | 0.226 | >50 | 48.9 |
| BR07.DG | B | 0.256 | 0.003 | 0.037 | 0.127 | 0.113 | 0.048 | 0.022 | 1.58 | 0.133 | 0.002 | 0.472 | 0.100 | 0.638 | 0.458 |
| BX08.16 | B | 0.061 | 0.002 | 0.0008 | 0.003 | 0.008 | 0.006 | 0.002 | 0.330 | 0.010 | 0.040 | 0.100 | 0.131 | 0.011 | 0.09 |
| CAAN.A2 | B | 0.511 | 0.014 | 0.009 | 0.018 | 0.079 | 0.036 | 0.008 | 1.15 | 0.021 | 0.001 | 0.289 | 2.78 | 2.83 | 0.630 |
| CNE10 | B | 0.197 | 0.005 | 0.008 | 0.020 | 0.060 | 0.011 | 0.007 | 0.756 | 0.021 | >50 | 0.155 | 0.302 | 1.08 | 0.014 |
| CNE12 | B | 0.331 | 0.010 | 0.008 | 0.023 | 0.066 | 0.031 | 0.004 | 0.703 | 0.015 | 0.010 | 0.190 | 0.239 | 1.41 | 0.617 |
| CNE14 | B | 0.212 | 0.008 | 0.006 | 0.019 | 0.043 | 0.023 | 0.006 | 0.317 | 0.011 | 0.004 | 0.064 | 0.556 | 1.02 | 0.230 |
| CNE4 | B | 0.497 | 0.014 | 0.025 | 0.044 | 0.187 | 0.090 | 0.022 | 0.733 | 2.16 | 0.010 | 0.240 | 0.106 | 0.236 | 0.098 |
| CNE57 | B | 0.135 | 0.005 | 0.009 | 0.016 | 0.035 | 0.016 | 0.004 | 0.532 | 0.030 | >50 | 0.165 | 0.217 | 0.774 | 0.154 |
| HO86.8 | B | 1.21 | 0.024 | 0.674 | 0.096 | 0.211 | 0.034 | 0.010 | >50 | >50 | >50 | 1.86 | 0.440 | 0.220 | 0.036 |
| HT593.1 | B | 0.730 | 0.030 | 0.030 | 0.031 | 0.114 | 0.126 | 0.024 | 0.531 | >50 | >50 | 0.194 | 0.067 | 0.198 | 0.119 |
| HXB2.DG | B | 0.209 | 0.002 | 0.003 | 0.003 | 0.012 | 0.017 | 0.002 | 0.050 | >50 | 17.3 | 0.011 | 0.010 | 0.043 | 0.016 |
| JRCSF.JB | B | 0.469 | 0.017 | 0.014 | 0.006 | 0.011 | 0.008 | 0.003 | 0.350 | 0.063 | 0.070 | 0.162 | 0.721 | 0.010 | 0.005 |
| JRFL.JB | B | 0.558 | 0.017 | 0.015 | 0.035 | 0.091 | 0.053 | 0.011 | 0.042 | 0.038 | 0.020 | 0.009 | 0.278 | 0.119 | 0.021 |
| MN.3 | B | 0.140 | 0.008 | 0.009 | 0.015 | 0.035 | 0.025 | 0.001 | 0.034 | >50 | 0.009 | 0.009 | 0.011 | 0.009 | 0.009 |
| PVO.04 | B | 0.456 | 0.029 | 0.027 | 0.113 | 0.189 | 0.171 | 0.050 | 0.508 | 0.189 | 45.0 | 0.244 | 3.49 | 0.756 | 0.373 |
| QH0515.01 | B | 3.11 | 0.093 | 0.163 | 0.107 | 0.137 | 0.427 | 0.028 | 1.15 | 2.91 | >50 | 0.326 | 2.02 | 1.08 | 0.361 |
| QH0692.42 | B | 1.06 | 0.020 | 0.037 | 0.088 | 0.142 | 0.222 | 0.047 | 1.58 | 1.05 | 0.100 | 0.579 | 0.164 | 0.800 | 0.721 |
| REJO.67 | B | 0.407 | 0.011 | 0.008 | 0.006 | 0.013 | 0.012 | 0.003 | 0.103 | 2.34 | 0.003 | 0.041 | 0.167 | 0.012 | 0.005 |
| RHPA.7 | B | 0.336 | 0.010 | 0.008 | 0.031 | 0.056 | 0.063 | 0.016 | 0.064 | 0.038 | >50 | 0.026 | 1.12 | 0.084 | 0.049 |
| SC422.8 | B | 0.229 | 0.006 | 0.007 | 0.047 | 0.105 | 0.105 | 0.013 | 0.142 | 0.116 | >50 | 0.118 | 0.310 | 0.173 | 0.155 |
| SF162.LS | B | 0.020 | 0.0009 | 0.0006 | 0.004 | 0.008 | 0.016 | 0.002 | 0.285 | 0.007 | >50 | 0.072 | 0.431 | 0.330 | 0.109 |
| SS1196.01 | B | 0.068 | 0.001 | 0.002 | 0.006 | 0.015 | 0.022 | 0.003 | 0.255 | 0.014 | 0.068 | 0.132 | 0.155 | 0.037 | 0.041 |
| THRO.18 | B | 0.225 | 0.006 | 0.016 | 0.031 | 0.124 | 0.037 | 0.022 | 4.39 | >50 | >50 | 1.93 | 0.120 | 0.226 | 0.148 |
| THJO.58 | B | 1.35 | 0.034 | 0.017 | 0.047 | 0.089 | 0.126 | 0.011 | 0.128 | 1.70 | 0.001 | 0.147 | 2.48 | 0.175 | 0.268 |
| TRO.11 | B | 0.218 | 0.006 | 0.005 | 0.020 | 0.033 | 0.028 | 0.007 | 0.619 | 0.022 | >50 | 0.152 | 0.133 | 0.264 | 0.153 |
| WITO.33 | B | 0.221 | 0.008 | 0.008 | 0.010 | 0.017 | 0.011 | 0.004 | 0.140 | 0.534 | 7.24 | 0.076 | 0.097 | 0.002 | 0.008 |
| X2278.C2.B6 | B | 0.057 | 0.004 | 0.001 | 0.012 | 0.022 | 0.024 | 0.003 | 0.121 | 0.028 | 0.0003 | 0.033 | 0.463 | 0.032 | 0.038 |
| YU2.DG | B | 0.339 | 0.013 | 0.005 | 0.017 | 0.045 | 0.082 | 0.008 | 0.067 | 0.041 | >50 | 0.028 | 0.512 | 0.214 | 0.045 |
| BJOX002000.03.2 | BC | 0.084 | 0.005 | 0.002 | 0.010 | 0.020 | 0.015 | 0.004 | >50 | 0.025 | 45.0 | 0.070 | 0.458 | 0.006 | 0.009 |
| CH038.12 | BC | 0.077 | 0.002 | 0.001 | 0.006 | 0.020 | 0.009 | 0.003 | 0.333 | 0.013 | >50 | 0.115 | 0.408 | 0.102 | 0.056 |
| CH070.1 | BC | 0.035 | 0.001 | 0.001 | 0.003 | 0.004 | 0.003 | 0.002 | 7.56 | 0.015 | >50 | 0.143 | 1.81 | 0.002 | 0.002 |
| CH117.4 | BC | 0.017 | 0.0008 | 0.0006 | 0.003 | 0.005 | 0.003 | 0.001 | 0.105 | >50 | >50 | 0.043 | 0.282 | 0.003 | 0.0010 |
| CH119.10 | BC | 0.162 | 0.006 | 0.003 | 0.013 | 0.029 | 0.013 | 0.004 | 0.829 | 0.032 | 38.2 | 0.066 | 0.869 | 0.169 | 0.103 |
| CH181.12 | BC | 0.027 | 0.002 | 0.004 | 0.018 | 0.017 | 0.003 | 0.013 | 0.445 | 0.034 | 10.6 | 0.096 | 0.697 | 0.002 | 0.0010 |
| CNE15 | BC | 0.187 | 0.006 | 0.005 | 0.010 | 0.015 | 0.008 | 0.005 | 0.151 | 9.30 | >50 | 0.060 | 1.02 | 0.008 | 0.0106 |
| CNE19 | BC | 0.039 | 0.001 | 0.0007 | 0.003 | 0.006 | 0.003 | 0.0008 | 0.215 | 0.011 | 0.001 | 0.038 | 0.423 | 0.012 | 0.005 |
| CNE20 | BC | 0.052 | 0.002 | 0.001 | 0.005 | 0.007 | 0.005 | 0.001 | 11.0 | 0.006 | >50 | 0.028 | 0.402 | 0.013 | 0.005 |

FIG. 14A (countinued)

| Virus ID | Clade | Penta-nab 2.0 IgG3C LS | Penta-nab 2.0 ScFv | Penta-nab 2.0 Reverse ScFv | Penta-Nab 4.0 ScFv | Penta-Nab 4.0 Reverse ScFv | Penta-Nab 4.0_Stem_HC-LS_v2 | HexaNab 1.0 Reverse ScFv | VRC01 | PGT121 | 35022 | N6 | 10E8v4 | 10E8v4 x PGDM 1400/ VRC01 | 10E8v4 x PGDM 1400/ N6-LS |
|---|---|---|---|---|---|---|---|---|---|---|---|---|---|---|---|
| CNE21 | BC | 0.083 | 0.004 | 0.004 | 0.010 | 0.012 | 0.008 | 0.003 | 0.310 | 0.014 | 0.062 | 0.066 | 0.242 | 0.008 | 0.003 |
| CNE40 | BC | 0.076 | 0.004 | 0.003 | 0.010 | 0.018 | 0.029 | 0.002 | 0.485 | 0.279 | 0.006 | 0.019 | 0.010 | 0.087 | 0.035 |
| CNE7 | BC | 0.149 | 0.006 | 0.006 | 0.022 | 0.057 | 0.027 | 0.006 | 0.397 | 0.047 | 0.003 | 0.069 | 0.089 | 0.019 | 0.022 |
| 286.36 | C | 0.113 | 0.003 | 0.002 | 0.006 | 0.008 | 0.009 | 0.003 | 0.393 | 0.013 | 0.009 | 0.121 | 1.67 | 0.006 | 0.018 |
| 288.38 | C | 0.022 | 0.001 | 0.003 | 0.004 | 0.015 | 0.005 | 0.006 | 1.80 | 0.018 | >50 | 0.366 | 0.580 | 0.061 | 0.024 |
| 0013095-2.11 | C | 0.023 | 0.001 | 0.002 | 0.002 | 0.006 | 0.003 | 0.0009 | 0.127 | >50 | >50 | 0.054 | 0.031 | 0.009 | 0.002 |
| 001428-2.42 | C | 0.089 | 0.003 | 0.002 | 0.005 | 0.007 | 0.003 | 0.003 | 0.022 | 0.037 | >50 | 0.012 | 3.56 | 0.006 | 0.002 |
| 0077_V1.C16 | C | 0.126 | 0.008 | 0.003 | 0.014 | 0.033 | 0.015 | 0.005 | 1.18 | >50 | 0.005 | 0.068 | 2.08 | 0.028 | 0.022 |
| 00836-2.5 | C | 0.141 | 0.004 | 0.008 | 0.007 | 0.035 | 0.010 | 0.004 | 0.183 | >50 | >50 | 0.012 | 0.607 | 0.029 | 0.016 |
| 0921.V2.C14 | C | 0.060 | 0.003 | 0.002 | 0.009 | 0.026 | 0.006 | 0.006 | 0.277 | >50 | >50 | 0.119 | 1.05 | 0.027 | 0.007 |
| 16055-2.3 | C | 0.083 | 0.003 | 0.001 | 0.007 | 0.013 | 0.007 | 0.003 | 0.087 | 0.364 | >50 | 0.036 | 0.910 | 0.005 | 0.004 |
| 16845-2.22 | C | 0.520 | 0.016 | 0.014 | 0.014 | 0.078 | 0.092 | 0.009 | 3.75 | 2.52 | >50 | 0.608 | 0.034 | 0.542 | 0.198 |
| 16936-2.21 | C | 0.028 | 0.0007 | 0.0007 | 0.002 | 0.004 | 0.010 | 0.0008 | 0.208 | 0.012 | 0.001 | 0.078 | 0.244 | 0.011 | 0.004 |
| 25710-2.43 | C | 0.065 | 0.003 | 0.001 | 0.009 | 0.010 | 0.003 | 0.003 | 0.487 | 0.023 | >50 | 0.083 | 0.056 | 0.025 | 0.009 |
| 25711-2.4 | C | 0.163 | 0.006 | 0.003 | 0.014 | 0.044 | 0.021 | 0.005 | 0.535 | 0.016 | >50 | 0.087 | 0.561 | 0.602 | 0.215 |
| 25925-2.22 | C | 0.073 | 0.002 | 0.001 | 0.007 | 0.011 | 0.004 | 0.003 | 0.610 | 0.050 | >50 | 0.129 | 0.395 | 0.015 | 0.004 |
| 26191-2.48 | C | 0.096 | 0.004 | 0.002 | 0.013 | 0.032 | 0.009 | 0.005 | 0.196 | 0.096 | >50 | 0.093 | 1.28 | 0.002 | 0.006 |
| 3168.V4.C10 | C | 0.302 | 0.011 | 0.009 | 0.054 | 0.112 | 0.043 | 0.029 | 0.175 | 0.526 | 0.004 | 0.153 | 1.86 | 0.104 | 0.114 |
| 3637.V5.C3 | C | 27.7 | 1.47 | >50 | 9.57 | >50 | 30.6 | 0.384 | 2.98 | >50 | >50 | 0.331 | 2.31 | 5.40 | 1.12 |
| 3873.V1.C24 | C | 0.037 | 0.007 | 0.002 | 0.006 | 0.012 | 0.022 | 0.002 | 1.08 | 0.040 | >50 | 0.117 | 3.16 | 0.014 | 0.006 |
| 426c | C | 1.36 | 0.030 | 0.072 | 0.096 | 0.773 | 0.160 | 0.027 | 1.86 | >50 | >50 | 0.256 | 1.09 | 1.58 | 0.322 |
| 6322.V4.C1 | C | 0.206 | 0.015 | 0.0007 | 0.0008 | 0.003 | 0.028 | 0.001 | >50 | >50 | >50 | 0.269 | 1.37 | 0.032 | 0.004 |
| 6471.V1.C16 | C | >50 | >50 | >50 | >50 | >50 | >50 | 0.426 | >50 | >50 | >50 | >50 | 7.55 | >50 | >50 |
| 6631.V3.C10 | C | 6.50 | 0.351 | 0.507 | 0.292 | 3.38 | 1.13 | 0.055 | >50 | >50 | >50 | 0.115 | 1.55 | >50 | 0.510 |
| 6644.V2.C33 | C | 0.159 | 0.005 | 0.004 | 0.005 | 0.007 | 0.007 | 0.002 | 0.294 | 0.034 | 0.037 | 0.102 | 0.136 | 0.016 | 0.012 |
| 6785.V5.C14 | C | 0.228 | 0.008 | 0.002 | 0.013 | 0.024 | 0.011 | 0.009 | 0.462 | 0.063 | >50 | 0.293 | 3.11 | 0.003 | 0.015 |
| 6838.V1.C35 | C | 0.092 | 0.003 | 0.001 | 0.005 | 0.010 | 0.007 | 0.001 | 0.358 | 0.066 | >50 | 0.065 | 0.620 | 0.012 | 0.013 |
| 96ZM651.02 | C | 0.150 | 0.005 | 0.003 | 0.006 | 0.019 | 0.017 | 0.003 | 0.824 | 0.025 | >50 | 0.109 | 0.081 | 0.085 | 0.043 |
| BR025.9 | C | 0.064 | 0.002 | 0.001 | 0.004 | 0.008 | 0.007 | 0.002 | 0.378 | 0.010 | 0.005 | 0.047 | 0.634 | 0.018 | 0.006 |
| CAP210.E8 | C | 0.106 | 0.003 | 0.001 | 0.009 | 0.039 | 0.013 | 0.005 | >50 | 5.55 | 0.019 | >50 | 0.798 | 0.201 | 0.014 |
| CAP244.D3 | C | 0.239 | 0.004 | 0.002 | 0.002 | 0.021 | 0.077 | 0.015 | 0.989 | >50 | >50 | 0.168 | 0.519 | 0.338 | 0.055 |
| CAP256.206.C9 | C | 0.085 | 0.003 | 0.0003 | 0.001 | 0.003 | 0.004 | 0.0007 | 0.649 | 0.020 | 0.033 | 0.194 | 1.34 | 0.020 | 0.006 |
| CAP45.G3 | C | 0.059 | 0.002 | 0.0006 | 0.002 | 0.010 | 0.003 | 0.001 | 6.09 | 1.04 | 0.016 | 0.067 | 0.666 | 0.008 | 0.002 |
| Ce1176.A3 | C | 0.079 | 0.003 | 0.002 | 0.007 | 0.022 | 0.009 | 0.006 | 3.12 | 0.027 | 0.005 | 0.334 | 0.431 | 0.0010 | 0.011 |
| CE703010217.B6 | C | 0.065 | 0.001 | 0.0006 | 0.001 | 0.004 | 0.006 | 0.0008 | 0.248 | 0.009 | >50 | 0.034 | 0.135 | 0.017 | 0.005 |
| CNE30 | C | 0.935 | 0.020 | 0.029 | 0.062 | 0.188 | 0.044 | 0.045 | 0.863 | 0.126 | >50 | 0.253 | 0.582 | 1.17 | 0.630 |
| CNE31 | C | 0.389 | 0.017 | 0.024 | 0.096 | 0.206 | 0.151 | 0.014 | 1.05 | 0.676 | >50 | 0.394 | 1.28 | 0.382 | 0.266 |
| CNE53 | C | 0.274 | 0.008 | 0.009 | 0.013 | 0.037 | 0.027 | 0.007 | 0.114 | 0.028 | >50 | 0.068 | 0.263 | 0.031 | 0.036 |
| CNE58 | C | 0.075 | 0.005 | 0.002 | 0.007 | 0.010 | 0.008 | 0.002 | 0.210 | 11.3 | 0.070 | 0.029 | 0.304 | 0.010 | 0.004 |
| DU123.06 | C | 0.029 | 0.0002 | 0.001 | 0.003 | 0.006 | 0.004 | 0.001 | 5.07 | 0.048 | >50 | 0.081 | 0.113 | 0.021 | 0.008 |
| DU151.02 | C | 0.068 | 0.002 | 0.002 | 0.009 | 0.012 | 0.015 | 0.003 | 11.9 | 0.012 | 8.00 | 0.068 | 0.418 | 0.012 | 0.014 |
| DU156.12 | C | 0.047 | 0.002 | 0.001 | 0.005 | 0.009 | 0.005 | 0.001 | 0.094 | 0.016 | >50 | 0.016 | 0.030 | 0.019 | 0.004 |

FIG. 14A (countinued)

| Virus ID | Clade | Penta-nab 2.0 IgG3C LS | Penta-nab 2.0 ScFv | Penta-nab 2.0 Reverse ScFv | Penta-Nab 4.0 ScFv | Penta-Nab 4.0 Reverse ScFv | Penta-Nab 4.0_Stem_HC-LS_v2 | HexaNab 1.0 Reverse ScFv | VRC01 | PGT121 | 35022 | N6 | 10E8v4 | 10E8v4 x PGDM 1400/ VRC01 | 10E8v4 x PGDM 1400/ N6-LS |
|---|---|---|---|---|---|---|---|---|---|---|---|---|---|---|---|
| DU172.17 | C | 0.159 | 0.003 | 0.004 | 0.004 | 0.021 | 0.014 | 0.003 | >50 | 0.063 | >50 | 0.040 | 0.085 | 1.07 | 0.066 |
| DU422.01 | C | 0.162 | 0.004 | 0.003 | 0.020 | 0.067 | 0.026 | 0.009 | >50 | 0.063 | >50 | 0.046 | 0.366 | 2.96 | 0.090 |
| MW965.26 | C | 0.025 | 0.003 | 0.003 | 0.005 | 0.008 | 0.019 | 0.001 | 0.045 | 0.019 | 5.60 | 0.013 | 0.011 | 0.009 | 0.002 |
| S018.18 | C | 0.030 | 0.001 | 0.006 | 0.030 | 0.033 | 0.008 | 0.012 | 0.041 | 0.005 | >50 | 0.014 | 0.854 | 0.004 | 0.004 |
| TV1.29 | C | 0.069 | 0.004 | 0.002 | 0.006 | 0.009 | 0.007 | 0.002 | >50 | 0.176 | >50 | >50 | 0.368 | 0.009 | 0.002 |
| TZA125.17 | C | 0.103 | 0.004 | 0.001 | 0.008 | 0.027 | 0.020 | 0.005 | >50 | 1.75 | >50 | 1.56 | 0.358 | 0.083 | 0.045 |
| TZBD.02 | C | 0.502 | 0.140 | 0.004 | 0.012 | 0.020 | 0.018 | 0.013 | 0.111 | 0.034 | >50 | 0.061 | 3.08 | 0.006 | 0.010 |
| ZA012.29 | C | 0.154 | 0.010 | 0.004 | 0.021 | 0.032 | 0.024 | 0.012 | 0.297 | 0.012 | >50 | 0.041 | 1.40 | 0.031 | 0.030 |
| ZM0106.9 | C | 0.187 | 0.008 | 0.003 | 0.010 | 0.023 | 0.017 | 0.007 | 0.239 | 0.012 | >50 | 0.044 | >50 | 0.016 | 0.022 |
| ZM109.4 | C | 0.113 | 0.005 | 0.001 | 0.011 | 0.032 | 0.026 | 0.004 | 0.154 | 1.87 | >50 | 0.090 | 0.208 | 0.021 | 0.030 |
| ZM135.10a | C | 0.199 | 0.004 | 0.002 | 0.006 | 0.026 | 0.057 | 0.004 | 1.29 | 0.788 | >50 | 0.225 | 0.151 | 0.036 | 0.021 |
| ZM176.66 | C | 0.066 | 0.002 | 0.0008 | 0.003 | 0.010 | 0.007 | 0.002 | 0.050 | 4.65 | >50 | 0.015 | 0.917 | 0.005 | 0.004 |
| ZM197.7 | C | 0.225 | 0.005 | 0.004 | 0.036 | 0.069 | 0.050 | 0.009 | 0.603 | >50 | >50 | 0.178 | 0.102 | 0.049 | 0.055 |
| ZM214.15 | C | 0.179 | 0.007 | 0.002 | 0.100 | 0.574 | 0.477 | 0.114 | 1.20 | 0.362 | >50 | 0.178 | 2.22 | 1.87 | 0.591 |
| ZM215.8 | C | 0.054 | 0.003 | 0.001 | 0.002 | 0.005 | 0.005 | 0.001 | 0.401 | 0.034 | 0.015 | 0.091 | 0.063 | 0.004 | 0.002 |
| ZM233.6 | C | 0.037 | 0.002 | 0.002 | 0.003 | 0.007 | 0.004 | 0.0009 | 3.37 | 0.827 | 0.005 | 0.125 | 0.293 | 0.005 | 0.006 |
| ZM249.1 | C | 0.091 | 0.002 | 0.002 | 0.007 | 0.034 | 0.017 | 0.003 | 0.110 | >50 | 0.001 | 0.031 | 0.936 | 0.003 | 0.007 |
| ZM253.12 | C | 0.056 | 0.002 | 0.0009 | 0.003 | 0.006 | 0.004 | 0.002 | 1.20 | 0.003 | >50 | 0.256 | 3.82 | 0.016 | 0.004 |
| ZM55.28a | C | 0.160 | 0.009 | 0.007 | 0.042 | 0.075 | 0.043 | 0.014 | 0.293 | 0.087 | >50 | 0.035 | 3.23 | 0.084 | 0.024 |
| 3326.V4.C3 | CD | 0.041 | 0.002 | 0.001 | 0.003 | 0.015 | 0.007 | 0.002 | 0.075 | >50 | >50 | 0.005 | 1.06 | 0.014 | 0.003 |
| 3337.V2.C6 | CD | 0.033 | 0.001 | 0.001 | 0.012 | 0.051 | 0.013 | 0.008 | 0.098 | 1.70 | 0.0009 | 0.021 | 0.853 | 0.059 | 0.012 |
| 3817.v2.c59 | CD | 0.140 | 0.011 | 0.101 | 0.399 | 7.45 | 0.028 | 0.086 | >50 | 20.6 | >50 | 0.293 | 0.845 | 2.48 | 0.055 |
| 191821.E6.1 | D | 0.230 | 0.014 | 0.0105 | 0.089 | 0.144 | 0.046 | 0.021 | 0.622 | >50 | >50 | 0.211 | 2.57 | 0.069 | 0.073 |
| 231965.c1 | D | 0.199 | 0.015 | 0.014 | 0.019 | 0.060 | 0.021 | 0.017 | 0.489 | >50 | >50 | 0.080 | 3.08 | 0.029 | 0.017 |
| 247-23 | D | 0.098 | 0.004 | 0.002 | 0.008 | 0.018 | 0.005 | 0.002 | 2.45 | >50 | 0.001 | 0.181 | 0.224 | 0.024 | 0.009 |
| 3016.v5.c45 | D | 0.066 | 0.004 | 0.003 | 0.008 | 0.048 | 0.020 | 0.020 | 0.106 | >50 | >50 | 0.035 | 0.312 | 0.005 | 0.014 |
| 57128.vrc15 | D | 0.047 | 0.004 | 0.002 | 0.007 | 0.028 | 0.010 | 0.005 | >50 | 1.47 | 0.043 | 0.720 | 0.161 | 0.056 | 0.030 |
| 6405.v4.c34 | D | 0.687 | 0.015 | 0.009 | 0.017 | 0.078 | 0.067 | 0.016 | 1.82 | 0.038 | 0.004 | 0.136 | 0.853 | 4.08 | 0.575 |
| A03349M1.vrc4a | D | 0.380 | 0.011 | 0.002 | 0.014 | 0.034 | 0.035 | 0.002 | 4.56 | 0.089 | 0.0009 | 1.15 | 0.318 | 0.213 | 0.157 |
| A07412M1.vrc12 | D | 0.140 | 0.006 | 0.017 | 0.070 | 0.097 | 0.019 | 0.020 | 0.145 | 0.043 | >50 | 0.080 | 0.516 | 0.007 | 0.018 |
| NKU3006.ec1 | D | 2.22 | 0.157 | 0.134 | 0.287 | 1.33 | 1.81 | 0.016 | 0.542 | >50 | 0.004 | 0.388 | 0.466 | 1.10 | 0.572 |
| UG021.16 | D | 0.468 | 0.027 | 0.072 | 0.092 | 0.092 | 0.105 | 0.029 | 0.511 | 1.11 | >50 | 0.071 | 0.096 | 0.027 | 0.010 |
| UG024.2 | D | 0.209 | 0.016 | 0.066 | 0.200 | 0.253 | 0.176 | 0.021 | 0.279 | >50 | >50 | 0.041 | 0.070 | 0.038 | 0.028 |
| P0402.c2.11 | G | 0.011 | 0.001 | 0.0009 | 0.002 | 0.002 | 0.006 | 0.0007 | 0.165 | 0.012 | 0.006 | 0.058 | 0.221 | 0.007 | 0.002 |
| P1981.C5.3 | G | 0.045 | 0.003 | 0.001 | 0.003 | 0.008 | 0.005 | 0.002 | 0.326 | 0.009 | 0.0003 | 0.232 | 0.078 | 0.036 | 0.028 |
| X1193.c1 | G | 0.150 | 0.009 | 0.001 | 0.007 | 0.017 | 0.021 | 0.003 | 0.167 | 0.052 | 0.020 | 0.110 | 0.595 | 0.055 | 0.040 |
| X1254.c3 | G | 0.249 | 0.016 | 0.007 | 0.015 | 0.045 | 0.073 | 0.011 | 0.054 | 0.030 | >50 | 0.033 | 0.880 | 0.021 | 0.092 |
| X1632.S2.B10 | G | 0.100 | 0.003 | 0.001 | 0.009 | 0.022 | 0.013 | 0.003 | 0.161 | >50 | 0.564 | 0.084 | 0.258 | 0.0010 | 0.013 |
| X2088.c9 | G | 0.258 | 0.017 | 0.007 | 0.019 | 0.086 | 0.044 | 0.021 | >50 | 0.007 | >50 | 0.063 | >50 | >50 | 0.297 |
| X2131.C1.B5 | G | 0.066 | 0.003 | 0.001 | 0.005 | 0.010 | 0.013 | 0.002 | 0.546 | 0.014 | >50 | 0.140 | 0.045 | 0.088 | 0.071 |
| SIVmac251.30.SG3 | NA | >50 | >50 | >50 | >50 | >50 | >50 | 3.37 | >50 | >50 | >50 | >50 | >50 | >50 | >50 |
| SVA.MLV | NA | >50 | >50 | >50 | >50 | >50 | >50 | >50 | >50 | >50 | >50 | >50 | >50 | >50 | >50 |

FIG. 14A (countinued)

| | Pentanab 2.0 IgG3C LS | Pentanab 2.0 ScFv | Penta-Nab 2.0 Reverse ScFv | Penta-Nab 4.0 ScFv | Penta-Nab 4.0 Reverse ScFv | PentaNab 4.0_Stem_HC-LS_vs | HexaNab1.0 Reverse ScFv | VRC01 | PGT121 | 35022 | N6 | 10E8v4 | 10E8v4 x PGDM 1400/ VRC01 | 10E8V4 x PGDM1400 /N6-LS |
|---|---|---|---|---|---|---|---|---|---|---|---|---|---|---|
| # Viruses | 208 | 208 | 208 | 208 | 208 | 208 | 208 | 208 | 208 | 208 | 208 | 208 | 208 | 208 |
| Total VS Neutralized | | | | | | | | | | | | | | |
| IC50 <50ug/ml | 207 | 207 | 206 | 207 | 206 | 207 | 208 | 188 | 135 | 94 | 202 | 203 | 204 | 207 |
| IC50 <10ug/ml | 206 | 207 | 206 | 207 | 206 | 206 | 208 | 185 | 132 | 89 | 202 | 203 | 204 | 206 |
| IC50 <1.0ug/ml | 194 | 206 | 206 | 206 | 202 | 204 | 208 | 149 | 113 | 79 | 196 | 147 | 187 | 204 |
| IC50 <0.1ug/ml | 85 | 202 | 199 | 195 | 177 | 185 | 204 | 35 | 91 | 75 | 109 | 32 | 150 | 165 |
| IC50 <0.01ug/ml | 0 | 149 | 165 | 106 | 41 | 65 | 145 | 0 | 10 | 45 | 5 | 2 | 54 | 82 |
| % VS Neutralized | | | | | | | | | | | | | | |
| IC50 <50ug/ml | 100 | 100 | 99 | 100 | 99 | 100 | 100 | 90 | 65 | 45 | 97 | 98 | 98 | 100 |
| IC50 <10ug/ml | 99 | 100 | 99 | 100 | 99 | 99 | 100 | 89 | 63 | 43 | 97 | 98 | 98 | 99 |
| IC50 <1.0ug/ml | 93 | 99 | 99 | 99 | 97 | 98 | 100 | 72 | 54 | 38 | 94 | 71 | 90 | 98 |
| IC50 <0.1ug/ml | 41 | 97 | 96 | 94 | 85 | 89 | 98 | 17 | 44 | 36 | 52 | 15 | 72 | 79 |
| IC50 <0.01ug/ml | 0 | 72 | 79 | 51 | 20 | 31 | 70 | 0 | 5 | 22 | 2 | 1 | 26 | 39 |
| Median IC50 | 0.139 | 0.005 | 0.003 | 0.009 | 0.023 | 0.017 | 0.005 | 0.328 | 0.038 | 0.010 | 0.086 | 0.463 | 0.022 | 0.015 |
| Geometric Mean | 0.143 | 0.006 | 0.004 | 0.011 | 0.028 | 0.020 | 0.005 | 0.339 | 0.076 | 0.025 | 0.091 | 0.419 | 0.034 | 0.021 |

FIG. 14B

SEQUENCE LISTING

```
<160> NUMBER OF SEQ ID NOS: 108

<210> SEQ ID NO 1
<211> LENGTH: 143
<212> TYPE: PRT
<213> ORGANISM: Artificial Sequence
<220> FEATURE:
<223> OTHER INFORMATION: Synthetic: VRC26.25 VH
```

```
<400> SEQUENCE: 1

Gln Val Gln Leu Val Glu Ser Gly Gly Gly Val Val Gln Pro Gly Thr
1               5                   10                  15

Ser Leu Arg Leu Ser Cys Ala Ala Ser Gln Phe Arg Phe Asp Gly Tyr
            20                  25                  30

Gly Met His Trp Val Arg Gln Ala Pro Gly Lys Gly Leu Glu Trp Val
        35                  40                  45

Ala Ser Ile Ser His Asp Gly Ile Lys Lys Tyr His Ala Glu Lys Val
    50                  55                  60

Trp Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Leu Tyr Tyr Cys
                85                  90                  95

Ala Lys Asp Leu Arg Glu Asp Glu Cys Glu Glu Trp Trp Ser Asp Asp
            100                 105                 110

Phe Gly Lys Gln Leu Pro Cys Ala Lys Ser Arg Gly Gly Leu Val Gly
        115                 120                 125

Ile Ala Asp Asn Trp Gly Gln Gly Thr Met Val Thr Val Ser Ser
    130                 135                 140


<210> SEQ ID NO 2
<211> LENGTH: 8
<212> TYPE: PRT
<213> ORGANISM: Artificial Sequence
<220> FEATURE:
<223> OTHER INFORMATION: Synthetic: VRC26.25 VH CDR1

<400> SEQUENCE: 2

Gln Phe Arg Phe Asp Gly Tyr Gly
1               5


<210> SEQ ID NO 3
<211> LENGTH: 8
<212> TYPE: PRT
<213> ORGANISM: Artificial Sequence
<220> FEATURE:
<223> OTHER INFORMATION: Synthetic: VRC26.25 VH CDR2

<400> SEQUENCE: 3

Ile Ser His Asp Gly Ile Lys Lys
1               5


<210> SEQ ID NO 4
<211> LENGTH: 36
<212> TYPE: PRT
<213> ORGANISM: Artificial Sequence
<220> FEATURE:
<223> OTHER INFORMATION: Synthetic: VRC26.25 VH CDR3

<400> SEQUENCE: 4

Ala Lys Asp Leu Arg Glu Asp Glu Cys Glu Glu Trp Trp Ser Asp Asp
1               5                   10                  15

Phe Gly Lys Gln Leu Pro Cys Ala Lys Ser Arg Gly Gly Leu Val Gly
            20                  25                  30

Ile Ala Asp Asn
        35


<210> SEQ ID NO 5
<211> LENGTH: 112
<212> TYPE: PRT
<213> ORGANISM: Artificial Sequence
```

<220> FEATURE:
<223> OTHER INFORMATION: Synthetic: VRC26.25 VL

<400> SEQUENCE: 5

Gln Ser Val Leu Thr Gln Pro Pro Ser Val Ser Ala Ala Pro Gly Gln
1 5 10 15

Lys Val Thr Ile Ser Cys Ser Gly Asn Thr Ser Asn Ile Gly Asn Asn
20 25 30

Phe Val Ser Trp Tyr Gln Gln Arg Pro Gly Arg Ala Pro Gln Leu Leu
35 40 45

Ile Tyr Glu Thr Asp Lys Arg Pro Ser Gly Ile Pro Asp Arg Phe Ser
50 55 60

Ala Ser Lys Ser Gly Thr Ser Gly Thr Leu Ala Ile Thr Gly Leu Gln
65 70 75 80

Thr Gly Asp Glu Ala Asp Tyr Tyr Cys Ala Thr Trp Ala Ala Ser Leu
85 90 95

Ser Ser Ala Arg Val Phe Gly Thr Gly Thr Lys Val Ile Val Leu Val
100 105 110

<210> SEQ ID NO 6
<211> LENGTH: 8
<212> TYPE: PRT
<213> ORGANISM: Artificial Sequence
<220> FEATURE:
<223> OTHER INFORMATION: Synthetic: VRC26.25 VL CDR1

<400> SEQUENCE: 6

Thr Ser Asn Ile Gly Asn Asn Phe
1 5

<210> SEQ ID NO 7
<211> LENGTH: 3
<212> TYPE: PRT
<213> ORGANISM: Artificial Sequence
<220> FEATURE:
<223> OTHER INFORMATION: Synthetic: VRC26.25 VL CDR2

<400> SEQUENCE: 7

Glu Thr Asp
1

<210> SEQ ID NO 8
<211> LENGTH: 12
<212> TYPE: PRT
<213> ORGANISM: Artificial Sequence
<220> FEATURE:
<223> OTHER INFORMATION: Synthetic: VRC26.25 VL CDR3

<400> SEQUENCE: 8

Ala Thr Trp Ala Ala Ser Leu Ser Ser Ala Arg Val
1 5 10

<210> SEQ ID NO 9
<211> LENGTH: 140
<212> TYPE: PRT
<213> ORGANISM: Artificial Sequence
<220> FEATURE:
<223> OTHER INFORMATION: Synthetic: PGDM1400 VH

<400> SEQUENCE: 9

Gln Ala Gln Leu Val Gln Ser Gly Pro Glu Val Arg Lys Pro Gly Thr
1 5 10 15

Ser Val Lys Val Ser Cys Lys Ala Pro Gly Asn Thr Leu Lys Thr Tyr

```
            20                  25                  30

Asp Leu His Trp Val Arg Ser Val Pro Gly Gln Gly Leu Gln Trp Met
        35                  40                  45

Gly Trp Ile Ser His Glu Gly Asp Lys Lys Val Ile Val Glu Arg Phe
    50                  55                  60

Lys Ala Lys Val Thr Ile Asp Trp Asp Arg Ser Thr Asn Thr Ala Tyr
65                  70                  75                  80

Leu Gln Leu Ser Gly Leu Thr Ser Gly Asp Thr Ala Val Tyr Tyr Cys
                85                  90                  95

Ala Lys Gly Ser Lys His Arg Leu Arg Asp Tyr Ala Leu Asp Asp Asp
            100                 105                 110

Gly Ala Leu Asn Trp Ala Val Asp Val Asp Tyr Leu Ser Asn Leu Glu
        115                 120                 125

Phe Trp Gly Gln Gly Thr Ala Val Thr Val Ser Ser
    130                 135                 140


<210> SEQ ID NO 10
<211> LENGTH: 8
<212> TYPE: PRT
<213> ORGANISM: Artificial Sequence
<220> FEATURE:
<223> OTHER INFORMATION: Synthetic: PGDM1400 VH CDR1

<400> SEQUENCE: 10

Gly Asn Thr Leu Lys Thr Tyr Asp
1               5


<210> SEQ ID NO 11
<211> LENGTH: 8
<212> TYPE: PRT
<213> ORGANISM: Artificial Sequence
<220> FEATURE:
<223> OTHER INFORMATION: Synthetic: PGDM1400 VH CDR2

<400> SEQUENCE: 11

Ile Ser His Glu Gly Asp Lys Lys
1               5


<210> SEQ ID NO 12
<211> LENGTH: 33
<212> TYPE: PRT
<213> ORGANISM: Artificial Sequence
<220> FEATURE:
<223> OTHER INFORMATION: Synthetic: PGDM1400 VH CDR3

<400> SEQUENCE: 12

Ala Lys Gly Ser Lys His Arg Leu Arg Asp Tyr Ala Leu Asp Asp Asp
1               5                   10                  15

Gly Ala Leu Asn Trp Ala Val Asp Val Asp Tyr Leu Ser Asn Leu Glu
            20                  25                  30

Phe


<210> SEQ ID NO 13
<211> LENGTH: 112
<212> TYPE: PRT
<213> ORGANISM: Artificial Sequence
<220> FEATURE:
<223> OTHER INFORMATION: Synthetic: PGDM1400 VL

<400> SEQUENCE: 13

Asp Phe Val Leu Thr Gln Ser Pro His Ser Leu Ser Val Thr Pro Gly
1               5                   10                  15
```

```
Glu Ser Ala Ser Ile Ser Cys Lys Ser Ser His Ser Leu Ile His Gly
            20                  25                  30

Asp Arg Asn Asn Tyr Leu Ala Trp Tyr Val Gln Lys Pro Gly Arg Ser
        35                  40                  45

Pro Gln Leu Leu Ile Tyr Leu Ala Ser Ser Arg Ala Ser Gly Val Pro
    50                  55                  60

Asp Arg Phe Ser Gly Ser Gly Ser Asp Lys Asp Phe Thr Leu Lys Ile
65                  70                  75                  80

Ser Arg Val Glu Thr Glu Asp Val Gly Thr Tyr Tyr Cys Met Gln Gly
                85                  90                  95

Arg Glu Ser Pro Trp Thr Phe Gly Gln Gly Thr Lys Val Asp Ile Lys
            100                 105                 110


<210> SEQ ID NO 14
<211> LENGTH: 11
<212> TYPE: PRT
<213> ORGANISM: Artificial Sequence
<220> FEATURE:
<223> OTHER INFORMATION: Synthetic: PGDM1400 VL CDR1

<400> SEQUENCE: 14

His Ser Leu Ile His Gly Asp Arg Asn Asn Tyr
1               5                   10


<210> SEQ ID NO 15
<211> LENGTH: 3
<212> TYPE: PRT
<213> ORGANISM: Artificial Sequence
<220> FEATURE:
<223> OTHER INFORMATION: Synthetic: PGDM1400 VL CDR2

<400> SEQUENCE: 15

Leu Ala Ser
1


<210> SEQ ID NO 16
<211> LENGTH: 9
<212> TYPE: PRT
<213> ORGANISM: Artificial Sequence
<220> FEATURE:
<223> OTHER INFORMATION: Synthetic: PGDM1400 VL CDR3

<400> SEQUENCE: 16

Met Gln Gly Arg Glu Ser Pro Trp Thr
1               5


<210> SEQ ID NO 17
<211> LENGTH: 132
<212> TYPE: PRT
<213> ORGANISM: Artificial Sequence
<220> FEATURE:
<223> OTHER INFORMATION: Synthetic: PGT121 VH

<400> SEQUENCE: 17

Gln Met Gln Leu Gln Glu Ser Gly Pro Gly Leu Val Lys Pro Ser Glu
1               5                   10                  15

Thr Leu Ser Leu Thr Cys Ser Val Ser Gly Ala Ser Ile Ser Asp Ser
            20                  25                  30

Tyr Trp Ser Trp Ile Arg Arg Ser Pro Gly Lys Gly Leu Glu Trp Ile
        35                  40                  45

Gly Tyr Val His Lys Ser Gly Asp Thr Asn Tyr Ser Pro Ser Leu Lys
    50                  55                  60
```

```
Ser Arg Val Asn Leu Ser Leu Asp Thr Ser Lys Asn Gln Val Ser Leu
65                  70                  75                  80

Ser Leu Val Ala Ala Thr Ala Ala Asp Ser Gly Lys Tyr Tyr Cys Ala
                85                  90                  95

Arg Thr Leu His Gly Arg Arg Ile Tyr Gly Ile Val Ala Phe Asn Glu
            100                 105                 110

Trp Phe Thr Tyr Phe Tyr Met Asp Val Trp Gly Asn Gly Thr Gln Val
        115                 120                 125

Thr Val Ser Ser
    130


<210> SEQ ID NO 18
<211> LENGTH: 8
<212> TYPE: PRT
<213> ORGANISM: Artificial Sequence
<220> FEATURE:
<223> OTHER INFORMATION: Synthetic: PGT121 VH CDR1

<400> SEQUENCE: 18

Gly Ala Ser Ile Ser Asp Ser Tyr
1               5


<210> SEQ ID NO 19
<211> LENGTH: 7
<212> TYPE: PRT
<213> ORGANISM: Artificial Sequence
<220> FEATURE:
<223> OTHER INFORMATION: Synthetic: PGT121 VH CDR2

<400> SEQUENCE: 19

Val His Lys Ser Gly Asp Thr
1               5


<210> SEQ ID NO 20
<211> LENGTH: 26
<212> TYPE: PRT
<213> ORGANISM: Artificial Sequence
<220> FEATURE:
<223> OTHER INFORMATION: Synthetic: PGT121 VH CDR3

<400> SEQUENCE: 20

Ala Arg Thr Leu His Gly Arg Arg Ile Tyr Gly Ile Val Ala Phe Asn
1               5                   10                  15

Glu Trp Phe Thr Tyr Phe Tyr Met Asp Val
            20                  25


<210> SEQ ID NO 21
<211> LENGTH: 105
<212> TYPE: PRT
<213> ORGANISM: Artificial Sequence
<220> FEATURE:
<223> OTHER INFORMATION: Synthetic: PGT121 VL

<400> SEQUENCE: 21

Ser Asp Ile Ser Val Ala Pro Gly Glu Thr Ala Arg Ile Ser Cys Gly
1               5                   10                  15

Glu Lys Ser Leu Gly Ser Arg Ala Val Gln Trp Tyr Gln His Arg Ala
            20                  25                  30

Gly Gln Ala Pro Ser Leu Ile Ile Tyr Asn Asn Gln Asp Arg Pro Ser
        35                  40                  45

Gly Ile Pro Glu Arg Phe Ser Gly Ser Pro Asp Ser Pro Phe Gly Thr
    50                  55                  60
```

```
Thr Ala Thr Leu Thr Ile Thr Ser Val Glu Ala Gly Asp Glu Ala Asp
65                  70                  75                  80

Tyr Tyr Cys His Ile Trp Asp Ser Arg Val Pro Thr Lys Trp Val Phe
                85                  90                  95

Gly Gly Gly Thr Thr Leu Thr Val Leu
            100                 105


<210> SEQ ID NO 22
<211> LENGTH: 6
<212> TYPE: PRT
<213> ORGANISM: Artificial Sequence
<220> FEATURE:
<223> OTHER INFORMATION: Synthetic: PGT121 VL CDR1

<400> SEQUENCE: 22

Ser Leu Gly Ser Arg Ala
1               5


<210> SEQ ID NO 23
<211> LENGTH: 3
<212> TYPE: PRT
<213> ORGANISM: Artificial Sequence
<220> FEATURE:
<223> OTHER INFORMATION: Synthetic: PGT121 VL CDR2

<400> SEQUENCE: 23

Asn Asn Gln
1


<210> SEQ ID NO 24
<211> LENGTH: 12
<212> TYPE: PRT
<213> ORGANISM: Artificial Sequence
<220> FEATURE:
<223> OTHER INFORMATION: Synthetic: PGT121 VL CDR3

<400> SEQUENCE: 24

His Ile Trp Asp Ser Arg Val Pro Thr Lys Trp Val
1               5                   10


<210> SEQ ID NO 25
<211> LENGTH: 122
<212> TYPE: PRT
<213> ORGANISM: Artificial Sequence
<220> FEATURE:
<223> OTHER INFORMATION: Synthetic: N6 VH

<400> SEQUENCE: 25

Arg Ala His Leu Val Gln Ser Gly Thr Ala Met Lys Lys Pro Gly Ala
1               5                   10                  15

Ser Val Arg Val Ser Cys Gln Thr Ser Gly Tyr Thr Phe Thr Ala His
            20                  25                  30

Ile Leu Phe Trp Phe Arg Gln Ala Pro Gly Arg Gly Leu Glu Trp Val
        35                  40                  45

Gly Trp Ile Lys Pro Gln Tyr Gly Ala Val Asn Phe Gly Gly Gly Phe
    50                  55                  60

Arg Asp Arg Val Thr Leu Thr Arg Asp Val Tyr Arg Glu Ile Ala Tyr
65                  70                  75                  80

Met Asp Ile Arg Gly Leu Lys Pro Asp Asp Thr Ala Val Tyr Tyr Cys
                85                  90                  95

Ala Arg Asp Arg Ser Tyr Gly Asp Ser Ser Trp Ala Leu Asp Ala Trp
            100                 105                 110
```

```
Gly Gln Gly Thr Thr Val Val Val Ser Ala
        115                 120


<210> SEQ ID NO 26
<211> LENGTH: 8
<212> TYPE: PRT
<213> ORGANISM: Artificial Sequence
<220> FEATURE:
<223> OTHER INFORMATION: Synthetic: N6 VH CDR1

<400> SEQUENCE: 26

Gly Tyr Thr Phe Thr Ala His Ile
1               5


<210> SEQ ID NO 27
<211> LENGTH: 8
<212> TYPE: PRT
<213> ORGANISM: Artificial Sequence
<220> FEATURE:
<223> OTHER INFORMATION: Synthetic: N6 VH CDR2

<400> SEQUENCE: 27

Ile Lys Pro Gln Tyr Gly Ala Val
1               5


<210> SEQ ID NO 28
<211> LENGTH: 2
<212> TYPE: PRT
<213> ORGANISM: Artificial Sequence
<220> FEATURE:
<223> OTHER INFORMATION: Synthetic: N6 VH CDR3

<400> SEQUENCE: 28

Ala Arg
1


<210> SEQ ID NO 29
<211> LENGTH: 103
<212> TYPE: PRT
<213> ORGANISM: Artificial Sequence
<220> FEATURE:
<223> OTHER INFORMATION: Synthetic: N6 VL

<400> SEQUENCE: 29

Tyr Ile His Val Thr Gln Ser Pro Ser Ser Leu Ser Val Ser Ile Gly
1               5                   10                  15

Asp Arg Val Thr Ile Asn Cys Gln Thr Ser Gln Gly Val Gly Ser Asp
            20                  25                  30

Leu His Trp Tyr Gln His Lys Pro Gly Arg Ala Pro Lys Leu Leu Ile
        35                  40                  45

His His Thr Ser Ser Val Glu Asp Gly Val Pro Ser Arg Phe Ser Gly
    50                  55                  60

Ser Gly Phe His Thr Ser Phe Asn Leu Thr Ile Ser Asp Leu Gln Ala
65                  70                  75                  80

Asp Asp Ile Ala Thr Tyr Tyr Cys Gln Val Leu Gln Phe Phe Gly Arg
                85                  90                  95

Gly Ser Arg Leu His Ile Lys
            100


<210> SEQ ID NO 30
<211> LENGTH: 6
<212> TYPE: PRT
<213> ORGANISM: Artificial Sequence
```

```
<220> FEATURE:
<223> OTHER INFORMATION: Synthetic: N6 VL CDR1

<400> SEQUENCE: 30

Gln Gly Val Gly Ser Asp
1               5

<210> SEQ ID NO 31
<211> LENGTH: 3
<212> TYPE: PRT
<213> ORGANISM: Artificial Sequence
<220> FEATURE:
<223> OTHER INFORMATION: Synthetic: N6 VL CDR2

<400> SEQUENCE: 31

His Thr Ser
1

<210> SEQ ID NO 32
<211> LENGTH: 5
<212> TYPE: PRT
<213> ORGANISM: Artificial Sequence
<220> FEATURE:
<223> OTHER INFORMATION: Synthetic: N6 VL CDR3

<400> SEQUENCE: 32

Gln Val Leu Gln Phe
1               5

<210> SEQ ID NO 33
<211> LENGTH: 131
<212> TYPE: PRT
<213> ORGANISM: Artificial Sequence
<220> FEATURE:
<223> OTHER INFORMATION: Synthetic: 35O22 VH

<400> SEQUENCE: 33

Gln Gly Gln Leu Val Gln Ser Gly Ala Glu Leu Lys Lys Pro Gly Ala
1               5                   10                  15

Ser Val Lys Ile Ser Cys Lys Thr Ser Gly Tyr Arg Phe Asn Phe Tyr
                20                  25                  30

His Ile Asn Trp Ile Arg Gln Thr Ala Gly Arg Gly Pro Glu Trp Met
            35                  40                  45

Gly Trp Ile Ser Pro Tyr Ser Gly Asp Lys Asn Leu Ala Pro Ala Phe
        50                  55                  60

Gln Asp Arg Val Ile Met Thr Thr Asp Thr Glu Val Pro Val Thr Ser
65                  70                  75                  80

Phe Thr Ser Thr Gly Ala Ala Tyr Met Glu Ile Arg Asn Leu Lys Phe
                85                  90                  95

Asp Asp Thr Gly Thr Tyr Phe Cys Ala Lys Gly Leu Leu Arg Asp Gly
            100                 105                 110

Ser Ser Thr Trp Leu Pro Tyr Leu Trp Gly Gln Gly Thr Leu Leu Thr
        115                 120                 125

Val Ser Ser
    130

<210> SEQ ID NO 34
<211> LENGTH: 8
<212> TYPE: PRT
<213> ORGANISM: Artificial Sequence
<220> FEATURE:
<223> OTHER INFORMATION: Synthetic: 35O22 VH CDR1
```

```
<400> SEQUENCE: 34

Gly Tyr Arg Phe Asn Phe Tyr His
1               5

<210> SEQ ID NO 35
<211> LENGTH: 8
<212> TYPE: PRT
<213> ORGANISM: Artificial Sequence
<220> FEATURE:
<223> OTHER INFORMATION: Synthetic: 35O22 VH CDR2

<400> SEQUENCE: 35

Ile Ser Pro Tyr Ser Gly Asp Lys
1               5

<210> SEQ ID NO 36
<211> LENGTH: 24
<212> TYPE: PRT
<213> ORGANISM: Artificial Sequence
<220> FEATURE:
<223> OTHER INFORMATION: Synthetic: 35O22 VH CDR3

<400> SEQUENCE: 36

Asp Asp Thr Gly Thr Tyr Phe Cys Ala Lys Gly Leu Leu Arg Asp Gly
1               5                   10                  15

Ser Ser Thr Trp Leu Pro Tyr Leu
            20

<210> SEQ ID NO 37
<211> LENGTH: 110
<212> TYPE: PRT
<213> ORGANISM: Artificial Sequence
<220> FEATURE:
<223> OTHER INFORMATION: Synthetic: 35O22 VL

<400> SEQUENCE: 37

Gln Ser Val Leu Thr Gln Ser Ala Ser Val Ser Gly Ser Leu Gly Gln
1               5                   10                  15

Ser Val Thr Ile Ser Cys Thr Gly Pro Asn Ser Val Cys Cys Ser His
            20                  25                  30

Lys Ser Ile Ser Trp Tyr Gln Trp Pro Pro Gly Arg Ala Pro Thr Leu
        35                  40                  45

Ile Ile Tyr Glu Asp Asn Glu Arg Ala Pro Gly Ile Ser Pro Arg Phe
    50                  55                  60

Ser Gly Tyr Lys Ser Tyr Trp Ser Ala Tyr Leu Thr Ile Ser Asp Leu
65                  70                  75                  80

Arg Pro Glu Asp Glu Thr Thr Tyr Tyr Cys Cys Ser Tyr Thr His Asn
                85                  90                  95

Ser Gly Cys Val Phe Gly Thr Gly Thr Lys Val Ser Val Leu
            100                 105                 110

<210> SEQ ID NO 38
<211> LENGTH: 9
<212> TYPE: PRT
<213> ORGANISM: Artificial Sequence
<220> FEATURE:
<223> OTHER INFORMATION: Synthetic: 35O22 VL CDR1

<400> SEQUENCE: 38

Asn Ser Val Cys Cys Ser His Lys Ser
1               5
```

```
<210> SEQ ID NO 39
<211> LENGTH: 3
<212> TYPE: PRT
<213> ORGANISM: Artificial Sequence
<220> FEATURE:
<223> OTHER INFORMATION: Synthetic: 35O22 VL CDR2

<400> SEQUENCE: 39

Glu Asp Asn
1

<210> SEQ ID NO 40
<211> LENGTH: 10
<212> TYPE: PRT
<213> ORGANISM: Artificial Sequence
<220> FEATURE:
<223> OTHER INFORMATION: Synthetic: 35O22 VL CDR3

<400> SEQUENCE: 40

Cys Ser Tyr Thr His Asn Ser Gly Cys Val
1               5                   10

<210> SEQ ID NO 41
<211> LENGTH: 131
<212> TYPE: PRT
<213> ORGANISM: Artificial Sequence
<220> FEATURE:
<223> OTHER INFORMATION: Synthetic: 10E8v4 VH

<400> SEQUENCE: 41

Glu Val Arg Leu Val Glu Ser Gly Gly Gly Leu Val Lys Pro Gly Gly
1               5                   10                  15

Ser Leu Arg Leu Ser Cys Ser Ala Ser Gly Phe Asp Phe Asp Asn Ala
            20                  25                  30

Trp Met Thr Trp Val Arg Gln Pro Pro Gly Lys Gly Leu Glu Trp Val
        35                  40                  45

Gly Arg Ile Thr Gly Pro Gly Glu Gly Trp Ser Val Asp Tyr Ala Glu
    50                  55                  60

Ser Val Lys Gly Arg Phe Thr Ile Ser Arg Asp Asn Thr Lys Asn Thr
65                  70                  75                  80

Leu Tyr Leu Glu Met Asn Asn Val Arg Thr Glu Asp Thr Gly Tyr Tyr
                85                  90                  95

Phe Cys Ala Arg Thr Gly Lys Tyr Tyr Asp Phe Trp Ser Gly Tyr Pro
            100                 105                 110

Pro Gly Glu Glu Tyr Phe Gln Asp Trp Gly Gln Gly Thr Leu Val Ile
        115                 120                 125

Val Ser Ser
    130

<210> SEQ ID NO 42
<211> LENGTH: 8
<212> TYPE: PRT
<213> ORGANISM: Artificial Sequence
<220> FEATURE:
<223> OTHER INFORMATION: Synthetic: 10E8v4 VH CDR1

<400> SEQUENCE: 42

Gly Phe Asp Phe Asp Asn Ala Trp
1               5

<210> SEQ ID NO 43
<211> LENGTH: 10
<212> TYPE: PRT
```

-continued

<213> ORGANISM: Artificial Sequence
<220> FEATURE:
<223> OTHER INFORMATION: Synthetic: 10E8v4 VH CDR2

<400> SEQUENCE: 43

Ile Thr Gly Pro Gly Glu Gly Trp Ser Val
1 5 10

<210> SEQ ID NO 44
<211> LENGTH: 28
<212> TYPE: PRT
<213> ORGANISM: Artificial Sequence
<220> FEATURE:
<223> OTHER INFORMATION: Synthetic: 10E8v4 VH CDR3

<400> SEQUENCE: 44

Thr Gly Tyr Tyr Phe Cys Ala Arg Thr Gly Lys Tyr Tyr Asp Phe Trp
1 5 10 15

Ser Gly Tyr Pro Pro Gly Glu Glu Tyr Phe Gln Asp
20 25

<210> SEQ ID NO 45
<211> LENGTH: 108
<212> TYPE: PRT
<213> ORGANISM: Artificial Sequence
<220> FEATURE:
<223> OTHER INFORMATION: Synthetic: 10E8v4 VL

<400> SEQUENCE: 45

Ser Glu Leu Thr Gln Asp Pro Ala Val Ser Val Ala Leu Lys Gln Thr
1 5 10 15

Val Thr Ile Thr Cys Arg Gly Asp Ser Leu Arg Ser His Tyr Ala Ser
20 25 30

Trp Tyr Gln Lys Lys Pro Gly Gln Ala Pro Val Leu Leu Phe Tyr Gly
35 40 45

Lys Asn Asn Arg Pro Ser Gly Ile Pro Asp Arg Phe Ser Gly Ser Ala
50 55 60

Ser Gly Asn Arg Ala Ser Leu Thr Ile Thr Gly Ala Gln Ala Glu Asp
65 70 75 80

Glu Ala Asp Tyr Tyr Cys Ser Ser Arg Asp Lys Ser Gly Ser Arg Leu
85 90 95

Ser Val Phe Gly Gly Gly Thr Lys Leu Thr Val Leu
100 105

<210> SEQ ID NO 46
<211> LENGTH: 11
<212> TYPE: PRT
<213> ORGANISM: Artificial Sequence
<220> FEATURE:
<223> OTHER INFORMATION: Synthetic: 10E8v4 VL CDR1

<400> SEQUENCE: 46

Arg Gly Asp Ser Leu Arg Ser His Tyr Ala Ser
1 5 10

<210> SEQ ID NO 47
<211> LENGTH: 7
<212> TYPE: PRT
<213> ORGANISM: Artificial Sequence
<220> FEATURE:
<223> OTHER INFORMATION: Synthetic: 10E8v4 VL CDR2

<400> SEQUENCE: 47

```
Gly Lys Asn Asn Arg Pro Ser
1               5


<210> SEQ ID NO 48
<211> LENGTH: 12
<212> TYPE: PRT
<213> ORGANISM: Artificial Sequence
<220> FEATURE:
<223> OTHER INFORMATION: Synthetic: 10E8v4 VL CDR3

<400> SEQUENCE: 48

Ser Ser Arg Asp Lys Ser Gly Ser Arg Leu Ser Val
1               5                   10


<210> SEQ ID NO 49
<211> LENGTH: 131
<212> TYPE: PRT
<213> ORGANISM: Artificial Sequence
<220> FEATURE:
<223> OTHER INFORMATION: Synthetic: 10E8v4_S100cF VH

<400> SEQUENCE: 49

Glu Val Arg Leu Val Glu Ser Gly Gly Gly Leu Val Lys Pro Gly Gly
1               5                   10                  15

Ser Leu Arg Leu Ser Cys Ser Ala Ser Gly Phe Asp Phe Asp Asn Ala
            20                  25                  30

Trp Met Thr Trp Val Arg Gln Pro Pro Gly Lys Gly Leu Glu Trp Val
        35                  40                  45

Gly Arg Ile Thr Gly Pro Gly Glu Gly Trp Ser Val Asp Tyr Ala Glu
    50                  55                  60

Ser Val Lys Gly Arg Phe Thr Ile Ser Arg Asp Asn Thr Lys Asn Thr
65                  70                  75                  80

Leu Tyr Leu Glu Met Asn Asn Val Arg Thr Glu Asp Thr Gly Tyr Tyr
                85                  90                  95

Phe Cys Ala Arg Thr Gly Lys Tyr Tyr Asp Phe Trp Phe Gly Tyr Pro
            100                 105                 110

Pro Gly Glu Glu Tyr Phe Gln Asp Trp Gly Gln Gly Thr Leu Val Ile
        115                 120                 125

Val Ser Ser
    130


<210> SEQ ID NO 50
<211> LENGTH: 28
<212> TYPE: PRT
<213> ORGANISM: Artificial Sequence
<220> FEATURE:
<223> OTHER INFORMATION: Synthetic: 10E8v4_S100cF VH CDR3

<400> SEQUENCE: 50

Thr Gly Tyr Tyr Phe Cys Ala Arg Thr Gly Lys Tyr Tyr Asp Phe Trp
1               5                   10                  15

Phe Gly Tyr Pro Pro Gly Glu Glu Tyr Phe Gln Asp
            20                  25


<210> SEQ ID NO 51
<211> LENGTH: 131
<212> TYPE: PRT
<213> ORGANISM: Artificial Sequence
<220> FEATURE:
<223> OTHER INFORMATION: Synthetic: 10E8v4_V5R_S100cF VH

<400> SEQUENCE: 51
```

```
Glu Val Arg Leu Arg Glu Ser Gly Gly Gly Leu Val Lys Pro Gly Gly
1               5                   10                  15

Ser Leu Arg Leu Ser Cys Ser Ala Ser Gly Phe Asp Phe Asp Asn Ala
            20                  25                  30

Trp Met Thr Trp Val Arg Gln Pro Pro Gly Lys Gly Leu Glu Trp Val
        35                  40                  45

Gly Arg Ile Thr Gly Pro Gly Glu Gly Trp Ser Val Asp Tyr Ala Glu
    50                  55                  60

Ser Val Lys Gly Arg Phe Thr Ile Ser Arg Asp Asn Thr Lys Asn Thr
65                  70                  75                  80

Leu Tyr Leu Glu Met Asn Asn Val Arg Thr Glu Asp Thr Gly Tyr Tyr
                85                  90                  95

Phe Cys Ala Arg Thr Gly Lys Tyr Tyr Asp Phe Trp Phe Gly Tyr Pro
            100                 105                 110

Pro Gly Glu Glu Tyr Phe Gln Asp Trp Gly Gln Gly Thr Leu Val Ile
        115                 120                 125

Val Ser Ser
    130
```

<210> SEQ ID NO 52
<211> LENGTH: 429
<212> TYPE: DNA
<213> ORGANISM: Artificial Sequence
<220> FEATURE:
<223> OTHER INFORMATION: Synthetic: VRC26.25 VH (Original Seq)

<400> SEQUENCE: 52

```
caggtgcagt tggtggagtc tgggggaggc gtggtccagc ctgggacgtc cctgagactc      60

tcctgtgcag cctctcaatt caggtttgat ggttatggca tgcactgggt ccgccaggcc     120

ccaggcaagg ggctggagtg ggtggcatct atatcacatg atggaattaa aaagtatcac     180

gcagaaaaag tgtggggccg cttcaccatc tccagagaca attccaagaa cacactgtat     240

ctacaaatga acagcctgcg acctgaggac acggctctct actactgtgc gaaagatttg     300

cgagaagacg aatgtgaaga gtggtggtcg gatgattttg ggaaacaact cccttgcgca     360

aagtcacgcg gcggcttggt tggaattgct gataactggg gccaagggac aatggtcacc     420

gtctcttca                                                             429
```

<210> SEQ ID NO 53
<211> LENGTH: 333
<212> TYPE: DNA
<213> ORGANISM: Artificial Sequence
<220> FEATURE:
<223> OTHER INFORMATION: Synthetic: VRC26.25 VL (Original Seq)

<400> SEQUENCE: 53

```
cagtctgtgc tgacgcagcc gccctcagtg tctgcggccc caggacagaa ggtcaccatc      60

tcctgctctg gaaacacctc caacattggc aataattttg tgtcctggta ccaacagcgc     120

cccggcagag ccccccaact cctcatttat gaaactgaca agcgaccctc agggattcct     180

gaccgattct ctgcttccaa gtctggtacg tcaggcaccc tggccatcac cgggctgcag     240

actggggacg aggccgatta ttactgcgcc acatgggctg ccagcctgag ttccgcgcgt     300

gtcttcggaa ctgggaccaa ggtcatcgtc cta                                 333
```

<210> SEQ ID NO 54
<211> LENGTH: 393
<212> TYPE: DNA

```
<213> ORGANISM: Artificial Sequence
<220> FEATURE:
<223> OTHER INFORMATION: Synthetic: 35O22 VH (Original Seq)

<400> SEQUENCE: 54

cagggtcaac tagtccagtc tggagctgaa ttgaaaaagc ctggcgcctc ggtgaagatt     60

tcctgtaaga cttcgggtta taggtttaat ttctatcata ttaattggat tcgacaaact    120

gcaggacgtg gacctgagtg gatgggatgg atcagccctt acagtggtga caaaaacctc    180

gcacctgcct ttcaagacag agtcattatg acgacagaca cagaagtccc tgtgacctca    240

ttcacgtcca cgggcgcagc ctacatggaa ataaggaacc tgaaatttga cgacacaggc    300

acctatttct gtgcaaaagg cctcctgcgt gacggttcgt cgacgtggct tccttatttg    360

tggggccagg gtaccctact caccgtctcg tca                                 393


<210> SEQ ID NO 55
<211> LENGTH: 330
<212> TYPE: DNA
<213> ORGANISM: Artificial Sequence
<220> FEATURE:
<223> OTHER INFORMATION: Synthetic: 35O22 VL (Original Seq)

<400> SEQUENCE: 55

cagtctgtgc tgacgcagtc tgcctccgtg tctgggtctc ttggacagtc ggtcaccatc     60

tcctgcactg gacccaatag tgtttgttgc agtcacaaat ctatctcctg gtatcagtgg    120

cccccaggca gagcccccac actcatcatt tatgaggaca atgaaagggc cccgggaatc    180

tctcctcgct tctctggcta caagtcgtat tggtcggcct acttgacaat ctctgatctc    240

cggcctgaag acgagaccac ttactactgt tgctcataca ctcacaatag cggctgtgtc    300

ttcgggactg ggaccaaggt ctccgtcttg                                     330


<210> SEQ ID NO 56
<211> LENGTH: 393
<212> TYPE: DNA
<213> ORGANISM: Artificial Sequence
<220> FEATURE:
<223> OTHER INFORMATION: Synthetic: 10E8v4 VH (Original Seq)

<400> SEQUENCE: 56

gaggttagac tggtggagtc aggagggggg cttgtgaagc ccggtgggtc tctccgcctg     60

agctgttctg cctccggctt tgatttcgat aacgcctgga tgacctgggt caggcagcct    120

ccaggtaagg gactggagtg ggtgggaaga atcacaggtc caggcgaggg ctggtccgtg    180

gactacgcgg aatctgttaa agggcggttt acaatctcaa gggacaatac caagaatacc    240

ttgtatttgg agatgaacaa cgtgagaact gaagacaccg gatattactt ctgtgccaga    300

acaggcaaat actacgactt ctggtccggc tatccccctg gcgaggaata ttttcaagac    360

tggggtcagg gaacccttgt tatcgtgtcc tcc                                 393


<210> SEQ ID NO 57
<211> LENGTH: 324
<212> TYPE: DNA
<213> ORGANISM: Artificial Sequence
<220> FEATURE:
<223> OTHER INFORMATION: Synthetic: 10E8v4 VL (Original Seq)

<400> SEQUENCE: 57

tccgaactga ctcaggaccc tgccgtctct gtggcactga agcagactgt gactattact     60

tgccgaggcg actcactgcg gagccactac gcttcctggt atcagaagaa acccggccag    120
```

-continued gcacctgtgc tgctgttcta cggaaagaac aataggccat ctggcatccc cgaccgcttt 180
tctggcagtg catcagggaa ccgagccagt ctgaccatta ccggcgccca ggctgaggac 240
gaagccgatt actattgcag ctcccgggat aagagcggct ccagactgag cgtgttcgga 300
ggaggaacta aactgaccgt cctc 324

<210> SEQ ID NO 58
<211> LENGTH: 429
<212> TYPE: DNA
<213> ORGANISM: Artificial Sequence
<220> FEATURE:
<223> OTHER INFORMATION: Synthetic: VRC26.25 VH (Optimized Seq 1)

<400> SEQUENCE: 58
caggtgcagc tggtggagag cggcggcggc gtggtgcagc caggcacctc cctgaggctg 60
tcttgtgcag caagccagtt cagatttgat ggctacggca tgcactgggt gcgccaggca 120
ccaggcaagg gcctggagtg ggtagcctct atcagccacg acggcatcaa gaagtaccac 180
gccgagaaag tgtggggcag gttcaccatc tcccgcgata actctaaaaa cacactgtat 240
ctgcagatga actccctgag gcccgaggac accgccctgt actattgcgc caaggacctg 300
cgcgaggatg agtgtgagga gtggtggtcc gacgattttg gcaagcagct gccttgcgca 360
aagagcaggg gaggcctggt gggaatcgcc gataattggg gccagggcac catggtgaca 420
gtgtctagc 429

<210> SEQ ID NO 59
<211> LENGTH: 429
<212> TYPE: DNA
<213> ORGANISM: Artificial Sequence
<220> FEATURE:
<223> OTHER INFORMATION: Synthetic: VRC26.25 VH (Optimized Seq 2)

<400> SEQUENCE: 59
caggtgcagc tggtggagtc cggaggagga gtggtgcagc caggcacctc tctgaggctg 60
agctgtgcag catcccagtt cagatttgat ggctacggaa tgcactgggt gaggcaggca 120
ccaggcaagg gactggagtg ggtggccagc atctcccacg acggcatcaa gaagtaccac 180
gccgagaaag tgtggggcag gttcaccatc tctcgcgata acagcaagaa tacactgtat 240
ctgcagatga acagcctgag gcccgaggac accgccctgt actattgcgc caaggacctg 300
cgcgaggatg agtgtgagga gtggtggtcc gacgattttg gcaagcagct gccttgcgca 360
aagagcaggg gaggactggt gggaatcgcc gacaattggg gccagggcac catggtgaca 420
gtgagcagc 429

<210> SEQ ID NO 60
<211> LENGTH: 336
<212> TYPE: DNA
<213> ORGANISM: Artificial Sequence
<220> FEATURE:
<223> OTHER INFORMATION: Synthetic: VRC26.25 VL (Optimized Seq 1)

<400> SEQUENCE: 60
cagagcgtgc tgacccagcc accttccgtg tctgccgcac caggacagaa ggtgaccatc 60
agctgttccg gcaacacatc caatatcggc aacaatttcg tgtcttggta ccagcagagg 120
ccaggaaggg caccacagct gctgatctat gagacagaca agcggccttc cggcatccca 180
gatagatttt ctgccagcaa gtccggcacc agcggcacac tggcaatcac cggcctgcag 240
acaggcgacg aagctgatta ctattgcgca acctgggcag cctccctgag ctccgccagg 300
gtgttcggaa ccggaacaaa agtgatcgtg ctggtg 336

<210> SEQ ID NO 61
<211> LENGTH: 336
<212> TYPE: DNA
<213> ORGANISM: Artificial Sequence
<220> FEATURE:
<223> OTHER INFORMATION: Synthetic: VRC26.25 VL (Optimized Seq 2)

<400> SEQUENCE: 61
cagagcgtgc tgacccagcc accttccgtg tctgccgcac caggacagaa ggtgaccatc 60
agctgttccg gcaacacatc caatatcggc aacaatttcg tgtcttggta ccagcagagg 120
cctggaagag caccacagct gctgatctat gagacagaca agaggccctc cggcatccct 180
gatcgctttt ctgccagcaa gtccggcacc agcggcacac tggcaatcac cggactgcag 240
acaggcgacg aggcagatta ctattgcgca acctgggcag cctccctgtc tagcgccagg 300
gtgttcggca ccggcacaaa agtgatcgtg ctggtg 336

<210> SEQ ID NO 62
<211> LENGTH: 420
<212> TYPE: DNA
<213> ORGANISM: Artificial Sequence
<220> FEATURE:
<223> OTHER INFORMATION: Synthetic: PGDM1400 VH (Optimized Seq 1)

<400> SEQUENCE: 62
caggcacagc tggtgcagag cggacccgaa gtgagaaaac ctgggactag cgtcaaagtg 60
tcatgtaaag cccctggaaa taccctgaag acctacgatc tgcactgggt gcggtccgtg 120
cctggacagg gcctgcagtg gatgggatgg atctctcacg agggcgacaa gaaagtgatc 180
gtggagcggt tcaaggccaa ggtgacaatc gattgggaca gatccaccaa cacagcctac 240
ctgcagctgt ctggcctgac cagcggcgat acagccgtgt actactgtgc caagggctct 300
aagcaccggc tgagagacta cgccctggac gatgacggcg ccctgaactg ggccgtggat 360
gtggactatc tgtccaatct ggagttctgg ggacagggaa ccgcagtgac agtgagctcc 420

<210> SEQ ID NO 63
<211> LENGTH: 420
<212> TYPE: DNA
<213> ORGANISM: Artificial Sequence
<220> FEATURE:
<223> OTHER INFORMATION: Synthetic: PGDM1400 VH (Optimized Seq 2)

<400> SEQUENCE: 63
caggcacagc tggtgcagag cggaccagag gtgaggaagc caggcacctc tgtgaaggtg 60
agctgtaagg cccctggcaa caccctgaag acatacgatc tgcactgggt gcggtctgtg 120
ccaggacagg gcctgcagtg gatgggatgg atcagccacg agggcgacaa gaaagtgatc 180
gtggagcggt ttaaggccaa ggtgacaatc gattgggaca gaagcaccaa tacagcctat 240
ctgcagctgt ccggcctgac ctctggcgat acagccgtgt actattgcgc caagggctcc 300
aagcaccggc tgagagacta cgccctggac gatgacggcg ccctgaattg ggcagtggac 360
gtggactatc tgagtaatct ggagttttgg gggcagggca ccgcagtgac agtgtctagc 420

<210> SEQ ID NO 64
<211> LENGTH: 336
<212> TYPE: DNA
<213> ORGANISM: Artificial Sequence
<220> FEATURE:
<223> OTHER INFORMATION: Synthetic: PGDM1400 VL (Optimized Seq 1)

<400> SEQUENCE: 64
gattttgtgc tgacccagtc tccacacagc ctgtccgtga cacccggcga gtctgccagc 60
atctcctgca agtctagcca cagcctgatc cacggcgaca ggaacaatta cctggcctgg 120
tacgtgcaga agccaggccg cagccctcag ctgctgatct atctggcatc ctctagggcc 180
tccggagtgc cagatcgctt ctctggcagc ggctccgata aggactttac cctgaagatc 240
agccgggtgg agacagagga cgtgggcaca tactattgta tgcagggccg agaatcacct 300
tggacatttg ggcagggaac taaagtcgac atcaaa 336

<210> SEQ ID NO 65
<211> LENGTH: 336
<212> TYPE: DNA
<213> ORGANISM: Artificial Sequence
<220> FEATURE:
<223> OTHER INFORMATION: Synthetic: PGDM1400 VL (Optimized Seq 2)

<400> SEQUENCE: 65
gatttcgtgc tgacccagtc tccacatagt ctgagcgtga cacccggcga aagcgcatca 60
atttcttgta aatcatctca tagtctgatc cacggcgata ggaacaatta cctggcctgg 120
tacgtgcaga agccaggccg cagccctcag ctgctgatct acctggcaag ctccagggca 180
tccggagtgc cagatcgctt ctctggcagc ggctccgata aggactttac cctgaagatc 240
tcccgggtgg agacagagga cgtgggcaca tactattgca tgcagggcag agagtctcct 300
tggaccttcg gccagggcac aaaggtggac atcaag 336

<210> SEQ ID NO 66
<211> LENGTH: 393
<212> TYPE: DNA
<213> ORGANISM: Artificial Sequence
<220> FEATURE:
<223> OTHER INFORMATION: Synthetic: 35O22 VH (Optimized Seq 1)

<400> SEQUENCE: 66
cagggccagc tggtgcagag cggagcagag ctgaagaagc ctggagccag cgtgaagatc 60
tcctgtaaga catctggcta ccggttcaac ttttatcaca tcaattggat caggcagacc 120
gcaggaaggg gaccagagtg gatgggctgg atctccccct actctggcga taagaacctg 180
gccccagcct tccaggacag agtgatcatg accacagata ccgaggtgcc agtgaccagc 240
ttcacctcca ccggagccgc ctacatggag atcaggaatc tgaagttcga cgatacaggc 300
acctattttt gcgcaaaggg cctgctgagg gacggctcct ctacctggct gccttacctg 360
tggggacagg gcaccctgct gacagtgagc tcc 393

<210> SEQ ID NO 67
<211> LENGTH: 393
<212> TYPE: DNA
<213> ORGANISM: Artificial Sequence
<220> FEATURE:
<223> OTHER INFORMATION: Synthetic: 35O22 VH (Optimized Seq 2)

<400> SEQUENCE: 67
cagggccagc tggtgcagag cggagcagag ctgaagaagc caggagcctc tgtgaagatc 60
agctgtaaga catccggcta ccggttcaac ttttatcaca tcaattggat caggcagacc 120
gcaggaaggg gaccagagtg gatgggctgg atctccccct actctggcga taagaacctg 180

-continued

```
gccccagcct tccaggacag agtgatcatg accacagata ccgaggtgcc agtgaccagc    240

ttcacctcca ccggagccgc ctacatggag atccggaatc tgaagttcga cgatacaggc    300

acctattttt gcgccaaggg cctgctgaga gacggctcta gcacatggct gccatacctg    360

tggggacagg gcaccctgct gacagtgtcc tct                                 393
```

<210> SEQ ID NO 68
<211> LENGTH: 330
<212> TYPE: DNA
<213> ORGANISM: Artificial Sequence
<220> FEATURE:
<223> OTHER INFORMATION: Synthetic: 35O22 VL (Optimized Seq 1)

<400> SEQUENCE: 68

```
cagtccgtgc tgacccagtc tgccagcgtg tccggctctc tgggacagag cgtgaccatc     60

tcctgtacag gccccaacag cgtgtgctgt agccacaaga gcatctcctg gtaccagtgg    120

cctccaggaa gggcacctac cctgatcatc tatgaggaca atgagcgggc cccaggcatc    180

tcccccagat tctctggcta caagtcttat tggagcgcct acctgacaat cagcgacctg    240

cgccccgagg atgagacaac atactattgc tgttcctata cccacaactc tggctgcgtg    300

tttggcacag gcaccaaggt gtccgtgctg                                     330
```

<210> SEQ ID NO 69
<211> LENGTH: 330
<212> TYPE: DNA
<213> ORGANISM: Artificial Sequence
<220> FEATURE:
<223> OTHER INFORMATION: Synthetic: 35O22 VL (Optimized Seq 2)

<400> SEQUENCE: 69

```
caaagcgtgc tgacccagtc cgcctctgtg agcggctccc tgggccagtc tgtgaccatc     60

agctgtacag gccccaactc cgtgtgctgt tctcacaagt ctatcagctg gtaccagtgg    120

ccaccaggaa gggcacctac cctgatcatc tatgaggaca atgagagggc accaggaatc    180

agccctcgct tctccggcta caagtcttat tggagcgcct acctgaccat ttccgacctg    240

cgccccgagg atgagaccac atactattgc tgtagctata cccacaactc cggctgcgtg    300

tttggcacag gcaccaaggt gagcgtgctg                                     330
```

<210> SEQ ID NO 70
<211> LENGTH: 393
<212> TYPE: DNA
<213> ORGANISM: Artificial Sequence
<220> FEATURE:
<223> OTHER INFORMATION: Synthetic: 10E8v4_V5R_S100cF VH (Optimized Seq)

<400> SEQUENCE: 70

```
gaggtgcggc tgcgggagag cggcggcggc ctggtgaagc caggcggctc tctgagactg     60

tcctgttctg ccagcggctt cgactttgat aatgcctgga tgacatgggt gcggcagcct    120

cctggcaagg ggctggagtg ggtgggaaga atcaccggac caggagaggg atggtctgtg    180

gactacgccg agagcgtgaa gggccggttc accatcagca gagataacac taaaaataca    240

ctgtatctgg agatgaacaa tgtgcggacc gaggacacag gctactattt ctgcgccaga    300

accggcaagt actatgattt ctggtttggc taccccccctg gcgaggagta ttttcaggac    360

tggggccagg gcaccctggt catcgtgagc agc                                 393
```

<210> SEQ ID NO 71
<211> LENGTH: 324

<212> TYPE: DNA
<213> ORGANISM: Artificial Sequence
<220> FEATURE:
<223> OTHER INFORMATION: Synthetic: 10E8v4 VL

<400> SEQUENCE: 71
agcgagctga cccaggaccc cgccgtgtcc gtggccctga agcagacagt gaccatcaca 60
tgcaggggcg actccctgcg ctctcactac gccagctggt atcagaagaa gccaggacag 120
gcacccgtgc tgctgttcta cggcaagaac aatcggcctt ccggcatccc agatagattt 180
tccggctctg ccagcggaaa cagggccagc ctgaccatca caggagcaca ggcagaggat 240
gaagcagatt actattgttc ctctcgggac aagtccggct ctagactgag cgtgttcggc 300
ggcggaacca agctgacagt gctg 324

<210> SEQ ID NO 72
<211> LENGTH: 1402
<212> TYPE: PRT
<213> ORGANISM: Artificial Sequence
<220> FEATURE:
<223> OTHER INFORMATION: Synthetic: PentaNAb1.0
10E8v4-5X-35O22-5X-N6-5X-PGT121-5X-VRC26.25-His

<400> SEQUENCE: 72

Met Gly Trp Ser Cys Ile Ile Leu Phe Leu Val Ala Thr Ala Thr Gly
1 5 10 15

Val His Ser Ser Glu Leu Thr Gln Asp Pro Ala Val Ser Val Ala Leu
20 25 30

Lys Gln Thr Val Thr Ile Thr Cys Arg Gly Asp Ser Leu Arg Ser His
35 40 45

Tyr Ala Ser Trp Tyr Gln Lys Lys Pro Gly Gln Ala Pro Val Leu Leu
50 55 60

Phe Tyr Gly Lys Asn Asn Arg Pro Ser Gly Ile Pro Asp Arg Phe Ser
65 70 75 80

Gly Ser Ala Ser Gly Asn Arg Ala Ser Leu Thr Ile Thr Gly Ala Gln
85 90 95

Ala Glu Asp Glu Ala Asp Tyr Tyr Cys Ser Ser Arg Asp Lys Ser Gly
100 105 110

Ser Arg Leu Ser Val Phe Gly Gly Gly Thr Lys Leu Thr Val Leu Gly
115 120 125

Gly Gly Gly Ser Gly Gly Gly Gly Ser Gly Gly Gly Gly Ser Glu Val
130 135 140

Arg Leu Val Glu Ser Gly Gly Gly Leu Val Lys Pro Gly Gly Ser Leu
145 150 155 160

Arg Leu Ser Cys Ser Ala Ser Gly Phe Asp Phe Asp Asn Ala Trp Met
165 170 175

Thr Trp Val Arg Gln Pro Pro Gly Lys Gly Leu Glu Trp Val Gly Arg
180 185 190

Ile Thr Gly Pro Gly Glu Gly Trp Ser Val Asp Tyr Ala Glu Ser Val
195 200 205

Lys Gly Arg Phe Thr Ile Ser Arg Asp Asn Thr Lys Asn Thr Leu Tyr
210 215 220

Leu Glu Met Asn Asn Val Arg Thr Glu Asp Thr Gly Tyr Tyr Phe Cys
225 230 235 240

Ala Arg Thr Gly Lys Tyr Tyr Asp Phe Trp Ser Gly Tyr Pro Pro Gly
245 250 255

Glu Glu Tyr Phe Gln Asp Trp Gly Gln Gly Thr Leu Val Ile Val Ser

-continued

```
            260                 265                 270

Ser Gly Gly Gly Gly Ser Gly Gly Gly Gly Ser Gly Gly Gly Gly Ser
        275                 280                 285

Gly Gly Gly Gly Ser Gly Gly Gly Gly Ser Gln Ser Val Leu Thr Gln
    290                 295                 300

Ser Ala Ser Val Ser Gly Ser Leu Gly Gln Ser Val Thr Ile Ser Cys
305                 310                 315                 320

Thr Gly Pro Asn Ser Val Cys Cys Ser His Lys Ser Ile Ser Trp Tyr
                325                 330                 335

Gln Trp Pro Pro Gly Arg Ala Pro Thr Leu Ile Ile Tyr Glu Asp Asn
            340                 345                 350

Glu Arg Ala Pro Gly Ile Ser Pro Arg Phe Ser Gly Tyr Lys Ser Tyr
        355                 360                 365

Trp Ser Ala Tyr Leu Thr Ile Ser Asp Leu Arg Pro Glu Asp Glu Thr
    370                 375                 380

Thr Tyr Tyr Cys Cys Ser Tyr Thr His Asn Ser Gly Cys Val Phe Gly
385                 390                 395                 400

Thr Gly Thr Lys Val Ser Val Leu Gly Gly Gly Gly Ser Gly Gly Gly
                405                 410                 415

Gly Ser Gly Gly Gly Gly Ser Gln Gly Gln Leu Val Gln Ser Gly Ala
            420                 425                 430

Glu Leu Lys Lys Pro Gly Ala Ser Val Lys Ile Ser Cys Lys Thr Ser
        435                 440                 445

Gly Tyr Arg Phe Asn Phe Tyr His Ile Asn Trp Ile Arg Gln Thr Ala
    450                 455                 460

Gly Arg Gly Pro Glu Trp Met Gly Trp Ile Ser Pro Tyr Ser Gly Asp
465                 470                 475                 480

Lys Asn Leu Ala Pro Ala Phe Gln Asp Arg Val Ile Met Thr Thr Asp
                485                 490                 495

Thr Glu Val Pro Val Thr Ser Phe Thr Ser Thr Gly Ala Ala Tyr Met
            500                 505                 510

Glu Ile Arg Asn Leu Lys Phe Asp Asp Thr Gly Thr Tyr Phe Cys Ala
        515                 520                 525

Lys Gly Leu Leu Arg Asp Gly Ser Ser Thr Trp Leu Pro Tyr Leu Trp
    530                 535                 540

Gly Gln Gly Thr Leu Leu Thr Val Ser Ser Gly Gly Gly Gly Ser Gly
545                 550                 555                 560

Gly Gly Gly Ser Gly Gly Gly Gly Ser Gly Gly Gly Gly Ser Gly Gly
                565                 570                 575

Gly Gly Ser Tyr Ile His Val Thr Gln Ser Pro Ser Ser Leu Ser Val
            580                 585                 590

Ser Ile Gly Asp Arg Val Thr Ile Asn Cys Gln Thr Ser Gln Gly Val
        595                 600                 605

Gly Ser Asp Leu His Trp Tyr Gln His Lys Pro Gly Arg Ala Pro Lys
    610                 615                 620

Leu Leu Ile His His Thr Ser Ser Val Glu Asp Gly Val Pro Ser Arg
625                 630                 635                 640

Phe Ser Gly Ser Gly Phe His Thr Ser Phe Asn Leu Thr Ile Ser Asp
                645                 650                 655

Leu Gln Ala Asp Asp Ile Ala Thr Tyr Tyr Cys Gln Val Leu Gln Phe
            660                 665                 670

Phe Gly Arg Gly Ser Arg Leu His Ile Lys Gly Gly Gly Gly Ser Gly
        675                 680                 685
```

```
Gly Gly Gly Ser Gly Gly Gly Gly Ser Arg Ala His Leu Val Gln Ser
    690                 695                 700

Gly Thr Ala Met Lys Lys Pro Gly Ala Ser Val Arg Val Ser Cys Gln
705                 710                 715                 720

Thr Ser Gly Tyr Thr Phe Thr Ala His Ile Leu Phe Trp Phe Arg Gln
                725                 730                 735

Ala Pro Gly Arg Gly Leu Glu Trp Val Gly Trp Ile Lys Pro Gln Tyr
            740                 745                 750

Gly Ala Val Asn Phe Gly Gly Gly Phe Arg Asp Arg Val Thr Leu Thr
        755                 760                 765

Arg Asp Val Tyr Arg Glu Ile Ala Tyr Met Asp Ile Arg Gly Leu Lys
    770                 775                 780

Pro Asp Asp Thr Ala Val Tyr Tyr Cys Ala Arg Asp Arg Ser Tyr Gly
785                 790                 795                 800

Asp Ser Ser Trp Ala Leu Asp Ala Trp Gly Gln Gly Thr Thr Val Val
                805                 810                 815

Val Ser Ala Gly Gly Gly Gly Ser Gly Gly Gly Gly Ser Gly Gly Gly
            820                 825                 830

Gly Ser Gly Gly Gly Gly Ser Gly Gly Gly Gly Ser Ser Asp Ile Ser
        835                 840                 845

Val Ala Pro Gly Glu Thr Ala Arg Ile Ser Cys Gly Glu Lys Ser Leu
    850                 855                 860

Gly Ser Arg Ala Val Gln Trp Tyr Gln His Arg Ala Gly Gln Ala Pro
865                 870                 875                 880

Ser Leu Ile Ile Tyr Asn Asn Gln Asp Arg Pro Ser Gly Ile Pro Glu
                885                 890                 895

Arg Phe Ser Gly Ser Pro Asp Ser Pro Phe Gly Thr Thr Ala Thr Leu
            900                 905                 910

Thr Ile Thr Ser Val Glu Ala Gly Asp Glu Ala Asp Tyr Tyr Cys His
        915                 920                 925

Ile Trp Asp Ser Arg Val Pro Thr Lys Trp Val Phe Gly Gly Gly Thr
    930                 935                 940

Thr Leu Thr Val Leu Gly Gly Gly Gly Ser Gly Gly Gly Gly Ser Gly
945                 950                 955                 960

Gly Gly Gly Ser Gln Met Gln Leu Gln Glu Ser Gly Pro Gly Leu Val
                965                 970                 975

Lys Pro Ser Glu Thr Leu Ser Leu Thr Cys Ser Val Ser Gly Ala Ser
            980                 985                 990

Ile Ser Asp Ser Tyr Trp Ser Trp  Ile Arg Arg Ser Pro  Gly Lys Gly
        995                 1000                 1005

Leu Glu  Trp Ile Gly Tyr Val  His Lys Ser Gly Asp  Thr Asn Tyr
    1010                 1015                 1020

Ser Pro  Ser Leu Lys Ser Arg  Val Asn Leu Ser Leu  Asp Thr Ser
    1025                 1030                 1035

Lys Asn  Gln Val Ser Leu Ser  Leu Val Ala Ala Thr  Ala Ala Asp
    1040                 1045                 1050

Ser Gly  Lys Tyr Tyr Cys Ala  Arg Thr Leu His Gly  Arg Arg Ile
    1055                 1060                 1065

Tyr Gly  Ile Val Ala Phe Asn  Glu Trp Phe Thr Tyr  Phe Tyr Met
    1070                 1075                 1080

Asp Val  Trp Gly Asn Gly Thr  Gln Val Thr Val Ser  Ser Gly Gly
    1085                 1090                 1095
```

-continued

```
Gly Gly  Ser Gly Gly Gly Gly  Ser Gly Gly Gly Gly  Ser Gly Gly
    1100                 1105                 1110

Gly Gly  Ser Gly Gly Gly Gly  Ser Gln Ser Val Leu  Thr Gln Pro
    1115                 1120                 1125

Pro Ser  Val Ser Ala Ala Pro  Gly Gln Lys Val Thr  Ile Ser Cys
    1130                 1135                 1140

Ser Gly  Asn Thr Ser Asn Ile  Gly Asn Asn Phe Val  Ser Trp Tyr
    1145                 1150                 1155

Gln Gln  Arg Pro Gly Arg Ala  Pro Gln Leu Leu Ile  Tyr Glu Thr
    1160                 1165                 1170

Asp Lys  Arg Pro Ser Gly Ile  Pro Asp Arg Phe Ser  Ala Ser Lys
    1175                 1180                 1185

Ser Gly  Thr Ser Gly Thr Leu  Ala Ile Thr Gly Leu  Gln Thr Gly
    1190                 1195                 1200

Asp Glu  Ala Asp Tyr Tyr Cys  Ala Thr Trp Ala Ala  Ser Leu Ser
    1205                 1210                 1215

Ser Ala  Arg Val Phe Gly Thr  Gly Thr Lys Val Ile  Val Leu Val
    1220                 1225                 1230

Gly Gly  Gly Gly Ser Gly Gly  Gly Gly Ser Gly Gly  Gly Gly Ser
    1235                 1240                 1245

Gln Val  Gln Leu Val Glu Ser  Gly Gly Gly Val Val  Gln Pro Gly
    1250                 1255                 1260

Thr Ser  Leu Arg Leu Ser Cys  Ala Ala Ser Gln Phe  Arg Phe Asp
    1265                 1270                 1275

Gly Tyr  Gly Met His Trp Val  Arg Gln Ala Pro Gly  Lys Gly Leu
    1280                 1285                 1290

Glu Trp  Val Ala Ser Ile Ser  His Asp Gly Ile Lys  Lys Tyr His
    1295                 1300                 1305

Ala Glu  Lys Val Trp Gly Arg  Phe Thr Ile Ser Arg  Asp Asn Ser
    1310                 1315                 1320

Lys Asn  Thr Leu Tyr Leu Gln  Met Asn Ser Leu Arg  Pro Glu Asp
    1325                 1330                 1335

Thr Ala  Leu Tyr Tyr Cys Ala  Lys Asp Leu Arg Glu  Asp Glu Cys
    1340                 1345                 1350

Glu Glu  Trp Trp Ser Asp Tyr  Tyr Asp Phe Gly Lys  Gln Leu Pro
    1355                 1360                 1365

Cys Ala  Lys Ser Arg Gly Gly  Leu Val Gly Ile Ala  Asp Asn Trp
    1370                 1375                 1380

Gly Gln  Gly Thr Met Val Thr  Val Ser Ser Gly Ser  Gly His His
    1385                 1390                 1395

His His  His His
    1400
```

<210> SEQ ID NO 73
<211> LENGTH: 1402
<212> TYPE: PRT
<213> ORGANISM: Artificial Sequence
<220> FEATURE:
<223> OTHER INFORMATION: Synthetic: PentaNAb2.0
10E8v4_S100cF-5X-35O22-5X-N6-5X-PGT121-5X-VRC26.25-His

<400> SEQUENCE: 73

```
Met Gly Trp Ser Cys Ile Ile Leu Phe Leu Val Ala Thr Ala Thr Gly
1               5                   10                  15

Val His Ser Ser Glu Leu Thr Gln Asp Pro Ala Val Ser Val Ala Leu
            20                  25                  30
```

-continued

```
Lys Gln Thr Val Thr Ile Thr Cys Arg Gly Asp Ser Leu Arg Ser His
        35                  40                  45

Tyr Ala Ser Trp Tyr Gln Lys Lys Pro Gly Gln Ala Pro Val Leu Leu
    50                  55                  60

Phe Tyr Gly Lys Asn Asn Arg Pro Ser Gly Ile Pro Asp Arg Phe Ser
65                  70                  75                  80

Gly Ser Ala Ser Gly Asn Arg Ala Ser Leu Thr Ile Thr Gly Ala Gln
                85                  90                  95

Ala Glu Asp Glu Ala Asp Tyr Tyr Cys Ser Ser Arg Asp Lys Ser Gly
            100                 105                 110

Ser Arg Leu Ser Val Phe Gly Gly Gly Thr Lys Leu Thr Val Leu Gly
        115                 120                 125

Gly Gly Gly Ser Gly Gly Gly Gly Ser Gly Gly Gly Gly Ser Glu Val
    130                 135                 140

Arg Leu Val Glu Ser Gly Gly Gly Leu Val Lys Pro Gly Gly Ser Leu
145                 150                 155                 160

Arg Leu Ser Cys Ser Ala Ser Gly Phe Asp Phe Asp Asn Ala Trp Met
                165                 170                 175

Thr Trp Val Arg Gln Pro Pro Gly Lys Gly Leu Glu Trp Val Gly Arg
            180                 185                 190

Ile Thr Gly Pro Gly Glu Gly Trp Ser Val Asp Tyr Ala Glu Ser Val
        195                 200                 205

Lys Gly Arg Phe Thr Ile Ser Arg Asp Asn Thr Lys Asn Thr Leu Tyr
    210                 215                 220

Leu Glu Met Asn Asn Val Arg Thr Glu Asp Thr Gly Tyr Tyr Phe Cys
225                 230                 235                 240

Ala Arg Thr Gly Lys Tyr Tyr Asp Phe Trp Phe Gly Tyr Pro Pro Gly
                245                 250                 255

Glu Glu Tyr Phe Gln Asp Trp Gly Gln Gly Thr Leu Val Ile Val Ser
            260                 265                 270

Ser Gly Gly Gly Gly Ser Gly Gly Gly Gly Ser Gly Gly Gly Gly Ser
        275                 280                 285

Gly Gly Gly Gly Ser Gly Gly Gly Gly Ser Gln Ser Val Leu Thr Gln
    290                 295                 300

Ser Ala Ser Val Ser Gly Ser Leu Gly Gln Ser Val Thr Ile Ser Cys
305                 310                 315                 320

Thr Gly Pro Asn Ser Val Cys Cys Ser His Lys Ser Ile Ser Trp Tyr
                325                 330                 335

Gln Trp Pro Pro Gly Arg Ala Pro Thr Leu Ile Ile Tyr Glu Asp Asn
            340                 345                 350

Glu Arg Ala Pro Gly Ile Ser Pro Arg Phe Ser Gly Tyr Lys Ser Tyr
        355                 360                 365

Trp Ser Ala Tyr Leu Thr Ile Ser Asp Leu Arg Pro Glu Asp Glu Thr
    370                 375                 380

Thr Tyr Tyr Cys Cys Ser Tyr Thr His Asn Ser Gly Cys Val Phe Gly
385                 390                 395                 400

Thr Gly Thr Lys Val Ser Val Leu Gly Gly Gly Gly Ser Gly Gly Gly
                405                 410                 415

Gly Ser Gly Gly Gly Gly Ser Gln Gly Gln Leu Val Gln Ser Gly Ala
            420                 425                 430

Glu Leu Lys Lys Pro Gly Ala Ser Val Lys Ile Ser Cys Lys Thr Ser
        435                 440                 445
```

-continued

```
Gly Tyr Arg Phe Asn Phe Tyr His Ile Asn Trp Ile Arg Gln Thr Ala
    450                 455                 460

Gly Arg Gly Pro Glu Trp Met Gly Trp Ile Ser Pro Tyr Ser Gly Asp
465                 470                 475                 480

Lys Asn Leu Ala Pro Ala Phe Gln Asp Arg Val Ile Met Thr Thr Asp
                485                 490                 495

Thr Glu Val Pro Val Thr Ser Phe Thr Ser Thr Gly Ala Ala Tyr Met
            500                 505                 510

Glu Ile Arg Asn Leu Lys Phe Asp Asp Thr Gly Thr Tyr Phe Cys Ala
        515                 520                 525

Lys Gly Leu Leu Arg Asp Gly Ser Ser Thr Trp Leu Pro Tyr Leu Trp
    530                 535                 540

Gly Gln Gly Thr Leu Leu Thr Val Ser Ser Gly Gly Gly Gly Ser Gly
545                 550                 555                 560

Gly Gly Gly Ser Gly Gly Gly Gly Ser Gly Gly Gly Gly Ser Gly Gly
                565                 570                 575

Gly Gly Ser Tyr Ile His Val Thr Gln Ser Pro Ser Ser Leu Ser Val
            580                 585                 590

Ser Ile Gly Asp Arg Val Thr Ile Asn Cys Gln Thr Ser Gln Gly Val
        595                 600                 605

Gly Ser Asp Leu His Trp Tyr Gln His Lys Pro Gly Arg Ala Pro Lys
    610                 615                 620

Leu Leu Ile His His Thr Ser Ser Val Glu Asp Gly Val Pro Ser Arg
625                 630                 635                 640

Phe Ser Gly Ser Gly Phe His Thr Ser Phe Asn Leu Thr Ile Ser Asp
                645                 650                 655

Leu Gln Ala Asp Asp Ile Ala Thr Tyr Tyr Cys Gln Val Leu Gln Phe
            660                 665                 670

Phe Gly Arg Gly Ser Arg Leu His Ile Lys Gly Gly Gly Gly Ser Gly
        675                 680                 685

Gly Gly Gly Ser Gly Gly Gly Gly Ser Arg Ala His Leu Val Gln Ser
    690                 695                 700

Gly Thr Ala Met Lys Lys Pro Gly Ala Ser Val Arg Val Ser Cys Gln
705                 710                 715                 720

Thr Ser Gly Tyr Thr Phe Thr Ala His Ile Leu Phe Trp Phe Arg Gln
                725                 730                 735

Ala Pro Gly Arg Gly Leu Glu Trp Val Gly Trp Ile Lys Pro Gln Tyr
            740                 745                 750

Gly Ala Val Asn Phe Gly Gly Gly Phe Arg Asp Arg Val Thr Leu Thr
        755                 760                 765

Arg Asp Val Tyr Arg Glu Ile Ala Tyr Met Asp Ile Arg Gly Leu Lys
    770                 775                 780

Pro Asp Asp Thr Ala Val Tyr Tyr Cys Ala Arg Asp Arg Ser Tyr Gly
785                 790                 795                 800

Asp Ser Ser Trp Ala Leu Asp Ala Trp Gly Gln Gly Thr Thr Val Val
                805                 810                 815

Val Ser Ala Gly Gly Gly Gly Ser Gly Gly Gly Gly Ser Gly Gly Gly
            820                 825                 830

Gly Ser Gly Gly Gly Gly Ser Gly Gly Gly Gly Ser Ser Asp Ile Ser
        835                 840                 845

Val Ala Pro Gly Glu Thr Ala Arg Ile Ser Cys Gly Glu Lys Ser Leu
    850                 855                 860

Gly Ser Arg Ala Val Gln Trp Tyr Gln His Arg Ala Gly Gln Ala Pro
```

-continued

```
865                 870                 875                 880

Ser Leu Ile Ile Tyr Asn Asn Gln Asp Arg Pro Ser Gly Ile Pro Glu
                885                 890                 895

Arg Phe Ser Gly Ser Pro Asp Ser Pro Phe Gly Thr Thr Ala Thr Leu
            900                 905                 910

Thr Ile Thr Ser Val Glu Ala Gly Asp Glu Ala Asp Tyr Tyr Cys His
        915                 920                 925

Ile Trp Asp Ser Arg Val Pro Thr Lys Trp Val Phe Gly Gly Gly Thr
    930                 935                 940

Thr Leu Thr Val Leu Gly Gly Gly Gly Ser Gly Gly Gly Gly Ser Gly
945                 950                 955                 960

Gly Gly Gly Ser Gln Met Gln Leu Gln Glu Ser Gly Pro Gly Leu Val
                965                 970                 975

Lys Pro Ser Glu Thr Leu Ser Leu Thr Cys Ser Val Ser Gly Ala Ser
            980                 985                 990

Ile Ser Asp Ser Tyr Trp Ser Trp  Ile Arg Arg Ser Pro  Gly Lys Gly
        995                 1000                1005

Leu Glu  Trp Ile Gly Tyr Val  His Lys Ser Gly Asp  Thr Asn Tyr
    1010                 1015                 1020

Ser Pro  Ser Leu Lys Ser Arg  Val Asn Leu Ser Leu  Asp Thr Ser
    1025                 1030                 1035

Lys Asn  Gln Val Ser Leu Ser  Leu Val Ala Ala Thr  Ala Ala Asp
    1040                 1045                 1050

Ser Gly  Lys Tyr Tyr Cys Ala  Arg Thr Leu His Gly  Arg Arg Ile
    1055                 1060                 1065

Tyr Gly  Ile Val Ala Phe Asn  Glu Trp Phe Thr Tyr  Phe Tyr Met
    1070                 1075                 1080

Asp Val  Trp Gly Asn Gly Thr  Gln Val Thr Val Ser  Ser Gly Gly
    1085                 1090                 1095

Gly Gly  Ser Gly Gly Gly Gly  Ser Gly Gly Gly Gly  Ser Gly Gly
    1100                 1105                 1110

Gly Gly  Ser Gly Gly Gly Gly  Ser Gln Ser Val Leu  Thr Gln Pro
    1115                 1120                 1125

Pro Ser  Val Ser Ala Ala Pro  Gly Gln Lys Val Thr  Ile Ser Cys
    1130                 1135                 1140

Ser Gly  Asn Thr Ser Asn Ile  Gly Asn Asn Phe Val  Ser Trp Tyr
    1145                 1150                 1155

Gln Gln  Arg Pro Gly Arg Ala  Pro Gln Leu Leu Ile  Tyr Glu Thr
    1160                 1165                 1170

Asp Lys  Arg Pro Ser Gly Ile  Pro Asp Arg Phe Ser  Ala Ser Lys
    1175                 1180                 1185

Ser Gly  Thr Ser Gly Thr Leu  Ala Ile Thr Gly Leu  Gln Thr Gly
    1190                 1195                 1200

Asp Glu  Ala Asp Tyr Tyr Cys  Ala Thr Trp Ala Ala  Ser Leu Ser
    1205                 1210                 1215

Ser Ala  Arg Val Phe Gly Thr  Gly Thr Lys Val Ile  Val Leu Val
    1220                 1225                 1230

Gly Gly  Gly Gly Ser Gly Gly  Gly Gly Ser Gly Gly  Gly Gly Ser
    1235                 1240                 1245

Gln Val  Gln Leu Val Glu Ser  Gly Gly Gly Val Val  Gln Pro Gly
    1250                 1255                 1260

Thr Ser  Leu Arg Leu Ser Cys  Ala Ala Ser Gln Phe  Arg Phe Asp
    1265                 1270                 1275
```

```
Gly Tyr  Gly Met His Trp Val  Arg Gln Ala Pro Gly  Lys Gly Leu
    1280                 1285                 1290

Glu Trp  Val Ala Ser Ile Ser  His Asp Gly Ile Lys  Lys Tyr His
    1295                 1300                 1305

Ala Glu  Lys Val Trp Gly Arg  Phe Thr Ile Ser Arg  Asp Asn Ser
    1310                 1315                 1320

Lys Asn  Thr Leu Tyr Leu Gln  Met Asn Ser Leu Arg  Pro Glu Asp
    1325                 1330                 1335

Thr Ala  Leu Tyr Tyr Cys Ala  Lys Asp Leu Arg Glu  Asp Glu Cys
    1340                 1345                 1350

Glu Glu  Trp Trp Ser Asp Tyr  Tyr Asp Phe Gly Lys  Gln Leu Pro
    1355                 1360                 1365

Cys Ala  Lys Ser Arg Gly Gly  Leu Val Gly Ile Ala  Asp Asn Trp
    1370                 1375                 1380

Gly Gln  Gly Thr Met Val Thr  Val Ser Ser Gly Ser  Gly His His
    1385                 1390                 1395

His His  His His
    1400
```

<210> SEQ ID NO 74
<211> LENGTH: 1402
<212> TYPE: PRT
<213> ORGANISM: Artificial Sequence
<220> FEATURE:
<223> OTHER INFORMATION: Synthetic: PentaNAb2.0 Reverse
      VRC26.25-5X-PGT121-5X-N6-5X-35O22-5X-10E8v4_S100cF-His

<400> SEQUENCE: 74

```
Met Gly Trp Ser Cys Ile Ile Leu Phe Leu Val Ala Thr Ala Thr Gly
1               5                   10                  15

Val His Ser Gln Val Gln Leu Val Glu Ser Gly Gly Gly Val Val Gln
            20                  25                  30

Pro Gly Thr Ser Leu Arg Leu Ser Cys Ala Ala Ser Gln Phe Arg Phe
        35                  40                  45

Asp Gly Tyr Gly Met His Trp Val Arg Gln Ala Pro Gly Lys Gly Leu
    50                  55                  60

Glu Trp Val Ala Ser Ile Ser His Asp Gly Ile Lys Lys Tyr His Ala
65                  70                  75                  80

Glu Lys Val Trp Gly Arg Phe Thr Ile Ser Arg Asp Asn Ser Lys Asn
                85                  90                  95

Thr Leu Tyr Leu Gln Met Asn Ser Leu Arg Pro Glu Asp Thr Ala Leu
            100                 105                 110

Tyr Tyr Cys Ala Lys Asp Leu Arg Glu Asp Glu Cys Glu Glu Trp Trp
        115                 120                 125

Ser Asp Tyr Tyr Asp Phe Gly Lys Gln Leu Pro Cys Ala Lys Ser Arg
    130                 135                 140

Gly Gly Leu Val Gly Ile Ala Asp Asn Trp Gly Gln Gly Thr Met Val
145                 150                 155                 160

Thr Val Ser Ser Gly Gly Gly Gly Ser Gly Gly Gly Gly Ser Gly Gly
                165                 170                 175

Gly Gly Ser Gln Ser Val Leu Thr Gln Pro Pro Ser Val Ser Ala Ala
            180                 185                 190

Pro Gly Gln Lys Val Thr Ile Ser Cys Ser Gly Asn Thr Ser Asn Ile
        195                 200                 205

Gly Asn Asn Phe Val Ser Trp Tyr Gln Gln Arg Pro Gly Arg Ala Pro
```

-continued

```
    210                 215                 220

Gln Leu Leu Ile Tyr Glu Thr Asp Lys Arg Pro Ser Gly Ile Pro Asp
225                 230                 235                 240

Arg Phe Ser Ala Ser Lys Ser Gly Thr Ser Gly Thr Leu Ala Ile Thr
                245                 250                 255

Gly Leu Gln Thr Gly Asp Glu Ala Asp Tyr Tyr Cys Ala Thr Trp Ala
            260                 265                 270

Ala Ser Leu Ser Ser Ala Arg Val Phe Gly Thr Gly Thr Lys Val Ile
        275                 280                 285

Val Leu Val Gly Gly Gly Gly Ser Gly Gly Gly Gly Ser Gly Gly Gly
    290                 295                 300

Gly Ser Gly Gly Gly Gly Ser Gly Gly Gly Gly Ser Gln Met Gln Leu
305                 310                 315                 320

Gln Glu Ser Gly Pro Gly Leu Val Lys Pro Ser Glu Thr Leu Ser Leu
                325                 330                 335

Thr Cys Ser Val Ser Gly Ala Ser Ile Ser Asp Ser Tyr Trp Ser Trp
            340                 345                 350

Ile Arg Arg Ser Pro Gly Lys Gly Leu Glu Trp Ile Gly Tyr Val His
        355                 360                 365

Lys Ser Gly Asp Thr Asn Tyr Ser Pro Ser Leu Lys Ser Arg Val Asn
    370                 375                 380

Leu Ser Leu Asp Thr Ser Lys Asn Gln Val Ser Leu Ser Leu Val Ala
385                 390                 395                 400

Ala Thr Ala Ala Asp Ser Gly Lys Tyr Tyr Cys Ala Arg Thr Leu His
                405                 410                 415

Gly Arg Arg Ile Tyr Gly Ile Val Ala Phe Asn Glu Trp Phe Thr Tyr
            420                 425                 430

Phe Tyr Met Asp Val Trp Gly Asn Gly Thr Gln Val Thr Val Ser Ser
        435                 440                 445

Gly Gly Gly Gly Ser Gly Gly Gly Gly Ser Gly Gly Gly Gly Ser Ser
    450                 455                 460

Asp Ile Ser Val Ala Pro Gly Glu Thr Ala Arg Ile Ser Cys Gly Glu
465                 470                 475                 480

Lys Ser Leu Gly Ser Arg Ala Val Gln Trp Tyr Gln His Arg Ala Gly
                485                 490                 495

Gln Ala Pro Ser Leu Ile Ile Tyr Asn Asn Gln Asp Arg Pro Ser Gly
            500                 505                 510

Ile Pro Glu Arg Phe Ser Gly Ser Pro Asp Ser Pro Phe Gly Thr Thr
        515                 520                 525

Ala Thr Leu Thr Ile Thr Ser Val Glu Ala Gly Asp Glu Ala Asp Tyr
    530                 535                 540

Tyr Cys His Ile Trp Asp Ser Arg Val Pro Thr Lys Trp Val Phe Gly
545                 550                 555                 560

Gly Gly Thr Thr Leu Thr Val Leu Gly Gly Gly Gly Ser Gly Gly Gly
                565                 570                 575

Gly Ser Gly Gly Gly Gly Ser Gly Gly Gly Gly Ser Gly Gly Gly Gly
            580                 585                 590

Ser Arg Ala His Leu Val Gln Ser Gly Thr Ala Met Lys Lys Pro Gly
        595                 600                 605

Ala Ser Val Arg Val Ser Cys Gln Thr Ser Gly Tyr Thr Phe Thr Ala
    610                 615                 620

His Ile Leu Phe Trp Phe Arg Gln Ala Pro Gly Arg Gly Leu Glu Trp
625                 630                 635                 640
```

```
Val Gly Trp Ile Lys Pro Gln Tyr Gly Ala Val Asn Phe Gly Gly Gly
                645                 650                 655

Phe Arg Asp Arg Val Thr Leu Thr Arg Asp Val Tyr Arg Glu Ile Ala
            660                 665                 670

Tyr Met Asp Ile Arg Gly Leu Lys Pro Asp Asp Thr Ala Val Tyr Tyr
        675                 680                 685

Cys Ala Arg Asp Arg Ser Tyr Gly Asp Ser Ser Trp Ala Leu Asp Ala
    690                 695                 700

Trp Gly Gln Gly Thr Thr Val Val Val Ser Ala Gly Gly Gly Gly Ser
705                 710                 715                 720

Gly Gly Gly Gly Ser Gly Gly Gly Gly Ser Tyr Ile His Val Thr Gln
                725                 730                 735

Ser Pro Ser Ser Leu Ser Val Ser Ile Gly Asp Arg Val Thr Ile Asn
            740                 745                 750

Cys Gln Thr Ser Gln Gly Val Gly Ser Asp Leu His Trp Tyr Gln His
        755                 760                 765

Lys Pro Gly Arg Ala Pro Lys Leu Leu Ile His His Thr Ser Ser Val
    770                 775                 780

Glu Asp Gly Val Pro Ser Arg Phe Ser Gly Ser Gly Phe His Thr Ser
785                 790                 795                 800

Phe Asn Leu Thr Ile Ser Asp Leu Gln Ala Asp Asp Ile Ala Thr Tyr
                805                 810                 815

Tyr Cys Gln Val Leu Gln Phe Phe Gly Arg Gly Ser Arg Leu His Ile
            820                 825                 830

Lys Gly Gly Gly Gly Ser Gly Gly Gly Gly Ser Gly Gly Gly Gly Ser
        835                 840                 845

Gly Gly Gly Gly Ser Gly Gly Gly Gly Ser Gln Gly Gln Leu Val Gln
    850                 855                 860

Ser Gly Ala Glu Leu Lys Lys Pro Gly Ala Ser Val Lys Ile Ser Cys
865                 870                 875                 880

Lys Thr Ser Gly Tyr Arg Phe Asn Phe Tyr His Ile Asn Trp Ile Arg
                885                 890                 895

Gln Thr Ala Gly Arg Gly Pro Glu Trp Met Gly Trp Ile Ser Pro Tyr
            900                 905                 910

Ser Gly Asp Lys Asn Leu Ala Pro Ala Phe Gln Asp Arg Val Ile Met
        915                 920                 925

Thr Thr Asp Thr Glu Val Pro Val Thr Ser Phe Thr Ser Thr Gly Ala
    930                 935                 940

Ala Tyr Met Glu Ile Arg Asn Leu Lys Phe Asp Asp Thr Gly Thr Tyr
945                 950                 955                 960

Phe Cys Ala Lys Gly Leu Leu Arg Asp Gly Ser Ser Thr Trp Leu Pro
                965                 970                 975

Tyr Leu Trp Gly Gln Gly Thr Leu Leu Thr Val Ser Ser Gly Gly Gly
            980                 985                 990

Gly Ser Gly Gly Gly Gly Ser Gly  Gly Gly Gly Ser Gln  Ser Val Leu
        995                 1000                1005

Thr Gln  Ser Ala Ser Val Ser  Gly Ser Leu Gly Gln  Ser Val Thr
    1010                1015                1020

Ile Ser  Cys Thr Gly Pro Asn  Ser Val Cys Cys Ser  His Lys Ser
    1025                1030                1035

Ile Ser  Trp Tyr Gln Trp Pro  Pro Gly Arg Ala Pro  Thr Leu Ile
    1040                1045                1050
```

```
Ile Tyr Glu Asp Asn Glu Arg Ala Pro Gly Ile Ser Pro Arg Phe
    1055                1060                1065

Ser Gly Tyr Lys Ser Tyr Trp Ser Ala Tyr Leu Thr Ile Ser Asp
    1070                1075                1080

Leu Arg Pro Glu Asp Glu Thr Thr Tyr Tyr Cys Cys Ser Tyr Thr
    1085                1090                1095

His Asn Ser Gly Cys Val Phe Gly Thr Gly Thr Lys Val Ser Val
    1100                1105                1110

Leu Gly Gly Gly Gly Ser Gly Gly Gly Gly Ser Gly Gly Gly Gly
    1115                1120                1125

Ser Gly Gly Gly Gly Ser Gly Gly Gly Gly Ser Glu Val Arg Leu
    1130                1135                1140

Val Glu Ser Gly Gly Gly Leu Val Lys Pro Gly Gly Ser Leu Arg
    1145                1150                1155

Leu Ser Cys Ser Ala Ser Gly Phe Asp Phe Asp Asn Ala Trp Met
    1160                1165                1170

Thr Trp Val Arg Gln Pro Pro Gly Lys Gly Leu Glu Trp Val Gly
    1175                1180                1185

Arg Ile Thr Gly Pro Gly Glu Gly Trp Ser Val Asp Tyr Ala Glu
    1190                1195                1200

Ser Val Lys Gly Arg Phe Thr Ile Ser Arg Asp Asn Thr Lys Asn
    1205                1210                1215

Thr Leu Tyr Leu Glu Met Asn Asn Val Arg Thr Glu Asp Thr Gly
    1220                1225                1230

Tyr Tyr Phe Cys Ala Arg Thr Gly Lys Tyr Tyr Asp Phe Trp Phe
    1235                1240                1245

Gly Tyr Pro Pro Gly Glu Glu Tyr Phe Gln Asp Trp Gly Gln Gly
    1250                1255                1260

Thr Leu Val Ile Val Ser Ser Gly Gly Gly Gly Ser Gly Gly Gly
    1265                1270                1275

Gly Ser Gly Gly Gly Gly Ser Ser Glu Leu Thr Gln Asp Pro Ala
    1280                1285                1290

Val Ser Val Ala Leu Lys Gln Thr Val Thr Ile Thr Cys Arg Gly
    1295                1300                1305

Asp Ser Leu Arg Ser His Tyr Ala Ser Trp Tyr Gln Lys Lys Pro
    1310                1315                1320

Gly Gln Ala Pro Val Leu Leu Phe Tyr Gly Lys Asn Asn Arg Pro
    1325                1330                1335

Ser Gly Ile Pro Asp Arg Phe Ser Gly Ser Ala Ser Gly Asn Arg
    1340                1345                1350

Ala Ser Leu Thr Ile Thr Gly Ala Gln Ala Glu Asp Glu Ala Asp
    1355                1360                1365

Tyr Tyr Cys Ser Ser Arg Asp Lys Ser Gly Ser Arg Leu Ser Val
    1370                1375                1380

Phe Gly Gly Gly Thr Lys Leu Thr Val Leu Gly Ser Gly His His
    1385                1390                1395

His His His His
    1400
```

<210> SEQ ID NO 75
<211> LENGTH: 1398
<212> TYPE: PRT
<213> ORGANISM: Artificial Sequence
<220> FEATURE:
<223> OTHER INFORMATION: Synthetic: PentaNAb3.0

10E8v4_S100cF-5X-35O22-5X-N6-5X-PGT121-5X-PGDM1400-His

<400> SEQUENCE: 75

Met Gly Trp Ser Cys Ile Ile Leu Phe Leu Val Ala Thr Ala Thr Gly
1 5 10 15

Val His Ser Ser Glu Leu Thr Gln Asp Pro Ala Val Ser Val Ala Leu
20 25 30

Lys Gln Thr Val Thr Ile Thr Cys Arg Gly Asp Ser Leu Arg Ser His
35 40 45

Tyr Ala Ser Trp Tyr Gln Lys Lys Pro Gly Gln Ala Pro Val Leu Leu
50 55 60

Phe Tyr Gly Lys Asn Asn Arg Pro Ser Gly Ile Pro Asp Arg Phe Ser
65 70 75 80

Gly Ser Ala Ser Gly Asn Arg Ala Ser Leu Thr Ile Thr Gly Ala Gln
85 90 95

Ala Glu Asp Glu Ala Asp Tyr Tyr Cys Ser Ser Arg Asp Lys Ser Gly
100 105 110

Ser Arg Leu Ser Val Phe Gly Gly Gly Thr Lys Leu Thr Val Leu Gly
115 120 125

Gly Gly Gly Ser Gly Gly Gly Gly Ser Gly Gly Gly Gly Ser Glu Val
130 135 140

Arg Leu Val Glu Ser Gly Gly Gly Leu Val Lys Pro Gly Gly Ser Leu
145 150 155 160

Arg Leu Ser Cys Ser Ala Ser Gly Phe Asp Phe Asp Asn Ala Trp Met
165 170 175

Thr Trp Val Arg Gln Pro Pro Gly Lys Gly Leu Glu Trp Val Gly Arg
180 185 190

Ile Thr Gly Pro Gly Glu Gly Trp Ser Val Asp Tyr Ala Glu Ser Val
195 200 205

Lys Gly Arg Phe Thr Ile Ser Arg Asp Asn Thr Lys Asn Thr Leu Tyr
210 215 220

Leu Glu Met Asn Asn Val Arg Thr Glu Asp Thr Gly Tyr Tyr Phe Cys
225 230 235 240

Ala Arg Thr Gly Lys Tyr Tyr Asp Phe Trp Phe Gly Tyr Pro Pro Gly
245 250 255

Glu Glu Tyr Phe Gln Asp Trp Gly Gln Gly Thr Leu Val Ile Val Ser
260 265 270

Ser Gly Gly Gly Gly Ser Gly Gly Gly Gly Ser Gly Gly Gly Gly Ser
275 280 285

Gly Gly Gly Gly Ser Gly Gly Gly Gly Ser Gln Ser Val Leu Thr Gln
290 295 300

Ser Ala Ser Val Ser Gly Ser Leu Gly Gln Ser Val Thr Ile Ser Cys
305 310 315 320

Thr Gly Pro Asn Ser Val Cys Cys Ser His Lys Ser Ile Ser Trp Tyr
325 330 335

Gln Trp Pro Pro Gly Arg Ala Pro Thr Leu Ile Ile Tyr Glu Asp Asn
340 345 350

Glu Arg Ala Pro Gly Ile Ser Pro Arg Phe Ser Gly Tyr Lys Ser Tyr
355 360 365

Trp Ser Ala Tyr Leu Thr Ile Ser Asp Leu Arg Pro Glu Asp Glu Thr
370 375 380

Thr Tyr Tyr Cys Cys Ser Tyr Thr His Asn Ser Gly Cys Val Phe Gly
385 390 395 400

-continued

```
Thr Gly Thr Lys Val Ser Val Leu Gly Gly Gly Gly Ser Gly Gly Gly
                405                 410                 415

Gly Ser Gly Gly Gly Gly Ser Gln Gly Gln Leu Val Gln Ser Gly Ala
            420                 425                 430

Glu Leu Lys Lys Pro Gly Ala Ser Val Lys Ile Ser Cys Lys Thr Ser
        435                 440                 445

Gly Tyr Arg Phe Asn Phe Tyr His Ile Asn Trp Ile Arg Gln Thr Ala
    450                 455                 460

Gly Arg Gly Pro Glu Trp Met Gly Trp Ile Ser Pro Tyr Ser Gly Asp
465                 470                 475                 480

Lys Asn Leu Ala Pro Ala Phe Gln Asp Arg Val Ile Met Thr Thr Asp
                485                 490                 495

Thr Glu Val Pro Val Thr Ser Phe Thr Ser Thr Gly Ala Ala Tyr Met
            500                 505                 510

Glu Ile Arg Asn Leu Lys Phe Asp Asp Thr Gly Thr Tyr Phe Cys Ala
        515                 520                 525

Lys Gly Leu Leu Arg Asp Gly Ser Ser Thr Trp Leu Pro Tyr Leu Trp
    530                 535                 540

Gly Gln Gly Thr Leu Leu Thr Val Ser Ser Gly Gly Gly Gly Ser Gly
545                 550                 555                 560

Gly Gly Gly Ser Gly Gly Gly Gly Ser Gly Gly Gly Gly Ser Gly Gly
                565                 570                 575

Gly Gly Ser Tyr Ile His Val Thr Gln Ser Pro Ser Ser Leu Ser Val
            580                 585                 590

Ser Ile Gly Asp Arg Val Thr Ile Asn Cys Gln Thr Ser Gln Gly Val
        595                 600                 605

Gly Ser Asp Leu His Trp Tyr Gln His Lys Pro Gly Arg Ala Pro Lys
    610                 615                 620

Leu Leu Ile His His Thr Ser Ser Val Glu Asp Gly Val Pro Ser Arg
625                 630                 635                 640

Phe Ser Gly Ser Gly Phe His Thr Ser Phe Asn Leu Thr Ile Ser Asp
                645                 650                 655

Leu Gln Ala Asp Asp Ile Ala Thr Tyr Tyr Cys Gln Val Leu Gln Phe
            660                 665                 670

Phe Gly Arg Gly Ser Arg Leu His Ile Lys Gly Gly Gly Gly Ser Gly
        675                 680                 685

Gly Gly Gly Ser Gly Gly Gly Gly Ser Arg Ala His Leu Val Gln Ser
    690                 695                 700

Gly Thr Ala Met Lys Lys Pro Gly Ala Ser Val Arg Val Ser Cys Gln
705                 710                 715                 720

Thr Ser Gly Tyr Thr Phe Thr Ala His Ile Leu Phe Trp Phe Arg Gln
                725                 730                 735

Ala Pro Gly Arg Gly Leu Glu Trp Val Gly Trp Ile Lys Pro Gln Tyr
            740                 745                 750

Gly Ala Val Asn Phe Gly Gly Gly Phe Arg Asp Arg Val Thr Leu Thr
        755                 760                 765

Arg Asp Val Tyr Arg Glu Ile Ala Tyr Met Asp Ile Arg Gly Leu Lys
    770                 775                 780

Pro Asp Asp Thr Ala Val Tyr Tyr Cys Ala Arg Asp Arg Ser Tyr Gly
785                 790                 795                 800

Asp Ser Ser Trp Ala Leu Asp Ala Trp Gly Gln Gly Thr Thr Val Val
                805                 810                 815

Val Ser Ala Gly Gly Gly Gly Ser Gly Gly Gly Gly Ser Gly Gly Gly
```

-continued

```
            820                 825                 830

Gly Ser Gly Gly Gly Gly Ser Gly Gly Gly Gly Ser Ser Asp Ile Ser
        835                 840                 845

Val Ala Pro Gly Glu Thr Ala Arg Ile Ser Cys Gly Glu Lys Ser Leu
    850                 855                 860

Gly Ser Arg Ala Val Gln Trp Tyr Gln His Arg Ala Gly Gln Ala Pro
865                 870                 875                 880

Ser Leu Ile Ile Tyr Asn Asn Gln Asp Arg Pro Ser Gly Ile Pro Glu
                885                 890                 895

Arg Phe Ser Gly Ser Pro Asp Ser Pro Phe Gly Thr Thr Ala Thr Leu
            900                 905                 910

Thr Ile Thr Ser Val Glu Ala Gly Asp Glu Ala Asp Tyr Tyr Cys His
        915                 920                 925

Ile Trp Asp Ser Arg Val Pro Thr Lys Trp Val Phe Gly Gly Gly Thr
    930                 935                 940

Thr Leu Thr Val Leu Gly Gly Gly Gly Ser Gly Gly Gly Gly Ser Gly
945                 950                 955                 960

Gly Gly Gly Ser Gln Met Gln Leu Gln Glu Ser Gly Pro Gly Leu Val
                965                 970                 975

Lys Pro Ser Glu Thr Leu Ser Leu Thr Cys Ser Val Ser Gly Ala Ser
            980                 985                 990

Ile Ser Asp Ser Tyr Trp Ser Trp  Ile Arg Arg Ser Pro  Gly Lys Gly
        995                 1000                1005

Leu Glu  Trp Ile Gly Tyr Val  His Lys Ser Gly Asp  Thr Asn Tyr
    1010                 1015                 1020

Ser Pro  Ser Leu Lys Ser Arg  Val Asn Leu Ser Leu  Asp Thr Ser
    1025                 1030                 1035

Lys Asn  Gln Val Ser Leu Ser  Leu Val Ala Ala Thr  Ala Ala Asp
    1040                 1045                 1050

Ser Gly  Lys Tyr Tyr Cys Ala  Arg Thr Leu His Gly  Arg Arg Ile
    1055                 1060                 1065

Tyr Gly  Ile Val Ala Phe Asn  Glu Trp Phe Thr Tyr  Phe Tyr Met
    1070                 1075                 1080

Asp Val  Trp Gly Asn Gly Thr  Gln Val Thr Val Ser  Ser Gly Gly
    1085                 1090                 1095

Gly Gly  Ser Gly Gly Gly Gly  Ser Gly Gly Gly Gly  Ser Gly Gly
    1100                 1105                 1110

Gly Gly  Ser Gly Gly Gly Gly  Ser Asp Phe Val Leu  Thr Gln Ser
    1115                 1120                 1125

Pro His  Ser Leu Ser Val Thr  Pro Gly Glu Ser Ala  Ser Ile Ser
    1130                 1135                 1140

Cys Lys  Ser Ser His Ser Leu  Ile His Gly Asp Arg  Asn Asn Tyr
    1145                 1150                 1155

Leu Ala  Trp Tyr Val Gln Lys  Pro Gly Arg Ser Pro  Gln Leu Leu
    1160                 1165                 1170

Ile Tyr  Leu Ala Ser Ser Arg  Ala Ser Gly Val Pro  Asp Arg Phe
    1175                 1180                 1185

Ser Gly  Ser Gly Ser Asp Lys  Asp Phe Thr Leu Lys  Ile Ser Arg
    1190                 1195                 1200

Val Glu  Thr Glu Asp Val Gly  Thr Tyr Tyr Cys Met  Gln Gly Arg
    1205                 1210                 1215

Glu Ser  Pro Trp Thr Phe Gly  Gln Gly Thr Lys Val  Asp Ile Lys
    1220                 1225                 1230
```

Gly Gly Gly Gly Ser Gly Gly Gly Gly Ser Gly Gly Gly Gly Ser
1235 1240 1245

Gln Ala Gln Leu Val Gln Ser Gly Pro Glu Val Arg Lys Pro Gly
1250 1255 1260

Thr Ser Val Lys Val Ser Cys Lys Ala Pro Gly Asn Thr Leu Lys
1265 1270 1275

Thr Tyr Asp Leu His Trp Val Arg Ser Val Pro Gly Gln Gly Leu
1280 1285 1290

Gln Trp Met Gly Trp Ile Ser His Glu Gly Asp Lys Lys Val Ile
1295 1300 1305

Val Glu Arg Phe Lys Ala Lys Val Thr Ile Asp Trp Asp Arg Ser
1310 1315 1320

Thr Asn Thr Ala Tyr Leu Gln Leu Ser Gly Leu Thr Ser Gly Asp
1325 1330 1335

Thr Ala Val Tyr Tyr Cys Ala Lys Gly Ser Lys His Arg Leu Arg
1340 1345 1350

Asp Tyr Ala Leu Tyr Asp Asp Asp Gly Ala Leu Asn Trp Ala Val
1355 1360 1365

Asp Val Asp Tyr Leu Ser Asn Leu Glu Phe Trp Gly Gln Gly Thr
1370 1375 1380

Ala Val Thr Val Ser Ser Gly Ser Gly His His His His His His
1385 1390 1395

<210> SEQ ID NO 76
<211> LENGTH: 1398
<212> TYPE: PRT
<213> ORGANISM: Artificial Sequence
<220> FEATURE:
<223> OTHER INFORMATION: Synthetic: PentaNAb3.0 Reverse
PGDM1400-5X-PGT121-5X-N6-5X-35O22-5X-10E8v4S100cF-His

<400> SEQUENCE: 76

Met Gly Trp Ser Cys Ile Ile Leu Phe Leu Val Ala Thr Ala Thr Gly
1 5 10 15

Val His Ser Gln Ala Gln Leu Val Gln Ser Gly Pro Glu Val Arg Lys
20 25 30

Pro Gly Thr Ser Val Lys Val Ser Cys Lys Ala Pro Gly Asn Thr Leu
35 40 45

Lys Thr Tyr Asp Leu His Trp Val Arg Ser Val Pro Gly Gln Gly Leu
50 55 60

Gln Trp Met Gly Trp Ile Ser His Glu Gly Asp Lys Lys Val Ile Val
65 70 75 80

Glu Arg Phe Lys Ala Lys Val Thr Ile Asp Trp Asp Arg Ser Thr Asn
85 90 95

Thr Ala Tyr Leu Gln Leu Ser Gly Leu Thr Ser Gly Asp Thr Ala Val
100 105 110

Tyr Tyr Cys Ala Lys Gly Ser Lys His Arg Leu Arg Asp Tyr Ala Leu
115 120 125

Tyr Asp Asp Asp Gly Ala Leu Asn Trp Ala Val Asp Val Asp Tyr Leu
130 135 140

Ser Asn Leu Glu Phe Trp Gly Gln Gly Thr Ala Val Thr Val Ser Ser
145 150 155 160

Gly Gly Gly Gly Ser Gly Gly Gly Gly Ser Gly Gly Gly Gly Ser Asp
165 170 175

Phe Val Leu Thr Gln Ser Pro His Ser Leu Ser Val Thr Pro Gly Glu

-continued

```
            180                 185                 190

Ser Ala Ser Ile Ser Cys Lys Ser Ser His Ser Leu Ile His Gly Asp
        195                 200                 205

Arg Asn Asn Tyr Leu Ala Trp Tyr Val Gln Lys Pro Gly Arg Ser Pro
    210                 215                 220

Gln Leu Leu Ile Tyr Leu Ala Ser Ser Arg Ala Ser Gly Val Pro Asp
225                 230                 235                 240

Arg Phe Ser Gly Ser Gly Ser Asp Lys Asp Phe Thr Leu Lys Ile Ser
                245                 250                 255

Arg Val Glu Thr Glu Asp Val Gly Thr Tyr Tyr Cys Met Gln Gly Arg
            260                 265                 270

Glu Ser Pro Trp Thr Phe Gly Gln Gly Thr Lys Val Asp Ile Lys Gly
        275                 280                 285

Gly Gly Gly Ser Gly Gly Gly Gly Ser Gly Gly Gly Gly Ser Gly Gly
    290                 295                 300

Gly Gly Ser Gly Gly Gly Gly Ser Gln Met Gln Leu Gln Glu Ser Gly
305                 310                 315                 320

Pro Gly Leu Val Lys Pro Ser Glu Thr Leu Ser Leu Thr Cys Ser Val
                325                 330                 335

Ser Gly Ala Ser Ile Ser Asp Ser Tyr Trp Ser Trp Ile Arg Arg Ser
            340                 345                 350

Pro Gly Lys Gly Leu Glu Trp Ile Gly Tyr Val His Lys Ser Gly Asp
        355                 360                 365

Thr Asn Tyr Ser Pro Ser Leu Lys Ser Arg Val Asn Leu Ser Leu Asp
    370                 375                 380

Thr Ser Lys Asn Gln Val Ser Leu Ser Leu Val Ala Ala Thr Ala Ala
385                 390                 395                 400

Asp Ser Gly Lys Tyr Tyr Cys Ala Arg Thr Leu His Gly Arg Arg Ile
                405                 410                 415

Tyr Gly Ile Val Ala Phe Asn Glu Trp Phe Thr Tyr Phe Tyr Met Asp
            420                 425                 430

Val Trp Gly Asn Gly Thr Gln Val Thr Val Ser Ser Gly Gly Gly Gly
        435                 440                 445

Ser Gly Gly Gly Gly Ser Gly Gly Gly Gly Ser Ser Asp Ile Ser Val
    450                 455                 460

Ala Pro Gly Glu Thr Ala Arg Ile Ser Cys Gly Glu Lys Ser Leu Gly
465                 470                 475                 480

Ser Arg Ala Val Gln Trp Tyr Gln His Arg Ala Gly Gln Ala Pro Ser
                485                 490                 495

Leu Ile Ile Tyr Asn Asn Gln Asp Arg Pro Ser Gly Ile Pro Glu Arg
            500                 505                 510

Phe Ser Gly Ser Pro Asp Ser Pro Phe Gly Thr Thr Ala Thr Leu Thr
        515                 520                 525

Ile Thr Ser Val Glu Ala Gly Asp Glu Ala Asp Tyr Tyr Cys His Ile
    530                 535                 540

Trp Asp Ser Arg Val Pro Thr Lys Trp Val Phe Gly Gly Gly Thr Thr
545                 550                 555                 560

Leu Thr Val Leu Gly Gly Gly Gly Ser Gly Gly Gly Gly Ser Gly Gly
                565                 570                 575

Gly Gly Ser Gly Gly Gly Gly Ser Gly Gly Gly Gly Ser Arg Ala His
            580                 585                 590

Leu Val Gln Ser Gly Thr Ala Met Lys Lys Pro Gly Ala Ser Val Arg
        595                 600                 605
```

-continued

```
Val Ser Cys Gln Thr Ser Gly Tyr Thr Phe Thr Ala His Ile Leu Phe
    610                 615                 620

Trp Phe Arg Gln Ala Pro Gly Arg Gly Leu Glu Trp Val Gly Trp Ile
625                 630                 635                 640

Lys Pro Gln Tyr Gly Ala Val Asn Phe Gly Gly Gly Phe Arg Asp Arg
                645                 650                 655

Val Thr Leu Thr Arg Asp Val Tyr Arg Glu Ile Ala Tyr Met Asp Ile
            660                 665                 670

Arg Gly Leu Lys Pro Asp Asp Thr Ala Val Tyr Tyr Cys Ala Arg Asp
        675                 680                 685

Arg Ser Tyr Gly Asp Ser Ser Trp Ala Leu Asp Ala Trp Gly Gln Gly
    690                 695                 700

Thr Thr Val Val Val Ser Ala Gly Gly Gly Gly Ser Gly Gly Gly Gly
705                 710                 715                 720

Ser Gly Gly Gly Gly Ser Tyr Ile His Val Thr Gln Ser Pro Ser Ser
                725                 730                 735

Leu Ser Val Ser Ile Gly Asp Arg Val Thr Ile Asn Cys Gln Thr Ser
            740                 745                 750

Gln Gly Val Gly Ser Asp Leu His Trp Tyr Gln His Lys Pro Gly Arg
        755                 760                 765

Ala Pro Lys Leu Leu Ile His His Thr Ser Ser Val Glu Asp Gly Val
    770                 775                 780

Pro Ser Arg Phe Ser Gly Ser Gly Phe His Thr Ser Phe Asn Leu Thr
785                 790                 795                 800

Ile Ser Asp Leu Gln Ala Asp Asp Ile Ala Thr Tyr Tyr Cys Gln Val
                805                 810                 815

Leu Gln Phe Phe Gly Arg Gly Ser Arg Leu His Ile Lys Gly Gly Gly
            820                 825                 830

Gly Ser Gly Gly Gly Gly Ser Gly Gly Gly Gly Ser Gly Gly Gly Gly
        835                 840                 845

Ser Gly Gly Gly Gly Ser Gln Gly Gln Leu Val Gln Ser Gly Ala Glu
    850                 855                 860

Leu Lys Lys Pro Gly Ala Ser Val Lys Ile Ser Cys Lys Thr Ser Gly
865                 870                 875                 880

Tyr Arg Phe Asn Phe Tyr His Ile Asn Trp Ile Arg Gln Thr Ala Gly
                885                 890                 895

Arg Gly Pro Glu Trp Met Gly Trp Ile Ser Pro Tyr Ser Gly Asp Lys
            900                 905                 910

Asn Leu Ala Pro Ala Phe Gln Asp Arg Val Ile Met Thr Thr Asp Thr
        915                 920                 925

Glu Val Pro Val Thr Ser Phe Thr Ser Thr Gly Ala Ala Tyr Met Glu
    930                 935                 940

Ile Arg Asn Leu Lys Phe Asp Asp Thr Gly Thr Tyr Phe Cys Ala Lys
945                 950                 955                 960

Gly Leu Leu Arg Asp Gly Ser Ser Thr Trp Leu Pro Tyr Leu Trp Gly
                965                 970                 975

Gln Gly Thr Leu Leu Thr Val Ser Ser Gly Gly Gly Gly Ser Gly Gly
            980                 985                 990

Gly Gly Ser Gly Gly Gly Gly Ser  Gln Ser Val Leu Thr  Gln Ser Ala
        995                 1000                1005

Ser Val  Ser Gly Ser Leu Gly  Gln Ser Val Thr Ile  Ser Cys Thr
    1010                1015                1020
```

-continued

```
Gly Pro  Asn Ser Val Cys Cys  Ser His Lys Ser Ile  Ser Trp Tyr
    1025                 1030                 1035

Gln Trp  Pro Pro Gly Arg Ala  Pro Thr Leu Ile Ile  Tyr Glu Asp
    1040                 1045                 1050

Asn Glu  Arg Ala Pro Gly Ile  Ser Pro Arg Phe Ser  Gly Tyr Lys
    1055                 1060                 1065

Ser Tyr  Trp Ser Ala Tyr Leu  Thr Ile Ser Asp Leu  Arg Pro Glu
    1070                 1075                 1080

Asp Glu  Thr Thr Tyr Tyr Cys  Cys Ser Tyr Thr His  Asn Ser Gly
    1085                 1090                 1095

Cys Val  Phe Gly Thr Gly Thr  Lys Val Ser Val Leu  Gly Gly Gly
    1100                 1105                 1110

Gly Ser  Gly Gly Gly Gly Ser  Gly Gly Gly Gly Ser  Gly Gly Gly
    1115                 1120                 1125

Gly Ser  Gly Gly Gly Gly Ser  Glu Val Arg Leu Val  Glu Ser Gly
    1130                 1135                 1140

Gly Gly  Leu Val Lys Pro Gly  Gly Ser Leu Arg Leu  Ser Cys Ser
    1145                 1150                 1155

Ala Ser  Gly Phe Asp Phe Asp  Asn Ala Trp Met Thr  Trp Val Arg
    1160                 1165                 1170

Gln Pro  Pro Gly Lys Gly Leu  Glu Trp Val Gly Arg  Ile Thr Gly
    1175                 1180                 1185

Pro Gly  Glu Gly Trp Ser Val  Asp Tyr Ala Glu Ser  Val Lys Gly
    1190                 1195                 1200

Arg Phe  Thr Ile Ser Arg Asp  Asn Thr Lys Asn Thr  Leu Tyr Leu
    1205                 1210                 1215

Glu Met  Asn Asn Val Arg Thr  Glu Asp Thr Gly Tyr  Tyr Phe Cys
    1220                 1225                 1230

Ala Arg  Thr Gly Lys Tyr Tyr  Asp Phe Trp Phe Gly  Tyr Pro Pro
    1235                 1240                 1245

Gly Glu  Glu Tyr Phe Gln Asp  Trp Gly Gln Gly Thr  Leu Val Ile
    1250                 1255                 1260

Val Ser  Ser Gly Gly Gly Gly  Ser Gly Gly Gly Gly  Ser Gly Gly
    1265                 1270                 1275

Gly Gly  Ser Ser Glu Leu Thr  Gln Asp Pro Ala Val  Ser Val Ala
    1280                 1285                 1290

Leu Lys  Gln Thr Val Thr Ile  Thr Cys Arg Gly Asp  Ser Leu Arg
    1295                 1300                 1305

Ser His  Tyr Ala Ser Trp Tyr  Gln Lys Lys Pro Gly  Gln Ala Pro
    1310                 1315                 1320

Val Leu  Leu Phe Tyr Gly Lys  Asn Asn Arg Pro Ser  Gly Ile Pro
    1325                 1330                 1335

Asp Arg  Phe Ser Gly Ser Ala  Ser Gly Asn Arg Ala  Ser Leu Thr
    1340                 1345                 1350

Ile Thr  Gly Ala Gln Ala Glu  Asp Glu Ala Asp Tyr  Tyr Cys Ser
    1355                 1360                 1365

Ser Arg  Asp Lys Ser Gly Ser  Arg Leu Ser Val Phe  Gly Gly Gly
    1370                 1375                 1380

Thr Lys  Leu Thr Val Leu Gly  Ser Gly His His His  His His His
    1385                 1390                 1395
```

<210> SEQ ID NO 77
<211> LENGTH: 1398
<212> TYPE: PRT

<213> ORGANISM: Artificial Sequence
<220> FEATURE:
<223> OTHER INFORMATION: Synthetic: PentaNAb4.0 10E8v4
V5R_S100cF-5X-35O22-5X-N6-5X-PGT121-5X-PGDM1400-His

<400> SEQUENCE: 77

```
Met Gly Trp Ser Cys Ile Ile Leu Phe Leu Val Ala Thr Ala Thr Gly
1               5                   10                  15

Val His Ser Ser Glu Leu Thr Gln Asp Pro Ala Val Ser Val Ala Leu
            20                  25                  30

Lys Gln Thr Val Thr Ile Thr Cys Arg Gly Asp Ser Leu Arg Ser His
        35                  40                  45

Tyr Ala Ser Trp Tyr Gln Lys Lys Pro Gly Gln Ala Pro Val Leu Leu
    50                  55                  60

Phe Tyr Gly Lys Asn Asn Arg Pro Ser Gly Ile Pro Asp Arg Phe Ser
65                  70                  75                  80

Gly Ser Ala Ser Gly Asn Arg Ala Ser Leu Thr Ile Thr Gly Ala Gln
                85                  90                  95

Ala Glu Asp Glu Ala Asp Tyr Tyr Cys Ser Ser Arg Asp Lys Ser Gly
            100                 105                 110

Ser Arg Leu Ser Val Phe Gly Gly Gly Thr Lys Leu Thr Val Leu Gly
        115                 120                 125

Gly Gly Gly Ser Gly Gly Gly Gly Ser Gly Gly Gly Gly Ser Glu Val
    130                 135                 140

Arg Leu Arg Glu Ser Gly Gly Gly Leu Val Lys Pro Gly Gly Ser Leu
145                 150                 155                 160

Arg Leu Ser Cys Ser Ala Ser Gly Phe Asp Phe Asp Asn Ala Trp Met
                165                 170                 175

Thr Trp Val Arg Gln Pro Pro Gly Lys Gly Leu Glu Trp Val Gly Arg
            180                 185                 190

Ile Thr Gly Pro Gly Glu Gly Trp Ser Val Asp Tyr Ala Glu Ser Val
        195                 200                 205

Lys Gly Arg Phe Thr Ile Ser Arg Asp Asn Thr Lys Asn Thr Leu Tyr
    210                 215                 220

Leu Glu Met Asn Asn Val Arg Thr Glu Asp Thr Gly Tyr Tyr Phe Cys
225                 230                 235                 240

Ala Arg Thr Gly Lys Tyr Tyr Asp Phe Trp Phe Gly Tyr Pro Pro Gly
                245                 250                 255

Glu Glu Tyr Phe Gln Asp Trp Gly Gln Gly Thr Leu Val Ile Val Ser
            260                 265                 270

Ser Gly Gly Gly Gly Ser Gly Gly Gly Gly Ser Gly Gly Gly Gly Ser
        275                 280                 285

Gly Gly Gly Gly Ser Gly Gly Gly Gly Ser Gln Ser Val Leu Thr Gln
    290                 295                 300

Ser Ala Ser Val Ser Gly Ser Leu Gly Gln Ser Val Thr Ile Ser Cys
305                 310                 315                 320

Thr Gly Pro Asn Ser Val Cys Cys Ser His Lys Ser Ile Ser Trp Tyr
                325                 330                 335

Gln Trp Pro Pro Gly Arg Ala Pro Thr Leu Ile Ile Tyr Glu Asp Asn
            340                 345                 350

Glu Arg Ala Pro Gly Ile Ser Pro Arg Phe Ser Gly Tyr Lys Ser Tyr
        355                 360                 365

Trp Ser Ala Tyr Leu Thr Ile Ser Asp Leu Arg Pro Glu Asp Glu Thr
    370                 375                 380
```

-continued

```
Thr Tyr Tyr Cys Cys Ser Tyr Thr His Asn Ser Gly Cys Val Phe Gly
385                 390                 395                 400

Thr Gly Thr Lys Val Ser Val Leu Gly Gly Gly Gly Ser Gly Gly Gly
                405                 410                 415

Gly Ser Gly Gly Gly Gly Ser Gln Gly Gln Leu Val Gln Ser Gly Ala
            420                 425                 430

Glu Leu Lys Lys Pro Gly Ala Ser Val Lys Ile Ser Cys Lys Thr Ser
        435                 440                 445

Gly Tyr Arg Phe Asn Phe Tyr His Ile Asn Trp Ile Arg Gln Thr Ala
    450                 455                 460

Gly Arg Gly Pro Glu Trp Met Gly Trp Ile Ser Pro Tyr Ser Gly Asp
465                 470                 475                 480

Lys Asn Leu Ala Pro Ala Phe Gln Asp Arg Val Ile Met Thr Thr Asp
                485                 490                 495

Thr Glu Val Pro Val Thr Ser Phe Thr Ser Thr Gly Ala Ala Tyr Met
            500                 505                 510

Glu Ile Arg Asn Leu Lys Phe Asp Asp Thr Gly Thr Tyr Phe Cys Ala
        515                 520                 525

Lys Gly Leu Leu Arg Asp Gly Ser Ser Thr Trp Leu Pro Tyr Leu Trp
    530                 535                 540

Gly Gln Gly Thr Leu Leu Thr Val Ser Ser Gly Gly Gly Gly Ser Gly
545                 550                 555                 560

Gly Gly Gly Ser Gly Gly Gly Gly Ser Gly Gly Gly Gly Ser Gly Gly
                565                 570                 575

Gly Gly Ser Tyr Ile His Val Thr Gln Ser Pro Ser Ser Leu Ser Val
            580                 585                 590

Ser Ile Gly Asp Arg Val Thr Ile Asn Cys Gln Thr Ser Gln Gly Val
        595                 600                 605

Gly Ser Asp Leu His Trp Tyr Gln His Lys Pro Gly Arg Ala Pro Lys
    610                 615                 620

Leu Leu Ile His His Thr Ser Ser Val Glu Asp Gly Val Pro Ser Arg
625                 630                 635                 640

Phe Ser Gly Ser Gly Phe His Thr Ser Phe Asn Leu Thr Ile Ser Asp
                645                 650                 655

Leu Gln Ala Asp Asp Ile Ala Thr Tyr Tyr Cys Gln Val Leu Gln Phe
            660                 665                 670

Phe Gly Arg Gly Ser Arg Leu His Ile Lys Gly Gly Gly Gly Ser Gly
        675                 680                 685

Gly Gly Gly Ser Gly Gly Gly Gly Ser Arg Ala His Leu Val Gln Ser
    690                 695                 700

Gly Thr Ala Met Lys Lys Pro Gly Ala Ser Val Arg Val Ser Cys Gln
705                 710                 715                 720

Thr Ser Gly Tyr Thr Phe Thr Ala His Ile Leu Phe Trp Phe Arg Gln
                725                 730                 735

Ala Pro Gly Arg Gly Leu Glu Trp Val Gly Trp Ile Lys Pro Gln Tyr
            740                 745                 750

Gly Ala Val Asn Phe Gly Gly Gly Phe Arg Asp Arg Val Thr Leu Thr
        755                 760                 765

Arg Asp Val Tyr Arg Glu Ile Ala Tyr Met Asp Ile Arg Gly Leu Lys
    770                 775                 780

Pro Asp Asp Thr Ala Val Tyr Tyr Cys Ala Arg Asp Arg Ser Tyr Gly
785                 790                 795                 800

Asp Ser Ser Trp Ala Leu Asp Ala Trp Gly Gln Gly Thr Thr Val Val
```

-continued

```
                805                 810                 815

Val Ser Ala Gly Gly Gly Gly Ser Gly Gly Gly Gly Ser Gly Gly Gly
            820                 825                 830

Gly Ser Gly Gly Gly Gly Ser Gly Gly Gly Gly Ser Ser Asp Ile Ser
        835                 840                 845

Val Ala Pro Gly Glu Thr Ala Arg Ile Ser Cys Gly Glu Lys Ser Leu
    850                 855                 860

Gly Ser Arg Ala Val Gln Trp Tyr Gln His Arg Ala Gly Gln Ala Pro
865                 870                 875                 880

Ser Leu Ile Ile Tyr Asn Asn Gln Asp Arg Pro Ser Gly Ile Pro Glu
                885                 890                 895

Arg Phe Ser Gly Ser Pro Asp Ser Pro Phe Gly Thr Thr Ala Thr Leu
            900                 905                 910

Thr Ile Thr Ser Val Glu Ala Gly Asp Glu Ala Asp Tyr Tyr Cys His
        915                 920                 925

Ile Trp Asp Ser Arg Val Pro Thr Lys Trp Val Phe Gly Gly Gly Thr
    930                 935                 940

Thr Leu Thr Val Leu Gly Gly Gly Gly Ser Gly Gly Gly Gly Ser Gly
945                 950                 955                 960

Gly Gly Gly Ser Gln Met Gln Leu Gln Glu Ser Gly Pro Gly Leu Val
                965                 970                 975

Lys Pro Ser Glu Thr Leu Ser Leu Thr Cys Ser Val Ser Gly Ala Ser
            980                 985                 990

Ile Ser Asp Ser Tyr Trp Ser Trp  Ile Arg Arg Ser Pro  Gly Lys Gly
        995                 1000                1005

Leu Glu  Trp Ile Gly Tyr Val  His Lys Ser Gly Asp  Thr Asn Tyr
    1010                1015                1020

Ser Pro  Ser Leu Lys Ser Arg  Val Asn Leu Ser Leu  Asp Thr Ser
    1025                1030                1035

Lys Asn  Gln Val Ser Leu Ser  Leu Val Ala Ala Thr  Ala Ala Asp
    1040                1045                1050

Ser Gly  Lys Tyr Tyr Cys Ala  Arg Thr Leu His Gly  Arg Arg Ile
    1055                1060                1065

Tyr Gly  Ile Val Ala Phe Asn  Glu Trp Phe Thr Tyr  Phe Tyr Met
    1070                1075                1080

Asp Val  Trp Gly Asn Gly Thr  Gln Val Thr Val Ser  Ser Gly Gly
    1085                1090                1095

Gly Gly  Ser Gly Gly Gly Gly  Ser Gly Gly Gly Gly  Ser Gly Gly
    1100                1105                1110

Gly Gly  Ser Gly Gly Gly Gly  Ser Asp Phe Val Leu  Thr Gln Ser
    1115                1120                1125

Pro His  Ser Leu Ser Val Thr  Pro Gly Glu Ser Ala  Ser Ile Ser
    1130                1135                1140

Cys Lys  Ser Ser His Ser Leu  Ile His Gly Asp Arg  Asn Asn Tyr
    1145                1150                1155

Leu Ala  Trp Tyr Val Gln Lys  Pro Gly Arg Ser Pro  Gln Leu Leu
    1160                1165                1170

Ile Tyr  Leu Ala Ser Ser Arg  Ala Ser Gly Val Pro  Asp Arg Phe
    1175                1180                1185

Ser Gly  Ser Gly Ser Asp Lys  Asp Phe Thr Leu Lys  Ile Ser Arg
    1190                1195                1200

Val Glu  Thr Glu Asp Val Gly  Thr Tyr Tyr Cys Met  Gln Gly Arg
    1205                1210                1215
```

Glu Ser Pro Trp Thr Phe Gly Gln Gly Thr Lys Val Asp Ile Lys
1220 1225 1230

Gly Gly Gly Gly Ser Gly Gly Gly Gly Ser Gly Gly Gly Gly Ser
1235 1240 1245

Gln Ala Gln Leu Val Gln Ser Gly Pro Glu Val Arg Lys Pro Gly
1250 1255 1260

Thr Ser Val Lys Val Ser Cys Lys Ala Pro Gly Asn Thr Leu Lys
1265 1270 1275

Thr Tyr Asp Leu His Trp Val Arg Ser Val Pro Gly Gln Gly Leu
1280 1285 1290

Gln Trp Met Gly Trp Ile Ser His Glu Gly Asp Lys Lys Val Ile
1295 1300 1305

Val Glu Arg Phe Lys Ala Lys Val Thr Ile Asp Trp Asp Arg Ser
1310 1315 1320

Thr Asn Thr Ala Tyr Leu Gln Leu Ser Gly Leu Thr Ser Gly Asp
1325 1330 1335

Thr Ala Val Tyr Tyr Cys Ala Lys Gly Ser Lys His Arg Leu Arg
1340 1345 1350

Asp Tyr Ala Leu Tyr Asp Asp Asp Gly Ala Leu Asn Trp Ala Val
1355 1360 1365

Asp Val Asp Tyr Leu Ser Asn Leu Glu Phe Trp Gly Gln Gly Thr
1370 1375 1380

Ala Val Thr Val Ser Ser Gly Ser Gly His His His His His His
1385 1390 1395

<210> SEQ ID NO 78
<211> LENGTH: 1398
<212> TYPE: PRT
<213> ORGANISM: Artificial Sequence
<220> FEATURE:
<223> OTHER INFORMATION: Synthetic: PentaNAb4.0 Reverse
PGDM1400-5X-PGT121-5X-N6-5X-35O22-5X-10E8v4 V5R S100cF-His

<400> SEQUENCE: 78

Met Gly Trp Ser Cys Ile Ile Leu Phe Leu Val Ala Thr Ala Thr Gly
1 5 10 15

Val His Ser Gln Ala Gln Leu Val Gln Ser Gly Pro Glu Val Arg Lys
20 25 30

Pro Gly Thr Ser Val Lys Val Ser Cys Lys Ala Pro Gly Asn Thr Leu
35 40 45

Lys Thr Tyr Asp Leu His Trp Val Arg Ser Val Pro Gly Gln Gly Leu
50 55 60

Gln Trp Met Gly Trp Ile Ser His Glu Gly Asp Lys Lys Val Ile Val
65 70 75 80

Glu Arg Phe Lys Ala Lys Val Thr Ile Asp Trp Asp Arg Ser Thr Asn
85 90 95

Thr Ala Tyr Leu Gln Leu Ser Gly Leu Thr Ser Gly Asp Thr Ala Val
100 105 110

Tyr Tyr Cys Ala Lys Gly Ser Lys His Arg Leu Arg Asp Tyr Ala Leu
115 120 125

Tyr Asp Asp Asp Gly Ala Leu Asn Trp Ala Val Asp Val Asp Tyr Leu
130 135 140

Ser Asn Leu Glu Phe Trp Gly Gln Gly Thr Ala Val Thr Val Ser Ser
145 150 155 160

Gly Gly Gly Gly Ser Gly Gly Gly Gly Ser Gly Gly Gly Gly Ser Asp

-continued

```
                165                 170                 175

Phe Val Leu Thr Gln Ser Pro His Ser Leu Ser Val Thr Pro Gly Glu
            180                 185                 190

Ser Ala Ser Ile Ser Cys Lys Ser Ser His Ser Leu Ile His Gly Asp
        195                 200                 205

Arg Asn Asn Tyr Leu Ala Trp Tyr Val Gln Lys Pro Gly Arg Ser Pro
    210                 215                 220

Gln Leu Leu Ile Tyr Leu Ala Ser Ser Arg Ala Ser Gly Val Pro Asp
225                 230                 235                 240

Arg Phe Ser Gly Ser Gly Ser Asp Lys Asp Phe Thr Leu Lys Ile Ser
                245                 250                 255

Arg Val Glu Thr Glu Asp Val Gly Thr Tyr Tyr Cys Met Gln Gly Arg
            260                 265                 270

Glu Ser Pro Trp Thr Phe Gly Gln Gly Thr Lys Val Asp Ile Lys Gly
        275                 280                 285

Gly Gly Gly Ser Gly Gly Gly Gly Ser Gly Gly Gly Gly Ser Gly Gly
    290                 295                 300

Gly Gly Ser Gly Gly Gly Gly Ser Gln Met Gln Leu Gln Glu Ser Gly
305                 310                 315                 320

Pro Gly Leu Val Lys Pro Ser Glu Thr Leu Ser Leu Thr Cys Ser Val
                325                 330                 335

Ser Gly Ala Ser Ile Ser Asp Ser Tyr Trp Ser Trp Ile Arg Arg Ser
            340                 345                 350

Pro Gly Lys Gly Leu Glu Trp Ile Gly Tyr Val His Lys Ser Gly Asp
        355                 360                 365

Thr Asn Tyr Ser Pro Ser Leu Lys Ser Arg Val Asn Leu Ser Leu Asp
    370                 375                 380

Thr Ser Lys Asn Gln Val Ser Leu Ser Leu Val Ala Ala Thr Ala Ala
385                 390                 395                 400

Asp Ser Gly Lys Tyr Tyr Cys Ala Arg Thr Leu His Gly Arg Arg Ile
                405                 410                 415

Tyr Gly Ile Val Ala Phe Asn Glu Trp Phe Thr Tyr Phe Tyr Met Asp
            420                 425                 430

Val Trp Gly Asn Gly Thr Gln Val Thr Val Ser Ser Gly Gly Gly Gly
        435                 440                 445

Ser Gly Gly Gly Gly Ser Gly Gly Gly Gly Ser Ser Asp Ile Ser Val
    450                 455                 460

Ala Pro Gly Glu Thr Ala Arg Ile Ser Cys Gly Glu Lys Ser Leu Gly
465                 470                 475                 480

Ser Arg Ala Val Gln Trp Tyr Gln His Arg Ala Gly Gln Ala Pro Ser
                485                 490                 495

Leu Ile Ile Tyr Asn Asn Gln Asp Arg Pro Ser Gly Ile Pro Glu Arg
            500                 505                 510

Phe Ser Gly Ser Pro Asp Ser Pro Phe Gly Thr Thr Ala Thr Leu Thr
        515                 520                 525

Ile Thr Ser Val Glu Ala Gly Asp Glu Ala Asp Tyr Tyr Cys His Ile
    530                 535                 540

Trp Asp Ser Arg Val Pro Thr Lys Trp Val Phe Gly Gly Gly Thr Thr
545                 550                 555                 560

Leu Thr Val Leu Gly Gly Gly Gly Ser Gly Gly Gly Gly Ser Gly Gly
                565                 570                 575

Gly Gly Ser Gly Gly Gly Gly Ser Gly Gly Gly Gly Ser Arg Ala His
            580                 585                 590
```

-continued

```
Leu Val Gln Ser Gly Thr Ala Met Lys Lys Pro Gly Ala Ser Val Arg
        595                 600                 605

Val Ser Cys Gln Thr Ser Gly Tyr Thr Phe Thr Ala His Ile Leu Phe
    610                 615                 620

Trp Phe Arg Gln Ala Pro Gly Arg Gly Leu Glu Trp Val Gly Trp Ile
625                 630                 635                 640

Lys Pro Gln Tyr Gly Ala Val Asn Phe Gly Gly Gly Phe Arg Asp Arg
                645                 650                 655

Val Thr Leu Thr Arg Asp Val Tyr Arg Glu Ile Ala Tyr Met Asp Ile
            660                 665                 670

Arg Gly Leu Lys Pro Asp Asp Thr Ala Val Tyr Tyr Cys Ala Arg Asp
        675                 680                 685

Arg Ser Tyr Gly Asp Ser Ser Trp Ala Leu Asp Ala Trp Gly Gln Gly
    690                 695                 700

Thr Thr Val Val Val Ser Ala Gly Gly Gly Gly Ser Gly Gly Gly Gly
705                 710                 715                 720

Ser Gly Gly Gly Gly Ser Tyr Ile His Val Thr Gln Ser Pro Ser Ser
                725                 730                 735

Leu Ser Val Ser Ile Gly Asp Arg Val Thr Ile Asn Cys Gln Thr Ser
            740                 745                 750

Gln Gly Val Gly Ser Asp Leu His Trp Tyr Gln His Lys Pro Gly Arg
        755                 760                 765

Ala Pro Lys Leu Leu Ile His His Thr Ser Ser Val Glu Asp Gly Val
    770                 775                 780

Pro Ser Arg Phe Ser Gly Ser Gly Phe His Thr Ser Phe Asn Leu Thr
785                 790                 795                 800

Ile Ser Asp Leu Gln Ala Asp Asp Ile Ala Thr Tyr Tyr Cys Gln Val
                805                 810                 815

Leu Gln Phe Phe Gly Arg Gly Ser Arg Leu His Ile Lys Gly Gly Gly
            820                 825                 830

Gly Ser Gly Gly Gly Gly Ser Gly Gly Gly Gly Ser Gly Gly Gly Gly
        835                 840                 845

Ser Gly Gly Gly Gly Ser Gln Gly Gln Leu Val Gln Ser Gly Ala Glu
    850                 855                 860

Leu Lys Lys Pro Gly Ala Ser Val Lys Ile Ser Cys Lys Thr Ser Gly
865                 870                 875                 880

Tyr Arg Phe Asn Phe Tyr His Ile Asn Trp Ile Arg Gln Thr Ala Gly
                885                 890                 895

Arg Gly Pro Glu Trp Met Gly Trp Ile Ser Pro Tyr Ser Gly Asp Lys
            900                 905                 910

Asn Leu Ala Pro Ala Phe Gln Asp Arg Val Ile Met Thr Thr Asp Thr
        915                 920                 925

Glu Val Pro Val Thr Ser Phe Thr Ser Thr Gly Ala Ala Tyr Met Glu
    930                 935                 940

Ile Arg Asn Leu Lys Phe Asp Asp Thr Gly Thr Tyr Phe Cys Ala Lys
945                 950                 955                 960

Gly Leu Leu Arg Asp Gly Ser Ser Thr Trp Leu Pro Tyr Leu Trp Gly
                965                 970                 975

Gln Gly Thr Leu Leu Thr Val Ser Ser Gly Gly Gly Gly Ser Gly Gly
            980                 985                 990

Gly Gly Ser Gly Gly Gly Gly Ser  Gln Ser Val Leu Thr  Gln Ser Ala
        995                 1000                1005
```

-continued

```
Ser Val  Ser Gly Ser Leu Gly  Gln Ser Val Thr Ile  Ser Cys Thr
    1010                 1015                 1020

Gly Pro  Asn Ser Val Cys Cys  Ser His Lys Ser Ile  Ser Trp Tyr
    1025                 1030                 1035

Gln Trp  Pro Pro Gly Arg Ala  Pro Thr Leu Ile Ile  Tyr Glu Asp
    1040                 1045                 1050

Asn Glu  Arg Ala Pro Gly Ile  Ser Pro Arg Phe Ser  Gly Tyr Lys
    1055                 1060                 1065

Ser Tyr  Trp Ser Ala Tyr Leu  Thr Ile Ser Asp Leu  Arg Pro Glu
    1070                 1075                 1080

Asp Glu  Thr Thr Tyr Tyr Cys  Cys Ser Tyr Thr His  Asn Ser Gly
    1085                 1090                 1095

Cys Val  Phe Gly Thr Gly Thr  Lys Val Ser Val Leu  Gly Gly Gly
    1100                 1105                 1110

Gly Ser  Gly Gly Gly Gly Ser  Gly Gly Gly Gly Ser  Gly Gly Gly
    1115                 1120                 1125

Gly Ser  Gly Gly Gly Gly Ser  Glu Val Arg Leu Arg  Glu Ser Gly
    1130                 1135                 1140

Gly Gly  Leu Val Lys Pro Gly  Gly Ser Leu Arg Leu  Ser Cys Ser
    1145                 1150                 1155

Ala Ser  Gly Phe Asp Phe Asp  Asn Ala Trp Met Thr  Trp Val Arg
    1160                 1165                 1170

Gln Pro  Pro Gly Lys Gly Leu  Glu Trp Val Gly Arg  Ile Thr Gly
    1175                 1180                 1185

Pro Gly  Glu Gly Trp Ser Val  Asp Tyr Ala Glu Ser  Val Lys Gly
    1190                 1195                 1200

Arg Phe  Thr Ile Ser Arg Asp  Asn Thr Lys Asn Thr  Leu Tyr Leu
    1205                 1210                 1215

Glu Met  Asn Asn Val Arg Thr  Glu Asp Thr Gly Tyr  Tyr Phe Cys
    1220                 1225                 1230

Ala Arg  Thr Gly Lys Tyr Tyr  Asp Phe Trp Phe Gly  Tyr Pro Pro
    1235                 1240                 1245

Gly Glu  Glu Tyr Phe Gln Asp  Trp Gly Gln Gly Thr  Leu Val Ile
    1250                 1255                 1260

Val Ser  Ser Gly Gly Gly Gly  Ser Gly Gly Gly Gly  Ser Gly Gly
    1265                 1270                 1275

Gly Gly  Ser Ser Glu Leu Thr  Gln Asp Pro Ala Val  Ser Val Ala
    1280                 1285                 1290

Leu Lys  Gln Thr Val Thr Ile  Thr Cys Arg Gly Asp  Ser Leu Arg
    1295                 1300                 1305

Ser His  Tyr Ala Ser Trp Tyr  Gln Lys Lys Pro Gly  Gln Ala Pro
    1310                 1315                 1320

Val Leu  Leu Phe Tyr Gly Lys  Asn Asn Arg Pro Ser  Gly Ile Pro
    1325                 1330                 1335

Asp Arg  Phe Ser Gly Ser Ala  Ser Gly Asn Arg Ala  Ser Leu Thr
    1340                 1345                 1350

Ile Thr  Gly Ala Gln Ala Glu  Asp Glu Ala Asp Tyr  Tyr Cys Ser
    1355                 1360                 1365

Ser Arg  Asp Lys Ser Gly Ser  Arg Leu Ser Val Phe  Gly Gly Gly
    1370                 1375                 1380

Thr Lys  Leu Thr Val Leu Gly  Ser Gly His His His  His His His
    1385                 1390                 1395
```

<210> SEQ ID NO 79
<211> LENGTH: 1605
<212> TYPE: PRT
<213> ORGANISM: Artificial Sequence
<220> FEATURE:
<223> OTHER INFORMATION: Synthetic: PentaNAb4.0 Reverse PGDM1400-5X-PGT121-5X-N6-5X-35O22-5X-10E8v4 V5R S100cF VH fused to IgG1 LS HC with His Tag

<400> SEQUENCE: 79

Met Gly Trp Ser Cys Ile Ile Leu Phe Leu Val Ala Thr Ala Thr Gly
1 5 10 15

Val His Ser Gln Ala Gln Leu Val Gln Ser Gly Pro Glu Val Arg Lys
20 25 30

Pro Gly Thr Ser Val Lys Val Ser Cys Lys Ala Pro Gly Asn Thr Leu
35 40 45

Lys Thr Tyr Asp Leu His Trp Val Arg Ser Val Pro Gly Gln Gly Leu
50 55 60

Gln Trp Met Gly Trp Ile Ser His Glu Gly Asp Lys Lys Val Ile Val
65 70 75 80

Glu Arg Phe Lys Ala Lys Val Thr Ile Asp Trp Asp Arg Ser Thr Asn
85 90 95

Thr Ala Tyr Leu Gln Leu Ser Gly Leu Thr Ser Gly Asp Thr Ala Val
100 105 110

Tyr Tyr Cys Ala Lys Gly Ser Lys His Arg Leu Arg Asp Tyr Ala Leu
115 120 125

Tyr Asp Asp Asp Gly Ala Leu Asn Trp Ala Val Asp Val Asp Tyr Leu
130 135 140

Ser Asn Leu Glu Phe Trp Gly Gln Gly Thr Ala Val Thr Val Ser Ser
145 150 155 160

Gly Gly Gly Gly Ser Gly Gly Gly Gly Ser Gly Gly Gly Gly Ser Asp
165 170 175

Phe Val Leu Thr Gln Ser Pro His Ser Leu Ser Val Thr Pro Gly Glu
180 185 190

Ser Ala Ser Ile Ser Cys Lys Ser Ser His Ser Leu Ile His Gly Asp
195 200 205

Arg Asn Asn Tyr Leu Ala Trp Tyr Val Gln Lys Pro Gly Arg Ser Pro
210 215 220

Gln Leu Leu Ile Tyr Leu Ala Ser Ser Arg Ala Ser Gly Val Pro Asp
225 230 235 240

Arg Phe Ser Gly Ser Gly Ser Asp Lys Asp Phe Thr Leu Lys Ile Ser
245 250 255

Arg Val Glu Thr Glu Asp Val Gly Thr Tyr Tyr Cys Met Gln Gly Arg
260 265 270

Glu Ser Pro Trp Thr Phe Gly Gln Gly Thr Lys Val Asp Ile Lys Gly
275 280 285

Gly Gly Gly Ser Gly Gly Gly Gly Ser Gly Gly Gly Gly Ser Gly Gly
290 295 300

Gly Gly Ser Gly Gly Gly Gly Ser Gln Met Gln Leu Gln Glu Ser Gly
305 310 315 320

Pro Gly Leu Val Lys Pro Ser Glu Thr Leu Ser Leu Thr Cys Ser Val
325 330 335

Ser Gly Ala Ser Ile Ser Asp Ser Tyr Trp Ser Trp Ile Arg Arg Ser
340 345 350

Pro Gly Lys Gly Leu Glu Trp Ile Gly Tyr Val His Lys Ser Gly Asp
355 360 365

-continued

```
Thr Asn Tyr Ser Pro Ser Leu Lys Ser Arg Val Asn Leu Ser Leu Asp
    370                 375                 380

Thr Ser Lys Asn Gln Val Ser Leu Ser Leu Val Ala Ala Thr Ala Ala
385                 390                 395                 400

Asp Ser Gly Lys Tyr Tyr Cys Ala Arg Thr Leu His Gly Arg Arg Ile
                405                 410                 415

Tyr Gly Ile Val Ala Phe Asn Glu Trp Phe Thr Tyr Phe Tyr Met Asp
            420                 425                 430

Val Trp Gly Asn Gly Thr Gln Val Thr Val Ser Ser Gly Gly Gly Gly
        435                 440                 445

Ser Gly Gly Gly Gly Ser Gly Gly Gly Gly Ser Ser Asp Ile Ser Val
    450                 455                 460

Ala Pro Gly Glu Thr Ala Arg Ile Ser Cys Gly Glu Lys Ser Leu Gly
465                 470                 475                 480

Ser Arg Ala Val Gln Trp Tyr Gln His Arg Ala Gly Gln Ala Pro Ser
                485                 490                 495

Leu Ile Ile Tyr Asn Asn Gln Asp Arg Pro Ser Gly Ile Pro Glu Arg
            500                 505                 510

Phe Ser Gly Ser Pro Asp Ser Pro Phe Gly Thr Thr Ala Thr Leu Thr
        515                 520                 525

Ile Thr Ser Val Glu Ala Gly Asp Glu Ala Asp Tyr Tyr Cys His Ile
    530                 535                 540

Trp Asp Ser Arg Val Pro Thr Lys Trp Val Phe Gly Gly Gly Thr Thr
545                 550                 555                 560

Leu Thr Val Leu Gly Gly Gly Gly Ser Gly Gly Gly Gly Ser Gly Gly
                565                 570                 575

Gly Gly Ser Gly Gly Gly Gly Ser Gly Gly Gly Gly Ser Arg Ala His
            580                 585                 590

Leu Val Gln Ser Gly Thr Ala Met Lys Lys Pro Gly Ala Ser Val Arg
        595                 600                 605

Val Ser Cys Gln Thr Ser Gly Tyr Thr Phe Thr Ala His Ile Leu Phe
    610                 615                 620

Trp Phe Arg Gln Ala Pro Gly Arg Gly Leu Glu Trp Val Gly Trp Ile
625                 630                 635                 640

Lys Pro Gln Tyr Gly Ala Val Asn Phe Gly Gly Gly Phe Arg Asp Arg
                645                 650                 655

Val Thr Leu Thr Arg Asp Val Tyr Arg Glu Ile Ala Tyr Met Asp Ile
            660                 665                 670

Arg Gly Leu Lys Pro Asp Asp Thr Ala Val Tyr Tyr Cys Ala Arg Asp
        675                 680                 685

Arg Ser Tyr Gly Asp Ser Ser Trp Ala Leu Asp Ala Trp Gly Gln Gly
    690                 695                 700

Thr Thr Val Val Val Ser Ala Gly Gly Gly Gly Ser Gly Gly Gly Gly
705                 710                 715                 720

Ser Gly Gly Gly Gly Ser Tyr Ile His Val Thr Gln Ser Pro Ser Ser
                725                 730                 735

Leu Ser Val Ser Ile Gly Asp Arg Val Thr Ile Asn Cys Gln Thr Ser
            740                 745                 750

Gln Gly Val Gly Ser Asp Leu His Trp Tyr Gln His Lys Pro Gly Arg
        755                 760                 765

Ala Pro Lys Leu Leu Ile His His Thr Ser Ser Val Glu Asp Gly Val
    770                 775                 780
```

```
Pro Ser Arg Phe Ser Gly Ser Gly Phe His Thr Ser Phe Asn Leu Thr
785                 790                 795                 800

Ile Ser Asp Leu Gln Ala Asp Asp Ile Ala Thr Tyr Tyr Cys Gln Val
                805                 810                 815

Leu Gln Phe Phe Gly Arg Gly Ser Arg Leu His Ile Lys Gly Gly Gly
            820                 825                 830

Gly Ser Gly Gly Gly Gly Ser Gly Gly Gly Gly Ser Gly Gly Gly Gly
        835                 840                 845

Ser Gly Gly Gly Gly Ser Gln Gly Gln Leu Val Gln Ser Gly Ala Glu
    850                 855                 860

Leu Lys Lys Pro Gly Ala Ser Val Lys Ile Ser Cys Lys Thr Ser Gly
865                 870                 875                 880

Tyr Arg Phe Asn Phe Tyr His Ile Asn Trp Ile Arg Gln Thr Ala Gly
                885                 890                 895

Arg Gly Pro Glu Trp Met Gly Trp Ile Ser Pro Tyr Ser Gly Asp Lys
            900                 905                 910

Asn Leu Ala Pro Ala Phe Gln Asp Arg Val Ile Met Thr Thr Asp Thr
        915                 920                 925

Glu Val Pro Val Thr Ser Phe Thr Ser Thr Gly Ala Ala Tyr Met Glu
    930                 935                 940

Ile Arg Asn Leu Lys Phe Asp Asp Thr Gly Thr Tyr Phe Cys Ala Lys
945                 950                 955                 960

Gly Leu Leu Arg Asp Gly Ser Ser Thr Trp Leu Pro Tyr Leu Trp Gly
                965                 970                 975

Gln Gly Thr Leu Leu Thr Val Ser Ser Gly Gly Gly Gly Ser Gly Gly
            980                 985                 990

Gly Gly Ser Gly Gly Gly Gly Ser  Gln Ser Val Leu Thr  Gln Ser Ala
        995                 1000                1005

Ser Val  Ser Gly Ser Leu Gly  Gln Ser Val Thr Ile  Ser Cys Thr
    1010                1015                1020

Gly Pro  Asn Ser Val Cys Cys  Ser His Lys Ser Ile  Ser Trp Tyr
    1025                1030                1035

Gln Trp  Pro Pro Gly Arg Ala  Pro Thr Leu Ile Ile  Tyr Glu Asp
    1040                1045                1050

Asn Glu  Arg Ala Pro Gly Ile  Ser Pro Arg Phe Ser  Gly Tyr Lys
    1055                1060                1065

Ser Tyr  Trp Ser Ala Tyr Leu  Thr Ile Ser Asp Leu  Arg Pro Glu
    1070                1075                1080

Asp Glu  Thr Thr Tyr Tyr Cys  Cys Ser Tyr Thr His  Asn Ser Gly
    1085                1090                1095

Cys Val  Phe Gly Thr Gly Thr  Lys Val Ser Val Leu  Gly Gly Gly
    1100                1105                1110

Gly Ser  Gly Gly Gly Gly Ser  Gly Gly Gly Gly Ser  Gly Gly Gly
    1115                1120                1125

Gly Ser  Gly Gly Gly Gly Ser  Glu Val Arg Leu Arg  Glu Ser Gly
    1130                1135                1140

Gly Gly  Leu Val Lys Pro Gly  Gly Ser Leu Arg Leu  Ser Cys Ser
    1145                1150                1155

Ala Ser  Gly Phe Asp Phe Asp  Asn Ala Trp Met Thr  Trp Val Arg
    1160                1165                1170

Gln Pro  Pro Gly Lys Gly Leu  Glu Trp Val Gly Arg  Ile Thr Gly
    1175                1180                1185

Pro Gly  Glu Gly Trp Ser Val  Asp Tyr Ala Glu Ser  Val Lys Gly
```

```
    1190                1195                1200

Arg Phe  Thr Ile Ser Arg Asp  Asn Thr Lys Asn Thr  Leu Tyr Leu
    1205                1210                1215

Glu Met  Asn Asn Val Arg Thr  Glu Asp Thr Gly Tyr  Tyr Phe Cys
    1220                1225                1230

Ala Arg  Thr Gly Lys Tyr Tyr  Asp Phe Trp Phe Gly  Tyr Pro Pro
    1235                1240                1245

Gly Glu  Glu Tyr Phe Gln Asp  Trp Gly Gln Gly Thr  Leu Val Ile
    1250                1255                1260

Val Ser  Ser Ala Ser Thr Lys  Gly Pro Ser Val Phe  Pro Leu Ala
    1265                1270                1275

Pro Ser  Ser Lys Ser Thr Ser  Gly Gly Thr Ala Ala  Leu Gly Cys
    1280                1285                1290

Leu Val  Lys Asp Tyr Phe Pro  Glu Pro Val Thr Val  Ser Trp Asn
    1295                1300                1305

Ser Gly  Ala Leu Thr Ser Gly  Val His Thr Phe Pro  Ala Val Leu
    1310                1315                1320

Gln Ser  Ser Gly Leu Tyr Ser  Leu Ser Ser Val Val  Thr Val Pro
    1325                1330                1335

Ser Ser  Ser Leu Gly Thr Gln  Thr Tyr Ile Cys Asn  Val Asn His
    1340                1345                1350

Lys Pro  Ser Asn Thr Lys Val  Asp Lys Lys Val Glu  Pro Lys Ser
    1355                1360                1365

Cys Asp  Lys Thr His Thr Cys  Pro Pro Cys Pro Ala  Pro Glu Leu
    1370                1375                1380

Leu Gly  Gly Pro Ser Val Phe  Leu Phe Pro Pro Lys  Pro Lys Asp
    1385                1390                1395

Thr Leu  Met Ile Ser Arg Thr  Pro Glu Val Thr Cys  Val Val Val
    1400                1405                1410

Asp Val  Ser His Glu Asp Pro  Glu Val Lys Phe Asn  Trp Tyr Val
    1415                1420                1425

Asp Gly  Val Glu Val His Asn  Ala Lys Thr Lys Pro  Arg Glu Glu
    1430                1435                1440

Gln Tyr  Asn Ser Thr Tyr Arg  Val Val Ser Val Leu  Thr Val Leu
    1445                1450                1455

His Gln  Asp Trp Leu Asn Gly  Lys Glu Tyr Lys Cys  Lys Val Ser
    1460                1465                1470

Asn Lys  Ala Leu Pro Ala Pro  Ile Glu Lys Thr Ile  Ser Lys Ala
    1475                1480                1485

Lys Gly  Gln Pro Arg Glu Pro  Gln Val Tyr Thr Leu  Pro Pro Ser
    1490                1495                1500

Arg Glu  Glu Met Thr Lys Asn  Gln Val Ser Leu Thr  Cys Leu Val
    1505                1510                1515

Lys Gly  Phe Tyr Pro Ser Asp  Ile Ala Val Glu Trp  Glu Ser Asn
    1520                1525                1530

Gly Gln  Pro Glu Asn Asn Tyr  Lys Thr Thr Pro Pro  Val Leu Asp
    1535                1540                1545

Ser Asp  Gly Ser Phe Phe Leu  Tyr Ser Lys Leu Thr  Val Asp Lys
    1550                1555                1560

Ser Arg  Trp Gln Gln Gly Asn  Val Phe Ser Cys Ser  Val Leu His
    1565                1570                1575

Glu Ala  Leu His Ser His Tyr  Thr Gln Lys Ser Leu  Ser Leu Ser
    1580                1585                1590
```

-continued

Pro Gly Lys Gly Ser Gly His His His His His His
1595 1600 1605

<210> SEQ ID NO 80
<211> LENGTH: 1632
<212> TYPE: PRT
<213> ORGANISM: Artificial Sequence
<220> FEATURE:
<223> OTHER INFORMATION: Synthetic: PentaNAb4.0 Reverse PGDM1400-5X-PGT121-5X-N6-5X-35O22-5X-10E8v4 V5R S100cF VH-VL-fused to IgG1 LS FC with His Tag

<400> SEQUENCE: 80

Met Gly Trp Ser Cys Ile Ile Leu Phe Leu Val Ala Thr Ala Thr Gly
1 5 10 15

Val His Ser Gln Ala Gln Leu Val Gln Ser Gly Pro Glu Val Arg Lys
20 25 30

Pro Gly Thr Ser Val Lys Val Ser Cys Lys Ala Pro Gly Asn Thr Leu
35 40 45

Lys Thr Tyr Asp Leu His Trp Val Arg Ser Val Pro Gly Gln Gly Leu
50 55 60

Gln Trp Met Gly Trp Ile Ser His Glu Gly Asp Lys Lys Val Ile Val
65 70 75 80

Glu Arg Phe Lys Ala Lys Val Thr Ile Asp Trp Asp Arg Ser Thr Asn
85 90 95

Thr Ala Tyr Leu Gln Leu Ser Gly Leu Thr Ser Gly Asp Thr Ala Val
100 105 110

Tyr Tyr Cys Ala Lys Gly Ser Lys His Arg Leu Arg Asp Tyr Ala Leu
115 120 125

Tyr Asp Asp Asp Gly Ala Leu Asn Trp Ala Val Asp Val Asp Tyr Leu
130 135 140

Ser Asn Leu Glu Phe Trp Gly Gln Gly Thr Ala Val Thr Val Ser Ser
145 150 155 160

Gly Gly Gly Gly Ser Gly Gly Gly Gly Ser Gly Gly Gly Gly Ser Asp
165 170 175

Phe Val Leu Thr Gln Ser Pro His Ser Leu Ser Val Thr Pro Gly Glu
180 185 190

Ser Ala Ser Ile Ser Cys Lys Ser Ser His Ser Leu Ile His Gly Asp
195 200 205

Arg Asn Asn Tyr Leu Ala Trp Tyr Val Gln Lys Pro Gly Arg Ser Pro
210 215 220

Gln Leu Leu Ile Tyr Leu Ala Ser Ser Arg Ala Ser Gly Val Pro Asp
225 230 235 240

Arg Phe Ser Gly Ser Gly Ser Asp Lys Asp Phe Thr Leu Lys Ile Ser
245 250 255

Arg Val Glu Thr Glu Asp Val Gly Thr Tyr Tyr Cys Met Gln Gly Arg
260 265 270

Glu Ser Pro Trp Thr Phe Gly Gln Gly Thr Lys Val Asp Ile Lys Gly
275 280 285

Gly Gly Gly Ser Gly Gly Gly Gly Ser Gly Gly Gly Gly Ser Gly Gly
290 295 300

Gly Gly Ser Gly Gly Gly Gly Ser Gln Met Gln Leu Gln Glu Ser Gly
305 310 315 320

Pro Gly Leu Val Lys Pro Ser Glu Thr Leu Ser Leu Thr Cys Ser Val
325 330 335

```
Ser Gly Ala Ser Ile Ser Asp Ser Tyr Trp Ser Trp Ile Arg Arg Ser
            340                 345                 350

Pro Gly Lys Gly Leu Glu Trp Ile Gly Tyr Val His Lys Ser Gly Asp
        355                 360                 365

Thr Asn Tyr Ser Pro Ser Leu Lys Ser Arg Val Asn Leu Ser Leu Asp
    370                 375                 380

Thr Ser Lys Asn Gln Val Ser Leu Ser Leu Val Ala Ala Thr Ala Ala
385                 390                 395                 400

Asp Ser Gly Lys Tyr Tyr Cys Ala Arg Thr Leu His Gly Arg Arg Ile
                405                 410                 415

Tyr Gly Ile Val Ala Phe Asn Glu Trp Phe Thr Tyr Phe Tyr Met Asp
            420                 425                 430

Val Trp Gly Asn Gly Thr Gln Val Thr Val Ser Ser Gly Gly Gly Gly
        435                 440                 445

Ser Gly Gly Gly Gly Ser Gly Gly Gly Gly Ser Ser Asp Ile Ser Val
    450                 455                 460

Ala Pro Gly Glu Thr Ala Arg Ile Ser Cys Gly Glu Lys Ser Leu Gly
465                 470                 475                 480

Ser Arg Ala Val Gln Trp Tyr Gln His Arg Ala Gly Gln Ala Pro Ser
                485                 490                 495

Leu Ile Ile Tyr Asn Asn Gln Asp Arg Pro Ser Gly Ile Pro Glu Arg
            500                 505                 510

Phe Ser Gly Ser Pro Asp Ser Pro Phe Gly Thr Thr Ala Thr Leu Thr
        515                 520                 525

Ile Thr Ser Val Glu Ala Gly Asp Glu Ala Asp Tyr Tyr Cys His Ile
    530                 535                 540

Trp Asp Ser Arg Val Pro Thr Lys Trp Val Phe Gly Gly Gly Thr Thr
545                 550                 555                 560

Leu Thr Val Leu Gly Gly Gly Gly Ser Gly Gly Gly Gly Ser Gly Gly
                565                 570                 575

Gly Gly Ser Gly Gly Gly Gly Ser Gly Gly Gly Gly Ser Arg Ala His
            580                 585                 590

Leu Val Gln Ser Gly Thr Ala Met Lys Lys Pro Gly Ala Ser Val Arg
        595                 600                 605

Val Ser Cys Gln Thr Ser Gly Tyr Thr Phe Thr Ala His Ile Leu Phe
    610                 615                 620

Trp Phe Arg Gln Ala Pro Gly Arg Gly Leu Glu Trp Val Gly Trp Ile
625                 630                 635                 640

Lys Pro Gln Tyr Gly Ala Val Asn Phe Gly Gly Gly Phe Arg Asp Arg
                645                 650                 655

Val Thr Leu Thr Arg Asp Val Tyr Arg Glu Ile Ala Tyr Met Asp Ile
            660                 665                 670

Arg Gly Leu Lys Pro Asp Asp Thr Ala Val Tyr Tyr Cys Ala Arg Asp
        675                 680                 685

Arg Ser Tyr Gly Asp Ser Ser Trp Ala Leu Asp Ala Trp Gly Gln Gly
    690                 695                 700

Thr Thr Val Val Val Ser Ala Gly Gly Gly Gly Ser Gly Gly Gly Gly
705                 710                 715                 720

Ser Gly Gly Gly Gly Ser Tyr Ile His Val Thr Gln Ser Pro Ser Ser
                725                 730                 735

Leu Ser Val Ser Ile Gly Asp Arg Val Thr Ile Asn Cys Gln Thr Ser
            740                 745                 750

Gln Gly Val Gly Ser Asp Leu His Trp Tyr Gln His Lys Pro Gly Arg
```

```
        755                 760                 765

Ala Pro Lys Leu Leu Ile His His Thr Ser Ser Val Glu Asp Gly Val
    770                 775                 780

Pro Ser Arg Phe Ser Gly Ser Gly Phe His Thr Ser Phe Asn Leu Thr
785                 790                 795                 800

Ile Ser Asp Leu Gln Ala Asp Asp Ile Ala Thr Tyr Tyr Cys Gln Val
                805                 810                 815

Leu Gln Phe Phe Gly Arg Gly Ser Arg Leu His Ile Lys Gly Gly Gly
            820                 825                 830

Gly Ser Gly Gly Gly Gly Ser Gly Gly Gly Gly Ser Gly Gly Gly Gly
        835                 840                 845

Ser Gly Gly Gly Gly Ser Gln Gly Gln Leu Val Gln Ser Gly Ala Glu
    850                 855                 860

Leu Lys Lys Pro Gly Ala Ser Val Lys Ile Ser Cys Lys Thr Ser Gly
865                 870                 875                 880

Tyr Arg Phe Asn Phe Tyr His Ile Asn Trp Ile Arg Gln Thr Ala Gly
                885                 890                 895

Arg Gly Pro Glu Trp Met Gly Trp Ile Ser Pro Tyr Ser Gly Asp Lys
            900                 905                 910

Asn Leu Ala Pro Ala Phe Gln Asp Arg Val Ile Met Thr Thr Asp Thr
        915                 920                 925

Glu Val Pro Val Thr Ser Phe Thr Ser Thr Gly Ala Ala Tyr Met Glu
    930                 935                 940

Ile Arg Asn Leu Lys Phe Asp Asp Thr Gly Thr Tyr Phe Cys Ala Lys
945                 950                 955                 960

Gly Leu Leu Arg Asp Gly Ser Ser Thr Trp Leu Pro Tyr Leu Trp Gly
                965                 970                 975

Gln Gly Thr Leu Leu Thr Val Ser Ser Gly Gly Gly Gly Ser Gly Gly
            980                 985                 990

Gly Gly Ser Gly Gly Gly Gly Ser  Gln Ser Val Leu Thr  Gln Ser Ala
        995                 1000                 1005

Ser Val  Ser Gly Ser Leu Gly  Gln Ser Val Thr Ile  Ser Cys Thr
    1010                 1015                 1020

Gly Pro  Asn Ser Val Cys Cys  Ser His Lys Ser Ile  Ser Trp Tyr
    1025                 1030                 1035

Gln Trp  Pro Pro Gly Arg Ala  Pro Thr Leu Ile Ile  Tyr Glu Asp
    1040                 1045                 1050

Asn Glu  Arg Ala Pro Gly Ile  Ser Pro Arg Phe Ser  Gly Tyr Lys
    1055                 1060                 1065

Ser Tyr  Trp Ser Ala Tyr Leu  Thr Ile Ser Asp Leu  Arg Pro Glu
    1070                 1075                 1080

Asp Glu  Thr Thr Tyr Tyr Cys  Cys Ser Tyr Thr His  Asn Ser Gly
    1085                 1090                 1095

Cys Val  Phe Gly Thr Gly Thr  Lys Val Ser Val Leu  Gly Gly Gly
    1100                 1105                 1110

Gly Ser  Gly Gly Gly Gly Ser  Gly Gly Gly Gly Ser  Gly Gly Gly
    1115                 1120                 1125

Gly Ser  Gly Gly Gly Gly Ser  Glu Val Arg Leu Arg  Glu Ser Gly
    1130                 1135                 1140

Gly Gly  Leu Val Lys Pro Gly  Gly Ser Leu Arg Leu  Ser Cys Ser
    1145                 1150                 1155

Ala Ser  Gly Phe Asp Phe Asp  Asn Ala Trp Met Thr  Trp Val Arg
    1160                 1165                 1170
```

Gln Pro Pro Gly Lys Gly Leu Glu Trp Val Gly Arg Ile Thr Gly
1175 1180 1185

Pro Gly Glu Gly Trp Ser Val Asp Tyr Ala Glu Ser Val Lys Gly
1190 1195 1200

Arg Phe Thr Ile Ser Arg Asp Asn Thr Lys Asn Thr Leu Tyr Leu
1205 1210 1215

Glu Met Asn Asn Val Arg Thr Glu Asp Thr Gly Tyr Tyr Phe Cys
1220 1225 1230

Ala Arg Thr Gly Lys Tyr Tyr Asp Phe Trp Phe Gly Tyr Pro Pro
1235 1240 1245

Gly Glu Glu Tyr Phe Gln Asp Trp Gly Gln Gly Thr Leu Val Ile
1250 1255 1260

Val Ser Ser Gly Gly Gly Gly Ser Gly Gly Gly Gly Ser Gly Gly
1265 1270 1275

Gly Gly Ser Ser Glu Leu Thr Gln Asp Pro Ala Val Ser Val Ala
1280 1285 1290

Leu Lys Gln Thr Val Thr Ile Thr Cys Arg Gly Asp Ser Leu Arg
1295 1300 1305

Ser His Tyr Ala Ser Trp Tyr Gln Lys Lys Pro Gly Gln Ala Pro
1310 1315 1320

Val Leu Leu Phe Tyr Gly Lys Asn Asn Arg Pro Ser Gly Ile Pro
1325 1330 1335

Asp Arg Phe Ser Gly Ser Ala Ser Gly Asn Arg Ala Ser Leu Thr
1340 1345 1350

Ile Thr Gly Ala Gln Ala Glu Asp Glu Ala Asp Tyr Tyr Cys Ser
1355 1360 1365

Ser Arg Asp Lys Ser Gly Ser Arg Leu Ser Val Phe Gly Gly Gly
1370 1375 1380

Thr Lys Leu Thr Val Leu Gly Ser Gly Pro Lys Ser Cys Asp Lys
1385 1390 1395

Thr His Thr Cys Pro Pro Cys Pro Ala Pro Glu Leu Leu Gly Gly
1400 1405 1410

Pro Ser Val Phe Leu Phe Pro Pro Lys Pro Lys Asp Thr Leu Met
1415 1420 1425

Ile Ser Arg Thr Pro Glu Val Thr Cys Val Val Val Asp Val Ser
1430 1435 1440

His Glu Asp Pro Glu Val Lys Phe Asn Trp Tyr Val Asp Gly Val
1445 1450 1455

Glu Val His Asn Ala Lys Thr Lys Pro Arg Glu Glu Gln Tyr Asn
1460 1465 1470

Ser Thr Tyr Arg Val Val Ser Val Leu Thr Val Leu His Gln Asp
1475 1480 1485

Trp Leu Asn Gly Lys Glu Tyr Lys Cys Lys Val Ser Asn Lys Ala
1490 1495 1500

Leu Pro Ala Pro Ile Glu Lys Thr Ile Ser Lys Ala Lys Gly Gln
1505 1510 1515

Pro Arg Glu Pro Gln Val Tyr Thr Leu Pro Pro Ser Arg Glu Glu
1520 1525 1530

Met Thr Lys Asn Gln Val Ser Leu Thr Cys Leu Val Lys Gly Phe
1535 1540 1545

Tyr Pro Ser Asp Ile Ala Val Glu Trp Glu Ser Asn Gly Gln Pro
1550 1555 1560

-continued

```
Glu Asn  Asn Tyr Lys Thr Thr  Pro Pro Val Leu Asp  Ser Asp Gly
    1565                 1570                 1575

Ser Phe  Phe Leu Tyr Ser Lys  Leu Thr Val Asp Lys  Ser Arg Trp
    1580                 1585                 1590

Gln Gln  Gly Asn Val Phe Ser  Cys Ser Val Leu His  Glu Ala Leu
    1595                 1600                 1605

His Ser  His Tyr Thr Gln Lys  Ser Leu Ser Leu Ser  Pro Gly Lys
    1610                 1615                 1620

Gly Ser  Gly His His His His  His His
    1625                 1630
```

<210> SEQ ID NO 81
<211> LENGTH: 4233
<212> TYPE: DNA
<213> ORGANISM: Artificial Sequence
<220> FEATURE:
<223> OTHER INFORMATION: Synthetic: PentaNAb1.0
10E8v4-5X-35O22-5X-N6-5X-PGT121-5X-VRC26.25-His

<400> SEQUENCE: 81

```
gaattcgccg ccaccatggg atggagctgt attattctgt ttctggtcgc taccgctacc     60

ggagtgcatt cttctgaact gacccaggac cccgccgtga gcgtggccct gaagcagacc    120

gtgacaatca cctgcagggg cgacagcctg cgctcccact acgccagctg gtatcagaag    180

aagcctggcc aggccccagt gctgctgttc tacggcaaga acaataggcc ctccggcatc    240

cctgatcgct tttccggctc tgccagcgga aacagggcca gcctgacaat caccggagca    300

caggcagagg acgaggcaga ttactattgc agctcccggg acaagtccgg ctctagactg    360

agcgtgttcg gcggcggcac caagctgaca gtgctgggag gaggaggcag cggcggagga    420

ggctccggag gcggcggctc tgaggtgcgg ctggtggagt ctggaggagg cctggtgaag    480

ccaggaggca gcctgagact gagctgttcc gcctctggct tcgactttga taatgcctgg    540

atgacatggg tgcggcagcc acctggcaag ggcctggagt gggtgggaag aatcaccgga    600

ccaggagagg gatggtctgt ggactacgcc gagagcgtga agggccggtt caccatctcc    660

agagataaca ccaagaatac actgtatctg gagatgaaca atgtgcggac cgaggacaca    720

ggctactatt tctgcgccag aaccggcaag tactatgatt tttggagcgg ctacccaccc    780

ggcgaggagt attttcagga ctggggccag ggcaccctgg tcatcgtgag cagcggcggc    840

ggcggcagcg gcggcggcgg ctccggagga ggcggctctg gaggaggagg cagcggggga    900

gggggcagcc agtccgtgct gacccagtct gccagcgtgt ccggctctct gggacagagc    960

gtgaccatct cctgtacagg ccccaacagc gtgtgctgta gccacaagag catctcctgg   1020

taccagtggc ctccaggaag ggcacctacc ctgatcatct atgaggacaa tgagcgggcc   1080

ccaggcatct cccccagatt ctctggctac aagtcttatt ggagcgccta cctgacaatc   1140

agcgacctgc gccccgagga tgagacaaca tactattgct gttcctatac ccacaactct   1200

ggctgcgtgt ttggcacagg caccaaggtg tccgtgctgg gcggcggcgg cagcgggggc   1260

gggggctccg gagggggcgg ctctcagggc cagctggtgc agagcggagc agagctgaag   1320

aagcctggag ccagcgtgaa gatctcctgt aagacatctg gctaccggtt caacttttat   1380

cacatcaatt ggatcaggca gaccgcagga aggggaccag agtggatggg ctggatctcc   1440

ccctactctg gcgataagaa cctggcccca gccttccagg acagagtgat catgaccaca   1500

gataccgagg tgccagtgac cagcttcacc tccaccggag ccgcctacat ggagatcagg   1560

aatctgaagt tcgacgatac aggcacctat ttttgcgcaa agggcctgct gagggacggc   1620
```

-continued

```
tcctctacct ggctgcctta cctgtgggga cagggcaccc tgctgacagt gagctccggc   1680
ggcgggggca gcggcggcgg gggctccgga ggaggaggct ctggaggagg gggcagcgga   1740
ggaggcggct cctacatcca cgtgacccag tccccatcta gcctgtctgt gagcatcggc   1800
gatcgggtga ccatcaactg tcagacatct cagggcgtgg gcagcgacct gcactggtat   1860
cagcacaagc ctggcagggc cccaaagctg ctgatccacc acacatcctc tgtggaggat   1920
ggagtgccaa gccgcttctc cggctctgga ttccacacct cctttaatct gacaatctct   1980
gacctgcagg ccgacgatat cgccacctac tattgccagg tgctgcagtt ctttggccgg   2040
ggctccagac tgcacatcaa gggaggagga ggctccgggg gcggaggctc tggcggcggc   2100
ggcagccggg cccacctggt gcagagcggc accgccatga agaagcctgg cgccagcgtg   2160
agagtgtcct gtcagacatc tggctacacc ttcaccgccc acatcctgtt ctggtttagg   2220
caggcaccag gaagaggcct ggagtgggtg ggctggatca agccccagta tggagcagtg   2280
aacttcggag gaggctttcg ggacagagtg acactgaccc gggacgtgta cagagagatc   2340
gcctatatgg atatcagggg cctgaagcca gacgataccg ccgtgtacta ttgcgccagg   2400
gaccgctcct acggcgatag ctcctgggca ctggacgcat ggggacaggg caccacagtg   2460
gtggtgagcg ccggcggcgg aggctccggc ggcgggggct ctggaggagg cggcagcgga   2520
gggggaggct ccggaggggg aggctctagc gacatctccg tggcccctgg cgagacagcc   2580
agaatctctt gtggcgagaa gtctctgggc agcagggccg tgcagtggta ccagcacagg   2640
gcaggacagg caccatctct gatcatctat aacaatcagg ataggccaag cggcatccct   2700
gagcggttca gcggctcccc cgacagccct tttggcacca cagccacact gaccatcaca   2760
tccgtggagg caggcgacga agccgattac tattgccaca tctgggattc cagagtgcca   2820
accaagtggg tgttcggagg aggaaccaca ctgacagtgc tgggaggggg gggctctggc   2880
ggcgggggca gcgggggagg aggctcccag atgcagctgc aggagagcgg accaggcctg   2940
gtgaagccta gcgagacact gagcctgaca tgttctgtga gcggcgcctc catctctgac   3000
agctactggt cttggatcag acggagcccc ggcaagggcc tggaatggat cggctacgtg   3060
cacaagtccg gcgatacaaa ctattcccca tctctgaagt ctcgggtgaa cctgtctctg   3120
gacaccagca agaatcaggt gagcctgtcc ctggtggcag caaccgcagc agatagcggc   3180
aagtactatt gcgccagaac actgcacggc aggcgcatct acggcatcgt ggcctttaac   3240
gagtggttca cctactttta tatggacgtg tggggcaatg gcacccaggt gacagtgtcc   3300
tctggcgggg gcggctccgg aggcggaggc tctggcgggg gcggcagcgg cgggggcggc   3360
tccgggggag gcggctctca gagcgtgctg acccagccac cttccgtgtc tgccgcacca   3420
ggacagaagg tgaccatcag ctgttccggc aacacatcca atatcggcaa caatttcgtg   3480
tcttggtacc agcagaggcc aggaagggca ccacagctgc tgatctatga gacagacaag   3540
cggccttccg gcatcccaga tagattttct gccagcaagt ccggcaccag cggcacactg   3600
gcaatcaccg gcctgcagac aggcgacgaa gctgattact attgcgcaac ctgggcagcc   3660
tccctgagct ccgccagggt gttcggaacc ggaacaaaag tgatcgtgct ggtgggcggc   3720
ggaggctctg gcggaggcgg cagcggcggg gggggctccc aggtgcagct ggtggagagc   3780
ggcggcggcg tggtgcagcc aggcacctcc ctgaggctgt cttgtgcagc aagccagttc   3840
agatttgatg gctacggcat gcactgggtg cgccaggcac caggcaaggg cctggagtgg   3900
gtagcctcta tcagccacga cggcatcaag aagtaccacg ccgagaaagt gtggggcagg   3960
```

-continued

```
ttcaccatct cccgcgataa ctctaaaaac acactgtatc tgcagatgaa ctccctgagg   4020

cccgaggaca ccgccctgta ctattgcgcc aaggacctgc gcgaggatga gtgtgaggag   4080

tggtggtccg actactatga ttttggcaag cagctgcctt gcgcaaagag caggggaggc   4140

ctggtgggaa tcgccgataa ttggggccag ggcaccatgg tgacagtgtc tagcggatcc   4200

ggacaccacc atcaccatca ttagtgaaag ctt                                4233
```

<210> SEQ ID NO 82
<211> LENGTH: 5052
<212> TYPE: DNA
<213> ORGANISM: Artificial Sequence
<220> FEATURE:
<223> OTHER INFORMATION: Synthetic: PentaNAb2.0
10E8v4_S100cF-5X-35O22-5X-N6-5X-PGT121-5X-VRC26.25-His

<400> SEQUENCE: 82

```
gaattcgccg ccaccatggg atggagctgt attattctgt ttctggtcgc taccgctacc     60

ggagtgcatt cttctgaact gacccaggac cccgccgtga gcgtggccct gaagcagacc    120

gtgacaatca cctgcagggg cgacagcctg cgctcccact acgccagctg gtatcagaag    180

aagcctggcc aggccccagt gctgctgttc tacggcaaga acaataggcc ctccggcatc    240

cctgatcgct tttccggctc tgccagcgga aacagggcca gcctgacaat caccggagca    300

caggcagagg acgaggcaga ttactattgc agctcccggg acaagtccgg ctctagactg    360

agcgtgttcg gcggcggcac caagctgaca gtgctgggag gaggaggcag cggcggagga    420

ggctccggag gcggcggctc tgaggtgcgg ctggtggagt ctggaggagg cctggtgaag    480

ccaggaggca gcctgagact gagctgttcc gcctctggct tcgactttga taatgcctgg    540

atgacatggg tgcggcagcc acctggcaag ggcctggagt gggtgggaag aatcaccgga    600

ccaggagagg gatggtctgt ggactacgcc gagagcgtga agggccggtt caccatctcc    660

agagataaca ccaagaatac actgtatctg gagatgaaca atgtgcggac cgaggacaca    720

ggctactatt tctgcgccag aaccggcaag tactatgatt tttggtttgg ctacccaccc    780

ggcgaggagt attttcagga ctggggccag ggcaccctgg tcatcgtgag cagcggcggc    840

ggcggcagcg gcggcggcgg ctccggagga ggcggctctg gaggaggagg cagcggggga    900

gggggcagcc agtccgtgct gacccagtct gccagcgtgt ccggctctct gggacagagc    960

gtgaccatct cctgtacagg ccccaacagc gtgtgctgta gccacaagag catctcctgg   1020

taccagtggc ctccaggaag ggcacctacc ctgatcatct atgaggacaa tgagcgggcc   1080

ccaggcatct cccccagatt ctctggctac aagtcttatt ggagcgccta cctgacaatc   1140

agcgacctgc gccccgagga tgagacaaca tactattgct gttcctatac ccacaactct   1200

ggctgcgtgt ttggcacagg caccaaggtg tccgtgctgg gcggcggcgg cagcgggggc   1260

gggggctccg gagggggcgg ctctcagggc cagctggtgc agagcggagc agagctgaag   1320

aagcctggag ccagcgtgaa gatctcctgt aagacatctg gctaccggtt caacttttat   1380

cacatcaatt ggatcaggca gaccgcagga aggggaccag agtggatggg ctggatctcc   1440

ccctactctg gcgataagaa cctggcccca gccttccagg acagagtgat catgaccaca   1500

gataccgagg tgccagtgac cagcttcacc tccaccggag ccgcctacat ggagatcagg   1560

aatctgaagt tcgacgatac aggcacctat ttttgcgcaa agggcctgct gagggacggc   1620

tcctctacct ggctgcctta cctgtgggga cagggcaccc tgctgacagt gagctccggc   1680

ggcgggggca gcggcggcgg gggctccgga ggaggaggct ctggaggagg gggcagcgga   1740
```

-continued

```
ggaggcggct cctacatcca cgtgacccag tccccatcta gcctgtctgt gagcatcggc   1800
gatcgggtga ccatcaactg tcagacatct cagggcgtgg gcagcgacct gcactggtat   1860
cagcacaagc ctggcagggc cccaaagctg ctgatccacc acacatcctc tgtggaggat   1920
ggagtgccaa gccgcttctc cggctctgga ttccacacct cctttaatct gacaatctct   1980
gacctgcagg ccgacgatat cgccacctac tattgccagg tgctgcagtt ctttggccgg   2040
ggctccagac tgcacatcaa gggaggagga ggctccgggg gcggaggctc tggcggcggc   2100
ggcagccggg cccacctggt gcagagcggc accgccatga agaagcctgg cgccagcgtg   2160
agagtgtcct gtcagacatc tggctacacc ttcaccgccc acatcctgtt ctggtttagg   2220
caggcaccag gaagaggcct ggagtgggtg ggctggatca agccccagta tggagcagtg   2280
aacttcggag gaggctttcg ggacagagtg acactgaccc gggacgtgta cagagagatc   2340
gcctatatgg atatcagggg cctgaagcca gacgataccg ccgtgtacta ttgcgccagg   2400
gaccgctcct acggcgatag ctcctgggca ctggacgcat ggggacaggg caccacagtg   2460
gtggtgagcg ccggcggcgg aggctccggc ggcgggggct ctggaggagg cggcagcgga   2520
gggggaggct ccggaggggg aggctctagc gacatctccg tggcccctgg cgagacagcc   2580
agaatctctt gtggcgagaa gtctctgggc agcagggccg tgcagtggta ccagcacagg   2640
gcaggacagg caccatctct gatcatctat aacaatcagg ataggccaag cggcatccct   2700
gagcggttca gcggctcccc cgacagccct tttggcacca cagccacact gaccatcaca   2760
tccgtggagg caggcgacga agccgattac tattgccaca tctgggattc cagagtgcca   2820
accaagtggg tgttcggagg aggaaccaca ctgacagtgc tgggaggggg gggctctggc   2880
ggcgggggca gcgggggagg aggctcccag atgcagctgc aggagagcgg accaggcctg   2940
gtgaagccta gcgagacact gagcctgaca tgttctgtga gcggcgcctc catctctgac   3000
agctactggt cttggatcag acggagcccc ggcaagggcc tggaatggat cggctacgtg   3060
cacaagtccg gcgatacaaa ctattcccca tctctgaagt ctcgggtgaa cctgtctctg   3120
gacaccagca agaatcaggt gagcctgtcc ctggtggcag caaccgcagc agatagcggc   3180
aagtactatt gcgccagaac actgcacggc aggcgcatct acggcatcgt ggcctttaac   3240
gagtggttca cctactttta tatggacgtg tggggcaatg gcacccaggt gacagtgtcc   3300
tctggcgggg gcggctccgg aggcggaggc tctggcgggg gcggcagcgg cgggggcggc   3360
tccgggggag gcggctctca gagcgtgctg acccagccac cttccgtgtc tgccgcacca   3420
ggacagaagg tgaccatcag ctgttccggc aacacatcca atatcggcaa caatttcgtg   3480
tcttggtacc agcagaggcc aggaagggca ccacagctgc tgatctatga gacagacaag   3540
cggccttccg gcatcccaga tagattttct gccagcaagt ccggcaccag cggcacactg   3600
gcaatcaccg gcctgcagac aggcgacgaa gctgattact attgcgcaac ctgggcagcc   3660
tccctgagct ccgccagggt gttcggaacc ggaacaaaag tgatcgtgct ggtgggcggc   3720
ggaggctctg gcggaggcgg cagcggcggg gggggctccc aggtgcagct ggtggagagc   3780
ggcggcggcg tggtgcagcc aggcacctcc ctgaggctgt cttgtgcagc aagccagttc   3840
agatttgatg gctacggcat gcactgggtg cgccaggcac caggcaaggg cctggagtgg   3900
gtagcctcta tcagccacga cggcatcaag aagtaccacg ccgagaaagt gtggggcagg   3960
ttcaccatct cccgcgataa ctctaaaaac acactgtatc tgcagatgaa ctccctgagg   4020
cccgaggaca ccgccctgta ctattgcgcc aaggacctgc gcgaggatga gtgtgaggag   4080
tggtggtccg actactatga ttttggcaag cagctgcctt gcgcaaagag caggggaggc   4140
```

```
ctggtgggaa tcgccgataa ttggggccag ggcaccatgg tgacagtgtc tagcggatcc   4200

ggagagctga agacccctct gggcgatacc acacacacat ccccacggag ccccgagcca   4260

aagtcctctg acaccccacc ccctagccct agatcccctg agccaaagag ctccgataca   4320

ccaccccctt ctccaaggag ccccgagcct aagtctagcg acaccccacc cccttgcccc   4380

cgctgtccag caccagagct gctgggagga ccaagcgtgt tcctgtttcc acccaagcct   4440

aaggatacac tgatgatctc tcgcaccccc gaggtgacat gcgtggtggt ggacgtgagc   4500

cacgaggacc ccgaggtgaa gttcaactgg tacgtggacg gcgtggaggt gcacaatgcc   4560

aagaccaagc ccagggagga gcagtacaac agcacctatc gcgtggtgtc cgtgctgaca   4620

gtgctgcacc aggactggct gaacggcaag gagtacaagt gcaaggtgtc caataaggcc   4680

ctgcctgccc caatcgagaa gacaatcagc aaggcaaagg gacagccaag ggagccacag   4740

gtgtacaccc tgcctccaag ccgcgaggag atgaccaaga accaggtgtc cctgacatgt   4800

ctggtgaagg gcttctatcc tagcgatatc gccgtggagt gggagtccaa tggccagcca   4860

gagaacaatt acaagaccac acccccctgtg ctggactccg atggctcttt ctttctgtat   4920

tctaagctga ccgtggacaa gagccggtgg cagcagggca acgtgttcag ctgctctgtg   4980

ctgcacgaag ccctgcacag ccattacacc cagaagagcc tgagcctgag ccccggaaaa   5040

tagtgaaagc tt                                                       5052
```

```
<210> SEQ ID NO 83
<211> LENGTH: 4232
<212> TYPE: DNA
<213> ORGANISM: Artificial Sequence
<220> FEATURE:
<223> OTHER INFORMATION: Synthetic: PentaNAb2.0 Reverse
      VRC26.25-5X-PGT121-5X-N6-5X-35O22-5X-10E8v4_S100cF-His

<400> SEQUENCE: 83
```

```
gaattcgccg ccaccatggg ctggagctgc atcatcctgt tcctggtggc aaccgcaaca     60

ggagtgcaca gccaggtgca gctggtggag tccggaggag gagtggtgca gccaggcacc    120

tctctgaggc tgagctgtgc agcatcccag ttcagatttg atggctacgg aatgcactgg    180

gtgaggcagg caccaggcaa gggactggag tgggtggcca gcatctccca cgacggcatc    240

aagaagtacc acgccgagaa agtgtggggc aggttcacca tctctcgcga taacagcaag    300

aatacactgt atctgcagat gaacagcctg aggcccgagg acaccgccct gtactattgc    360

gccaaggacc tgcgcgagga tgagtgtgag gagtggtggt ccgactacta tgattttggc    420

aagcagctgc cttgcgcaaa gagcagggga ggactggtgg gaatcgccga caattggggc    480

cagggcacca tggtgacagt gagcagcgga ggaggaggct ctggaggagg aggcagcgga    540

ggcggcggct ctcagagcgt gctgacccag ccaccttccg tgtctgccgc accaggacag    600

aaggtgacca tcagctgttc cggcaacaca tccaatatcg gcaacaattt cgtgtcttgg    660

taccagcaga ggcctggaag agcaccacag ctgctgatct atgagacaga caagaggccc    720

tccggcatcc ctgatcgctt ttctgccagc aagtccggca ccagcggcac actggcaatc    780

accggactgc agacaggcga cgaggcagat tactattgcg caacctgggc agcctccctg    840

tctagcgcca gggtgttcgg caccggcaca aaagtgatcg tgctggtggg aggaggaggc    900

tccggcggcg gggctctgg cggcggcggc agcggaggag gcggctccgg aggaggcggc    960

tctcagatgc agctgcagga gagcggacca ggactggtga agccttccga gaccctgtct   1020

ctgacatgtt ctgtgagcgg cgcctccatc tctgatagct actggagctg gatcagacgg   1080
```

-continued

```
agccctggca agggcctgga gtggatcggc tacgtgcaca agtctggcga tacaaactat   1140
tccccatctc tgaagagccg ggtgaacctg agcctggaca cctccaagaa tcaggtgagc   1200
ctgtccctgg tggcagcaac cgcagcagac agcggcaagt actattgcgc cagaacactg   1260
cacggcaggc gcatctacgg catcgtggcc tttaacgagt ggttcaccta cttttatatg   1320
gacgtgtggg gcaatggcac ccaggtgaca gtgtcctctg gcggcggcgg ctctggcgga   1380
ggaggcagcg gaggaggagg cagctccgac atctctgtgg cacctggaga gaccgcaagg   1440
atcagctgtg gagagaagtc tctgggcagc agggccgtgc agtggtacca gcacagggca   1500
ggacaggcac catccctgat catctataac aatcaggacc ggccatctgg catccccgag   1560
agattctctg gcagccccga tagccctttt ggcaccacag ccaccctgac aatcacctcc   1620
gtggaggccg gcgacgaagc agattactat tgccacatct gggactccag agtgccaacc   1680
aagtgggtgt tcggaggagg aaccacactg acagtgctgg gcggcggagg ctccggcggg   1740
ggcggctctg gaggcggcgg cagcggaggg ggcggctccg gcggcggcgg ctctagggca   1800
cacctggtgc agagcggaac cgcaatgaag aagcctggcg cctctgtgcg cgtgagctgt   1860
cagacatccg gctacacctt caccgcccac atcctgttct ggtttaggca ggcaccagga   1920
agaggactgg agtgggtggg ctggatcaag ccccagtatg gagcagtgaa cttcggagga   1980
ggctttcggg acagagtgac actgacccgg gacgtgtaca gagagatcgc ctatatggat   2040
atcaggggcc tgaagcccga cgataccgcc gtgtactatt gcgccaggga ccgctcctac   2100
ggcgattcta gctgggcact ggacgcatgg ggacagggaa ccacagtggt ggtgagcgcc   2160
ggaggcgggg gcagcggcgg cgggggctcc ggaggcggag gctcttacat ccacgtgacc   2220
cagtcccctt cctctctgtc cgtgtctatc ggcgatcgcg tgaccatcaa ctgtcagaca   2280
agccagggag tgggctccga cctgcactgg tatcagcaca agcctggcag ggccccaaag   2340
ctgctgatcc accacacaag ctccgtggag gatggagtgc caagccgctt cagcggctcc   2400
ggattccaca ccagctttaa tctgacaatc tccgacctgc aggccgacga tatcgccacc   2460
tactattgcc aggtgctgca gttctttggc aggggctccc gcctgcacat caagggcggc   2520
ggcggctctg gggcggggg cagcggcggg gggggctccg gggaggaggg ctctggcgga   2580
gggggcagcc agggccagct ggtgcagagc ggagcagagc tgaagaagcc aggagcctct   2640
gtgaagatca gctgtaagac atccggctac cggttcaact tttatcacat caattggatc   2700
aggcagaccg caggaagggg accagagtgg atgggctgga tctcccccta ctctggcgat   2760
aagaacctgg ccccagcctt ccaggacaga gtgatcatga ccacagatac cgaggtgcca   2820
gtgaccagct tcacctccac cggagccgcc tacatggaga tccggaatct gaagttcgac   2880
gatacaggca cctatttttg cgccaagggc ctgctgagag acggctctag cacatggctg   2940
ccatacctgt ggggacaggg caccctgctg acagtgtcct ctggaggagg aggctccggg   3000
ggcggcggct ctggaggagg aggctctcaa agcgtgctga cccagtccgc ctctgtgagc   3060
ggctccctgg gccagtctgt gaccatcagc tgtacaggcc ccaactccgt gtgctgttct   3120
cacaagtcta tcagctggta ccagtggcca ccaggaaggg cacctaccct gatcatctat   3180
gaggacaatg agagggcacc aggaatcagc cctcgcttct ccggctacaa gtcttattgg   3240
agcgcctacc tgaccatttc cgacctgcgc cccgaggatg agaccacata ctattgctgt   3300
agctataccc acaactccgg ctgcgtgttt ggcacaggca ccaaggtgag cgtgctggga   3360
ggaggggggct ctggcggcgg gggcagcggc ggaggcggct ccggaggggg cggctctggc   3420
```

ggaggcggca gcgaggtgcg gctggtggag agcggcggcg gcctggtgaa gccaggcggc 3480
tctctgagac tgtcctgttc tgccagcggc ttcgactttg ataatgcctg gatgacatgg 3540
gtgcggcagc ctcctggcaa ggggctggag tgggtgggaa gaatcaccgg accaggagag 3600
ggatggtctg tggactacgc cgagagcgtg aagggccggt tcaccatcag cagagataac 3660
actaaaaata cactgtatct ggagatgaac aatgtgcgga ccgaggacac aggctactat 3720
ttctgcgcca gaaccggcaa gtactatgat ttctggtttg gctacccccc tggcgaggag 3780
tattttcagg actggggcca gggcaccctg gtcatcgtga gcagcggcgg gggaggctcc 3840
ggcggggggg gctctggagg agggggctct agcgagctga cccaggaccc cgccgtgtcc 3900
gtggccctga agcagacagt gaccatcaca tgcaggggcg actccctgcg ctctcactac 3960
gccagctggt atcagaagaa gccaggacag gcacccgtgc tgctgttcta cggcaagaac 4020
aatcggcctt ccggcatccc agatagattt tccggctctg ccagcggaaa cagggccagc 4080
ctgaccatca caggagcaca ggcagaggat gaagcagatt actattgttc ctctcgggac 4140
aagtccggct ctagactgag cgtgttcggc ggcggaacca agctgacagt gctgggatcc 4200
ggccaccacc atcaccatca ttagtgaagc tt 4232

<210> SEQ ID NO 84
<211> LENGTH: 4221
<212> TYPE: DNA
<213> ORGANISM: Artificial Sequence
<220> FEATURE:
<223> OTHER INFORMATION: Synthetic: PentaNAb3.0
10E8v4_S100cF-5X-35O22-5X-N6-5X-PGT121-5X-PGDM1400-His

<400> SEQUENCE: 84
gaattcgccg ccaccatggg atggagctgt attattctgt ttctggtcgc taccgctacc 60
ggagtgcatt cttctgaact gacccaggac cccgccgtga gcgtggccct gaagcagacc 120
gtgacaatca cctgcagggg cgacagcctg cgctcccact acgccagctg gtatcagaag 180
aagcctggcc aggccccagt gctgctgttc tacggcaaga acaataggcc ctccggcatc 240
cctgatcgct tttccggctc tgccagcgga aacagggcca gcctgacaat caccggagca 300
caggcagagg acgaggcaga ttactattgc agctcccggg acaagtccgg ctctagactg 360
agcgtgttcg gcggcggcac caagctgaca gtgctgggag gaggaggcag cggcggagga 420
ggctccggag gcggcggctc tgaggtgcgg ctggtggagt ctggaggagg cctggtgaag 480
ccaggaggca gcctgagact gagctgttcc gcctctggct tcgactttga taatgcctgg 540
atgacatggg tgcggcagcc acctggcaag ggcctggagt gggtgggaag aatcaccgga 600
ccaggagagg gatggtctgt ggactacgcc gagagcgtga agggccggtt caccatctcc 660
agagataaca ccaagaatac actgtatctg gagatgaaca atgtgcggac cgaggacaca 720
ggctactatt tctgcgccag aaccggcaag tactatgatt tttggtttgg ctacccaccc 780
ggcgaggagt attttcagga ctggggccag ggcaccctgg tcatcgtgag cagcggcggc 840
ggcggcagcg gcggcggcgg ctccggagga ggcggctctg gaggaggagg cagcggggga 900
gggggcagcc agtccgtgct gacccagtct gccagcgtgt ccggctctct gggacagagc 960
gtgaccatct cctgtacagg ccccaacagc gtgtgctgta gccacaagag catctcctgg 1020
taccagtggc ctccaggaag ggcacctacc ctgatcatct atgaggacaa tgagcgggcc 1080
ccaggcatct cccccagatt ctctggctac aagtcttatt ggagcgccta cctgacaatc 1140
agcgacctgc gccccgagga tgagacaaca tactattgct gttcctatac ccacaactct 1200

-continued

```
ggctgcgtgt ttggcacagg caccaaggtg tccgtgctgg gcggcggcgg cagcgggggc   1260
gggggctccg gagggggcgg ctctcagggc cagctggtgc agagcggagc agagctgaag   1320
aagcctggag ccagcgtgaa gatctcctgt aagacatctg gctaccggtt caacttttat   1380
cacatcaatt ggatcaggca gaccgcagga aggggaccag agtggatggg ctggatctcc   1440
ccctactctg gcgataagaa cctggcccca gccttccagg acagagtgat catgaccaca   1500
gataccgagg tgccagtgac cagcttcacc tccaccggag ccgcctacat ggagatcagg   1560
aatctgaagt tcgacgatac aggcacctat ttttgcgcaa agggcctgct gagggacggc   1620
tcctctacct ggctgcctta cctgtgggga cagggcaccc tgctgacagt gagctccggc   1680
ggcgggggca gcggcggcgg gggctccgga ggaggaggct ctggaggagg gggcagcgga   1740
ggaggcggct cctacatcca cgtgacccag tccccatcta gcctgtctgt gagcatcggc   1800
gatcgggtga ccatcaactg tcagacatct cagggcgtgg gcagcgacct gcactggtat   1860
cagcacaagc ctggcagggc cccaaagctg ctgatccacc acacatcctc tgtggaggat   1920
ggagtgccaa gccgcttctc cggctctgga ttccacacct cctttaatct gacaatctct   1980
gacctgcagg ccgacgatat cgccacctac tattgccagg tgctgcagtt ctttggccgg   2040
ggctccagac tgcacatcaa gggaggagga ggctccgggg gcggaggctc tggcggcggc   2100
ggcagccggg cccacctggt gcagagcggc accgccatga agaagcctgg cgccagcgtg   2160
agagtgtcct gtcagacatc tggctacacc ttcaccgccc acatcctgtt ctggtttagg   2220
caggcaccag gaagaggcct ggagtgggtg ggctggatca agccccagta tggagcagtg   2280
aacttcggag gaggctttcg ggacagagtg acactgaccc gggacgtgta cagagagatc   2340
gcctatatgg atatcagggg cctgaagcca gacgataccg ccgtgtacta ttgcgccagg   2400
gaccgctcct acggcgatag ctcctgggca ctggacgcat ggggacaggg caccacagtg   2460
gtggtgagcg ccggcggcgg aggctccggc ggcgggggct ctggaggagg cggcagcgga   2520
gggggaggct ccggaggggg aggctctagc gacatctccg tggcccctgg cgagacagcc   2580
agaatctctt gtggcgagaa gtctctgggc agcagggccg tgcagtggta ccagcacagg   2640
gcaggacagg caccatctct gatcatctat aacaatcagg ataggccaag cggcatccct   2700
gagcggttca gcggctcccc cgacagccct tttggcacca cagccacact gaccatcaca   2760
tccgtggagg caggcgacga agccgattac tattgccaca tctgggattc cagagtgcca   2820
accaagtggg tgttcggagg aggaaccaca ctgacagtgc tgggaggggg gggctctggc   2880
ggcgggggca gcgggggagg aggctcccag atgcagctgc aggagagcgg accaggcctg   2940
gtgaagccta gcgagacact gagcctgaca tgttctgtga gcggcgcctc catctctgac   3000
agctactggt cttggatcag acggagcccc ggcaagggcc tggaatggat cggctacgtg   3060
cacaagtccg gcgatacaaa ctattcccca tctctgaagt ctcgggtgaa cctgtctctg   3120
gacaccagca agaatcaggt gagcctgtcc ctggtggcag caaccgcagc agatagcggc   3180
aagtactatt gcgccagaac actgcacggc aggcgcatct acggcatcgt ggcctttaac   3240
gagtggttca cctactttta tatggacgtg tggggcaatg gcacccaggt gacagtgtcc   3300
tctggcgggg gcggctccgg aggcggaggc tctggcgggg gcggcagcgg cgggggcggc   3360
tccgggggag gcggctctga tttcgtgctg acccagtctc cacatagtct gagcgtgaca   3420
cccggcgaaa gcgcatcaat ttcttgtaaa tcatctcata gtctgatcca cggcgatagg   3480
aacaattacc tggcctggta cgtgcagaag ccaggccgca gccctcagct gctgatctac   3540
ctggcaagct ccagggcatc cggagtgcca gatcgcttct ctggcagcgg ctccgataag   3600
```

gactttaccc tgaagatctc ccgggtggag acagaggacg tgggcacata ctattgcatg 3660
cagggcagag agtctccttg gaccttcggc cagggcacaa aggtggacat caagggagga 3720
ggaggcagcg gcggaggagg ctccggcggc ggcggctctc aggcacagct ggtgcagagc 3780
ggaccagagg tgaggaagcc aggcacctct gtgaaggtga gctgtaaggc ccctggcaac 3840
accctgaaga catacgatct gcactgggtg cggtctgtgc caggacaggg cctgcagtgg 3900
atgggatgga tcagccacga gggcgacaag aaagtgatcg tggagcggtt taaggccaag 3960
gtgacaatcg attgggacag aagcaccaat acagcctatc tgcagctgtc cggcctgacc 4020
tctggcgata cagccgtgta ctattgcgcc aagggctcca agcaccggct gagagactac 4080
gccctgtatg acgatgacgg cgccctgaat tgggcagtgg acgtggacta tctgagtaat 4140
ctggagtttt gggggcaggg caccgcagtg acagtgtcta gcggatccgg acaccaccat 4200
caccatcatt agtgaaagct t 4221

<210> SEQ ID NO 85
<211> LENGTH: 4221
<212> TYPE: DNA
<213> ORGANISM: Artificial Sequence
<220> FEATURE:
<223> OTHER INFORMATION: Synthetic: PentaNAb3.0 Reverse
PGDM1400-5X-PGT121-5X-N6-5X-35O22-5X-10E8v4S100cF-His

<400> SEQUENCE: 85
gaattcgccg ccaccatggg ctggagctgc atcatcctgt tcctggtggc aaccgcaaca 60
ggagtgcaca gccaggcaca gctggtgcag agcggacccg aagtgagaaa acctgggact 120
agcgtcaaag tgtcatgtaa agcccctgga aataccctga agacctacga tctgcactgg 180
gtgcggtccg tgcctggaca gggcctgcag tggatgggat ggatctctca cgagggcgac 240
aagaaagtga tcgtggagcg gttcaaggcc aaggtgacaa tcgattggga cagatccacc 300
aacacagcct acctgcagct gtctggcctg accagcggcg atacagccgt gtactactgt 360
gccaagggct ctaagcaccg gctgagagac tacgccctgt atgacgatga cggcgccctg 420
aactgggccg tggatgtgga ctatctgtcc aatctggagt tctggggaca gggaaccgca 480
gtgacagtga gctccggagg aggaggctcc ggcggcggag gctctggggg aggcggcagc 540
gattttgtgc tgacccagtc tccacacagc ctgtccgtga cacccggcga gtctgccagc 600
atctcctgca agtctagcca cagcctgatc cacggcgaca ggaacaatta cctggcctgg 660
tacgtgcaga agccaggccg cagccctcag ctgctgatct atctggcatc ctctagggcc 720
tccggagtgc cagatcgctt ctctggcagc ggctccgata aggactttac cctgaagatc 780
agccgggtgg agacagagga cgtgggcaca tactattgta tgcagggccg agaatcacct 840
tggacatttg ggcagggaac taaagtcgac atcaaagggg gggggggctc cggcggcggg 900
ggctctggcg gcggcggcag cggaggaggc ggctccggag gaggcggctc tcagatgcag 960
ctgcaggaga gcggaccagg actggtgaag ccttccgaga ccctgtctct gacatgttct 1020
gtgagcggcg cctccatctc tgatagctac tggagctgga tcagacggag ccctggcaag 1080
ggcctggagt ggatcggcta cgtgcacaag tctggcgata caaactattc cccatctctg 1140
aagagccggg tgaacctgag cctggacacc tccaagaatc aggtgagcct gtccctggtg 1200
gcagcaaccg cagcagacag cggcaagtac tattgcgcca gaacactgca cggcaggcgc 1260
atctacggca tcgtggcctt taacgagtgg ttcacctact tttatatgga cgtgtggggc 1320
aatggcaccc aggtgacagt gtcctctggc ggcggcggct ctggcggagg aggcagcgga 1380
ggaggaggca gctccgacat ctctgtggca cctggagaga ccgcaaggat cagctgtgga 1440
gagaagtctc tgggcagcag ggccgtgcag tggtaccagc acagggcagg acaggcacca 1500
tccctgatca tctataacaa tcaggaccgg ccatctggca tccccgagag attctctggc 1560
agccccgata gccctttgg caccacagcc accctgacaa tcacctccgt ggaggccggc 1620
gacgaagcag attactattg ccacatctgg gactccagag tgccaaccaa gtgggtgttc 1680
ggaggaggaa ccacactgac agtgctgggc ggcggaggct ccggcggggg cggctctgga 1740
ggcggcggca gcggaggggg cggctccggc ggcggcggct ctagggcaca cctggtgcag 1800
agcggaaccg caatgaagaa gcctggcgcc tctgtgcgcg tgagctgtca gacatccggc 1860
tacaccttca ccgcccacat cctgttctgg tttaggcagg caccaggaag aggactggag 1920
tgggtgggct ggatcaagcc ccagtatgga gcagtgaact tcggaggagg ctttcgggac 1980
agagtgacac tgacccggga cgtgtacaga gagatcgcct atatggatat caggggcctg 2040
aagcccgacg ataccgccgt gtactattgc gccagggacc gctcctacgg cgattctagc 2100
tgggcactgg acgcatgggg acagggaacc acagtggtgg tgagcgccgg aggcgggggc 2160
agcggcggcg gggctccgg aggcggaggc tcttacatcc acgtgaccca gtccccttcc 2220
tctctgtccg tgtctatcgg cgatcgcgtg accatcaact gtcagacaag ccagggagtg 2280
ggctccgacc tgcactggta tcagcacaag cctggcaggg ccccaaagct gctgatccac 2340
cacacaagct ccgtggagga tggagtgcca agccgcttca gcggctccgg attccacacc 2400
agctttaatc tgacaatctc cgacctgcag gccgacgata tcgccaccta ctattgccag 2460
gtgctgcagt tctttggcag gggctcccgc ctgcacatca agggcggcgg cggctctggg 2520
ggcgggggca gcggcggggg gggctccggg ggaggaggct ctggcggagg gggcagccag 2580
ggccagctgg tgcagagcgg agcagagctg aagaagccag gagcctctgt gaagatcagc 2640
tgtaagacat ccggctaccg gttcaacttt tatcacatca attggatcag gcagaccgca 2700
ggaaggggac cagagtggat gggctggatc tccccctact ctggcgataa gaacctggcc 2760
ccagccttcc aggacagagt gatcatgacc acagataccg aggtgccagt gaccagcttc 2820
acctccaccg gagccgccta catggagatc cggaatctga agttcgacga tacaggcacc 2880
tatttttgcg ccaagggcct gctgagagac ggctctagca catggctgcc atacctgtgg 2940
ggacagggca ccctgctgac agtgtcctct ggaggaggag gctccggggg cggcggctct 3000
ggaggaggag gctctcaaag cgtgctgacc cagtccgcct ctgtgagcgg ctccctgggc 3060
cagtctgtga ccatcagctg tacaggcccc aactccgtgt gctgttctca caagtctatc 3120
agctggtacc agtggccacc aggaagggca cctaccctga tcatctatga ggacaatgag 3180
agggcaccag gaatcagccc tcgcttctcc ggctacaagt cttattggag cgcctacctg 3240
accatttccg acctgcgccc cgaggatgag accacatact attgctgtag ctatacccac 3300
aactccggct gcgtgtttgg cacaggcacc aaggtgagcg tgctgggagg agggggctct 3360
ggcggcgggg gcagcggcgg aggcggctcc ggagggggcg gctctggcgg aggcggcagc 3420
gaggtgcggc tggtggagag cggcggcggc ctggtgaagc caggcggctc tctgagactg 3480
tcctgttctg ccagcggctt cgactttgat aatgcctgga tgacatgggt gcggcagcct 3540
cctggcaagg ggctggagtg ggtgggaaga atcaccggac caggagaggg atggtctgtg 3600
gactacgccg agagcgtgaa gggccggttc accatcagca gagataacac taaaaataca 3660
ctgtatctgg agatgaacaa tgtgcggacc gaggacacag gctactattt ctgcgccaga 3720

```
accggcaagt actatgattt ctggtttggc taccccccctg gcgaggagta ttttcaggac   3780

tggggccagg gcaccctggt catcgtgagc agcggcgggg gaggctccgg cgggggggggc   3840

tctggaggag gggctctag cgagctgacc caggaccccg ccgtgtccgt ggccctgaag   3900

cagacagtga ccatcacatg caggggcgac tccctgcgct ctcactacgc cagctggtat   3960

cagaagaagc caggacaggc acccgtgctg ctgttctacg gcaagaacaa tcggccttcc   4020

ggcatcccag atagattttc cggctctgcc agcggaaaca gggccagcct gaccatcaca   4080

ggagcacagg cagaggatga agcagattac tattgttcct ctcgggacaa gtccggctct   4140

agactgagcg tgttcggcgg cggaaccaag ctgacagtgc tgggatccgg acaccaccat   4200

caccatcatt agtgaaagct t                                               4221
```

<210> SEQ ID NO 86
<211> LENGTH: 4221
<212> TYPE: DNA
<213> ORGANISM: Artificial Sequence
<220> FEATURE:
<223> OTHER INFORMATION: Synthetic: PentaNAb4.0 10E8v4
      V5R_S100cF-5X-35O22-5X-N6-5X-PGT121-5X-PGDM1400-His

<400> SEQUENCE: 86

```
gaattcgccg ccaccatggg atggagctgt attattctgt ttctggtcgc taccgctacc     60

ggagtgcatt cttctgaact gacccaggac cccgccgtga gcgtggccct gaagcagacc    120

gtgacaatca cctgcagggg cgacagcctg cgctcccact acgccagctg gtatcagaag    180

aagcctggcc aggccccagt gctgctgttc tacggcaaga acaataggcc ctccggcatc    240

cctgatcgct tttccggctc tgccagcgga aacagggcca gcctgacaat caccggagca    300

caggcagagg acgaggcaga ttactattgc agctcccggg acaagtccgg ctctagactg    360

agcgtgttcg gcggcggcac caagctgaca gtgctgggag gaggaggcag cggcggagga    420

ggctccggag gcggcggctc tgaggtgcgg ctgcgggagt ctggaggagg cctggtgaag    480

ccaggaggca gcctgagact gagctgttcc gcctctggct tcgactttga taatgcctgg    540

atgacatggg tgcggcagcc acctggcaag ggcctggagt gggtgggaag aatcaccgga    600

ccaggagagg gatggtctgt ggactacgcc gagagcgtga agggccggtt caccatctcc    660

agagataaca ccaagaatac actgtatctg gagatgaaca atgtgcggac cgaggacaca    720

ggctactatt tctgcgccag aaccggcaag tactatgatt tttggtttgg ctacccaccc    780

ggcgaggagt attttcagga ctggggccag ggcaccctgg tcatcgtgag cagcggcggc    840

ggcggcagcg gcggcggcgg ctccggagga ggcggctctg gaggaggagg cagcggggga    900

gggggcagcc agtccgtgct gacccagtct gccagcgtgt ccggctctct gggacagagc    960

gtgaccatct cctgtacagg ccccaacagc gtgtgctgta gccacaagag catctcctgg   1020

taccagtggc ctccaggaag ggcacctacc ctgatcatct atgaggacaa tgagcgggcc   1080

ccaggcatct cccccagatt ctctggctac aagtcttatt ggagcgccta cctgacaatc   1140

agcgacctgc gccccgagga tgagacaaca tactattgct gttcctatac ccacaactct   1200

ggctgcgtgt ttggcacagg caccaaggtg tccgtgctgg gcggcggcgg cagcgggggc   1260

gggggctccg gagggggcgg ctctcagggc cagctggtgc agagcggagc agagctgaag   1320

aagcctggag ccagcgtgaa gatctcctgt aagacatctg gctatcggtt caacttttat   1380

cacatcaatt ggatcaggca gaccgcagga aggggaccag agtggatggg ctggatctcc   1440

ccctactctg gcgataagaa cctggcccca gccttccagg acagagtgat catgaccaca   1500
```

```
gataccgagg tgccagtgac cagcttcacc tccaccggag ccgcctacat ggagatcagg   1560
aatctgaagt tcgacgatac aggcacctat ttttgcgcaa agggcctgct gagggacggc   1620
tcctctacct ggctgcctta cctgtgggga cagggcaccc tgctgacagt gagctccggc   1680
ggcgggggca gcggcggcgg gggctccgga ggaggaggct ctggaggagg gggcagcgga   1740
ggaggcggct cctacatcca cgtgacccag tccccatcta gcctgtctgt gagcatcggc   1800
gatcgggtga ccatcaactg tcagacatct cagggcgtgg gcagcgacct gcactggtat   1860
cagcacaagc ctggcagggc cccaaagctg ctgatccacc acacatcctc tgtggaggat   1920
ggagtgccaa gccgcttctc cggctctgga ttccacacct cctttaatct gacaatctct   1980
gacctgcagg ccgacgatat cgccacctac tattgccagg tgctgcagtt ctttggccgg   2040
ggctccagac tgcacatcaa gggaggagga ggctccgggg gcggaggctc tggcggcggc   2100
ggcagccggg cccacctggt gcagagcggc accgccatga agaagcctgg cgccagcgtg   2160
agagtgtcct gtcagacatc tggctacacc ttcaccgccc acatcctgtt ctggtttagg   2220
caggcaccag gaagaggcct ggagtgggtg ggctggatca agccccagta tggagcagtg   2280
aacttcggag gaggctttcg ggacagagtg acactgaccc gggacgtgta cagagagatc   2340
gcctatatgg atatcagggg cctgaagcca gacgataccg ccgtgtacta ttgcgccagg   2400
gaccgctcct acggcgatag ctcctgggca ctggacgcat ggggacaggg caccacagtg   2460
gtggtgagcg ccggcggcgg aggctccggc ggcgggggct ctggaggagg cggcagcgga   2520
gggggaggct ccggaggggg aggctctagc gacatctccg tggcccctgg cgagacagcc   2580
agaatctctt gtggcgagaa gtctctgggc agcagggccg tgcagtggta ccagcacagg   2640
gcaggacagg caccatctct gatcatctat aacaatcagg ataggccaag cggcatccct   2700
gagcggttca gcggctcccc cgacagccct tttggcacca cagccacact gaccatcaca   2760
tccgtggagg caggcgacga agccgattac tattgccaca tctgggattc cagagtgcca   2820
accaagtggg tgttcggagg aggaaccaca ctgacagtgc tgggaggggg gggctctggc   2880
ggcgggggca gcgggggagg aggctcccag atgcagctgc aggagagcgg accaggcctg   2940
gtgaagccta gcgagacact gagcctgaca tgttctgtga gcggcgcctc catctctgac   3000
agctactggt cttggatcag acggagcccc ggcaagggcc tggaatggat cggctacgtg   3060
cacaagtccg gcgatacaaa ctattcccca tctctgaagt ctcgggtgaa cctgtctctg   3120
gacaccagca agaatcaggt gagcctgtcc ctggtggcag caaccgcagc agatagcggc   3180
aagtactatt gcgccagaac actgcacggc aggcgcatct acggcatcgt ggcctttaac   3240
gagtggttca cctactttta tatggacgtg tggggcaatg gcacccaggt gacagtgtcc   3300
tctggcgggg gcggctccgg aggcggaggc tctggcgggg gcggcagcgg cgggggcggc   3360
tccgggggag gcggctctga tttcgtgctg acccagtctc cacatagtct gagcgtgaca   3420
cccggcgaaa gcgcatcaat ttcttgtaaa tcatctcata gtctgatcca cggcgatagg   3480
aacaattacc tggcctggta cgtgcagaag ccaggccgca gccctcagct gctgatctac   3540
ctggcaagct ccagggcatc cggagtgcca gatcgcttct ctggcagcgg ctccgataag   3600
gactttaccc tgaagatctc ccgggtggag acagaggacg tgggcacata ctattgcatg   3660
cagggcagag agtctccttg gaccttcggc cagggcacaa aggtggacat caagggagga   3720
ggaggcagcg gcggaggagg ctccggcggc ggcggctctc aggcacagct ggtgcagagc   3780
ggaccagagg tgaggaagcc aggcacctct gtgaaggtga gctgtaaggc ccctggcaac   3840
accctgaaga catacgatct gcactgggtg cggtctgtgc caggacaggg cctgcagtgg   3900
```

atgggatgga tcagccacga gggcgacaag aaagtgatcg tggagcggtt taaggccaag 3960
gtgacaatcg attgggacag aagcaccaat acagcctatc tgcagctgtc cggcctgacc 4020
tctggcgata cagccgtgta ctattgcgcc aagggctcca agcaccggct gagagactac 4080
gccctgtatg acgatgacgg cgccctgaat tgggcagtgg acgtggacta tctgagtaat 4140
ctggagtttt gggggcaggg caccgcagtg acagtgtcta gcggatccgg acaccaccat 4200
caccatcatt agtgaaagct t 4221

<210> SEQ ID NO 87
<211> LENGTH: 4221
<212> TYPE: DNA
<213> ORGANISM: Artificial Sequence
<220> FEATURE:
<223> OTHER INFORMATION: Synthetic: PentaNAb4.0 Reverse
PGDM1400-5X-PGT121-5X-N6-5X-35O22-5X-10E8v4 V5R S100cF-His

<400> SEQUENCE: 87
gaattcgccg ccaccatggg ctggagctgc atcatcctgt tcctggtggc aaccgcaaca 60
ggagtgcaca gccaggcaca gctggtgcag agcggacccg aagtgagaaa acctgggact 120
agcgtcaaag tgtcatgtaa agcccctgga aataccctga agacctacga tctgcactgg 180
gtgcggtccg tgcctggaca gggcctgcag tggatgggat ggatctctca cgagggcgac 240
aagaaagtga tcgtggagcg gttcaaggcc aaggtgacaa tcgattggga cagatccacc 300
aacacagcct acctgcagct gtctggcctg accagcggcg atacagccgt gtactactgt 360
gccaagggct ctaagcaccg gctgagagac tacgccctgt atgacgatga cggcgccctg 420
aactgggccg tggatgtgga ctatctgtcc aatctggagt tctggggaca gggaaccgca 480
gtgacagtga gctccggagg aggaggctcc ggcggcggag gctctggggg aggcggcagc 540
gattttgtgc tgacccagtc tccacacagc ctgtccgtga cacccggcga gtctgccagc 600
atctcctgca agtctagcca cagcctgatc cacggcgaca ggaacaatta cctggcctgg 660
tacgtgcaga agccaggccg cagccctcag ctgctgatct atctggcatc ctctagggcc 720
tccggagtgc cagatcgctt ctctggcagc ggctccgata aggactttac cctgaagatc 780
agccgggtgg agacagagga cgtgggcaca tactattgta tgcagggccg agaatcacct 840
tggacatttg ggcagggaac taaagttgac atcaaagggg ggggggggctc cggcggcggg 900 ggctctggcg gcggcggcag cggaggaggc ggctccggag gaggcggctc tcagatgcag 960
ctgcaggaga gcggaccagg actggtgaag ccttccgaga ccctgtctct gacatgttct 1020
gtgagcggcg cctccatctc tgatagctac tggagctgga tcagacggag ccctggcaag 1080
ggcctggagt ggatcggcta cgtgcacaag tctggcgata caaactattc cccatctctg 1140
aagagccggg tgaacctgag cctggacacc tccaagaatc aggtgagcct gtccctggtg 1200
gcagcaaccg cagcagacag cggcaagtac tattgcgcca gaacactgca cggcaggcgc 1260
atctacggca tcgtggcctt taacgagtgg ttcacctact tttatatgga cgtgtggggc 1320
aatggcaccc aggtgacagt gtcctctggc ggcggcggct ctggcggagg aggcagcgga 1380
ggaggaggca gctccgacat ctctgtggca cctggagaga ccgcaaggat cagctgtgga 1440
gagaagtctc tgggcagcag ggccgtgcag tggtaccagc acagggcagg acaggcacca 1500
tccctgatca tctataacaa tcaggaccgg ccatctggca tccccgagag attctctggc 1560
agccccgata gcccttttgg caccacagcc accctgacaa tcacctccgt ggaggccggc 1620
gacgaagcag attactattg ccacatctgg gactccagag tgccaaccaa gtgggtgttc 1680

-continued

```
ggaggaggaa ccacactgac agtgctgggc ggcggaggct ccggcggggg cggctctgga   1740
ggcggcggca gcggaggggg cggctccggc ggcggcggct ctagggcaca cctggtgcag   1800
agcggaaccg caatgaagaa gcctggcgcc tctgtgcgcg tgagctgtca gacatccggc   1860
tacaccttca ccgcccacat cctgttctgg tttaggcagg caccaggaag aggactggag   1920
tgggtgggct ggatcaagcc ccagtatgga gcagtgaact tcggaggagg ctttcgggac   1980
agagtgacac tgacccggga cgtgtacaga gagatcgcct atatggatat caggggcctg   2040
aagcccgacg ataccgccgt gtactattgc gccagggacc gctcctacgg cgattctagc   2100
tgggcactgg acgcatgggg acagggaacc acagtggtgg tgagcgccgg aggcgggggc   2160
agcggcggcg gggctccgg aggcggaggc tcttacatcc acgtgaccca gtccccttcc   2220
tctctgtccg tgtctatcgg cgatcgcgtg accatcaact gtcagacaag ccagggagtg   2280
ggctccgacc tgcactggta tcagcacaag cctggcaggg ccccaaagct gctgatccac   2340
cacacaagct ccgtggagga tggagtgcca agccgcttca gcggctccgg attccacacc   2400
agctttaatc tgacaatctc cgacctgcag gccgacgata tcgccaccta ctattgccag   2460
gtgctgcagt tctttggcag ggctcccgc ctgcacatca agggcggcgg cggctctggg   2520
ggcgggggca gcggcggggg gggctccggg ggaggaggct ctggcggagg gggcagccag   2580
ggccagctgg tgcagagcgg agcagagctg aagaagccag gagcctctgt gaagatcagc   2640
tgtaagacat ccggctatcg gttcaacttt tatcacatca attggatcag gcagaccgca   2700
ggaaggggac cagagtggat gggctggatc tccccctact ctggcgataa gaacctggcc   2760
ccagccttcc aggacagagt gatcatgacc acagataccg aggtgccagt gaccagcttc   2820
acctccaccg gagccgccta catggagatc cggaatctga agttcgacga tacaggcacc   2880
tatttttgcg ccaagggcct gctgagagac ggctctagca catggctgcc atacctgtgg   2940
ggacagggca ccctgctgac agtgtcctct ggaggaggag gctccggggg cggcggctct   3000
ggaggaggag gctctcaaag cgtgctgacc cagtccgcct ctgtgagcgg ctccctgggc   3060
cagtctgtga ccatcagctg tacaggcccc aactccgtgt gctgttctca caagtctatc   3120
agctggtacc agtggccacc aggaagggca cctaccctga tcatctatga ggacaatgag   3180
agggcaccag gaatcagccc tcgcttctcc ggctacaagt cttattggag cgcctacctg   3240
accatttccg acctgcgccc cgaggatgag accacatact attgctgtag ctatacccac   3300
aactccggct gcgtgtttgg cacaggcacc aaggtgagcg tgctgggagg agggggctct   3360
ggcggcgggg gcagcggcgg aggcggctcc ggagggggcg gctctggcgg aggcggcagc   3420
gaggtgcggc tgcgggagag cggcggcggc ctggtgaagc caggcggctc tctgagactg   3480
tcctgttctg ccagcggctt cgactttgat aatgcctgga tgacatgggt gcggcagcct   3540
cctggcaagg ggctggagtg ggtgggaaga atcaccggac caggagaggg atggtctgtg   3600
gactacgccg agagcgtgaa gggccggttc accatcagca gagataacac taaaaataca   3660
ctgtatctgg agatgaacaa tgtgcggacc gaggacacag gctactattt ctgcgccaga   3720
accggcaagt actatgattt ctggtttggc taccccctg gcgaggagta ttttcaggac   3780
tggggccagg gcaccctggt catcgtgagc agcggcgggg gaggctccgg cgggggggc   3840
tctggaggag gggctctag cgagctgacc caggaccccg ccgtgtccgt ggccctgaag   3900
cagacagtga ccatcacatg caggggcgac tccctgcgct ctcactacgc cagctggtat   3960
cagaagaagc caggacaggc acccgtgctg ctgttctacg gcaagaacaa tcggccttcc   4020
```

```
ggcatcccag atagattttc cggctctgcc agcggaaaca gggccagcct gaccatcaca   4080

ggagcacagg cagaggatga agcagattac tattgttcct ctcgggacaa gtccggctct   4140

agactgagcg tgttcggcgg cggaaccaag ctgacagtgc tgggatccgg acaccaccat   4200

caccatcatt agtgaaagct t                                             4221
```

<210> SEQ ID NO 88
<211> LENGTH: 4791
<212> TYPE: DNA
<213> ORGANISM: Artificial Sequence
<220> FEATURE:
<223> OTHER INFORMATION: Synthetic: PentaNAb4.0 Reverse PGDM1400-5X-PGT121-5X-N6-5X-35O22-5X-10E8v4 V5R S100cFvVH-fused to IgG1 LS HC with His Tag

<400> SEQUENCE: 88

```
atgggctgga gctgcatcat cctgttcctg gtggcaaccg caacaggagt gcacagccag     60

gcacagctgg tgcagagcgg acccgaagtg agaaaacctg ggactagcgt caaagtgtca    120

tgtaaagccc ctggaaatac cctgaagacc tacgatctgc actgggtgcg gtccgtgcct    180

ggacagggcc tgcagtggat gggatggatc tctcacgagg gcgacaagaa agtgatcgtg    240

gagcggttca aggccaaggt gacaatcgat tgggacagat ccaccaacac agcctacctg    300

cagctgtctg gcctgaccag cggcgataca gccgtgtact actgtgccaa gggctctaag    360

caccggctga gagactacgc cctgtatgac gatgacggcg ccctgaactg ggccgtggat    420

gtggactatc tgtccaatct ggagttctgg ggacagggaa ccgcagtgac agtgagctcc    480

ggaggaggag gctccggcgg cggaggctct gggggaggcg gcagcgattt tgtgctgacc    540

cagtctccac acagcctgtc cgtgacaccc ggcgagtctg ccagcatctc ctgcaagtct    600

agccacagcc tgatccacgg cgacaggaac aattacctgg cctggtacgt gcagaagcca    660

ggccgcagcc ctcagctgct gatctatctg gcatcctcta gggcctccgg agtgccagat    720

cgcttctctg gcagcggctc cgataaggac tttaccctga agatcagccg ggtggagaca    780

gaggacgtgg gcacatacta ttgtatgcag ggccgagaat caccttggac atttgggcag    840

ggaactaaag ttgacatcaa agggggggggg ggctccggcg gcgggggctc tggcggcggc    900

ggcagcggag gaggcggctc cggaggaggc ggctctcaga tgcagctgca ggagagcgga    960

ccaggactgg tgaagccttc cgagaccctg tctctgacat gttctgtgag cggcgcctcc   1020

atctctgata gctactggag ctggatcaga cggagccctg gcaagggcct ggagtggatc   1080

ggctacgtgc acaagtctgg cgatacaaac tattccccat ctctgaagag ccgggtgaac   1140

ctgagcctgg acacctccaa gaatcaggtg agcctgtccc tggtggcagc aaccgcagca   1200

gacagcggca agtactattg cgccagaaca ctgcacggca ggcgcatcta cggcatcgtg   1260

gcctttaacg agtggttcac ctacttttat atggacgtgt ggggcaatgg cacccaggtg   1320

acagtgtcct ctggcggcgg cggctctggc ggaggaggca gcggaggagg aggcagctcc   1380

gacatctctg tggcacctgg agagaccgca aggatcagct gtggagagaa gtctctgggc   1440

agcagggccg tgcagtggta ccagcacagg gcaggacagg caccatccct gatcatctat   1500

aacaatcagg accggccatc tggcatcccc gagagattct ctggcagccc cgatagccct   1560

tttggcacca cagccaccct gacaatcacc tccgtggagg ccggcgacga agcagattac   1620

tattgccaca tctgggactc cagagtgcca accaagtggg tgttcggagg aggaaccaca   1680

ctgacagtgc tgggcggcgg aggctccggc gggggcggct ctggaggcgg cggcagcgga   1740

gggggcggct ccggcggcgg cggctctagg gcacacctgg tgcagagcgg aaccgcaatg   1800
```

aagaagcctg gcgcctctgt gcgcgtgagc tgtcagacat ccggctacac cttcaccgcc 1860
cacatcctgt tctggtttag gcaggcacca ggaagaggac tggagtgggt gggctggatc 1920
aagccccagt atggagcagt gaacttcgga ggaggctttc gggacagagt gacactgacc 1980
cgggacgtgt acagagagat cgcctatatg gatatcaggg gcctgaagcc cgacgatacc 2040
gccgtgtact attgcgccag ggaccgctcc tacggcgatt ctagctgggc actggacgca 2100
tggggacagg gaaccacagt ggtggtgagc gccggaggcg ggggcagcgg cggcgggggc 2160
tccggaggcg gaggctctta catccacgtg acccagtccc cttcctctct gtccgtgtct 2220
atcggcgatc gcgtgaccat caactgtcag acaagccagg gagtgggctc cgacctgcac 2280
tggtatcagc acaagcctgg cagggcccca aagctgctga tccaccacac aagctccgtg 2340
gaggatggag tgccaagccg cttcagcggc tccggattcc acaccagctt taatctgaca 2400
atctccgacc tgcaggccga cgatatcgcc acctactatt gccaggtgct gcagttcttt 2460
ggcaggggct cccgcctgca catcaagggc ggcggcggct ctgggggcgg gggcagcggc 2520
gggggggct ccgggggagg aggctctggc ggagggggca gccagggcca gctggtgcag 2580
agcggagcag agctgaagaa gccaggagcc tctgtgaaga tcagctgtaa gacatccggc 2640
tatcggttca acttttatca catcaattgg atcaggcaga ccgcaggaag gggaccagag 2700
tggatgggct ggatctcccc ctactctggc gataagaacc tggccccagc cttccaggac 2760
agagtgatca tgaccacaga taccgaggtg ccagtgacca gcttcacctc caccggagcc 2820
gcctacatgg agatccggaa tctgaagttc gacgatacag gcacctattt ttgcgccaag 2880
ggcctgctga gagacggctc tagcacatgg ctgccatacc tgtggggaca gggcaccctg 2940
ctgacagtgt cctctggagg aggaggctcc gggggcggcg gctctggagg aggaggctct 3000
caaagcgtgc tgacccagtc cgcctctgtg agcggctccc tgggccagtc tgtgaccatc 3060
agctgtacag gccccaactc cgtgtgctgt tctcacaagt ctatcagctg gtaccagtgg 3120
ccaccaggaa gggcacctac cctgatcatc tatgaggaca atgagagggc accaggaatc 3180
agccctcgct tctccggcta caagtcttat tggagcgcct acctgaccat ttccgacctg 3240
cgccccgagg atgagaccac atactattgc tgtagctata cccacaactc cggctgcgtg 3300
tttggcacag gcaccaaggt gagcgtgctg ggaggagggg gctctggcgg cgggggcagc 3360
ggcggaggcg gctccggagg gggcggctct ggcggaggcg gcagcgaggt gcggctgcgg 3420
gagagcggcg gcggcctggt gaagccaggc ggctctctga gactgtcctg ttctgccagc 3480
ggcttcgact ttgataatgc ctggatgaca tgggtgcggc agcctcctgg caaggggctg 3540
gagtgggtgg gaagaatcac cggaccagga gagggatggt ctgtggacta cgccgagagc 3600
gtgaagggcc ggttcaccat cagcagagat aacactaaaa atacactgta tctggagatg 3660
aacaatgtgc ggaccgagga cacaggctac tatttctgcg ccagaaccgg caagtactat 3720
gatttctggt ttggctaccc ccctggcgag gagtattttc aggactgggg ccagggcacc 3780
ctggtcatcg tgagcagcgc gtcgaccaag ggcccatcgg tcttccccct ggcaccctcc 3840
tccaagagca cctctggggg cacagcggcc ctgggctgcc tggtcaagga ctacttcccc 3900
gaacctgtga cggtgtcgtg gaactcaggc gccctgacca gcggcgtgca caccttcccg 3960
gctgtcctac agtcctcagg actctactcc ctcagcagcg tggtgaccgt gccctccagc 4020
agcttgggca cccagaccta catctgcaac gtgaatcaca agcccagcaa caccaaggtg 4080
gacaagaaag ttgagcccaa atcttgtgac aaaactcaca catgcccacc gtgcccagca 4140

```
cctgaactcc tgggggggacc gtcagtcttc ctcttcccc caaaacccaa ggacaccctc   4200

atgatctccc ggacccctga ggtcacatgc gtggtggtgg acgtgagcca cgaagaccct   4260

gaggtcaagt tcaactggta cgtggacggc gtggaggtgc ataatgccaa gacaaagccg   4320

cgggaggagc agtacaacag cacgtaccgt gtggtcagcg tcctcaccgt cctgcaccag   4380

gactggctga atggcaagga gtacaagtgc aaggtctcca acaaagccct cccagccccc   4440

atcgagaaaa ccatctccaa agccaaaggg cagccccgag aaccacaggt gtacaccctg   4500

cccccatccc gggaggagat gaccaagaac caggtcagcc tgacctgcct ggtcaaaggc   4560

ttctatccca gcgacatcgc cgtggagtgg gagagcaatg ggcagccgga gaacaactac   4620

aagaccacgc ctcccgtgct ggactccgac ggctccttct tcctctacag caagctcacc   4680

gtggacaaga gcaggtggca gcaggggaac gtcttctcat gctccgtgct gcatgaggct   4740

ctgcacagcc actacacgca gaagagcctc tccctgtctc cgggtaaatg a            4791
```

<210> SEQ ID NO 89
<211> LENGTH: 4884
<212> TYPE: DNA
<213> ORGANISM: Artificial Sequence
<220> FEATURE:
<223> OTHER INFORMATION: Synthetic: PentaNAb4.0 Reverse PGDM1400-5X-PGT121-5X-N6-5X-35O22-5X-10E8v4 V5R S100cF VH-VL-fused to IgG1 LS FC with His Tag

<400> SEQUENCE: 89

```
gaattcgccg ccaccatggg ctggagctgc atcatcctgt tcctggtggc aaccgcaaca     60

ggagtgcaca gccaggcaca gctggtgcag agcggacccg aagtgagaaa acctgggact    120

agcgtcaaag tgtcatgtaa agcccctgga aataccctga agacctacga tctgcactgg    180

gtgcggtccg tgcctggaca gggcctgcag tggatgggat ggatctctca cgagggcgac    240

aagaaagtga tcgtggagcg gttcaaggcc aaggtgacaa tcgattggga cagatccacc    300

aacacagcct acctgcagct gtctggcctg accagcggcg atacagccgt gtactactgt    360

gccaagggct ctaagcaccg gctgagagac tacgccctgt atgacgatga cggcgccctg    420

aactgggccg tggatgtgga ctatctgtcc aatctggagt tctggggaca gggaaccgca    480

gtgacagtga gctccggagg aggaggctcc ggcggcggag gctctggggg aggcggcagc    540

gattttgtgc tgacccagtc tccacacagc ctgtccgtga cacccggcga gtctgccagc    600

atctcctgca agtctagcca cagcctgatc cacggcgaca ggaacaatta cctggcctgg    660

tacgtgcaga agccaggccg cagccctcag ctgctgatct atctggcatc ctctagggcc    720

tccggagtgc cagatcgctt ctctggcagc ggctccgata aggactttac cctgaagatc    780

agccgggtgg agacagagga cgtgggcaca tactattgta tgcagggccg agaatcacct    840

tggacatttg ggcagggaac taaagttgac atcaaagggg gggggggctc cggcggcggg    900

ggctctggcg gcggcggcag cggaggaggc ggctccggag gaggcggctc tcagatgcag    960

ctgcaggaga gcggaccagg actggtgaag ccttccgaga ccctgtctct gacatgttct   1020

gtgagcggcg cctccatctc tgatagctac tggagctgga tcagacggag ccctggcaag   1080

ggcctggagt ggatcggcta cgtgcacaag tctggcgata caaactattc cccatctctg   1140

aagagccggg tgaacctgag cctggacacc tccaagaatc aggtgagcct gtccctggtg   1200

gcagcaaccg cagcagacag cggcaagtac tattgcgcca gaacactgca cggcaggcgc   1260

atctacggca tcgtggcctt taacgagtgg ttcacctact tttatatgga cgtgtggggc   1320

aatggcaccc aggtgacagt gtcctctggc ggcggcggct ctggcggagg aggcagcgga   1380
```

-continued

```
ggaggaggca gctccgacat ctctgtggca cctggagaga ccgcaaggat cagctgtgga   1440
gagaagtctc tgggcagcag ggccgtgcag tggtaccagc acagggcagg acaggcacca   1500
tccctgatca tctataacaa tcaggaccgg ccatctggca tccccgagag attctctggc   1560
agccccgata gccctttttgg caccacagcc accctgacaa tcacctccgt ggaggccggc   1620
gacgaagcag attactattg ccacatctgg gactccagag tgccaaccaa gtgggtgttc   1680
ggaggaggaa ccacactgac agtgctgggc ggcggaggct ccggcggggg cggctctgga   1740
ggcggcggca gcggaggggg cggctccggc ggcggcggct ctagggcaca cctggtgcag   1800
agcggaaccg caatgaagaa gcctggcgcc tctgtgcgcg tgagctgtca gacatccggc   1860
tacaccttca ccgcccacat cctgttctgg tttaggcagg caccaggaag aggactggag   1920
tgggtgggct ggatcaagcc ccagtatgga gcagtgaact tcggaggagg ctttcgggac   1980
agagtgacac tgacccggga cgtgtacaga gagatcgcct atatggatat caggggcctg   2040
aagcccgacg ataccgccgt gtactattgc gccagggacc gctcctacgg cgattctagc   2100
tgggcactgg acgcatgggg acagggaacc acagtggtgg tgagcgccgg aggcgggggc   2160
agcggcggcg ggggctccgg aggcggaggc tcttacatcc acgtgaccca gtccccttcc   2220
tctctgtccg tgtctatcgg cgatcgcgtg accatcaact gtcagacaag ccagggagtg   2280
ggctccgacc tgcactggta tcagcacaag cctggcaggg ccccaaagct gctgatccac   2340
cacacaagct ccgtggagga tggagtgcca agccgcttca gcggctccgg attccacacc   2400
agctttaatc tgacaatctc cgacctgcag gccgacgata tcgccaccta ctattgccag   2460
gtgctgcagt tctttggcag ggctcccgc ctgcacatca agggcggcgg cggctctggg   2520
ggcgggggca gcggcggggg gggctccggg ggaggaggct ctggcggagg gggcagccag   2580
ggccagctgg tgcagagcgg agcagagctg aagaagccag gagcctctgt gaagatcagc   2640
tgtaagacat ccggctatcg gttcaacttt tatcacatca attggatcag gcagaccgca   2700
ggaaggggac cagagtggat gggctggatc tccccctact ctggcgataa gaacctggcc   2760
ccagccttcc aggacagagt gatcatgacc acagataccg aggtgccagt gaccagcttc   2820
acctccaccg gagccgccta catggagatc cggaatctga agttcgacga tacaggcacc   2880
tatttttgcg ccaagggcct gctgagagac ggctctagca catggctgcc atacctgtgg   2940
ggacagggca ccctgctgac agtgtcctct ggaggaggag gctccggggg cggcggctct   3000
ggaggaggag gctctcaaag cgtgctgacc cagtccgcct ctgtgagcgg ctccctgggc   3060
cagtctgtga ccatcagctg tacaggcccc aactccgtgt gctgttctca caagtctatc   3120
agctggtacc agtggccacc aggaagggca cctaccctga tcatctatga ggacaatgag   3180
agggcaccag gaatcagccc tcgcttctcc ggctacaagt cttattggag cgcctacctg   3240
accatttccg acctgcgccc cgaggatgag accacatact attgctgtag ctatacccac   3300
aactccggct gcgtgtttgg cacaggcacc aaggtgagcg tgctgggagg agggggctct   3360
ggcggcgggg gcagcggcgg aggcggctcc ggagggggcg gctctggcgg aggcggcagc   3420
gaggtgcggc tgcgggagag cggcggcggc ctggtgaagc caggcggctc tctgagactg   3480
tcctgttctg ccagcggctt cgactttgat aatgcctgga tgacatgggt gcggcagcct   3540
cctggcaagg ggctggagtg ggtgggaaga atcaccggac caggagaggg atggtctgtg   3600
gactacgccg agagcgtgaa gggccggttc accatcagca gagataacac taaaaataca   3660
ctgtatctgg agatgaacaa tgtgcggacc gaggacacag gctactattt ctgcgccaga   3720
```

-continued

```
accggcaagt actatgattt ctggtttggc tacccccctg gcgaggagta ttttcaggac   3780

tggggccagg gcaccctggt catcgtgagc agcggcgggg gaggctccgg cggggggggc   3840

tctggaggag ggggctctag cgagctgacc caggaccccg ccgtgtccgt ggccctgaag   3900

cagacagtga ccatcacatg caggggcgac tccctgcgct ctcactacgc cagctggtat   3960

cagaagaagc caggacaggc acccgtgctg ctgttctacg gcaagaacaa tcggccttcc   4020

ggcatcccag atagattttc cggctctgcc agcggaaaca gggccagcct gaccatcaca   4080

ggagcacagg cagaggatga agcagattac tattgttcct ctcgggacaa gtccggctct   4140

agactgagcg tgttcggcgg cggaaccaag ctgacagtgc tgggatcccc caaatcttgt   4200

gacaaaactc acacatgccc accgtgccca gcacctgaac tcctgggggg accgtcagtc   4260

ttcctcttcc ccccaaaacc caaggacacc ctcatgatct cccggacccc tgaggtcaca   4320

tgcgtggtgg tggacgtgag ccacgaagac cctgaggtca agttcaactg gtacgtggac   4380

ggcgtggagg tgcataatgc caagacaaag ccgcgggagg agcagtacaa cagcacgtac   4440

cgtgtggtca gcgtcctcac cgtcctgcac caggactggc tgaatggcaa ggagtacaag   4500

tgcaaggtct ccaacaaagc cctcccagcc cccatcgaga aaaccatctc caaagccaaa   4560

gggcagcccc gagaaccaca ggtgtacacc ctgcccccat cccgggagga gatgaccaag   4620

aaccaggtca gcctgacctg cctggtcaaa ggcttctatc ccagcgacat cgccgtggag   4680

tgggagagca atgggcagcc ggagaacaac tacaagacca cgcctcccgt gctggactcc   4740

gacggctcct tcttcctcta cagcaagctc accgtggaca agagcaggtg gcagcagggg   4800

aacgtcttct catgctccgt gctgcatgag gctctgcaca gccactacac gcagaagagc   4860

ctctccctgt ctccgggtaa atga                                          4884
```

<210> SEQ ID NO 90
<211> LENGTH: 1398
<212> TYPE: PRT
<213> ORGANISM: Artificial Sequence
<220> FEATURE:
<223> OTHER INFORMATION: Synthetic: PentaNAb4.0 Reverse ScFv Amino acid sequence

<400> SEQUENCE: 90

```
Met Gly Trp Ser Cys Ile Ile Leu Phe Leu Val Ala Thr Ala Thr Gly
1               5                   10                  15

Val His Ser Gln Ala Gln Leu Val Gln Ser Gly Pro Glu Val Arg Lys
            20                  25                  30

Pro Gly Thr Ser Val Lys Val Ser Cys Lys Ala Pro Gly Asn Thr Leu
        35                  40                  45

Lys Thr Tyr Asp Leu His Trp Val Arg Ser Val Pro Gly Gln Gly Leu
    50                  55                  60

Gln Trp Met Gly Trp Ile Ser His Glu Gly Asp Lys Lys Val Ile Val
65                  70                  75                  80

Glu Arg Phe Lys Ala Lys Val Thr Ile Asp Trp Asp Arg Ser Thr Asn
                85                  90                  95

Thr Ala Tyr Leu Gln Leu Ser Gly Leu Thr Ser Gly Asp Thr Ala Val
            100                 105                 110

Tyr Tyr Cys Ala Lys Gly Ser Lys His Arg Leu Arg Asp Tyr Ala Leu
        115                 120                 125

Tyr Asp Asp Asp Gly Ala Leu Asn Trp Ala Val Asp Val Asp Tyr Leu
    130                 135                 140

Ser Asn Leu Glu Phe Trp Gly Gln Gly Thr Ala Val Thr Val Ser Ser
```

-continued

```
145                 150                 155                 160

Gly Gly Gly Gly Ser Gly Gly Gly Gly Ser Gly Gly Gly Gly Ser Asp
                165                 170                 175

Phe Val Leu Thr Gln Ser Pro His Ser Leu Ser Val Thr Pro Gly Glu
            180                 185                 190

Ser Ala Ser Ile Ser Cys Lys Ser Ser His Ser Leu Ile His Gly Asp
        195                 200                 205

Arg Asn Asn Tyr Leu Ala Trp Tyr Val Gln Lys Pro Gly Arg Ser Pro
    210                 215                 220

Gln Leu Leu Ile Tyr Leu Ala Ser Ser Arg Ala Ser Gly Val Pro Asp
225                 230                 235                 240

Arg Phe Ser Gly Ser Gly Ser Asp Lys Asp Phe Thr Leu Lys Ile Ser
                245                 250                 255

Arg Val Glu Thr Glu Asp Val Gly Thr Tyr Tyr Cys Met Gln Gly Arg
            260                 265                 270

Glu Ser Pro Trp Thr Phe Gly Gln Gly Thr Lys Val Asp Ile Lys Gly
        275                 280                 285

Gly Gly Gly Ser Gly Gly Gly Gly Ser Gly Gly Gly Gly Ser Gly Gly
    290                 295                 300

Gly Gly Ser Gly Gly Gly Gly Ser Gln Met Gln Leu Gln Glu Ser Gly
305                 310                 315                 320

Pro Gly Leu Val Lys Pro Ser Glu Thr Leu Ser Leu Thr Cys Ser Val
                325                 330                 335

Ser Gly Ala Ser Ile Ser Asp Ser Tyr Trp Ser Trp Ile Arg Arg Ser
            340                 345                 350

Pro Gly Lys Gly Leu Glu Trp Ile Gly Tyr Val His Lys Ser Gly Asp
        355                 360                 365

Thr Asn Tyr Ser Pro Ser Leu Lys Ser Arg Val Asn Leu Ser Leu Asp
    370                 375                 380

Thr Ser Lys Asn Gln Val Ser Leu Ser Leu Val Ala Ala Thr Ala Ala
385                 390                 395                 400

Asp Ser Gly Lys Tyr Tyr Cys Ala Arg Thr Leu His Gly Arg Arg Ile
                405                 410                 415

Tyr Gly Ile Val Ala Phe Asn Glu Trp Phe Thr Tyr Phe Tyr Met Asp
            420                 425                 430

Val Trp Gly Asn Gly Thr Gln Val Thr Val Ser Ser Gly Gly Gly Gly
        435                 440                 445

Ser Gly Gly Gly Gly Ser Gly Gly Gly Gly Ser Ser Asp Ile Ser Val
    450                 455                 460

Ala Pro Gly Glu Thr Ala Arg Ile Ser Cys Gly Glu Lys Ser Leu Gly
465                 470                 475                 480

Ser Arg Ala Val Gln Trp Tyr Gln His Arg Ala Gly Gln Ala Pro Ser
                485                 490                 495

Leu Ile Ile Tyr Asn Asn Gln Asp Arg Pro Ser Gly Ile Pro Glu Arg
            500                 505                 510

Phe Ser Gly Ser Pro Asp Ser Pro Phe Gly Thr Thr Ala Thr Leu Thr
        515                 520                 525

Ile Thr Ser Val Glu Ala Gly Asp Glu Ala Asp Tyr Tyr Cys His Ile
    530                 535                 540

Trp Asp Ser Arg Val Pro Thr Lys Trp Val Phe Gly Gly Gly Thr Thr
545                 550                 555                 560

Leu Thr Val Leu Gly Gly Gly Gly Ser Gly Gly Gly Gly Ser Gly Gly
                565                 570                 575
```

-continued

Gly Gly Ser Gly Gly Gly Gly Ser Gly Gly Gly Gly Ser Arg Ala His
580 585 590

Leu Val Gln Ser Gly Thr Ala Met Lys Lys Pro Gly Ala Ser Val Arg
595 600 605

Val Ser Cys Gln Thr Ser Gly Tyr Thr Phe Thr Ala His Ile Leu Phe
610 615 620

Trp Phe Arg Gln Ala Pro Gly Arg Gly Leu Glu Trp Val Gly Trp Ile
625 630 635 640

Lys Pro Gln Tyr Gly Ala Val Asn Phe Gly Gly Gly Phe Arg Asp Arg
645 650 655

Val Thr Leu Thr Arg Asp Val Tyr Arg Glu Ile Ala Tyr Met Asp Ile
660 665 670

Arg Gly Leu Lys Pro Asp Asp Thr Ala Val Tyr Tyr Cys Ala Arg Asp
675 680 685

Arg Ser Tyr Gly Asp Ser Ser Trp Ala Leu Asp Ala Trp Gly Gln Gly
690 695 700

Thr Thr Val Val Val Ser Ala Gly Gly Gly Gly Ser Gly Gly Gly Gly
705 710 715 720

Ser Gly Gly Gly Gly Ser Tyr Ile His Val Thr Gln Ser Pro Ser Ser
725 730 735

Leu Ser Val Ser Ile Gly Asp Arg Val Thr Ile Asn Cys Gln Thr Ser
740 745 750

Gln Gly Val Gly Ser Asp Leu His Trp Tyr Gln His Lys Pro Gly Arg
755 760 765

Ala Pro Lys Leu Leu Ile His His Thr Ser Ser Val Glu Asp Gly Val
770 775 780

Pro Ser Arg Phe Ser Gly Ser Gly Phe His Thr Ser Phe Asn Leu Thr
785 790 795 800

Ile Ser Asp Leu Gln Ala Asp Asp Ile Ala Thr Tyr Tyr Cys Gln Val
805 810 815

Leu Gln Phe Phe Gly Arg Gly Ser Arg Leu His Ile Lys Gly Gly Gly
820 825 830

Gly Ser Gly Gly Gly Gly Ser Gly Gly Gly Gly Ser Gly Gly Gly Gly
835 840 845

Ser Gly Gly Gly Gly Ser Gln Gly Gln Leu Val Gln Ser Gly Ala Glu
850 855 860

Leu Lys Lys Pro Gly Ala Ser Val Lys Ile Ser Cys Lys Thr Ser Gly
865 870 875 880

Tyr Arg Phe Asn Phe Tyr His Ile Asn Trp Ile Arg Gln Thr Ala Gly
885 890 895

Arg Gly Pro Glu Trp Met Gly Trp Ile Ser Pro Tyr Ser Gly Asp Lys
900 905 910

Asn Leu Ala Pro Ala Phe Gln Asp Arg Val Ile Met Thr Thr Asp Thr
915 920 925

Glu Val Pro Val Thr Ser Phe Thr Ser Thr Gly Ala Ala Tyr Met Glu
930 935 940

Ile Arg Asn Leu Lys Phe Asp Asp Thr Gly Thr Tyr Phe Cys Ala Lys
945 950 955 960

Gly Leu Leu Arg Asp Gly Ser Ser Thr Trp Leu Pro Tyr Leu Trp Gly
965 970 975

Gln Gly Thr Leu Leu Thr Val Ser Ser Gly Gly Gly Gly Ser Gly Gly
980 985 990

-continued

```
Gly Gly Ser Gly Gly Gly Gly Ser  Gln Ser Val Leu Thr  Gln Ser Ala
        995                 1000                 1005

Ser Val  Ser Gly Ser Leu Gly  Gln Ser Val Thr Ile  Ser Cys Thr
    1010                 1015                 1020

Gly Pro  Asn Ser Val Cys Cys  Ser His Lys Ser Ile  Ser Trp Tyr
    1025                 1030                 1035

Gln Trp  Pro Pro Gly Arg Ala  Pro Thr Leu Ile Ile  Tyr Glu Asp
    1040                 1045                 1050

Asn Glu  Arg Ala Pro Gly Ile  Ser Pro Arg Phe Ser  Gly Tyr Lys
    1055                 1060                 1065

Ser Tyr  Trp Ser Ala Tyr Leu  Thr Ile Ser Asp Leu  Arg Pro Glu
    1070                 1075                 1080

Asp Glu  Thr Thr Tyr Tyr Cys  Cys Ser Tyr Thr His  Asn Ser Gly
    1085                 1090                 1095

Cys Val  Phe Gly Thr Gly Thr  Lys Val Ser Val Leu  Gly Gly Gly
    1100                 1105                 1110

Gly Ser  Gly Gly Gly Gly Ser  Gly Gly Gly Gly Ser  Gly Gly Gly
    1115                 1120                 1125

Gly Ser  Gly Gly Gly Gly Ser  Glu Val Arg Leu Arg  Glu Ser Gly
    1130                 1135                 1140

Gly Gly  Leu Val Lys Pro Gly  Gly Ser Leu Arg Leu  Ser Cys Ser
    1145                 1150                 1155

Ala Ser  Gly Phe Asp Phe Asp  Asn Ala Trp Met Thr  Trp Val Arg
    1160                 1165                 1170

Gln Pro  Pro Gly Lys Gly Leu  Glu Trp Val Gly Arg  Ile Thr Gly
    1175                 1180                 1185

Pro Gly  Glu Gly Trp Ser Val  Asp Tyr Ala Glu Ser  Val Lys Gly
    1190                 1195                 1200

Arg Phe  Thr Ile Ser Arg Asp  Asn Thr Lys Asn Thr  Leu Tyr Leu
    1205                 1210                 1215

Glu Met  Asn Asn Val Arg Thr  Glu Asp Thr Gly Tyr  Tyr Phe Cys
    1220                 1225                 1230

Ala Arg  Thr Gly Lys Tyr Tyr  Asp Phe Trp Phe Gly  Tyr Pro Pro
    1235                 1240                 1245

Gly Glu  Glu Tyr Phe Gln Asp  Trp Gly Gln Gly Thr  Leu Val Ile
    1250                 1255                 1260

Val Ser  Ser Gly Gly Gly Gly  Ser Gly Gly Gly Gly  Ser Gly Gly
    1265                 1270                 1275

Gly Gly  Ser Ser Glu Leu Thr  Gln Asp Pro Ala Val  Ser Val Ala
    1280                 1285                 1290

Leu Lys  Gln Thr Val Thr Ile  Thr Cys Arg Gly Asp  Ser Leu Arg
    1295                 1300                 1305

Ser His  Tyr Ala Ser Trp Tyr  Gln Lys Lys Pro Gly  Gln Ala Pro
    1310                 1315                 1320

Val Leu  Leu Phe Tyr Gly Lys  Asn Asn Arg Pro Ser  Gly Ile Pro
    1325                 1330                 1335

Asp Arg  Phe Ser Gly Ser Ala  Ser Gly Asn Arg Ala  Ser Leu Thr
    1340                 1345                 1350

Ile Thr  Gly Ala Gln Ala Glu  Asp Glu Ala Asp Tyr  Tyr Cys Ser
    1355                 1360                 1365

Ser Arg  Asp Lys Ser Gly Ser  Arg Leu Ser Val Phe  Gly Gly Gly
    1370                 1375                 1380

Thr Lys  Leu Thr Val Leu Gly  Ser Gly His His His  His His His
```

-continued 1385 1390 1395

<210> SEQ ID NO 91
<211> LENGTH: 4197
<212> TYPE: DNA
<213> ORGANISM: Artificial Sequence
<220> FEATURE:
<223> OTHER INFORMATION: Synthetic: PentaNAb4.0 Reverse ScFv DNA sequence

<400> SEQUENCE: 91
atgggctgga gctgcatcat cctgttcctg gtggcaaccg caacaggagt gcacagccag 60
gcacagctgg tgcagagcgg acccgaagtg agaaaacctg ggactagcgt caaagtgtca 120
tgtaaagccc ctggaaatac cctgaagacc tacgatctgc actgggtgcg gtccgtgcct 180
ggacagggcc tgcagtggat gggatggatc tctcacgagg gcgacaagaa agtgatcgtg 240
gagcggttca aggccaaggt gacaatcgat tgggacagat ccaccaacac agcctacctg 300
cagctgtctg gcctgaccag cggcgataca gccgtgtact actgtgccaa gggctctaag 360
caccggctga gagactacgc cctgtatgac gatgacggcg ccctgaactg ggccgtggat 420
gtggactatc tgtccaatct ggagttctgg ggacagggaa ccgcagtgac agtgagctcc 480
ggaggaggag gctccggcgg cggaggctct gggggaggcg gcagcgattt tgtgctgacc 540
cagtctccac acagcctgtc cgtgacaccc ggcgagtctg ccagcatctc ctgcaagtct 600
agccacagcc tgatccacgg cgacaggaac aattacctgg cctggtacgt gcagaagcca 660
ggccgcagcc ctcagctgct gatctatctg gcatcctcta gggcctccgg agtgccagat 720
cgcttctctg gcagcggctc cgataaggac tttaccctga agatcagccg ggtggagaca 780
gaggacgtgg gcacatacta ttgtatgcag ggccgagaat caccttggac atttgggcag 840
ggaactaaag ttgacatcaa aggggggggg ggctccggcg gcgggggctc tggcggcggc 900
ggcagcggag gaggcggctc cggaggaggc ggctctcaga tgcagctgca ggagagcgga 960
ccaggactgg tgaagccttc cgagaccctg tctctgacat gttctgtgag cggcgcctcc 1020
atctctgata gctactggag ctggatcaga cggagccctg gcaagggcct ggagtggatc 1080
ggctacgtgc acaagtctgg cgatacaaac tattccccat ctctgaagag ccgggtgaac 1140
ctgagcctgg acacctccaa gaatcaggtg agcctgtccc tggtggcagc aaccgcagca 1200
gacagcggca agtactattg cgccagaaca ctgcacggca ggcgcatcta cggcatcgtg 1260
gcctttaacg agtggttcac ctacttttat atggacgtgt ggggcaatgg cacccaggtg 1320
acagtgtcct ctggcggcgg cggctctggc ggaggaggca gcggaggagg aggcagctcc 1380
gacatctctg tggcacctgg agagaccgca aggatcagct gtggagagaa gtctctgggc 1440
agcagggccg tgcagtggta ccagcacagg gcaggacagg caccatccct gatcatctat 1500
aacaatcagg accggccatc tggcatcccc gagagattct ctggcagccc cgatagccct 1560
tttggcacca cagccaccct gacaatcacc tccgtggagg ccggcgacga agcagattac 1620
tattgccaca tctgggactc cagagtgcca accaagtggg tgttcggagg aggaaccaca 1680
ctgacagtgc tgggcggcgg aggctccggc gggggcggct ctggaggcgg cggcagcgga 1740
gggggcggct ccggcggcgg cggctctagg gcacacctgg tgcagagcgg aaccgcaatg 1800
aagaagcctg gcgcctctgt gcgcgtgagc tgtcagacat ccggctacac cttcaccgcc 1860
cacatcctgt tctggtttag gcaggcacca ggaagaggac tggagtgggt gggctggatc 1920
aagccccagt atggagcagt gaacttcgga ggaggctttc gggacagagt gacactgacc 1980

```
cgggacgtgt acagagagat cgcctatatg gatatcaggg gcctgaagcc cgacgatacc   2040

gccgtgtact attgcgccag ggaccgctcc tacggcgatt ctagctgggc actggacgca   2100

tggggacagg gaaccacagt ggtggtgagc gccggaggcg gggcagcgg cggcgggggc   2160

tccggaggcg gaggctctta catccacgtg acccagtccc cttcctctct gtccgtgtct   2220

atcggcgatc gcgtgaccat caactgtcag acaagccagg gagtgggctc cgacctgcac   2280

tggtatcagc acaagcctgg cagggcccca aagctgctga tccaccacac aagctccgtg   2340

gaggatggag tgccaagccg cttcagcggc tccggattcc acaccagctt taatctgaca   2400

atctccgacc tgcaggccga cgatatcgcc acctactatt gccaggtgct gcagttcttt   2460

ggcaggggct cccgcctgca catcaagggc ggcggcggct ctgggggcgg gggcagcggc   2520

gggggggct ccgggggagg aggctctggc ggagggggca gccagggcca gctggtgcag   2580

agcggagcag agctgaagaa gccaggagcc tctgtgaaga tcagctgtaa gacatccggc   2640

tatcggttca acttttatca catcaattgg atcaggcaga ccgcaggaag gggaccagag   2700

tggatgggct ggatctcccc ctactctggc gataagaacc tggccccagc cttccaggac   2760

agagtgatca tgaccacaga taccgaggtg ccagtgacca gcttcacctc caccggagcc   2820

gcctacatgg agatccggaa tctgaagttc gacgatacag gcacctattt ttgcgccaag   2880

ggcctgctga gagacggctc tagcacatgg ctgccatacc tgtggggaca gggcaccctg   2940

ctgacagtgt cctctggagg aggaggctcc gggggcggcg gctctggagg aggaggctct   3000

caaagcgtgc tgacccagtc cgcctctgtg agcggctccc tgggccagtc tgtgaccatc   3060

agctgtacag gccccaactc cgtgtgctgt tctcacaagt ctatcagctg gtaccagtgg   3120

ccaccaggaa gggcacctac cctgatcatc tatgaggaca atgagagggc accaggaatc   3180

agccctcgct tctccggcta caagtcttat tggagcgcct acctgaccat ttccgacctg   3240

cgccccgagg atgagaccac atactattgc tgtagctata cccacaactc cggctgcgtg   3300

tttggcacag gcaccaaggt gagcgtgctg ggaggagggg gctctggcgg cgggggcagc   3360

ggcggaggcg gctccggagg gggcggctct ggcggaggcg gcagcgaggt gcggctgcgg   3420

gagagcggcg gcggcctggt gaagccaggc ggctctctga gactgtcctg ttctgccagc   3480

ggcttcgact ttgataatgc ctggatgaca tgggtgcggc agcctcctgg caaggggctg   3540

gagtgggtgg gaagaatcac cggaccagga gagggatggt ctgtggacta cgccgagagc   3600

gtgaagggcc ggttcaccat cagcagagat aacactaaaa atacactgta tctggagatg   3660

aacaatgtgc ggaccgagga cacaggctac tatttctgcg ccagaaccgg caagtactat   3720

gatttctggt ttggctaccc ccctggcgag gagtattttc aggactgggg ccagggcacc   3780

ctggtcatcg tgagcagcgg cgggggaggc tccggcgggg ggggctctgg aggagggggc   3840

tctagcgagc tgacccagga ccccgccgtg tccgtggccc tgaagcagac agtgaccatc   3900

acatgcaggg gcgactccct gcgctctcac tacgccagct ggtatcagaa gaagccagga   3960

caggcacccg tgctgctgtt ctacggcaag aacaatcggc cttccggcat cccagataga   4020

ttttccggct ctgccagcgg aaacagggcc agcctgacca tcacaggagc acaggcagag   4080

gatgaagcag attactattg ttcctctcgg gacaagtccg gctctagact gagcgtgttc   4140

ggcggcggaa ccaagctgac agtgctggga tccggtcacc accatcacca ccactag      4197
```

<210> SEQ ID NO 92
<211> LENGTH: 1667
<212> TYPE: PRT
<213> ORGANISM: Artificial Sequence

```
<220> FEATURE:
<223> OTHER INFORMATION: Synthetic: HexaNAb1.0 Reverse ScFv
      (dB4C7/UB-421)-5X-PGDM1400-5X-PGT121-5X-N6-5X-35O22-5X-10E8v4 V5R
      S100cF-His

<400> SEQUENCE: 92

Met Gly Trp Ser Cys Ile Ile Leu Phe Leu Val Ala Thr Ala Thr Gly
1               5                   10                  15

Val His Ser Asp Ile Val Leu Thr Gln Ser Pro Ala Ser Leu Ala Val
            20                  25                  30

Ser Leu Gly Gln Arg Ala Thr Ile Thr Cys Lys Ala Gly Gln Ser Val
        35                  40                  45

Asp Tyr Asp Gly Asp Ser Tyr Met Asn Trp Tyr Gln Gln Lys Pro Gly
    50                  55                  60

Gln Pro Pro Lys Leu Leu Ile Tyr Val Ala Ser Asn Leu Glu Ser Gly
65                  70                  75                  80

Ile Pro Ala Arg Phe Ser Gly Ser Gly Ser Gly Thr Asp Phe Thr Leu
                85                  90                  95

Asn Ile His Pro Val Glu Glu Asn Asp Ala Ala Thr Tyr Tyr Cys Gln
            100                 105                 110

Gln Ser Tyr Lys Asp Pro Leu Thr Phe Gly Gln Gly Thr Lys Leu Glu
        115                 120                 125

Ile Lys Gly Gly Gly Gly Ser Gly Gly Gly Gly Ser Gly Gly Gly Gly
    130                 135                 140

Ser Gln Val Gln Leu Val Gln Ser Gly Pro Glu Leu Lys Lys Pro Gly
145                 150                 155                 160

Ala Ser Val Lys Val Ser Cys Lys Ala Ser Gly Tyr Thr Phe Thr Asp
                165                 170                 175

Tyr Val Ile His Trp Val Lys Gln Ala Thr Gly Gln Gly Leu Glu Trp
            180                 185                 190

Ile Gly Glu Ile Tyr Pro Gly Ser Gly Ser Ala Tyr Ser Asn Ala Lys
        195                 200                 205

Phe Lys Asp Arg Val Thr Met Thr Ala Asp Lys Ser Ser Asn Thr Ala
    210                 215                 220

Tyr Met Glu Leu Ser Ser Leu Thr Ser Asp Asp Thr Ala Val Tyr Phe
225                 230                 235                 240

Cys Ala Arg Arg Gly Asn Gly Thr Gly Phe Ala Tyr Trp Gly Gln Gly
                245                 250                 255

Thr Leu Val Thr Val Ser Ser Gly Gly Gly Gly Ser Gly Gly Gly Gly
            260                 265                 270

Ser Gly Gly Gly Gly Ser Gly Gly Gly Gly Ser Gly Gly Gly Gly Ser
        275                 280                 285

Gln Ala Gln Leu Val Gln Ser Gly Pro Glu Val Arg Lys Pro Gly Thr
    290                 295                 300

Ser Val Lys Val Ser Cys Lys Ala Pro Gly Asn Thr Leu Lys Thr Tyr
305                 310                 315                 320

Asp Leu His Trp Val Arg Ser Val Pro Gly Gln Gly Leu Gln Trp Met
                325                 330                 335

Gly Trp Ile Ser His Glu Gly Asp Lys Lys Val Ile Val Glu Arg Phe
            340                 345                 350

Lys Ala Lys Val Thr Ile Asp Trp Asp Arg Ser Thr Asn Thr Ala Tyr
        355                 360                 365

Leu Gln Leu Ser Gly Leu Thr Ser Gly Asp Thr Ala Val Tyr Tyr Cys
    370                 375                 380
```

-continued

```
Ala Lys Gly Ser Lys His Arg Leu Arg Asp Tyr Ala Leu Tyr Asp Asp
385                 390                 395                 400

Asp Gly Ala Leu Asn Trp Ala Val Asp Val Asp Tyr Leu Ser Asn Leu
                405                 410                 415

Glu Phe Trp Gly Gln Gly Thr Ala Val Thr Val Ser Ser Gly Gly Gly
            420                 425                 430

Gly Ser Gly Gly Gly Gly Ser Gly Gly Gly Gly Ser Asp Phe Val Leu
        435                 440                 445

Thr Gln Ser Pro His Ser Leu Ser Val Thr Pro Gly Glu Ser Ala Ser
    450                 455                 460

Ile Ser Cys Lys Ser Ser His Ser Leu Ile His Gly Asp Arg Asn Asn
465                 470                 475                 480

Tyr Leu Ala Trp Tyr Val Gln Lys Pro Gly Arg Ser Pro Gln Leu Leu
                485                 490                 495

Ile Tyr Leu Ala Ser Ser Arg Ala Ser Gly Val Pro Asp Arg Phe Ser
            500                 505                 510

Gly Ser Gly Ser Asp Lys Asp Phe Thr Leu Lys Ile Ser Arg Val Glu
        515                 520                 525

Thr Glu Asp Val Gly Thr Tyr Tyr Cys Met Gln Gly Arg Glu Ser Pro
    530                 535                 540

Trp Thr Phe Gly Gln Gly Thr Lys Val Asp Ile Lys Gly Gly Gly Gly
545                 550                 555                 560

Ser Gly Gly Gly Gly Ser Gly Gly Gly Gly Ser Gly Gly Gly Gly Ser
                565                 570                 575

Gly Gly Gly Gly Ser Gln Met Gln Leu Gln Glu Ser Gly Pro Gly Leu
            580                 585                 590

Val Lys Pro Ser Glu Thr Leu Ser Leu Thr Cys Ser Val Ser Gly Ala
        595                 600                 605

Ser Ile Ser Asp Ser Tyr Trp Ser Trp Ile Arg Arg Ser Pro Gly Lys
    610                 615                 620

Gly Leu Glu Trp Ile Gly Tyr Val His Lys Ser Gly Asp Thr Asn Tyr
625                 630                 635                 640

Ser Pro Ser Leu Lys Ser Arg Val Asn Leu Ser Leu Asp Thr Ser Lys
                645                 650                 655

Asn Gln Val Ser Leu Ser Leu Val Ala Ala Thr Ala Ala Asp Ser Gly
            660                 665                 670

Lys Tyr Tyr Cys Ala Arg Thr Leu His Gly Arg Arg Ile Tyr Gly Ile
        675                 680                 685

Val Ala Phe Asn Glu Trp Phe Thr Tyr Phe Tyr Met Asp Val Trp Gly
    690                 695                 700

Asn Gly Thr Gln Val Thr Val Ser Ser Gly Gly Gly Gly Ser Gly Gly
705                 710                 715                 720

Gly Gly Ser Gly Gly Gly Gly Ser Ser Asp Ile Ser Val Ala Pro Gly
                725                 730                 735

Glu Thr Ala Arg Ile Ser Cys Gly Glu Lys Ser Leu Gly Ser Arg Ala
            740                 745                 750

Val Gln Trp Tyr Gln His Arg Ala Gly Gln Ala Pro Ser Leu Ile Ile
        755                 760                 765

Tyr Asn Asn Gln Asp Arg Pro Ser Gly Ile Pro Glu Arg Phe Ser Gly
    770                 775                 780

Ser Pro Asp Ser Pro Phe Gly Thr Thr Ala Thr Leu Thr Ile Thr Ser
785                 790                 795                 800

Val Glu Ala Gly Asp Glu Ala Asp Tyr Tyr Cys His Ile Trp Asp Ser
```

-continued

```
                805                 810                 815

Arg Val Pro Thr Lys Trp Val Phe Gly Gly Gly Thr Thr Leu Thr Val
            820                 825                 830

Leu Gly Gly Gly Gly Ser Gly Gly Gly Gly Ser Gly Gly Gly Gly Ser
        835                 840                 845

Gly Gly Gly Gly Ser Gly Gly Gly Gly Ser Arg Ala His Leu Val Gln
    850                 855                 860

Ser Gly Thr Ala Met Lys Lys Pro Gly Ala Ser Val Arg Val Ser Cys
865                 870                 875                 880

Gln Thr Ser Gly Tyr Thr Phe Thr Ala His Ile Leu Phe Trp Phe Arg
                885                 890                 895

Gln Ala Pro Gly Arg Gly Leu Glu Trp Val Gly Trp Ile Lys Pro Gln
            900                 905                 910

Tyr Gly Ala Val Asn Phe Gly Gly Gly Phe Arg Asp Arg Val Thr Leu
        915                 920                 925

Thr Arg Asp Val Tyr Arg Glu Ile Ala Tyr Met Asp Ile Arg Gly Leu
    930                 935                 940

Lys Pro Asp Asp Thr Ala Val Tyr Tyr Cys Ala Arg Asp Arg Ser Tyr
945                 950                 955                 960

Gly Asp Ser Ser Trp Ala Leu Asp Ala Trp Gly Gln Gly Thr Thr Val
                965                 970                 975

Val Val Ser Ala Gly Gly Gly Gly Ser Gly Gly Gly Gly Ser Gly Gly
            980                 985                 990

Gly Gly Ser Tyr Ile His Val Thr  Gln Ser Pro Ser Ser  Leu Ser Val
        995                 1000                1005

Ser Ile  Gly Asp Arg Val Thr  Ile Asn Cys Gln Thr  Ser Gln Gly
    1010                1015                1020

Val Gly  Ser Asp Leu His Trp  Tyr Gln His Lys Pro  Gly Arg Ala
    1025                1030                1035

Pro Lys  Leu Leu Ile His His  Thr Ser Ser Val Glu  Asp Gly Val
    1040                1045                1050

Pro Ser  Arg Phe Ser Gly Ser  Gly Phe His Thr Ser  Phe Asn Leu
    1055                1060                1065

Thr Ile  Ser Asp Leu Gln Ala  Asp Asp Ile Ala Thr  Tyr Tyr Cys
    1070                1075                1080

Gln Val  Leu Gln Phe Phe Gly  Arg Gly Ser Arg Leu  His Ile Lys
    1085                1090                1095

Gly Gly  Gly Gly Ser Gly Gly  Gly Gly Ser Gly Gly  Gly Gly Ser
    1100                1105                1110

Gly Gly  Gly Gly Ser Gly Gly  Gly Gly Ser Gln Gly  Gln Leu Val
    1115                1120                1125

Gln Ser  Gly Ala Glu Leu Lys  Lys Pro Gly Ala Ser  Val Lys Ile
    1130                1135                1140

Ser Cys  Lys Thr Ser Gly Tyr  Arg Phe Asn Phe Tyr  His Ile Asn
    1145                1150                1155

Trp Ile  Arg Gln Thr Ala Gly  Arg Gly Pro Glu Trp  Met Gly Trp
    1160                1165                1170

Ile Ser  Pro Tyr Ser Gly Asp  Lys Asn Leu Ala Pro  Ala Phe Gln
    1175                1180                1185

Asp Arg  Val Ile Met Thr Thr  Asp Thr Glu Val Pro  Val Thr Ser
    1190                1195                1200

Phe Thr  Ser Thr Gly Ala Ala  Tyr Met Glu Ile Arg  Asn Leu Lys
    1205                1210                1215
```

Phe Asp Asp Thr Gly Thr Tyr Phe Cys Ala Lys Gly Leu Leu Arg
1220 1225 1230

Asp Gly Ser Ser Thr Trp Leu Pro Tyr Leu Trp Gly Gln Gly Thr
1235 1240 1245

Leu Leu Thr Val Ser Ser Gly Gly Gly Gly Ser Gly Gly Gly Gly
1250 1255 1260

Ser Gly Gly Gly Gly Ser Gln Ser Val Leu Thr Gln Ser Ala Ser
1265 1270 1275

Val Ser Gly Ser Leu Gly Gln Ser Val Thr Ile Ser Cys Thr Gly
1280 1285 1290

Pro Asn Ser Val Cys Cys Ser His Lys Ser Ile Ser Trp Tyr Gln
1295 1300 1305

Trp Pro Pro Gly Arg Ala Pro Thr Leu Ile Ile Tyr Glu Asp Asn
1310 1315 1320

Glu Arg Ala Pro Gly Ile Ser Pro Arg Phe Ser Gly Tyr Lys Ser
1325 1330 1335

Tyr Trp Ser Ala Tyr Leu Thr Ile Ser Asp Leu Arg Pro Glu Asp
1340 1345 1350

Glu Thr Thr Tyr Tyr Cys Cys Ser Tyr Thr His Asn Ser Gly Cys
1355 1360 1365

Val Phe Gly Thr Gly Thr Lys Val Ser Val Leu Gly Gly Gly Gly
1370 1375 1380

Ser Gly Gly Gly Gly Ser Gly Gly Gly Gly Ser Gly Gly Gly Gly
1385 1390 1395

Ser Gly Gly Gly Gly Ser Glu Val Arg Leu Arg Glu Ser Gly Gly
1400 1405 1410

Gly Leu Val Lys Pro Gly Gly Ser Leu Arg Leu Ser Cys Ser Ala
1415 1420 1425

Ser Gly Phe Asp Phe Asp Asn Ala Trp Met Thr Trp Val Arg Gln
1430 1435 1440

Pro Pro Gly Lys Gly Leu Glu Trp Val Gly Arg Ile Thr Gly Pro
1445 1450 1455

Gly Glu Gly Trp Ser Val Asp Tyr Ala Glu Ser Val Lys Gly Arg
1460 1465 1470

Phe Thr Ile Ser Arg Asp Asn Thr Lys Asn Thr Leu Tyr Leu Glu
1475 1480 1485

Met Asn Asn Val Arg Thr Glu Asp Thr Gly Tyr Tyr Phe Cys Ala
1490 1495 1500

Arg Thr Gly Lys Tyr Tyr Asp Phe Trp Phe Gly Tyr Pro Pro Gly
1505 1510 1515

Glu Glu Tyr Phe Gln Asp Trp Gly Gln Gly Thr Leu Val Ile Val
1520 1525 1530

Ser Ser Gly Gly Gly Gly Ser Gly Gly Gly Gly Ser Gly Gly Gly
1535 1540 1545

Gly Ser Ser Glu Leu Thr Gln Asp Pro Ala Val Ser Val Ala Leu
1550 1555 1560

Lys Gln Thr Val Thr Ile Thr Cys Arg Gly Asp Ser Leu Arg Ser
1565 1570 1575

His Tyr Ala Ser Trp Tyr Gln Lys Lys Pro Gly Gln Ala Pro Val
1580 1585 1590

Leu Leu Phe Tyr Gly Lys Asn Asn Arg Pro Ser Gly Ile Pro Asp
1595 1600 1605

-continued

```
Arg Phe  Ser Gly Ser Ala Ser  Gly Asn Arg Ala Ser  Leu Thr Ile
    1610                 1615                 1620

Thr Gly  Ala Gln Ala Glu Asp  Glu Ala Asp Tyr Tyr  Cys Ser Ser
    1625                 1630                 1635

Arg Asp  Lys Ser Gly Ser Arg  Leu Ser Val Phe Gly  Gly Gly Thr
    1640                 1645                 1650

Lys Leu  Thr Val Leu Gly Ser  Gly His His His His  His His
    1655                 1660                 1665
```

<210> SEQ ID NO 93
<211> LENGTH: 5004
<212> TYPE: DNA
<213> ORGANISM: Artificial Sequence
<220> FEATURE:
<223> OTHER INFORMATION: Synthetic: HexaNAb1.0 Reverse ScFv DNA sequence

<400> SEQUENCE: 93

```
atgggctgga gctgcatcat cctgttcctg gtggcaaccg caacaggagt gcacagcgac     60

atcgtgctga cccagtctcc tgccagcctg gccgtgagcc tgggacagag ggccaccatc    120

acatgcaagg ccggccagtc tgtggactac gatggcgaca gctacatgaa ctggtatcag    180

cagaagccag gccagccccc taagctgctg atctatgtgg cctccaatct ggagtctggc    240

atccctgcac gcttcagcgg ctccggctct ggaaccgact tcaccctgaa catccaccca    300

gtggaggaga atgacgccgc cacctactat tgccagcaga gctacaagga ccccctgacc    360

ttcggccagg gcacaaagct ggagatcaag ggaggaggag gcagcggggg aggaggctcc    420

ggaggcggcg gctctcaggt gcagctggtg cagtccggac cagagctgaa gaagccagga    480

gccagcgtga aggtgtcctg taaggcctct ggctacacct tcacagatta tgtgatccac    540

tgggtgaagc aggcaacagg acagggcctg gagtggatcg gagagatcta cccaggcagc    600

ggctccgcct attccaacgc caagtttaag gatcgggtga ccatgacagc cgacaagagc    660

tccaataccg cctatatgga gctgtctagc ctgacctctg acgatacagc cgtgtacttc    720

tgtgcccgga gaggcaacgg cacaggcttt gcctattggg gccagggcac cctggtgaca    780

gtgtcctctg gaggaggagg cagcggcggc ggcggctccg gaggaggcgg ctctggcggc    840

ggcggcagcg gaggaggcgg ctcccaggca cagctggtgc agagcggacc cgaagtgaga    900

aaacctggga ctagcgtcaa agtgtcatgt aaagcccctg gaaataccct gaagacctac    960

gatctgcact gggtgcggtc cgtgcctgga cagggcctgc agtggatggg atggatctct   1020

cacgagggcg acaagaaagt gatcgtggag cggttcaagg ccaaggtgac aatcgattgg   1080

gacagatcca ccaacacagc ctacctgcag ctgtctggcc tgaccagcgg cgatacagcc   1140

gtgtactact gtgccaaggg ctctaagcac cggctgagag actacgccct gtatgacgat   1200

gacggcgccc tgaactgggc cgtggatgtg gactatctgt ccaatctgga gttctgggga   1260

cagggaaccg cagtgacagt gagctccgga ggaggaggct ccggcggcgg aggctctggg   1320

ggaggcggca gcgattttgt gctgacccag tctccacaca gcctgtccgt gacacccggc   1380

gagtctgcca gcatctcctg caagtctagc cacagcctga tccacggcga caggaacaat   1440

tacctggcct ggtacgtgca gaagccaggc cgcagccctc agctgctgat ctatctggca   1500

tcctctaggg cctccggagt gccagatcgc ttctctggca gcggctccga taaggacttt   1560

accctgaaga tcagccgggt ggagacagag gacgtgggca catactattg tatgcagggc   1620

cgagaatcac cttggacatt tgggcaggga actaaagttg acatcaaagg ggggggggc    1680

tccggcggcg gggctctgg cggcggcggc agcggaggag gcggctccgg aggaggcggc   1740
```

tctcagatgc agctgcagga gagcggacca ggactggtga agccttccga gaccctgtct 1800
ctgacatgtt ctgtgagcgg cgcctccatc tctgatagct actggagctg gatcagacgg 1860
agccctggca agggcctgga gtggatcggc tacgtgcaca agtctggcga tacaaactat 1920
tccccatctc tgaagagccg ggtgaacctg agcctggaca cctccaagaa tcaggtgagc 1980
ctgtccctgg tggcagcaac cgcagcagac agcggcaagt actattgcgc cagaacactg 2040
cacggcaggc gcatctacgg catcgtggcc tttaacgagt ggttcaccta cttttatatg 2100
gacgtgtggg gcaatggcac ccaggtgaca gtgtcctctg gcggcggcgg ctctggcgga 2160
ggaggcagcg gaggaggagg cagctccgac atctctgtgg cacctggaga gaccgcaagg 2220
atcagctgtg gagagaagtc tctgggcagc agggccgtgc agtggtacca gcacagggca 2280
ggacaggcac catccctgat catctataac aatcaggacc ggccatctgg catccccgag 2340
agattctctg gcagccccga tagccctttt ggcaccacag ccaccctgac aatcacctcc 2400
gtggaggccg gcgacgaagc agattactat tgccacatct gggactccag agtgccaacc 2460
aagtgggtgt tcggaggagg aaccacactg acagtgctgg gcggcggagg ctccggcggg 2520
ggcggctctg gaggcggcgg cagcggaggg ggcggctccg gcggcggcgg ctctagggca 2580
cacctggtgc agagcggaac cgcaatgaag aagcctggcg cctctgtgcg cgtgagctgt 2640
cagacatccg gctacacctt caccgcccac atcctgttct ggtttaggca ggcaccagga 2700
agaggactgg agtgggtggg ctggatcaag ccccagtatg gagcagtgaa cttcggagga 2760
ggctttcggg acagagtgac actgacccgg gacgtgtaca gagagatcgc ctatatggat 2820
atcaggggcc tgaagcccga cgataccgcc gtgtactatt gcgccaggga ccgctcctac 2880
ggcgattcta gctgggcact ggacgcatgg ggacagggaa ccacagtggt ggtgagcgcc 2940
ggaggcgggg gcagcggcgg cgggggctcc ggaggcggag gctcttacat ccacgtgacc 3000
cagtcccctt cctctctgtc cgtgtctatc ggcgatcgcg tgaccatcaa ctgtcagaca 3060
agccagggag tgggctccga cctgcactgg tatcagcaca agcctggcag ggccccaaag 3120
ctgctgatcc accacacaag ctccgtggag gatggagtgc caagccgctt cagcggctcc 3180
ggattccaca ccagctttaa tctgacaatc tccgacctgc aggccgacga tatcgccacc 3240
tactattgcc aggtgctgca gttctttggc aggggctccc gcctgcacat caagggcggc 3300
ggcggctctg gggcggggg cagcggcggg gggggctccg ggggaggagg ctctggcgga 3360
gggggcagcc agggccagct ggtgcagagc ggagcagagc tgaagaagcc aggagcctct 3420
gtgaagatca gctgtaagac atccggctat cggttcaact tttatcacat caattggatc 3480
aggcagaccg caggaagggg accagagtgg atgggctgga tctcccccta ctctggcgat 3540
aagaacctgg ccccagcctt ccaggacaga gtgatcatga ccacagatac cgaggtgcca 3600
gtgaccagct tcacctccac cggagccgcc tacatggaga tccggaatct gaagttcgac 3660
gatacaggca cctatttttg cgccaagggc ctgctgagag acggctctag cacatggctg 3720
ccatacctgt ggggacaggg caccctgctg acagtgtcct ctggaggagg aggctccggg 3780
ggcggcggct ctggaggagg aggctctcaa agcgtgctga cccagtccgc ctctgtgagc 3840
ggctccctgg gccagtctgt gaccatcagc tgtacaggcc ccaactccgt gtgctgttct 3900
cacaagtcta tcagctggta ccagtggcca ccaggaaggg cacctaccct gatcatctat 3960
gaggacaatg agagggcacc aggaatcagc cctcgcttct ccggctacaa gtcttattgg 4020
agcgcctacc tgaccatttc cgacctgcgc cccgaggatg agaccacata ctattgctgt 4080

-continued

```
agctataccc acaactccgg ctgcgtgttt ggcacaggca ccaaggtgag cgtgctggga   4140

ggagggggct ctggcggcgg gggcagcggc ggaggcggct ccggaggggg cggctctggc   4200

ggaggcggca gcgaggtgcg gctgcgggag agcggcggcg gcctggtgaa gccaggcggc   4260

tctctgagac tgtcctgttc tgccagcggc ttcgactttg ataatgcctg gatgacatgg   4320

gtgcggcagc ctcctggcaa ggggctggag tgggtgggaa gaatcaccgg accaggagag   4380

ggatggtctg tggactacgc cgagagcgtg aagggccggt tcaccatcag cagagataac   4440

actaaaaata cactgtatct ggagatgaac aatgtgcgga ccgaggacac aggctactat   4500

ttctgcgcca gaaccggcaa gtactatgat ttctggtttg gctacccccc tggcgaggag   4560

tattttcagg actggggcca gggcaccctg gtcatcgtga gcagcggcgg gggaggctcc   4620

ggcggggggg gctctggagg agggggctct agcgagctga cccaggaccc cgccgtgtcc   4680

gtggccctga agcagacagt gaccatcaca tgcaggggcg actccctgcg ctctcactac   4740

gccagctggt atcagaagaa gccaggacag gcacccgtgc tgctgttcta cggcaagaac   4800

aatcggcctt ccggcatccc agatagattt tccggctctg ccagcggaaa cagggccagc   4860

ctgaccatca caggagcaca ggcagaggat gaagcagatt actattgttc ctctcgggac   4920

aagtccggct ctagactgag cgtgttcggc ggcggaacca agctgacagt gctgggatcc   4980

ggtcaccacc atcaccacca ctag                                           5004
```

<210> SEQ ID NO 94
<211> LENGTH: 1041
<212> TYPE: PRT
<213> ORGANISM: Artificial Sequence
<220> FEATURE:
<223> OTHER INFORMATION: Synthetic: PentaNAb4.0 Stem HC LS_v2 Amino acid sequence

<400> SEQUENCE: 94

```
Met Gly Trp Ser Cys Ile Ile Leu Phe Leu Val Ala Thr Ala Thr Gly
1               5                   10                  15

Val His Ser Gln Ala Gln Leu Val Gln Ser Gly Pro Glu Val Arg Lys
            20                  25                  30

Pro Gly Thr Ser Val Lys Val Ser Cys Lys Ala Pro Gly Asn Thr Leu
        35                  40                  45

Lys Thr Tyr Asp Leu His Trp Val Arg Ser Val Pro Gly Gln Gly Leu
    50                  55                  60

Gln Trp Met Gly Trp Ile Ser His Glu Gly Asp Lys Lys Val Ile Val
65                  70                  75                  80

Glu Arg Phe Lys Ala Lys Val Thr Ile Asp Trp Asp Arg Ser Thr Asn
                85                  90                  95

Thr Ala Tyr Leu Gln Leu Ser Gly Leu Thr Ser Gly Asp Thr Ala Val
            100                 105                 110

Tyr Tyr Cys Ala Lys Gly Ser Lys His Arg Leu Arg Asp Tyr Ala Leu
        115                 120                 125

Tyr Asp Asp Asp Gly Ala Leu Asn Trp Ala Val Asp Val Asp Tyr Leu
    130                 135                 140

Ser Asn Leu Glu Phe Trp Gly Gln Gly Thr Ala Val Thr Val Ser Ser
145                 150                 155                 160

Gly Gly Gly Gly Ser Gly Gly Gly Gly Ser Gly Gly Gly Gly Ser Asp
                165                 170                 175

Phe Val Leu Thr Gln Ser Pro His Ser Leu Ser Val Thr Pro Gly Glu
            180                 185                 190
```

-continued

```
Ser Ala Ser Ile Ser Cys Lys Ser Ser His Ser Leu Ile His Gly Asp
        195                 200                 205

Arg Asn Asn Tyr Leu Ala Trp Tyr Val Gln Lys Pro Gly Arg Ser Pro
    210                 215                 220

Gln Leu Leu Ile Tyr Leu Ala Ser Ser Arg Ala Ser Gly Val Pro Asp
225                 230                 235                 240

Arg Phe Ser Gly Ser Gly Ser Asp Lys Asp Phe Thr Leu Lys Ile Ser
                245                 250                 255

Arg Val Glu Thr Glu Asp Val Gly Thr Tyr Tyr Cys Met Gln Gly Arg
            260                 265                 270

Glu Ser Pro Trp Thr Phe Gly Gln Gly Thr Lys Val Asp Ile Lys Gly
        275                 280                 285

Gly Gly Gly Ser Gly Gly Gly Gly Ser Gly Gly Gly Gly Ser Gly Gly
    290                 295                 300

Gly Gly Ser Gly Gly Gly Gly Ser Gln Met Gln Leu Gln Glu Ser Gly
305                 310                 315                 320

Pro Gly Leu Val Lys Pro Ser Glu Thr Leu Ser Leu Thr Cys Ser Val
                325                 330                 335

Ser Gly Ala Ser Ile Ser Asp Ser Tyr Trp Ser Trp Ile Arg Arg Ser
            340                 345                 350

Pro Gly Lys Gly Leu Glu Trp Ile Gly Tyr Val His Lys Ser Gly Asp
        355                 360                 365

Thr Asn Tyr Ser Pro Ser Leu Lys Ser Arg Val Asn Leu Ser Leu Asp
    370                 375                 380

Thr Ser Lys Asn Gln Val Ser Leu Ser Leu Val Ala Ala Thr Ala Ala
385                 390                 395                 400

Asp Ser Gly Lys Tyr Tyr Cys Ala Arg Thr Leu His Gly Arg Arg Ile
                405                 410                 415

Tyr Gly Ile Val Ala Phe Asn Glu Trp Phe Thr Tyr Phe Tyr Met Asp
            420                 425                 430

Val Trp Gly Asn Gly Thr Gln Val Thr Val Ser Ser Gly Gly Gly Gly
        435                 440                 445

Ser Gly Gly Gly Gly Ser Gly Gly Gly Gly Ser Ser Asp Ile Ser Val
    450                 455                 460

Ala Pro Gly Glu Thr Ala Arg Ile Ser Cys Gly Glu Lys Ser Leu Gly
465                 470                 475                 480

Ser Arg Ala Val Gln Trp Tyr Gln His Arg Ala Gly Gln Ala Pro Ser
                485                 490                 495

Leu Ile Ile Tyr Asn Asn Gln Asp Arg Pro Ser Gly Ile Pro Glu Arg
            500                 505                 510

Phe Ser Gly Ser Pro Asp Ser Pro Phe Gly Thr Thr Ala Thr Leu Thr
        515                 520                 525

Ile Thr Ser Val Glu Ala Gly Asp Glu Ala Asp Tyr Tyr Cys His Ile
    530                 535                 540

Trp Asp Ser Arg Val Pro Thr Lys Trp Val Phe Gly Gly Gly Thr Thr
545                 550                 555                 560

Leu Thr Val Leu Gly Gly Gly Gly Ser Gly Gly Gly Gly Ser Gly Gly
                565                 570                 575

Gly Gly Ser Gly Gly Gly Gly Ser Gly Gly Gly Gly Ser Arg Ala His
            580                 585                 590

Leu Val Gln Ser Gly Thr Ala Met Lys Lys Pro Gly Ala Ser Val Arg
        595                 600                 605

Val Ser Cys Gln Thr Ser Gly Tyr Thr Phe Thr Ala His Ile Leu Phe
```

-continued

```
    610                 615                 620

Trp Phe Arg Gln Ala Pro Gly Arg Gly Leu Glu Trp Val Gly Trp Ile
625                 630                 635                 640

Lys Pro Gln Tyr Gly Ala Val Asn Phe Gly Gly Gly Phe Arg Asp Arg
                645                 650                 655

Val Thr Leu Thr Arg Asp Val Tyr Arg Glu Ile Ala Tyr Met Asp Ile
            660                 665                 670

Arg Gly Leu Lys Pro Asp Asp Thr Ala Val Tyr Tyr Cys Ala Arg Asp
        675                 680                 685

Arg Ser Tyr Gly Asp Ser Ser Trp Ala Leu Asp Ala Trp Gly Gln Gly
    690                 695                 700

Thr Thr Val Val Val Ser Ala Ala Ser Thr Lys Gly Pro Ser Val Phe
705                 710                 715                 720

Pro Leu Ala Pro Ser Ser Lys Ser Thr Ser Gly Gly Thr Ala Ala Leu
                725                 730                 735

Gly Cys Leu Val Lys Asp Tyr Phe Pro Glu Pro Val Thr Val Ser Trp
            740                 745                 750

Asn Ser Gly Ala Leu Thr Ser Gly Val His Thr Phe Pro Ala Val Leu
        755                 760                 765

Gln Ser Ser Gly Leu Tyr Ser Leu Ser Ser Val Val Thr Val Pro Ser
    770                 775                 780

Ser Ser Leu Gly Thr Gln Thr Tyr Ile Cys Asn Val Asn His Lys Pro
785                 790                 795                 800

Ser Asn Thr Lys Val Asp Lys Lys Val Glu Pro Lys Ser Cys Asp Lys
                805                 810                 815

Thr His Thr Cys Pro Pro Cys Pro Ala Pro Glu Leu Leu Gly Gly Pro
            820                 825                 830

Ser Val Phe Leu Phe Pro Pro Lys Pro Lys Asp Thr Leu Met Ile Ser
        835                 840                 845

Arg Thr Pro Glu Val Thr Cys Val Val Val Asp Val Ser His Glu Asp
    850                 855                 860

Pro Glu Val Lys Phe Asn Trp Tyr Val Asp Gly Val Glu Val His Asn
865                 870                 875                 880

Ala Lys Thr Lys Pro Arg Glu Glu Gln Tyr Asn Ser Thr Tyr Arg Val
                885                 890                 895

Val Ser Val Leu Thr Val Leu His Gln Asp Trp Leu Asn Gly Lys Glu
            900                 905                 910

Tyr Lys Cys Lys Val Ser Asn Lys Ala Leu Pro Ala Pro Ile Glu Lys
        915                 920                 925

Thr Ile Ser Lys Ala Lys Gly Gln Pro Arg Glu Pro Gln Val Tyr Thr
    930                 935                 940

Leu Pro Pro Ser Arg Glu Glu Met Thr Lys Asn Gln Val Ser Leu Thr
945                 950                 955                 960

Cys Leu Val Lys Gly Phe Tyr Pro Ser Asp Ile Ala Val Glu Trp Glu
                965                 970                 975

Ser Asn Gly Gln Pro Glu Asn Asn Tyr Lys Thr Thr Pro Pro Val Leu
            980                 985                 990

Asp Ser Asp Gly Ser Phe Phe Leu  Tyr Ser Lys Leu Thr  Val Asp Lys
        995                 1000                1005

Ser Arg  Trp Gln Gln Gly Asn  Val Phe Ser Cys Ser  Val Leu His
    1010                1015                1020

Glu Ala  Leu His Ser His Tyr  Thr Gln Lys Ser Leu  Ser Leu Ser
    1025                1030                1035
```

```
Pro Gly  Lys
    1040


<210> SEQ ID NO 95
<211> LENGTH: 3126
<212> TYPE: DNA
<213> ORGANISM: Artificial Sequence
<220> FEATURE:
<223> OTHER INFORMATION: Synthetic: PentaNAb4.0 Stem HC LS_v2 DNA
      sequence

<400> SEQUENCE: 95

atgggctgga gctgcatcat cctgttcctg gtggcaaccg caaccggtgt gcacagccag     60

gcacagctgg tgcagagcgg acccgaagtg agaaaacctg ggactagcgt caaagtgtca    120

tgtaaagccc ctggaaatac cctgaagacc tacgatctgc actgggtgcg gtccgtgcct    180

ggacagggcc tgcagtggat gggatggatc tctcacgagg gcgacaagaa agtgatcgtg    240

gagcggttca aggccaaggt gacaatcgat tgggacagat ccaccaacac agcctacctg    300

cagctgtctg gcctgaccag cggcgataca gccgtgtact actgtgccaa gggctctaag    360

caccggctga gagactacgc cctgtatgac gatgacggcg ccctgaactg ggccgtggat    420

gtggactatc tgtccaatct ggagttctgg ggacagggaa ccgcagtgac agtgagctcc    480

ggaggaggag gctccggcgg cggaggctct gggggaggcg gcagcgattt tgtgctgacc    540

cagtctccac acagcctgtc cgtgacaccc ggcgagtctg ccagcatctc ctgcaagtct    600

agccacagcc tgatccacgg cgacaggaac aattacctgg cctggtacgt gcagaagcca    660

ggccgcagcc ctcagctgct gatctatctg gcatcctcta gggcctccgg agtgccagat    720

cgcttctctg gcagcggctc cgataaggac tttaccctga agatcagccg ggtggagaca    780

gaggacgtgg gcacatacta ttgtatgcag ggccgagaat caccttggac atttgggcag    840

ggaactaaag ttgacatcaa aggggggggg ggctccggcg gcgggggctc tggcggcggc    900

ggcagcggag gaggcggctc cggaggaggc ggctctcaga tgcagctgca ggagagcgga    960

ccaggactgg tgaagccttc cgagaccctg tctctgacat gttctgtgag cggcgcctcc   1020

atctctgata gctactggag ctggatcaga cggagccctg gcaagggcct ggagtggatc   1080

ggctacgtgc acaagtctgg cgatacaaac tattccccat ctctgaagag ccgggtgaac   1140

ctgagcctgg acacctccaa gaatcaggtg agcctgtccc tggtggcagc aaccgcagca   1200

gacagcggca agtactattg cgccagaaca ctgcacggca ggcgcatcta cggcatcgtg   1260

gcctttaacg agtggttcac ctacttttat atggacgtgt ggggcaatgg cacccaggtg   1320

acagtgtcct ctggcggcgg cggctctggc ggaggaggca gcggaggagg aggcagctcc   1380

gacatctctg tggcacctgg agagaccgca aggatcagct gtggagagaa gtctctgggc   1440

agcagggccg tgcagtggta ccagcacagg gcaggacagg caccatccct gatcatctat   1500

aacaatcagg accggccatc tggcatcccc gagagattct ctggcagccc cgatagccct   1560

tttggcacca cagccaccct gacaatcacc tccgtggagg ccggcgacga agcagattac   1620

tattgccaca tctgggactc cagagtgcca accaagtggg tgttcggagg aggaaccaca   1680

ctgacagtgc tgggcggcgg aggctccggc gggggcggct ctggaggcgg cggcagcgga   1740

gggggcggct ccggcggcgg cggctctagg gcacacctgg tgcagagcgg aaccgcaatg   1800

aagaagcctg gcgcctctgt gcgcgtgagc tgtcagacat ccggctacac cttcaccgcc   1860

cacatcctgt tctggtttag gcaggcacca ggaagaggac tggagtgggt gggctggatc   1920
```

```
aagccccagt atggagcagt gaacttcgga ggaggctttc gggacagagt gacactgacc   1980
cgggacgtgt acagagagat cgcctatatg gatatcaggg gcctgaagcc cgacgatacc   2040
gccgtgtact attgcgccag ggaccgctcc tacggcgatt ctagctgggc actggacgca   2100
tggggacagg gaaccacagt ggtggtgagc gccgcgtcga ccaagggccc atcggtcttc   2160
cccctggcac cctcctccaa gagcacctct gggggcacag cggccctggg ctgcctggtc   2220
aaggactact tccccgaacc tgtgacggtg tcgtggaact caggcgccct gaccagcggc   2280
gtgcacacct tcccggctgt cctacagtcc tcaggactct actccctcag cagcgtggtg   2340
accgtgccct ccagcagctt gggcacccag acctacatct gcaacgtgaa tcacaagccc   2400
agcaacacca aggtggacaa gaaagttgag cccaaatctt gtgacaaaac tcacacatgc   2460
ccaccgtgcc cagcacctga actcctgggg ggaccgtcag tcttcctctt ccccccaaaa   2520
cccaaggaca ccctcatgat ctcccggacc cctgaggtca catgcgtggt ggtggacgtg   2580
agccacgaag accctgaggt caagttcaac tggtacgtgg acggcgtgga ggtgcataat   2640
gccaagacaa agccgcggga ggagcagtac aacagcacgt accgtgtggt cagcgtcctc   2700
accgtcctgc accaggactg gctgaatggc aaggagtaca agtgcaaggt ctccaacaaa   2760
gccctcccag cccccatcga gaaaaccatc tccaaagcca aagggcagcc ccgagaacca   2820
caggtgtaca ccctgccccc atcccgggag gagatgacca agaaccaggt cagcctgacc   2880
tgcctggtca aaggcttcta tcccagcgac atcgccgtgg agtgggagag caatgggcag   2940
ccggagaaca actacaagac cacgcctccc gtgctggact ccgacggctc cttcttcctc   3000
tacagcaagc tcaccgtgga caagagcagg tggcagcagg ggaacgtctt ctcatgctcc   3060
gtgctgcatg aggctctgca cagccactac acgcagaaga gcctctccct gtctccgggt   3120
aaatga                                                              3126
```

```
<210> SEQ ID NO 96
<211> LENGTH: 789
<212> TYPE: PRT
<213> ORGANISM: Artificial Sequence
<220> FEATURE:
<223> OTHER INFORMATION: Synthetic: PentaNAb4.0 Stem HC LS_v2 (light
      chain) N6 KC-CK-35O22-5X-10E8v4 S100cF

<400> SEQUENCE: 96

Met Gly Trp Ser Cys Ile Ile Leu Phe Leu Val Ala Thr Ala Thr Gly
1               5                   10                  15

Val His Ser Tyr Ile His Val Thr Gln Ser Pro Ser Ser Leu Ser Val
            20                  25                  30

Ser Ile Gly Asp Arg Val Thr Ile Asn Cys Gln Thr Ser Gln Gly Val
        35                  40                  45

Gly Ser Asp Leu His Trp Tyr Gln His Lys Pro Gly Arg Ala Pro Lys
    50                  55                  60

Leu Leu Ile His His Thr Ser Ser Val Glu Asp Gly Val Pro Ser Arg
65                  70                  75                  80

Phe Ser Gly Ser Gly Phe His Thr Ser Phe Asn Leu Thr Ile Ser Asp
                85                  90                  95

Leu Gln Ala Asp Asp Ile Ala Thr Tyr Tyr Cys Gln Val Leu Gln Phe
            100                 105                 110

Phe Gly Arg Gly Ser Arg Leu His Ile Lys Arg Thr Val Ala Ala Pro
        115                 120                 125

Ser Val Phe Ile Phe Pro Pro Ser Asp Glu Gln Leu Lys Ser Gly Thr
    130                 135                 140
```

```
Ala Ser Val Val Cys Leu Leu Asn Asn Phe Tyr Pro Arg Glu Ala Lys
145                 150                 155                 160

Val Gln Trp Lys Val Asp Asn Ala Leu Gln Ser Gly Asn Ser Gln Glu
                165                 170                 175

Ser Val Thr Glu Gln Asp Ser Lys Asp Ser Thr Tyr Ser Leu Ser Ser
            180                 185                 190

Thr Leu Thr Leu Ser Lys Ala Asp Tyr Glu Lys His Lys Val Tyr Ala
        195                 200                 205

Cys Glu Val Thr His Gln Gly Leu Ser Ser Pro Val Thr Lys Ser Phe
    210                 215                 220

Asn Arg Gly Glu Cys Gly Gly Gly Gly Ser Gly Gly Gly Gly Ser Gly
225                 230                 235                 240

Gly Gly Gly Ser Gly Gly Gly Gly Ser Gly Gly Gly Gly Ser Gln Gly
                245                 250                 255

Gln Leu Val Gln Ser Gly Ala Glu Leu Lys Lys Pro Gly Ala Ser Val
            260                 265                 270

Lys Ile Ser Cys Lys Thr Ser Gly Tyr Arg Phe Asn Phe Tyr His Ile
        275                 280                 285

Asn Trp Ile Arg Gln Thr Ala Gly Arg Gly Pro Glu Trp Met Gly Trp
    290                 295                 300

Ile Ser Pro Tyr Ser Gly Asp Lys Asn Leu Ala Pro Ala Phe Gln Asp
305                 310                 315                 320

Arg Val Ile Met Thr Thr Asp Thr Glu Val Pro Val Thr Ser Phe Thr
                325                 330                 335

Ser Thr Gly Ala Ala Tyr Met Glu Ile Arg Asn Leu Lys Phe Asp Asp
            340                 345                 350

Thr Gly Thr Tyr Phe Cys Ala Lys Gly Leu Leu Arg Asp Gly Ser Ser
        355                 360                 365

Thr Trp Leu Pro Tyr Leu Trp Gly Gln Gly Thr Leu Leu Thr Val Ser
    370                 375                 380

Ser Gly Gly Gly Gly Ser Gly Gly Gly Gly Ser Gly Gly Gly Gly Ser
385                 390                 395                 400

Gln Ser Val Leu Thr Gln Ser Ala Ser Val Ser Gly Ser Leu Gly Gln
                405                 410                 415

Ser Val Thr Ile Ser Cys Thr Gly Pro Asn Ser Val Cys Cys Ser His
            420                 425                 430

Lys Ser Ile Ser Trp Tyr Gln Trp Pro Pro Gly Arg Ala Pro Thr Leu
        435                 440                 445

Ile Ile Tyr Glu Asp Asn Glu Arg Ala Pro Gly Ile Ser Pro Arg Phe
    450                 455                 460

Ser Gly Tyr Lys Ser Tyr Trp Ser Ala Tyr Leu Thr Ile Ser Asp Leu
465                 470                 475                 480

Arg Pro Glu Asp Glu Thr Thr Tyr Tyr Cys Cys Ser Tyr Thr His Asn
                485                 490                 495

Ser Gly Cys Val Phe Gly Thr Gly Thr Lys Val Ser Val Leu Gly Gly
            500                 505                 510

Gly Gly Ser Gly Gly Gly Gly Ser Gly Gly Gly Gly Ser Gly Gly Gly
        515                 520                 525

Gly Ser Gly Gly Gly Gly Ser Glu Val Arg Leu Val Glu Ser Gly Gly
    530                 535                 540

Gly Leu Val Lys Pro Gly Gly Ser Leu Arg Leu Ser Cys Ser Ala Ser
545                 550                 555                 560
```

```
Gly Phe Asp Phe Asp Asn Ala Trp Met Thr Trp Val Arg Gln Pro Pro
                565                 570                 575

Gly Lys Gly Leu Glu Trp Val Gly Arg Ile Thr Gly Pro Gly Glu Gly
            580                 585                 590

Trp Ser Val Asp Tyr Ala Glu Ser Val Lys Gly Arg Phe Thr Ile Ser
        595                 600                 605

Arg Asp Asn Thr Lys Asn Thr Leu Tyr Leu Glu Met Asn Asn Val Arg
    610                 615                 620

Thr Glu Asp Thr Gly Tyr Tyr Phe Cys Ala Arg Thr Gly Lys Tyr Tyr
625                 630                 635                 640

Asp Phe Trp Phe Gly Tyr Pro Pro Gly Glu Glu Tyr Phe Gln Asp Trp
                645                 650                 655

Gly Gln Gly Thr Leu Val Ile Val Ser Ser Gly Gly Gly Gly Ser Gly
            660                 665                 670

Gly Gly Gly Ser Gly Gly Gly Gly Ser Ser Glu Leu Thr Gln Asp Pro
        675                 680                 685

Ala Val Ser Val Ala Leu Lys Gln Thr Val Thr Ile Thr Cys Arg Gly
    690                 695                 700

Asp Ser Leu Arg Ser His Tyr Ala Ser Trp Tyr Gln Lys Lys Pro Gly
705                 710                 715                 720

Gln Ala Pro Val Leu Leu Phe Tyr Gly Lys Asn Asn Arg Pro Ser Gly
                725                 730                 735

Ile Pro Asp Arg Phe Ser Gly Ser Ala Ser Gly Asn Arg Ala Ser Leu
            740                 745                 750

Thr Ile Thr Gly Ala Gln Ala Glu Asp Glu Ala Asp Tyr Tyr Cys Ser
        755                 760                 765

Ser Arg Asp Lys Ser Gly Ser Arg Leu Ser Val Phe Gly Gly Gly Thr
    770                 775                 780

Lys Leu Thr Val Leu
785
```

<210> SEQ ID NO 97
<211> LENGTH: 2334
<212> TYPE: DNA
<213> ORGANISM: Artificial Sequence
<220> FEATURE:
<223> OTHER INFORMATION: Synthetic: LC: N6 KC-CK-35O22-5X-10E8v4 V5R S100cF DNA sequence

<400> SEQUENCE: 97

```
atgggctgga gctgcatcat cctgttcctg gtggcaaccg caacaggagt gcacagctac     60

atccacgtga cccagtcccc ttcctctctg tccgtgtcta tcggcgatcg cgtgaccatc    120

aactgtcaga caagccaggg agtgggctcc gacctgcact ggtatcagca caagcctggc    180

agggccccaa agctgctgat ccaccacaca agctccgtgg aggatggagt gccaagccgc    240

ttcagcggct ccggattcca caccagcttt aatctgacaa tctccgacct gcaggccgac    300

gatatcgcca cctactattg ccaggtgctg cagttctttg gcaggggctc ccgcctgcac    360

atcaagcgta cggtggctgc accatctgtc ttcatcttcc cgccatctga tgagcagttg    420

aaatctggaa ctgcctctgt tgtgtgcctg ctgaataact tctatcccag agaggccaaa    480

gtacagtgga aggtggataa cgccctccaa tcgggtaact cccaggagag tgtcacagag    540

caggacagca aggacagcac ctacagcctc agcagcaccc tgacgctgag caaagcagac    600

tacgagaaac acaaagtcta cgcctgcgaa gtcacccatc agggcctgag ctcgcccgtc    660

acaaagagct tcaacagggg agagtgtgga ggagggggct ctggcggcgg gggcagcggc    720
```

```
ggaggcggct ccggaggggg cggctctggc ggaggcggca gccagggcca gctggtgcag    780

agcggagcag agctgaagaa gccaggagcc tctgtgaaga tcagctgtaa gacatccggc    840

taccggttca acttttatca catcaattgg atcaggcaga ccgcaggaag ggaccagag    900

tggatgggct ggatctcccc ctactctggc gataagaacc tggccccagc cttccaggac    960

agagtgatca tgaccacaga taccgaggtg ccagtgacca gcttcacctc caccggagcc   1020

gcctacatgg agatccggaa tctgaagttc gacgatacag gcacctattt ttgcgccaag   1080

ggcctgctga gagacggctc tagcacatgg ctgccatacc tgtggggaca gggcaccctg   1140

ctgacagtgt cctctggagg aggaggctcc gggggcggcg gctctggagg aggaggctct   1200

caaagcgtgc tgacccagtc cgcctctgtg agcggctccc tgggccagtc tgtgaccatc   1260

agctgtacag gccccaactc cgtgtgctgt tctcacaagt ctatcagctg gtaccagtgg   1320

ccaccaggaa gggcacctac cctgatcatc tatgaggaca atgagagggc accaggaatc   1380

agccctcgct tctccggcta caagtcttat tggagcgcct acctgaccat ttccgacctg   1440

cgccccgagg atgagaccac atactattgc tgtagctata cccacaactc cggctgcgtg   1500

tttggcacag gcaccaaggt gagcgtgctg ggaggagggg gctctggcgg cgggggcagc   1560

ggcggaggcg gctccggagg gggcggctct ggcggaggcg gcagcgaggt gcggctggtg   1620

gagagcggcg gcggcctggt gaagccaggc ggctctctga gactgtcctg ttctgccagc   1680

ggcttcgact ttgataatgc ctggatgaca tgggtgcggc agcctcctgg caaggggctg   1740

gagtgggtgg gaagaatcac cggaccagga gagggatggt ctgtggacta cgccgagagc   1800

gtgaagggcc ggttcaccat cagcagagat aacactaaaa atacactgta tctggagatg   1860

aacaatgtgc ggaccgagga cacaggctac tatttctgcg ccagaaccgg caagtactat   1920

gatttctggt ttggctaccc ccctggcgag gagtattttc aggactgggg ccagggcacc   1980

ctggtcatcg tgagcagcgg cgggggaggc tccggcgggg ggggctctgg aggagggggc   2040

tctagcgagc tgacccagga ccccgccgtg tccgtggccc tgaagcagac agtgaccatc   2100

acatgcaggg gcgactccct gcgctctcac tacgccagct ggtatcagaa gaagccagga   2160

caggcacccg tgctgctgtt ctacggcaag aacaatcggc cttccggcat cccagataga   2220

ttttccggct ctgccagcgg aaacagggcc agcctgacca tcacaggagc acaggcagag   2280

gatgaagcag attactattg ttcctctcgg gacaagtccg gctctagact gagc         2334
```

<210> SEQ ID NO 98
<211> LENGTH: 118
<212> TYPE: PRT
<213> ORGANISM: Artificial Sequence
<220> FEATURE:
<223> OTHER INFORMATION: Synthetic: mAb dB4C7/UB-421s perfect heavy chain Fv region

<400> SEQUENCE: 98

```
Gln Val Gln Leu Val Gln Ser Gly Pro Glu Leu Lys Lys Pro Gly Ala
1               5                   10                  15

Ser Val Lys Val Ser Cys Lys Ala Ser Gly Tyr Thr Phe Thr Asp Tyr
            20                  25                  30

Val Ile His Trp Val Lys Gln Ala Thr Gly Gln Gly Leu Glu Trp Ile
        35                  40                  45

Gly Glu Ile Tyr Pro Gly Ser Gly Ser Ala Tyr Ser Asn Ala Lys Phe
    50                  55                  60

Lys Asp Arg Val Thr Met Thr Ala Asp Lys Ser Ser Asn Thr Ala Tyr
```

```
65                  70                  75                  80

Met Glu Leu Ser Ser Leu Thr Ser Asp Asp Thr Ala Val Tyr Phe Cys
                85                  90                  95

Ala Arg Arg Gly Asn Gly Thr Gly Phe Ala Tyr Trp Gly Gln Gly Thr
            100                 105                 110

Leu Val Thr Val Ser Ser
        115
```

<210> SEQ ID NO 99
<211> LENGTH: 111
<212> TYPE: PRT
<213> ORGANISM: Artificial Sequence
<220> FEATURE:
<223> OTHER INFORMATION: Synthetic: mAb dB4C7/UB-421s perfect light chain Fv region

<400> SEQUENCE: 99

```
Asp Ile Val Leu Thr Gln Ser Pro Ala Ser Leu Ala Val Ser Leu Gly
1               5                   10                  15

Gln Arg Ala Thr Ile Thr Cys Lys Ala Gly Gln Ser Val Asp Tyr Asp
            20                  25                  30

Gly Asp Ser Tyr Met Asn Trp Tyr Gln Gln Lys Pro Gly Gln Pro Pro
        35                  40                  45

Lys Leu Leu Ile Tyr Val Ala Ser Asn Leu Glu Ser Gly Ile Pro Ala
    50                  55                  60

Arg Phe Ser Gly Ser Gly Ser Gly Thr Asp Phe Thr Leu Asn Ile His
65                  70                  75                  80

Pro Val Glu Glu Asn Asp Ala Ala Thr Tyr Tyr Cys Gln Gln Ser Tyr
                85                  90                  95

Lys Asp Pro Leu Thr Phe Gly Gln Gly Thr Lys Leu Glu Ile Lys
            100                 105                 110
```

<210> SEQ ID NO 100
<211> LENGTH: 5
<212> TYPE: PRT
<213> ORGANISM: Artificial Sequence
<220> FEATURE:
<223> OTHER INFORMATION: Synthetic: CDR1 of Heavy Chain of murine

<400> SEQUENCE: 100

```
Asp Tyr Val Ile His
1               5
```

<210> SEQ ID NO 101
<211> LENGTH: 17
<212> TYPE: PRT
<213> ORGANISM: Artificial Sequence
<220> FEATURE:
<223> OTHER INFORMATION: Synthetic: CDR2 of Heavy Chain of murine

<400> SEQUENCE: 101

```
Glu Ile Tyr Pro Gly Ser Gly Ser Ala Tyr Ser Asn Ala Lys Phe Lys
1               5                   10                  15

Asp
```

<210> SEQ ID NO 102
<211> LENGTH: 9
<212> TYPE: PRT
<213> ORGANISM: Artificial Sequence
<220> FEATURE:
<223> OTHER INFORMATION: Synthetic: CDR3 of Heavy Chain of murine

<400> SEQUENCE: 102

Arg Gly Asn Gly Thr Gly Phe Ala Tyr
1               5

<210> SEQ ID NO 103
<211> LENGTH: 15
<212> TYPE: PRT
<213> ORGANISM: Artificial Sequence
<220> FEATURE:
<223> OTHER INFORMATION: Synthetic: CDR1 of Light Chain of murine

<400> SEQUENCE: 103

Lys Ala Gly Gln Ser Val Asp Tyr Asp Gly Asp Ser Tyr Met Asn
1               5                   10                  15

<210> SEQ ID NO 104
<211> LENGTH: 7
<212> TYPE: PRT
<213> ORGANISM: Artificial Sequence
<220> FEATURE:
<223> OTHER INFORMATION: Synthetic: CDR2 of Light Chain of murine

<400> SEQUENCE: 104

Val Ala Ser Asn Leu Glu Ser
1               5

<210> SEQ ID NO 105
<211> LENGTH: 9
<212> TYPE: PRT
<213> ORGANISM: Artificial Sequence
<220> FEATURE:
<223> OTHER INFORMATION: Synthetic: CDR3 of Light Chain of murine

<400> SEQUENCE: 105

Gln Gln Ser Tyr Lys Asp Pro Leu Thr
1               5

<210> SEQ ID NO 106
<211> LENGTH: 5025
<212> TYPE: DNA
<213> ORGANISM: Artificial Sequence
<220> FEATURE:
<223> OTHER INFORMATION: Synthetic: PentaNAb2.0

<400> SEQUENCE: 106
atgggatgga gctgtattat tctgtttctg gtcgctaccg ctaccggagt gcattcttct 60
gaactgaccc aggaccccgc cgtgagcgtg gccctgaagc agaccgtgac aatcacctgc 120
aggggcgaca gcctgcgctc ccactacgcc agctggtatc agaagaagcc tggccaggcc 180
ccagtgctgc tgttctacgg caagaacaat aggccctccg gcatccctga tcgcttttcc 240
ggctctgcca gcggaaacag ggccagcctg acaatcaccg gagcacaggc agaggacgag 300
gcagattact attgcagctc ccgggacaag tccggctcta gactgagcgt gttcggcggc 360
ggcaccaagc tgacagtgct gggaggagga ggcagcggcg gaggaggctc cggaggcggc 420
ggctctgagg tgcggctggt ggagtctgga ggaggcctgg tgaagccagg aggcagcctg 480
agactgagct gttccgcctc tggcttcgac tttgataatg cctggatgac atgggtgcgg 540
cagccacctg gcaagggcct ggagtgggtg ggaagaatca ccggaccagg agagggatgg 600
tctgtggact acgccgagag cgtgaagggc cggttcacca tctccagaga taacaccaag 660
aatacactgt atctggagat gaacaatgtg cggaccgagg acacaggcta ctatttctgc 720
gccagaaccg gcaagtacta tgatttttgg tttggctacc cacccggcga ggagtatttt 780

-continued

```
caggactggg gccagggcac cctggtcatc gtgagcagcg gcggcggcgg cagcggcggc    840
ggcggctccg gaggaggcgg ctctggagga ggaggcagcg ggggaggggg cagccagtcc    900
gtgctgaccc agtctgccag cgtgtccggc tctctgggac agagcgtgac catctcctgt    960
acaggcccca acagcgtgtg ctgtagccac aagagcatct cctggtacca gtggcctcca   1020
ggaagggcac ctaccctgat catctatgag gacaatgagc gggccccagg catctccccc   1080
agattctctg gctacaagtc ttattggagc gcctacctga caatcagcga cctgcgcccc   1140
gaggatgaga caacatacta ttgctgttcc tatacccaca actctggctg cgtgtttggc   1200
acaggcacca aggtgtccgt gctgggcggc ggcggcagcg ggggcggggg ctccggaggg   1260
ggcggctctc agggccagct ggtgcagagc ggagcagagc tgaagaagcc tggagccagc   1320
gtgaagatct cctgtaagac atctggctac cggttcaact tttatcacat caattggatc   1380
aggcagaccg caggaagggg accagagtgg atgggctgga tctcccccta ctctggcgat   1440
aagaacctgg ccccagcctt ccaggacaga gtgatcatga ccacagatac cgaggtgcca   1500
gtgaccagct tcacctccac cggagccgcc tacatggaga tcaggaatct gaagttcgac   1560
gatacaggca cctatttttg cgcaaagggc ctgctgaggg acggctcctc tacctggctg   1620
ccttacctgt ggggacaggg caccctgctg acagtgagct ccggcggcgg gggcagcggc   1680
ggcgggggct ccggaggagg aggctctgga ggagggggca gcggaggagg cggctcctac   1740
atccacgtga cccagtcccc atctagcctg tctgtgagca tcggcgatcg ggtgaccatc   1800
aactgtcaga catctcaggg cgtgggcagc gacctgcact ggtatcagca caagcctggc   1860
agggccccaa agctgctgat ccaccacaca tcctctgtgg aggatggagt gccaagccgc   1920
ttctccggct ctggattcca cacctccttt aatctgacaa tctctgacct gcaggccgac   1980
gatatcgcca cctactattg ccaggtgctg cagttctttg gccggggctc cagactgcac   2040
atcaagggag gaggaggctc cgggggcgga ggctctggcg gcggcggcag ccgggcccac   2100
ctggtgcaga gcggcaccgc catgaagaag cctggcgcca gcgtgagagt gtcctgtcag   2160
acatctggct acaccttcac cgcccacatc ctgttctggt ttaggcaggc accaggaaga   2220
ggcctggagt gggtgggctg gatcaagccc cagtatggag cagtgaactt cggaggaggc   2280
tttcgggaca gagtgacact gacccgggac gtgtacagag agatcgccta tatggatatc   2340
aggggcctga agccagacga taccgccgtg tactattgcg ccagggaccg ctcctacggc   2400
gatagctcct gggcactgga cgcatgggga cagggcacca cagtggtggt gagcgccggc   2460
ggcggaggct ccggcggcgg gggctctgga ggaggcggca gcggaggggg aggctccgga   2520
gggggaggct ctagcgacat ctccgtggcc cctggcgaga cagccagaat ctcttgtggc   2580
gagaagtctc tgggcagcag ggccgtgcag tggtaccagc acagggcagg acaggcacca   2640
tctctgatca tctataacaa tcaggatagg ccaagcggca tccctgagcg gttcagcggc   2700
tcccccgaca gcccttttgg caccacagcc acactgacca tcacatccgt ggaggcaggc   2760
gacgaagccg attactattg ccacatctgg gattccagag tgccaaccaa gtgggtgttc   2820
ggaggaggaa ccacactgac agtgctggga ggggggggct ctggcggcgg gggcagcggg   2880
ggaggaggct cccagatgca gctgcaggag agcggaccag gcctggtgaa gcctagcgag   2940
acactgagcc tgacatgttc tgtgagcggc gcctccatct ctgacagcta ctggtcttgg   3000
atcagacgga gccccggcaa gggcctggaa tggatcggct acgtgcacaa gtccggcgat   3060
acaaactatt ccccatctct gaagtctcgg gtgaacctgt ctctggacac cagcaagaat   3120
```

```
caggtgagcc tgtccctggt ggcagcaacc gcagcagata gcggcaagta ctattgcgcc   3180

agaacactgc acggcaggcg catctacggc atcgtggcct ttaacgagtg gttcacctac   3240

ttttatatgg acgtgtgggg caatggcacc caggtgacag tgtcctctgg cgggggcggc   3300

tccggaggcg gaggctctgg cgggggcggc agcggcgggg gcggctccgg gggaggcggc   3360

tctcagagcg tgctgaccca gccaccttcc gtgtctgccg caccaggaca gaaggtgacc   3420

atcagctgtt ccggcaacac atccaatatc ggcaacaatt tcgtgtcttg gtaccagcag   3480

aggccaggaa gggcaccaca gctgctgatc tatgagacag acaagcggcc ttccggcatc   3540

ccagatagat tttctgccag caagtccggc accagcggca cactggcaat caccggcctg   3600

cagacaggcg acgaagctga ttactattgc gcaacctggg cagcctccct gagctccgcc   3660

agggtgttcg gaaccggaac aaaagtgatc gtgctggtgg gcggcggagg ctctggcgga   3720

ggcggcagcg gcgggggggg ctcccaggtg cagctggtgg agagcggcgg cggcgtggtg   3780

cagccaggca cctccctgag gctgtcttgt gcagcaagcc agttcagatt tgatggctac   3840

ggcatgcact gggtgcgcca ggcaccaggc aagggcctgg agtgggtagc ctctatcagc   3900

cacgacggca tcaagaagta ccacgccgag aaagtgtggg gcaggttcac catctcccgc   3960

gataactcta aaaacacact gtatctgcag atgaactccc tgaggcccga ggacaccgcc   4020

ctgtactatt gcgccaagga cctgcgcgag gatgagtgtg aggagtggtg gtccgactac   4080

tatgattttg gcaagcagct gccttgcgca aagagcaggg gaggcctggt gggaatcgcc   4140

gataattggg gccagggcac catggtgaca gtgtctagcg gatccggaga gctgaagacc   4200

cctctgggcg ataccacaca cacatcccca cggagccccg agccaaagtc ctctgacacc   4260

ccacccccta gccctagatc ccctgagcca aagagctccg atacaccacc cccttctcca   4320

aggagccccg agcctaagtc tagcgacacc ccaccccctt gcccccgctg tccagcacca   4380

gagctgctgg gaggaccaag cgtgttcctg tttccaccca agcctaagga tacactgatg   4440

atctctcgca cccccgaggt gacatgcgtg gtggtggacg tgagccacga ggaccccgag   4500

gtgaagttca actggtacgt ggacggcgtg gaggtgcaca atgccaagac caagcccagg   4560

gaggagcagt acaacagcac ctatcgcgtg gtgtccgtgc tgacagtgct gcaccaggac   4620

tggctgaacg gcaaggagta caagtgcaag gtgtccaata aggccctgcc tgccccaatc   4680

gagaagacaa tcagcaaggc aaagggacag ccaagggagc cacaggtgta caccctgcct   4740

ccaagccgcg aggagatgac caagaaccag gtgtccctga catgtctggt gaagggcttc   4800

tatcctagcg atatcgccgt ggagtgggag tccaatggcc agccagagaa caattacaag   4860

accacacccc ctgtgctgga ctccgatggc tctttctttc tgtattctaa gctgaccgtg   4920

gacaagagcc ggtggcagca gggcaacgtg ttcagctgct ctgtgctgca cgaagccctg   4980

cacagccatt acacccagaa gagcctgagc ctgagccccg gaaaa                   5025
```

<210> SEQ ID NO 107
<211> LENGTH: 1675
<212> TYPE: PRT
<213> ORGANISM: Artificial Sequence
<220> FEATURE:
<223> OTHER INFORMATION: Synthetic: PentaNAb2.0

<400> SEQUENCE: 107

```
Met Gly Trp Ser Cys Ile Ile Leu Phe Leu Val Ala Thr Ala Thr Gly
1               5                   10                  15

Val His Ser Ser Glu Leu Thr Gln Asp Pro Ala Val Ser Val Ala Leu
            20                  25                  30
```

-continued

```
Lys Gln Thr Val Thr Ile Thr Cys Arg Gly Asp Ser Leu Arg Ser His
        35                  40                  45

Tyr Ala Ser Trp Tyr Gln Lys Lys Pro Gly Gln Ala Pro Val Leu Leu
    50                  55                  60

Phe Tyr Gly Lys Asn Asn Arg Pro Ser Gly Ile Pro Asp Arg Phe Ser
65                  70                  75                  80

Gly Ser Ala Ser Gly Asn Arg Ala Ser Leu Thr Ile Thr Gly Ala Gln
                85                  90                  95

Ala Glu Asp Glu Ala Asp Tyr Tyr Cys Ser Ser Arg Asp Lys Ser Gly
            100                 105                 110

Ser Arg Leu Ser Val Phe Gly Gly Gly Thr Lys Leu Thr Val Leu Gly
        115                 120                 125

Gly Gly Gly Ser Gly Gly Gly Gly Ser Gly Gly Gly Gly Ser Glu Val
    130                 135                 140

Arg Leu Val Glu Ser Gly Gly Gly Leu Val Lys Pro Gly Gly Ser Leu
145                 150                 155                 160

Arg Leu Ser Cys Ser Ala Ser Gly Phe Asp Phe Asp Asn Ala Trp Met
                165                 170                 175

Thr Trp Val Arg Gln Pro Pro Gly Lys Gly Leu Glu Trp Val Gly Arg
            180                 185                 190

Ile Thr Gly Pro Gly Glu Gly Trp Ser Val Asp Tyr Ala Glu Ser Val
        195                 200                 205

Lys Gly Arg Phe Thr Ile Ser Arg Asp Asn Thr Lys Asn Thr Leu Tyr
    210                 215                 220

Leu Glu Met Asn Asn Val Arg Thr Glu Asp Thr Gly Tyr Tyr Phe Cys
225                 230                 235                 240

Ala Arg Thr Gly Lys Tyr Tyr Asp Phe Trp Phe Gly Tyr Pro Pro Gly
                245                 250                 255

Glu Glu Tyr Phe Gln Asp Trp Gly Gln Gly Thr Leu Val Ile Val Ser
            260                 265                 270

Ser Gly Gly Gly Gly Ser Gly Gly Gly Gly Ser Gly Gly Gly Gly Ser
        275                 280                 285

Gly Gly Gly Gly Ser Gly Gly Gly Gly Ser Gln Ser Val Leu Thr Gln
    290                 295                 300

Ser Ala Ser Val Ser Gly Ser Leu Gly Gln Ser Val Thr Ile Ser Cys
305                 310                 315                 320

Thr Gly Pro Asn Ser Val Cys Cys Ser His Lys Ser Ile Ser Trp Tyr
                325                 330                 335

Gln Trp Pro Pro Gly Arg Ala Pro Thr Leu Ile Ile Tyr Glu Asp Asn
            340                 345                 350

Glu Arg Ala Pro Gly Ile Ser Pro Arg Phe Ser Gly Tyr Lys Ser Tyr
        355                 360                 365

Trp Ser Ala Tyr Leu Thr Ile Ser Asp Leu Arg Pro Glu Asp Glu Thr
    370                 375                 380

Thr Tyr Tyr Cys Cys Ser Tyr Thr His Asn Ser Gly Cys Val Phe Gly
385                 390                 395                 400

Thr Gly Thr Lys Val Ser Val Leu Gly Gly Gly Gly Ser Gly Gly Gly
                405                 410                 415

Gly Ser Gly Gly Gly Gly Ser Gln Gly Gln Leu Val Gln Ser Gly Ala
            420                 425                 430

Glu Leu Lys Lys Pro Gly Ala Ser Val Lys Ile Ser Cys Lys Thr Ser
        435                 440                 445
```

```
Gly Tyr Arg Phe Asn Phe Tyr His Ile Asn Trp Ile Arg Gln Thr Ala
    450                 455                 460

Gly Arg Gly Pro Glu Trp Met Gly Trp Ile Ser Pro Tyr Ser Gly Asp
465                 470                 475                 480

Lys Asn Leu Ala Pro Ala Phe Gln Asp Arg Val Ile Met Thr Thr Asp
                485                 490                 495

Thr Glu Val Pro Val Thr Ser Phe Thr Ser Thr Gly Ala Ala Tyr Met
            500                 505                 510

Glu Ile Arg Asn Leu Lys Phe Asp Asp Thr Gly Thr Tyr Phe Cys Ala
        515                 520                 525

Lys Gly Leu Leu Arg Asp Gly Ser Ser Thr Trp Leu Pro Tyr Leu Trp
    530                 535                 540

Gly Gln Gly Thr Leu Leu Thr Val Ser Ser Gly Gly Gly Gly Ser Gly
545                 550                 555                 560

Gly Gly Gly Ser Gly Gly Gly Gly Ser Gly Gly Gly Gly Ser Gly Gly
                565                 570                 575

Gly Gly Ser Tyr Ile His Val Thr Gln Ser Pro Ser Ser Leu Ser Val
            580                 585                 590

Ser Ile Gly Asp Arg Val Thr Ile Asn Cys Gln Thr Ser Gln Gly Val
        595                 600                 605

Gly Ser Asp Leu His Trp Tyr Gln His Lys Pro Gly Arg Ala Pro Lys
    610                 615                 620

Leu Leu Ile His His Thr Ser Ser Val Glu Asp Gly Val Pro Ser Arg
625                 630                 635                 640

Phe Ser Gly Ser Gly Phe His Thr Ser Phe Asn Leu Thr Ile Ser Asp
                645                 650                 655

Leu Gln Ala Asp Asp Ile Ala Thr Tyr Tyr Cys Gln Val Leu Gln Phe
            660                 665                 670

Phe Gly Arg Gly Ser Arg Leu His Ile Lys Gly Gly Gly Gly Ser Gly
        675                 680                 685

Gly Gly Gly Ser Gly Gly Gly Gly Ser Arg Ala His Leu Val Gln Ser
    690                 695                 700

Gly Thr Ala Met Lys Lys Pro Gly Ala Ser Val Arg Val Ser Cys Gln
705                 710                 715                 720

Thr Ser Gly Tyr Thr Phe Thr Ala His Ile Leu Phe Trp Phe Arg Gln
                725                 730                 735

Ala Pro Gly Arg Gly Leu Glu Trp Val Gly Trp Ile Lys Pro Gln Tyr
            740                 745                 750

Gly Ala Val Asn Phe Gly Gly Gly Phe Arg Asp Arg Val Thr Leu Thr
        755                 760                 765

Arg Asp Val Tyr Arg Glu Ile Ala Tyr Met Asp Ile Arg Gly Leu Lys
    770                 775                 780

Pro Asp Asp Thr Ala Val Tyr Tyr Cys Ala Arg Asp Arg Ser Tyr Gly
785                 790                 795                 800

Asp Ser Ser Trp Ala Leu Asp Ala Trp Gly Gln Gly Thr Thr Val Val
                805                 810                 815

Val Ser Ala Gly Gly Gly Gly Ser Gly Gly Gly Gly Ser Gly Gly Gly
            820                 825                 830

Gly Ser Gly Gly Gly Gly Ser Gly Gly Gly Gly Ser Ser Asp Ile Ser
        835                 840                 845

Val Ala Pro Gly Glu Thr Ala Arg Ile Ser Cys Gly Glu Lys Ser Leu
    850                 855                 860

Gly Ser Arg Ala Val Gln Trp Tyr Gln His Arg Ala Gly Gln Ala Pro
```

-continued

```
865                 870                 875                 880

Ser Leu Ile Ile Tyr Asn Asn Gln Asp Arg Pro Ser Gly Ile Pro Glu
                885                 890                 895

Arg Phe Ser Gly Ser Pro Asp Ser Pro Phe Gly Thr Thr Ala Thr Leu
            900                 905                 910

Thr Ile Thr Ser Val Glu Ala Gly Asp Glu Ala Asp Tyr Tyr Cys His
        915                 920                 925

Ile Trp Asp Ser Arg Val Pro Thr Lys Trp Val Phe Gly Gly Gly Thr
    930                 935                 940

Thr Leu Thr Val Leu Gly Gly Gly Gly Ser Gly Gly Gly Gly Ser Gly
945                 950                 955                 960

Gly Gly Gly Ser Gln Met Gln Leu Gln Glu Ser Gly Pro Gly Leu Val
                965                 970                 975

Lys Pro Ser Glu Thr Leu Ser Leu Thr Cys Ser Val Ser Gly Ala Ser
            980                 985                 990

Ile Ser Asp Ser Tyr Trp Ser Trp  Ile Arg Arg Ser Pro  Gly Lys Gly
        995                 1000                1005

Leu Glu  Trp Ile Gly Tyr Val  His Lys Ser Gly Asp  Thr Asn Tyr
    1010                 1015                1020

Ser Pro  Ser Leu Lys Ser Arg  Val Asn Leu Ser Leu  Asp Thr Ser
    1025                 1030                1035

Lys Asn  Gln Val Ser Leu Ser  Leu Val Ala Ala Thr  Ala Ala Asp
    1040                 1045                1050

Ser Gly  Lys Tyr Tyr Cys Ala  Arg Thr Leu His Gly  Arg Arg Ile
    1055                 1060                1065

Tyr Gly  Ile Val Ala Phe Asn  Glu Trp Phe Thr Tyr  Phe Tyr Met
    1070                 1075                1080

Asp Val  Trp Gly Asn Gly Thr  Gln Val Thr Val Ser  Ser Gly Gly
    1085                 1090                1095

Gly Gly  Ser Gly Gly Gly Gly  Ser Gly Gly Gly Gly  Ser Gly Gly
    1100                 1105                1110

Gly Gly  Ser Gly Gly Gly Gly  Ser Gln Ser Val Leu  Thr Gln Pro
    1115                 1120                1125

Pro Ser  Val Ser Ala Ala Pro  Gly Gln Lys Val Thr  Ile Ser Cys
    1130                 1135                1140

Ser Gly  Asn Thr Ser Asn Ile  Gly Asn Asn Phe Val  Ser Trp Tyr
    1145                 1150                1155

Gln Gln  Arg Pro Gly Arg Ala  Pro Gln Leu Leu Ile  Tyr Glu Thr
    1160                 1165                1170

Asp Lys  Arg Pro Ser Gly Ile  Pro Asp Arg Phe Ser  Ala Ser Lys
    1175                 1180                1185

Ser Gly  Thr Ser Gly Thr Leu  Ala Ile Thr Gly Leu  Gln Thr Gly
    1190                 1195                1200

Asp Glu  Ala Asp Tyr Tyr Cys  Ala Thr Trp Ala Ala  Ser Leu Ser
    1205                 1210                1215

Ser Ala  Arg Val Phe Gly Thr  Gly Thr Lys Val Ile  Val Leu Val
    1220                 1225                1230

Gly Gly  Gly Gly Ser Gly Gly  Gly Gly Ser Gly Gly  Gly Gly Ser
    1235                 1240                1245

Gln Val  Gln Leu Val Glu Ser  Gly Gly Gly Val Val  Gln Pro Gly
    1250                 1255                1260

Thr Ser  Leu Arg Leu Ser Cys  Ala Ala Ser Gln Phe  Arg Phe Asp
    1265                 1270                1275
```

```
Gly Tyr  Gly Met His Trp Val  Arg Gln Ala Pro Gly  Lys Gly Leu
    1280                 1285                 1290

Glu Trp  Val Ala Ser Ile Ser  His Asp Gly Ile Lys  Lys Tyr His
    1295                 1300                 1305

Ala Glu  Lys Val Trp Gly Arg  Phe Thr Ile Ser Arg  Asp Asn Ser
    1310                 1315                 1320

Lys Asn  Thr Leu Tyr Leu Gln  Met Asn Ser Leu Arg  Pro Glu Asp
    1325                 1330                 1335

Thr Ala  Leu Tyr Tyr Cys Ala  Lys Asp Leu Arg Glu  Asp Glu Cys
    1340                 1345                 1350

Glu Glu  Trp Trp Ser Asp Tyr  Tyr Asp Phe Gly Lys  Gln Leu Pro
    1355                 1360                 1365

Cys Ala  Lys Ser Arg Gly Gly  Leu Val Gly Ile Ala  Asp Asn Trp
    1370                 1375                 1380

Gly Gln  Gly Thr Met Val Thr  Val Ser Ser Gly Ser  Gly Glu Leu
    1385                 1390                 1395

Lys Thr  Pro Leu Gly Asp Thr  Thr His Thr Ser Pro  Arg Ser Pro
    1400                 1405                 1410

Glu Pro  Lys Ser Ser Asp Thr  Pro Pro Pro Ser Pro  Arg Ser Pro
    1415                 1420                 1425

Glu Pro  Lys Ser Ser Asp Thr  Pro Pro Pro Ser Pro  Arg Ser Pro
    1430                 1435                 1440

Glu Pro  Lys Ser Ser Asp Thr  Pro Pro Pro Cys Pro  Arg Cys Pro
    1445                 1450                 1455

Ala Pro  Glu Leu Leu Gly Gly  Pro Ser Val Phe Leu  Phe Pro Pro
    1460                 1465                 1470

Lys Pro  Lys Asp Thr Leu Met  Ile Ser Arg Thr Pro  Glu Val Thr
    1475                 1480                 1485

Cys Val  Val Val Asp Val Ser  His Glu Asp Pro Glu  Val Lys Phe
    1490                 1495                 1500

Asn Trp  Tyr Val Asp Gly Val  Glu Val His Asn Ala  Lys Thr Lys
    1505                 1510                 1515

Pro Arg  Glu Glu Gln Tyr Asn  Ser Thr Tyr Arg Val  Val Ser Val
    1520                 1525                 1530

Leu Thr  Val Leu His Gln Asp  Trp Leu Asn Gly Lys  Glu Tyr Lys
    1535                 1540                 1545

Cys Lys  Val Ser Asn Lys Ala  Leu Pro Ala Pro Ile  Glu Lys Thr
    1550                 1555                 1560

Ile Ser  Lys Ala Lys Gly Gln  Pro Arg Glu Pro Gln  Val Tyr Thr
    1565                 1570                 1575

Leu Pro  Pro Ser Arg Glu Glu  Met Thr Lys Asn Gln  Val Ser Leu
    1580                 1585                 1590

Thr Cys  Leu Val Lys Gly Phe  Tyr Pro Ser Asp Ile  Ala Val Glu
    1595                 1600                 1605

Trp Glu  Ser Asn Gly Gln Pro  Glu Asn Asn Tyr Lys  Thr Thr Pro
    1610                 1615                 1620
```

-continued

```
Pro Val Leu Asp Ser Asp Gly Ser Phe Phe Leu Tyr Ser Lys Leu
    1625            1630                1635

Thr Val Asp Lys Ser Arg Trp Gln Gln Gly Asn Val Phe Ser Cys
    1640            1645                1650

Ser Val Leu His Glu Ala Leu His Ser His Tyr Thr Gln Lys Ser
    1655            1660                1665

Leu Ser Leu Ser Pro Gly Lys
    1670            1675

<210> SEQ ID NO 108
<211> LENGTH: 24
<212> TYPE: PRT
<213> ORGANISM: Artificial Sequence
<220> FEATURE:
<223> OTHER INFORMATION: Synthetic: membrane-proximal external region or
      MPER

<400> SEQUENCE: 108

Leu Leu Glu Leu Asp Lys Trp Ala Ser Leu Trp Asn Trp Phe Asx Ile
1               5                  10                  15

Thr Asn Trp Leu Trp Tyr Ile Lys
                20
```

MULTISPECIFIC ANTIBODIES TARGETING MULTIPLE EPITOPES ON THE HIV-1 ENVELOPE

This application claims priority to U.S. Provisional Application No. 62/749,510, filed Oct. 23, 2018 and U.S. Provisional Application No. 62/748,228 filed Oct. 19, 2018. The entire disclosures of all of the foregoing applications are incorporated by reference herein.

This invention was made with government support under A1136756 awarded by the National Institutes of Health. The government has certain rights in the invention.

FIELD OF THE INVENTION

The field of the invention relates to medicine, infectious disease and in particular antibodies which can neutralize HIV-1 virus strains.

SEQUENCE LISTING

This application includes an electronically submitted sequence listing in .txt format. The .txt file contains a sequence listing entitled 1475-59 PCT ST25.txt. and is 294,336 bytes in size. The sequence listing contained in this .txt file is part of the specification and is hereby incorporated by reference herein in its entirety.

BACKGROUND OF THE INVENTION

The acquired immunodeficiency syndrome (AIDS) is caused by the human immunodeficiency virus type 1 (HIV-1) (Gallo et al., Science 224, 500-503. (1984); Barre-Sinoussi et al., Science 220, 868-871. (1983)), and results from infection and depletion of human CD4+ lymphocytes. HIV-1 infection of CD4+ host cells is mediated by the viral envelope glycoproteins (Env), which are displayed as trimeric spikes that sparsely coat the surface of the HIV virion. Each trimeric Env complex is composed of three of each exterior envelope glycoprotein, gp120, and the gp41 transmembrane envelope glycoprotein (Kowalski et al., Science 237, 1351-1355. (1987); Lu et al., Nat Struct Biol 2, 1075-1082 (1995). This trimeric Env complex is the main target of neutralizing antibody responses [reviewed by (Wyatt et al., Science 280, 1884-1888. (1998)].

Over the past two decades, advances in the treatment of human immunodeficiency virus (HIV) infection have led to dramatic improvements in health outcomes of infected individuals receiving antiretroviral therapy (ART). Nonetheless, the vast majority of HIV-infected individuals must remain on continuous, life-long ART in order to maintain suppression of HIV replication and prevent progression to AIDS. While effective at suppressing HIV replication, current ART requires life-long adherence to daily medication regimens and is associated with significant costs, cumulative toxicities, and the potential for emergence of drug-resistant virus.

Consequently, there has been considerable interest in strategies that would allow for discontinuation of ART while maintaining suppression of plasma viremia for prolonged periods. In this regard, recent advances in immunogen and antibody cloning technologies have led to the isolation of several highly potent and broadly neutralizing HIV-specific antibodies (bNAb) from B cells of infected individuals. Some bNAbs have exhibited strong activities against HIV and SIV in vitro, in infected animals, and in infected individuals who were not receiving ART.

Recently, broadly neutralizing antibodies (bNAbs) have been explored as prevention and therapy agents for the treatment and management of HIV-1, as they can i) inhibit virus entry by neutralizing the free infectious virus particles, ii) prevent virus cell-to-cell spread, and iii) eliminate virus-infected cells by binding the Env molecules expressed on the surface of the infected cells and triggering antibody-dependent cell-mediated cytotoxicity (ADCC) through interactions between the IgG Fc region and the Fc receptors on effector cells (primarily NK cells) [reviewed in Burton et al., Nat Immunol 16, 571-576 (2015)]. Furthermore, the repertoire of isolated bNAbs has drastically increased recently as the process for bNAb isolation and characterization has accelerated with the integration of emerging functional and structural information and new technologies of single B cell sorting and cloning (Burton et al., Proc Natl Acad Sci USA 88, 10134-10137 (1991); Buchacher et al., AIDS Res Hum Retroviruses 10, 359-369 (1994); Huang et al., Nature 491, 406-412 (2012); Scheid et al., Science 333, 1633-1637 (2011); Wu et al., Science 329, 856-861 (2010); Walker et al., Nature 477, 466-470 (2011)). The characterization of HIV-1 bNAbs and their cognate epitopes on the Env spikes has identified five conserved Env sites of vulnerability including, in the order from the apex to the stem of Env: the V1/V2-glycan region, the V3-glycan region, the CD4-binding site (CD4bs), the gp120-gp41 interface (Burton et al., Nat Immunol 16, 571-576 (2015)), and the gp41 membrane proximal external region (MPER) (Burton et al., Nat Immunol 16, 571-576 (2015); Kwong et al., Nat Rev Immunol 13, 693-701 (2013)) (FIG. 1).

Administration of a single bNAb as a therapeutic agent has successfully cleared phase I safety clinical trials, demonstrating temporary HIV-1 viremia suppression in the majority of patients (Caskey et al., Nature 522, 487-491 (2015); Ledgerwood et al., Clin Exp Immunol 182, 289-301 (2015)). Unfortunately, the HIV virus rapidly develops resistance mutations under the selective pressure of single bNAb, suggesting that passive treatment with a single bNAb is unlikely to result in long-term viremia suppression (Caskey et al., Nature 522, 487-491 (2015); Lynch et al., Sci Transl Med 7, 319ra206 (2015); Bar et al., N Engl J Med 375, 2037-2050 (2016); Caskey et al., Nat Med 23, 185-191 (2017)). Fortunately, some Env mutations associated with bNAb resistance can reduce viral fitness, suggesting that simultaneously targeting different Env epitopes may compromise viral replication (Tebit et al., AIDS Rev 9, 75-87 (2007); Sather et al., J Virol 86, 12676-12685 (2012); Lynch et al., J Virol 89, 4201-4213 (2015); Pietzsch et al., J Exp Med 207, 1995-2002 (2010)). The quick onset of escaping virus quasi species in these clinical trials with single bNAb agent strongly highlights the need to develop combinational therapy regimens to control virus rebound by preventing emergence of resistant virus. Additionally, in vitro data from previous studies have demonstrated that combinatorial bNAb therapies display a substantial gain of neutralization potency and breadth when two or more bNAbs targeting independent epitopes are combined (Kong et al., J Virol 89, 2659-2671 (2015); Doria-Rose et al., J Virol 86, 3393-3397 (2012)). This in vitro data is further supported by a number of in vivo animal studies in which dual-, triple-, and penta-combinations of bNAbs resulted in improved protective efficacy compared to mono bNAb therapy (Shingai et al., Nature 503, 277-280 (2013); Klein et al., Nature 492, 118-122 (2012)).

Collectively, these findings suggest that passive immunotherapy with a bNAb(s) could potentially prevent plasma viral rebound in HIV-infected individuals following cessation of ART. For this reason, we recently conducted a clinical trial to investigate whether VRC01 could prevent plasma viral rebound upon discontinuation of ART. While multiple infusions of VRC01 were safe and well-tolerated, the majority of patients experienced plasma viral rebound due to pre-existing and emergent VRC01-resistant HIV despite adequate levels of antibody in plasma (Lynch, Sci Transl Med 7, 319ra206 (2015); Bar et al., N Engl J Med 375, 2037-2050 (2016)). Therefore, therapeutic strategies involving passive transfer of bNAbs may require a combination of bNAbs that targets multiple regions on HIV Env protein in order to achieve sustained virologic control upon withdrawal of ART.

Of note, the potential significance of the above concept was recently highlighted in an animal experiment in which a trimeric antibody consisting of VRC01, PGDM1400, and 10E8 showed profound potency and breadth against a mixture of SHIV (Xu et al., Science 358, 85-90 (2017)). Building upon these findings, it is of great importance to explore the effect of multimeric bNAbs (or bNAb-like molecules) that possess broad and potent neutralization capacity against highly heterogeneous infectious viral isolates.

While antibody cocktails demonstrated improved efficacy in preclinical studies, multispecific "single agents" are desirable for manufacturing purposes (Hu et al., Adv Drug Deliv Rev 98, 19-34 (2016) as well as for improved avidity that may result in enhanced neutralization breadth and potency (Galimidi et al., Cell 160, 433-446 (2015)). Previous bispecific bNAb designs utilizing CrossMab technology to combine two bNAb Fabs first proved the concept that empirical combinations of bNAb functional moieties in bi-valence format could achieve breadth and coverage (94-97%) superior to individual parental bNAbs (70-90%) (Asokan et al., J Virol 89, 12501-12512 (2015)). These empirical combinations were recently improved upon with cross-over dual variable (CODV) technology to develop Tri-NAbs with improved potency and breadth (Xu et al., Science 358, 85-90 (2017)). In addition, using tandem ScFvs format, we engineered a trispecific HIV-1 neutralizing antibody and two tetra-specific antibodies, consisting of functional moieties of three and four HIV bNAbs, respectively (Steinhardt et al., Nat Commun 9, 877 (2018)) (PCT/US2017/057053), which displays elevated neutralization breadth and potency compared to the parental bNAbs.

This background information is provided for informational purposes only. No admission is necessarily intended, nor should it be construed, that any of the preceding information constitutes prior art against the present invention.

SUMMARY OF THE INVENTION

It is to be understood that both the foregoing general description of the embodiments and the following detailed description are exemplary, and thus do not restrict the scope of the embodiments.

Provided herein are multispecific neutralizing antibodies against HIV which in some embodiments utilize a tandem ScFv format to combine five HIV Env bNAb moieties via structure-based rational design. In some embodiments, these antibodies can achieve simultaneous engagement of five separate epitopes by each respective individual bNAb functional moiety to achieve superior binding avidity, profoundly enhanced viral inhibition breadth and potency, and ADCC functions.

By targeting >3 Env epitopes, these multi-NAbs display near pan-isolate neutralization breadth (99.6% coverage), high potency (GMT IC50=0.006 μg/mL) as assessed by a 208 virus panel and effectively neutralize viral quasi-species isolated from VRC01 clinical trials that are frequently resistant to VRC01. Furthermore, the data herein suggest that these multi-NAbs possess substantially higher antibody-dependent cell-mediated cytotoxicity (ADCC) capacity than their parental bNAbs. Taken together, the data suggest that multi-NAbs may be used as a novel candidate format for the treatment and management of persistent HIV-1 infection.

In some embodiments, the present disclosure describes synergistically combined epitope-binding moieties from five bNAbs that target the CD4 binding site, V2 and V3 conserved glycans, gp120/gp41 interface, as well as the membrane exterior proximal region into a 'single' penta-specific antibody (penta-NAb). The penta-Nabs exhibited superior degrees of inhibition against pseudo-typed viruses, exceptional neutralization capacity over individual bNAbs, and the capacity to neutralize replication-competent HIV isolates from infected individuals.

In one aspect, the invention provides a multispecific anti-HIV antibody that binds to multiple epitopes on HIV envelope protein, wherein the antibody comprises:

i. an amino acid sequence that binds to a V1/V2 apex glycan epitope;

ii. an amino acid sequence that binds to a V3-base glycan region epitope;

iii. an amino acid sequence that binds to a CD4 binding site (CD4bs) epitope;

iv. an amino acid sequence that binds to a gp120/gp41 interface epitope; and v. an amino acid sequence that binds to a membrane proximal external region (MPER) epitope.

In some embodiments, the amino acid sequences of parts i-v) comprise amino acid sequences of single chain fragment variable (ScFv) moieties, wherein each ScFv moiety comprises an amino acid sequence from a light chain variable region (VL) and an amino acid sequence from a heavy chain variable region (VH) of an antibody. In some embodiments, the VL and VH sequences are separated by one or more linking amino acids. In some embodiments, the linking amino acids comprise one or more tetra-glycine serine ($G_4S$) linkers. In some embodiments, the antibody further comprises an Fc region of an immunoglobulin or a variant thereof. In some embodiments, the antibody comprises a first and second polypeptide chain, wherein the first and second polypeptide chains each comprise five ScFv moieties, wherein each ScFv moiety on a single chain recognizes an individual epitope, wherein each ScFv moiety comprises an amino acid sequence from a light chain variable region (VL) and an amino acid sequence from a heavy chain variable region (VH) of an antibody and an Fc region of an immunoglobulin or a variant thereof.

In some embodiments, the amino acid sequence that binds to the epitope of the V1/V2-glycan region comprises an amino acid sequence from an antibody selected from the group consisting of VRC26.25 and PGDM1400; the amino acid sequence that binds to the epitope of the V3-glycan region comprises an amino acid sequence from antibody PGT121; the amino acid sequence that binds to the epitope of the CD4-binding site (CD4bs) comprises an amino acid sequence from antibody N6; the amino acid sequence that binds to the epitope of the gp120/gp41 interface comprises an amino acid sequence from antibody 35O22; and the amino acid sequence that binds to the epitope of the membrane proximal external region (MPER) comprises an amino acid sequence from an antibody selected from the group consisting of 10E8v4, 10E8v4_S100cF, and 10E8v4_V5R_S100cF.

In some embodiments, the amino acid sequence from the antibody VRC26.25 comprises an amino acid sequence from the VH region comprising CDR H1, CDR H2 and CDR H3, wherein CDR H1 comprises QFRFDGYG, CDR H2 comprises ISHDGIKK and CDR H3 comprises AKDLREDECEEWWSDDFGKQLPCAKSRGGLVGIADN; and an amino acid sequence from the VL region comprising CDR L1, CDR L2 and CDR L3, wherein CDR L1 comprises TSNIGNNF, CDR L2 comprises ETD and CDR L3 comprises ATWAASLSSARV;

the amino acid sequence from the antibody PGDM1400 comprises an amino acid sequence from the VH region comprising CDR H1, CDR H2 and CDR H3, wherein CDR H1 comprises GNTLKTYD, CDR H2 comprises ISHEGDKK and CDR H3 comprises AKGSKHRLRDYALDDDGALNWAVDVDYLSNLEF; and an amino acid sequence from the VL region comprising CDR L1, CDR L2 and CDR L3, wherein CDR L1 comprises HSLIHGDRNNY, CDR L2 comprises LAS and CDR L3 comprises MQGRESPWT;

the amino acid sequence from the antibody PGT121 comprises an amino acid sequence from the VH region comprising CDR H1, CDR H2 and CDR H3, wherein CDR H1 comprises GASISDSY, CDR H2 comprises VHKSGDT and CDR H3 comprises ARTLHGRRIYGIVAFNEWFTYFYMDV; and an amino acid sequence from the VL region comprising CDR L1, CDR L2 and CDR L3, wherein CDR L1 comprises SLGSRA, CDR L2 comprises NNQ and CDR L3 comprises HIWDSRVPTKWV;

the amino acid sequence from the antibody N6 comprises an amino acid sequence from the VH region comprising CDR H1, CDR H2 and CDR H3, wherein CDR H1 comprises GYTFTAHI, CDR H2 comprises IKPQYGAV and CDR H3 comprises AR; and an amino acid sequence from the VL region comprising CDR L1, CDR L2 and CDR L3, wherein CDR L1 comprises QGVGSD, CDR L2 comprises HTS and CDR L3 comprises QVLQF;

the amino acid sequence from the antibody 35O22 comprises an amino acid sequence from the VH region comprising CDR H1, CDR H2 and CDR H3, wherein CDR H1 comprises GYRFNFYH, CDR H2 comprises ISPYSGDK and CDR H3 comprises DDTGTYFCAKGLLRDGSSTWLPYL; and an amino acid sequence from the VL region comprising CDR L1, CDR L2 and CDR L3, wherein CDR L1 comprises NSVCCSHKS, CDR L2 comprises EDN and CDR L3 comprises CSYTHNSGCV;

the amino acid sequence from the antibody 10E8v4 comprises an amino acid sequence from the VH region comprising CDR H1, CDR H2 and CDR H3, wherein CDR H1 comprises GFDFDNAW, CDR H2 comprises ITGPGEGWSV and CDR H3 comprises TGYYFCARTGKYYDFWSGYPPGEEYFQD; and an amino acid sequence from the VL region comprising CDR L1, CDR L2 and CDR L3, wherein CDR L1 comprises RGDSLRSHYAS, CDR L2 comprises GKNNRPS and CDR L3 comprises SSRDKSGSRLSV;

the amino acid sequence from the antibody 10E8v4 S100cF comprises an amino acid sequence from the VH region comprising CDR H1, CDR H2 and CDR H3, wherein CDR H1 comprises GFDFDNAW, CDR H2 comprises ITGPGEGWSV and CDR H3 comprises TGYYFCARTGKYYDFWFGYPPGEEYFQD; and an amino acid sequence from the VL region comprising CDR L1, CDR L2 and CDR L3, wherein CDR L1 comprises RGDSLRSHYAS, CDR L2 comprises GKNNRPS and CDR L3 comprises SSRDKSGSRLSV;

the amino acid sequence from the antibody 10E8v4_V5R_S100cF comprises an amino acid sequence from the VH region comprising CDR H1, CDR H2 and CDR H3, wherein CDR H1 comprises GFDFDNAW, CDR H2 comprises ITGPGEGWSV and CDR H3 comprises TGYYFCARTGKYYDFWFGYPPGEEYFQD; and an amino acid sequence from the VL region comprising CDR L1, CDR L2 and CDR L3, wherein CDR L1 comprises RGDSLRSHYAS, CDR L2 comprises GKNNRPS and CDR L3 comprises SSRDKSGSRLSV.

In another aspect, the invention provides one or more vectors comprising a nucleic acid encoding the antibody or polypeptide of the invention.

In another aspect, the invention provides a cell comprising the one or more vectors of the invention.

In another aspect, the invention provides an engineered cell that expresses an antibody of the invention. In some embodiments, the cell is an immune cell. In some embodiments, the cell is a B cell.

In another aspect, the invention provides a pharmaceutical composition comprising an antibody of the invention and/or cells of the invention and a pharmaceutically acceptable carrier.

In another aspect, the invention provides a method for treating or preventing HIV infection in a subject, comprising administering to the subject an effective amount of a composition comprising an effective amount of a multispecific antibody as described herein.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE FIGURES

The skilled artisan will understand that the drawings, described below, are for illustration purposes only. The drawings are not intended to limit the scope of the present teachings in any way.

FIG. 4. (A) IC50 values (μg/ml) for PentaNAb2.0 and other antibodies tested in a 208 virus panel. The IC50 was adjusted to account for the molarity difference between the antibodies. (B) Summary of IC50 values for PentaNAb2.0 and other antibodies.

FIG. 8. (A-C) Spatial distance of bNAb functional moieties.

FIG. 12A-B. Design of a multi-specific antibody HexaNAb 1.0 ScFv which contains PentaNAb4.0 Reverse ScFv with variable domains of dB4C7/UB-421, an anti-CD4 antibody.

FIG. 14A-B depicts the neutralization profiles of PentaNAb2.0 Reverse ScFv, PentaNAb4.0 Forward ScFv, PentaNAb4.0 Reverse ScFv, HexaNAb 1.0 ScFv and PentaNAb4.0 Stem HC LS v2 IgG tested with a 208-virus panel (FIGS. 14A & B). The PentaNAb2.0 Reverse ScFv has incremental improvement in potency (IC 50 geometric mean) compared to the initial design, PentaNAb2.0 ScFv. The HexaNAb 1.0 ScFv (FIG. 12) shows 100% virus neutralization breadth and promising potency (IC50 geometric mean ~0.005 ug/mL) (FIGS. 14 A & B). The PentaNAb4.0 Stem HC LS v2 IgG demonstrates 99.5% virus coverage (207/208 viruses tested) and high potency (IC50 geometric mean ~0.02 ug/mL) (FIGS. 14A & B).

DETAILED DESCRIPTION OF THE INVENTION

Figure 1:
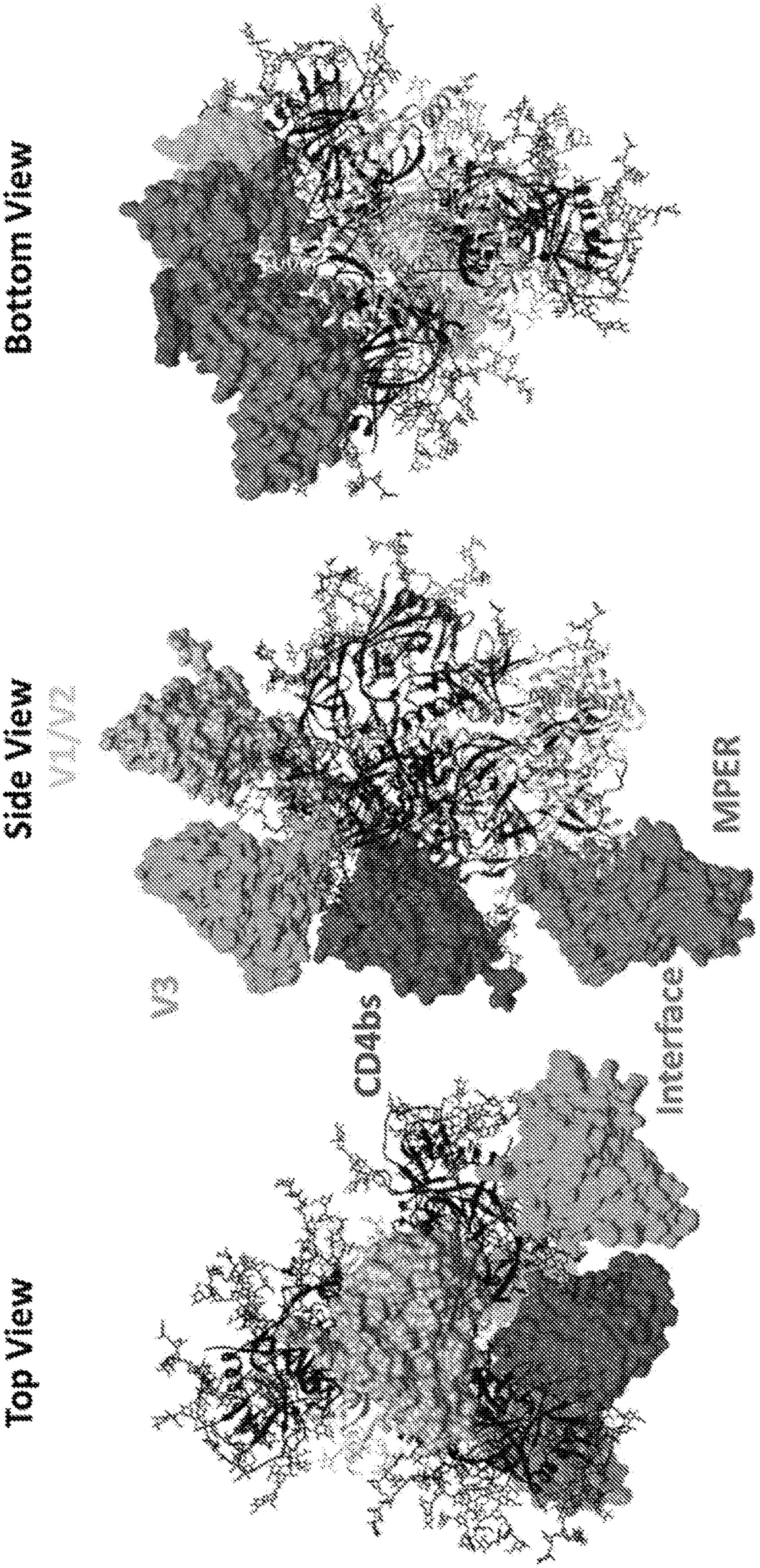
FIG. 1. HIV-1 Env major epitope clusters and their spatial relationships.

The present disclosure is based on the discovery of highly neutralizing and potent HIV antibodies that are capable of engaging at least five epitopes on HIV envelope protein. In some embodiments, the antibody comprises single-chain variable fragment (ScFv) domains of five bNAbs, specific for the HIV-1 envelope epitopes that have been joined to form penta-specific ScFvs (penta-ScFvs). The penta-ScFv crosslinks adjacent HIV-1 envelope protomers and demonstrates superior neutralization breadth over its parental bNAbs. The epitopes recognized are the V1/V2 glycan region, the V3-glycan region, the CD4-binding site (CD4bs), the gp120-gp41 interface, and the gp41 membrane proximal external region (MPER). Furthermore, the present disclosure shows that using an Fc moiety to combine two penta-ScFv molecules that recognize the same series of HIV-1 epitopes in either the forward or reverse orientation resulted in a penta-specific bNAb, which displays near-pan neutralization breadth potently. Thus, penta-specific antibodies combining functional moieties of Env bNAbs could achieve exceptional neutralization capacity with profoundly augmented avidity. The penta-specific antibodies described herein can be used in studies aimed at preventing HIV disease progression or mother to child transmission, and curing HIV. Furthermore, the approach described herein, that combines multi-functional moieties of individual bNAbs with profoundly elevated avidity and cooperative effect of multivalence interactions, may be applied to generate superior antibody-based anti-viral therapeutics against other infectious agents.

For the purpose of interpreting this specification, the following definitions will apply and whenever appropriate, terms used in the singular will also include the plural and vice versa. In the event that any definition set forth below conflicts with the usage of that word in any other document, including any document incorporated herein by reference, the definition set forth below shall always control for purposes of interpreting this specification and its associated claims unless a contrary meaning is clearly intended (for example in the document where the term is originally used). The use of "or" means "and/or" unless stated otherwise. As used in the specification and claims, the singular form "a," "an" and "the" include plural references unless the context clearly dictates otherwise. For example, the term "a cell" includes a plurality of cells, including mixtures thereof. The use of "comprise," "comprises," "comprising," "include," "includes," and "including" are interchangeable and not intended to be limiting. Furthermore, where the description of one or more embodiments uses the term "comprising," those skilled in the art would understand that, in some specific instances, the embodiment or embodiments can be alternatively described using the language "consisting essentially of" and/or "consisting of."

Abbreviations for amino acids are used throughout this disclosure and follow the standard nomenclature known in the art. For example, as would be understood by those of ordinary skill in the art, Alanine is Ala or A; Arginine is Arg or R; Asparagine is Asn or N; Aspartic Acid is Asp or D; Cysteine is Cys or C; Glutamic acid is Glu or E; Glutamine is Gln or Q; Glycine is Gly or G; Histidine is His or H; Isoleucine is Ile or I; Leucine is Leu or L; Lysine is Lys or K; Methionine is Met or M; Phenylalanine is Phe or F; Proline is Pro or P; Serine is Ser or S; Threonine is Thr or T; Tryptophan is Trp or W; Tyrosine is Tyr or Y; and Valine is Val or V.

As used herein, the term "about" means plus or minus 10% of the numerical value of the number with which it is being used.

The term "broad neutralizing antibody" refers to an antibody which inhibits HIV-1 infection, as defined by at least about 50% inhibition of infection in vitro, in more than 50%, 60%, 70%, 80%, 90%, 95%, 99% or greater, of a large panel of (greater than 100) HIV-1 envelope pseudotyped viruses and/or viral isolates. In some embodiments, the broad neutralizing antibody is an antibody that inhibits HIV-1 infection as defined by at least about 70%, 80%, 90%, 91%, 92%, 93%, 94%, 95%, 96%, 97%, 98%, 99% or 100% inhibition of infection in vitro in more than about 50%, 60%, 70%, 80%, 90%, 95%, 99% or greater, of a large panel of (greater than 100) HIV-1 envelope pseudotyped viruses and/or viral isolates. In some embodiments, the disclosure relates to a composition comprising one or a plurality of broad neutralizing antibodies.

As used herein, the term "in combination with," is not intended to imply that the therapy or the therapeutic agents must be administered at the same time and/or formulated for delivery together, although these methods of delivery are within the scope described herein.

The therapeutic agents can be administered concurrently with, prior to, or subsequent to, one or more other additional therapies or therapeutic agents.

The term "antibody" means a molecule that recognizes and specifically binds to a target, such as a protein, polypeptide, peptide, carbohydrate, polynucleotide, lipid, or combinations of the foregoing through at least one antigen recognition site within a variable region of the molecule, or any functional fragment, mutant, variant, or derivative thereof which retains the epitope binding features of an immunoglobulin molecule. As used herein, the term "antibody" encompasses intact polyclonal antibodies, intact monoclonal antibodies, antibody fragments (such as Fab, Fab', F(ab')2, and Fv fragments, dual affinity retargeting antibodies (DART)), single chain Fv (scFv) mutants, multispecific antibodies such as pentaspecific antibodies generated from at least five intact immunoglobulins, chimeric antibodies, humanized antibodies, human antibodies, fusion proteins comprising an antigen determination portion of an antibody, and any other modified immunoglobulin molecule comprising an antigen recognition site so long as the antibodies exhibit the desired biological activity.

In some embodiments, the antibody can comprise a sequence from any of the five major classes of immunoglobulins: IgA, IgD, IgE, IgG, and IgM, or subclasses (isotypes) thereof (e.g. IgG1, IgG2, IgG3, IgG4, IgA1 and IgA2), based on the identity of their heavy-chain constant domains referred to as alpha, delta, epsilon, gamma, and mu, respectively. The different classes of immunoglobulins have different and well known subunit structures and three-dimensional configurations. Antibodies can be naked or conjugated to other molecules such as toxins, radioisotopes, etc.

In a full-length antibody, each heavy chain is comprised of a heavy chain variable region (abbreviated herein as HCVR or VH) and a heavy chain constant region. The heavy chain constant region is comprised of three domains, CHI, CH2 and CH3. Each light chain is comprised of a light chain variable region (abbreviated herein as LCVR or VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is generally composed of three CDRs and four FRs, arranged from amino-terminus to carboxy-terminus in the following order: FR1, CDR1, FR2, CDR2, FR3, CDR3, FR4.

A "conservative amino acid substitution" is one in which one amino acid residue is replaced with another amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., asparagine, glutamine, serine, threonine, tyrosine, cysteine), nonpolar side chains (e.g., glycine, alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). For example, substitution of a phenylalanine for a tyrosine is a conservative substitution. In certain embodiments, conservative substitutions in the sequences of the polypeptides and antibodies of the invention do not abrogate the binding of the polypeptide or antibody containing the amino acid sequence, to the antigen(s), i.e., the envelope protein to which the polypeptide or antibody binds. Methods of identifying nucleotide and amino acid conservative substitutions which do not eliminate antigen binding are well-known in the art (see, e.g., Brummell et al., Biochem. 32: 1180-1187 (1993); Kobayashi et al., Protein Eng. 12(10):879-884 (1999); and Burks et al., Proc. Natl. Acad. Sci. USA 94:412-417 (1997)).

As used herein, the term "CDR" refers to the complementarity determining region within antibody variable sequences. In some embodiments, there are three CDRs in each of the variable regions of the heavy chain and the light chain of an antibody, which are designated CDR1, CDR2 and CDR3, for each of the variable regions. The term "CDR set" as used herein refers to a group of three CDRs that occur in a single variable region capable of binding the antigen. The exact boundaries of these CDRs have been defined differently according to different systems. The system described by Kabat (Kabat et al., Sequences of Proteins of Immunological Interest (National Institutes of Health, Bethesda, Md. (1987) and (1991)) not only provides an unambiguous residue numbering system applicable to any variable region of an antibody, but also provides precise residue boundaries defining the three CDRs. These CDRs may be referred to as Kabat CDRs. Chothia and coworkers (Chothia et al., J. Mol. Biol. 196:901-917 (1987) and Chothia et al., Nature 342:877-883 (1989)) found that certain sub-portions within Kabat CDRs adopt nearly identical peptide backbone conformations, despite having great diversity at the level of amino acid sequence. These sub-portions were designated as LI, L2 and L3 or HI, H2 and H3 where the "L" and the "H" designates the light chain and the heavy chains regions, respectively. These regions may be referred to as Chothia CDRs, which have boundaries that overlap with Kabat CDRs. Other boundaries defining CDRs overlapping with the Kabat CDRs have been described by Padlan (FASEB J. 9:133-139 (1995)) and MacCallum (J Mol Biol 262(5):732-45 (1996)). Still other CDR boundary definitions may not strictly follow one of the above systems, but will nonetheless overlap with the Kabat CDRs, although they may be shortened or lengthened in light of prediction or experimental findings that particular residues or groups of residues or even entire CDRs do not significantly impact antigen binding. The methods used herein may utilize CDRs defined according to any of these systems, although preferred embodiments use Kabat or Chothia defined CDRs.

As used herein, the term "fragment" is defined as a physically contiguous portion of the primary structure of a biomolecule. In the case of polypeptides, a fragment may be defined by a contiguous portion of the amino acid sequence of a protein and may be at least 3-5 amino acids, at least 6-10 amino acids, at least 11-15 amino acids, at least 16-24 amino acids, at least 25-30 amino acids, at least 30-45 amino acids and up to the full length of the protein minus a few amino acids. In the case of polynucleotides, a fragment is defined by a contiguous portion of the nucleic acid sequence of a polynucleotide and may be at least 9-15 nucleotides, at least 15-30 nucleotides, at least 31-45 nucleotides, at least 46-74 nucleotides, at least 75-90 nucleotides, and at least 90-130 nucleotides. In some embodiments, fragments of bio molecules are immunogenic fragments.

In some embodiments, the term "functional fragment" means any portion of a polypeptide or amino acid sequence that is of a sufficient length to retain at least partial biological function that is similar to or substantially similar to the parental polypeptide or amino acid sequence upon which the fragment is based. If the fragment is a functional fragment of an antibody or antibody-like molecule, the fragment can possess a binding avidity for one or a plurality of antigens. In some embodiments, a functional fragment is a polypeptide that comprises 80, 85, 90, 95, 96, 97, 98, or 99% sequence identity of any variable region of a polypeptide antibody disclosed herein and has sufficient length to retain at least partial binding affinity to one or a plurality of antigens that bind to the amino acid sequence. In some embodiments, the fragment has a length of at least about 10, about 20, about 30, about 40, about 50, about 60, about 70, about 80, about 90, or about 100 contiguous amino acids. In some embodiments, the fragment is a fragment of any amino acid sequence disclosed herein and has a length of at least about 50 amino acids. In some embodiments, the fragment has a length of at least about 100, 150, 200, 250, 300, 350, 400, 450, 500, or 550 amino acids.

The term "antigen binding portion" or "antigen binding fragment" of an antibody (or simply "antibody portion" or "antibody fragment"), as used herein, refers to one or more fragments of an antibody that retain the ability to specifically bind to an antigen (e.g., HIV gp120). It has been shown that the antigen-binding function of an antibody can be performed by fragments of a full-length antibody. Such antibody embodiments can be multi-specific formats; specifically binding to two or more different antigens. Examples of binding fragments encompassed within the term "antigen-binding portion" or "antigen binding fragment" of an antibody include (i) a Fab fragment, a monovalent fragment consisting of the VL, VH, CL and CHI domains; (ii) a F(ab')2 fragment, a bivalent fragment comprising two Fab fragments linked by a disulfide bridge at the hinge region; (iii) a Fd fragment consisting of the VH and CHI domains; (iv) a Fv fragment consisting of the VL and VH domains of a single arm of an antibody, (v) a dAb fragment (Ward et al, (1989) Nature 341:544-546, Winter et al., PCT publication WO 90/05144 Al herein incorporated by reference), which comprises a single variable domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) Science 242:423-426; and Huston et al. (1988) Proc. Natl. Acad. Sci. USA 85:5879-5883). Such single chain antibodies are also intended to be encompassed within the term "antigen-binding portion" or "antigen binding fragment" of an antibody. Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger, P., et al. (1993) Proc. Natl. Acad. Sci. USA 90:6444-6448; Poljak, R. J., et al. (1994) Structure 2:1121-1123). Such antibody binding portions are known in the art (Kontermann and Dubel eds., Antibody Engineering (2001) Springer-Verlag. New York. 790 pp. (ISBN 3-540-41354-5).

The term "multispecific antibody" refers to an antibody or antibody-like molecule, or fragment thereof, capable of binding two or more related or unrelated targets, or antigens. Antibody specificity refers to selective recognition of the antibody for a particular epitope, or amino acid sequence, of an antigen. Natural antibodies, for example, are monospecific. Pentaspecific antibodies are antibodies which have five different antigen-binding specificities.

The term "epitope" includes any polypeptide determinant capable of specific binding to an antibody. In certain embodiments, epitope determinants include chemically active surface groupings of molecules such as amino acids, sugar side chains, phosphoryl, or sulfonyl, and, in certain embodiments, may have specific three-dimensional structural characteristics, and or specific charge characteristics. An epitope is a region of an antigen that is bound by an antibody.

The term "antigen" refers to a polypeptide that can stimulate the production of antibodies or a T cell response in an animal, including polypeptides that are injected or absorbed into an animal. An antigen reacts with the products of specific humoral or cellular immunity.

The term "HIV Envelope protein (Env)" refers to the glycoprotein that is found on the surface of HIV. The HIV envelope protein is initially synthesized as a longer precursor protein of 845-870 amino acids in size, designated gp160. gp160 forms a homotrimer and undergoes glycosylation within the Golgi apparatus. In vivo, it is then cleaved by a cellular protease into gp120 and gp41. gp120 contains most of the external, surface-exposed, domains of the HIV envelope glycoprotein complex, and it is gp120 which binds both to cellular CD4 receptors and to cellular chemokine receptors (such as CCR5). gp41 contains a transmembrane domain and remains in a trimeric configuration within the membrane of the virus or the membrane of a host cell; it interacts with gp120 in a noncovalent manner. The mature gp120 wildtype polypeptides have about 500 amino acids in the primary sequence. gp120 is heavily N-glycosylated giving rise to an apparent molecular weight of 120 kD. The polypeptide is comprised of five conserved regions (C1-05) and five regions of high variability (V1-V5). Exemplary sequence of wt gp120 polypeptides are shown on GENBANK, for example accession numbers AAB05604 and AAD12142 (as available on Oct. 16, 2009), incorporated by reference herein. It is understood that there are numerous variation in the sequence of gp120 from what is given in GENBANK, for example accession numbers AAB05604 and AAD12142, and that these variants are skill recognized in the art as gp120. The gp120 core has a molecular structure, which includes two domains: an "inner" domain (which faces gp41) and an "outer" domain (which is mostly exposed on the surface of the oligomeric envelope glycoprotein complex). The two gp120 domains are separated by a "bridging sheet" that is not part of either domain. The gp120 core includes 25 beta strands, 5 alpha helices, and 10 defined loop segments.

The term "CD4 binding site (CD4BS) antibodies" refers to antibodies that bind to the CD4 binding surface of a gp120 polypeptide. The antibodies interfere with or prevent CD4 from binding to a gp120 polypeptide.

The term "V3 loops" refers to a loop of about 35 amino acids critical for the binding of the co-receptor and determination of which of the co-receptors will bind. In certain examples the V3 loop includes residues 296-331.

The term "membrane-proximal external region or MPER" refers to a highly conserved region of the gp41 envelope protein. The MPER comprises the last 24 C-terminal amino acids of the gp41 ectodomain, LLELDKWASLWNWF(N/D)ITNWLWYIK (aa 660 to 683) (Zwick et al. J Virol. 2005 January; 79(2): 1252-61).

The term "V1V2 glycan antibody" refers to antibodies that bind to the V1V2 apex and associated conserved glycans N160 and/or N156.

The term "gp120/gp41 interface antibody" refers to antibodies that bind to a conserved epitope that stretches across gp120 and gp41.

The term "vector," as used herein, is intended to refer to a nucleic acid molecule. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome.

Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" may be used interchangeably as the plasmid is the most commonly used form of vector. However, the disclosure is intended to include such other forms of expression vectors, such as viral vectors (e.g., replication defective retroviruses, adenoviruses and adeno-associated viruses), which serve equivalent functions.

"Polynucleotide" or "nucleic acid" as used interchangeably herein, refers to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase or by a synthetic reaction. A polynucleotide may comprise modified nucleotides, such as methylated nucleotides and their analogs. A sequence of nucleotides may be interrupted by non-nucleotide components. A polynucleotide may comprise modification(s) made after synthesis, such as conjugation to a label. Other types of modifications include, for example, "caps," substitution of one or more of the naturally occurring nucleotides with an analog, internucleotide modifications such as, for example, those with uncharged linkages (e.g., methyl phosphonates, phosphotriesters, phosphoamidates, carbamates, etc.) and with charged linkages (e.g., phosphorothioates, phosphorodithioates, etc.), those containing pendant moieties, such as, for example, proteins (e.g., nucleases, toxins, antibodies, signal peptides, ply-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotides(s). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid or semi-solid supports. The 5' and 3' terminal OH can be phosphorylated or substituted with amines or organic capping group moieties of from 1 to 20 carbon atoms. Other hydroxyls may also be derivatized to standard protecting groups. Polynucleotides can also contain analogous forms of ribose or deoxyribose sugars that are generally known in the art, including, for example, 2'-O-methyl-, 2'-O-allyl-, 2'-fluoro- or 2'-azido-ribose, carbocyclic sugar analogs, .alpha.-anomeric sugars, epimeric sugars such as arabinose, xyloses or lyxoses, pyranose sugars, furanose sugars, sedoheptuloses, acyclic analogs, and basic nucleoside analogs such as methyl riboside. One or more phosphodiester linkages may be replaced by alternative linking groups. These alternative linking groups include, but are not limited to, embodiments wherein phosphate is replaced by P(0)S ("thioate"), P(S)S ("dithioate"), (0)NR2 ("amidate"), P(0)R, P(0)OR, CO, or CH2 ("formacetal"), in which each R or R' is independently H or substituted or unsubstituted alkyl (1-20C) optionally containing an ether (—0-) linkage, aryl, alkenyl, cycloalkyl, cycloalkenyl or araldyl. Not all linkages in a polynucleotide need be identical. The preceding description applies to all polynucleotides referred to herein, including RNA and DNA.

The term "host cell" as used herein is intended to refer to a cell into which exogenous DNA has been introduced. It should be understood that such terms are intended to refer not only to the particular subject cell, but, to the progeny of such a cell. Because certain modifications may occur in succeeding generations due to either mutation or environmental influences, such progeny may not, in fact, be identical to the parent cell, but are still included within the scope of the term "host cell" as used herein. The host cells can include prokaryotic and eukaryotic cells selected from any of the Kingdoms of life. In some embodiments, eukaryotic cells include protist, fungal, plant and animal cells. In some embodiments, host cells include but are not limited to the prokaryotic cell line *E. coli*; mammalian cell lines CHO, HEK 293 and COS; the insect cell line Sf9; and the fungal cell *Saccharomyces cerevisiae*. In some embodiments, the host cell is an immune cell.

Standard techniques may be used for recombinant DNA, oligonucleotide synthesis, and tissue culture and transformation (e.g., electroporation, lipofection). Enzymatic reactions and purification techniques may be performed according to manufacturer's specifications or as commonly accomplished in the art or as described herein. The foregoing techniques and procedures may be generally performed according to conventional methods well known in the art and as described in various general and more specific references that are cited and discussed throughout the present specification. See e.g., Sambrook et al. Molecular Cloning: A Laboratory Manual (2d ed., Cold Spring Harbor Laboratory Press, Cold Spring Harbor, N.Y. (1989)), which is incorporated herein by reference for any purpose.

The term "inhibit" and its various grammatical forms is used to refer to a restraining, blocking, or limiting of the range or extent of a certain biological event or effect.

The term "effective amount," is used herein to include the amount of an agent (e.g. a multispecific antibody) that, when administered to a patient for treating an infection, is sufficient to effect treatment of the disease (e.g., by diminishing, ameliorating or maintaining the existing disease or one or more symptoms of disease or its related comorbidities). The "effective amount" may vary depending on the agent, how it is administered, the disease and its severity and the history, age, weight, family history, genetic makeup, stage of pathological processes, the types of preceding or concomitant treatments, if any, and other individual characteristics of the patient to be treated. An effective amount includes an amount that results in a clinically relevant change or stabilization, as appropriate, of an indicator of a disease or condition. "Effective amount" refers to an amount of a compound, material, or composition, as described herein effective to achieve a particular biological result such as, but not limited to, biological results disclosed, described, or exemplified herein. Such results may include, but are not limited to, the effective reduction of symptoms associated with any of the disease states mentioned herein, as determined by any means suitable in the art. The effective amount of the composition may be dependent on any number of variables, including without limitation, the species, breed, size, height, weight, age, overall health of the subject, the type of formulation, the mode or manner or administration, the type and/or severity of the particular condition being treated, or the need to modulate the activity of the molecular pathway induced by association of the analog to its receptor. The appropriate effective amount can be routinely determined by those of skill in the art using routine optimization techniques and the skilled and informed judgment of the practitioner and other factors evident to those skilled in the art. An effective dose of the antibodies or mutants or variants described herein may provide partial or complete biological activity as compared to the biological activity induced by the wild-type or naturally occurring polypeptides upon which the antibodies or mutants or variants are derived. A therapeutically effective dose of the antibodies or mutants or variants described herein may provide a sustained biochemical or biological effect and/or an increased resistance to degradation when placed in solution as compared with the normal affect observed when the naturally occurring and fully processed translated protein is administered to the same subject.

An "immunoconjugate" is an antibody or multispecific antibody conjugated to one or more heterologous molecule (s), including but not limited to a cytotoxic agent.

The term "cytotoxic agent" as used herein refers to a substance that inhibits or prevents a cellular function and/or causes cell death or destruction. Cytotoxic agents include, but are not limited to, radioactive isotopes; growth inhibitory agents; enzymes and fragments thereof such as nucleolytic enzymes; antibiotics; toxins such as small molecule toxins or enzymatically active toxins of bacterial, fungal, plant or animal origin, including fragments and/or variants thereof.

The term "administer" as used herein means to give or to apply. The term "administering" as used herein includes in vivo administration.

The term "linker" refers to a chemical moiety that connects one peptide sequence to another, e.g., one antibody or antigen binding fragment to another. Linkers can also be used to attach antibodies to labels or solid substrates. A linker can include amino acids. Linkers can be straight or branched, saturated or unsaturated carbon chains. They can also include one or more heteroatoms within the chain.

The term "pharmaceutical composition" refers to a preparation which is in such form as to permit the biological activity of an active ingredient contained therein to be effective, and which contains no additional components which are unacceptably toxic to a subject to which the composition would be administered. A pharmaceutical composition of the present disclosure can be administered by a variety of methods known in the art. As will be appreciated by the skilled artisan, the route and/or mode of administration will vary depending upon the desired results. To administer an antibody according to the disclosure by certain routes of administration, it may be necessary to coat the antibody with, or coadminister the antibody with, a material to prevent its inactivation. For example, the antibody may be administered to a subject in an appropriate carrier, for example, liposomes, or a diluent. Pharmaceutically acceptable diluents include saline and aqueous buffer solutions.

A "pharmaceutically acceptable carrier" refers to an ingredient in a pharmaceutical formulation, other than an active ingredient, which is nontoxic to a subject. Pharmaceutically acceptable carriers includes any and all solvents, dispersion media, coatings, antibacterial and antifungal agents, isotonic and absorption delaying agents, and the like that are physiologically compatible. In one embodiment, the carrier is suitable for intravenous, intramuscular, subcutaneous, parenteral, spinal or epidermal administration (e.g. by injection or infusion).

The pharmaceutical compositions according to the disclosure can also contain adjuvants such as preservatives, wetting agents, emulsifying agents and dispersing agents. Prevention of presence of microorganisms may be ensured both by sterilization procedures, supra, and by the inclusion of various antibacterial and antifungal agents, for example, paraben, chlorobutanol, phenol, sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

The term "subject" is used throughout the specification to describe an animal to which one or more compositions comprising the antibody or antibodies disclosed herein. In some embodiment, the subject is a human. The term "subject" and "patient" may be interchangeably used. In some instances in the description of the present disclosure, the term "patient" will refer to human patients suffering from a particular disease or disorder. In some embodiments, the subject may be a human suspected of having or being identified as at risk to develop HIV infection. In some embodiments, the subject is suspected of having or has been diagnosed with HIV or HIV-1 infection or AIDS. In some embodiments, the subject may be a human suspected of having or being identified as at risk to develop AIDS or an AIDS-associated disorder. In some embodiments, the subject may be a mammal. In some embodiments, the subject may be a non-human animal. In one embodiment, the subject is a human, such as a human being treated or assessed for an HIV infection; or a human having an HIV infection that would benefit from a multispecific antibody as described herein. In some embodiments, the subject is in need of the treatment being administered.

In some embodiments, the compositions or pharmaceutical compositions comprise crystalline forms or lyophilized forms of the antibodies, antibody—like molecules or salts thereof.

The term "treat" or "treating" includes abrogating, substantially inhibiting, slowing or reversing the progression of a disease, condition or disorder, substantially ameliorating clinical or esthetical symptoms of a condition, substantially preventing the appearance of clinical or esthetical symptoms of a disease, condition, or disorder, and protecting from harmful or annoying symptoms. The term "treat" or "treating" as used herein further refers to accomplishing one or more of the following: (a) reducing the severity of the disorder; (b) limiting development of symptoms characteristic of the disorder(s) being treated; (c) limiting worsening of symptoms characteristic of the disorder(s) being treated; (d) limiting recurrence of the disorder(s) in patients that have previously had the disorder(s); and (e) limiting recurrence of symptoms in patients that were previously symptomatic for the disorder(s).

The term "potency" as used herein refers to the neutralization capacity, i.e. the $IC_{50}$ or $IC_{80}$ of the antibody, or fragment thereof. The term "IC50" as used herein refers to the concentration of an inhibitor, such as a multispecific antibody, where the response or biological activity is reduced by half. The term "$IC_{80}$" as used herein refers to the concentration of an inhibitor (e.g. a multispecific antibody) where the response or biological activity is reduced by eighty percent.

Humanization and primatization refer to in cases where the multi-specific antibodies or the five antibodies forming the multi-specific fusion antibody are non-human antibodies, the antibody can be "humanized" to reduce immunogenicity to a human recipient. Methods for humanizing non-human antibodies have been described in the art. See, e.g., Jones et al., Nature 321:522-525 (1986); Riechmann et al, Nature 332:323-327 (1988); Verhoeyen et al., Science 239: 1534-1536 (1988), and U.S. Pat. No. 4,816,567. Generally, residues from the variable domain of a non-human antibody are "imported" into a human immunoglobulin molecule, resulting in antibodies in which some hypervariable region residues and possibly some FR residues of a human antibody are substituted by residues from analogous sites of non-human antibodies. It is important to humanize a non-human antibody while retaining high affinity for the antigen. To this end, three dimensional immunoglobulin models are commonly available and suitable for use in analyzing proposed humanized sequences in comparison to the parental non-human antibodies. Such analysis permits identification of residues likely involved in recognition and binding of the antigen, and therefore rational design of humanized sequences that retain the specificity and affinity for the antigen.

In some embodiments, multispecific antibodies are formed from anti-HIV human or humanized antibodies. Similarly, a penta-specific fusion antibody or the five antibodies forming the fusion can be "primatized" to reduce immunogenicity to another primate, non-human recipient, e.g., a rhesus recipient. Residues from the variable domain of a donor antibody (such as a non-primate antibody or an antibody of a primate species different from the recipient primate) are "imported" into a nonhuman primate recipient immunoglobulin molecule, resulting in antibodies in which some hypervariable region residues and possibly some FR residues of a nonhuman primate antibody are substituted by residues from analogous sites of donor antibodies. Alternatively, primatized antibodies can be made for use in a desirable primate species by using a recipient immunoglobulin having non-primate sequences or sequences from a different primate species by introducing the Fc fragment, and/or residues, including particularly framework region residues, from the desirable primate, into the recipient immunoglobulin.

By "affinity maturation" is meant when one or more hypervariable region residues of an antibody can be substituted to select for variants that have improved biological properties relative to the parent antibody by employing, e.g., affinity maturation using phage or yeast display. For example, the Fab region of an anti-HIV antibody can be mutated at several sites selected based on available structural information to generate all possible amino substitutions at each site. The antibody variants thus generated are displayed in a monovalent fashion from phage particles or on the surface of yeast cells. The displayed variants are then screened for their biological activity (e.g. binding affinity).

Anti-HIV Antibodies

In some embodiments, the invention provides multispecific antibodies that are broadly neutralizing antibodies against HIV.

HIV-1 is among the most genetically diverse viral pathogens. Of the three main branches of the HIV-1 phylogenetic tree, the M (main), N (new), and O (outlier) groups, group M viruses are the most widespread, accounting for over 99% of global infections. This group is presently divided into nine distinct genetic subtypes, or clades (A through K), based on full-length sequences. Env is the most variable HIV-1 gene, with up to 35% sequence diversity between clades, 20% sequence diversity within clades, and up to 10% sequence diversity in a single infected person (Shankarappa, R. et al. 1999. *J. Virol.* 73:10489-10502). Clade B is dominant in Europe, the Americas, and Australia. Clade C is common in southern Africa, China, and India and presently infects more people worldwide than any other Glade (McCutchan, F E. 2000. Understanding the genetic diversity of HIV-1. AIDS 14(Suppl. 3):531-544). Clades A and D are prominent in central and eastern Africa.

In some embodiments, the invention provides multispecific antibodies that are broadly neutralizing against HIV. In some embodiments, the antibody has a particularly high potency in neutralizing HIV infection in vitro across multiple clades as shown in the Table 1 and FIG. 4A herein. In some embodiments, only low concentrations are required in order to neutralize a given amount of virus. This facilitates higher levels of protection while administering lower amounts of antibody.

In some embodiments, the invention provides a multispecific anti-HIV antibody that binds to multiple epitopes on HIV envelope protein, wherein the antibody comprises:

i. an amino acid sequence that binds to a V1/V2 apex glycan epitope;
ii. an amino acid sequence that binds to a V3-base glycan region epitope;
iii. an amino acid sequence that binds to a CD4 binding site (CD4bs) epitope;
iv. an amino acid sequence that binds to a gp120/gp41 interface epitope; and
v. an amino acid sequence that binds to a membrane proximal external region (MPER) epitope.

The amino acid sequences of parts i-v) of the multispecific anti-HIV antibody can be present on one or more polypeptide chains. In some embodiments, the amino acid sequences of parts i-v) are present on a single polypeptide chain. In some embodiments, the multispecific anti-HIV antibody comprises two polypeptide chains, with each chain comprising amino acid sequences of parts i-v). In some embodiments, the antibody simultaneously binds the multiple epitopes.

In some embodiments, the multispecific anti-HIV antibody is capable of neutralizing at least 99% of the HIV viruses listed in Table 1 with an IC50 value of less than 50 μg/mL. In some embodiments, the multispecific anti-HIV antibody is capable of neutralizing at least 99.5% of the HIV pseudoviruses listed in Table 1 with an IC50 value of less than 50 μg/mL. In some embodiments, the multispecific anti-HIV antibody has an IC50 geomean of less than or equal to 0.10 μg/ml. In some embodiments, the multispecific anti-HIV antibody has an IC50 geomean of less than or equal to 0.072 μg/ml. In some embodiments, the multispecific anti-HIV antibody has an IC50 geomean of less than or equal to 0.006 μg/ml.

TABLE 1

List of HIV-1 Pseudovirus Panel: 208 Total Pseudoviruses Included.

| Virus ID | Clade |
|---|---|
| 0260.v5.c36 | A |
| 0330.v4.c3 | A |
| 0439.v5.c1 | A |
| 3365.v2.c20 | A |
| 3415.v1.c1 | A |
| 3718.v3.c11 | A |
| 398-F1_F6_20 | A |
| BB201.B42 | A |
| BB539.2B13 | A |
| BG505.W6M.C2 | A |
| BI369.9A | A |
| BS208.B1 | A |
| KER2008.12 | A |
| KER2018.11 | A |
| KNH1209.18 | A |
| MB201.A1 | A |
| MB539.2B7 | A |
| MI369.A5 | A |
| MS208.A1 | A |
| Q23.17 | A |
| Q259.17 | A |
| Q769.d22 | A |
| Q769.h5 | A |
| Q842.d12 | A |
| QH209.14M.A2 | A |
| RW020.2 | A |
| UG037.8 | A |
| 246-F3.C10.2 | AC |
| 3301.V1.C24 | AC |
| 3589.V1.C4 | AC |

TABLE 1-continued

List of HIV-1 Pseudovirus Panel: 208 Total Pseudoviruses Included.

| Virus ID | Clade |
|---|---|
| 6540.v4.c1 | AC |
| 6545.V4.C1 | AC |
| 0815.V3.C3 | ACD |
| 6095.V1.C10 | ACD |
| 3468.V1.C12 | AD |
| Q168.a2 | AD |
| Q461.e2 | AD |
| 620345.c1 | AE |
| BJOX009000.02.4 | AE |
| BJOX010000.06.2 | AE |
| BJOX025000.01.1 | AE |
| BJOX028000.10.3 | AE |
| C1080.c3 | AE |
| C2101.c1 | AE |
| C3347.c11 | AE |
| C4118.09 | AE |
| CM244.ec1 | AE |
| CNE3 | AE |
| CNE5 | AE |
| CNE55 | AE |
| CNE56 | AE |
| CNE59 | AE |
| CNE8 | AE |
| M02138 | AE |
| R1166.c1 | AE |
| R2184.c4 | AE |
| R3265.c6 | AE |
| TH023.6 | AE |
| TH966.8 | AE |
| TH976.17 | AE |
| 235-47 | AG |
| 242-14 | AG |
| 263-8 | AG |
| 269-12 | AG |
| 271-11 | AG |
| 928-28 | AG |
| DJ263.8 | AG |
| T250-4 | AG |
| T251-18 | AG |
| T253-11 | AG |
| T255-34 | AG |
| T257-31 | AG |
| T266-60 | AG |
| T278-50 | AG |
| T280-5 | AG |
| T33-7 | AG |
| 3988.25 | B |
| 5768.04 | B |
| 6101.10 | B |
| 6535.3 | B |
| 7165.18 | B |
| 45_01dG5 | B |
| 89.6.DG | B |
| AC10.29 | B |
| ADA.DG | B |
| Bal.01 | B |
| BaL.26 | B |
| BG1168.01 | B |
| BL01.DG | B |
| BR07.DG | B |
| BX08.16 | B |
| CAAN.A2 | B |
| CNE10 | B |
| CNE12 | B |
| CNE14 | B |
| CNE4 | B |
| CNE57 | B |
| HO86.8 | B |
| HT593.1 | B |
| HXB2.DG | B |
| JRCSF.JB | B |
| JRFL.JB | B |
| MN.3 | B |
| PVO.04 | B |
| QH0515.01 | B |

TABLE 1-continued

List of HIV-1 Pseudovirus Panel: 208 Total Pseudoviruses Included.

| Virus ID | Clade |
|---|---|
| QH0692.42 | B |
| REJO.67 | B |
| RHPA.7 | B |
| SC422.8 | B |
| SF162.LS | B |
| SS1196.01 | B |
| THRO.18 | B |
| TRJO.58 | B |
| TRO.11 | B |
| WITO.33 | B |
| X2278.C2.B6 | B |
| YU2.DG | B |
| BJOX002000.03.2 | BC |
| CH038.12 | BC |
| CH070.1 | BC |
| CH117.4 | BC |
| CH119.10 | BC |
| CH181.12 | BC |
| CNE15 | BC |
| CNE19 | BC |
| CNE20 | BC |
| CNE21 | BC |
| CNE40 | BC |
| CNE7 | BC |
| 286.36 | C |
| 288.38 | C |
| 0013095-2.11 | C |
| 001428-2.42 | C |
| 0077_V1.C16 | C |
| 00836-2.5 | C |
| 0921.V2.C14 | C |
| 16055-2.3 | C |
| 16845-2.22 | C |
| 16936-2.21 | C |
| 25710-2.43 | C |
| 25711-2.4 | C |
| 25925-2.22 | C |
| 26191-2.48 | C |
| 3168.V4.C10 | C |
| 3637.V5.C3 | C |
| 3873.V1.C24 | C |
| 426c | C |
| 6322.V4.C1 | C |
| 6471.V1.C16 | C |
| 6631.V3.C10 | C |
| 6644.V2.C33 | C |
| 6785.V5.C14 | C |
| 6838.V1.C35 | C |
| 96ZM651.02 | C |
| BR025.9 | C |
| CAP210.E8 | C |
| CAP244.D3 | C |
| CAP256.206.C9 | C |
| CAP45.G3 | C |
| Ce1176.A3 | C |
| CE703010217.B6 | C |
| CNE30 | C |
| CNE31 | C |
| CNE53 | C |
| CNE58 | C |
| DU123.06 | C |
| DU151.02 | C |
| DU156.12 | C |
| DU172.17 | C |
| DU422.01 | C |
| MW965.26 | C |
| SO18.18 | C |
| TV1.29 | C |
| TZA125.17 | C |
| TZBD.02 | C |
| ZA012.29 | C |
| ZM106.9 | C |
| ZM109.4 | C |
| ZM135.10a | C |
| ZM176.66 | C |
| ZM197.7 | C |
| ZM214.15 | C |
| ZM215.8 | C |
| ZM233.6 | C |
| ZM249.1 | C |
| ZM53.12 | C |
| ZM55.28a | C |
| 3326.V4.C3 | CD |
| 3337.V2.C6 | CD |
| 3817.v2.c59 | CD |
| 191821.E6.1 | D |
| 231965.c1 | D |
| 247-23 | D |
| 3016.v5.c45 | D |
| 57128.vrc15 | D |
| 6405.v4.c34 | D |
| A03349M1.vrc4a | D |
| A07412M1.vrc12 | D |
| NKU3006.ec1 | D |
| UG021.16 | D |
| UG024.2 | D |
| P0402.c2.11 | G |
| P1981.C5.3 | G |
| X1193.c1 | G |
| X1254.c3 | G |
| X1632.S2.B10 | G |
| X2088.c9 | G |
| X2131.C1.B5 | G |

In some embodiments, the amino acid sequences of parts i-v) comprise amino acid sequences of single chain fragment variable (ScFv) moieties, wherein each ScFv moiety comprises an amino acid sequence from a light chain variable region (VL) and an amino acid sequence from a heavy chain variable region (VH) of an antibody. In some embodiments, one or more of the ScFv moieties is organized such that the VL is at the amino terminal end of the ScFv moiety and the VH is at the carboxy terminal end of the ScFv moiety. In some embodiments, one or more of the ScFv moieties is organized such that the VH is at the amino terminal end of the ScFv moiety and the VL is at the carboxy terminal end of the ScFv moiety. In some embodiments, each ScFv moiety is organized such that the VL is at the amino terminal end of the ScFv moiety and the VH is at the carboxy terminal end of the ScFv moiety.

In some embodiments, the amino acid sequences that bind to the various epitope are separated from each other by one more linking amino acids. In some embodiments, the VL and VH sequences are separated by one or more linking amino acids. The linking amino acid sequences are not limiting. In some embodiments, the linking amino acids comprise one or more tetra-glycine serine ($G_4S$) linkers. In some embodiments, the VL and VH sequences are separated by 1-10 tetra-glycine serine ($G_4S$) linkers. In some embodiments, the VL and VH sequences are separated by 3 tetra-glycine serine ($G_4S$) linkers.

In some embodiments, one or more of the polypeptide chains of the multispecific anti-HIV antibody can further comprises an Fc region of an immunoglobulin or a variant thereof. In some embodiments, the immunoglobulin is IgG. In some embodiments, the immunoglobulin is IgG1. In some embodiments, the antibody comprises an IgG1 Fc region variant comprising mutations corresponding to M428L and N434S. In some embodiments, the antibody comprises an immunoglobulin Fc region that has been modified to facilitate heterodimerization.

In some embodiments, the antibody further comprises a sequence tag that facilitates purification of the antibody. In some embodiments, the sequence tag comprises a polyhistidine tag.

In some embodiments, the multispecific anti-HIV antibody comprises a first and second polypeptide chain, wherein the first and second polypeptide chains each comprise a. five ScFv moieties, wherein each ScFv moiety on a single chain recognizes an individual epitope (V1/V2 apex glycan, V3-base glycan region, CD4 binding site (CD4bs), gp120/gp41 interface, membrane proximal external region (MPER), wherein each ScFv moiety comprises an amino acid sequence from a light chain variable region (VL) and an amino acid sequence from a heavy chain variable region (VH) of an antibody; and b. an Fc region of an immunoglobulin or a variant thereof.

In some embodiments, the ScFv moieties are separated on the polypeptide chain by one or more linking amino acids. In some embodiments, the linking amino acids comprise one or more tetra-glycine serine ($G_4S$) linkers. In some embodiments, each ScFv moiety is separated by 5 tetra-glycine serine ($G_4S$) linkers.

In some embodiments, the amino acid sequences of parts i-v) are organized on a single polypeptide chain in the following order, from its N-terminus to its C-terminus:

i. an amino acid sequence that binds to the V1/V2 apex glycan epitope;
ii. an amino acid sequence that binds to the V3-base glycan region epitope;
iii. an amino acid sequence that binds to the CD4 binding site (CD4bs) epitope;
iv. an amino acid sequence that binds to the gp120/gp41 interface epitope; and
v. an amino acid sequence that binds to the membrane proximal external region (MPER) epitope.

In some embodiments, the amino acid sequences of parts i-v) are organized on a single polypeptide chain in the following order, from its N-terminus to its C-terminus:

i. an amino acid sequence that binds to the membrane proximal external region (MPER) epitope;
ii. an amino acid sequence that binds to the gp120/gp41 interface epitope;
iii. an amino acid sequence that binds to the CD4 binding site (CD4bs) epitope;
iv. an amino acid sequence that binds to the V3-base glycan region epitope; and
v. an amino acid sequence that binds to the V1/V2 apex glycan epitope.

In some embodiments, the multispecific anti-HIV antibody comprises a first and second polypeptide chain, wherein the amino acid sequences of parts i-v) are organized in the following order, from its N-terminus to its C-terminus:

i. an amino acid sequence that binds to the membrane proximal external region (MPER) epitope;
ii. an amino acid sequence that binds to the gp120/gp41 interface epitope;
iii. an amino acid sequence that binds to the CD4 binding site (CD4bs) epitope;
iv. an amino acid sequence that binds to the V3-base glycan region epitope;
v. an amino acid sequence that binds to the V1/V2 apex glycan epitope; and
vi. an Fc region of an immunoglobulin or a variant thereof.

In some embodiments, the multispecific anti-HIV antibody comprises a first and second polypeptide chain, wherein the amino acid sequences of parts i-v) are organized in the following order, from its N-terminus to its C-terminus:

i. an amino acid sequence that binds to the V1/V2 apex glycan epitope;
ii. an amino acid sequence that binds to the V3-base glycan region epitope;
iii. an amino acid sequence that binds to the CD4 binding site (CD4bs) epitope;
iv. an amino acid sequence that binds to the gp120/gp41 interface epitope;
v. an amino acid sequence that binds to the membrane proximal external region (MPER) epitope; and
vi. an Fc region of an immunoglobulin or a variant thereof.

In some embodiments, the multispecific anti-HIV antibody comprises 1) a first polypeptide chain, wherein the amino acid sequences of parts i-v) are organized in the following order, from its N-terminus to its C-terminus:
   i. an amino acid sequence that binds to the membrane proximal external region (MPER) epitope;
   ii. an amino acid sequence that binds to the gp120/gp41 interface epitope;
   iii. an amino acid sequence that binds to the CD4 binding site (CD4bs) epitope;
   iv. an amino acid sequence that binds to the V3-base glycan region epitope;
   v. an amino acid sequence that binds to the V1/V2 apex glycan epitope; and
   vi. an Fc region of an immunoglobulin or a variant thereof; and
2) a second polypeptide chain, wherein the amino acid sequences of parts i-v) are organized in the following order, from its N-terminus to its C-terminus:
   i. an amino acid sequence that binds to the V1/V2 apex glycan epitope;
   ii. an amino acid sequence that binds to the V3-base glycan region epitope;
   iii. an amino acid sequence that binds to the CD4 binding site (CD4bs) epitope;
   iv. an amino acid sequence that binds to the gp120/gp41 interface epitope;
   v. an amino acid sequence that binds to the membrane proximal external region (MPER) epitope; and
   vi. an Fc region of an immunoglobulin or a variant thereof.

In some embodiments, the amino acid sequence that binds to the epitope of the V1/V2-glycan region comprises an amino acid sequence from an antibody selected from the group consisting of VRC26.25 and PGDM1400; the amino acid sequence that binds to the epitope of the V3-glycan region comprises an amino acid sequence from antibody PGT121; the amino acid sequence that binds to the epitope of the CD4-binding site (CD4bs) comprises an amino acid sequence from antibody N6; the amino acid sequence that binds to the epitope of the gp120/gp41 interface comprises an amino acid sequence from antibody 35O22; and the amino acid sequence that binds to the epitope of the membrane proximal external region (MPER) comprises an amino acid sequence from an antibody selected from the group consisting of 10E8v4, 10E8v4 S100cF, and 10E8v4_V5R_S100cF.

In some embodiments, the amino acid sequence from the antibody VRC26.25 comprises an amino acid sequence from the VH region comprising CDR H1, CDR H2 and CDR H3, wherein CDR H1 comprises QFRFDGYG, CDR H2 comprises ISHDGIKK and CDR H3 comprises AKDLREDE- CEEWWSDDFGKQLPCAKSRGGLVGIADN; and an amino acid sequence from the VL region comprising CDR L1, CDR L2 and CDR L3, wherein CDR L1 comprises TSNIGNNF, CDR L2 comprises ETD and CDR L3 comprises ATWAASLSSARV;

In some embodiments, the amino acid sequence from the antibody PGDM1400 comprises an amino acid sequence from the VH region comprising CDR H1, CDR H2 and CDR H3, wherein CDR H1 comprises GNTLKTYD, CDR H2 comprises ISHEGDKK and CDR H3 comprises AKGSKHRLRDYALDDDGALNWAVDVDYLSNLEF; and an amino acid sequence from the VL region comprising CDR L1, CDR L2 and CDR L3, wherein CDR L1 comprises HSLIHGDRNNY, CDR L2 comprises LAS and CDR L3 comprises MQGRESPWT.

In some embodiments, the amino acid sequence from the antibody PGT121 comprises an amino acid sequence from the VH region comprising CDR H1, CDR H2 and CDR H3, wherein CDR H1 comprises GASISDSY, CDR H2 comprises VHKSGDT and CDR H3 comprises ARTLHGRRIYGIVAFNEWFTYFYMDV; and an amino acid sequence from the VL region comprising CDR L1, CDR L2 and CDR L3, wherein CDR L1 comprises SLGSRA, CDR L2 comprises NNQ and CDR L3 comprises HIWDSRVPTKWV.

In some embodiments, the amino acid sequence from the antibody N6 comprises an amino acid sequence from the VH region comprising CDR H1, CDR H2 and CDR H3, wherein CDR H1 comprises GYTFTAHI, CDR H2 comprises IKPQYGAV and CDR H3 comprises AR; and an amino acid sequence from the VL region comprising CDR L1, CDR L2 and CDR L3, wherein CDR L1 comprises QGVGSD, CDR L2 comprises HTS and CDR L3 comprises QVLQF.

In some embodiments, the amino acid sequence from the antibody 35O22 comprises an amino acid sequence from the VH region comprising CDR H1, CDR H2 and CDR H3, wherein CDR H1 comprises GYRFNFYH, CDR H2 comprises ISPYSGDK and CDR H3 comprises DDTGTYFCAKGLLRDGSSTWLPYL; and an amino acid sequence from the VL region comprising CDR L1, CDR L2 and CDR L3, wherein CDR L1 comprises NSVCCSHKS, CDR L2 comprises EDN and CDR L3 comprises CSYTHNSGCV.

In some embodiments, the amino acid sequence from the antibody 10E8v4 comprises an amino acid sequence from the VH region comprising CDR H1, CDR H2 and CDR H3, wherein CDR H1 comprises GFDFDNAW, CDR H2 comprises ITGPGEGWSV and CDR H3 comprises TGYYFCARTGKYYDFWSGYPPGEEYFQD; and an amino acid sequence from the VL region comprising CDR L1, CDR L2 and CDR L3, wherein CDR L1 comprises RGDSLRSHYAS, CDR L2 comprises GKNNRPS and CDR L3 comprises SSRDKSGSRLSV.

In some embodiments, the amino acid sequence from the antibody 10E8v4 S100cF comprises an amino acid sequence from the VH region comprising CDR H1, CDR H2 and CDR H3, wherein CDR H1 comprises GFDFDNAW, CDR H2 comprises ITGPGEGWSV and CDR H3 comprises TGYYFCARTGKYYDFWFGYPPGEEYFQD; and an amino acid sequence from the VL region comprising CDR L1, CDR L2 and CDR L3, wherein CDR L1 comprises RGDSLRSHYAS, CDR L2 comprises GKNNRPS and CDR L3 comprises SSRDKSGSRLSV.

In some embodiments, the amino acid sequence from the antibody 10E8v4_V5R_S100cF comprises an amino acid sequence from the VH region comprising CDR H1, CDR H2 and CDR H3, wherein CDR H1 comprises GFDFDNAW, CDR H2 comprises ITGPGEGWSV and CDR H3 comprises TGYYFCARTGKYYDFWFGYPPGEEYFQD; and an amino acid sequence from the VL region comprising CDR L1, CDR L2 and CDR L3, wherein CDR L1 comprises RGDSLRSHYAS, CDR L2 comprises GKNNRPS and CDR L3 comprises SSRDKSGSRLSV.

In some embodiments, the amino acid sequence from the antibody VRC26.25 comprises the VH region or a variant thereof comprising 1, 2, 3, or 4 conservative amino acid substitutions, wherein the VH region comprises SEQ ID NO:1; and the VL region or a variant thereof comprising 1, 2, 3, or 4 conservative amino acid substitutions, wherein the VL region comprises amino acids SEQ ID NO:5.

In some embodiments, the amino acid sequence from the antibody PGDM1400 comprises the VH region or a variant thereof comprising 1, 2, 3, or 4 conservative amino acid substitutions, wherein the VH region comprises SEQ ID NO:9; and the VL region or a variant thereof comprising 1, 2, 3, or 4 conservative amino acid substitutions, wherein the VL region comprises amino acids SEQ ID NO:13.

In some embodiments, the amino acid sequence from the antibody PGT121 comprises the VH region or a variant thereof comprising 1, 2, 3, or 4 conservative amino acid substitutions, wherein the VH region comprises SEQ ID NO:17; and the VL region or a variant thereof comprising 1, 2, 3, or 4 conservative amino acid substitutions, wherein the VL region comprises amino acids SEQ ID NO:21.

In some embodiments, the amino acid sequence from the antibody N6 comprises the VH region or a variant thereof comprising 1, 2, 3, or 4 conservative amino acid substitutions, wherein the VH region comprises SEQ ID NO:25; and the VL region or a variant thereof comprising 1, 2, 3, or 4 conservative amino acid substitutions, wherein the VL region comprises amino acids SEQ ID NO:29.

In some embodiments, the amino acid sequence from the antibody 35O22 comprises the VH region or a variant thereof comprising 1, 2, 3, or 4 conservative amino acid substitutions, wherein the VH region comprises SEQ ID NO:33; and the VL region or a variant thereof comprising 1, 2, 3, or 4 conservative amino acid substitutions, wherein the VL region comprises amino acids SEQ ID NO:37.

In some embodiments, the amino acid sequence from the antibody 10E8v4 comprises the VH region or a variant thereof comprising 1, 2, 3, or 4 conservative amino acid substitutions, wherein the VH region comprises SEQ ID NO:41; and VL region or a variant thereof comprising 1, 2, 3, or 4 conservative amino acid substitutions, wherein the VL region comprises amino acids SEQ ID NO:45.

In some embodiments, the amino acid sequence from the antibody 10E8v4 S100cF comprises the VH region or a variant thereof comprising 1, 2, 3, or 4 conservative amino acid substitutions, wherein the VH region comprises SEQ ID NO:49; and the VL region or a variant thereof comprising 1, 2, 3, or 4 conservative amino acid substitutions, wherein the VL region comprises amino acids SEQ ID NO:45.

In some embodiments, the amino acid sequence from the antibody 10E8v4_V5R_S100cF comprises the VH region or a variant thereof comprising 1, 2, 3, or 4 conservative amino acid substitutions, wherein the VH region comprises SEQ ID NO:51; and the VL region or a variant thereof comprising 1, 2, 3, or 4 conservative amino acid substitutions, wherein the VL region comprises amino acids SEQ ID NO:45.

Variable regions and CDR sequences of the antibodies described herein are shown in Table 2, below.

TABLE 2

| Amino Acid Sequences of variable domains and CDR sequences. | | |
|---|---|---|
| SEQ ID NO | DESCRIPTION | AMINO ACID SEQUENCE |
| 1 | VRC26.25 VH | QVQLVESGGGVVQPGTSLRLSCAASQFRFDGYGMHWVRQAPGKGLEWVASISHDGIKKYHAEKVWGRFTISRDNSKNTLYLQMNSLRPEDTALYYCAKDLREDECEEWWSDDFGKQLPCAKSRGGLVGIADNWGQGTMVTVSS |
| 2 | VRC26.25 VH CDR1 | QFRFDGYG |
| 3 | VRC26.25 VH CDR2 | ISHDGIKK |
| 4 | VRC26.25 VH CDR3 | AKDLREDECEEWWSDDFGKQLPCAKSRGGLVGIADN |
| 5 | VRC26.25 VL | QSVLTQPPSVSAAPGQKVTISCSGNTSNIGNNFVSWYQQRPGRAPQLLIYETDKRPSGIPDRFSASKSGTSGTLAITGLQTGDEADYYCATWAASLSSARVFGTGTKVIVLV |
| 6 | VRC26.25 VL CDR1 | TSNIGNNF |
| 7 | VRC26.25 VL CDR2 | ETD |
| 8 | VRC26.25 VL CDR3 | ATWAASLSSARV |
| 9 | PGDM1400 VH | QAQLVQSGPEVRKPGTSVKVSCKAPGNTLKTYDLHWVRSVPGQGLQWMGWISHEGDKKVIVERFKAKVTIDWDRSTNTAYLQLSGLTSGDTAVYYCAKGSKHRLRDYALDDDGALNWAVDVDYLSNLEFWGQGTAVTVSS |
| 10 | PGDM1400 VH CDR1 | GNTLKTYD |
| 11 | PGDM1400 VH CDR2 | ISHEGDKK |
| 12 | PGDM1400 VH CDR3 | AKGSKHRLRDYALDDDGALNWAVDVDYLSNLEF |
| 13 | PGDM1400 VL | DFVLTQSPHSLSVTPGESASISCKSSHSLIHGDRNNYLAWYVQKPGRSPQLLIYLASSRASGVPDRFSGSGSDKDFTLKISRVETEDVGTYYCMQGRESPWTFGQGTKVDIK |
| 14 | PGDM1400 VL CDR1 | HSLIHGDRNNY |
| 15 | PGDM1400 VL CDR2 | LAS |
| 16 | PGDM1400 VL CDR3 | MQGRESPWT |
| 17 | PGT121 VH | QMQLQESGPGLVKPSETLSLTCSVSGASISDSYWSWIRRSPGKGLEWIGYVHKSGDTNYSPSLKSRVNLSLDTSKNQVSLSLVAATAADSGKYYCARTLHGRRIYGIVAFNEWFTYFYMDVWGNGTQVTVSS |
| 18 | PGT121 VH CDR1 | GASISDSY |
| 19 | PGT121 VH CDR2 | VHKSGDT |
| 20 | PGT121 VH CDR3 | ARTLHGRRIYGIVAFNEWFTYFYMDV |
| 21 | PGT121 VL | SDISVAPGETARISCGEKSLGSRAVQWYQHRAGQAPSLIIYNNQDRPSGIPERFSGSPDSPFGTTATLTITSVEAGDEADYYCHIWDSRVPTKWVFGGGTTLTVL |
| 22 | PGT121 VL CDR1 | SLGSRA |
| 23 | PGT121 VL CDR2 | NNQ |
| 24 | PGT121 VL CDR3 | HIWDSRVPTKWV |
| 25 | N6 VH | RAHLVQSGTAMKKPGASVRVSCQTSGYTFTAHILFWFRQAPGRGLEWVGWIKPQYGAVNFGGGFRDRVTLTRDVYREIAYMDIRGLKPDDTAVYYCARDRSYGDSSWALDAWGQGTTVVVSA |
| 26 | N6 VH CDR1 | GYTFTAHI |
| 27 | N6 VH CDR2 | IKPQYGAV |
| 28 | N6 VH CDR3 | AR |

TABLE 2-continued

| Amino Acid Sequences of variable domains and CDR sequences. | | |
|---|---|---|
| SEQ ID NO | DESCRIPTION | AMINO ACID SEQUENCE |
| 29 | N6 VL | YIHVTQSPSSLSVSIGDRVTINCQTSQGVGSDLHWYQHKP GRAPKLLIHHTSSVEDGVPSRFSGSGFHTSFNLTISDLQA DDIATYYCQVLQFFGRGSRLHIK |
| 30 | N6 VL CDR1 | QGVGSD |
| 31 | N6 VL CDR2 | HTS |
| 32 | N6 VL CDR3 | QVLQF |
| 33 | 35O22 VH | QGQLVQSGAELKKPGASVKISCKTSGYRFNFYHINWIRQT AGRGPEWMGWISPYSGDKNLAPAFQDRVIMTTDTEVPVTS FTSTGAAYMEIRNLKFDDTGTYFCAKGLLRDGSSTWLPYL WGQGTLLTVSS |
| 34 | 35O22 VH CDR1 | GYRFNFYH |
| 35 | 35O22 VH CDR2 | ISPYSGDK |
| 36 | 35O22 VH CDR3 | DDTGTYFCAKGLLRDGSSTWLPYL |
| 37 | 35O22 VL | QSVLTQSASVSGSLGQSVTISCTGPNSVCCSHKSISWYQW PPGRAPTLIIYEDNERAPGISPRFSGYKSYWSAYLTISDL RPEDETTYYCCSYTHNSGCVFGTGTKVSVL |
| 38 | 35O22 VL CDR1 | NSVCCSHKS |
| 39 | 35O22 VL CDR2 | EDN |
| 40 | 35O22 VL CDR3 | CSYTHNSGCV |
| 41 | 10E8v4 VH | EVRLVESGGGLVKPGGSLRLSCSASGFDFDNAWMTWVRQP PGKGLEWVGRITGPGEGWSVDYAESVKGRFTISRDNTKNT LYLEMNNVRTEDTGYYFCARTGKYYDFWSGYPPGEEYFQD WGQGTLVIVSS |
| 42 | 10E8v4 VH CDR1 | GFDFDNAW |
| 43 | 10E8v4 VH CDR2 | ITGPGEGWSV |
| 44 | 10E8v4 VH CDR3 | TGYYFCARTGKYYDFWSGYPPGEEYFQD |
| 45 | 10E8v4 VL | SELTQDPAVSVALKQTVTITCRGDSLRSHYASWYQKKPGQ APVLLFYGKNNRPSGIPDRFSGSASGNRASLTITGAQAED EADYYCSSRDKSGSRLSVFGGGTKLTVL |
| 46 | 10E8v4 VL CDR1 | RGDSLRSHYAS |
| 47 | 10E8v4 VL CDR2 | GKNNRPS |
| 48 | 10E8v4 VL CDR3 | SSRDKSGSRLSV |
| 49 | 10E8v4_S100cF VH | EVRLVESGGGLVKPGGSLRLSCSASGFDFDNAWMTWVRQP PGKGLEWVGRITGPGEGWSVDYAESVKGRFTISRDNTKNT LYLEMNNVRTEDTGYYFCARTGKYYDFWFGYPPGEEYFQD WGQGTLVIVSS |
| 10E8v4 VH CDR1 | 10E8v4_S100cF VH CDR1 | GFDFDNAW |
| 10E8v4 VH CDR2 | 10E8v4_S100cF VH CDR2 | ITGPGEGWSV |
| 50 | 10E8v4_S100cF VH CDR3 | TGYYFCARTGKYYDFWFGYPPGEEYFQD |
| 51 | 10E8v4_V5R_S100cF VH | EVRLRESGGGLVKPGGSLRLSCSASGFDFDNAWMTWVRQP PGKGLEWVGRITGPGEGWSVDYAESVKGRFTISRDNTKNT LYLEMNNVRTEDTGYYFCARTGKYYDFWFGYPPGEEYFQD WGQGTLVIVSS |
| 10E8v4 VH CDR1 | 10E8v4_V5R_S100cF VH CDR1 | GFDFDNAW |
| 10E8v4 VH CDR2 | 10E8v4_V5R_S100cF VH CDR2 | ITGPGEGWSV |

TABLE 2-continued

Amino Acid Sequences of variable domains and CDR sequences.

| SEQ ID NO | DESCRIPTION | AMINO ACID SEQUENCE |
|---|---|---|
| 10E8v4_S100cF VHBCDR3 | 10E8v4_V5R_S100cF VH CDR3 | TGYYFCARTGKYYDFWFGYPPGEEYFQD |

In some embodiments, the multispecific anti-HIV antibody is capable of binding five different antigen targets. The disclosure features a multispecific antibody that binds five non-overlapping epitopes. In some embodiments, the multispecific anti-HIV antibody comprises an amino acid sequence selected from any of SEQ ID NOS:72-80, as shown below in Table 3.

TABLE 3

Penta-Nab names, orientations of variable light and variable heavy chains, and amino acid sequences.

| SEQ ID NO: | Name | Orientation | Amino Acid Sequence |
|---|---|---|---|
| 72 | PentaNAb$_{1.0}$ | 10E8v4-5X-35O22-5X-N6-5X-PGT121-5X-VRC26.25-His | MGWSCIILFLVATATGVHSSELTQDPAVSVALKQTVTITCRGDSLRSHYASWYQKKPGQAPVLLFYGKNNRPSGIPDRFSGSASGNRASLTITGAQAEDEADYYCSSRDKSGSRLSVFGGGTKLTVLGGGGSGGGGSGGGGSEVRLVESGGGLVKPGGSLRLSCSASGFDFDNAWMTWVRQPPGKGLEWVGRITGPGEGWSVDYAESVKGRFTISRDNTKNTLYLEMNNVRTEDTGYYFCARTGKYYDFWSGYPPGEEYFQDWGQGTLVIVSSGGGGSGGGGSGGGGSGGGGSGGGGSQSVLTQSASVSGSLGQSVTISCTGPNSVCCSKKSISWYQWPPGRAPTLIIYEDNERAPGISPRFSGYKSYWSAYLTISDLRPEDETTYYCCSYTHNSGCVFGTGTKVSVLGGGGSGGGGSGGGGSQGQLVQSGAELKKPGASVKISCKTSGYRFNFYHINWIRQTAGRGPEWMGWISPYSGDKNLAPAFQDRVIMTTDTEVPVTSFTSTGAAYMEIRNLKFDDTGTYFCAKGLLRDGSSTWLPYLWGQGTLLTVSSGGGGSGGGGSGGGGSGGGGSGGGGSYIHVTQSPSSLSVSIGDRVTINCQTSQGVGSDLHWYQHKPGRAPKLLIHHTSSVEDGVPSRFSGSGFHTSFNLTISDLQADDIATYYCQVLQFFGRGSRLHIKGGGGSGGGGSGGGGSRAHLVQSGTAMKKPGASVRVSCQTSGYTFTAHILFWFRQAPGRGLEWVGWIKPQYGAVNFGGGFRDRVTLTRDVYREIAYMDIRGLKPDDTAVYYCARDRSYGDSSWALDAWGQGTTVVVSAGGGGSGGGGSGGGGSGGGGSGGGGSSDISVAPGETARISCGEKSLGSRAVQWYQHPAGQAPSLIIYNNQDRPSGIPERFSGSPDSPFGTTATLTITSVEAGDEADYYCHIWDSRVPTKWVFGGGTTLTVLGGGGSGGGGSGGGGSQMQLQESGPGLVKPSETLSLTCSVSGASISDSYWSWIRRSPGKGLEWIGYVHKSGDTNYSPSLKSRVNLSLDTSKNQVSLSLVAATAADSGKYYCARTLHGRRIYGIVAFNEWFTYFYMDVWGNGTQVTVSSGGGGSGGGGSGGGGSGGGGSGGGGSQSVLTQPPSVSAAPGQKVTISCSGNTSNIGNNFVSWYQQRPGPAPQLLIYETDKRPSGIPDRFSASKSGTSGTLAITGLQTGDEADYYCATWAASLSSARVFGTGTKVIVLVGGGGSGGGGSGGGGSQVQLVESGGGVVQPGTSLRLSCAASQFRFDGYGMHWVRQAPGKGLEWVASISHDGIKKYHAEKVWGRFTISRDNSKMTLYLQMNSLRPEDTALYYCAKDLREDECEEWWSDYYDFGKQLPCAKSRGGLVGIADNWGQGTMVTVSSGSGHHHHHH |
| 73 | PentaNAb$_{2.0}$ | 10E8v4_S100cF-5X-35O22-5X-N6-5X-PGT121-5X-VRC26.25-His | MGWSCIILFLVATATGVHSSELTQDPAYSVALKQTVTITCRGDSLRSHYASWYQKKPGQAPVLLFYGKNNRPSGIPDRFSGSASGNRASLTITGAQAEDEADYYCSSRDKSGSRLSVFGGGTKLTVLGGGGSGGGGSGGGGSEVRLVESGGGLVKPGGSLRLSCSASGFDFDNAWMTWVRQPPGKGLEWVGRITGPGEGWSVDYAESVKGRFTISRDNTKNTLYLEMNNVRTEDTGYYFCARTGKYYDFWFGYPPGEEYFQDWGQGTLVIVSSGGGGSGGGGSGGGGSGGGGSGGGGSQSVLTQSASVSGSLGQSVTISCTGPNSVCCSHKSISWYQWPPGRAPTLIIYEDNERAPGISPRFSGYKSYWSAYLTISDLRPEDETTYYCCSYTHNSGCVFGTGTKVSVLGGGGSGGGGSGGGGSQGQLVQSGAELKKPGASVKISCKTSGYRFNFYHINWIRQTAGRGPEWMGWISPYSGDKNLAPAFQBRVIMTTDTEVPVTSFTSTGAAYMEIRNLKFDDTGTYFCAKGLLRDGSSTWLPYLWGQGTLLTVSSGGGGSGGGGSGGGGSGGGGSGGGGSYIHVTQSPSSLSVSIGDRVTINCQTSQGVGSDLHWYQHKPGRAPKLLIHHTSSVEDGVPSRFSGSGFHTSFNLTISDLQADDIATYYCQVLQFFGRGSRLHIKGGGGSGGGGSGGGGSRAHLVQSGTAMKKPGASVRVSCQTSGYTFTAHIL |

TABLE 3-continued

Penta-Nab names, orientations of variable light and variable heavy chains, and amino acid sequences.

| SEQ ID NO: | Name | Orientation | Amino Acid Sequence |
|---|---|---|---|
| | | | FWFRQAPGRGLEWVGWIKPQYGAVNFGGGFRDRVTLTRDVYREIAYMDIRGLKPDDTAVYYCARDRSYGDSSWALDAWGQGTTVVVSAGGGGSGGGGSGGGGSGGGGSGGGGSSDISVAPGETARISCGEKSLGSRAVQWYQHRAGQAPSLIIYNNQDRPSGIPERFSGSPDSPFGTTATLTITSVEAGDEADYYCHIWDSRVPTKWVFGGGTTLTVLGGGGSGGGGSGGGGSQMQLQESGPGLVKPSETLSLTCSVSGASISDSYWSWIRRSPGKGLEWIGYVHKSGDTNYSPSLKSRVNLSLDTSKNQVSLSLVAATAADSGKYYCARTLHGRRIYGIVAFNEWFTYFYMDVWGNGTQVTVSSGGGGSGGGGSGGGGSGGGGSGGGGSQSVLTQPPSVSAAPGQKVTISCSGNTSNIGNNFVSWYQQRPGRAPQLLIYETDKRPSGIPDRFSASKSGTSGTLAITGLQTGDEADYYCATWAASLSSARVFGTGTKVIVTVGGGGSGGGGSGGGGSQVQLVESGGGVVQPGTSLRLSCAASQFRFDGYGMHWVRQAPGKGLEWVASISRDGIKKYHAEKVWGRFTISRDNSKNTLYLQMNSLRPEDTALYYCAKDLREDECEEWWSDYYDFGKQLPCAKSRGGLVGIADNWGQGTMVTVSSGSGHHHKHH |
| 74 | PentaNA $b_{2.0}$ Reverse | VRC26.25-5X-PGT121-5X-N6-5X-35O22-5X-10E8v4_S100cF-His | MGWSCIILFLVATATGVHSQVQLVESGGGVVQPGTSLRLSCAASQFRFDGYGMHWVRQAPGKGLEWVASISHDGIKKYHAEKVWGRFTISRDNSKNTLYLQMNSLRPEDTALYYCAKDLREDECEEWWSDYYDFGKQLPCAKSRGGLVGIADNWGQGTMVTVSSGGGGSGGGSGGGGSQSVLTQPPSVSAAPGQKVTISCSGNTSNIGNNFVSWYQQRPGRAPQLLIYETDKRPSGIPDRFSASKSGTSGTLAITGLQTGDEADYYCATWAASLSSARVFGTGTKVIVLVGGGGSGGGGSGGGGSGGGGSGGGGSQMQLQESGPGLVKPSETLSLTCSVSGASISDSYWSWIRRSPGKGLEWIGYVHKSGDTNYSPSLKSRVNLSLDTSKNQVSLSLVAATAADSGKYYCARTLHGRRIYGIVAFNEWFTYFYMDVWGNGTQVTVSSGGGGSGGGGSGGGGSSDISVAPGETARISCGEKSLGSRAVQWYQHRAGQAPSLIIYNNQDRPSGIPERFSGSPDSPFGTTATLTITSVEAGDEADYYCHIWDSRVPTKWVFGGGTTLTVLGGGGSGGGGSGGGGSGGGGSGGGGSRAHLVQSGTAMKKPGASVRVSCQTSGYTFTAHILFWFRQAPGRGLEWVGWIKPQYGAVNFGGGFRDRVTLTRDVYREIAYMDIRGLKPDDTAVYYCARDRSYGDSSWALDAWGQGTTVVVSAGGGGSGGGGSGGGGSYIHVTQSPSSLSVSIGDRVTINCQTSQGVGSDLHWYQHKPGRAPKLLIHHTSSVEDGVPSRFSGSGFHTSFNLTISDLQADDIATYYCQVLQFFGRGSRLHIKGGGGSGGGGSGGGGSGGGGSGGGGSQGQLVQSGAELKKPGASVKISCKTSGYRFNFYHINWIRQTAGRGPEWMGWISPYSGDKNLAPAFQDRVIMTTDTEVPVTSFTSTGAAYMEIRNLKFDDTGTYFCAKGLLRDGSSTWLPYLWGQGTLLTVSSGGGGSGGGGSGGGGSQSVLTQSASVSGSLGQSVTISCTGPNSVCCSHKSISWYQWPPGRAFTLIIYEDNERAPGISPRFSGYKSYWSAYLTISDLRPEDETTYYCCSYTHNSGCVFGTGTKVSVLGGGGSGGGGSGGGGSGGGGSGGGGSEVRLVESGGGLVKPGGSLRLSCSASGFDFDNAWMTWVRQPPGKGLEWVGRITGPGEGWSVDYAESVKGRFTISRDNTKNTLYLEMNNVRTEDTGYYFCARTGKYYDFWFGYPPGEEYFQDWGQGTLVIVSSGGGGSGGGGSGGGGSSELTQDPAYSVALKQTVTITCRGDSLRSHYASWYQKKPGQAPVLLFYGKNNRPSGIFDRFSGSASGNRASLTITGAQAEDEADYYCSSRDKSGSRLSVFGGGTKLTVLGSGHHHHHH |
| 75 | PentaNA $b_{3.0}$ | 10E8v4_S100cF-5X-35O22-5X-N6-5X-PGT121-5X-PGDM1400-His | MGWSCIILFLVATATGVHSSELTQDPAVSVALKQTVTITCRGDSLRSHYASWYQKKPGQAPVLLFYGKNNRPSGIPDRFSGSASGNRASLTITGAQAEDEADYYCSSRDKSGSRLSVFGGGTKLTVLGGGGSGGGGSGGGGSEVRLVESGGGLVKPGGSLRLSCSASGFDFDNAWMTWVRQPPGKGLSWVGRITGPGEGWSVDYAESVKGRFTISRDNTKNTLYLEMNNVRTEDTGYYFCARTGKYYDFWFGYPPGEEYFQDWGQGTLVIVSSGGGGSGGGGSGGGGSGGGGSGGGGSQSVLTQSASVSGSLGQSVTISCTGPNSVCCSHKSISWYQWPPGRAPTLIIYEDNERAPGISPRFSGYKSYWSAYLTISDLRPEDETTYYCCSYTHNSGCVFGTGTKVSVLGGGGSGGGGSGGGGSQGQLVQSGAELKKFGASVKISCKTSGYRFNFYHINWIRQTAGRGPEWMGWISPYSGDKNLAPAFQDRVIMTTDTEVPVTSFTSTGAAYMEIRNLKFDDTGTYFCAKGLLRDGSSTWLPYLWGQGTLLTVSSGGGGSGGGGSGGGGSGGGGSGGGGSYIHVTQSPSSLSVSIGDRVTINCQTSQGVGSDLHWYQHKPGRAPKLLIHHTSSVEDGVPSRFSGSGFHTSFNLTISDLQADDIATYYCQVLQFFGRGSRLHIKGGGGSGGGGSGGGGSRAHLVQSGTAMKKPGASVRVSCQTSGYTFTAHILFWFRQAPGRGLEWVGWIKPQYGAVNFGGGFRDRVTLTRDVYREIAYMDIRGLKPDDTAVYYCARDRSYGDSSWALDAWGQGTTVVVSAGGGGSGGGGSGGGGSGGGGSGGGGSSDISVAPGETARISCGEKSLGSPAVQWYQHRAGQAPSLIIYNNQDRPSGIPERFSGSPDSPFGTTATLTITSVEAGDEADYYCMIWDSRVPTKWVFGGGTTL |

TABLE 3-continued

Penta-Nab names, orientations of variable light and variable heavy chains, and amino acid sequences.

| SEQ ID NO: | Name | Orientation | Amino Acid Sequence |
|---|---|---|---|
| | | | TVLGGGGSGGGGSGGGGSQMQLQESGPGLVKPSETLSLTCSVS<br>GASISDSYWSWIRRSPGKGLEWIGYVHKSGDTNYSPSLKSRVN<br>LSLDTSKNQVSLSLVAATAADSGKYYCARTLHGRRIYGIVAFN<br>EWFTYFYMDVWGNGTQVTVSSGGGGSGGGGSGGGGSGGGGSGG<br>GGSDFVLTQSPHSLSVTPGESASISCKSSHSLIHGDRNNYLAW<br>YVQKPGRSPQLLIYLASSRASGVPDRFSGSGSDKDFTLKISRV<br>ETEDVGTYYCMQGRESPWTFGQGTKVDIKGGGGSGGGGSGGGG<br>SQAQLVQSGPEVRKPGTSVKVSCKAPGNTLKTYDLHWVRSVPG<br>QGLQWMGWISHEGDKKVIVERFKAKVTIDWDRSTNTAYLQLSG<br>LTSGDTAVYYCAKGSKHRLRDYALYDDDGALNWAVDVDYLSNL<br>EFWGQGTAVTVSSGSGHHHHHH |
| 76 | PentaNAb$_{3.0}$ Reverse | PGDM1400-5X-PGT121-5X-N6-5X-35O22-5X-10E8v4S100cF-His | MGWSCIILFLVATATGVHSQAQLVQSGPEVRKPGTSVKVSCKA<br>PGNTLKTYDLHWVRSVPGQGLQWMGWISHEGDKKVIVERFKAK<br>VTIDWDRSTNTAYLQLSGLTSGDTAVYYCAKGSKHRLRDYALY<br>DDDGALNWAVDVDYLSNLEFWGQGTAVTVSSGGGGSGGGGSGG<br>GGSDFVLTQSPHSLSVTPGESASISCKSSHSLIHGDRNNYLAW<br>YVQKPGRSPQLLIYLASSRASGVPDRFSGSGSDKDFTLKISRV<br>ETEDVGTYYCMQGRESPWTFGQGTKVDIKGGGGSGGGGSGGGG<br>SGGGGSGGGGSQMQLQESGPGLVKPSETLSLTCSVSGASISDS<br>YWSWIRRSPGKGLEWIGYVHKSGDTNYSPSLKSRVNLSLDTSK<br>NQVSLSLVAATAADSGKYYCARTLHGRRIYGIVAFNEWFTYFY<br>MDVWGNGTQVTVSSGGGGSGGGGSGGGGSSDISVAPGETARIS<br>CGEKSLGSRAVQWYQHRAGQAPSLIIYNNQDRPSGIPERFSGS<br>PDSPFGTTATLTITSVEAGDEADYYCHIWDSRVPTKWVFGGGT<br>TLTVLGGGGSGGGGSGGGGSGGGGSGGGGSRAHLVQSGTAMKK<br>PGASVRVSCQTSGYTFTAHILFWFRQAPGRGLEWVGWIKPQYG<br>AVNFGGGFRDRVTLTRDVYREIAYMDIRGLKPDDTAVYYCARD<br>RSYGDSSWALDAWCQGTTVVVSAGGGGSGGGGSGGGGSYIHVT<br>QSPSSLSVSIGDRVTINCQTSQGVGSDLKWYQHKPGRAPKLLI<br>HHTSSVEDGVPSRFSGSGFKTSFNLTISDLQADDIATYYCQVL<br>QFFGRGSRLHIKGGGGSGGGGSGGGGSGGGGSGGGGSQGQLVQ<br>SGAELKKPGASVKISCKTSGYRFNFYHINWIRQTAGRGPEWMG<br>WISPYSGDKNLAPAFQDRVIMTTDTEVPVTSFTSTGAAYMEIR<br>NLKFDDTGTYFCAKGLLRDGSSTWLPYLWGQGTLLTVSSGGGG<br>SGGGGSGGGGSQSVLTQSASVSGSLGQSVTISCTGPNSVCCSH<br>KSISWYQWPPGRAFTLIIYEDNERAPGISPRFSGYKSYWSAYL<br>TISDLRPEDETTYYCCSYTHNSGCVFGTGTKVSVLGGGGSGGG<br>GSGGGGSGGGGSGGGGSEVRLVESGGGLVKPGGSLRLSCSASG<br>FDFDNAWMTWVRQPPGKGLEWVGPITGPGEGWSVDYAESVKGR<br>FTISRDNTKNTLYLEMNNVRTEDTGYYFCARTGKYYDFWFGYP<br>PGEEYFQDWGQGTLVTVSSGGGGSGGGGSGGGGSSELTQDPAV<br>SVALKQTVTITCRGDSLRSHYASWYQKKPGQAPVLLFYGKNNR<br>PSGIPDRFSGSASGNRASLTITGAQAEDSADYYCSSRPKSGSR<br>LSVFGGGTKLTVLGSGHHHHHH |
| 77 | PentaNAb$_{4.0}$ | 10E8v4 V5R_S100cF-5X-35O22-5X-N6-SX-PGT121-5X-PGTDM1400-His | MGWSCIILFINATATGVHSSELTQDPAVSVALKQTVTITCRGD<br>SLRSHYASWYQKKPGQAPVLLFYGKNNRPSGIPDRFSGSASGN<br>RASLTITGAQAEDEADYYCSSRDKSGSPISVFGGGTKLTVLGG<br>GGSGGGGSGGGGSEVRLRESGGGLVKPGGSLRLSCSASGFDFD<br>NAWMTWVRQPPGKGLEWVGRITGPGEGWSVDYAESVKGRFTIS<br>RDNTKNTLYLEMNNVRTEDTGYYFCARTGKYYDFWFGYPPGEE<br>YFQDWGQGTLVIVSSGGGGSGGGGSGGGGSGGGGSGGGGSQSV<br>LTQSASVSGSLGQSVTISCTGPNSVCCSHKSISWYQWPPGRAP<br>TLIIYEDNERAPGISPRFSGYKSYWSAYLTISDLRPEDETTYY<br>CCSYTHNSGCVFGTGTKVSVLGGGGSGGGGSGGGGSQGQLVQS<br>GAELKKPGASVKISCKTSGYRFNFYHINWIRQTAGRGPEWMGW<br>ISPYSGDKNLAPAFQDRVIMTTDTEVPVTSFTSTGAAYMEIRN<br>LKFDDTGTYFCAKGLLRDGSSTWLPYLWGQGTLLTVSSGGGGS<br>GGGGSGGGGSGGGGSGGGGSYIHVTQSPSSLSVSIGDRVTINC<br>QTSQGVGSDLHVYQHKPGRAPKLLIHHTSSVEDGVPSRFSGSG<br>FHTSFNLTISDLQADDIATYYCQVLQFFGRGSRLHIKGGGGSG<br>GGGSGGGGSRAHLVQSGTAMKKPGASVRVSCQTSGYTFTAHIL<br>FWFRQAPGRGLEWVGWIKPQYGAVNFGGGFRDRVTLTRDVYRE<br>IAYMDIRGLKPDDTAVYYCARDRSYGDSSWALDAWGQGTTVVV<br>SAGGGGSGGGGSGGGGSGGGGSGGGGSSDISVAPGETARISCG<br>EKSLGSRAVQWYQHRAGQAPSLIIYNNQDRPSGIPERFSGSPD<br>SPFGTTATLTITSVEAGDEADYYCHIWDSRVPTKWVFGGGTTL<br>TVLGGGGSGGGGSGGGGSQMQLQESGPGLVKPSETLSLTCSVS<br>GASISDSYWSWIRRSPGKGLEWIGYVHKSGDTNYSPSLKSRVN<br>LSLDTSKNQVSLSLVAATAADSGKYYCARTLHGRRIYGIVAFN<br>EWFTYFYMDVWGNGTQVTVSSGGGGSGGGGSGGGGSGGGGSGG<br>GGSDFVLTQSPHSLSVTPGSSASISCKSSHSLIHGDRNNYLAW |

TABLE 3-continued

Penta-Nab names, orientations of variable light and variable heavy chains, and amino acid sequences.

| SEQ ID NO: | Name | Orientation | Amino Acid Sequence |
|---|---|---|---|
| | | | YVQKPGRSPQLLIYLASSRASGVPDRFSGSGSDKDFTLKISRV<br>ETEDVGTYYCMQGRESPWTFGQGTKVDIKGGGGSGGGGSGGGG<br>SQAQLVQSGPEVRKPGTSVKVSCKAPGNTLKTYDLHWVRSVPG<br>QGLQWMGWISHEGDKKVTVERFKAKVTIDWDRSTNTAYLQLSG<br>LTSGDTAVYYCAKGSKHRLRDYALYDDDGALNWAVDVDYLSNL<br>EFWGQGTAVTVSSGSGHHHHHH |
| 78 | PentaNA b$_{4.0}$ Reverse | PGDM1400-5X-PGT121-5X-N6-5X-35022-5X-10E8v4 V5R S100cF-His | MGWSCIILFLVATATGVHSQAQLVQSGPEVRKPGTSVKVSCKA<br>PGNTLKTYDLHWVRSVPGQGLQWMGWISHEGDKKVIVERFKAK<br>VTIDWDRSTNTAYLQLSGLTSGDTAVYYCAKGSKHRLRDYALY<br>DDDGALNWAVDVDYLSNLEFWGQGTAVTVSSGGGGSGEGGSGG<br>GGSDFVLTQSPHSLSVTPGESASISCKSSHSLIHGDRNNYLAW<br>YVQKPGRSPQLLIYLASSRASGVPDRFSGSGSDKDFTLKISRV<br>ETEDVGTYYCMQGRESPWTFGQGTKVDIKGGGGSGGGGSGGGG<br>SGGGGSGGGGSQMQLQESGPGLVKPSETLSLTCSVSGASISDS<br>YWSWIRRSPGKGLEWIGYVHKSGDTNYSPSLKSRVNLSLDTSK<br>NQVSLSLVAATAADSGKYYCARTLHGRRIYGIVAFNEWFTYFY<br>MDVWGNGTQVTVSSGGGGSGGGGSGGGGSSDISVAPGETARIS<br>CGEKSLGSRAVQWYQHRAGQAPSLIIYNNQDRPSGIPERFSGS<br>PDSPFGTTATLTITSVEAGDEADYYCHIWDSRVPTKWVFGGGT<br>TLTVLGGGGSGGEGSGGGGSEGGGSGGGGSRAHLVQSGTAMKK<br>PGASVRVSCQTSGYTFTAHILFWFRQAPGRGLEWVGWIKPQWG<br>AVNFGGGFRDPVTITRDVYRETAYMDIRGLKPDDTAVYYCARD<br>RSYGDSSWALDAWGQGTTVVVSAGGGGSGGGGSGGGGSYIHVT<br>QSPSSLSVSIGDRVTINCQTSQGVGSDLHWYQHKPGRAPKLLI<br>HHTSSVEDEVPSRFSGSGFHTSFNLTISDLQADDIATYYCQVL<br>QFFGRGSRLHIKGGGGSGGGGSGGGGSGGGGSEGGGSQGQLVQ<br>SGAELKKPGASVKISCKTSGYRFNFYHINWIRQTAGRGPEWMG<br>WISPYSGDKNLAPAFQDRVIMTTDTEVPVTSFTSTGAAYMEIR<br>NLKFDDTGTYFCAKGLLRDGSSTWLPYLWGQGYLLTVSSGGGG<br>SGGGGSGGGGSQSVITQSASVSGSLGQSVTISCTGPNSVCCSH<br>KSISWYQWPPGRAPTLIIYEDNERAPGISPRFSGYKSYWSAYL<br>TISDLRPEDETTYYCCSYTHNSGCVFGTGTKVSVLGGGGSGGG<br>GSGGGGSGGGGSGGGGSEVRLRESGGGLVKPGGSLRLSCSASG<br>FDFDNAWMTWVRQPPGKGLEWVGRITGPGEGWSVDYAESVKGR<br>FTISRDNTKNTLYLEMNNVRTEDTGYYFCARTGKYYDFWFGYP<br>PGEEYFQDWGQGTLVIVSSGGGGSGGGGSGGGGSSELTQDPAV<br>SVALKQTVTITCRGDSLRSHYASWYQKKPGQAPVLLFYGKNNR<br>PSGIPDRFSGSASGNRASLTITGAQAEDEADYYCSSRDESGSR<br>LSVFGGGTKLTVLGSGHHHHHH |
| 79 | PentaNA b$_{4.0}$ Reverse | PGDM1400-5X-PGT121-5X-N6-5X-35022-5X-10E8v4 V5R S100cF VH fused to ***IgG1 LS HC with His Tag*** | MGWSCIILFLVATATGVHSQAQLVQSGPEVRKPGTSVKVSCKA<br>PGNTLKTYDLHWVRSVPGQGLQWMGWISHEGDKKVIVERFKAK<br>VTIDWDRSTNTAYLQLSGLTSGDTAVYYCAKGSKHRLRDYALY<br>DDDGALNWAVDVDYLSNLEFWGQGTAVTVSSGGGGSGEGGSGG<br>GGSDFVLTQSPHSLSVTPGESASISCKSSHSLIHGDPNNYLAW<br>YVQKPGRSPQLLIYLASSRASGVPDRFSGSGSDKDFTLKISRV<br>ETEDVGTYYCMQGRESPWTFGQGTKVDIKGGGGSGGGGSGGGG<br>SGGGGSGGGGSQMQLQESGPGLVKPSETLSLTCSVSGASISDS<br>YWSWIRRSPGKGLEWIGYVHKSGDTNYSPSLKSRVNLSLDTSK<br>NQVSLSLVAATAADSGKYYCARTLHGRRIYGIVAFNEWFTYFY<br>MDVWGNGTQVTVSSGGGGSGGGGSGGGGSSDISVAPGETARIS<br>CGEKSLGSRAVQWYQHRAGQAPSLIIYNNQDRPSGIPERFSGS<br>PDSPFGTTATLTITSVEAGDEADYYCHIWDSRVPTKWVFGGGT<br>TLTVLGGGGSGGGGSGGGGSGGGGSGGGGSRAHLVQSGTAMKK<br>PGASVRVSCQTSGYTFTAHILFWFRQAPGRGLEWVGWIKPQYG<br>AVNFGGGFRDRVTLTRDVYREIAYMDIRGLKPDDTAVYYCARD<br>RSYGDSSWALDAWGQGTTVVVSAGGGGSGGGGSGGGGSYIHVT<br>QSPSSLSVSIGDRVTINCQTSQGVGSDLHWYQHKPGPAPKLLI<br>HHTSSVEDGVPSRFSGSGFHTSFNLTISDLQADDIATYYCQVL<br>QFFGRGSRLHIKGGGGSGGGGSGGGGSGGGGSGGGGSQGQLVQ<br>SGAELKKPGASVKISCKTSGYRFNFYHINWIRQTAGRGPEWMG<br>WISPYSGDKNLAPAFQDRVIMTTDTEVPVTSFTSTGAAYMEIR<br>NLKFDDTGTYFCAKGLLRDGSSTWLPYLWGQGTLLTVSSGGGG<br>SGGGGSGGGGSQSVLTQSASVSGSLGQSVTISCTGPNSVCCSH<br>KSISWYQWPPGRAPTLIIYEDNERAPGISPRFSGYKSYWSAYL<br>TISDLRPEDETTYYCCSYTHNSGCVFGTGTKVSVLGGGGSGGG<br>GSGGGGSGGGGSGGGGSEVRLRESGGGLVKPGGSLRLSCSASG<br>FDFDNAWMTWVRQPPGKGLEWVGRITGPGEGWSVDYAESVKGR<br>FTISRDNTKNTLYLEMNNVRTEDTGYYFCARTGKYYDFWFGYP<br>PGEEYFQDWGQGTLVIVSS***ASTKGPSVFPLAPSSKSTSGGTAA***<br>***LGCLVKDYFPEPVTVSWNSGALTSGVHTFPAVLQSSGLYSLSS***<br>***VVTVPSSSLGTQTYICNVNHKPSNTKVDKKVEPKSCDKTHTCP*** |

TABLE 3-continued

Penta-Nab names, orientations of variable light and variable heavy chains, and amino acid sequences.

| SEQ ID NO: | Name | Orientation | Amino Acid Sequence |
|---|---|---|---|
| | | | ***PCPAPELLGGPSVFLFPPKPKDTLMISRTPEVTCVVVDVSHED<br>PEVKFNWYVDGVEVHNAKTKPREEQYNSTYRVVSVLTVLHQDW<br>LNGKEYKCKVSNKALPAPIEKTISKAKGQPREPQVYTLPPSRE<br>EMTKNQVSLTCLVKGFYPSDIAVEWESNGQPENNYKTTPPVLD<br>SDGSFFLYSKLTVDKSRWQQGNVFSCSVLHEALHSHYTQKSLS<br>LSKGKGSGHHHHHH*** |
| 80 | PentaNAb$_{4.0}$ Reverse | PGDM1400-5X-PGT121-5X-N6-5X-35022-5X-10E8v4 V5R S100cF VH-VL-fused to ***IgG1 LS FC with His Tag*** | MGWSCIILFLVATATGVHSQAQLVQSGPEVRKPGTSVKVSCKA<br>PGNTLKTYDLHWVRSVPGQGLQWMGWISHEGDKKVIVERFKAK<br>VTIDWDRSTNTAYLQLSGLTSGDTAVYYCAKGSKHRLPDYALY<br>DDDGAINWAVDVDYLSNLEFWGQGTAVTVSSGGGGSGGGGSGG<br>GGSDFVLTQSPHSLSVTPGESASISCKSSHSLIHGDRNNYLAW<br>YVQKPGRSPQLLIYLASSRASGVPDRFSGSGSDKDFTLKISRV<br>ETEDVGTYYCMQGRESPWTFGQGYKVDIKGGGGSGGGGSGGGG<br>SGGGGSGGGGSQMQLQESGPGLVKPSETLSLTCSVSGASISDS<br>YWSWIRRSPGKGLEWIGYVHKSGDTNYSPSLKSRVNLSLDTSK<br>NQVSLSLVAATAADSGKYYCARTLHGRRIYGIVAFNEWFTYFY<br>MDVWGNGTQVTVSSGGGGSGGGGSGGGGSSDISVAPGETARIS<br>CGEKSLGSRAVQWYQHRAGQAPSLIIYNNQDRPSGIPERFSGS<br>PDSPFGTTATLTITSVEAGDEADYYCHIWDSRVPTKWVFGGGT<br>TLTVLGGGGSGGGGSGGGGSGGGGSGGGGSRAHLVQSGTAMKK<br>PGASVRVSCQTSGYTFTAHILFWFRQAPGRGLEWVGWIKPQYG<br>AVNFGGGFRDRVTLTRDVYREIAYMDIRGLKPDDTAVYYCARD<br>RSYGDSSWALDAWGQGTTVVVSAGGGGSGGGGSGGGGSYIHVT<br>QSPSSLSVSIGDRVTINCQTSQGVGSDLHWYQHKPGRAPKLLI<br>HHTSSVEDGVPSRFSGSGFHTSFNLTISDLQADDIATYYCQVL<br>QFFGRGSRLHIKGGGGSGGGGSGGGGSGGGGSGGGGSQGQLVQ<br>SGAELKKPGASVKISCKTSGYRFNFYHINWIRQTAGRGPEWMG<br>WISPYSGDKNLAPAFQDRVIMTTDTEVPVTSFTSTGAAYMEIR<br>NLKFDDTGTYFCAKGLLRDGSSTWLPYLWGQGTLLTVSSGGGG<br>SGGGGSGGGGSQSVLTQSASVSGSLGQSVTISCTGPNSVCCSH<br>KSISWYQWPPGRAPTLIIYEDNERAPGISPRFSGYKSYWSAYL<br>TISDLRPEDETTYYCCSYTHNSGCVFGTGTKVSVLGGGGSGGG<br>GSGGGGSGGGGSGGGGSEVRLRESGGGLVKPGGSLRLSCSASG<br>FDFDNAWMTWVRQPPGKGLEWVGRITGPGEGWSVDYAESVKGR<br>FTISRDNTKNTLYLEMNNVRTEDTGYYFCARTGKYYDFWFGYP<br>PGEEYFQDWGQGTLVIVSSGGGGSGGGGSGGGGSSELTQDPAV<br>SVALKQTVTITCRGDSLRSHYASWYQKKPGQAPVLLFYGKNNR<br>PSGIPDRFSGSASGNRASLTITGAQAEDEADYYCSSRDKSGSR<br>LSVFGGGTKLTVL***gsgPKSCDKTHTCPPCPAPELLGGPSVFLF<br>PPKPKDTLMISRTPEVTCVVVDVSHEDPEVKFNWYVDGVEVHN<br>AKTKPREEQYNSTYRVVSVLTVLHQDWLNGKEYKCKVSNKALP<br>APIEKTISKAKGQPREPQVYTLPPSREEMTNQVSLTCLVKGF<br>YPSDIAVEWESNGQPENNYKTTPPVLDSDGSFFLYSKLTVDKS<br>RWQQGNVFSCSVLHEALHSHYTQKSLSLSPGKGSGHHHHHH*** |

In some embodiments, 3D structure information of broadly neutralizing antibodies (bNAbs) in complex with HIV-1 envelope glycoproteins (Env) was used to perform rational design of penta-specific antibodies (PentaNAbs) capable of targeting five major Env neutralizing epitopes. In some embodiments, "PentaNAbs" as referred to herein comprise five functional single chain fragment variable (ScFv) moieties connected in tandem via (G4S)n linkers, such that penta-valence engagement of five individual epitopes on the HIV-1 Env by each respective moiety is possible. The bNAb functional moieties incorporated in the design target five major HIV neutralization epitopes including the i) V1/V2 apex glycan, ii) V3-base glycan, iii) CD4 binding site, iv) gp120/gp41 interface, and v) the membrane proximal external region (MPER). In addition, these PentaScFv entities can be fused to the fragment crystallizable region (Fc) region of IgG1 to accommodate effector functions in a Penta-IgG format.

The term "protomer" is the structural unit of an oligomeric protein unit. A protomer may span a single segment of a protein's primary structure, or may be composed of one or more different protein sequences that spans across a protein's three-dimensional folded or unfolded protein structure. A protomer may be a repeating structural unit.

In some embodiments, to design the Penta-specific ScFv and bNAbs, the physical distance between the compatible N/C termini of parental bNAb variable heavy (VH) and light chain (VL) domains was estimated to identify the shortest linker combinations allowing optimal VH/VL connection within each bNAb ScFv entity. In some embodiments multiple tandem (G4S)n linkers were used. In some embodiments, at least three G4S linkers were used between the VH and VL domains of a bNAb in the PentaScFv or Penta-bNAb molecule. The number of G4S linkers between VH and VL regions is not limiting and may not be required. In some embodiments there is no linker between the VH and VL regions. The number of G4S linkers between VH and VL domains of a bNab may include at least one, at least two, at least three, at least four, at least five, at least six, at least seven, at least eight, at least nine, at least ten, at least eleven, at least twelve, at least thirteen, at least fourteen, or at least fifteen linkers. In some embodiments multiple tandem (G4S)n linkers can be used between individual bNab moieties in the PentaScFv and Penta-bNAb molecules. In some embodiments at least five G4S linkers were used between individual bNAbs. The number of G4S linkers between individual bNabs may include at least one, at least two, at least three, at least four, at least five, at least six, at least seven, at least eight, at least nine, at least ten, at least eleven, at least twelve, at least thirteen, at least fourteen, or at least fifteen linkers.

In some embodiments, five G4S linkers were used to connect moieties of bNAbs targeting the V1V2 (e.g. VRC26.25) and V3 (e.g. PGT121) glycans. A linker of sufficient length (e.g. a linker with five G4S units) can be utilized to connect VRC26.25 or PGDM1400 with PGT121. In some embodiments, epitopes located on adjacent protomers of the HIV-1 trimer are often more proximate to each other than those on the same protomer. Thus, in some embodiments, two functional bNAb moieties can be arranged binding to the same protomer (intra-protomer mode) and in some cases to separate protomers (inter-protomers) of the HIV-1 Env trimer. In some embodiments, the shortest distance between the CD4bs targeting bNAb moiety, N6 (with VRC01 as surrogate), and the gp120/gp41 interface targeting 35O22 entity was determined to be an intra-protomer distance. Using the model in PDB 5FYK, the distance between the 35O22 and N6 functional variable domains were determined to be 57 Å between the C-terminus of 35O22 VH domain and the N-terminus of N6 VL domain with the topology of 35O22(VL-VH)-N6(VL-VH), and 47 Å between the C-terminus of N6 VL and the N-terminus of 35O22 VH with the topology of N6(VH-VL)-35O22(VH-VL), respectively. Thus, five G4S linkers can be used to connect N6 and 35O22. The length of the linkers is not limiting and may be varied.

In some embodiments, five G4S linkers can be used to connect the V3-glycan targeting PGT121 and the CD4bs targeting N6 ScFv entities. The shortest distance between PGT122 (a surrogate for PGT121) and VRC01 (a surrogate for N6) was previously determined between adjacent protomers within an Env trimer (inter-protomer). Using the PDB model 5FYK, the distances between the VRC01 and PGT121 functional variable domains were determined as the follows: 37 Å between the C-terminus of VRC01 VH domain and the N-terminus of PGT121 VL domain with VRC01(VL-VH)-PGT121(VL-VH) topology, and 53 Å between the C-terminus of PGT121 VL and the N-terminus of VRC01 VH with PGT121(VH-VL)-VRC01(VH-VL) topology. Furthermore, negative stain electron microscopy data demonstrated that one of the Bi-ScFvs previously generated, dVRC01(VL-VH)-5X-PGT121(VL-VH), was able to simultaneously engage both the PGT121 and VRC01 epitopes in an inter-protomer manner as predicted (31), which supports rationale for this linker design.

In some embodiments, the shortest distances between the gp120/gp41 interface targeting 35O22 entity and the MPER targeting 10E8v4 entity was determined to be inter-protomer manner. Using PDB 5IQ7 superimposed with PDB 5FYK, a model for Env engaged with both 35O22 and 10E8 was generated. In this model, the distance between the 10E8v4 and 35O22 functional variable domains were determined to be 48 Å between the C-terminus of 10E8v4 VH domain and the N-terminus of 35O22 VL domain with the topology of 10E8v4(VL-VH)-35O22(VL-VH), and 25 Å between the C-terminus of 35O22 VL and the N-terminus of 10E8v4 VH with the topology of 35O22(VH-VL)-10E8v4(VH-VL) respectively. Therefore, five G4S linkers can be used to connect 35O22 and 10E8v4. The linkers used are not limiting and can be optimized.

The type of linker between VH and VL domains of a bNAb is not limited to the use of G4S linkers. The type of linker between individual bNAbs is not limited to the use of G4S linkers. The length, sequence, and/or identity between the linkers separating the VH and VL regions and the linkers separating the individual bNAb moieties may be the same or may be different. The relationship between the types and characteristics of linkers used is not limiting. Such linkers are typically polypeptide sequences of between about 1 and 200 amino acids. The linkers can be any combination of natural or unnatural amino acids, and the sequence identity of the linkers is not limiting. Linkers can be flexible or rigid amino acid subsequences which are synthesized as part of a recombinant fusion protein.

The linkers may be flexible, the linkers may be rigid, or the linkers may be cleavable. Linkers may offer many other advantages for the production of fusion proteins, such as improving biological activity, increasing expression yield, and achieving desirable pharmacokinetic profiles. As such, the linkers in certain embodiments are not limiting and may be optimized for length, flexibility, rigidity, identity, cleavability, chemical composition, or other physical or chemical properties, for reasons that may or may not affect yield, half-life, biological activity, neutralization activity, pharmacokinetic properties, bioavailability, binding affinity, protein size, or stoichiometric binding ratios.

In some embodiments, the linker can be non-peptide based. A chemical linker may be used to connect protein sequences. Such linkers are known to persons of skill in the art. For example, poly(ethylene glycol) linkers are available from Shearwater Polymers, Inc. Huntsville, Ala. These linkers optionally have amide linkages, sulfhydryl linkages, or heterofunctional linkages. In addition to covalent linkage of bNab sequences and linkers, non-covalent methods can be used to produce molecules with bNabs and linkers. Disulfide bonds may be used to form linkers. Chemical conjugation methods are known to persons of skill in the art and may be used to link VH and VL regions, or individual bNab moieties.

In some embodiments, the disclosure relates to an antibody comprising a variable portion and a constant portion, the variable portion comprising any one or plurality of variable heavy and/or light antibody fragments (such as a scFv fragment) capable of binding to the epitopes disclosed herein, and the constant portion comprising an IgG-like domain.

The antibody can be modified to improve certain biological properties of the antibody, e.g., to improve stability, to enhance or reduce effector functions such as antigen-dependent cell-mediated cytoxicity (ADCC) and/or complement dependent cytotoxicity (CDC) of the antibody, improved or decreased internalization and/or recycling, among others.

In certain embodiments, the multispecific antibody as described herein further includes a modification in the Fc region. In certain embodiments, the multispecific antibodies of the disclosure include mutations that increase binding to the neonatal Fc receptor (FcRn), which recycles IgG in intestinal epithelial cells and increases levels in the serum, extended half-life, enhanced mucosal localization, and conferred more efficient protection against lentivirus infection relative to the wild-type antibody. Enhanced neonatal Fc receptor function improves protection against primate SHIV infection. Such mutations are described, for example in Ko et al. (Nature 514, 642-645 (2014)).

For example, the Fc fragment of some antibodies (derived from human Ig4) can be replaced with human IgG1 that increases effector function mediated through FcRs (except FcRn). Such modification may improve the stability of the resulting antibody by about 5 fold. In another example, the IgG1 Fc fragment can be modified to improve the recycling of the antibody via the antibody salvage pathway.

Still another type of modification involves alteration of the glycosylation pattern of a parent antibody, including deletions of one or more carbohydrate moieties found in the parent antibody, or addition of one or more carbohydrates (via addition of one or more glycosylation sites) that are not present in the parent antibody.

In some embodiments, "knob into hole" technology (J. B. Ridgway, L. G. Presta, P. Carter, 'Knobs-into-holes' engineering of antibody CH3 domains for heavy chain heterodimerization. Protein Eng 9, 617-621 (1996)) can be utilized to generate a heterodimer of the "Forward" and "Reverse" PentaNAb arms, with LS mutations (M428L/N434S) in the Fc fragment for elongated antibody in vivo half-lives as well as improved biodistribution into the mucosal compartment. The use of this "knob into hole" technology is not limiting any method of generating PentaNAb dimers known to persons of skill in the art may be used.

PentaNAbs fused to a C-terminal fragment crystallizable region (Fc) region of IgG1, which may or may not contain a Hinge, CH2, and CH3 domains, can accommodate effector functions in a Penta-IgG format. The Fc region may or may not be fused to the C-terminus of each pentaNAb. Such recombinant formats are known to persons of skill in the art. The formats may include, but are not limited to the use of diabodies, minibodies, scFab, or scFv-zippers. For example, the types of recombinant formats may be found in the literature (See Frenzel A, Hust M, and Schirrmann T., *Frontiers in Immunology.* 2013; 4:217).

In some embodiments, two Forwards PentaNAbs can be combined through the use of the Fc regions of IgG1. In some embodiments, one Forward PentaNAb can be combined with one Reverse PentaNAb through the use of Fc regions of IgG1. The combinations of Forward and Reverse PentaNAbs are advantageous but not limiting.

Polynucleotides

In some embodiments, the invention encompasses polynucleotides comprising polynucleotides that encode a polypeptide as described herein, such as a sequence of an HIV antibody or a fragment of such a polypeptide. For example, in some embodiments, the invention provides a polynucleotide comprising a nucleic acid sequence that encodes a multi specific antibody to HIV Env protein or encodes a fragment of such an antibody. The polynucleotides of the invention can be in the form of RNA or in the form of DNA. DNA includes cDNA, genomic DNA, and synthetic DNA; and can be double-stranded or single-stranded, and if single stranded can be the coding strand or non-coding (anti-sense) strand.

In some embodiments, the polynucleotides are isolated. In certain embodiments, the polynucleotides are substantially pure.

In some embodiments, the invention provides isolated nucleic acid molecules that encode multispecific anti-HIV antibodies as described herein. In some embodiments, the invention provides isolated nucleic acid molecules that encode isolated variable domains of the antibodies described herein. In some embodiments, the nucleotide sequence is selected from any one of SEQ ID NOS:52-71 and SEQ ID NOS:81-89, as shown below in Table 4 and below.

In some embodiments, the invention provides a polynucleotide comprising a polynucleotide encoding a polypeptide comprising a sequence selected from the group consisting of SEQ ID NOS:1-51 and 72-80.

In some embodiments, the invention provides a polynucleotide comprising a polynucleotide encoding a polypeptide comprising the heavy or light chain variable region selected from the group consisting of SEQ ID NOS: 1, 5, 9, 13, 17 21, 25, 29, 33, 37, 41, 45, 49 and 51.

Also provided is a polynucleotide encoding a polypeptide comprising the heavy or light chain variable region having at least about 95%, at least about 96%, at least about 97%, at least about 98%, or at least about 99% sequence identity to any of SEQ ID NOS: 1, 5, 9, 13, 17 21, 25, 29, 33, 37, 41, 45, 49 and 51.

In some embodiments, the invention provides a polynucleotide comprising a polynucleotide encoding a polypeptide comprising an amino acid sequence selected from the group consisting of SEQ ID NOS:72-80 and SEQ ID NOS: 90, 92, 94, 96, 98, 99 and 107.

Also provided is a polynucleotide encoding a polypeptide having at least about 95%, at least about 96%, at least about 97%, at least about 98%, or at least about 99% sequence identity to any of SEQ ID NOS:72-80 and SEQ ID NOS: 90, 92, 94, 96, 98, 99 and 107.

The invention further provides a polynucleotide comprising a sequence selected from the group consisting of SEQ ID NOS:52-71 and SEQ ID NOS:81-89.

Also provided is a polynucleotide having at least 70%, 75%, 80%, 85%, 86%, 87%, 88%, 89%, 90%, 91%, 92%, 93%, 94%, 95%, 96%, 97%, 98%, or 99% sequence identity to any of SEQ ID NOS:52-71, SEQ ID NOS:81-89 and SEQ ID NOS 91, 93, 95, 97 and 106.

In some embodiments the polynucleotides comprise the coding sequence for the mature polypeptide fused in the same reading frame to a polynucleotide which aids, for example, in expression and secretion of a polypeptide from a host cell (e.g. a leader sequence which functions as a secretory sequence for controlling transport of a polypeptide from the cell). The polypeptide having a leader sequence is a preprotein and can have the leader sequence cleaved by the host cell to form the mature form of the polypeptide. The polynucleotides can also encode for a proprotein which is the mature protein plus additional 5' amino acid residues. A mature protein having a prosequence is a proprotein and is an inactive form of the protein. Once the prosequence is cleaved an active mature protein remains.

In certain embodiments the polynucleotides comprise the coding sequence for the mature polypeptide fused in the same reading frame to a marker sequence that allows, for example, for purification of the encoded polypeptide. For example, the marker sequence can be a hexa-histidine tag supplied by a pQE-9 vector to provide for purification of the mature polypeptide fused to the marker in the case of a bacterial host, or the marker sequence can be a hemagglutinin (HA) tag derived from the influenza hemagglutinin protein when a mammalian host (e.g. COS-7 cells) is used.

The present invention further relates to variants of the hereinabove described polynucleotides encoding, for example, fragments, analogs, and derivatives.

The polynucleotide variants can contain alterations in the coding regions, non-coding regions, or both. In some embodiments the polynucleotide variants contain alterations which produce silent substitutions, additions, or deletions, but do not alter the properties or activities of the encoded polypeptide. In some embodiments, nucleotide variants are produced by silent substitutions due to the degeneracy of the genetic code. Polynucleotide variants can be produced for a variety of reasons, e.g., to optimize codon expression for a particular host (change codons in the human mRNA to those preferred by a bacterial host such as *E. coli*).

Vectors and cells comprising the polynucleotides described herein are also provided. The term "vector" means a construct, which is capable of delivering, and expressing, one or more gene(s) or sequence(s) of interest in a host cell. Examples of vectors include, but are not limited to, viral vectors, naked DNA or RNA expression vectors, plasmid, cosmid or phage vectors, DNA or RNA expression vectors associated with cationic condensing agents, DNA or RNA expression vectors encapsulated in liposomes, and certain eukaryotic cells, such as producer cells. "Vector" also includes shuttle and expression vectors. In some embodiments, the vector is a plasmid construct and also includes an origin of replication (e.g., the ColE1 origin of replication) and a selectable marker (e.g., ampicillin or tetracycline resistance), for replication and selection, respectively. An "expression vector" refers to a vector that contains the necessary control sequences or regulatory elements for expression of the antibodies including antibody fragments of the invention, in bacterial or eukaryotic cells.

TABLE 4

Nucleotide Sequences of variable domain anti-HIV antibodies.

| SEQ ID NO | DESCRIPTION | NUCLEOTIDE SEQUENCE |
|---|---|---|
| 52 | VRC26.25 VH (Original Seq) | caggtgcagttggtggagtctgggggaggcgtggtccagcctgggacgtcc ctgagactctcctgtgcagcctctcaattcaggtttgatggttatggcatg cactgggtccgccaggccccaggcaaggggctggagtgggtggcatctata tcacatgatggaattaaaaagtatcacgcagaaaaagtgtggggccgcttc accatctccagagacaattccaagaacacactgtatctacaaatgaacagc ctgcgacctgaggacacggctctctactactgtgcgaaagatttgcgagaa gacgaatgtgaagagtggtggtcggatgattttgggaaacaactcccttgc gcaaagtcacgcggcggcttggttggaattgctgataactggggccaaggg acaatggtcaccgtctcttca |
| 53 | VRC26.25 VL (Original Seq) | cagtctgtgctgacgcagccgccctcagtgtctgcggccccaggacagaag gtcaccatctcctgctctggaaacacctccaacattggcaataattttgtg tcctggtaccaacagcgccccggcagagcccccccaactcctcatttatgaa actgacaagcgaccctcagggattcctgaccgattctctgcttccaagtct ggtacgtcaggcaccctggccatcaccgggctgcagactggggacgaggcc gattattactgcgccacatgggctgccagcctgagttccgcgcgtgtcttc ggaactgggaccaaggtcatcgtccta |
| 54 | 35O22 VH (Original Seq) | cagggtcaactagtccagtctggagctgaattgaaaaagcctggcgcctcg gtgaagatttcctgtaagacttcgggttataggtttaatttctatcatatt aattggattcgacaaactgcaggacgtggacctgagtggatgggatggatc agcccttacagtggtgacaaaaacctcgcacctgcctttcaagacagagtc attatgacgacagacacagaagtccctgtgacctcattcacgtccacgggc gcagcctacatggaaataaggaacctgaaatttgacgacacaggcacctat ttctgtgcaaaaggcctcctgcgtgacggttcgtcgacgtggcttccttat ttgtggggccagggtaccctactcaccgtctcgtca |
| 55 | 35O22 VL (Original Seq) | cagtctgtgctgacgcagtctgcctccgtgtctgggtctcttggacagtcg gtcaccatctcctgcactggacccaatagtgtttgttgcagtcacaaatct atctcctggtatcagtggcccccaggcagagcccccacactcatcatttat gaggacaatgaaagggccccgggaatctctcctcgcttctctggctacaag tcgtattggtcggcctacttgacaatctctgatctccggcctgaagacgag accacttactactgttgctcatacactcacaatagcggctgtgtcttcggg actgggaccaaggtctccgtcttg |
| 56 | 10E8v4 VH (Original Seq) | gaggttagactggtggagtcaggagggggcttgtgaagcccggtgggtct ctccgcctgagctgttctgcctccggctttgatttcgataacgcctggatg acctgggtcaggcagcctccaggtaagggactggagtgggtgggaagaatc acaggtccaggcgagggctggtccgtggactacgcggaatctgttaaaggg cggtttacaatctcaagggacaataccaagaataccttgtatttggagatg aacaacgtgagaactgaagacaccggatattacttctgtgccagaacaggc aaatactacgacttctggtccggctatccccctggcgaggaatattttcaa gactggggtcagggaacccttgttatcgtgtcctcc |
| 57 | 10E8v4 VL (Original Seq) | tccgaactgactcaggaccctgccgtctctgtggcactgaagcagactgtg actattacttgccgaggcgactcactgcggagccactacgcttcctggtat cagaagaaacccggccaggcacctgtgctgctgttctacggaaagaacaat aggccatctggcatccccgaccgcttttctggcagtgcatcagggaaccga gccagtctgaccattaccggcgcccaggctgaggacgaagccgattactat tgcagctcccgggataagagcggctccagactgagcgtgttcggaggagga actaaactgaccgtcctc |

TABLE 4-continued

| Nucleotide Sequences of variable domain anti-HIV antibodies. | | |
|---|---|---|
| SEQ ID NO | DESCRIPTION | NUCLEOTIDE SEQUENCE |
| 58 | VRC26.25 VH (Optimized Seq 1) | caggtgcagctggtggagagcggcggcggcgtggtgcagccaggcacctcc ctgaggctgtcttgtgcagcaagccagttcagatttgatggctacggcatg cactgggtgcgccaggcaccaggcaagggcctggagtgggtagcctctatc agccacgacggcatcaagaagtaccacgccgagaaagtgtggggcaggttc accatctcccgcgataactctaaaaacacactgtatctgcagatgaactcc ctgaggcccgaggacaccgccctgtactattgcgccaaggacctgcgcgag gatgagtgtgaggagtggtggtccgacgattttggcaagcagctgccttgc gcaaagagcaggggaggcctggtgggaatcgccgataattggggccagggc accatggtgacagtgtctagc |
| 59 | VRC26.25 VH (Optimized Seq 2) | caggtgcagctggtggagtccggaggaggagtggtgcagccaggcacctct ctgaggctgagctgtgcagcatcccagttcagatttgatggctacggaatg cactgggtgaggcaggcaccaggcaagggactggagtgggtggccagcatc tcccacgacggcatcaagaagtaccacgccgagaaagtgtggggcaggttc accatctctcgcgataacagcaagaatacactgtatctgcagatgaacagc ctgaggcccgaggacaccgccctgtactattgcgccaaggacctgcgcgag gatgagtgtgaggagtggtggtccgacgattttggcaagcagctgccttgc gcaaagagcaggggaggactggtgggaatcgccgacaattggggccagggc accatggtgacagtgagcagc |
| 60 | VRC26.25 VL (Optimized Seq 1) | cagagcgtgctgacccagccaccttccgtgtctgccgcaccaggacagaag gtgaccatcagctgttccggcaacacatccaatatcggcaacaatttcgtg tcttggtaccagcagaggccaggaagggcaccacagctgctgatctatgag acagacaagcggccttccggcatcccagatagattttctgccagcaagtcc ggcaccagcggcacactggcaatcaccggcctgcagacaggcgacgaagct gattactattgcgcaacctgggcagcctccctgagctccgccagggtgttc ggaaccggaacaaaagtgatcgtgctggtg |
| 61 | VRC26.25 VL (Optimized Seq 2) | cagagcgtgctgacccagccaccttccgtgtctgccgcaccaggacagaag gtgaccatcagctgttccggcaacacatccaatatcggcaacaatttcgtg tcttggtaccagcagaggcctggaagagcaccacagctgctgatctatgag acagacaagaggccctccggcatccctgatcgcttttctgccagcaagtcc ggcaccagcggcacactggcaatcaccggactgcagacaggcgacgaggca gattactattgcgcaacctgggcagcctccctgtctagcgccagggtgttc ggcaccggcacaaaagtgatcgtgctggtg |
| 62 | PGDM1400 VH (Optimized Seq 1) | caggcacagctggtgcagagcggacccgaagtgagaaaacctgggactagc gtcaaagtgtcatgtaaagcccctggaaataccctgaagacctacgatctg cactgggtgcggtccgtgcctggacagggcctgcagtggatgggatggatc tctcacgagggcgacaagaaagtgatcgtggagcggttcaaggccaaggtg acaatcgattgggacagatccaccaacacagcctacctgcagctgtctggc ctgaccagcggcgatacagccgtgtactactgtgccaagggctctaagcac cggctgagagactacgccctggacgatgacggcgccctgaactgggccgtg gatgtggactatctgtccaatctggagttctggggacagggaaccgcagtg acagtgagctcc |
| 63 | PGDM1400 VH (Optimized Seq 2) | caggcacagctggtgcagagcggaccagaggtgaggaagccaggcacctct gtgaaggtgagctgtaaggcccctggcaacaccctgaagacatacgatctg cactgggtgcggtctgtgccaggacagggcctgcagtggatgggatggatc agccacgagggcgacaagaaagtgatcgtggagcggtttaaggccaaggtg acaatcgattgggacagaagcaccaatacagcctatctgcagctgtccggc ctgacctctggcgatacagccgtgtactattgcgccaagggctccaagcac cggctgagagactacgccctggacgatgacggcgccctgaattgggcagtg gacgtggactatctgagtaatctggagttttgggggcagggcaccgcagtg acagtgtctagc |
| 64 | PGDM1400 VL (Optimized Seq 1) | gattttgtgctgacccagtctccacacagcctgtccgtgacacccggcgag tctgccagcatctcctgcaagtctagccacagcctgatccacggcgacagg aacaattacctggcctggtacgtgcagaagccaggccgcagccctcagctg ctgatctatctggcatcctctagggcctccggagtgccagatcgcttctct ggcagcggctccgataaggactttaccctgaagatcagccgggtggagaca gaggacgtgggcacatactattgtatgcagggccgagaatcaccttggaca tttgggcagggaactaaagtcgacatcaaa |
| 65 | PGDM1400 VL (Optimized Seq 2) | gatttcgtgctgacccagtctccacatagtctgagcgtgacacccggcgaa agcgcatcaatttcttgtaaatcatctcatagtctgatccacggcgatagg aacaattacctggcctggtacgtgcagaagccaggccgcagccctcagctg ctgatctacctggcaagctccagggcatccggagtgccagatcgcttctct ggcagcggctccgataaggactttaccctgaagatctcccgggtggagaca gaggacgtgggcacatactattgcatgcagggcagagagtctccttggacc ttcggccagggcacaaaggtggacatcaag |
| 66 | 35O22 VH (Optimized Seq 1) | cagggccagctggtgcagagcggagcagagctgaagaagcctggagccagc gtgaagatctcctgtaagacatctggctaccggttcaacttttatcacatc aattggatcaggcagaccgcaggaaggggaccagagtggatgggctggatc |

TABLE 4-continued

| Nucleotide Sequences of variable domain anti-HIV antibodies. | | |
|---|---|---|
| SEQ ID NO | DESCRIPTION | NUCLEOTIDE SEQUENCE |
| | | tcccccctactctggcgataagaacctggccccagccttccaggacagagtg<br>atcatgaccacagataccgaggtgccagtgaccagcttcacctccaccgga<br>gccgcctacatggagatcaggaatctgaagttcgacgatacaggcacctat<br>ttttgcgcaaagggcctgctgagggacggctcctctacctggctgccttac<br>ctgtggggacagggcaccctgctgacagtgagctcc |
| 67 | 35O22 VH (Optimized Seq 2) | cagggccagctggtgcagagcggagcagagctgaagaagccaggagcctct<br>gtgaagatcagctgtaagacatccggctaccggttcaacttttatcacatc<br>aattggatcaggcagaccgcaggaaggggaccagagtggatgggctggatc<br>tcccccctactctggcgataagaacctggccccagccttccaggacagagtg<br>atcatgaccacagataccgaggtgccagtgaccagcttcacctccaccgga<br>gccgcctacatggagatccggaatctgaagttcgacgatacaggcacctat<br>ttttgcgccaagggcctgctgagagacggctctagcacatggctgccatac<br>ctgtggggacagggcaccctgctgacagtgtcctct |
| 68 | 35O22 VL (Optimized Seq 1) | cagtccgtgctgacccagtctgccagcgtgtccggctctctgggacagagc<br>gtgaccatctcctgtacaggccccaacagcgtgtgctgtagccacaagagc<br>atctcctggtaccagtggcctccaggaagggcacctaccctgatcatctat<br>gaggacaatgagcgggccccaggcatctcccccagattctctggctacaag<br>tcttattggagcgcctacctgacaatcagcgacctgcgccccgaggatgag<br>acaacatactattgctgttcctatacccacaactctggctgcgtgtttggc<br>acaggcaccaaggtgtccgtgctg |
| 69 | 35O22 VL (Optimized Seq 2) | caaagcgtgctgacccagtccgcctctgtgagcggctccctgggccagtct<br>gtgaccatcagctgtacaggccccaactccgtgtgctgttctcacaagtct<br>atcagctggtaccagtggccaccaggaagggcacctaccctgatcatctat<br>gaggacaatgagagggcaccaggaatcagccctcgcttctccggctacaag<br>tcttattggagcgcctacctgaccatttccgacctgcgccccgaggatgag<br>accacatactattgctgtagctatacccacaactccggctgcgtgtttggc<br>acaggcaccaaggtgagcgtgctg |
| 70 | 10E8v4_V5R_S100cF VH (Optimized Seq) | gaggtgcggctgcgggagagcggcggcggcctggtgaagccaggcggctct<br>ctgagactgtcctgttctgccagcggcttcgactttgataatgcctggatg<br>acatgggtgcggcagcctcctggcaaggggctggagtgggtgggaagaatc<br>accggaccaggagagggatggtctgtggactacgccgagagcgtgaagggc<br>cggttcaccatcagcagagataacactaaaaatacactgtatctggagatg<br>aacaatgtgcggaccgaggacacaggctactatttctgcgccagaaccggc<br>aagtactatgatttctggtttggctaccccccctggcgaggagtattttcag<br>gactggggccagggcaccctggtcatcgtgagcagc |
| 71 | 10E8v4 VL | agcgagctgacccaggaccccgccgtgtccgtggccctgaagcagacagtg<br>accatcacatgcaggggcgactccctgcgctctcactacgccagctggtat<br>cagaagaagccaggacaggcacccgtgctgctgttctacggcaagaacaat<br>cggccttccggcatcccagatagattttccggctctgccagcggaaacagg<br>gccagcctgaccatcacaggagcacaggcagaggatgaagcagattactat<br>tgttcctctcgggacaagtccggctctagactgagcgtgttcggcggcgga<br>accaagctgacagtgctg |

Nucleotide sequences of the Penta-Nabs shown in Table 3 are provided below.

1. PentaNAb$_{1.0}$ 10E8v4-5X-35O22-5X-N6-5X-PGT121-5X-VRC26.25-His

SEQ ID NO: 81

GAATTCGCCGCCACCATGGGATGGAGCTGTATTATTCTGTTTCTGGTCGC

TACCGCTACCGGAGTGCATTCTTCTGAACTGACCCAGGACCCCGCCGTGA

GCGTGGCCCTGAAGCAGACCGTGACAATCACCTGCAGGGGCGACAGCCTG

CGCTCCCACTACGCCAGCTGGTATCAGAAGAAGCCTGGCCAGGCCCCAGT

GCTGCTGTTCTACGGCAAGAACAATAGGCCCTCCGGCATCCCTGATCGCT

TTTCCGGCTCTGCCAGCGGAAACAGGGCCAGCCTGACAATCACCGGAGCA

CAGGCAGAGGACGAGGCAGATTACTATTGCAGCTCCCGGGACAAGTCCGG

CTCTAGACTGAGCGTGTTCGGCGGCGGCACCAAGCTGACAGTGCTGGGAG

-continued

GAGGAGGCAGCGGCGGAGGAGGCTCCGGAGGCGGCGGCTCTGAGGTGCGG

CTGGTGGAGTCTGGAGGAGGCCTGGTGAAGCCAGGAGGCAGCCTGAGACT

GAGCTGTTCCGCCTCTGGCTTCGACTTTGATAATGCCTGGATGACATGGG

TGCGGCAGCCACCTGGCAAGGGCCTGGAGTGGGTGGGAAGAATCACCGGA

CCAGGAGAGGGATGGTCTGTGGACTACGCCGAGAGCGTGAAGGGCCGGTT

CACCATCTCCAGAGATAACACCAAGAATACACTGTATCTGGAGATGAACA

ATGTGCGGACCGAGGACACAGGCTACTATTTCTGCGCCAGAACCGGCAAG

TACTATGATTTTTGGAGCGGCTACCCACCCGGCGAGGAGTATTTTCAGGA

CTGGGGCCAGGGCACCCTGGTCATCGTGAGCAGCGGCGGCGGCGGCAGCG

GCGGCGGCGGCTCCGGAGGAGGCGGCTCTGGAGGAGGAGGCAGCGGGGGA

GGGGGCAGCCAGTCCGTGCTGACCCAGTCTGCCAGCGTGTCCGGCTCTCT

GGGACAGAGCGTGACCATCTCCTGTACAGGCCCCAACAGCGTGTGCTGTA

-continued

GCCACAAGAGCATCTCCTGGTACCAGTGGCCTCCAGGAAGGGCACCTACC

CTGATCATCTATGAGGACAATGAGCGGGCCCCAGGCATCTCCCCCAGATT

CTCTGGCTACAAGTCTTATTGGAGCGCCTACCTGACAATCAGCGACCTGC

GCCCCGAGGATGAGACAACATACTATTGCTGTTCCTATACCCACAACTCT

GGCTGCGTGTTTGGCACAGGCACCAAGGTGTCCGTGCTGGGCGGCGGCGG

CAGCGGGGGCGGGGGCTCCGGAGGGGGCGGCTCTCAGGGCCAGCTGGTGC

AGAGCGGAGCAGAGCTGAAGAAGCCTGGAGCCAGCGTGAAGATCTCCTGT

AAGACATCTGGCTACCGGTTCAACTTTTATCACATCAATTGGATCAGGCA

GACCGCAGGAAGGGGACCAGAGTGGATGGGCTGGATCTCCCCCTACTCTG

GCGATAAGAACCTGGCCCCAGCCTTCCAGGACAGAGTGATCATGACCACA

GATACCGAGGTGCCAGTGACCAGCTTCACCTCCACCGGAGCCGCCTACAT

GGAGATCAGGAATCTGAAGTTCGACGATACAGGCACCTATTTTTGCGCAA

AGGGCCTGCTGAGGGACGGCTCCTCTACCTGGCTGCCTTACCTGTGGGGA

CAGGGCACCCTGCTGACAGTGAGCTCCGGCGGCGGGGGCAGCGGCGGCGG

GGGCTCCGGAGGAGGAGGCTCTGGAGGAGGGGGCAGCGGAGGAGGCGGCT

CCTACATCCACGTGACCCAGTCCCCATCTAGCCTGTCTGTGAGCATCGGC

GATCGGGTGACCATCAACTGTCAGACATCTCAGGGCGTGGGCAGCGACCT

GCACTGGTATCAGCACAAGCCTGGCAGGGCCCCAAAGCTGCTGATCCACC

ACACATCCTCTGTGGAGGATGGAGTGCCAAGCCGCTTCTCCGGCTCTGGA

TTCCACACCTCCTTTAATCTGACAATCTCTGACCTGCAGGCCGACGATAT

CGCCACCTACTATTGCCAGGTGCTGCAGTTCTTTGGCCGGGGCTCCAGAC

TGCACATCAAGGGAGGAGGAGGCTCCGGGGGCGGAGGCTCTGGCGGCGGC

GGCAGCCGGGCCCACCTGGTGCAGAGCGGCACCGCCATGAAGAAGCCTGG

CGCCAGCGTGAGAGTGTCCTGTCAGACATCTGGCTACACCTTCACCGCCC

ACATCCTGTTCTGGTTTAGGCAGGCACCAGGAAGAGGCCTGGAGTGGGTG

GGCTGGATCAAGCCCCAGTATGGAGCAGTGAACTTCGGAGGAGGCTTTCG

GGACAGAGTGACACTGACCCGGGACGTGTACAGAGAGATCGCCTATATGG

ATATCAGGGGCCTGAAGCCAGACGATACCGCCGTGTACTATTGCGCCAGG

GACCGCTCCTACGGCGATAGCTCCTGGGCACTGGACGCATGGGGACAGGG

CACCACAGTGGTGGTGAGCGCCGGCGGCGGAGGCTCCGGCGGCGGGGGCT

CTGGAGGAGGCGGCAGCGGAGGGGGAGGCTCCGGAGGGGGAGGCTCTAGC

GACATCTCCGTGGCCCCTGGCGAGACAGCCAGAATCTCTTGTGGCGAGAA

GTCTCTGGGCAGCAGGGCCGTGCAGTGGTACCAGCACAGGGCAGGACAGG

CACCATCTCTGATCATCTATAACAATCAGGATAGGCCAAGCGGCATCCCT

GAGCGGTTCAGCGGCTCCCCCGACAGCCCTTTTGGCACCACAGCCACACT

GACCATCACATCCGTGGAGGCAGGCGACGAAGCCGATTACTATTGCCACA

TCTGGGATTCCAGAGTGCCAACCAAGTGGGTGTTCGGAGGAGGAACCACA

CTGACAGTGCTGGGAGGGGGGGGCTCTGGCGGCGGGGGCAGCGGGGGAGG

AGGCTCCCAGATGCAGCTGCAGGAGAGCGGACCAGGCCTGGTGAAGCCTA

GCGAGACACTGAGCCTGACATGTTCTGTGAGCGGCGCCTCCATCTCTGAC

AGCTACTGGTCTTGGATCAGACGGAGCCCCGGCAAGGGCCTGGAATGGAT

CGGCTACGTGCACAAGTCCGGCGATACAAACTATTCCCCATCTCTGAAGT

CTCGGGTGAACCTGTCTCTGGACACCAGCAAGAATCAGGTGAGCCTGTCC

CTGGTGGCAGCAACCGCAGCAGATAGCGGCAAGTACTATTGCGCCAGAAC

ACTGCACGGCAGGCGCATCTACGGCATCGTGGCCTTTAACGAGTGGTTCA

CCTACTTTTATATGGACGTGTGGGGCAATGGCACCCAGGTGACAGTGTCC

TCTGGCGGGGGCGGCTCCGGAGGCGGAGGCTCTGGCGGGGGCGGCAGCGG

CGGGGGCGGCTCCGGGGGAGGCGGCTCTCAGAGCGTGCTGACCCAGCCAC

CTTCCGTGTCTGCCGCACCAGGACAGAAGGTGACCATCAGCTGTTCCGGC

AACACATCCAATATCGGCAACAATTTCGTGTCTTGGTACCAGCAGAGGCC

AGGAAGGGCACCACAGCTGCTGATCTATGAGACAGACAAGCGGCCTTCCG

GCATCCCAGATAGATTTTCTGCCAGCAAGTCCGGCACCAGCGGCACACTG

GCAATCACCGGCCTGCAGACAGGCGACGAAGCTGATTACTATTGCGCAAC

CTGGGCAGCCTCCCTGAGCTCCGCCAGGGTGTTCGGAACCGGAACAAAAG

TGATCGTGCTGGTGGGCGGCGGAGGCTCTGGCGGAGGCGGCAGCGGCGGG

GGGGGCTCCCAGGTGCAGCTGGTGGAGAGCGGCGGCGGCGTGGTGCAGCC

AGGCACCTCCCTGAGGCTGTCTTGTGCAGCAAGCCAGTTCAGATTTGATG

GCTACGGCATGCACTGGGTGCGCCAGGCACCAGGCAAGGGCCTGGAGTGG

GTAGCCTCTATCAGCCACGACGGCATCAAGAAGTACCACGCCGAGAAAGT

GTGGGGCAGGTTCACCATCTCCCGCGATAACTCTAAAAACACACTGTATC

TGCAGATGAACTCCCTGAGGCCCGAGGACACCGCCCTGTACTATTGCGCC

AAGGACCTGCGCGAGGATGAGTGTGAGGAGTGGTGGTCCGACTACTATGA

TTTTGGCAAGCAGCTGCCTTGCGCAAAGAGCAGGGGAGGCCTGGTGGGAA

TCGCCGATAATTGGGGCCAGGGCACCATGGTGACAGTGTCTAGCGGATCC

GGACACCACCATCACCATCATTAGTGAAAGCTT

2. PentaNAb$_{2.0}$ 10 E8v4_S100cF-5X-35O22-5X-N6-5X-PGT121-5X-VRC26.25-His

SEQ ID NO: 82

GAATTCGCCGCCACCATGGGATGGAGCTGTATTATTCTGTTTCTGGTCGC

TACCGCTACCGGAGTGCATTCTTCTGAACTGACCCAGGACCCCGCCGTGA

GCGTGGCCCTGAAGCAGACCGTGACAATCACCTGCAGGGGCGACAGCCTG

CGCTCCCACTACGCCAGCTGGTATCAGAAGAAGCCTGGCCAGGCCCCAGT

GCTGCTGTTCTACGGCAAGAACAATAGGCCCTCCGGCATCCCTGATCGCT

TTTCCGGCTCTGCCAGCGGAAACAGGGCCAGCCTGACAATCACCGGAGCA

CAGGCAGAGGACGAGGCAGATTACTATTGCAGCTCCCGGGACAAGTCCGG

CTCTAGACTGAGCGTGTTCGGCGGCGGCACCAAGCTGACAGTGCTGGGAG

GAGGAGGCAGCGGCGGAGGAGGCTCCGGAGGCGGCGGCTCTGAGGTGCGG

CTGGTGGAGTCTGGAGGAGGCCTGGTGAAGCCAGGAGGCAGCCTGAGACT

GAGCTGTTCCGCCTCTGGCTTCGACTTTGATAATGCCTGGATGACATGGG

TGCGGCAGCCACCTGGCAAGGGCCTGGAGTGGGTGGGAAGAATCACCGGA

CCAGGAGAGGGATGGTCTGTGGACTACGCCGAGAGCGTGAAGGGCCGGTT

-continued

CACCATCTCCAGAGATAACACCAAGAATACACTGTATCTGGAGATGAACA

ATGTGCGGACCGAGGACACAGGCTACTATTTCTGCGCCAGAACCGGCAAG

TACTATGATTTTTGGTTTGGCTACCCACCCGGCGAGGAGTATTTTCAGGA

CTGGGGCCAGGGCACCCTGGTCATCGTGAGCAGCGGCGGCGGCGGCAGCG

GCGGCGGCGGCTCCGGAGGAGGCGGCTCTGGAGGAGGAGGCAGCGGGGGA

GGGGGCAGCCAGTCCGTGCTGACCCAGTCTGCCAGCGTGTCCGGCTCTCT

GGGACAGAGCGTGACCATCTCCTGTACAGGCCCCAACAGCGTGTGCTGTA

GCCACAAGAGCATCTCCTGGTACCAGTGGCCTCCAGGAAGGGCACCTACC

CTGATCATCTATGAGGACAATGAGCGGGCCCCAGGCATCTCCCCCAGATT

CTCTGGCTACAAGTCTTATTGGAGCGCCTACCTGACAATCAGCGACCTGC

GCCCCGAGGATGAGACAACATACTATTGCTGTTCCTATACCCACAACTCT

GGCTGCGTGTTTGGCACAGGCACCAAGGTGTCCGTGCTGGGCGGCGGCGG

CAGCGGGGGCGGGGGCTCCGGAGGGGGCGGCTCTCAGGGCCAGCTGGTGC

AGAGCGGAGCAGAGCTGAAGAAGCCTGGAGCCAGCGTGAAGATCTCCTGT

AAGACATCTGGCTACCGGTTCAACTTTTATCACATCAATTGGATCAGGCA

GACCGCAGGAAGGGGACCAGAGTGGATGGGCTGGATCTCCCCCTACTCTG

GCGATAAGAACCTGGCCCCAGCCTTCCAGGACAGAGTGATCATGACCACA

GATACCGAGGTGCCAGTGACCAGCTTCACCTCCACCGGAGCCGCCTACAT

GGAGATCAGGAATCTGAAGTTCGACGATACAGGCACCTATTTTTGCGCAA

AGGGCCTGCTGAGGGACGGCTCCTCTACCTGGCTGCCTTACCTGTGGGGA

CAGGGCACCCTGCTGACAGTGAGCTCCGGCGGCGGGGGCAGCGGCGGCGG

GGGCTCCGGAGGAGGAGGCTCTGGAGGAGGGGGCAGCGGAGGAGGCGGCT

CCTACATCCACGTGACCCAGTCCCCATCTAGCCTGTCTGTGAGCATCGGC

GATCGGGTGACCATCAACTGTCAGACATCTCAGGGCGTGGGCAGCGACCT

GCACTGGTATCAGCACAAGCCTGGCAGGGCCCCAAAGCTGCTGATCCACC

ACACATCCTCTGTGGAGGATGGAGTGCCAAGCCGCTTCTCCGGCTCTGGA

TTCCACACCTCCTTTAATCTGACAATCTCTGACCTGCAGGCCGACGATAT

CGCCACCTACTATTGCCAGGTGCTGCAGTTCTTTGGCCGGGGCTCCAGAC

TGCACATCAAGGGAGGAGGAGGCTCCGGGGGCGGAGGCTCTGGCGGCGGC

GGCAGCCGGGCCCACCTGGTGCAGAGCGGCACCGCCATGAAGAAGCCTGG

CGCCAGCGTGAGAGTGTCCTGTCAGACATCTGGCTACACCTTCACCGCCC

ACATCCTGTTCTGGTTTAGGCAGGCACCAGGAAGAGGCCTGGAGTGGGTG

GGCTGGATCAAGCCCCAGTATGGAGCAGTGAACTTCGGAGGAGGCTTTCG

GGACAGAGTGACACTGACCCGGGACGTGTACAGAGAGATCGCCTATATGG

ATATCAGGGGCCTGAAGCCAGACGATACCGCCGTGTACTATTGCGCCAGG

GACCGCTCCTACGGCGATAGCTCCTGGGCACTGGACGCATGGGGACAGGG

CACCACAGTGGTGGTGAGCGCCGGCGGCGGAGGCTCCGGCGGCGGGGGCT

CTGGAGGAGGCGGCAGCGGAGGGGGAGGCTCCGGAGGGGGAGGCTCTAGC

GACATCTCCGTGGCCCCTGGCGAGACAGCCAGAATCTCTTGTGGCGAGAA

GTCTCTGGGCAGCAGGGCCGTGCAGTGGTACCAGCACAGGGCAGGACAGG

-continued

CACCATCTCTGATCATCTATAACAATCAGGATAGGCCAAGCGGCATCCCT

GAGCGGTTCAGCGGCTCCCCCGACAGCCCTTTTGGCACCACAGCCACACT

GACCATCACATCCGTGGAGGCAGGCGACGAAGCCGATTACTATTGCCACA

TCTGGGATTCCAGAGTGCCAACCAAGTGGGTGTTCGGAGGAGGAACCACA

CTGACAGTGCTGGGAGGGGGGGGCTCTGGCGGCGGGGGCAGCGGGGGAGG

AGGCTCCCAGATGCAGCTGCAGGAGAGCGGACCAGGCCTGGTGAAGCCTA

GCGAGACACTGAGCCTGACATGTTCTGTGAGCGGCGCCTCCATCTCTGAC

AGCTACTGGTCTTGGATCAGACGGAGCCCCGGCAAGGGCCTGGAATGGAT

CGGCTACGTGCACAAGTCCGGCGATACAAACTATTCCCCATCTCTGAAGT

CTCGGGTGAACCTGTCTCTGGACACCAGCAAGAATCAGGTGAGCCTGTCC

CTGGTGGCAGCAACCGCAGCAGATAGCGGCAAGTACTATTGCGCCAGAAC

ACTGCACGGCAGGCGCATCTACGGCATCGTGGCCTTTAACGAGTGGTTCA

CCTACTTTTATATGGACGTGTGGGGCAATGGCACCCAGGTGACAGTGTCC

TCTGGCGGGGGCGGCTCCGGAGGCGGAGGCTCTGGCGGGGGCGGCAGCGG

CGGGGGCGGCTCCGGGGGAGGCGGCTCTCAGAGCGTGCTGACCCAGCCAC

CTTCCGTGTCTGCCGCACCAGGACAGAAGGTGACCATCAGCTGTTCCGGC

AACACATCCAATATCGGCAACAATTTCGTGTCTTGGTACCAGCAGAGGCC

AGGAAGGGCACCACAGCTGCTGATCTATGAGACAGACAAGCGGCCTTCCG

GCATCCCAGATAGATTTTCTGCCAGCAAGTCCGGCACCAGCGGCACACTG

GCAATCACCGGCCTGCAGACAGGCGACGAAGCTGATTACTATTGCGCAAC

CTGGGCAGCCTCCCTGAGCTCCGCCAGGGTGTTCGGAACCGGAACAAAAG

TGATCGTGCTGGTGGGCGGCGGAGGCTCTGGCGGAGGCGGCAGCGGCGGG

GGGGGCTCCCAGGTGCAGCTGGTGGAGAGCGGCGGCGGCGTGGTGCAGCC

AGGCACCTCCCTGAGGCTGTCTTGTGCAGCAAGCCAGTTCAGATTTGATG

GCTACGGCATGCACTGGGTGCGCCAGGCACCAGGCAAGGGCCTGGAGTGG

GTAGCCTCTATCAGCCACGACGGCATCAAGAAGTACCACGCCGAGAAAGT

GTGGGGCAGGTTCACCATCTCCCGCGATAACTCTAAAAACACACTGTATC

TGCAGATGAACTCCCTGAGGCCCGAGGACACCGCCCTGTACTATTGCGCC

AAGGACCTGCGCGAGGATGAGTGTGAGGAGTGGTGGTCCGACTACTATGA

TTTTGGCAAGCAGCTGCCTTGCGCAAAGAGCAGGGGAGGCCTGGTGGGAA

TCGCCGATAATTGGGGCCAGGGCACCATGGTGACAGTGTCTAGCGGATCC

GGAGAGCTGAAGACCCCTCTGGGCGATACCACACACACATCCCCACGGAG

CCCCGAGCCAAAGTCCTCTGACACCCCACCCCCTAGCCCTAGATCCCCTG

AGCCAAAGAGCTCCGATACACCACCCCCTTCTCCAAGGAGCCCCGAGCCT

AAGTCTAGCGACACCCCACCCCCTTGCCCCCGCTGTCCAGCACCAGAGCT

GCTGGGAGGACCAAGCGTGTTCCTGTTTCCACCCAAGCCTAAGGATACAC

TGATGATCTCTCGCACCCCCGAGGTGACATGCGTGGTGGTGGACGTGAGC

CACGAGGACCCCGAGGTGAAGTTCAACTGGTACGTGGACGGCGTGGAGGT

GCACAATGCCAAGACCAAGCCCAGGGAGGAGCAGTACAACAGCACCTATC

GCGTGGTGTCCGTGCTGACAGTGCTGCACCAGGACTGGCTGAACGGCAAG

GAGTACAAGTGCAAGGTGTCCAATAAGGCCCTGCCTGCCCCAATCGAGAA

-continued

GACAATCAGCAAGGCAAAGGGACAGCCAAGGGAGCCACAGGTGTACACCC
TGCCTCCAAGCCGCGAGGAGATGACCAAGAACCAGGTGTCCCTGACATGT
CTGGTGAAGGGCTTCTATCCTAGCGATATCGCCGTGGAGTGGGAGTCCAA
TGGCCAGCCAGAGAACAATTACAAGACCACACCCCCTGTGCTGGACTCCG
ATGGCTCTTTCTTTCTGTATTCTAAGCTGACCGTGGACAAGAGCCGGTGG
CAGCAGGGCAACGTGTTCAGCTGCTCTGTGCTGCACGAAGCCCTGCACAG
CCATTACACCCAGAAGAGCCTGAGCCTGAGCCCCGGAAAATAGTGAAAGC
TT

3. PentaNAb$_{2.0}$ Reverse VRC26.25-5X-PGT121-5X-N6-5X-35O22-5X-10E8v4_S100cF-His

SEQ ID NO: 83

GAATTCGCCGCCACCATGGGCTGGAGCTGCATCATCCTGTTCCTGGTG
GCAACCGCAACAGGAGTGCACAGCCAGGTGCAGCTGGTGGAGTCCGG
AGGAGGAGTGGTGCAGCCAGGCACCTCTCTGAGGCTGAGCTGTGCAG
CATCCCAGTTCAGATTTGATGGCTACGGAATGCACTGGGTGAGGCAGG
CACCAGGCAAGGGACTGGAGTGGGTGGCCAGCATCTCCCACGACGGC
ATCAAGAAGTACCACGCCGAGAAAGTGTGGGGCAGGTTCACCATCTCT
CGCGATAACAGCAAGAATACACTGTATCTGCAGATGAACAGCCTGAG
GCCCGAGGACACCGCCCTGTACTATTGCGCCAAGGACCTGCGCGAGGA
TGAGTGTGAGGAGTGGTGGTCCGACTACTATGATTTTGGCAAGCAGCT
GCCTTGCGCAAAGAGCAGGGGAGGACTGGTGGGAATCGCCGACAATT
GGGGCCAGGGCACCATGGTGACAGTGAGCAGCGGAGGAGGAGGCTCT
GGAGGAGGAGGCAGCGGA
GGCGGCGGCTCTCAGAGCGTGCTGACCCAGCCACCTTCCGTGTCTGCC
GCACCAGGACAGAAGGTGACCATCAGCTGTTCCGGCAACACATCCAAT
ATCGGCAACAATTTCGTGTCTTGGTACCAGCAGAGGCCTGGAAGAGCA
CCACAGCTGCTGATCTATGAGACAGACAAGAGGCCCTCCGGCATCCCT
GATCGCTTTTCTGCCAGCAAGTCCGGCACCAGCGGCACACTGGCAATC
ACCGGACTGCAGACAGGCGACGAGGCAGATTACTATTGCGCAACCTG
GGCAGCCTCCCTG
TCTAGCGCCAGGGTGTTCGGCACCGGCACAAAAGTGATCGTGCTGGTG
GGAGGAGGAGGCTCCGGCGGCGGGGGCTCTGGCGGCGGCGGCAGCGG
AGGAGGCGGCTCCGGAGGAGGCGGCTCTCAGATGCAGCTGCAGGAGA
GCGGACCAGGACTGGTGAAGCCTTCCGAGACCCTGTCTCTGACATGTT
CTGTGAGCGGCGCCTCCATCTCTGATAGCTACTGGAGCTGGATCAGAC
GGAGCCCTGGCAAGGGCCTGGAGTGGATCGGCTACGTGCACAAGTCT
GGCGATACAAACTATTCCCCATCTCTGAAGAGCCGGGTGAACCTGAGC
CTGGACACCTCCAAGAATCAGGTGAGCCTGTCCCTGGTGGCAGCAACC
GCAGCAGACACAGCGGCAAGTACTATTGCGCCAGAACACTGCACGGCAG
GCGCATCTACGGCATCGTGGCCTTTAACGAGTGGTTCACCTACTTTTAT

-continued

ATGGACGTGTGGGGCAATGGCACCCAGGTGACAGTGTCCTCTGGCGGC
GGCGGCTCTGGCGGAGGAGGCAGCGGAGGAGGAGGCAGCTCCGACAT
CTCTGTGGCACCTGGAGAGACCGCAAGGATCAGCTGTGGAGAGAAGT
CTCTGGGCAGCAGGGCCGTGCAGTGGTACCAGCACAGGGCAGGACAG
GCACCATCCCTGATCATCTATAACAATCAGGACCGGCCATCTGGCATC
CCCGAGAGATTCTCTGGCAGCCCCGATAGCCCTTTTGGCACCACAGCC
ACCCTGACAATCACCTCCGTGGAGGCCGGCGACGAAGCAGATTACTAT
TGCCACATCTGGGACTCCAGAGTGCCAACCAAGTGGGTGTTCGGAGGA
GGAACCACACTGACAGTGCTGGGCGGCGGAGGCTCCGGCGGGGGCGG
CTCTGGAGGCGGCGGCAGCGGAGGGGGCGGCTCCGGCGGCGGCGGCT
CTAGGGCACACCTGGTGCAGAGCGGAACCGCAATGAAGAAGCCTGGC
GCCTCTGTGCGCGTGAGCTGTCAGACATCCGGCTACACCTTCACCGCC
CACATCCTGTTCTGGTTTAGGCAGGCACCAGGAAGAGGACTGGAGTGG
GTGGGCTGGATCAAGCCCCAGTATGGAGCAGTGAACTTCGGAGGA
GGCTTTCGGGACAGAGTGACACTGACCCGGGACGTGTACAGAGAGAT
CGCCTATATGGATATCAGGGGCCTGAAGCCCGACGATACCGCCGTGTA
CTATTGCGCCAGGGACCGCTCCTACGGCGATTCTAGCTGGGCACTGGA
CGCATGGGGACAGGGAACCACAGTGGTGGTGAGCGCCGGAGGCGGGG
GCAGCGGCGGCGGGGGCTCCGGAGGCGGAGGCTCTTACATCCACGTG
ACCCAGTCCCCTTCCTCTCTGTCCGTGTCTATCGGCGATCGCGTGACCA
TCAACTGTCAGACAAGCCAGGGAGTGGGCTCCGACCTGCACTGGTATC
AGCACAAGCCTGGCAGGGCCCCAAAGCTGCTGATCCACCACACAAGC
TCCGTGGAGGATGGAGTGCCAAGCCGCTTCAGCGGCTCCGGATTCCAC
ACCAGCTTTAATCTGACAATCTCCGACCTGCAGGCCGACGATATCGCC
ACCTACTATTGCCAGGTGCTGCAGTTCTTTGGCAGGGGCTCCCGCCTGC
ACATCAAGGGCGGCGGCGGCTCTGGGGGCGGGGGCAGCGGCGGGGGG
GGCTCCGGGGGAGGAGGCTCTGGCGGAGGGGGCAGCCAGGGCCAGCT
GGTGCAGAGCGGAGCAGAGCTGAAGAAGCCAGGAGCCTCTGTGAAGA
TCAGCTGTAAGACATCCGGCTACCGGTTCAACTTTTATCACATCAATTG
GATCAGGCAGACCGCAGGAAGGGGACCAGAGTGGATGGGCTGGATCT
CCCCCTACTCTGGCGATAAGAACCTGGCCCCAGCCTTCCAGGACAGAG
TGATCATGACCACAGATACCGAGGTGCCAGTGACCAGCTTCACCTCCA
CCGGAGCCGCCTACATGGAGATCCGGAATCTGAAGTTCGACGATACAG
GCACCTATTTTTGCGCCAAGGGCCTGCTGAGAGACGGCTCTAGCACAT
GGCTGCCATACCTGTGGGGACAGGGCACCCTGCTGACAGTGTCCTCTG
GAGGAGGAGGCTCCGGGGGCGGCGGCTCTGGAGGAGGAGGCTCTCAA
AGCGTGCTGACCCAGTCCGCCTCTGTGAGCGGCTCCCTGGGCCAGTCT
GTGACCATCAGCTGTACAGGCCCCAACTCCGTGTGCTGTTCTCACAAG
TCTATCAGCTGGTACCAGTGGCCACCAGGAAGGGCACCTACCCTGATC
ATCTATGAGGACAATGAGAGGGCACCAGGAATCAGCCCTCGCTTCTCC
GGCTACAAGTCTTATTGGAGCGCCTACCTGACCATTTCCGACCTGCGC

-continued

CCCGAGGATGAGACCACATACTATTGCTGTAGCTATACCCACAACTCC
GGCTGCGTGTTTGGCACAGGCACCAAGGTGAGCGTGCTGGGAGGAGG
GGGCTCTGGCGGCGGGGGCAGCGGCGGAGGCGGCTCCGGAGGGGGCG
GCTCTGGCGGAGGCGGCAGCGAGGTGCGGCTGGTGGAGAGCGGCGGC
GGCCTGGTGAAGCCAGGCGGCTCTCTGAGACTGTCCTGTTCTGCCAGC
GGCTTCGACTTTGATAATGCCTGGATGACATGGGTGCGGCAGCCTCCT
GGCAAGGGGCTGGAGTGGGTGGGAAGAATCACCGGACCAGGAGAGG
GATGGTCTGTGGACTACGCCGAGAGCGTGAAGGGCCGGTTCACCATCA
GCAGAGATAACACTAAAAATACACTGTATCTGGAGATGAACAATGTG
CGGACCGAGGACACAGGCTACTATTTCTGCGCCAGAACCGGCAAGTAC
TATGATTTCTGGTTTGGCTACCCCCCTGGCGAGGAGTATTTTCAGGACT
GGGGCCAGGGCACCCTGGTCATCGTGAGCAGCGGCGGGGGAGGCTCC
GGCGGGGGGGGCTCTGGAGGAGGGGGCTCTAGCGAGCTGACCCAGGA
CCCCGCCGTGTCCGTGGCCCTGAAGCAGACAGTGACCATCACATGCAG
GGGCGACTCCCTGCGCTCTCACTACGCCAGCTGGTATCAGAAGAAGCC
AGGACAGGCACCCGTGCTGCTGTTCTACGGCAAGAACAATCGGCCTTC
CGGCATCCCAGATAGATTTTCCGGCTCTGCCAGCGGAAACAGGGCCAG
CCTGACCATCACAGGAGCACAGGCAGAGGATGAAGCAGATTACTATT
GTTCCTCTCGGGACAAGTCCGGCTCTAGACTGAGCGTGTTCGGCGGCG
GAACCAAGCTGACAGTGCTGGGATCCGGCCACCACCATCACCATCATT
AGTGAAGCTT

4. PentaNAb$_{3.0}$ 10 E8v4_S100cF-5X-35O22-5X-N6-5X-PGT121-5X-PGDM1400-His

SEQ ID NO: 84

GAATTCGCCG CCACCATGGG ATGGAGCTGT ATTATTCTGT
TTCTGGTCGC TACCGCTACC GGAGTGCATT CTTCTGAACT
GACCCAGGAC CCCGCCGTGA GCGTGGCCCT GAAGCAGACC
GTGACAATCA CCTGCAGGGG CGACAGCCTG CGCTCCCACT
ACGCCAGCTG GTATCAGAAG AAGCCTGGCC AGGCCCCAGT
GCTGCTGTTC TACGGCAAGA ACAATAGGCC CTCCGGCATC
CCTGATCGCT TTTCCGGCTC TGCCAGCGGA AACAGGGCCA
GCCTGACAAT CACCGGAGCA CAGGCAGAGG ACGAGGCAGA
TTACTATTGC AGCTCCCGGG ACAAGTCCGG CTCTAGACTG
AGCGTGTTCG GCGGCGGCAC CAAGCTGACA GTGCTGGGAG
GAGGAGGCAG CGGCGGAGGA GGCTCCGGAG GCGGCGGCTC
TGAGGTGCGG CTGGTGGAGT CTGGAGGAGG CCTGGTGAAG
CCAGGAGGCA GCCTGAGACT GAGCTGTTCC GCCTCTGGCT
TCGACTTTGA TAATGCCTGG ATGACATGGG TGCGGCAGCC
ACCTGGCAAG GGCCTGGAGT GGGTGGGAAG AATCACCGGA
CCAGGAGAGG GATGGTCTGT GGACTACGCC GAGAGCGTGA

-continued

AGGGCCGGTT CACCATCTCC AGAGATAACA CCAAGAATAC
ACTGTATCTG GAGATGAACA ATGTGCGGAC CGAGGACACA
GGCTACTATT TCTGCGCCAG AACCGGCAAG TACTATGATT
TTTGGTTTGG CTACCCACCC GGCGAGGAGT ATTTTCAGGA
CTGGGGCCAG GGCACCCTGG TCATCGTGAG CAGCGGCGGC
GGCGGCAGCG GCGGCGGCGG CTCCGGAGGA GGCGGCTCTG
GAGGAGGAGG CAGCGGGGGA GGGGGCAGCC AGTCCGTGCT
GACCCAGTCT GCCAGCGTGT CCGGCTCTCT GGGACAGAGC
GTGACCATCT CCTGTACAGG CCCCAACAGC GTGTGCTGTA
GCCACAAGAG CATCTCCTGG TACCAGTGGC CTCCAGGAAG
GGCACCTACC CTGATCATCT ATGAGGACAA TGAGCGGGCC
CCAGGCATCT CCCCCAGATT CTCTGGCTAC AAGTCTTATT
GGAGCGCCTA CCTGACAATC AGCGACCTGC GCCCCGAGGA
TGAGACAACA TACTATTGCT GTTCCTATAC CCACAACTCT
GGCTGCGTGT TTGGCACAGG CACCAAGGTG TCCGTGCTGG
GCGGCGGCGG CAGCGGGGGC GGGGGCTCCG GAGGGGGCGG
CTCTCAGGGC CAGCTGGTGC AGAGCGGAGC AGAGCTGAAG
AAGCCTGGAG CCAGCGTGAA GATCTCCTGT AAGACATCTG
GCTACCGGTT CAACTTTTAT CACATCAATT GGATCAGGCA
GACCGCAGGA AGGGGACCAG AGTGGATGGG CTGGATCTCC
CCCTACTCTG GCGATAAGAA CCTGGCCCCA GCCTTCCAGG
ACAGAGTGAT CATGACCACA GATACCGAGG TGCCAGTGAC
CAGCTTCACC TCCACCGGAG CCGCCTACAT GGAGATCAGG
AATCTGAAGT TCGACGATAC AGGCACCTAT TTTTGCGCAA
AGGGCCTGCT GAGGGACGGC TCCTCTACCT GGCTGCCTTA
CCTGTGGGGA CAGGGCACCC TGCTGACAGT GAGCTCCGGC
GGCGGGGGCA GCGGCGGCGG GGGCTCCGGA GGAGGAGGCT
CTGGAGGAGG GGGCAGCGGA GGAGGCGGCT CCTACATCCA
CGTGACCCAG TCCCCATCTA GCCTGTCTGT GAGCATCGGC
GATCGGGTGA CCATCAACTG TCAGACATCT CAGGGCGTGG
GCAGCGACCT GCACTGGTAT CAGCACAAGC CTGGCAGGGC
CCCAAAGCTG CTGATCCACC ACACATCCTC TGTGGAGGAT
GGAGTGCCAA GCCGCTTCTC CGGCTCTGGA TTCCACACCT
CCTTTAATCT GACAATCTCT GACCTGCAGG CCGACGATAT
CGCCACCTAC TATTGCCAGG TGCTGCAGTT CTTTGGCCGG
GGCTCCAGAC TGCACATCAA GGGAGGAGGA GGCTCCGGGG
GCGGAGGCTC TGGCGGCGGC GGCAGCCGGG CCCACCTGGT
GCAGAGCGGC ACCGCCATGA AGAAGCCTGG CGCCAGCGTG
AGAGTGTCCT GTCAGACATC TGGCTACACC TTCACCGCCC
ACATCCTGTT CTGGTTTAGG CAGGCACCAG GAAGAGGCCT
GGAGTGGGTG GGCTGGATCA AGCCCCAGTA TGGAGCAGTG

-continued

AACTTCGGAG GAGGCTTTCG GGACAGAGTG ACACTGACCC
GGGACGTGTA CAGAGAGATC GCCTATATGG ATATCAGGGG
CCTGAAGCCA GACGATACCG CCGTGTACTA TTGCGCCAGG
GACCGCTCCT ACGGCGATAG CTCCTGGGCA CTGGACGCAT
GGGGACAGGG CACCACAGTG GTGGTGAGCG CCGGCGGCGG
AGGCTCCGGC GGCGGGGGCT CTGGAGGAGG CGGCAGCGGA
GGGGGAGGCT CCGGAGGGGG AGGCTCTAGC GACATCTCCG
TGGCCCCTGG CGAGACAGCC AGAATCTCTT GTGGCGAGAA
GTCTCTGGGC AGCAGGGCCG TGCAGTGGTA CCAGCACAGG
GCAGGACAGG CACCATCTCT GATCATCTAT AACAATCAGG
ATAGGCCAAG CGGCATCCCT GAGCGGTTCA GCGGCTCCCC
CGACAGCCCT TTTGGCACCA CAGCCACACT GACCATCACA
TCCGTGGAGG CAGGCGACGA AGCCGATTAC TATTGCCACA
TCTGGGATTC CAGAGTGCCA ACCAAGTGGG TGTTCGGAGG
AGGAACCACA CTGACAGTGC TGGGAGGGGG GGGCTCTGGC
GGCGGGGGCA GCGGGGGAGG AGGCTCCCAG ATGCAGCTGC
AGGAGAGCGG ACCAGGCCTG GTGAAGCCTA GCGAGACACT
GAGCCTGACA TGTTCTGTGA GCGGCGCCTC CATCTCTGAC
AGCTACTGGT CTTGGATCAG ACGGAGCCCC GGCAAGGGCC
TGGAATGGAT CGGCTACGTG CACAAGTCCG GCGATACAAA
CTATTCCCCA TCTCTGAAGT CTCGGGTGAA CCTGTCTCTG
GACACCAGCA AGAATCAGGT GAGCCTGTCC CTGGTGGCAG
CAACCGCAGC AGATAGCGGC AAGTACTATT GCGCCAGAAC
ACTGCACGGC AGGCGCATCT ACGGCATCGT GGCCTTTAAC
GAGTGGTTCA CCTACTTTTA TATGGACGTG TGGGGCAATG
GCACCCAGGT GACAGTGTCC TCTGGCGGGG GCGGCTCCGG
AGGCGGAGGC TCTGGCGGGG GCGGCAGCGG CGGGGGCGGC
TCCGGGGGAG GCGGCTCTGA TTTCGTGCTG ACCCAGTCTC
CACATAGTCT GAGCGTGACA CCCGGCGAAA GCGCATCAAT
TTCTTGTAAA TCATCTCATA GTCTGATCCA CGGCGATAGG
AACAATTACC TGGCCTGGTA CGTGCAGAAG CCAGGCCGCA
GCCCTCAGCT GCTGATCTAC CTGGCAAGCT CCAGGGCATC
CGGAGTGCCA GATCGCTTCT CTGGCAGCGG CTCCGATAAG
GACTTTACCC TGAAGATCTC CCGGGTGGAG ACAGAGGACG
TGGGCACATA CTATTGCATG CAGGGCAGAG AGTCTCCTTG
GACCTTCGGC CAGGGCACAA AGGTGGACAT CAAGGGAGGA
GGAGGCAGCG GCGGAGGAGG CTCCGGCGGC GGCGGCTCTC
AGGCACAGCT GGTGCAGAGC GGACCAGAGG TGAGGAAGCC
AGGCACCTCT GTGAAGGTGA GCTGTAAGGC CCCTGGCAAC
ACCCTGAAGA CATACGATCT GCACTGGGTG CGGTCTGTGC

-continued

CAGGACAGGG CCTGCAGTGG ATGGGATGGA TCAGCCACGA
GGGCGACAAG AAAGTGATCG TGGAGCGGTT TAAGGCCAAG
GTGACAATCG ATTGGGACAG AAGCACCAAT ACAGCCTATC
TGCAGCTGTC CGGCCTGACC TCTGGCGATA CAGCCGTGTA
CTATTGCGCC AAGGGCTCCA AGCACCGGCT GAGAGACTAC
GCCCTGTATG ACGATGACGG CGCCCTGAAT TGGGCAGTGG
ACGTGGACTA TCTGAGTAAT CTGGAGTTTT GGGGGCAGGG
CACCGCAGTG ACAGTGTCTA
GCGGATCCGGACACCACCATCACCATCATTAGTGAAAGCTT

5. PentaNAb$_{3.0}$Reverse PGDM1400-5X-PGT121-5X-N6-5X-35O22-5X-10E8v4S100cF-His

SEQ ID NO: 85

GAATTCGCCG CCACCATGGG CTGGAGCTGC ATCATCCTGT
TCCTGGTGGC AACCGCAACA GGAGTGCACA GCCAGGCACA
GCTGGTGCAG AGCGGACCCG AAGTGAGAAA ACCTGGGACT
AGCGTCAAAG TGTCATGTAA AGCCCCTGGA AATACCCTGA
AGACCTACGA TCTGCACTGG GTGCGGTCCG TGCCTGGACA
GGGCCTGCAG TGGATGGGAT GGATCTCTCA CGAGGGCGAC
AAGAAAGTGA TCGTGGAGCG GTTCAAGGCC AAGGTGACAA
TCGATTGGGA CAGATCCACC AACACAGCCT ACCTGCAGCT
GTCTGGCCTG ACCAGCGGCG ATACAGCCGT GTACTACTGT
GCCAAGGGCT CTAAGCACCG GCTGAGAGAC TACGCCCTGT
ATGACGATGA CGGCGCCCTG AACTGGGCCG TGGATGTGGA
CTATCTGTCC AATCTGGAGT TCTGGGGACA GGGAACCGCA
GTGACAGTGA GCTCCGGAGG AGGAGGCTCC GGCGGCGGAG
GCTCTGGGGG AGGCGGCAGC GATTTTGTGC TGACCCAGTC
TCCACACAGC CTGTCCGTGA CACCCGGCGA GTCTGCCAGC
ATCTCCTGCA AGTCTAGCCA CAGCCTGATC CACGGCGACA
GGAACAATTA CCTGGCCTGG TACGTGCAGA AGCCAGGCCG
CAGCCCTCAG CTGCTGATCT ATCTGGCATC CTCTAGGGCC
TCCGGAGTGC CAGATCGCTT CTCTGGCAGC GGCTCCGATA
AGGACTTTAC CCTGAAGATC AGCCGGGTGG AGACAGAGGA
CGTGGGCACA TACTATTGTA TGCAGGGCCG AGAATCACCT
TGGACATTTG GGCAGGGAAC TAAAGTCGAC ATCAAAGGGG
GGGGGGGCTC CGGCGGCGGG GGCTCTGGCG GCGGCGGCAG
CGGAGGAGGC GGCTCCGGAG GAGGCGGCTC TCAGATGCAG
CTGCAGGAGA GCGGACCAGG ACTGGTGAAG CCTTCCGAGA
CCCTGTCTCT GACATGTTCT GTGAGCGGCG CCTCCATCTC
TGATAGCTAC TGGAGCTGGA TCAGACGGAG CCCTGGCAAG
GGCCTGGAGT GGATCGGCTA CGTGCACAAG TCTGGCGATA
CAAACTATTC CCCATCTCTG AAGAGCCGGG TGAACCTGAG

-continued

CCTGGACACC TCCAAGAATC AGGTGAGCCT GTCCCTGGTG
GCAGCAACCG CAGCAGACAG CGGCAAGTAC TATTGCGCCA
GAACACTGCA CGGCAGGCGC ATCTACGGCA TCGTGGCCTT
TAACGAGTGG TTCACCTACT TTTATATGGA CGTGTGGGGC
AATGGCACCC AGGTGACAGT GTCCTCTGGC GGCGGCGGCT
CTGGCGGAGG AGGCAGCGGA GGAGGAGGCA GCTCCGACAT
CTCTGTGGCA CCTGGAGAGA CCGCAAGGAT CAGCTGTGGA
GAGAAGTCTC TGGGCAGCAG GGCCGTGCAG TGGTACCAGC
ACAGGGCAGG ACAGGCACCA TCCCTGATCA TCTATAACAA
TCAGGACCGG CCATCTGGCA TCCCCGAGAG ATTCTCTGGC
AGCCCCGATA GCCCTTTTGG CACCACAGCC ACCCTGACAA
TCACCTCCGT GGAGGCCGGC GACGAAGCAG ATTACTATTG
CCACATCTGG GACTCCAGAG TGCCAACCAA GTGGGTGTTC
GGAGGAGGAA CCACACTGAC AGTGCTGGGC GGCGGAGGCT
CCGGCGGGGG CGGCTCTGGA GGCGGCGGCA GCGGAGGGGG
CGGCTCCGGC GGCGGCGGCT CTAGGGCACA CCTGGTGCAG
AGCGGAACCG CAATGAAGAA GCCTGGCGCC TCTGTGCGCG
TGAGCTGTCA GACATCCGGC TACACCTTCA CCGCCCACAT
CCTGTTCTGG TTTAGGCAGG CACCAGGAAG AGGACTGGAG
TGGGTGGGCT GGATCAAGCC CCAGTATGGA GCAGTGAACT
TCGGAGGAGG CTTTCGGGAC AGAGTGACAC TGACCCGGGA
CGTGTACAGA GAGATCGCCT ATATGGATAT CAGGGGCCTG
AAGCCCGACG ATACCGCCGT GTACTATTGC GCCAGGGACC
GCTCCTACGG CGATTCTAGC TGGGCACTGG ACGCATGGGG
ACAGGGAACC ACAGTGGTGG TGAGCGCCGG AGGCGGGGGC
AGCGGCGGCG GGGGCTCCGG AGGCGGAGGC TCTTACATCC
ACGTGACCCA GTCCCCTTCC TCTCTGTCCG TGTCTATCGG
CGATCGCGTG ACCATCAACT GTCAGACAAG CCAGGGAGTG
GGCTCCGACC TGCACTGGTA TCAGCACAAG CCTGGCAGGG
CCCCAAAGCT GCTGATCCAC CACACAAGCT CCGTGGAGGA
TGGAGTGCCA AGCCGCTTCA GCGGCTCCGG ATTCCACACC
AGCTTTAATC TGACAATCTC CGACCTGCAG GCCGACGATA
TCGCCACCTA CTATTGCCAG GTGCTGCAGT TCTTTGGCAG
GGGCTCCCGC CTGCACATCA AGGGCGGCGG CGGCTCTGGG
GGCGGGGGCA GCGGCGGGGG GGGCTCCGGG GGAGGAGGCT
CTGGCGGAGG GGGCAGCCAG GGCCAGCTGG TGCAGAGCGG
AGCAGAGCTG AAGAAGCCAG GAGCCTCTGT GAAGATCAGC
TGTAAGACAT CCGGCTACCG GTTCAACTTT TATCACATCA
ATTGGATCAG GCAGACCGCA GGAAGGGGAC CAGAGTGGAT
GGGCTGGATC TCCCCCTACT CTGGCGATAA GAACCTGGCC

-continued

CCAGCCTTCC AGGACAGAGT GATCATGACC ACAGATACCG
AGGTGCCAGT GACCAGCTTC ACCTCCACCG GAGCCGCCTA
CATGGAGATC CGGAATCTGA AGTTCGACGA TACAGGCACC
TATTTTTGCG CCAAGGGCCT GCTGAGAGAC GGCTCTAGCA
CATGGCTGCC ATACCTGTGG GGACAGGGCA CCCTGCTGAC
AGTGTCCTCT GGAGGAGGAG GCTCCGGGGG CGGCGGCTCT
GGAGGAGGAG GCTCTCAAAG CGTGCTGACC CAGTCCGCCT
CTGTGAGCGG CTCCCTGGGC CAGTCTGTGA CCATCAGCTG
TACAGGCCCC AACTCCGTGT GCTGTTCTCA CAAGTCTATC
AGCTGGTACC AGTGGCCACC AGGAAGGGCA CCTACCCTGA
TCATCTATGA GGACAATGAG AGGGCACCAG GAATCAGCCC
TCGCTTCTCC GGCTACAAGT CTTATTGGAG CGCCTACCTG
ACCATTTCCG ACCTGCGCCC CGAGGATGAG ACCACATACT
ATTGCTGTAG CTATACCCAC AACTCCGGCT GCGTGTTTGG
CACAGGCACC AAGGTGAGCG TGCTGGGAGG AGGGGGCTCT
GGCGGCGGGG GCAGCGGCGG AGGCGGCTCC GGAGGGGGCG
GCTCTGGCGG AGGCGGCAGC GAGGTGCGGC TGGTGGAGAG
CGGCGGCGGC CTGGTGAAGC CAGGCGGCTC TCTGAGACTG
TCCTGTTCTG CCAGCGGCTT CGACTTTGAT AATGCCTGGA
TGACATGGGT GCGGCAGCCT CCTGGCAAGG GGCTGGAGTG
GGTGGGAAGA ATCACCGGAC CAGGAGAGGG ATGGTCTGTG
GACTACGCCG AGAGCGTGAA GGGCCGGTTC ACCATCAGCA
GAGATAACAC TAAAAATACA CTGTATCTGG AGATGAACAA
TGTGCGGACC GAGGACACAG GCTACTATTT CTGCGCCAGA
ACCGGCAAGT ACTATGATTT CTGGTTTGGC TACCCCCCTG
GCGAGGAGTA TTTTCAGGAC TGGGGCCAGG GCACCCTGGT
CATCGTGAGC AGCGGCGGGG GAGGCTCCGG CGGGGGGGGC
TCTGGAGGAG GGGGCTCTAG CGAGCTGACC CAGGACCCCG
CCGTGTCCGT GGCCCTGAAG CAGACAGTGA CCATCACATG
CAGGGGCGAC TCCCTGCGCT CTCACTACGC CAGCTGGTAT
CAGAAGAAGC CAGGACAGGC ACCCGTGCTG CTGTTCTACG
GCAAGAACAA TCGGCCTTCC GGCATCCCAG ATAGATTTTC
CGGCTCTGCC AGCGGAAACA GGGCCAGCCT GACCATCACA
GGAGCACAGG CAGAGGATGA AGCAGATTAC TATTGTTCCT
CTCGGGACAA GTCCGGCTCT AGACTGAGCG TGTTCGGCGG
CGGAACCAAG CTGACAGTGC
TGGGATCCGGACACCACCATCACCATCATTAGTGAAAGCTT

6. PentaNAb4.0 10E8v4 V5R_S100cF-5X-35O22-5X-N6-5X-PGT121-5X-PGDM1400-His

SEQ ID NO: 86 gaattcgccgccaccatgggatggagctgtattattctgtttctggtcgctaccgctacc
ggagtgcattcttctgaactgacccaggaccccgccgtgagcgtggccctgaagcagacc
gtgacaatcacctgcaggggcgacagcctgcgctcccactacgccagctggtatcagaag
aagcctggccaggccccagtgctgctgttctacggcaagaacaataggccctccggcatc
cctgatcgcttttccggctctgccagcggaaacagggccagcctgacaatcaccggagca
caggcagaggacgaggcagattactattgcagctcccgggacaagtccggctctagactg
agcgtgttcggcggcggcaccaagctgacagtgctgggaggaggaggcagcggcggagga
ggctccggaggcggcggctctgaggtgcggctgCGGgagtctggaggaggcctggtgaag
ccaggaggcagcctgagactgagctgttccgcctctggcttcgactttgataatgcctgg
atgacatgggtgcggcagccacctggcaagggcctggagtgggtgggaagaatcaccgga
ccaggagagggatggtctgtggactacgccgagagcgtgaagggccggttcaccatctcc
agagataacaccaagaatacactgtatctggagatgaacaatgtgcggaccgaggacaca
ggctactatttctgcgccagaaccggcaagtactatgattttggtttggctacccaccc
ggcgaggagtattttcaggactggggccagggcaccctggtcatcgtgagcagcggcggc
ggcggcagcggcggcggcggctccggaggaggcggctctggaggaggaggcagcggggga
gggggcagccagtccgtgctgacccagtctgccagcgtgtccggctctctgggacagagc
gtgaccatctcctgtacaggccccaacagcgtgtgctgtagccacaagagcatctcctgg
taccagtggcctccaggaagggcacctaccctgatcatctatgaggacaatgagcgggcc
ccaggcatctcccccagattctctggctacaagtcttattggagcgcctacctgacaatc
agcgacctgcgccccgaggatgagacaacatactattgctgttcctatacccacaactct
ggctgcgtgtttggcacaggcaccaaggtgtccgtgctgggcggcggcggcagcgggggc
gggggctccggagggggcggctctcagggccagctggtgcagagcggagcagagctgaag
aagcctggagccagcgtgaagatctcctgtaagacatctggcTATcggttcaacttttat
cacatcaattggatcaggcagaccgcaggaaggggaccagagtggatgggctggatctcc
ccctactctggcgataagaacctggccccagccttccaggacagagtgatcatgaccaca
gataccgaggtgccagtgaccagcttcacctccaccggagccgcctacatggagatcagg
aatctgaagttcgacgatacaggcacctatttttgcgcaaagggcctgctgagggacggc
tcctctacctggctgccttacctgtggggacagggcaccctgctgacagtgagctccggc
ggcgggggcagcggcggcgggggctccggaggaggaggctctggaggagggggcagcgga
ggaggcggctcctacatccacgtgacccagtccccatctagcctgtctgtgagcatcggc
gatcgggtgaccatcaactgtcagacatctcagggcgtgggcagcgacctgcactggtat
cagcacaagcctggcagggccccaaagctgctgatccaccacacatcctctgtggaggat
ggagtgccaagccgcttctccggctctggattccacacctcctttaatctgacaatctct
gacctgcaggccgacgatatcgccacctactattgccaggtgctgcagttctttggccgg
ggctccagactgcacatcaagggaggaggaggctccgggggcggaggctctggcggcggc
ggcagccgggcccacctggtgcagagcggcaccgccatgaagaagcctggcgccagcgtg
agagtgtcctgtcagacatctggctacaccttcaccgcccacatcctgttctggtttagg
caggcaccaggaagaggcctggagtgggtgggctggatcaagccccagtatggagcagtg
aacttcggaggaggctttcgggacagagtgacactgacccgggacgtgtacagagagatc -continued gcctatatggatatcaggggcctgaagccagacgataccgccgtgtactattgcgccagg
gaccgctcctacggcgatagctcctgggcactggacgcatggggacagggcaccacagtg
gtggtgagcgccggcggcggaggctccggcggcgggggctctggaggaggcggcagcgga
gggggaggctccggagggggaggctctagcgacatctccgtggcccctggcgagacagcc
agaatctcttgtggcgagaagtctctgggcagcagggccgtgcagtggtaccagcacagg
gcaggacaggcaccatctctgatcatctataacaatcaggataggccaagcggcatccct
gagcggttcagcggctcccccgacagcccttttggcaccacagccacactgaccatcaca
tccgtggaggcaggcgacgaagccgattactattgccacatctgggattccagagtgcca
accaagtgggtgttcggaggaggaaccacactgacagtgctgggagggggggctctggc
ggcgggggcagcgggggaggaggctcccagatgcagctgcaggagagcggaccaggcctg
gtgaagcctagcgagacactgagcctgacatgttctgtgagcggcgcctccatctctgac
agctactggtcttggatcagacggagccccggcaagggcctggaatggatcggctacgtg
cacaagtccggcgatacaaactattccccatctctgaagtctcgggtgaacctgtctctg
gacaccagcaagaatcaggtgagcctgtccctggtggcagcaaccgcagcagatagcggc
aagtactattgcgccagaacactgcacggcaggcgcatctacggcatcgtggcctttaac
gagtggttcacctacttttatatggacgtgtggggcaatggcacccaggtgacagtgtcc
tctggcgggggcggctccggaggcggaggctctggcgggggcggcagcggcgggggcggc
tccgggggaggcggctctgatttcgtgctgacccagtctccacatagtctgagcgtgaca
cccggcgaaagcgcatcaatttcttgtaaatcatctcatagtctgatccacggcgatagg
aacaattacctggcctggtacgtgcagaagccaggccgcagccctcagctgctgatctac
ctggcaagctccagggcatccggagtgccagatcgcttctctggcagcggctccgataag
gactttaccctgaagatctcccgggtggagacagaggacgtgggcacatactattgcatg
cagggcagagagtctccttggaccttcggccagggcacaaaggtggacatcaagggagga
ggaggcagcggcggaggaggctccggcggcggcggctctcaggcacagctggtgcagagc
ggaccagaggtgaggaagccaggcacctctgtgaaggtgagctgtaaggcccctggcaac
accctgaagacatacgatctgcactgggtgcggtctgtgccaggacagggcctgcagtgg
atgggatggatcagccacgagggcgacaagaaagtgatcgtggagcggtttaaggccaag
gtgacaatcgattgggacagaagcaccaatacagcctatctgcagctgtccggcctgacc
tctggcgatacagccgtgtactattgcgccaagggctccaagcaccggctgagagactac
gccctgtatgacgatgacggcgccctgaattgggcagtggacgtggactatctgagtaat
ctggagttttgggggcagggcaccgcagtgacagtgtctagcggatccGGACACCACCATCACCAT
CATTAGTGAAAGCTT 7. PentaNAb$_{4.0}$ Reverse PGDM1400-5X-PGT121-5X-N6-5X-35O22-5X-10E8v4 V5R_S100cF-His SEQ ID NO: 87
gaattcgccgccaccatgggctggagctgcatcatcctgttcctggtggcaaccgcaaca
ggagtgcacagccaggcacagctggtgcagagcggacccgaagtgagaaaacctgggact
agcgtcaaagtgtcatgtaaagcccctggaaataccctgaagacctacgatctgcactgg
gtgcggtccgtgcctggacagggcctgcagtggatgggatggatctctcacgagggcgac
aagaaagtgatcgtggagcggttcaaggccaaggtgacaatcgattgggacagatccacc -continued aacacagcctacctgcagctgtctggcctgaccagcggcgatacagccgtgtactactgt gccaagggctctaagcaccggctgagagactacgccctgtatgacgatgacggcgccctg aactgggccgtggatgtggactatctgtccaatctggagttctggggacagggaaccgca gtgacagtgagctccggaggaggaggctccggcggcggaggctctgggggaggcggcagc gattttgtgctgacccagtctccacacagcctgtccgtgacacccggcgagtctgccagc atctcctgcaagtctagccacagcctgatccacggcgacaggaacaattacctggcctgg tacgtgcagaagccaggccgcagccctcagctgctgatctatctggcatcctctagggcc tccggagtgccagatcgcttctctggcagcggctccgataaggactttaccctgaagatc agccgggtggagacagaggacgtgggcacatactattgtatgcagggccgagaatcacct tggacatttgggcagggaactaaaGTTgacatcaaaggggggggggggctccggcggcggg ggctctggcggcggcggcagcggaggaggcggctccggaggaggcggctctcagatgcag ctgcaggagagcggaccaggactggtgaagccttccgagaccctgtctctgacatgttct gtgagcggcgcctccatctctgatagctactggagctggatcagacggagccctggcaag ggcctggagtggatcggctacgtgcacaagtctggcgatacaaactattccccatctctg aagagccgggtgaacctgagcctggacacctccaagaatcaggtgagcctgtccctggtg gcagcaaccgcagcagacagcggcaagtactattgcgccagaacactgcacggcaggcgc atctacggcatcgtggcctttaacgagtggttcacctacttttatatggacgtgtggggc aatggcacccaggtgacagtgtcctctggcggcggcggctctggcggaggaggcagcgga ggaggaggcagctccgacatctctgtggcacctggagagaccgcaaggatcagctgtgga gagaagtctctgggcagcagggccgtgcagtggtaccagcacagggcaggacaggcacca tccctgatcatctataacaatcaggaccggccatctggcatccccgagagattctctggc agccccgatagcccttttggcaccacagccaccctgacaatcacctccgtggaggccggc gacgaagcagattactattgccacatctgggactccagagtgccaaccaagtgggtgttc ggaggaggaaccacactgacagtgctgggcggcggaggctccggcgggggcggctctgga ggcggcggcagcggagggggcggctccggcggcggcggctctagggcacacctggtgcag agcggaaccgcaatgaagaagcctggcgcctctgtgcgcgtgagctgtcagacatccggc tacaccttcaccgcccacatcctgttctggtttaggcaggcaccaggaagaggactggag tgggtgggctggatcaagccccagtatggagcagtgaacttcggaggaggctttcgggac agagtgacactgacccgggacgtgtacagagagatcgcctatatggatatcaggggcctg aagcccgacgataccgccgtgtactattgcgccagggaccgctcctacggcgattctagc tgggcactggacgcatggggacagggaaccacagtggtggtgagcgccggaggcgggggc agcggcggcgggggctccggaggcggaggctcttacatccacgtgacccagtccccttcc tctctgtccgtgtctatcggcgatcgcgtgaccatcaactgtcagacaagccagggagtg ggctccgacctgcactggtatcagcacaagcctggcagggccccaaagctgctgatccac cacacaagctccgtggaggatggagtgccaagccgcttcagcggctccggattccacacc agctttaatctgacaatctccgacctgcaggccgacgatatcgccacctactattgccag gtgctgcagttctttggcaggggctcccgcctgcacatcaagggcggcggcggctctggg ggcgggggcagcggcgggggggggctccgggggaggaggctctggcggagggggcagccag ggccagctggtgcagagcggagcagagctgaagaagccaggagcctctgtgaagatcagc tgtaagacatccggcTATcggttcaacttttatcacatcaattggatcaggcagaccgca -continued ggaaggggaccagagtggatgggctggatctcccccctactctggcgataagaacctggcc ccagccttccaggacagagtgatcatgaccacagataccgaggtgccagtgaccagcttc acctccaccggagccgcctacatggagatccggaatctgaagttcgacgatacaggcacc tatttttgcgccaagggcctgctgagagacggctctagcacatggctgccatacctgtgg ggacagggcaccctgctgacagtgtcctctggaggaggaggctccgggggcggcggctct ggaggaggaggctctcaaagcgtgctgacccagtccgcctctgtgagcggctccctgggc cagtctgtgaccatcagctgtacaggccccaactccgtgtgctgttctcacaagtctatc agctggtaccagtggccaccaggaagggcacctaccctgatcatctatgaggacaatgag agggcaccaggaatcagccctcgcttctccggctacaagtcttattggagcgcctacctg accatttccgacctgcgccccgaggatgagaccacatactattgctgtagctatacccac aactccggctgcgtgtttggcacaggcaccaaggtgagcgtgctgggaggagggggctct ggcggcgggggcagcggcggaggcggctccggagggggcggctctggcggaggcggcagc gaggtgcggctgCGGgagagcggcggcggcctggtgaagccaggcggctctctgagactg tcctgttctgccagcggcttcgactttgataatgcctggatgacatgggtgcggcagcct cctggcaaggggctggagtgggtgggaagaatcaccggaccaggagagggatggtctgtg gactacgccgagagcgtgaagggccggttcaccatcagcagagataacactaaaaataca ctgtatctggagatgaacaatgtgcggaccgaggacacaggctactatttctgcgccaga accggcaagtactatgatttctggtttggctacccccctggcgaggagtattttcaggac tggggccagggcaccctggtcatcgtgagcagcggcgggggaggctccggcgggggggc tctggaggagggggctctagcgagctgacccaggaccccgccgtgtccgtggccctgaag cagacagtgaccatcacatgcaggggcgactccctgcgctctcactacgccagctggtat cagaagaagccaggacaggcacccgtgctgctgttctacggcaagaacaatcggccttcc ggcatcccagatagattttccggctctgccagcggaaacagggccagcctgaccatcaca ggagcacaggcagaggatgaagcagattactattgttcctctcgggacaagtccggctct agactgagcgtgttcggcggcggaaccaagctgacagtgctgggatccGGACACCACCATCACCA

TCATTAGTGAAAGCTT

8. PentaNAb$_{4.0}$ Reverse PGDM1400-5X-PGT121-5X-N6-5X-35O22-5X-10E8v4 V5R S100cFvVH-fused to IgG1 LS HC with His Tag

SEQ ID NO: 88

SEQ ID NO: 88

ATGGGCTGGAGCTGCATCATCCTGTTCCTGGTGGCAACCGCAACAGGA

GTGCACAGCCAGGCACAGCTGGTGCAGAGCGGACCCGAAGTGAGAAA

ACCTGGGACTAGCGTCAAAGTGTCATGTAAAGCCCCTGGAAATACCCT

GAAGACCTACGATCTGCACTGGGTGCGGTCCGTGCCTGGACAGGGCCT

GCAGTGGATGGGATGGATCTCTCACGAGGGCGACAAGAAAGTGATCG

TGGAGCGGTTCAAGGCCAAGGTGACAATCGATTGGGACAGATCCACC

AACACAGCCTACCTGCAGCTGTCTGGCCTGACCAGCGGCGATACAGCC

GTGTACTACTGTGCCAAGGGCTCTAAGCACCGGCTGAGAGACTACGCC

CTGTATGACGATGACGGCGCCCTGAACTGGGCCGTGGATGTGGACTAT

CTGTCCAATCTGGAGTTCTGGGGACAGGGAACCGCAGTGACAGTGAGC

-continued

TCCGGAGGAGGAGGCTCCGGCGGCGGAGGCTCTGGGGGAGGCGGCAG

CGATTTTGTGCTGACCCAGTCTCCACACAGCCTGTCCGTGACACCCGG

CGAGTCTGCCAGCATCTCCTGCAAGTCTAGCCACAGCCTGATCCACGG

CGACAGGAACAATTACCTGGCCTGGTACGTGCAGAAGCCAGGCCGCA

GCCCTCAGCTGCTGATCTATCTGGCATCCTCTAGGGCCTCCGGAGTGCC

AGATCGCTTCTCTGGCAGCGGCTCCGATAAGGACTTTACCCTGAAGAT

CAGCCGGGTGGAGACAGAGGACGTGGGCACATACTATTGTATGCAGG

GCCGAGAATCACCTTGGACATTTGGGCAGGGAACTAAAGTTGACATCA

AAGGGGGGGGGGGCTCCGGCGGCGGGGGCTCTGGCGGCGGCGGCAGC

GGAGGAGGCGGCTCCGGAGGAGGCGGCTCTCAGATGCAGCTGCAGGA

GAGCGGACCAGGACTGGTGAAGCCTTCCGAGACCCTGTCTCTGACATG

TTCTGTGAGCGGCGCCTCCATCTCTGATAGCTACTGGAGCTGGATCAG

ACGGAGCCCTGGCAAGGGCCTGGAGTGGATCGGCTACGTGCACAAGT

-continued

CTGGCGATACAAACTATTCCCCATCTCTGAAGAGCCGGGTGAACCTGA

GCCTGGACACCTCCAAGAATCAGGTGAGCCTGTCCCTGGTGGCAGCAA

CCGCAGCAGACAGCGGCAAGTACTATTGCGCCAGAACACTGCACGGC

AGGCGCATCTACGGCATCGTGGCCTTTAACGAGTGGTTCACCTACTTTT

ATATGGACGTGTGGGGCAATGGCACCCAGGTGACAGTGTCCTCTGGCG

GCGGCGGCTCTGGCGGAGGAGGCAGCGGAGGAGGAGGCAGCTCCGAC

ATCTCTGTGGCACCTGGAGAGACCGCAAGGATCAGCTGTGGA

GAGAAGTCTCTGGGCAGCAGGGCCGTGCAGTGGTACCAGCACAGGGC

AGGACAGGCACCATCCCTGATCATCTATAACAATCAGGACCGGCCATC

TGGCATCCCCGAGAGATTCTCTGGCAGCCCCGATAGCCCTTTTGGCAC

CACAGCCACCCTGACAATCACCTCCGTGGAGGCCGGCGACGAAGCAG

ATTACTATTGCCACATCTGGGACTCCAGAGTGCCAACCAAGTGGGTGT

TCGGAGGAGGAACCACACTGACAGTGCTGGGCGGCGGAGGCTCCGGC

GGGGGCGGCTCTGGAGGCGGCGGCAGCGGAGGGGGCGGCTCCGGCGG

CGGCGGCTCTAGGGCACACCTGGTGCAGAGCGGAACCGCAATGAAGA

AGCCTGGCGCCTCTGTGCGCGTGAGCTGTCAGACATCCGGCTACACCT

TCACCGCCCACATCCTGTTCTGGTTTAGGCAGGCACCAGGAAGAGGAC

TGGAGTGGGTGGGCTGGATCAAGCCCCAGTATGGAGCAGTGAACTTCG

GAGGAGGCTTTCGGGACAGAGTGACACTGACCCGGGACGTGTACAGA

GAGATCGCCTATATGGATATCAGGGGCCTGAAGCCCGACGATACCGCC

GTGTACTATTGCGCCAGGGACCGCTCCTACGGCGATTCTAGCTGGGCA

CTGGACGCATGGGGACAGGGAACCACAGTGGTGGTGAGCGCCGGAGG

CGGGGGCAGCGGCGGCGGGGGCTCCGGAGGCGGAGGCTCTTACATCC

ACGTGACCCAGTCCCCTTCCTCTCTGTCCGTGTCTATCGGCGATCGCGT

GACCATCAACTGTCAGACAAGCCAGGGAGTG

GGCTCCGACCTGCACTGGTATCAGCACAAGCCTGGCAGGGCCCCAAAG

CTGCTGATCCACCACACAAGCTCCGTGGAGGATGGAGTGCCAAGCCGC

TTCAGCGGCTCCGGATTCCACACCAGCTTTAATCTGACAATCTCCGACC

TGCAGGCCGACGATATCGCCACCTACTATTGCCAGGTGCTGCAGTTCT

TTGGCAGGGGCTCCCGCCTGCACATCAAGGGCGGCGGCGGCTCTGGGG

GCGGGGGCAGCGGCGGGGGGGGCTCCGGGGGAGGAGGCTCTGGCGGA

GGGGGCAGCCAGGGCCAGCTGGTGCAGAGCGGAGCAGAGCTGAAGAA

GCCAGGAGCCTCTGTGAAGATCAGCTGTAAGACATCCGGCTATCGGTT

CAACTTTTATCACATCAATTGGATCAGGCAGACCGCAGGAAGGGGACC

AGAGTGGATGGGCTGGATCTCCCCCTACTCTGGCGATAAGAACCTGGC

CCCAGCCTTCCAGGACAGAGTGATCATGACCACAGATACCGAGGTGCC

AGTGACCAGCTTCACCTCCACCGGAGCCGCCTACATGGAGATCCGGAA

TCTGAAGTTCGACGATACAGGCACCTATTTTTGCGCCAAGGGCCTGCT

GAGAGACGGCTCTAGCACATGGCTGCCATACCTGTGGGGACAGGGCA

CCCTGCTGACAGTGTCCTCTGGAGGAGGAGGCTCCGGGGGCGGCGGCT

CTGGAGGAGGAGGCTCTCAAAGCGTGCTGACCCAGTCCGCCTCTGTGA

-continued

GCGGCTCCCTGGGCCAGTCTGTGACCATCAGCTGTACAGGCCCCAACT

CCGTGTGCTGTTCTCACAAGTCTATCAGCTGGTACCAGTGGCCACCAG

GAAGGGCACCTACCCTGATCATCTATGAGGACAATGAGAGGGCACCA

GGAATCAGCCCTCGCTTCTCCGGCTACAAGTCTTATTGGAGCGCCTAC

CTGACCATTTCCGACCTGCGCCCCGAGGATGAGACCACATACTATTGC

TGTAGCTATACCCACAACTCCGGCTGCGTGTTTGGCACAGGCACCAAG

GTGAGCGTGCTGGGAGGAGGGGGCTCTGGCGGCGGGGGCAGCGGCGG

AGGCGGCTCCGGAGGGGGCGGCTCTGGCGGAGGCGGCAGCGAGGTGC

GGCTGCGGGAGAGCGGCGGCGGCCTGGTGAAGCCAGGCGGCTCTCTG

AGACTGTCCTGTTCTGCCAGCGGCTTCGACTTTGATAATGCCTGGATGA

CATGGGTGCGGCAGCCTCCTGGCAAGGGGCTGGAGTGGGTGGGAAGA

ATCACCGGACCAGGAGAGGGATGGTCTGTGGACTACGCCGAGAGCGT

GAAGGGCCGGTTCACCATCAGCAGAGATAACACTAAAAATACACTGT

ATCTGGAGATGAACAATGTGCGGACCGAGGACACAGGCTACTATTTCT

GCGCCAGA

ACCGGCAAGTACTATGATTTCTGGTTTGGCTACCCCCCTGGCGAGGAG

TATTTTCAGGACTGGGGCCAGGGCACCCTGGTCATCGTGAGCAGCGCG

TCGACCAAGGGCCCATCGGTCTTCCCCCTGGCACCCTCCTCCAAGAGC

ACCTCTGGGGGCACAGCGGCCCTGGGCTGCCTGGTCAAGGACTACTTC

CCCGAACCTGTGACGGTGTCGTGGAACTCAGGCGCCCTGACCAGCGGC

GTGCACACCTTCCCGGCTGTCCTACAGTCCTCAGGACTCTACTCCCTCA

GCAGCGTGGTGACCGTGCCCTCCAGCAGCTTGGGCACCCAGACCTACA

TCTGCAACGTGAATCACAAGCCCAGCAACACCAAGGTGGACAAGAAA

GTTGAGCCCAAATCTTGTGACAAAACTCACACATGCCCACCGTGCCCA

GCACCTGAACTCCTGGGGGGACCGTCAGTCTTCCTCTTCCCCCCAAAA

CCCAAGGACACCCTCATGATCTCCCGGACCCCTGAGGTCACATGCGTG

GTGGTGGACGTGAGCCACGAAGACCCTGAGGTCAAGTTCAACTGGTAC

GTGGACGGCGTGGAGGTGCATAATGCCAAGACAAAGCCGCGGGAGGA

GCAGTACAACAGCACGTACCGTGTGGTCAGCGTCCTCACCGTCCTGCA

CCAGGACTGGCTGAATGGCAAGGAGTACAAGTGCAAGGTCTCCAACA

AAGCCCTCCCAGCCCCCATCGAGAAAACCATCTCCAAAGCCAAAGGG

CAGCCCCGAGAACCACAGGTGTACACCCTGCCCCCATCCCGGGAGGA

GATGACCAAGAACCAGGTCAGCCTGACCTGCCTGGTCAAAGGCTTCTA

TCCCAGCGACATCGCCGTGGAGTGGGAGAGCAATGGGCAGCCGGAGA

ACAACTACAAGACCACGCCTCCCGTGCTGGACTCCGACGGCTCCTTCT

TCCTCTACAGCAAGCTCACCGTGGACAAGAGCAGGTGGCAGCAGGGG

AACGTCTTCTCATGCTCCGTGCTGCATGAGGCTCTGCACAGCCACTAC

ACGCAGAAGAGCCTCTCCCTGTCTCCGGGTAAATGA

9. PentaNAb$_{4.0}$ Reverse PGDM1400-5X-PGT121-5X-N6-5X-35O22-5X-10E8v4 V5R S100cF VH-VL-fused to IgG1 LS FC with His Tag

SEQ ID NO: 89 gaattcgccgccaccatgggctggagctgcatcatcctgttcctggtggcaaccgcaaca ggagtgcacagccaggcacagctggtgcagagcggacccgaagtgagaaaacctgggact agcgtcaaagtgtcatgtaaagcccctggaaataccctgaagacctacgatctgcactgg gtgcggtccgtgcctggacagggcctgcagtggatgggatggatctctcacgagggcgac aagaaagtgatcgtggagcggttcaaggccaaggtgacaatcgattgggacagatccacc aacacagcctacctgcagctgtctggcctgaccagcggcgatacagccgtgtactactgt gccaagggctctaagcaccggctgagagactacgccctgtatgacgatgacggcgccctg aactgggccgtggatgtggactatctgtccaatctggagttctggggacagggaaccgca gtgacagtgagctccggaggaggaggctccggcggcggaggctctgggggaggcggcagc gattttgtgctgacccagtctccacacagcctgtccgtgacacccggcgagtctgccagc atctcctgcaagtctagccacagcctgatccacggcgacaggaacaattacctggcctgg tacgtgcagaagccaggccgcagccctcagctgctgatctatctggcatcctctagggcc tccggagtgccagatcgcttctctggcagcggctccgataaggactttaccctgaagatc agccgggtggagacagaggacgtgggcacatactattgtatgcagggccgagaatcacct tggacatttgggcagggaactaaaGTTgacatcaaaggggggggggggctccggcggcggg ggctctggcggcggcggcagcggaggaggcggctccggaggaggcggctctcagatgcag ctgcaggagagcggaccaggactggtgaagccttccgagaccctgtctctgacatgttct gtgagcggcgcctccatctctgatagctactggagctggatcagacggagccctggcaag ggcctggagtggatcggctacgtgcacaagtctggcgatacaaactattccccatctctg aagagccgggtgaacctgagcctggacacctccaagaatcaggtgagcctgtccctggtg gcagcaaccgcagcagacagcggcaagtactattgcgccagaacactgcacggcaggcgc atctacggcatcgtggcctttaacgagtggttcacctacttttatatggacgtgtggggc aatggcacccaggtgacagtgtcctctggcggcggcggctctggcggaggaggcagcgga ggaggaggcagctccgacatctctgtggcacctggagagaccgcaaggatcagctgtgga gagaagtctctgggcagcagggccgtgcagtggtaccagcacagggcaggacaggcacca tccctgatcatctataacaatcaggaccggccatctggcatccccgagagattctctggc agccccgatagcccttttggcaccacagccaccctgacaatcacctccgtggaggccggc gacgaagcagattactattgccacatctgggactccagagtgccaaccaagtgggtgttc ggaggaggaaccacactgacagtgctgggcggcggaggctccggcgggggcggctctgga ggcggcggcagcggagggggcggctccggcggcggcggctctagggcacacctggtgcag agcggaaccgcaatgaagaagcctggcgcctctgtgcgcgtgagctgtcagacatccggc tacaccttcaccgcccacatcctgttctggtttaggcaggcaccaggaagaggactggag tgggtgggctggatcaagccccagtatggagcagtgaacttcggaggaggattcgggac agagtgacactgacccgggacgtgtacagagagatcgcctatatggatatcaggggcctg aagcccgacgataccgccgtgtactattgcgccagggaccgctcctacggcgattctagc tgggcactggacgcatggggacagggaaccacagtggtggtgagcgccggaggcgggggc agcggcggcgggggctccggaggcggaggctcttacatccacgtgacccagtccccttcc tctctgtccgtgtctatcggcgatcgcgtgaccatcaactgtcagacaagccagggagtg ggctccgacctgcactggtatcagcacaagcctggcagggccccaaagctgctgatccac cacacaagctccgtggaggatggagtgccaagccgcttcagcggctccggattccacacc -continued

```
agctttaatctgacaatctccgacctgcaggccgacgatatcgccacctactattgccag
gtgctgcagttctttggcaggggctcccgcctgcacatcaagggcggcggcggctctggg
ggcgggggcagcggcgggggggggctccgggggaggaggctctggcggagggggcagccag
ggccagctggtgcagagcggagcagagctgaagaagccaggagcctctgtgaagatcagc
tgtaagacatccggcTATcggttcaacttttatcacatcaattggatcaggcagaccgca
ggaaggggaccagagtggatgggctggatctcccccctactctggcgataagaacctggcc
ccagccttccaggacagagtgatcatgaccacagataccgaggtgccagtgaccagcttc
acctccaccggagccgcctacatggagatccggaatctgaagttcgacgatacaggcacc
tatttttgcgccaagggcctgctgagagacggctctagcacatggctgccatacctgtgg
ggacagggcaccctgctgacagtgtcctctggaggaggaggctccgggggcggcggctct
ggaggaggaggctctcaaagcgtgctgacccagtccgcctctgtgagcggctccctgggc
cagtctgtgaccatcagctgtacaggccccaactccgtgtgctgttctcacaagtctatc
agctggtaccagtggccaccaggaagggcacctaccctgatcatctatgaggacaatgag
agggcaccaggaatcagccctcgcttctccggctacaagtcttattggagcgcctacctg
accatttccgacctgcgccccgaggatgagaccacatactattgctgtagctatacccac
aactccggctgcgtgtttggcacaggcaccaaggtgagcgtgctgggaggagggggctct
ggcggcgggggcagcggcggaggcggctccggagggggcggctctggcggaggcggcagc
gaggtgcggctgCGGgagagcggcggcggcctggtgaagccaggcggctctctgagactg
tcctgttctgccagcggcttcgactttgataatgcctggatgacatgggtgcggcagcct
cctggcaaggggctggagtgggtgggaagaatcaccggaccaggagagggatggtctgtg
gactacgccgagagcgtgaagggccggttcaccatcagcagagataacactaaaaataca
ctgtatctggagatgaacaatgtgcggaccgaggacacaggctactatttctgcgccaga
accggcaagtactatgatttctggtttggctacccccctggcgaggagtattttcaggac
tggggccagggcaccctggtcatcgtgagcagcggcgggggaggctccggcggggggggc
tctggaggagggggctctagcgagctgacccaggaccccgccgtgtccgtggccctgaag
cagacagtgaccatcacatgcaggggcgactccctgcgctctcactacgccagctggtat
cagaagaagccaggacaggcacccgtgctgctgttctacggcaagaacaatcggccttcc
ggcatcccagatagattttccggctctgccagcggaaacagggccagcctgaccatcaca
ggagcacaggcagaggatgaagcagattactattgttcctctcgggacaagtccggctct
agactgagcgtgttcggcggcggaaccaagctgacagtgctgggatccCCCAAATCTTGTGACAA
AACTCACACATGCCCACCGTGCCCAGCACCTGAACTCCTGGGGGGACC
GTCAGTCTTCCTCTTCCCCCCAAAACCCAAGGACACCCTCATGATCTCC
CGGACCCCTGAGGTCACATGCGTGGTGGTGGACGTGAGCCACGAAGA
CCCTGAGGTCAAGTTCAACTGGTACGTGGACGGCGTGGAGGTGCATAA
TGCCAAGACAAAGCCGCGGGAGGAGCAGTACAACAGCACGTACCGTG
TGGTCAGCGTCCTCACCGTCCTGCACCAGGACTGGCTGAATGGCAAGG
AGTACAAGTGCAAGGTCTCCAACAAAGCCCTCCCAGCCCCCATCGAGA
AAACCATCTCCAAAGCCAAAGGGCAGCCCCGAGAACCACAGGTGTAC
ACCCTGCCCCCATCCCGGGAGGAGATGACCAAGAACCAGGTCAGCCT
GACCTGCCTGGTCAAAGGCTTCTATCCCAGCGACATCGCCGTGGAGTG
GGAGAGCAATGGGCAGCCGGAGAACAACTACAAGACCACGCCTCCCG
```

-continued

```
TGCTGGACTCCGACGGCTCCTTCTTCCTCTACAGCAAGCTCACCGTGGA
CAAGAGCAGGTGGCAGCAGGGGAACGTCTTCTCATGCTCCGTGCTGCA
TGAGGCTCTGCACAGCCACTACACGCAGAAGAGCCTCTCCCTGTCTCC
GGGTAAATGA
```

Methods for producing antibodies, such as those disclosed herein, are known in the art. For example, DNA molecules encoding light chain variable regions and/or heavy chain variable regions can be chemically synthesized using the sequence information provided herein. Synthetic DNA molecules can be ligated to other appropriate nucleotide sequences, including, e.g., expression control sequences, to produce conventional gene expression constructs encoding the desired antibodies. Production of defined gene constructs is within routine skill in the art. Alternatively, the sequences provided herein can be cloned out of hybridomas by conventional hybridization techniques or polymerase chain reaction (PCR) techniques, using synthetic nucleic acid probes whose sequences are based on sequence information provided herein, or prior art sequence information regarding genes encoding the heavy and light chains.

Standard techniques of molecular biology may be used to prepare DNA sequences coding for the antibodies or fragments of the antibodies of the present invention. Desired DNA sequences may be synthesized completely or in part using oligonucleotide synthesis techniques. Site-directed mutagenesis and polymerase chain reaction (PCR) techniques may be used as appropriate.

Any suitable host cell/vector system may be used for expression of the DNA sequences encoding the antibody molecules of the present invention or fragments thereof. Bacterial, for example *E. coli*, and other microbial systems may be used, in part, for expression of antibody fragments such as Fab and F(ab')2 fragments, and especially Fv fragments and single chain antibody fragments, for example, single chain Fvs. Eukaryotic, e.g. mammalian, host cell expression systems may be used for production of larger antibody molecules, including complete antibody molecules. Suitable mammalian host cells include CHO, HEK293T, PER.C6, myeloma or hybridoma cells.

In some embodiments, antibodies according to the invention may be produced by i) expressing a nucleic acid sequence according to the invention in a cell, and ii) isolating the expressed antibody product. Additionally, the method may include iii) purifying the antibody.

For the antibodies of the present invention to be expressed, the protein coding sequence should be "operably linked" to regulatory or nucleic acid control sequences that direct transcription and translation of the protein. As used herein, a coding sequence and a nucleic acid control sequence or promoter are said to be "operably linked" when they are covalently linked in such a way as to place the expression or transcription and/or translation of the coding sequence under the influence or control of the nucleic acid control sequence. The "nucleic acid control sequence" can be any nucleic acid element, such as, but not limited to promoters, enhancers, IRES, introns, and other elements described herein that direct the expression of a nucleic acid sequence or coding sequence that is operably linked thereto. The term "promoter" will be used herein to refer to a group of transcriptional control modules that are clustered around the initiation site for RNA polymerase II and that when operationally linked to the protein coding sequences of the invention lead to the expression of the encoded protein. The expression of the antibodies of the present invention can be under the control of a constitutive promoter or of an inducible promoter, which initiates transcription only when exposed to some particular external stimulus, such as, without limitation, antibiotics such as tetracycline, hormones such as ecdysone, or heavy metals. The promoter can also be specific to a particular cell-type, tissue or organ. Many suitable promoters and enhancers are known in the art, and any such suitable promoter or enhancer may be used for expression of the antibodies of the invention. For example, suitable promoters and/or enhancers can be selected from the Eukaryotic Promoter Database (EPDB).

Nucleic acids encoding desired antibodies can be incorporated (ligated) into expression vectors, which can be introduced into host cells through conventional transfection or transformation techniques. Exemplary host cells are *E. coli* cells, Chinese hamster ovary (CHO) cells, human embryonic kidney 293 (HEK 293) cells, HeLa cells, baby hamster kidney (BHK) cells, monkey kidney cells (COS), human hepatocellular carcinoma cells (e.g., Hep G2), and myeloma cells that do not otherwise produce IgG protein. Transformed host cells can be grown under conditions that permit the host cells to express the genes that encode the immunoglobulin light and/or heavy chain variable regions. Specific expression and purification conditions will vary depending upon the expression system employed.

Following expression, the antibodies and/or antigens of the invention can be isolated and/or purified or concentrated using any suitable technique known in the art. For example, anion or cation exchange chromatography, phosphocellulose chromatography, hydrophobic interaction chromatography, affinity chromatography, immuno-affinity chromatography, hydroxyapatite chromatography, lectin chromatography, molecular sieve chromatography, isoelectric focusing, gel electrophoresis, or any other suitable method or combination of methods can be used.

In some embodiments, the antibodies can be made using recombinant DNA methods as described in U.S. Pat. No. 4,816,567. The polynucleotides encoding a monoclonal antibody can be isolated from mature B-cells or hybridoma cell, such as by RT-PCR using oligonucleotide primers that specifically amplify the genes encoding the heavy and light chains of the antibody, and their sequence is determined using conventional procedures. The isolated polynucleotides encoding the heavy and light chains are then cloned into suitable expression vectors, which when transfected into host cells such as *E. coli* cells, simian COS cells, Chinese hamster ovary (CHO) cells, or myeloma cells that do not otherwise produce immunoglobulin protein, monoclonal antibodies are generated by the host cells.

The anti-HIV antibodies can also include insertions, deletions, substitutions, or other selected modifications of particular regions or specific amino acids residues. It should be understood that the antibodies of the invention may differ from the exact sequences illustrated and described herein. Thus, the invention contemplates deletions, additions and substitutions to the sequences shown, so long as the sequences function in accordance with the methods of the invention. In this regard, particularly preferred substitutions will generally be conservative in nature, i.e., those substitutions that take place within a family of amino acids. For example, amino acids are generally divided into four families: (1) acidic—aspartate and glutamate; (2) basic—lysine, arginine, histidine; (3) non-polar—alanine, valine, leucine, isoleucine, proline, phenylalanine, methionine, tryptophan; and (4) uncharged polar—glycine, asparagine, glutamine, cystine, serine threonine, tyrosine. Phenylalanine, tryptophan, and tyrosine are sometimes classified as aromatic amino acids. For example, leucine can be replaced with isoleucine or valine, or vice versa; an aspartate with a glutamate or vice versa; a threonine with a serine or vice versa; or a similar conservative replacement of an amino acid with a structurally related amino acid can be made.

The polynucleotide(s) encoding a monoclonal antibody can further be modified in a number of different manners using recombinant DNA technology to generate alternative antibodies. In some embodiments, the constant domains of the light and heavy chains of, for example, a mouse monoclonal antibody can be substituted 1) for those regions of, for example, a human antibody to generate a chimeric antibody or 2) for a non-immunoglobulin polypeptide to generate a fusion antibody. In some embodiments, the constant regions are truncated or removed to generate the desired antibody fragment of a monoclonal antibody. Site-directed or high-density mutagenesis of the variable region can be used to optimize specificity, affinity, etc. of a monoclonal antibody.

For the purposes of the present invention, it should be appreciated that modified antibodies can comprise any type of variable region that provides for the association of the antibody with the polypeptides of HIV such as the envelope protein.

Besides their configuration, it is known in the art that the constant region mediates several effector functions. For example, binding of the Cl component of complement to antibodies activates the complement system. Activation of complement is important in the opsonisation and lysis of cell pathogens. The activation of complement also stimulates the inflammatory response and can also be involved in autoimmune hypersensitivity. Further, antibodies bind to cells via the Fc region, with a Fc receptor site on the antibody Fc region binding to a Fc receptor (FcR) on a cell. There are a number of Fc receptors which are specific for different classes of antibody, including IgG (gamma receptors), IgE (eta receptors), IgA (alpha receptors) and IgM (mu receptors). Binding of antibody to Fc receptors on cell surfaces triggers a number of important and diverse biological responses including engulfment and destruction of antibody-coated particles, clearance of immune complexes, lysis of antibody-coated target cells by killer cells (called antibody-dependent cell-mediated cytotoxicity, or ADCC), release of inflammatory mediators, placental transfer and control of immunoglobulin production.

In certain embodiments, the anti-HIV antibodies provide for altered effector functions that, in turn, affect the biological profile of the administered antibody. For example, the deletion or inactivation (through point mutations or other means) of a constant region domain can reduce Fc receptor binding of the circulating modified antibody thereby increasing tumor localization. In other cases it may be that constant region modifications, consistent with this invention, moderate complement binding and thus reduce the serum half-life and nonspecific association of a conjugated cytotoxin. Yet other modifications of the constant region can be used to eliminate disulfide linkages or oligosaccharide moieties that allow for enhanced localization due to increased antigen specificity or antibody flexibility. Similarly, modifications to the constant region in accordance with this invention can easily be made using well known biochemical or molecular engineering techniques well within the purview of the skilled artisan.

Methods

The multispecific anti-HIV antibodies of the invention are useful in a variety of applications including, but not limited to, therapeutic treatment methods, such as the treatment, cure, functional cure, or prevention of HIV infection. The methods of use may be in vitro, ex vivo, or in vivo methods.

In some embodiments, the multispecific antibodies disclosed herein may be used as neutralizing antibodies, passively administered or given via gene therapies.

In one aspect, the anti-HIV antibodies are useful for detecting the presence of HIV in a biological sample. The term "detecting" as used herein encompasses quantitative or qualitative detection. In certain embodiments, a biological sample comprises a cell or tissue.

Certain other methods can be used to detect binding of anti-HIV antibodies to antigens such as envelope protein. Such methods include, but are not limited to, antigen-binding assays that are well known in the art, such as western blots, radioimmunoassays, ELISA (enzyme linked immunosorbent assay), "sandwich" immunoassays, immunoprecipitation assays, fluorescent immunoassays, protein A immunoassays, and immunohistochemistry (IHC).

In certain embodiments, the antibodies are labeled. Labels include, but are not limited to, labels or moieties that are detected directly (such as fluorescent, chromophoric, electron-dense, chemiluminescent, and radioactive labels), as well as moieties, such as enzymes or ligands, that are detected indirectly, e.g., through an enzymatic reaction or molecular interaction.

In certain embodiments, the antibodies are immobilized on an insoluble matrix. Immobilization entails separating the antibody from any antigen that remains free in solution. This conventionally is accomplished by either insolubilizing the antibody before the assay procedure, as by adsorption to a water-insoluble matrix or surface (Bennich et al., U.S. Pat. No. 3,720,760), or by covalent coupling (for example, using glutaraldehyde cross-linking), or by insolubilizing the antibody after formation of a complex between the antibody and antigen, e.g., by immunoprecipitation.

The present invention provides for methods of treating or preventing HIV infection comprising administering a therapeutically effective amount of a multispecific antibody as described herein to a subject (e.g., a subject in need of treatment). In some embodiments, the subject is a human.

Subjects at risk for HIV-related diseases or disorders include patients who have come into contact with an infected person or who have been exposed to HIV-1 in some other way. Administration of a prophylactic agent can occur prior to the manifestation of symptoms characteristic of HIV-1-related disease or disorder, such that a disease or disorder is prevented or, alternatively, delayed in its progression.

Methods for preventing an increase in HIV-1 virus titer, virus replication, virus proliferation or an amount of an HIV-1 viral protein in a subject are further provided. In one embodiment, a method includes administering to the subject an amount of an anti-HIV antibody effective to prevent an increase in HIV-1 titer, virus replication or an amount of an HIV-1 protein of one or more HIV strains or isolates in the subject.

For in vivo treatment of human patients, the patient is usually administered or provided a pharmaceutical formulation including a multispecific anti-HIV antibody of the invention. When used for in vivo therapy, the antibodies of the invention are administered to the patient in therapeutically effective amounts (i.e., amounts that eliminate or reduce the patient's viral burden). The antibodies can be administered to a human patient, in accordance with known methods, such as intravenous administration, e.g., as a bolus or by continuous infusion over a period of time, by intramuscular, intraperitoneal, intracerobrospinal, subcutaneous, intra-articular, intrasynovial, intrathecal, oral, topical, or inhalation routes. The antibodies may be administered parenterally, when possible, at the target cell site, or intravenously. Intravenous or subcutaneous administration of the antibody is preferred in certain embodiments. Therapeutic compositions of the invention are administered to a patient or subject systemically, parenterally, or locally.

For parenteral administration, the antibodies can be formulated in a unit dosage injectable form (solution, suspension, emulsion) in association with a pharmaceutically acceptable, parenteral vehicle. Examples of such vehicles are water, saline, Ringer's solution, dextrose solution, and 5% human serum albumin. Nonaqueous vehicles such as fixed oils and ethyl oleate are also used. Liposomes are used as carriers. The vehicle contains minor amounts of additives such as substances that enhance isotonicity and chemical stability, e.g., buffers and preservatives. In some embodiments, the antibodies are typically formulated in such vehicles at concentrations of about 1 mg/ml to 10 mg/ml.

The dose and dosage regimen depends upon a variety of factors readily determined by a physician, such as the nature of the infection and the characteristics of the particular cytotoxic agent or growth inhibitory agent conjugated to the antibody (when used), e.g., its therapeutic index, the patient, and the patient's history. Generally, a therapeutically effective amount of an antibody is administered to a patient. In particular embodiments, the amount of antibody administered is in the range of about 0.1 mg/kg to about 20 mg/kg of patient body weight. Depending on the type and severity of the infection, about 0.1 mg/kg to about 20 mg/kg body weight (e.g., about 0.1-15 mg/kg/dose) of antibody is an initial candidate dosage for administration to the patient, whether, for example, by one or more separate administrations, or by continuous infusion. The progress of this therapy is readily monitored by conventional methods and assays and based on criteria known to the physician or other persons of skill in the art.

Antibodies of the invention can be coupled to a drug for delivery to a treatment site or coupled to a detectable label to facilitate imaging of a site comprising cells of interest, such as cells infected with HIV. Methods for coupling antibodies to drugs and detectable labels are well known in the art, as are methods for imaging using detectable labels. Labeled antibodies may be employed in a wide variety of assays, employing a wide variety of labels. Detection of the formation of an antibody-antigen complex between an antibody of the invention and an epitope of interest (an HIV epitope) can be facilitated by attaching a detectable substance to the antibody. Suitable detection means include the use of labels such as radionucleotides, enzymes, coenzymes, fluorescers, chemiluminescers, chromogens, enzyme substrates or co-factors, enzyme inhibitors, prosthetic group complexes, free radicals, particles, dyes, and the like. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, di chlorotriazinylamine fluorescein, dansyl chloride or phycoerythrin; an example of a luminescent material is luminol; examples of bioluminescent materials include luciferase, luciferin, and aequorin; and examples of suitable radioactive material include $^{125}I$, $^{131}I$, $^{35}S$, or .sup.3H. Such labeled reagents may be used in a variety of well-known assays, such as radioimmunoassays, enzyme immunoassays, e.g., ELISA, fluorescent immunoassays, and the like.

The antibodies can be tagged with such labels by known methods. For instance, coupling agents such as aldehydes, carbodiimides, dimaleimide, imidates, succinimides, bid-diazotized benzadine and the like are used to tag the antibodies with the above-described fluorescent, chemiluminescent, and enzyme labels. An enzyme is typically combined with an antibody using bridging molecules such as carbodiimides, periodate, diisocyanates, glutaraldehyde and the like. Various labeling techniques are described in Morrison, *Methods in Enzymology* 32b, 103 (1974), Syvanen et al., *J. Biol. Chem.* 284, 3762 (1973) and Bolton and Hunter, Biochem J. 133, 529(1973).

In one embodiment, the antibodies can be administered as immunoconjugates, conjugated to a second molecule. For example, the second molecule can be a toxin, a label, a radioisotope, a drug, or a chemical compound.

An antibody according to the invention may be conjugated to a therapeutic moiety such as a cytotoxin, a therapeutic agent, or a radioactive metal ion or radioisotope. Examples of radioisotopes include, but are not limited to, I-131, I-123, I-125, Y-90, Re-188, Re-186, At-211, Cu-67, Bi-212, Bi-213, Pd-109, Tc-99, In-111, and the like. Such antibody conjugates can be used for modifying a given biological response; the drug moiety is not to be construed as limited to classical chemical therapeutic agents. For example, the drug moiety may be a protein or polypeptide possessing a desired biological activity. Such proteins may include, for example, a toxin such as abrin, ricin A, *pseudomonas* exotoxin, or diphtheria toxin, TLR agonists (such as TLR7 agonist), or monomethylauristatin E.

Other therapeutic regimens can be combined with the administration of the anti-HIV antibody of the present invention. The combined administration includes co-administration, using separate formulations or a single pharmaceutical formulation, and consecutive administration in either order, wherein preferably there is a time period while both (or all) active agents simultaneously exert their biological activities. Preferably such combined therapy results in a synergistic therapeutic effect.

For any application, the antibody, antigen binding fragment, or nucleic acid encoding the antibody or antigen binding fragment can be combined with anti-retroviral therapy. Antiretroviral drugs are broadly classified by the phase of the retrovirus life-cycle that the drug inhibits. The disclosed antibodies can be administered in conjunction with nucleoside analog reverse-transcriptase inhibitors (such as zidovudine, didanosine, zalcitabine, stavudine, lamivudine, abacavir, emtricitabine, entecavir, and apricitabine), nucleotide reverse transcriptase inhibitors (such as tenofovir and adefovir), non-nucleoside reverse transcriptase inhibitors (such as efavirenz, nevirapine, delavirdine, etravirine, and rilpivirine), protease inhibitors (such as saquinavir, ritonavir, indinavir, nelfinavir, amprenavir, lopinavir, fosamprenavir, atazanavir, tipranavir, and darunavir), entry or fusion inhibitors (such as maraviroc and enfuvirtide), maturation inhibitors, (such as bevirimat and vivecon), or a broad spectrum inhibitors, such as natural antivirals. In some examples, a disclosed antibody or active fragment thereof or nucleic acids encoding such is administered in conjunction with IL-15, or conjugated to IL-15.

Single or multiple administrations of the compositions including the antibody, antigen binding fragment, or nucleic acid encoding the antibody or antigen binding fragment, that are disclosed herein, are administered depending on the dosage and frequency as required and tolerated by the patient. In any event, the composition should provide a sufficient quantity of at least one of the antibodies disclosed herein to effectively treat the patient. The dosage can be administered once, but may be applied periodically until either a therapeutic result is achieved or until side effects warrant discontinuation of therapy.

One approach to administration of nucleic acids is direct administration with plasmid DNA, such as with a mammalian expression plasmid. The nucleotide sequence encoding the disclosed antibody, or antibody binding fragments thereof, can be placed under the control of a promoter to increase expression. Another approach is to administer the nucleic acids in the form of mRNA.

In some embodiments, the subject is administered cells that are engineered to express the anti-HIV antibody. In some embodiments, the cells are engineered immune cells, such as B cells. In some embodiments, the cells are engineered, autologous cells.

In another approach to using nucleic acids, an anti-HIV antibody, or antibody binding fragment thereof can also be expressed by attenuated viral hosts or vectors or bacterial vectors. Recombinant vaccinia virus, adeno-associated virus (AAV), herpes virus, retrovirus, cytomegalovirus or other viral vectors can be used to express the antibody. For example, vaccinia vectors and methods useful protocols are described in U.S. Pat. No. 4,722,848. BCG (*Bacillus* Calmette Guerin) provides another vector for expression of the disclosed antibodies (see Stover, Nature 351:456-460, 1991).

Compositions

The present invention also encompasses compositions comprising one or more antibodies of the invention. In certain embodiments, the compositions are pharmaceutical compositions. In some embodiments, formulations are prepared for storage and use by combining an antibody with a pharmaceutically acceptable vehicle (e.g. carrier, excipient) (*Remington, The Science and Practice of Pharmacy* 20*th Edition* Mack Publishing, 2000). Suitable pharmaceutically acceptable vehicles include, but are not limited to, nontoxic buffers such as phosphate, citrate, and other organic acids; salts such as sodium chloride; antioxidants including ascorbic acid and methionine; preservatives (e.g. octadecyldimethylbenzyl ammonium chloride; hexamethonium chloride; benzalkonium chloride; benzethonium chloride; phenol, butyl or benzyl alcohol; alkyl parabens, such as methyl or propyl paraben; catechol; resorcinol; cyclohexanol; 3-pentanol; and m-cresol); low molecular weight polypeptides (e.g. less than about 10 amino acid residues); proteins such as serum albumin, gelatin, or immunoglobulins; hydrophilic polymers such as polyvinylpyrrolidone; amino acids such as glycine, glutamine, asparagine, histidine, arginine, or lysine; carbohydrates such as monosacchandes, disaccharides, glucose, mannose, or dextrins; chelating agents such as EDTA; sugars such as sucrose, mannitol, trehalose or sorbitol; salt-forming counter-ions such as sodium; metal complexes (e.g. Zn-protein complexes); and non-ionic surfactants such as TWEEN or polyethylene glycol (PEG).

For the treatment or prevention of HIV, the appropriate dosage of an antibody or combination of antibodies of the present invention can depend on a variety of factors, such as the severity and course of the disease, the responsiveness of the disease, whether the antibody or agent is administered for therapeutic or preventative purposes, previous therapy, patient's clinical history, and so on all at the discretion of the treating physician. The antibody or agent can be administered one time or over a series of treatments lasting from several days to several months, or until a cure is effected or a diminution of the disease state is achieved. The administering physician can easily determine optimum dosages, dosing methodologies and repetition rates. In certain embodiments, dosage is from 0.01 μg to 100 mg per kg of body weight, and can be given once or more daily, weekly, monthly or yearly. In certain embodiments, the antibody or combination of antibodies is given once every two weeks or once every three weeks. In certain embodiments, the dosage of the antibody is from about 0.1 mg to about 20 mg per kg of body weight. The treating physician can estimate repetition rates for dosing based on measured residence times and concentrations of the drug in bodily fluids or tissues.

Effective dosages and schedules for administering embodiments of the present invention can be determined empirically. In some embodiments, and effective amount of one or more antibodies are administered to neutralize, treat, prevent or eradicate HIV infection. In some embodiments, compositions comprising one or more nucleic acid molecules of the invention are administered to the subject. In some embodiments, genetic constructs capable of inducing production of antibodies of the present invention may be administered to a patient in need thereof.

Controlled-release parenteral formulations can be made as implants, oily injections, or as particulate systems. For a broad overview of protein delivery systems see, Banga, A. J., Therapeutic Peptides and Proteins: Formulation, Processing, and Delivery Systems, Technomic Publishing Company, Inc., Lancaster, Pa., (1995). Particulate systems include microspheres, microparticles, microcapsules, nanocapsules, nanospheres, and nanoparticles. Microcapsules contain the therapeutic protein, such as a cytotoxin or a drug, as a central core. In microspheres the therapeutic is dispersed throughout the particle. Particles, microspheres, and microcapsules smaller than about 1 μm are generally referred to as nanoparticles, nanospheres, and nanocapsules, respectively. Capillaries have a diameter of approximately 5 μm so that only nanoparticles are administered intravenously. Microparticles are typically around 100 μm in diameter and are administered subcutaneously or intramuscularly. See, for example, Kreuter, J., Colloidal Drug Delivery Systems, J. Kreuter, ed., Marcel Dekker, Inc., New York, N.Y., pp. 219-342 (1994); and Tice & Tabibi, Treatise on Controlled Drug Delivery, A. Kydonieus, ed., Marcel Dekker, Inc. New York, N.Y., pp. 315-339, (1992).

Polymers can be used for ion-controlled release of the antibody compositions disclosed herein. Various degradable and nondegradable polymeric matrices for use in controlled drug delivery are known in the art (Langer, Accounts Chem. Res. 26:537-542, 1993). For example, the block copolymer, polaxamer 407, exists as a viscous yet mobile liquid at low temperatures but forms a semisolid gel at body temperature. It has been shown to be an effective vehicle for formulation and sustained delivery of recombinant interleukin-2 and urease (Johnston et al., Pharm. Res. 9:425-434, 1992; and Pec et al., J. Parent. Sci. Tech. 44(2):58-65, 1990). Alternatively, hydroxyapatite has been used as a microcarrier for controlled release of proteins (Ijntema et al., Int. J. Pharm.

112:215-224, 1994). In yet another aspect, liposomes are used for controlled release as well as drug targeting of the lipid-capsulated drug (Betageri et al., Liposome Drug Delivery Systems, Technomic Publishing Co., Inc., Lancaster, Pa. (1993)). Numerous additional systems for controlled delivery of therapeutic proteins are known (see U.S. Pat. Nos. 5,055,303; 5,188,837; 4,235,871; 4,501,728; 4,837,028; 4,957,735; 5,019,369; 5,055,303; 5,514,670; 5,413,797; 5,268,164; 5,004,697; 4,902,505; 5,506,206; 5,271,961; 5,254,342 and 5,534,496).

In some embodiments, the compositions of the invention may be injectable suspensions, solutions, sprays, lyophilized powders, syrups, elixirs and the like. Any suitable form of composition may be used. To prepare such a composition, a nucleic acid or vector of the invention, having the desired degree of purity, is mixed with one or more pharmaceutically acceptable carriers and/or excipients. The carriers and excipients must be "acceptable" in the sense of being compatible with the other ingredients of the composition. Acceptable carriers, excipients, or stabilizers are nontoxic to recipients at the dosages and concentrations employed, and include, but are not limited to, water, saline, phosphate buffered saline, dextrose, glycerol, ethanol, or combinations thereof, buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™ PLURONICS™ or polyethylene glycol (PEG).

The compositions can be designed to introduce the antibodies, nucleic acids or expression vectors to a desired site of action and release it at an appropriate and controllable rate. Methods of preparing controlled-release formulations are known in the art. For example, controlled release preparations can be produced by the use of polymers to complex or absorb the immunogen and/or immunogenic composition. A controlled-release formulations can be prepared using appropriate macromolecules (for example, polyesters, polyamino acids, polyvinyl, pyrrolidone, ethylenevinylacetate, methylcellulose, carboxymethylcellulose, or protamine sulfate) known to provide the desired controlled release characteristics or release profile. Another possible method to control the duration of action by a controlled-release preparation is to incorporate the active ingredients into particles of a polymeric material such as, for example, polyesters, polyamino acids, hydrogels, polylactic acid, polyglycolic acid, copolymers of these acids, or ethylene vinylacetate copolymers. Alternatively, instead of incorporating these active ingredients into polymeric particles, it is possible to entrap these materials into microcapsules prepared, for example, by coacervation techniques or by interfacial polymerization, for example, hydroxymethylcellulose or gelatin-microcapsule and poly-(methylmethacrylate) microcapsule, respectively, in colloidal drug delivery systems (for example, liposomes, albumin microspheres, microemulsions, nano-particles and nanocapsules) or in macroemulsions. Such techniques are disclosed in New Trends and Developments in Vaccines, Voller et al. (eds.), University Park Press, Baltimore, Md., 1978 and Remington's Pharmaceutical Sciences, 16th edition.

The compositions can be administered using any suitable delivery method including, but not limited to, intramuscular, intravenous, intradermal, mucosal, and topical delivery. Such techniques are well known to those of skill in the art. More specific examples of delivery methods are intramuscular injection, intradermal injection, and subcutaneous injection. However, delivery need not be limited to injection methods. Further, delivery of DNA to animal tissue has been achieved by cationic liposomes (Watanabe et al., (1994) Mol. Reprod. Dev. 38:268-274; and WO 96/20013), direct injection of naked DNA into animal muscle tissue (Robinson et al., (1993) Vaccine 11:957-960; Hoffman et al., (1994) Vaccine 12: 1529-1533; Xiang et al., (1994) Virology 199: 132-140; Webster et al., (1994) Vaccine 12: 1495-1498; Davis et al., (1994) Vaccine 12: 1503-1509; and Davis et al., (1993) Hum. Mol. Gen. 2: 1847-1851), or intradermal injection of DNA using "gene gun" technology (Johnston et al., (1994) Meth. Cell Biol. 43:353-365). Alternatively, delivery routes can be oral, intranasal or by any other suitable route. Delivery also be accomplished via a mucosal surface such as the anal, vaginal or oral mucosa.

Dosing schedules (or regimens) can be readily determined for the particular subject and composition. Hence, the composition can be administered one or more times to the subject. Preferably, there is a set time interval between separate administrations of the composition. While this interval varies for every subject, typically it can range from 10 days to several weeks, and is often 2, 4, 6 or 8 weeks. In some embodiments, the interval can be typically from 2 to 6 weeks.

The compositions of the invention can be administered alone, or can be co-administered, or sequentially administered, with other HIV immunogens and/or HIV immunogenic compositions, e.g., with "other" immunological, antigenic or vaccine or therapeutic compositions thereby providing multivalent or "cocktail" or combination compositions of the invention and methods of employing them. Again, the ingredients and manner (sequential or co-administration) of administration, as well as dosages can be determined taking into consideration such factors as the age, sex, weight, species and condition of the particular subject, and the route of administration.

Kits

The present invention also includes kits useful in performing diagnostic and prognostic assays using the antibodies of the present invention. Kits of the invention include a suitable container comprising an HIV-1 antibody of the invention in either labeled or unlabeled form. In addition, when the antibody is supplied in a labeled form suitable for an indirect binding assay, the kit further includes reagents for performing the appropriate indirect assay. For example, the kit includes one or more suitable containers including enzyme substrates or derivatizing agents, depending on the nature of the label. Control samples and/or instructions are also included.

Application of the teachings of the present invention to a specific problem is within the capabilities of one having ordinary skill in the art in light of the teaching contained herein. Examples of the compositions and methods of the invention appear in the following non-limiting Examples.

EXAMPLES

Example 1. Multi-Specific Antibodies for HIV-1 and their Utility

Here, 3D structure information of broadly neutralizing antibodies (bNAbs) in complex with HIV-1 envelope glycoproteins (Env) was used to perform rational design of penta-specific antibodies (PentaNAbs) capable of targeting five major Env neutralizing epitopes. These inventions, herein referred to as "PentaNAbs", consist of five functional single chain fragment variable (ScFv) moieties connected in tandem via (G4S)n linkers, such that penta-valence engagement of five individual epitopes on the HIV-1 Env by each respective moiety is possible. The bNAb functional moieties incorporated in the design target five major HIV neutralization epitopes including the i) V1/V2 apex glycan, ii) V3-base glycan, iii) CD4 binding site, iv) gp120/gp41 interface, and v) the membrane proximal external region (MPER). The sequence information of the penta-specific antibodies is listed in Table 4. In addition, these PentaScFv entities were fused to the fragment crystallizable region (Fc) region of IgG1 to accommodate effector functions in a Penta-IgG format.

To design the PentaScFvs, the physical distance between the compatible N/C termini of parental bNAb variable heavy (VH) and light chain (VL) domains was estimated to identify the shortest linker combinations allowing optimal VH/VL connection within each bNAb ScFv entity. Furthermore, to generate molecules capable of simultaneously engaging ("draping" the HIV-1 Env) contiguous epitopes on the HIV-1 Env surface, the spatial relationship between each neighboring bNAb moiety in the state of cognate epitope binding was assessed. It was found that epitopes located on adjacent protomers of the HIV-1 trimer are often more proximate to each other than those on the same protomer. Thus, in some designs, two functional bNAb moieties binding to the same protomer (intra-protomer mode) were arranged and in some cases to separate protomers (inter-protomers) of the HIV-1 Env trimer. Finally, PentaNAbs with bNAb moieties connected from N to C terminus in two orientations were designed: from the MPER to V1V2 apex (forward order) or from the V1V2 apex to MPER (reverse order) followed by the Fc fragment to form PentaNAb IgG1 molecules. The purpose of these designs is to minimize potential steric hindrance imposed by the addition of Fc fragment to the C terminus of the connected ScFv entities. PentaNAb2.0 was initially constructed, which consists of functional moieties of five bNAbs including 10E8v4 S100cF, 35O22, N6, PGT121, and VRC26.25 to test the rationale. In this design, an molecular orientation was used, namely "Forward" orientation with which the MPER bNAb 10E8v4 S100cF moiety is at the N terminus of the PentaNAb and the V1V2 glycan bNAb VRC26.25 moiety on the distal side followed by Fc fragment.

Using a 208-virus panel representing the worldwide diverse circulating HIV-1 virus isolates to assess neutralization breath, PentaNAb2.0, in both ScFv and IgG form, displayed improved virus isolate coverage of 99.6%, as compared to individual bNAbs 10E8, VRC01, PGT121 and 35O22, which had 97.6%, 90.4%, 63.9%, and 45.2% coverage, respectively. Most significantly, the PentaNAb2.0, in both ScFv and IgG form, displayed significantly improved IC50 geomeans of 0.006 and 0.072 μg/mL, respectively, as compared to 10E8, which has an IC50 mean of 0.299 μg/mL with the best neutralization breadth among all known bNAbs. In addition, PentaNAb2.0 ScFv displays neutralization potency and breadth superior to previously engineered tri- and tetra-specific antibodies to HIV-1 Env. Furthermore, PentaNAb2.0, in both ScFv and IgG form effectively neutralizes VRC01-resistant replication-competent viral isolates from patients participated in the clinical trial involving passive transfer of VRC01. Finally, PentaNAbs were engineered with a "Reverse" orientation with which the V1V2 glycan bNAb VRC26.25 or PGDM1400 moiety is at the N terminus of the PentaNAb and the MPER bNAb 10E8v4 S100cF moiety on the distal side followed by Fc fragment. The neutralization capacities of these PentaNAb iterations were assessed with a panel of 26 HIV-1 Env-pseudoviruses in TZM-b1 target cells. It was found that all of the PentaNAbs in the ScFv format displayed a greater breadth and potency than their respective IgG1 counterparts with Fc fragment. Additionally, it was observed that the PentaNAbs in the "reverse" order displayed a greater potency than the "forward" order while maintaining the same breadth. Taken together, penta-specific antibodies were engineered that are capable of engaging five major neutralization epitopes of HIV-1 envelope glycoproteins possess superior antiviral activities to conventional HIV-1 bNAbs and previously engineered tri- and tetra-specific HIV-1 bNAbs, which may serve as effective agents for HIV-1 prevention, treatment and diagnosis.

Results

Figure 2B:
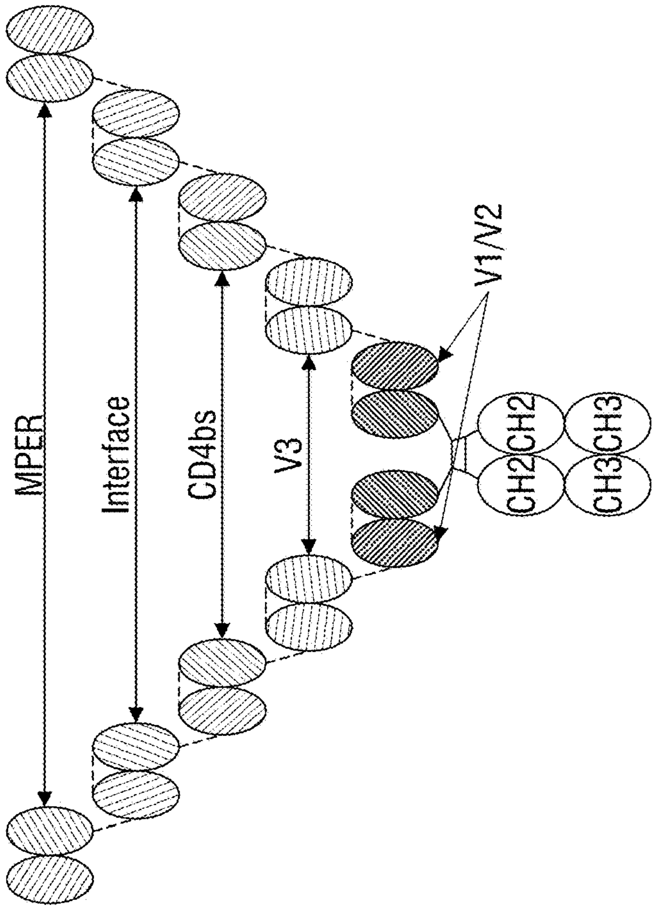
FIG. 2. Schematic of bNAb entities linked together in tandem to form PentaNAb 2.0. (A) Topology of PentaNAb design: from the Env MPER to the Env apex, with the shortest distance between bNAb entities marked. Modeling of Env trimer BG505 SOSIP.664 binding to five bNAbs targeting the five conserved epitopes including the V1V2 glycan, V3 base glycan, CD4 binding site (CD4bs), gp120/gp41 interface, and membrane proximate exterior region (MPER) simultaneously by superimposing individual bNAb Fab-Env complex structure, only VH-VL regions of Fab are shown. Env trimer in grey, and the bNAb moieties in color; (B) Scheme of the PentaNAb design, with MPER bNAb at the N terminus and V1V2 bNAb connected with CH2-CH3 domains of IgG Fc. Strategies of engineering penta-ScFv by joining the termini of VHs and VLs by linkers in dash lines optimized to accommodate individual VHs and VLs to achieve simultaneous epitope engagement; (C) Linear presentation of PentaNAb 2.0 design.
Figure 2A:
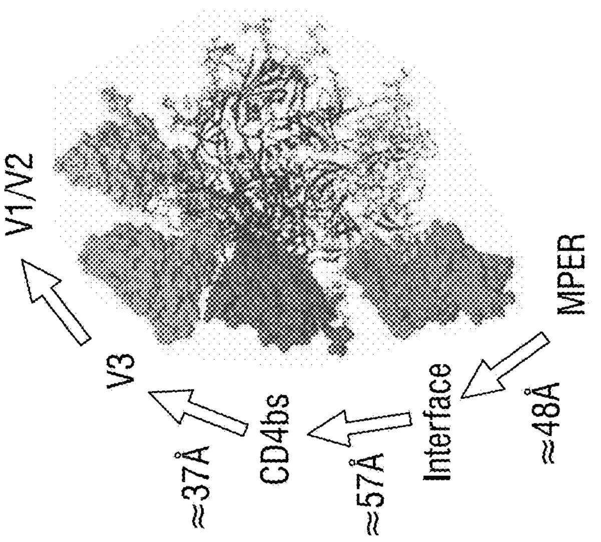
Figure 2C:
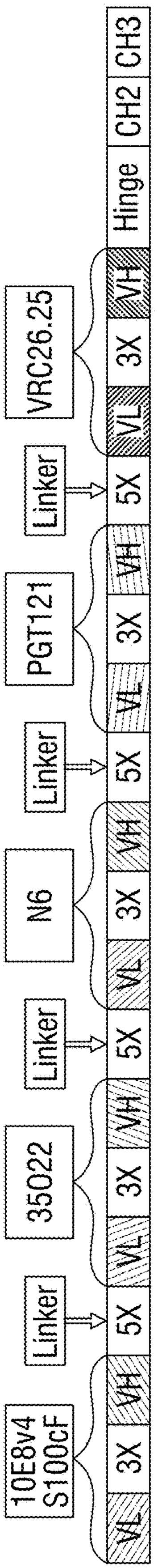

Spatial Relationships Between HIV-1 Env-Specific bNAb Epitopes and the Design of Connecting Linker Length To constitute PentaNAb molecules, five top lead antibodies displaying the best neutralization potency and breadth among bNAbs within each individual epitope cluster were first selected. For example, in one combination VRC26.25 or PGDM1400, PGT121, N6, 35O22, and 10E8v4 V5R S100cF from the V1/V2, V3-glycan, CD4bs, gp120/gp41 interface, and MPER epitope cluster, respectively were picked. In order to develop a PentaNAb capable of simultaneously engaging five separate epitopes, the physical distance between the compatible variable heavy (VH) and light (VL) chain region termini (e.g. VH C-terminus followed by N-terminus of VL) of the selected bNAbs was measured to identify the shortest combinations (FIG. 2). The PentaNAb was designed such that the VH and VL of each individual bNAb entity was connected between termini with flexible linkers such that the flexible linker would traverse the shortest unimpeded distance possible. It is believed that joining the individual entities of the PentaNAb between the termini with the shortest unimpeded distance in between would avoid excess linker length, which would i) improve protein folding, ii) improve the expression level/yield of the molecule, and iii) improve the coordination of simultaneous engagement of all five epitopes.

Five G4S linkers were used to connect moieties of bNAbs targeting the V1V2 (e.g. VRC26.25) and V3 (e.g. PGT121) glycans. The distance between V1/V2 and the V3-glycan targeting antibodies VRC26.25 or PGDM1400 and PGT121, respectively, was not determined as crystallography data of gp120 bound VRC26.25 or PGDM1400 is currently unavailable. Using the EMD data for VRC26.25 bound to BG505 SOSIP.664, EMD-5856 (Dona-Rose et al., Nature 509, 55-62 (2014)), the crystal structure of the VRC26.25 Fab (PDB: 5DT1) (Dona-Rose et al., J Virol 90, 76-91 (2015)), as well as the crystal structure of PGT122 bound BG505 SOSIP.664 (PDB: 5FYK) (Stewart-Jones et al., Cell 165, 813-826 (2016)), a model of VRC26.25 & PGT121 bound Env trimer were generated by manual superposition of BG505 trimer elements. This model was subsequently used to roughly estimate the spatial relationship between VRC26.25 and PGT121 with results similar to other modeling attempts using a combination of molecular dynamics (MD) and molecular dynamics flexible-fitting (MDFF) (Gorman et al., Nat Struct Mol Biol 23, 81-90 (2016)). Similarly this EM model, EMD-5856 (Dona-Rose et al., Nature 509, 55-62 (2014)), was used to manually fit the crystal structure of the PGDM1400 Fab (PDB: 4RQQ) (Sok et al., Proc Natl Acad Sci USA 111, 17624-17629 (2014)), with the crystal structure of PGT122 bound BG505 SOSIP.664 (PDB: 5FYK) (Stewart-Jones et al., Cell 165, 813-826 (2016)), to briefly estimate the spatial relationship between PGDM1400 and PGT121, since PGDM1400 approaches the gp120 apex with an angle similar to VRC26.25. According to the EM data, both VRC26.25 and PGDM1400 are quaternary-dependent antibodies targeting the V1/V2 epitope at the trimer apex (Dona-Rose et al., J Virol 90, 76-91 (2015); Sok et al., Proc Natl Acad Sci USA 111, 17624-17629 (2014)) (FIG. 1), with VH/VL termini close to one another. Based on the above stated analysis, a linker of sufficient length (e.g. a linker with five G4S units) is utilized to connect VRC26.25 or PGDM1400 with PGT121.

Five G4S linkers were used to connect the V3-glycan targeting PGT121 and the CD4bs targeting N6 ScFv entities. Previous studies determined that the shortest distance between PGT122 (a surrogate for PGT121) and VRC01 (a surrogate for N6) is between adjacent protomers within an Env trimer (inter-protomer). Using the PDB model 5FYK (Stewart-Jones et al., Cell 165, 813-826 (2016)), determined the distances between the VRC01 and PGT121 functional variable domains as the following: 37 Å between the C-terminus of VRC01 VH domain and the N-terminus of PGT121 VL domain with VRC01(VL-VH)-PGT121(VL-VH) topology, and 53 Å between the C-terminus of PGT121 VL and the N-terminus of VRC01 VH with PGT121(VH-VL)-VRC01(VH-VL) topology (FIG. 8A). Furthermore, negative stain electron microscopy data demonstrated that one of the Bi-ScFvs previously generated, dVRC01(VL-VH)-5X-PGT121(VL-VH), was able to simultaneously engage both the PGT121 and VRC01 epitopes in an inter-protomer manner as we had predicted (Steinhardt et al., Nat Commun 9, 877 (2018)), which supports rationale for this linker design.

The shortest distance between the CD4bs targeting bNAb moiety, N6 (with VRC01 as surrogate), and the gp120/gp41 interface targeting 35O22 entity was determined to be an intra-protomer distance. Using the model in PDB 5FYK (Stewart-Jones et al., Cell 165, 813-826 (2016)), the distance between the 35O22 and N6 functional variable domains were determined to be 57 Å between the C-terminus of 35O22 VH domain and the N-terminus of N6 VL domain with the topology of 35O22(VL-VH)-N6(VL-VH), and 47 Å between the C-terminus of N6 VL and the N-terminus of 35O22 VH with the topology of N6(VH-VL)-35O22(VH-VL) (FIG. 8B), respectively. Thus, five G4S linkers were used to connect N6 and 35O22.

Finally, the shortest distances between the gp120/gp41 interface targeting 35O22 entity and the MPER targeting 10E8v4 entity was determined to be inter-protomer manner. Using PDB 51Q7 superimposed with PDB 5FYK (Stewart-Jones et al., Cell 165, 813-826 (2016); Kwon et al., J Virol 90, 5899-5914 (2016)), a model for Env engaged with both 35O22 and 10E8 was generated. In this model, the distance between the 10E8v4 and 35O22 functional variable domains were determined to be 48 Å between the C-terminus of 10E8v4 VH domain and the N-terminus of 35O22 VL domain with the topology of 10E8v4(VL-VH)-35O22(VL-VH), and 25 Å between the C-terminus of 35O22 VL and the N-terminus of 10E8v4 VH with the topology of 35O22(VH-VL)-10E8v4(VH-VL) (FIG. 8C), respectively. Therefore, five G4S linkers were used to connect 35O22 and 10E8v4.

PentanAbs Display Exceptional Neutralization Potency and Breadth

Based on the analysis of spatial relationship between the five major bNAb epitopes on HIV-1 Env surface, and the design of connecting linker length stated above, PentaNAb2.0 (FIG. 2, Table 5) was composed consisting of bNAb moieties of VRC26.25, PGT121, N6, 35O22, and 10E8v4 S100cF from the V1/V2, V3-glycan, CD4bs, gp120/gp41 interface, and 1VIPER epitope cluster, respectively.

TABLE 5

Summary of PentaNAb names, order of individual antibody entities and orientation of variable light and variable heavy chains.

| Name | Order | Orientation |
|---|---|---|
| PentaNAb$_{1.0}$ | 10E8v4, 35O22, N6, PGT121, VRC26.25 | 10E8v4-5X-35O22-5X-N6-5X-PGT121-5X-VRC26.25 |
| PentaNAb$_{2.0}$ | 10E8v4 S100cF, 35O22, N6, PGT121, VRC26.25 | 10E8v4_S100cF-5X-35O22-5X-N6-5X-PGT121-5X-VRC26.25 |
| PentaNAb$_{2.0}$ Reverse | VRC26.25, PGT121, N6, 35O22, 10E8v4_S100cF | VRC26.25-5X-PGT121-5X-N6-35O22-10E8v4_S100cF |
| PentaNAb$_{3.0}$ | 10E8v4_S100cF, 35O22, N6, PGT121, PGDM1400 | 10E8v4_S100cF-5X-35O22-5X-N6-5X-PGT121-5X-PGDM1400 |
| PentaNAb$_{3.0}$ Reverse | PGDM1400, PGT121, N6, 35O22, 10E8v4_S100cF | PGDM1400-5X-PGT121-5X-N6-5X-35O22-5X-10E8v4_S100cF |
| PentaNAb$_{4.0}$ | 10E8v4 V5R_S100cF, 35O22, N6, PGT121, PGDM1400 | 10E8v4 V5R_S100cF-5X-35O22-5X-N6-5X-PGT121-5X-PGDM1400 |
| PentaNAb$_{4.0}$ Reverse | PGDM1400, PGT121, N6, 35O22, 10E8v4_V5R_S100cF | PGDM1400-5X-PGT121-5X-N6-5X-35O22-5X-10E8v4_V5R_S100cF |

The PentaNAb2.0-ScFvs and full length IgGs were expressed in mammalian 293FreeStyle cells and purified by Ni+ and protein A columns, respectively. All molecules were characterized by SDS-PAGE gels, size exclusion chromatography (SEC), and dynamic light scattering (DLS) (data not shown). Furthermore, the binding specificities of these constructs were validated by ELISA binding assay (not shown), and Bio-Layer Interferometry (BLI), which demonstrated binding to numerous Env ligands including the CD4bs specific RSC3 probe, an MPER peptide, and full length BG505 SOSIP.664 and JR-FL SOSIP.664 Env trimers (data not shown).

Figure 3A:
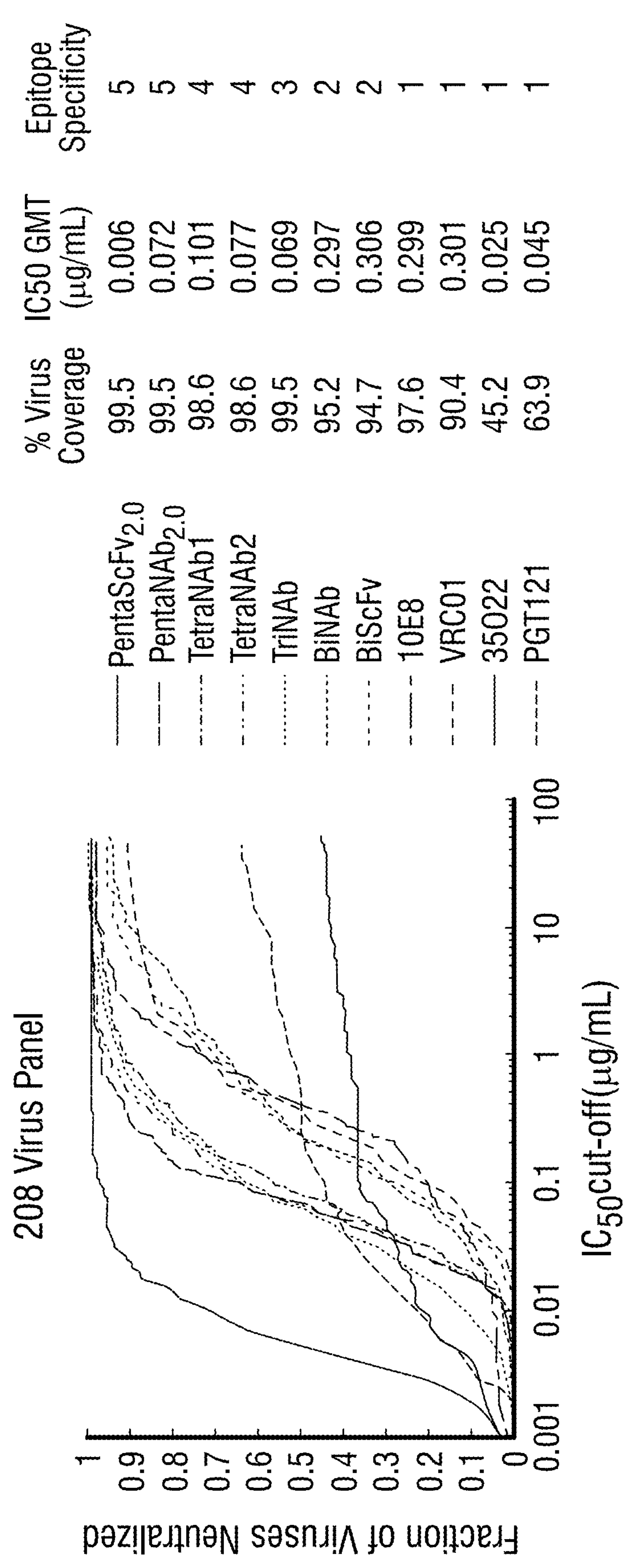
FIG. 3. Summary of neutralization breadth and potency of PentaNAb2.0 in a comprehensive panel of viruses, in comparison with other multi-specific antibody designs. (A) Comparison of potency-breadth curves and epitope specificities of Tri- and Penta-NAb against a panel of 208 circulating primary HIV-1 strains; (B) Heat maps of IC50, breadth and potency are shown as in (A) and FIG. 4. GMT, geometric mean of titer (IC50). The IC50 was adjusted to account for the molarity difference between the antibodies.
Figure 3B:
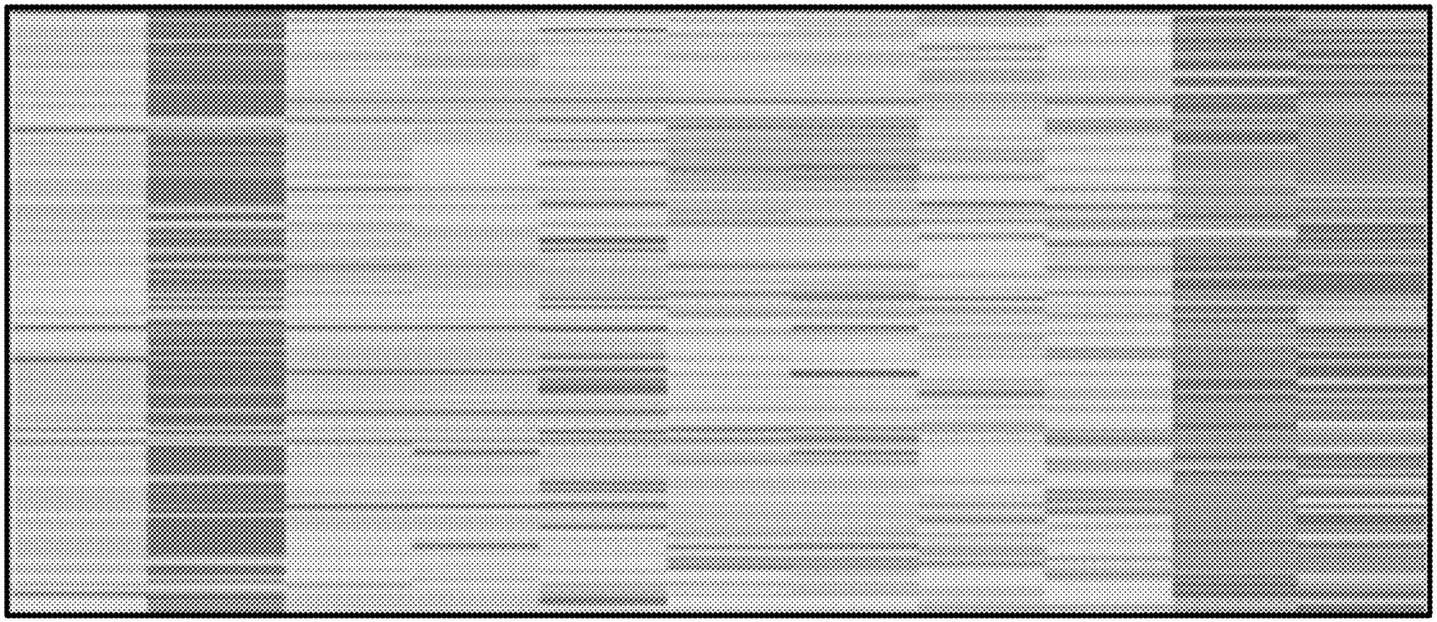

A comprehensive virus panel consisting of 208 pseudotype virus strains representing the worldwide diversified circulating HIV-1 virus isolates was used to analyze and compare the PentaNAb2.0 ScFv and IgG with TetraNAb, TriNAb and BiNAb designs in a previous invention disclosure (PCT/US2017/057053), as well as prototypic bNAbs including 10E8, VRC01 and PGT121. Both PentaNAb2.0 ScFv and IgG displayed substantially greater breadth and higher potency than the prototypical bNAbs and BiNAbs, while PentaNAb2.0 ScFv displays potency higher than TetraNAb and TriNAb (FIGS. 3A, 3B & 4) by approximately 10-fold. The PentaNAb2.0, in both ScFv and IgG form, displayed improved virus isolate coverage of 99.6%, as compared to bNAbs 10E8, VRC01 and PGT121, which had 97.6%, 90.4% and 63.9%, respectively. The PentaNAb2.0, in both ScFv and IgG form, displayed significantly improved IC50 geomeans of 0.006 and 0.072 μg/mL, respectively (FIGS. 3 & 4). Most significantly, with an IC50 mean of 0.006 μg/mL, the PentaNAb2.0 ScFv is the most potent HIV-1 multiNAb tested to date by the comprehensive 208-virus panel.

Figure 5A:
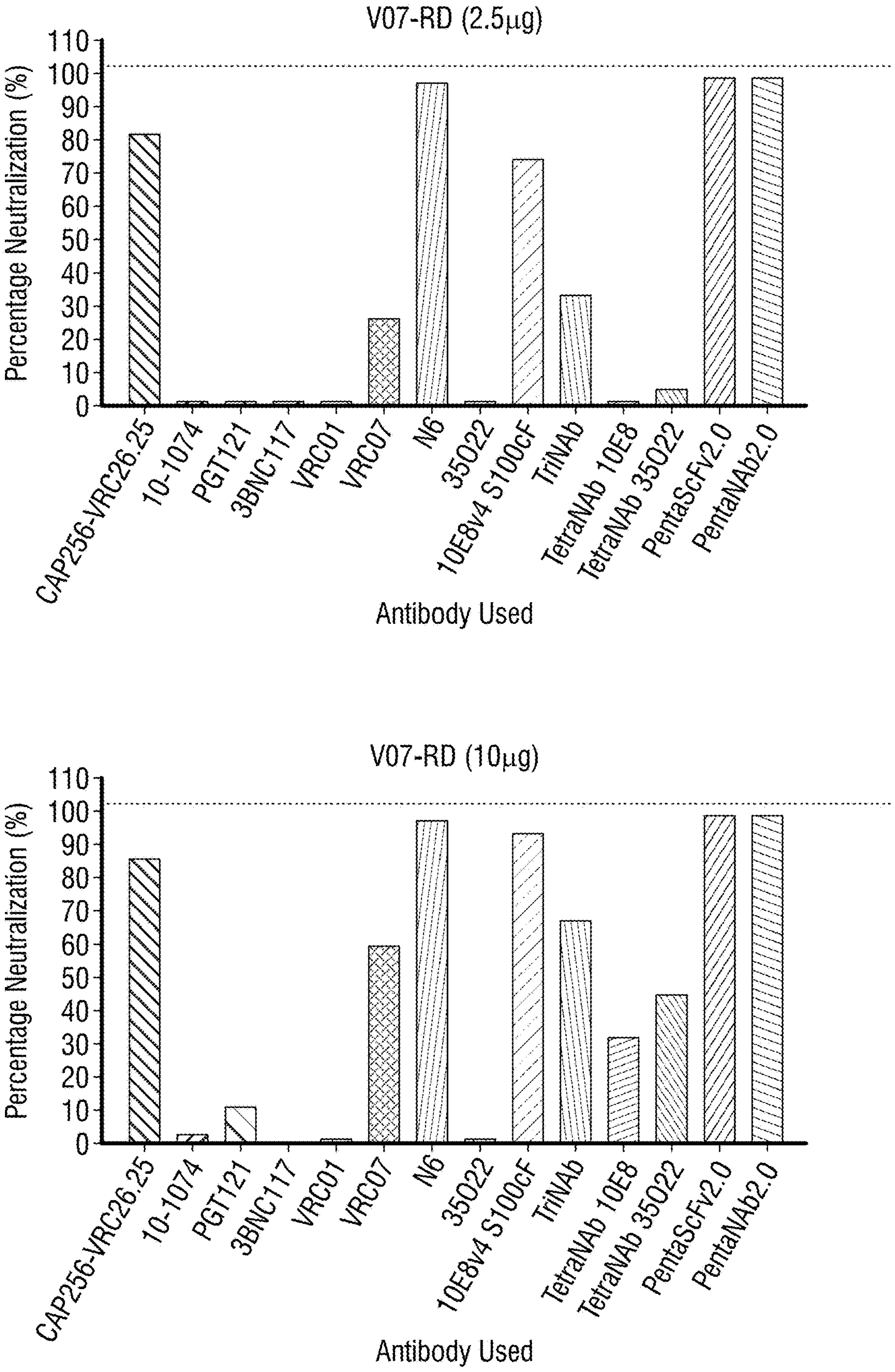
FIG. 5. Neutralization capacity of PentaNAbs tested against primary HIV-1 viruses isolated from patients involved in VRC01 therapy treatment. Neutralization of virus from patient V07-RD (A), and V09-RD (B), tested with antibodies at 2.5 μg/ml (left) and 10 μg/ml (right), respectively. (C) Summary of IC50/IC80 (μg/ml) for PentaNAbs tested against primary VRC01 resistant isolates. Neutralization IC50 and IC80 titers (μg/ml) of Penta-scFV and Penta-NAb IgG against HIV isolated from VRC01 clinical trial. The IC50 and IC80 values were adjusted to account for the molarity difference between the antibodies.
Figure 5B:
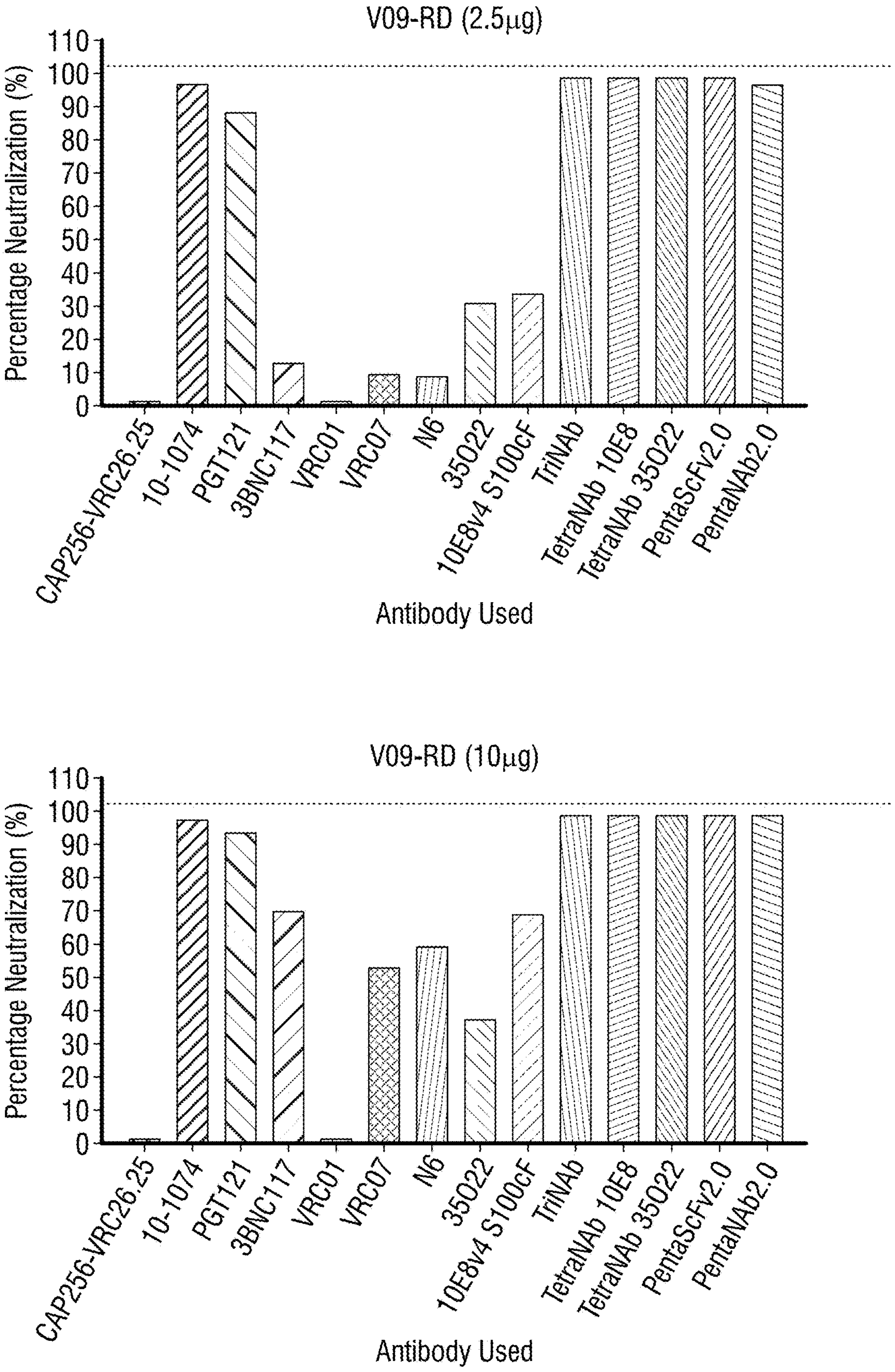

Finally, when tested against VRC01-resistant replication-competent viral isolates from patients participating in the clinical trial involving passive transfer of VRC01, the PentaNAb2.0 ScFv and IgG displayed neutralization capacity superior to previous multiNAb designs as well as the prototypical bNAbs (FIG. 5A-5C). Taken together, the data suggest that the PentaNAb could serve as a multifunctional therapeutic agent template for the prevention and treatment of HIV-1 infection, outperforming the conventional bNAbs and multi-specific bNAbs engineered previously.

Optimized bNAb Orientations Enhance the Potency of PentaNAbs

PentaNAb2.0 was initially designed and purified in the "Forward" orientation (FIG. 2). While PentaNAb2.0 ScFv shows superior potency to Tri- and Tetra-NAb designs, PentaNAb2.0 IgG with Fc fragment fused to the V1V2 glycan antibody moieties at the C terminus of the PentaNAb2.0 ScFv (FIG. 2) shows potency virtually identical to Tri- and Tetra-NAb designs. We hypothesized that the steric hindrance imposed by the Fc fragment to the potent V1V2 glycan antibody moieties such as VRC26.25 may result in deleterious effect on neutralization potency.

Figure 6:
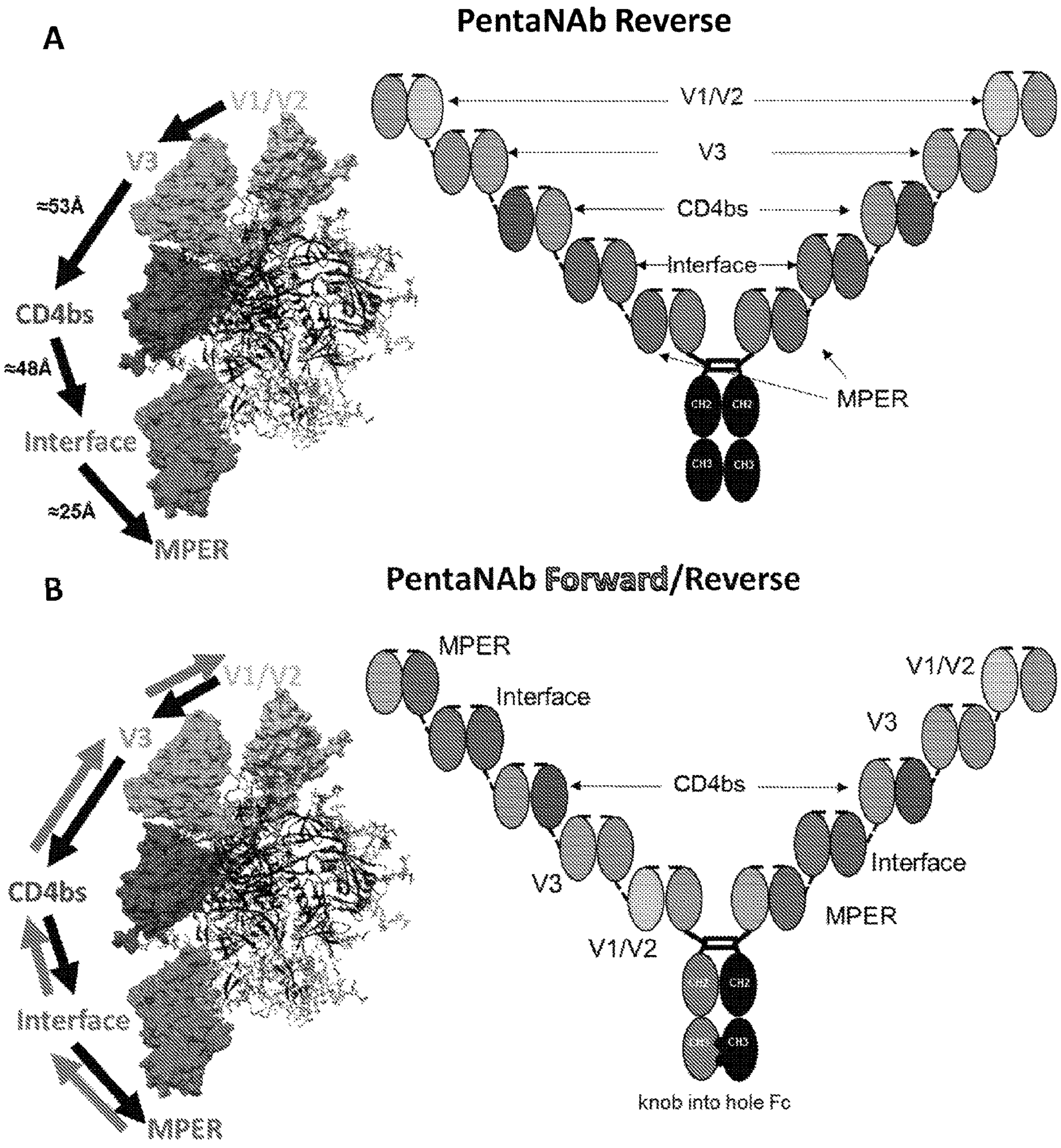
FIG. 6. Schemes of various iterations in which bNAb entities can be linked together in tandem to form PentaNAbs in the "Reverse" or "Forward/Reverse" orientation. (A) The "reverse" orientation of the PentaNAb design, in contrast to that in FIG. 2; (B) The PentaNAb "Forward/Reverse" orientation configuration conferred by IgG Fc bearing "knob-into-hole" mutations to form heterodimer.

To test this hypothesis, a series of Penta-ScFvs and full length IgGs (FIG. 2, FIG. 6) were generated, with combinations and permutations of VH-VL orientations and linker length for optimization (Table 4). Particularly, these designs include either i) the "Forward" orientation: 10E8v4(VL-VH)-35O22(VL-VH)-VRC01(VL-VH)-5X-PGT121(VL-VH)-VRC26.25/PGDM1400(VL-VH)-Fc whereby the Fc fragment connects with VRC26.25 or PGDM1400 (V1V2 glycan bNAb) and protrudes from the apex of the trimer (FIG. 2), or ii) the "Reverse" orientation: VRC26.25/PGDM1400(VH-VL)-PGT121(VH-VL)-VRC01(VH-VL)-35O22(VH-VL)-10E8v4(VH-VL)-Fc whereby the Fc fragment connects with 10E8v4 (MPER bNAb) and protrudes from the trimer MPER region (FIG. 6A). Additionally, "knob into hole" technology (Ridgway et al., Protein Eng 9, 617-621 (1996)) was utilized to generate a heterodimer of the "Forward" and "Reverse" PentaNAb arms for subsequent evaluation, with LS mutations (M428L/N434S) in the Fc fragment for elongated antibody in vivo half-lives as well as improved biodistribution into the mucosal compartment (Ko et al., Nature 514, 642-645 (2014)) (FIG. 6B).

Three selected Penta-ScFvs and full length IgGs were expressed in mammalian 293FreeStyle cells and purified by Ni+ and protein A columns (FIG. 7), respectively. All the proteins have expected molecular weight, as shown in representative SDS-PAGE gels (FIG. 7A), size exclusion chromatography (SEC), and dynamic light scattering (DLS) analysis (data not shown). Furthermore, the binding specificities of these antibodies were validated by ELISA binding assay (not shown), and Bio-Layer Interferometry (BLI) (data not shown).

Figures 7A, 7B:
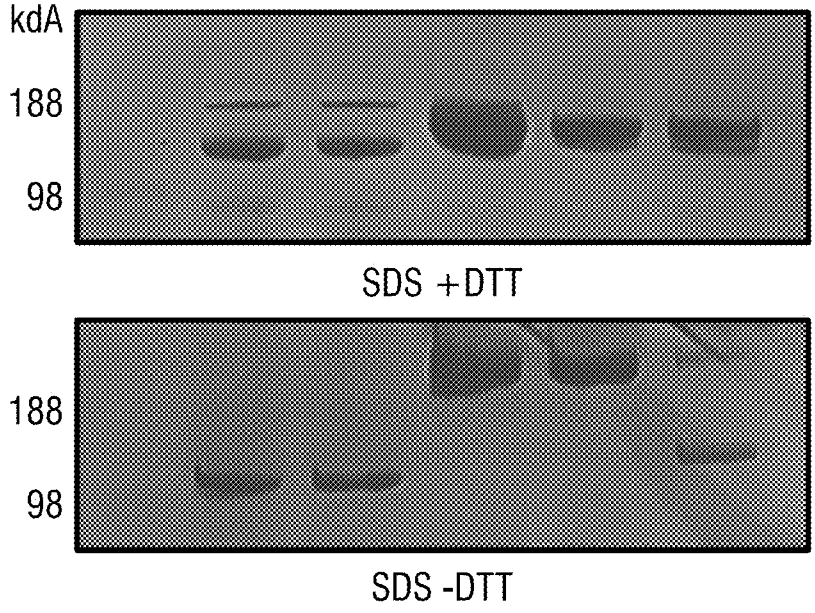
FIG. 7. Comparison of PentaNAbs in both the Forward, Reverse and Forward/Reverse orders. (A) SDS PAGE gel analysis for PentaNAbs; (B) Summary of neutralization breadth and potency of PentaNAbs against a 26-virus panel of high stringency; (C) Neutralization IC50 values of PentaNAbs against the 26-virus panel. The IC50 was adjusted to account for the molarity difference between the antibodies.

To compare the neutralization potency and breadth of the Penta-ScFvs and IgGs in the "Forward", "Reverse" and "Forward/Reverse" orientations, a virus panel of high stringency consisting of 26 tier-2 virus strains (FIGS. 7B & 7C) was used. Of the multiple iterations tested, it was found that the Penta-ScFv and Penta-IgG in the "Reverse" orientation displayed improved potency while maintaining the same breadth (virus coverage) as those in the "Forward" orientation (FIGS. 7B & 7C). Somewhat expectedly, the "Forward/Reverse" IgG orientation displayed a potency in between that of the "Forward" and "Reverse" IgG (FIGS. 7B & 7C). Thus, the "Reverse" orientation of Penta-ScFv and Penta-IgG could be applied to generate antiviral agent in the future.

Example 2. Design of Pentaspecific HIV Antibodies

Advances in the treatment of human immunodeficiency virus (HIV) infection have led to dramatic improvements in health outcomes of infected individuals receiving antiretroviral therapy (ART) over the course of the last several decades. By suppressing plasma viremia with ART, life expectancy has approached that of uninfected individuals, turning what was once an almost uniformly fatal illness into a manageable chronic disease. Nonetheless, the vast majority of HIV-infected individuals must remain on continuous therapy given that virus inevitably rebounds following discontinuation of ART. Furthermore, current ART requires life-long adherence to daily medication regimens and is associated with significant costs, cumulative toxicities, and the potential for emergence of drug-resistant virus. Consequently, intense efforts have been made in recent years to develop therapeutic strategies aimed at achieving ART-free virologic remission in infected individuals. Among those, recent discoveries of a number of highly potent broadly neutralizing HIV-specific antibodies (bNAbs) isolated from B cells of viremic HIV-infected individuals have materialized as a basis for realistic and feasible approaches for HIV prevention and immunotherapy.

Recent clinical trials conducted to assess the safety, tolerability, and virologic efficacy of multiple infusions of several bNAbs have shown to be safe, well-tolerated, and exhibit antiretroviral activities against HIV. However, these human trials have concomitantly shown that therapies involving single bNAbs are unlikely to suppress plasma viremia for prolonged periods of time due to both pre-existing and emergent HIV mutations that are resistant to the antibody-mediated neutralization. Therefore, it is of great interest to develop a combination approach to increase the specificity and potency of bNAbs (or bNAb-like) molecules against a broad spectrum of infectious HIV in patients. In order to achieve this goal, we have developed synergistically combined functional epitope-binding moieties from five bNAbs that target the CD4 binding site, V2 and V3 conserved glycans, gp120/gp41 interface, as well as the membrane exterior proximal region into a 'single' penta-specific antibody (penta-NAb).

Thus far, our penta-Nabs exhibited superior degrees of HIV inhibition (neutralization of 99.5% of a 208 pseudotyped HIV panel), exceptional neutralization capacity (IC50 at 0.006 μg/ml) compared to individual bNAbs, and the capacity to neutralize replication-competent HIV isolates from infected individuals whose virus became resistant to various single bNAbs inferring our penta-Nabs the potential to overcome immune-evasion and eliminate persistent HIV reservoirs.

In this example, it was proposed to:

1) generate multiple penta-Nabs by incorporating five candidate bNAbs exhibiting the highest levels of neutralization against >300 individual infectious viral isolates obtained from the persistent viral reservoir of infected individuals receiving ART.

2) engineer/modify the Fc region to extend the in vivo half-life of each penta-NAb.

3) generate several penta-bNAb/anti-CD3 antibody-based molecules that are capable of binding cell-surface Env and inducing CD8+ T cell-mediated killing of HIV reservoirs in vitro and in vivo.

4) measure the efficacy of penta-NAbs in NSG mice following administration of peripheral blood mononuclear cells (PBMCs) from ART-naïve, HIV-infected individuals whose viral reservoirs carry sensitive and/or resistant virus to individual bNAbs.

5) evaluate the capacity of penta-bNAbs and DART molecules to prevent plasma viral rebound in NSG mice injected with from HIV-infected individuals following discontinuation of ART The overall outcome of this study will provide the first proof of concept that a "5-in-1" antibody can achieve long-lasting broad-spectrum HIV inhibition in vivo, which will substantially advance our basic understanding of protective immunity against persistent virus infection and contribute to the development of safe and effective strategies toward ART-free virologic remission.

Results

Figure 9A:
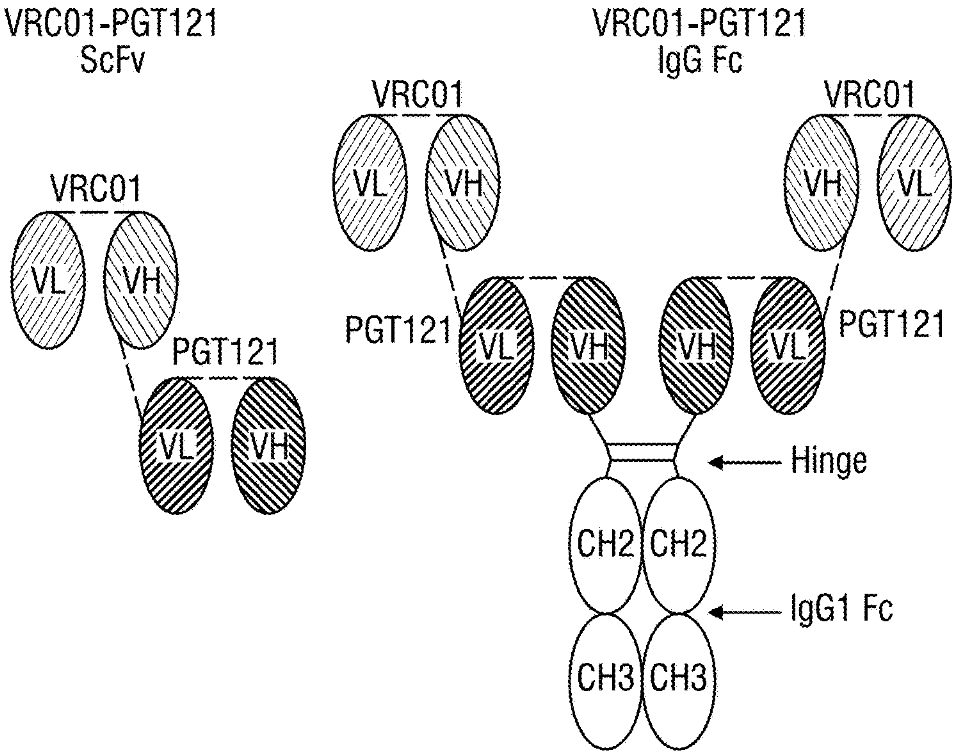
FIG. 9. Bi-ScFv and bi-NAb of VRC01-PGT121 design and EM analysis. (A) Schematic presentation of VRC01-PGT121 ScFv and full length IgG. (B) EM analysis of Env trimer BG505 SOSIP.664 and VRC01-PGT121 ScFv complex suggests bi-specific binding mode. Left, representative EM image of Env trimer BG505 SOSIP.664 and VRC01-PGT121 bi-ScFv complex. Arrows indicate ScFv molecules. Right, EM image of PGV04 (green) and PGT122 (blue) Fab complex with BG505 SOSIP.664 simultaneously.
Figure 9B:
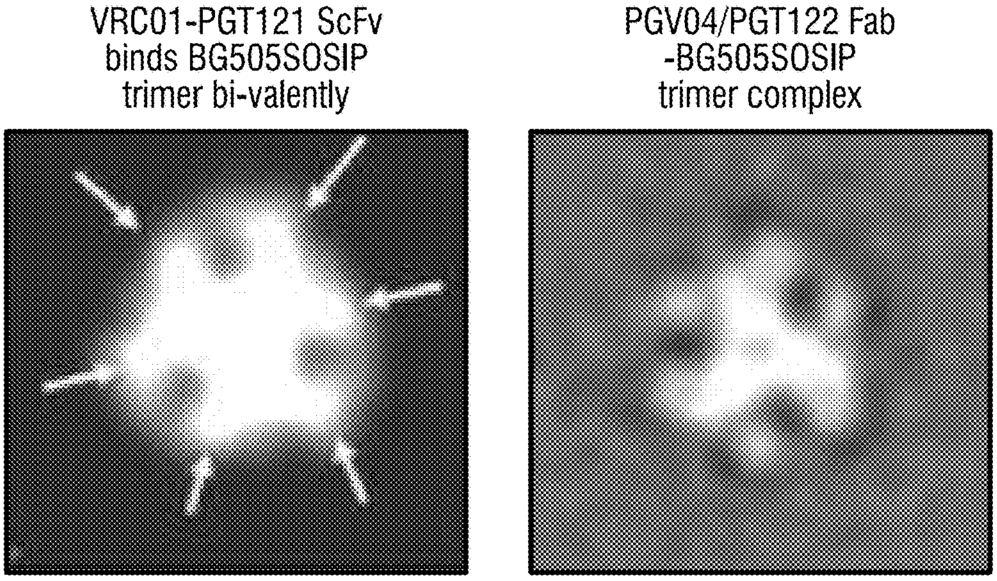

A clinical trial was previously conducted to investigate whether a bNAb VRC01 could prevent plasma viral rebound in infected individuals upon discontinuation of ART. While multiple infusions of VRC01 were safe and well-tolerated, the majority of patients experienced plasma viral rebound due to pre-existing and emergent antibody resistant HIV, suggesting therapeutic strategies involving passive transfer of bNAbs may require a combination(s) of bNAbs that targets more than one region on HIV Env protein in order to achieve sustained virologic control in HIV-infected individuals upon withdrawal of ART. Thus, building upon the outcome of the data, it was proposed to test HIV Env-specific antibodies possessing multi-functional moieties with improved antigen binding and/or virus neutralization capacities, which may translate into superior protective efficacy in subsequent studies. The preliminary data, derived from five of the constructs, demonstrated the feasibility of the methodology and linkage to the studies proposed here. Taking the first step toward generating multi-epitope targeting bNAbs, it was sought to test if one could engineer bi-specific single-chain variable fragment (bi-ScFv) consisting of bNAbs VRC01 and PGT121. As shown in FIG. 9A, a series of VRC01-PGT121 bi-ScFvs and full length IgGs were generated with combinations and permutations of VH-VL orientations and linker length. It was shown using single molecule electron microscopy (EM) analysis that the VRC01-PGT121 bi-ScFv binds Env trimer in a bi-specific manner (FIG. 9B). The virus neutralization capacity of the bispecific molecules (Bi-BNAb) against a virus panel consisting of 208 primary virus isolates was evaluated and demonstrated ~95% virus neutralization breadth, which is substantially expanded compared to that of the parent mAbs (VRC01 90% and PGT121 64%).

Using the knob-into-hole technology, the VRC01-PGT121 Bi-NAb was combined with 1) the moiety of MPER mAb 10E8 to form Tri-NAb; and 2) another Bi-NAb consisting of gp120/gp41 interface mAb and 10E8 in two different N-term to C-term orientations to form Tet-NAb 1 and 2. Finally, a scFV was created connecting variable regions of five bNAbs, namely penta-NAb, which engages all of the five conserved epitopes of HIV Env trimer (FIG. 2).

Figure 10:
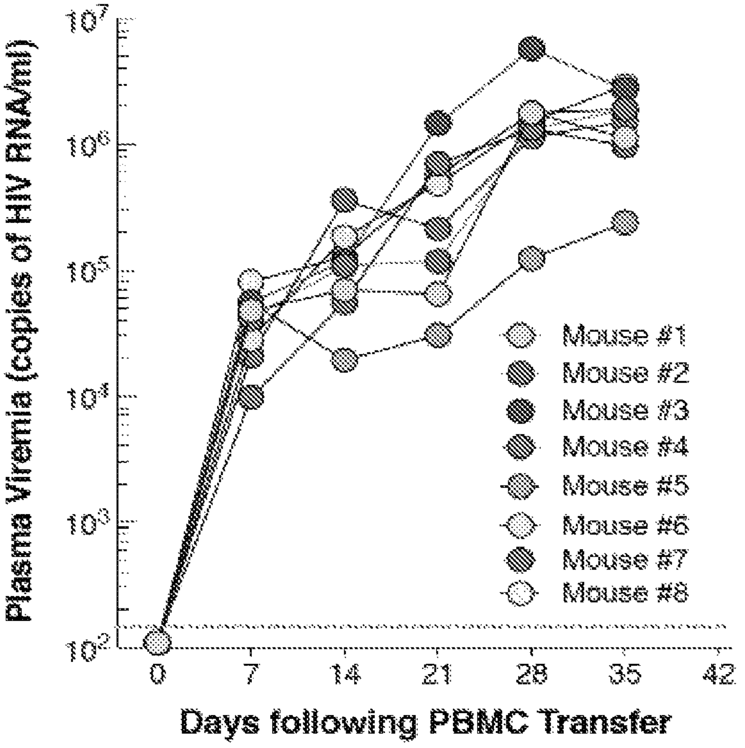
FIG. 10. Levels of HIV replication in NOD-scid IL2Re[11] (NSG) mice. PBMCs from an HIV-infected, ART-naïve individuals were injected to 8 mice and plasma viremia was monitored over time. The limit of detection was 20 copies/ml as measured by Roche Ampliprep/COBAS HIV-1 Test Version 2.

Interestingly, Tri-NAb, Tet-NAbs and Penta-NAb demonstrate remarkably improved neutralization breadth and potency compared to the parental mAbs (FIG. 3A). The superior neutralization breadth and potency possessed by the multi-epitope targeting NAbs are likely caused by cooperative and sometimes synergistic effect. Thus, the engineered multi-epitope targeting NAbs, which target three to five out of the five major conserved HIV Env neutralizing epitopes, could achieve nearly perfect virus coverage with IC50 geometric mean below 0.1 μg/ml. Furthermore, the neutralization capacity of the Penta-scFV and Penta-Nab was tested, which display neutralization breadth and potency outperforming the parental monoclonal antibodies and combinations (FIG. 5C). These multi-NAbs possessing remarkably improved breadth and potency represent excellent functional modules for next generation candidate therapeutic molecules. In order to generate in vivo efficacy data, NSG mice will be utilized that are injected with PBMCs from HIV-infected viremic and aviremic individuals. As shown in FIG. 10, all 8 mice exhibited robust HIV replication following transfer of 8×106 PBMCs from an viremic individual who was ART-naïve. These data demonstrate that the above animal system could be used to measure the efficacy of penta-NAbs and DART molecules against HIV derived from viral reservoirs from infected individuals who may carry sensitive and resistant HIV to certain bNAb.

Example 3

Figure 11:
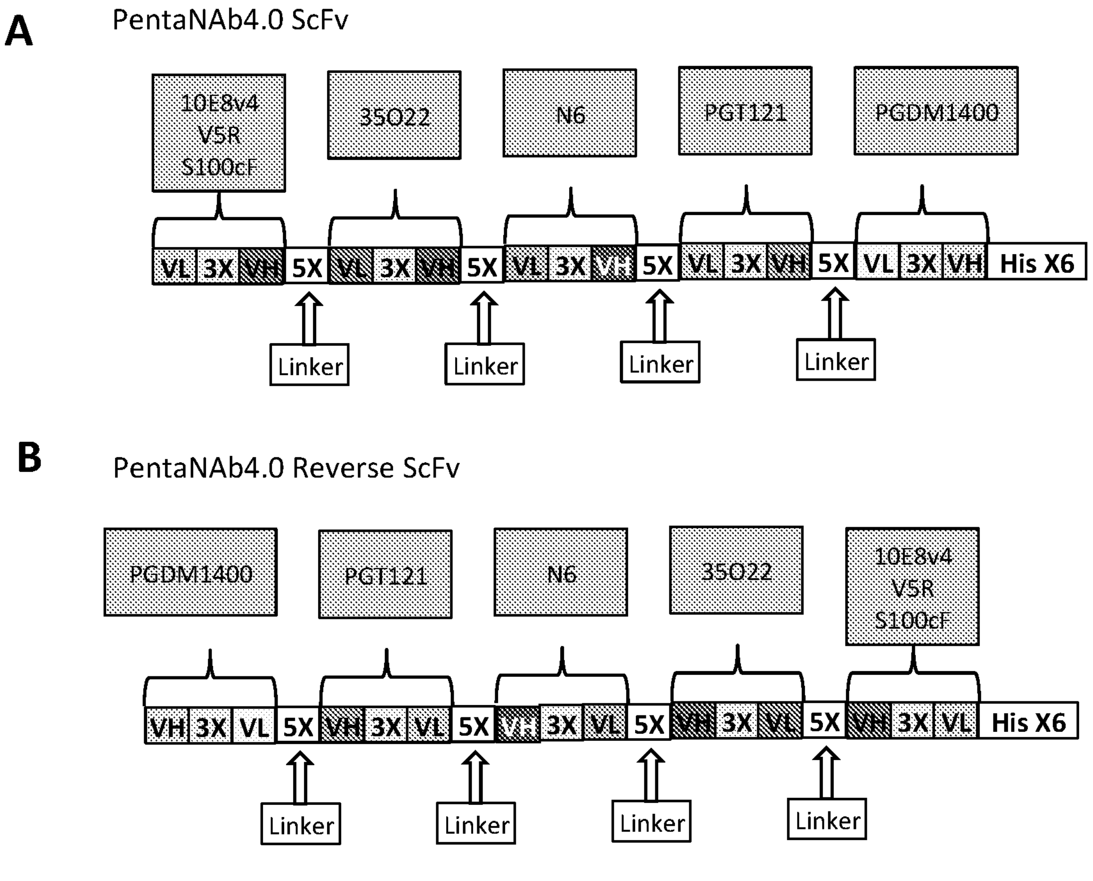
FIG. 11A-B. (A) Design of PentaNAb4.0 Forward ScFV (FIG. 11A) and PentaNAb 4.0 Reverse ScFv (FIG. 11B).

The neutralization profiles of PentaNAb2.0 Reverse ScFv, PentaNAb4.0 Forward ScFv (depicted in FIG. 11A), and PentaNAb4.0 Reverse ScFv (depicted in FIG. 11B) were tested with 208-virus panel (FIGS. 14A & B). It was confirmed that PentaNAb2.0 Reverse ScFv has incremental improvement in potency (IC 50 geometric mean) compared to the initial design, PentaNAb2.0 ScFv (FIGS. 14A & B).

A new multi-specific antibody was constructed, namely HexaNAb 1.0 ScFv (FIG. 12), which contains PentaNAb4.0 Reverse ScFv and variable domains of dB4C7/UB-421, an anti-CD4 antibody (N Engl J Med. 2019 Apr. 18; 380(16): 1535-1545. PMID: 30995373; patent U.S. Pat. No. 7,501,494B2) to 1) enhance the antiviral breadth, and 2) potentially inhibit the emergence of resistant virus variants as demonstrated by a recent clinical trial described in this cited reference. The HexaNAb 1.0 ScFv shows 100% virus neutralization breadth and promising potency (IC50 geometric mean 0.005 ug/mL) (FIGS. 14 A & B).

Figure 13:
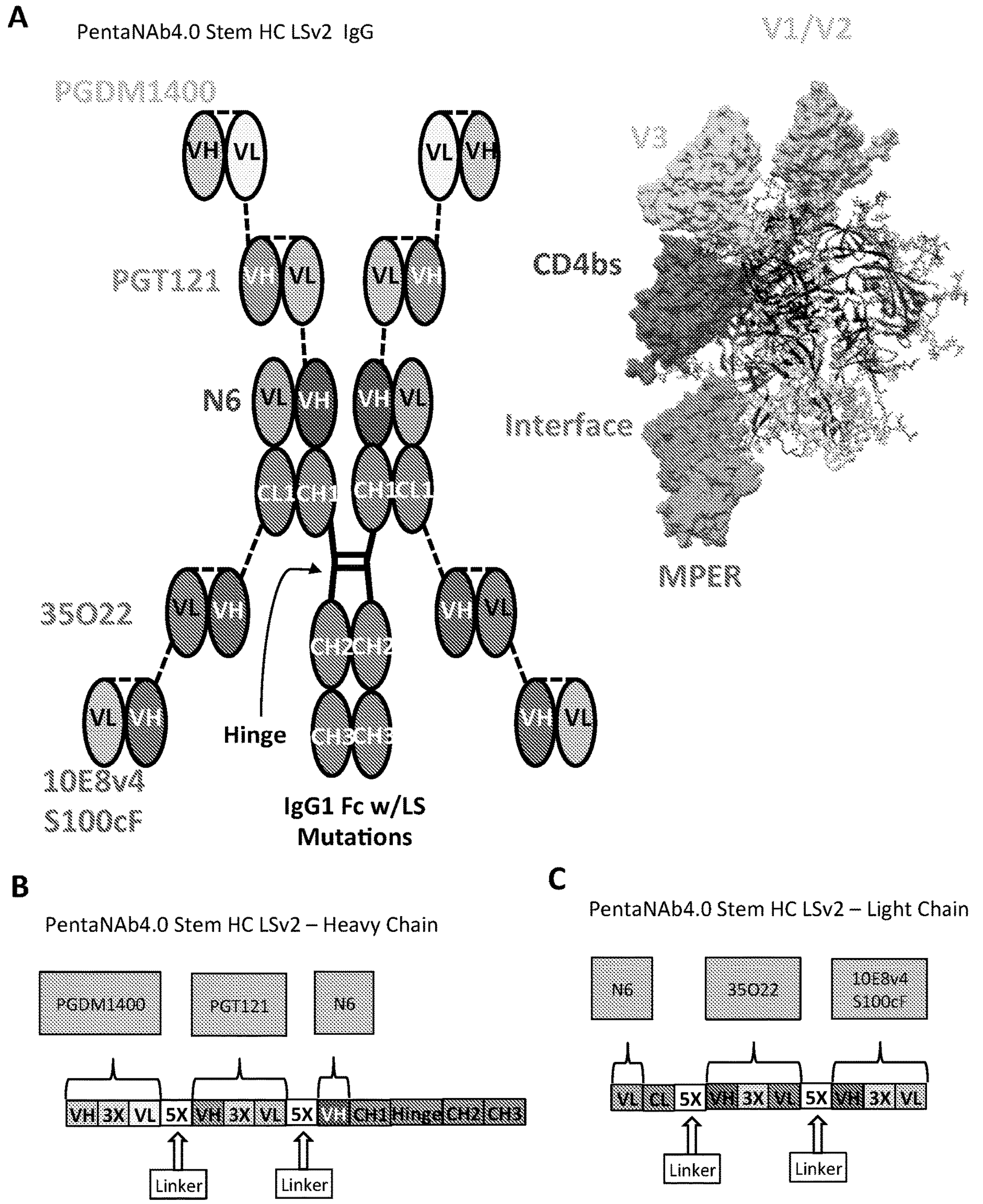
FIG. 13A-C. Design of a Penta-specific antibody in full-length IgG form, namely PentaNAb4.0 Stem HC LS v2 IgG (FIG. 13A), expressed as an IgG assembled from a heavy chain (FIG. 13B) and a light chain (FIG. 13C). The antibody contains the M428L/N434S (LS) mutation in the Fc domain to elongate antibody in vivo half-life. The heavy chain consists of V2 bNAb PGDM1400, V3 bNAb PGT121, and the VH domain of CD4bs bNAb N6 (FIG. 13B). The light chain contains the VL domain of N6 and 35O22 and 10E8v4 S100cF (FIG. 13C).

A new version of Penta-specific antibody in full-length IgG form was constructed (FIG. 13), namely PentaNAb4.0 Stem HC LS v2 IgG, expressed as an IgG assembled from a heavy chain and a light chain. With the M428L/N434S (LS) mutation in the Fc domain to elongate antibody in vivo half-life, the heavy chain consists of V2 bNAb PGDM1400, V3 bNAb PGT121, and the VH domain of CD4bs bNAb N6. The light chain contains the VL domain of N6 and 35O22 and 10E8v4 S100cF.

The PentaNAb4.0 Stem HC LS v2 IgG demonstrates 99.5% virus coverage (207/208 viruses tested) and high potency (IC50 geometric mean ~0.02 ug/mL) (FIGS. 14A & B), which is comparable to the Sanofi Tri-specific antibodies, 10E8v4xPGDM1400/VRC01 and 10E8v4xPGDM1400/N6-LS (FIG. 14B). The 5-specificity feature of the PentaNAb4.0 Stem HC LS v2 IgG may inhibit the emergence of neutralization resistant virus better than the other antibodies possessing less specificities (e.g. Tri-specific antibodies).

PentaNAb4.0 Reverse ScFv
[PGDM1400(VH-3X-VL)]-5X-[PGT121(VH-3X-VL)]-5X-[N6(VH-3X-VL)]-5X-
[35O22(VH-3X-VL)]-5X-[10E8v4 V5R S100cF(VH-3X-VL)]-His
Amino acid sequence (SEQ ID NO: 90)

MGWSCIILFLVATATGVHSQAQLVQSGPEVRKPGTSVKVSCKAPGNTLKTYDLHWVRSVPGQGLQWMGWISH

EGDKKVIVERFKAKVTIDWDRSTNTAYLQLSGLTSGDTAVYYCAKGSKHRLRDYALYDDDGALNWAVDVDYL

SNLEFWGQGTAVTVSSGGGGSGGGGSGGGGSDFVLTQSPHSLSVTPGESASISCKSSHSLIHGDRNNYLAWY

VQKPGRSPQLLIYLASSRASGVPDRFSGSGSDKDFTLKISRVETEDVGTYYCMQGRESPWTFGQGTKVDIKG

GGGSGGGGSGGGGSGGGGSGGGGSQMQLQESGPGLVKPSETLSLTCSVSGASISDSYWSWIRRSPGKGLEWI

GYVHKSGDTNYSPSLKSRVNLSLDTSKNQVSLSLVAATAADSGKYYCARTLHGRRIYGIVAFNEWFTYFYMD

VWGNGTQVTVSSGGGGSGGGGSGGGGSSDISVAPGETARISCGEKSLGSRAVQWYQHRAGQAPSLIIYNNQD

RPSGIPERFSGSPDSPFGTTATLTITSVEAGDEADYYCHIWDSRVPTKWVFGGGTTLTVLGGGGSGGGGSGG

GGSGGGGSGGGGSRAHLVQSGTAMKKPGASVRVSCQTSGYTFTAHILFWERQAPGRGLEWVGWIKPQYGAVN

FGGGFRDRVTLTRDVYREIAYMDIRGLKPDDTAVYYCARDRSYGDSSWALDAWGQGTTVVVSAGGGGSGGGG

SGGGGSYIHVTQSPSSLSVSIGDRVTINCQTSQGVGSDLHWYQHKPGRAPKLLIHHTSSVEDGVPSRFSGSG

FHTSFNLTISDLQADDIATYYCQVLQFFGRGSRLHIKGGGGSGGGGSGGGGSGGGGSGGGGSQGQLVQSGAE

LKKPGASVKISCKTSGYRFNFYHINWIRQTAGRGPEWMGWISPYSGDKNLAPAFQDRVIMTTDTEVPVTSFT

STGAAYMEIRNLKFDDTGTYFCAKGLLRDGSSTWLPYLWGQGTLLTVSSGGGGSGGGGSGGGGSQSVLTQSA

SVSGSLGQSVTISCTGPNSVCCSHKSISWYQWPPGRAPTLIIYEDNERAPGISPRFSGYKSYWSAYLTISDL

RPEDETTYYCCSYTHNSGCVFGTGTKVSVLGGGGSGGGGSGGGGSGGGGSGGGGSEVRLRESGGGLVKPGGS

LRLSCSASGFDFDNAWMTWVRQPPGKGLEWVGRITGPGEGWSVDYAESVKGRFTISRDNTKNTLYLEMNNVR

TEDTGYYFCARTGKYYDFWEGYPPGEEYFQDWGQGTLVIVSSGGGGSGGGGSGGGGSSELTQDPAVSVALKQ

TVTITCRGDSLRSHYASWYQKKPGQAPVLLFYGKNNRPSGIPDRFSGSASGNRASLTITGAQAEDEADYYCS

SRDKSGSRLSVFGGGTKLTVLGSGHHHHHH

DNA sequence (SEQ ID NO. 91)

ATGGGCTGGAGCTGCATCATCCTGTTCCTGGTGGCAACCGCAACAGGAGTGCACAGCCAGGCACAGCTGGTG

CAGAGCGGACCCGAAGTGAGAAAACCTGGGACTAGCGTCAAAGTGTCATGTAAAGCCCCTGGAAATACCCTG

AAGACCTACGATCTGCACTGGGTGCGGTCCGTGCCTGGACAGGGCCTGCAGTGGATGGGATGGATCTCTCAC

GAGGGCGACAAGAAAGTGATCGTGGAGCGGTTCAAGGCCAAGGTGACAATCGATTGGGACAGATCCACCAAC

ACAGCCTACCTGCAGCTGTCTGGCCTGACCAGCGGCGATACAGCCGTGTACTACTGTGCCAAGGGCTCTAAG

CACCGGCTGAGAGACTACGCCCTGTATGACGATGACGGCGCCCTGAACTGGGCCGTGGATGTGGACTATCTG

TCCAATCTGGAGTTCTGGGGACAGGGAACCGCAGTGACAGTGAGCTCCGGAGGAGGAGGCTCCGGCGGCGGA

GGCTCTGGGGGAGGCGGCAGCGATTTTGTGCTGACCCAGTCTCCACACAGCCTGTCCGTGACACCCGGCGAG

TCTGCCAGCATCTCCTGCAAGTCTAGCCACAGCCTGATCCACGGCGACAGGAACAATTACCTGGCCTGGTAC

GTGCAGAAGCCAGGCCGCAGCCCTCAGCTGCTGATCTATCTGGCATCCTCTAGGGCCTCCGGAGTGCCAGAT

CGCTTCTCTGGCAGCGGCTCCGATAAGGACTTTACCCTGAAGATCAGCCGGGTGGAGACAGAGGACGTGGGC

ACATACTATTGTATGCAGGGCCGAGAATCACCTTGGACATTTGGGCAGGGAACTAAAGTTGACATCAAAGGG

GGGGGGGGCTCCGGCGGCGGGGGCTCTGGCGGCGGCGGCAGCGGAGGAGGCGGCTCCGGAGGAGGCGGCTCT

CAGATGCAGCTGCAGGAGAGCGGACCAGGACTGGTGAAGCCTTCCGAGACCCTGTCTCTGACATGTTCTGTG

AGCGGCGCCTCCATCTCTGATAGCTACTGGAGCTGGATCAGACGGAGCCCTGGCAAGGGCCTGGAGTGGATC

GGCTACGTGCACAAGTCTGGCGATACAAACTATTCCCCATCTCTGAAGAGCCGGGTGAACCTGAGCCTGGAC

ACCTCCAAGAATCAGGTGAGCCTGTCCCTGGTGGCAGCAACCGCAGCAGACAGCGGCAAGTACTATTGCGCC

-continued

AGAACACTGCACGGCAGGCGCATCTACGGCATCGTGGCCTTTAACGAGTGGTTCACCTACTTTTATATGGAC

GTGTGGGGCAATGGCACCCAGGTGACAGTGTCCTCTGGCGGCGGCGGCTCTGGCGGAGGAGGCAGCGGAGGA

GGAGGCAGCTCCGACATCTCTGTGGCACCTGGAGAGACCGCAAGGATCAGCTGTGGAGAGAAGTCTCTGGGC

AGCAGGGCCGTGCAGTGGTACCAGCACAGGGCAGGACAGGCACCATCCCTGATCATCTATAACAATCAGGAC

CGGCCATCTGGCATCCCCGAGAGATTCTCTGGCAGCCCCGATAGCCCTTTTGGCACCACAGCCACCCTGACA

ATCACCTCCGTGGAGGCCGGCGACGAAGCAGATTACTATTGCCACATCTGGGACTCCAGAGTGCCAACCAAG

TGGGTGTTCGGAGGAGGAACCACACTGACAGTGCTGGGCGGCGGAGGCTCCGGCGGGGGCGGCTCTGGAGGC

GGCGGCAGCGGAGGGGGCGGCTCCGGCGGCGGCGGCTCTAGGGCACACCTGGTGCAGAGCGGAACCGCAATG

AAGAAGCCTGGCGCCTCTGTGCGCGTGAGCTGTCAGACATCCGGCTACACCTTCACCGCCCACATCCTGTTC

TGGTTTAGGCAGGCACCAGGAAGAGGACTGGAGTGGGTGGGCTGGATCAAGCCCCAGTATGGAGCAGTGAAC

TTCGGAGGAGGCTTTCGGGACAGAGTGACACTGACCCGGGACGTGTACAGAGAGATCGCCTATATGGATATC

AGGGGCCTGAAGCCCGACGATACCGCCGTGTACTATTGCGCCAGGGACCGCTCCTACGGCGATTCTAGCTGG

GCACTGGACGCATGGGGACAGGGAACCACAGTGGTGGTGAGCGCCGGAGGCGGGGGCAGCGGCGGCGGGGGC

TCCGGAGGCGGAGGCTCTTACATCCACGTGACCCAGTCCCCTTCCTCTCTGTCCGTGTCTATCGGCGATCGC

GTGACCATCAACTGTCAGACAAGCCAGGGAGTGGGCTCCGACCTGCACTGGTATCAGCACAAGCCTGGCAGG

GCCCCAAAGCTGCTGATCCACCACACAAGCTCCGTGGAGGATGGAGTGCCAAGCCGCTTCAGCGGCTCCGGA

TTCCACACCAGCTTTAATCTGACAATCTCCGACCTGCAGGCCGACGATATCGCCACCTACTATTGCCAGGTG

CTGCAGTTCTTTGGCAGGGGCTCCCGCCTGCACATCAAGGGCGGCGGCGGCTCTGGGGGCGGGGGCAGCGGC

GGGGGGGGCTCCGGGGGAGGAGGCTCTGGCGGAGGGGGCAGCCAGGGCCAGCTGGTGCAGAGCGGAGCAGAG

CTGAAGAAGCCAGGAGCCTCTGTGAAGATCAGCTGTAAGACATCCGGCTATCGGTTCAACTTTTATCACATC

AATTGGATCAGGCAGACCGCAGGAAGGGGACCAGAGTGGATGGGCTGGATCTCCCCCTACTCTGGCGATAAG

AACCTGGCCCCAGCCTTCCAGGACAGAGTGATCATGACCACAGATACCGAGGTGCCAGTGACCAGCTTCACC

TCCACCGGAGCCGCCTACATGGAGATCCGGAATCTGAAGTTCGACGATACAGGCACCTATTTTTGCGCCAAG

GGCCTGCTGAGAGACGGCTCTAGCACATGGCTGCCATACCTGTGGGGACAGGGCACCCTGCTGACAGTGTCC

TCTGGAGGAGGAGGCTCCGGGGGCGGCGGCTCTGGAGGAGGAGGCTCTCAAAGCGTGCTGACCCAGTCCGCC

TCTGTGAGCGGCTCCCTGGGCCAGTCTGTGACCATCAGCTGTACAGGCCCCAACTCCGTGTGCTGTTCTCAC

AAGTCTATCAGCTGGTACCAGTGGCCACCAGGAAGGGCACCTACCCTGATCATCTATGAGGACAATGAGAGG

GCACCAGGAATCAGCCCTCGCTTCTCCGGCTACAAGTCTTATTGGAGCGCCTACCTGACCATTTCCGACCTG

CGCCCCGAGGATGAGACCACATACTATTGCTGTAGCTATACCCACAACTCCGGCTGCGTGTTTGGCACAGGC

ACCAAGGTGAGCGTGCTGGGAGGAGGGGGCTCTGGCGGCGGGGGCAGCGGCGGAGGCGGCTCCGGAGGGGGC

GGCTCTGGCGGAGGCGGCAGCGAGGTGCGGCTGCGGGAGAGCGGCGGCGGCCTGGTGAAGCCAGGCGGCTCT

CTGAGACTGTCCTGTTCTGCCAGCGGCTTCGACTTTGATAATGCCTGGATGACATGGGTGCGGCAGCCTCCT

GGCAAGGGGCTGGAGTGGGTGGGAAGAATCACCGGACCAGGAGAGGGATGGTCTGTGGACTACGCCGAGAGC

GTGAAGGGCCGGTTCACCATCAGCAGAGATAACACTAAAAATACACTGTATCTGGAGATGAACAATGTGCGG

ACCGAGGACACAGGCTACTATTTCTGCGCCAGAACCGGCAAGTACTATGATTTCTGGTTTGGCTACCCCCCT

GGCGAGGAGTATTTTCAGGACTGGGGCCAGGGCACCCTGGTCATCGTGAGCAGCGGCGGGGGAGGCTCCGGC

GGGGGGGGCTCTGGAGGAGGGGGCTCTAGCGAGCTGACCCAGGACCCCGCCGTGTCCGTGGCCCTGAAGCAG

ACAGTGACCATCACATGCAGGGGCGACTCCCTGCGCTCTCACTACGCCAGCTGGTATCAGAAGAAGCCAGGA

-continued

CAGGCACCCGTGCTGCTGTTCTACGGCAAGAACAATCGGCCTTCCGGCATCCCAGATAGATTTTCCGGCTCT

GCCAGCGGAAACAGGGCCAGCCTGACCATCACAGGAGCACAGGCAGAGGATGAAGCAGATTACTATTGTTCC

TCTCGGGACAAGTCCGGCTCTAGACTGAGCGTGTTCGGCGGCGGAACCAAGCTGACAGTGCTGGGATCCGGT

CACCACCATCACCACCACTAG

HexaNAb1.0 Reverse ScFv
[dB4C7-UB-421(VL-3X-VH)]-5X-[PGDM1400(VH-3X-VL)]-5X-[PGT121(VH-3X-VL)]-5X-[N6(VH-3X-VL)]-5X-[35O22(VH-3X-VL)]-5X-[10E8v4 V5R S100cF(VH-3X-VL)]-His
Amino acid sequence (SEQ ID NO: 92)

MGWSCIILFLVATATGVHSDIVLTQSPASLAVSLGQRATITCKAGQSVDYDGDSYMNWYQQKPGQPPKLLIY

VASNLESGIPARFSGSGSGTDFTLNIHPVEENDAATYYCQQSYKDPLTFGQGTKLEIKGGGGSGGGGSGGGG

SQVQLVQSGPELKKPGASVKVSCKASGYTFTDYVIHWVKQATGQGLEWIGETYPGSGSAYSNAKFKDRVTMT

ADKSSNTAYMELSSLTSDDTAVYFCARRGNGTGFAYWGQGTLVTVSSGGGGSGGGGSGGGGSGGGGSGGGGS

QAQLVQSGPEVRKPGTSVKVSCKAPGNTLKTYDLHWVRSVPGQGLQWMGWISHEGDKKVIVERFKAKVTIDW

DRSTNTAYLQLSGLTSGDTAVYYCAKGSKHRLRDYALYDDDGALNWAVDVDYLSNLEFWGQGTAVTVSSGGG

GSGGGGSGGGGSDEVLTQSPHSLSVTPGESASISCKSSHSLIHGDRNNYLAWYVQKPGRSPQLLIYLASSRA

SGVPDRFSGSGSDKDFTLKISRVETEDVGTYYCMQGRESPWTFGQGTKVDIKGGGGSGGGGSGGGGSGGGGS

GGGGSQMQLQESGPGLVKPSETLSLTCSVSGASISDSYWSWIRRSPGKGLEWIGYVHKSGDTNYSPSLKSRV

NLSLDTSKNQVSLSLVAATAADSGKYYCARTLHGRRIYGIVAFNEWFTYFYMDVWGNGTQVTVSSGGGGSGG

GGSGGGGSSDISVAPGETARISCGEKSLGSRAVQWYQHRAGQAPSLIIYNNQDRPSGIPERFSGSPDSPFGT

TATLTITSVEAGDEADYYCHIWDSRVPTKWVFGGGTTLTVLGGGGSGGGGSGGGGSGGGGSGGGGSRAHLVQ

SGTAMKKPGASVRVSCQTSGYTFTAHILFWFRQAPGRGLEWVGWIKPQYGAVNFGGGFRDRVTLTRDVYREI

AYMDIRGLKPDDTAVYYCARDRSYGDSSWALDAWGQGTTVVVSAGGGGSGGGGSGGGGSYIHVTQSPSSLSV

SIGDRVTINCQTSQGVGSDLHWYQHKPGRAPKLLIHHTSSVEDGVPSRFSGSGFHTSFNLTISDLQADDIAT

YYCQVLQFFGRGSRLHIKGGGGSGGGGSGGGGSGGGGSGGGGSQGQLVQSGAELKKPGASVKISCKTSGYRF

NFYHINWIRQTAGRGPEWMGWISPYSGDKNLAPAFQDRVIMTTDTEVPVTSFTSTGAAYMEIRNLKFDDTGT

YFCAKGLLRDGSSTWLPYLWGQGTLLTVSSGGGGSGGGGSGGGGSQSVLTQSASVSGSLGQSVTISCTGPNS

VCCSHKSISWYQWPPGRAPTLIIYEDNERAPGISPRFSGYKSYWSAYLTISDLRPEDETTYYCCSYTHNSGC

VFGTGTKVSVLGGGGSGGGGSGGGGSGGGGSGGGGSEVRLRESGGGLVKPGGSLRLSCSASGFDFDNAWMTW

VRQPPGKGLEWVGRITGPGEGWSVDYAESVKGRFTISRDNTKNTLYLEMNNVRTEDTGYYFCARTGKYYDFW

FGYPPGEEYFQDWGQGTLVIVSSGGGGSGGGGSGGGGSSELTQDPAVSVALKQTVTITCRGDSLRSHYASWY

QKKPGQAPVLLFYGKNNRPSGIPDRFSGSASGNRASLTITGAQAEDEADYYCSSRDKSGSRLSVFGGGTKLT

VLGSGHHHHHH

DNA sequence (SEQ ID NO: 93)

ATGGGCTGGAGCTGCATCATCCTGTTCCTGGTGGCAACCGCAACAGGAGTGCACAGCGACATCGTGCTGACC

CAGTCTCCTGCCAGCCTGGCCGTGAGCCTGGGACAGAGGGCCACCATCACATGCAAGGCCGGCCAGTCTGTG

GACTACGATGGCGACAGCTACATGAACTGGTATCAGCAGAAGCCAGGCCAGCCCCCTAAGCTGCTGATCTAT

GTGGCCTCCAATCTGGAGTCTGGCATCCCTGCACGCTTCAGCGGCTCCGGCTCTGGAACCGACTTCACCCTG

AACATCCACCCAGTGGAGGAGAATGACGCCGCCACCTACTATTGCCAGCAGAGCTACAAGGACCCCCTGACC

TTCGGCCAGGGCACAAAGCTGGAGATCAAGGGAGGAGGAGGCAGCGGGGGAGGAGGCTCCGGAGGCGGCGGC

TCTCAGGTGCAGCTGGTGCAGTCCGGACCAGAGCTGAAGAAGCCAGGAGCCAGCGTGAAGGTGTCCTGTAAG

GCCTCTGGCTACACCTTCACAGATTATGTGATCCACTGGGTGAAGCAGGCAACAGGACAGGGCCTGGAGTGG

ATCGGAGAGATCTACCCAGGCAGCGGCTCCGCCTATTCCAACGCCAAGTTTAAGGATCGGGTGACCATGACA

-continued

GCCGACAAGAGCTCCAATACCGCCTATATGGAGCTGTCTAGCCTGACCTCTGACGATACAGCCGTGTACTTC
TGTGCCCGGAGAGGCAACGGCACAGGCTTTGCCTATTGGGGCCAGGGCACCCTGGTGACAGTGTCCTCTGGA
GGAGGAGGCAGCGGCGGCGGCGGCTCCGGAGGAGGCGGCTCTGGCGGCGGCGGCAGCGGAGGAGGCGGCTCC
CAGGCACAGCTGGTGCAGAGCGGACCCGAAGTGAGAAAACCTGGGACTAGCGTCAAAGTGTCATGTAAAGCC
CCTGGAAATACCCTGAAGACCTACGATCTGCACTGGGTGCGGTCCGTGCCTGGACAGGGCCTGCAGTGGATG
GGATGGATCTCTCACGAGGGCGACAAGAAAGTGATCGTGGAGCGGTTCAAGGCCAAGGTGACAATCGATTGG
GACAGATCCACCAACACAGCCTACCTGCAGCTGTCTGGCCTGACCAGCGGCGATACAGCCGTGTACTACTGT
GCCAAGGGCTCTAAGCACCGGCTGAGAGACTACGCCCTGTATGACGATGACGGCGCCCTGAACTGGGCCGTG
GATGTGGACTATCTGTCCAATCTGGAGTTCTGGGGACAGGGAACCGCAGTGACAGTGAGCTCCGGAGGAGGA
GGCTCCGGCGGCGGAGGCTCTGGGGGAGGCGGCAGCGATTTTGTGCTGACCCAGTCTCCACACAGCCTGTCC
GTGACACCCGGCGAGTCTGCCAGCATCTCCTGCAAGTCTAGCCACAGCCTGATCCACGGCGACAGGAACAAT
TACCTGGCCTGGTACGTGCAGAAGCCAGGCCGCAGCCCTCAGCTGCTGATCTATCTGGCATCCTCTAGGGCC
TCCGGAGTGCCAGATCGCTTCTCTGGCAGCGGCTCCGATAAGGACTTTACCCTGAAGATCAGCCGGGTGGAG
ACAGAGGACGTGGGCACATACTATTGTATGCAGGGCCGAGAATCACCTTGGACATTTGGGCAGGGAACTAAA
GTTGACATCAAAGGGGGGGGGGGCTCCGGCGGCGGGGGCTCTGGCGGCGGCGGCAGCGGAGGAGGCGGCTCC
GGAGGAGGCGGCTCTCAGATGCAGCTGCAGGAGAGCGGACCAGGACTGGTGAAGCCTTCCGAGACCCTGTCT
CTGACATGTTCTGTGAGCGGCGCCTCCATCTCTGATAGCTACTGGAGCTGGATCAGACGGAGCCCTGGCAAG
GGCCTGGAGTGGATCGGCTACGTGCACAAGTCTGGCGATACAAACTATTCCCCATCTCTGAAGAGCCGGGTG
AACCTGAGCCTGGACACCTCCAAGAATCAGGTGAGCCTGTCCCTGGTGGCAGCAACCGCAGCAGACAGCGGC
AAGTACTATTGCGCCAGAACACTGCACGGCAGGCGCATCTACGGCATCGTGGCCTTTAACGAGTGGTTCACC
TACTTTTATATGGACGTGTGGGGCAATGGCACCCAGGTGACAGTGTCCTCTGGCGGCGGCGGCTCTGGCGGA
GGAGGCAGCGGAGGAGGAGGCAGCTCCGACATCTCTGTGGCACCTGGAGAGACCGCAAGGATCAGCTGTGGA
GAGAAGTCTCTGGGCAGCAGGGCCGTGCAGTGGTACCAGCACAGGGCAGGACAGGCACCATCCCTGATCATC
TATAACAATCAGGACCGGCCATCTGGCATCCCCGAGAGATTCTCTGGCAGCCCCGATAGCCCTTTTGGCACC
ACAGCCACCCTGACAATCACCTCCGTGGAGGCCGGCGACGAAGCAGATTACTATTGCCACATCTGGGACTCC
AGAGTGCCAACCAAGTGGGTGTTCGGAGGAGGAACCACACTGACAGTGCTGGGCGGCGGAGGCTCCGGCGGG
GGCGGCTCTGGAGGCGGCGGCAGCGGAGGGGGCGGCTCCGGCGGCGGCGGCTCTAGGGCACACCTGGTGCAG
AGCGGAACCGCAATGAAGAAGCCTGGCGCCTCTGTGCGCGTGAGCTGTCAGACATCCGGCTACACCTTCACC
GCCCACATCCTGTTCTGGTTTAGGCAGGCACCAGGAAGAGGACTGGAGTGGGTGGGCTGGATCAAGCCCCAG
TATGGAGCAGTGAACTTCGGAGGAGGCTTTCGGGACAGAGTGACACTGACCCGGGACGTGTACAGAGAGATC
GCCTATATGGATATCAGGGGCCTGAAGCCCGACGATACCGCCGTGTACTATTGCGCCAGGGACCGCTCCTAC
GGCGATTCTAGCTGGGCACTGGACGCATGGGGACAGGGAACCACAGTGGTGGTGAGCGCCGGAGGCGGGGGC
AGCGGCGGCGGGGGCTCCGGAGGCGGAGGCTCTTACATCCACGTGACCCAGTCCCCTTCCTCTCTGTCCGTG
TCTATCGGCGATCGCGTGACCATCAACTGTCAGACAAGCCAGGGAGTGGGCTCCGACCTGCACTGGTATCAG
CACAAGCCTGGCAGGGCCCCAAAGCTGCTGATCCACCACACAAGCTCCGTGGAGGATGGAGTGCCAAGCCGC
TTCAGCGGCTCCGGATTCCACACCAGCTTTAATCTGACAATCTCCGACCTGCAGGCCGACGATATCGCCACC
TACTATTGCCAGGTGCTGCAGTTCTTTGGCAGGGGCTCCCGCCTGCACATCAAGGGCGGCGGCGGCTCTGGG
GGCGGGGGCAGCGGCGGGGGGGGCTCCGGGGGAGGAGGCTCTGGCGGAGGGGGCAGCCAGGGCCAGCTGGTG
CAGAGCGGAGCAGAGCTGAAGAAGCCAGGAGCCTCTGTGAAGATCAGCTGTAAGACATCCGGCTATCGGTTC
AACTTTTATCACATCAATTGGATCAGGCAGACCGCAGGAAGGGGACCAGAGTGGATGGGCTGGATCTCCCCC

-continued

TACTCTGGCGATAAGAACCTGGCCCCAGCCTTCCAGGACAGAGTGATCATGACCACAGATACCGAGGTGCCA

GTGACCAGCTTCACCTCCACCGGAGCCGCCTACATGGAGATCCGGAATCTGAAGTTCGACGATACAGGCACC

TATTTTTGCGCCAAGGGCCTGCTGAGAGACGGCTCTAGCACATGGCTGCCATACCTGTGGGGACAGGGCACC

CTGCTGACAGTGTCCTCTGGAGGAGGAGGCTCCGGGGGCGGCGGCTCTGGAGGAGGAGGCTCTCAAAGCGTG

CTGACCCAGTCCGCCTCTGTGAGCGGCTCCCTGGGCCAGTCTGTGACCATCAGCTGTACAGGCCCCAACTCC

GTGTGCTGTTCTCACAAGTCTATCAGCTGGTACCAGTGGCCACCAGGAAGGGCACCTACCCTGATCATCTAT

GAGGACAATGAGAGGGCACCAGGAATCAGCCCTCGCTTCTCCGGCTACAAGTCTTATTGGAGCGCCTACCTG

ACCATTTCCGACCTGCGCCCCGAGGATGAGACCACATACTATTGCTGTAGCTATACCCACAACTCCGGCTGC

GTGTTTGGCACAGGCACCAAGGTGAGCGTGCTGGGAGGAGGGGGCTCTGGCGGCGGGGGCAGCGGCGGAGGC

GGCTCCGGAGGGGGCGGCTCTGGCGGAGGCGGCAGCGAGGTGCGGCTGCGGGAGAGCGGCGGCGGCCTGGTG

AAGCCAGGCGGCTCTCTGAGACTGTCCTGTTCTGCCAGCGGCTTCGACTTTGATAATGCCTGGATGACATGG

GTGCGGCAGCCTCCTGGCAAGGGGCTGGAGTGGGTGGGAAGAATCACCGGACCAGGAGAGGGATGGTCTGTG

GACTACGCCGAGAGCGTGAAGGGCCGGTTCACCATCAGCAGAGATAACACTAAAAATACACTGTATCTGGAG

ATGAACAATGTGCGGACCGAGGACACAGGCTACTATTTCTGCGCCAGAACCGGCAAGTACTATGATTTCTGG

TTTGGCTACCCCCCTGGCGAGGAGTATTTTCAGGACTGGGGCCAGGGCACCCTGGTCATCGTGAGCAGCGGC

GGGGGAGGCTCCGGCGGGGGGGGCTCTGGAGGAGGGGGCTCTAGCGAGCTGACCCAGGACCCCGCCGTGTCC

GTGGCCCTGAAGCAGACAGTGACCATCACATGCAGGGGCGACTCCCTGCGCTCTCACTACGCCAGCTGGTAT

CAGAAGAAGCCAGGACAGGCACCCGTGCTGCTGTTCTACGGCAAGAACAATCGGCCTTCCGGCATCCCAGAT

AGATTTTCCGGCTCTGCCAGCGGAAACAGGGCCAGCCTGACCATCACAGGAGCACAGGCAGAGGATGAAGCA

GATTACTATTGTTCCTCTCGGGACAAGTCCGGCTCTAGACTGAGCGTGTTCGGCGGCGGAACCAAGCTGACA

GTGCTGGGATCCGGTCACCACCATCACCACCACTAG

PentaNAb4.0 Stem HC LS_v2
HC: PGDM1400-5X-PGT121-5X-N6 HC
[PGDM1400(VH-3X-VL)]-5X-[PGT121(VH-3X-VL)]-5X-[N6(VH)]-CH1-CH2-CH3
Amino acid sequence (SEQ ID NO: 94)

MGWSCIILFLVATATGVHSQAQLVQSGPEVRKPGTSVKVSCKAPGNTLKTYDLHWVRSVPGQGLQWMGWISH

EGDKKVIVERFKAKVTIDWDRSTNTAYLQLSGLTSGDTAVYYCAKGSKHRLRDYALYDDDGALNWAVDVDYL

SNLEFWGQGTAVTVSSGGGGSGGGGSGGGGSDFVLTQSPHSLSVTPGESASISCKSSHSLIHGDRNNYLAWY

VQKPGRSPQLLIYLASSRASGVPDRFSGSGSDKDFTLKISRVETEDVGTYYCMQGRESPWTFGQGTKVDIKG

GGGSGGGGSGGGGSGGGGSGGGGSQMQLQESGPGLVKPSETLSLTCSVSGASISDSYWSWIRRSPGKGLEWI

GYVHKSGDTNYSPSLKSRVNLSLDTSKNQVSLSLVAATAADSGKYYCARTLHGRRIYGIVAFNEWFTYFYMD

VWGNGTQVTVSSGGGGSGGGGSGGGGSSDISVAPGETARISCGEKSLGSRAVQWYQHRAGQAPSLITYNNQD

RPSGIPERFSGSPDSPFGTTATLTITSVEAGDEADYYCHIWDSRVPTKWVFGGGTTLTVLGGGGSGGGGSGG

GGSGGGGSGGGGSRAHLVQSGTAMKKPGASVRVSCQTSGYTFTAHILFWERQAPGRGLEWVGWIKPQYGAVN

FGGGFRDRVTLTRDVYREIAYMDIRGLKPDDTAVYYCARDRSYGDSSWALDAWGQGTTVVVSAASTKGPSVF

PLAPSSKSTSGGTAALGCLVKDYFPEPVTVSWNSGALTSGVHTFPAVLQSSGLYSLSSVVTVPSSSLGTQTY

ICNVNHKPSNTKVDKKVEPKSCDKTHTCPPCPAPELLGGPSVFLFPPKPKDTLMISRTPEVTCVVVDVSHED

PEVKFNWYVDGVEVHNAKTKPREEQYNSTYRVVSVLTVLHQDWLNGKEYKCKVSNKALPAPIEKTISKAKGQ

-continued

PREPQVYTLPPSREEMTKNQVSLTCLVKGFYPSDIAVEWESNGQPENNYKTTPPVLDSDGSFFLYSKLTVDK

SRWQQGNVFSCSVLHEALHSHYTQKSLSLSPGK

DNA sequence (SEQ ID NO: 95)

ATGGGCTGGAGCTGCATCATCCTGTTCCTGGTGGCAACCGCAACCGGTGTGCACAGCCAGGCACAGCTGGTG

CAGAGCGGACCCGAAGTGAGAAAACCTGGGACTAGCGTCAAAGTGTCATGTAAAGCCCCTGGAAATACCCTG

AAGACCTACGATCTGCACTGGGTGCGGTCCGTGCCTGGACAGGGCCTGCAGTGGATGGGATGGATCTCTCAC

GAGGGCGACAAGAAAGTGATCGTGGAGCGGTTCAAGGCCAAGGTGACAATCGATTGGGACAGATCCACCAAC

ACAGCCTACCTGCAGCTGTCTGGCCTGACCAGCGGCGATACAGCCGTGTACTACTGTGCCAAGGGCTCTAAG

CACCGGCTGAGAGACTACGCCCTGTATGACGATGACGGCGCCCTGAACTGGGCCGTGGATGTGGACTATCTG

TCCAATCTGGAGTTCTGGGGACAGGGAACCGCAGTGACAGTGAGCTCCGGAGGAGGAGGCTCCGGCGGCGGA

GGCTCTGGGGGAGGCGGCAGCGATTTTGTGCTGACCCAGTCTCCACACAGCCTGTCCGTGACACCCGGCGAG

TCTGCCAGCATCTCCTGCAAGTCTAGCCACAGCCTGATCCACGGCGACAGGAACAATTACCTGGCCTGGTAC

GTGCAGAAGCCAGGCCGCAGCCCTCAGCTGCTGATCTATCTGGCATCCTCTAGGGCCTCCGGAGTGCCAGAT

CGCTTCTCTGGCAGCGGCTCCGATAAGGACTTTACCCTGAAGATCAGCCGGGTGGAGACAGAGGACGTGGGC

ACATACTATTGTATGCAGGGCCGAGAATCACCTTGGACATTTGGGCAGGGAACTAAAGTTGACATCAAAGGG

GGGGGGGGCTCCGGCGGCGGGGGCTCTGGCGGCGGCGGCAGCGGAGGAGGCGGCTCCGGAGGAGGCGGCTCT

CAGATGCAGCTGCAGGAGAGCGGACCAGGACTGGTGAAGCCTTCCGAGACCCTGTCTCTGACATGTTCTGTG

AGCGGCGCCTCCATCTCTGATAGCTACTGGAGCTGGATCAGACGGAGCCCTGGCAAGGGCCTGGAGTGGATC

GGCTACGTGCACAAGTCTGGCGATACAAACTATTCCCCATCTCTGAAGAGCCGGGTGAACCTGAGCCTGGAC

ACCTCCAAGAATCAGGTGAGCCTGTCCCTGGTGGCAGCAACCGCAGCAGACAGCGGCAAGTACTATTGCGCC

AGAACACTGCACGGCAGGCGCATCTACGGCATCGTGGCCTTTAACGAGTGGTTCACCTACTTTTATATGGAC

GTGTGGGGCAATGGCACCCAGGTGACAGTGTCCTCTGGCGGCGGCGGCTCTGGCGGAGGAGGCAGCGGAGGA

GGAGGCAGCTCCGACATCTCTGTGGCACCTGGAGAGACCGCAAGGATCAGCTGTGGAGAGAAGTCTCTGGGC

AGCAGGGCCGTGCAGTGGTACCAGCACAGGGCAGGACAGGCACCATCCCTGATCATCTATAACAATCAGGAC

CGGCCATCTGGCATCCCCGAGAGATTCTCTGGCAGCCCCGATAGCCCTTTTGGCACCACAGCCACCCTGACA

ATCACCTCCGTGGAGGCCGGCGACGAAGCAGATTACTATTGCCACATCTGGGACTCCAGAGTGCCAACCAAG

TGGGTGTTCGGAGGAGGAACCACACTGACAGTGCTGGGCGGCGGAGGCTCCGGCGGGGGCGGCTCTGGAGGC

GGCGGCAGCGGAGGGGGCGGCTCCGGCGGCGGCGGCTCTAGGGCACACCTGGTGCAGAGCGGAACCGCAATG

AAGAAGCCTGGCGCCTCTGTGCGCGTGAGCTGTCAGACATCCGGCTACACCTTCACCGCCCACATCCTGTTC

TGGTTTAGGCAGGCACCAGGAAGAGGACTGGAGTGGGTGGGCTGGATCAAGCCCCAGTATGGAGCAGTGAAC

TTCGGAGGAGGCTTTCGGGACAGAGTGACACTGACCCGGGACGTGTACAGAGAGATCGCCTATATGGATATC

AGGGGCCTGAAGCCCGACGATACCGCCGTGTACTATTGCGCCAGGGACCGCTCCTACGGCGATTCTAGCTGG

GCACTGGACGCATGGGGACAGGGAACCACAGTGGTGGTGAGCGCCGCGTCGACCAAGGGCCCATCGGTCTTC

CCCCTGGCACCCTCCTCCAAGAGCACCTCTGGGGGCACAGCGGCCCTGGGCTGCCTGGTCAAGGACTACTTC

CCCGAACCTGTGACGGTGTCGTGGAACTCAGGCGCCCTGACCAGCGGCGTGCACACCTTCCCGGCTGTCCTA

CAGTCCTCAGGACTCTACTCCCTCAGCAGCGTGGTGACCGTGCCCTCCAGCAGCTTGGGCACCCAGACCTAC

ATCTGCAACGTGAATCACAAGCCCAGCAACACCAAGGTGGACAAGAAAGTTGAGCCCAAATCTTGTGACAAA

ACTCACACATGCCCACCGTGCCCAGCACCTGAACTCCTGGGGGGACCGTCAGTCTTCCTCTTCCCCCCAAAA

CCCAAGGACACCCTCATGATCTCCCGGACCCCTGAGGTCACATGCGTGGTGGTGGACGTGAGCCACGAAGAC

CCTGAGGTCAAGTTCAACTGGTACGTGGACGGCGTGGAGGTGCATAATGCCAAGACAAAGCCGCGGGAGGAG

CAGTACAACAGCACGTACCGTGTGGTCAGCGTCCTCACCGTCCTGCACCAGGACTGGCTGAATGGCAAGGAG

-continued

TACAAGTGCAAGGTCTCCAACAAAGCCCTCCCAGCCCCCATCGAGAAAACCATCTCCAAAGCCAAAGGGCAG

CCCCGAGAACCACAGGTGTACACCCTGCCCCCATCCCGGGAGGAGATGACCAAGAACCAGGTCAGCCTGACC

TGCCTGGTCAAAGGCTTCTATCCCAGCGACATCGCCGTGGAGTGGGAGAGCAATGGGCAGCCGGAGAACAAC

TACAAGACCACGCCTCCCGTGCTGGACTCCGACGGCTCCTTCTTCCTCTACAGCAAGCTCACCGTGGACAAG

AGCAGGTGGCAGCAGGGGAACGTCTTCTCATGCTCCGTGCTGCATGAGGCTCTGCACAGCCACTACACGCAG

AAGAGCCTCTCCCTGTCTCCGGGTAAATGA

LC: N6 KC-CK-35022-5X-10E8v4 V5R S100cF
[N6(VL)]-CL-5X-[35O22(VH-3X-VL)]-5X-[10E8v4 S100cF(VH-3X-VL)]
Amino acid sequence (SEQ ID NO: 96)

MGWSCIILFLVATATGVHSYIHVTQSPSSLSVSIGDRVTINCQTSQGVGSDLHWYQHKPGRAPKLLIHHTSS

VEDGVPSRFSGSGFHTSFNLTISDLQADDIATYYCQVLQFFGRGSRLHIKRTVAAPSVFIFPPSDEQLKSGT

ASVVCLLNNFYPREAKVQWKVDNALQSGNSQESVTEQDSKDSTYSLSSTLTLSKADYEKHKVYACEVTHQGL

SSPVTKSFNRGECGGGGSGGGGSGGGGSGGGGSGGGGSQGQLVQSGAELKKPGASVKISCKTSGYRFNFYHI

NWIRQTAGRGPEWMGWISPYSGDKNLAPAFQDRVIMTTDTEVPVTSFTSTGAAYMEIRNLKFDDTGTYFCAK

GLLRDGSSTWLPYLWGQGTLLTVSSGGGGSGGGGSGGGGSQSVLTQSASVSGSLGQSVTISCTGPNSVCCSH

KSISWYQWPPGRAPTLIIYEDNERAPGISPRFSGYKSYWSAYLTISDLRPEDETTYYCCSYTHNSGCVFGTG

TKVSVLGGGGSGGGGSGGGGSGGGGSGGGGSEVRLVESGGGLVKPGGSLRLSCSASGFDFDNAWMTWVRQPP

GKGLEWVGRITGPGEGWSVDYAESVKGRFTISRDNTKNTLYLEMNNVRTEDTGYYFCARTGKYYDFWFGYPP

GEEYFQDWGQGTLVIVSSGGGGSGGGGSGGGGSSELTQDPAVSVALKQTVTITCRGDSLRSHYASWYQKKPG

QAPVLLFYGKNNRPSGIPDRFSGSASGNRASLTITGAQAEDEADYYCSSRDKSGSRLSVFGGGTKLTVL

DNA sequence (SEQ ID NO: 97)

ATGGGCTGGAGCTGCATCATCCTGTTCCTGGTGGCAACCGCAACAGGAGTGCACAGCTACATCCAC

GTGACCCAGTCCCCTTCCTCTCTGTCCGTGTCTATCGGCGATCGCGTGACCATCAACTGTCAGACAAGCCAG

GGAGTGGGCTCCGACCTGCACTGGTATCAGCACAAGCCTGGCAGGGCCCCAAAGCTGCTGATCCACCACACA

AGCTCCGTGGAGGATGGAGTGCCAAGCCGCTTCAGCGGCTCCGGATTCCACACCAGCTTTAATCTGACAATC

TCCGACCTGCAGGCCGACGATATCGCCACCTACTATTGCCAGGTGCTGCAGTTCTTTGGCAGGGGCTCCCGC

CTGCACATCAAGCGTACGGTGGCTGCACCATCTGTCTTCATCTTCCCGCCATCTGATGAGCAGTTGAAATCT

GGAACTGCCTCTGTTGTGTGCCTGCTGAATAACTTCTATCCCAGAGAGGCCAAAGTACAGTGGAAGGTGGAT

AACGCCCTCCAATCGGGTAACTCCCAGGAGAGTGTCACAGAGCAGGACAGCAAGGACAGCACCTACAGCCTC

AGCAGCACCCTGACGCTGAGCAAAGCAGACTACGAGAAACACAAAGTCTACGCCTGCGAAGTCACCCATCAG

GGCCTGAGCTCGCCCGTCACAAAGAGCTTCAACAGGGGAGAGTGTGGAGGAGGGGGCTCTGGCGGCGGGGGC

AGCGGCGGAGGCGGCTCCGGAGGGGGCGGCTCTGGCGGAGGCGGCAGCCAGGGCCAGCTGGTGCAGAGCGGA

GCAGAGCTGAAGAAGCCAGGAGCCTCTGTGAAGATCAGCTGTAAGACATCCGGCTACCGGTTCAACTTTTAT

CACATCAATTGGATCAGGCAGACCGCAGGAAGGGGACCAGAGTGGATGGGCTGGATCTCCCCCTACTCTGGC

GATAAGAACCTGGCCCCAGCCTTCCAGGACAGAGTGATCATGACCACAGATACCGAGGTGCCAGTGACCAGC

TTCACCTCCACCGGAGCCGCCTACATGGAGATCCGGAATCTGAAGTTCGACGATACAGGCACCTATTTTTGC

GCCAAGGGCCTGCTGAGAGACGGCTCTAGCACATGGCTGCCATACCTGTGGGGACAGGGCACCCTGCTGACA

GTGTCCTCTGGAGGAGGAGGCTCCGGGGGCGGCGGCTCTGGAGGAGGAGGCTCTCAAAGCGTGCTGACCCAG

TCCGCCTCTGTGAGCGGCTCCCTGGGCCAGTCTGTGACCATCAGCTGTACAGGCCCCAACTCCGTGTGCTGT

TCTCACAAGTCTATCAGCTGGTACCAGTGGCCACCAGGAAGGGCACCTACCCTGATCATCTATGAGGACAAT

GAGAGGGCACCAGGAATCAGCCCTCGCTTCTCCGGCTACAAGTCTTATTGGAGCGCCTACCTGACCATTTCC

-continued

GACCTGCGCCCCGAGGATGAGACCACATACTATTGCTGTAGCTATACCCACAACTCCGGCTGCGTGTTTGGC

ACAGGCACCAAGGTGAGCGTGCTGGGAGGAGGGGGCTCTGGCGGCGGGGGCAGCGGCGGAGGCGGCTCCGGA

GGGGGCGGCTCTGGCGGAGGCGGCAGCGAGGTGCGGCTGGTGGAGAGCGGCGGCGGCCTGGTGAAGCCAGGC

GGCTCTCTGAGACTGTCCTGTTCTGCCAGCGGCTTCGACTTTGATAATGCCTGGATGACATGGGTGCGGCAG

CCTCCTGGCAAGGGGCTGGAGTGGGTGGGAAGAATCACCGGACCAGGAGAGGGATGGTCTGTGGACTACGCC

GAGAGCGTGAAGGGCCGGTTCACCATCAGCAGAGATAACACTAAAAATACACTGTATCTGGAGATGAACAAT

GTGCGGACCGAGGACACAGGCTACTATTTCTGCGCCAGAACCGGCAAGTACTATGATTTCTGGTTTGGCTAC

CCCCCTGGCGAGGAGTATTTTCAGGACTGGGGCCAGGGCACCCTGGTCATCGTGAGCAGCGGCGGGGGAGGC

TCCGGCGGGGGGGGCTCTGGAGGAGGGGGCTCTAGCGAGCTGACCCAGGACCCCGCCGTGTCCGTGGCCCTG

AAGCAGACAGTGACCATCACATGCAGGGGCGACTCCCTGCGCTCTCACTACGCCAGCTGGTATCAGAAGAAG

CCAGGACAGGCACCCGTGCTGCTGTTCTACGGCAAGAACAATCGGCCTTCCGGCATCCCAGATAGATTTTCC

GGCTCTGCCAGCGGAAACAGGGCCAGCCTGACCATCACAGGAGCACAGGCAGAGGATGAAGCAGATTACTAT

TGTTCCTCTCGGGACAAGTCCGGCTCTAGACTGAGC mAb dB4C7/UB-421's perfect heavy chain Fv region (SEQ ID NO 98)
QVQLVQSGPELKKPGASVKVSCKASGYTFTDYVIHWVKQATGQGLEWIGEIYPGSGSA
YSNAKFKDRVTMTADKSSNTAYMELSSLTSDDTAVYFCARRGNGTGFAYWGQGTLVT
VSS mAb dB4C7/UB-421's perfect light chain Fv region (SEQ ID NO. 99)
DIVLTQSPASLAVSLGQRATITCKAGQSVDYDGDSYMNWYQQKPGQPPKLLIYVASNLE
SGIPARFSGSGSGTDFTLNIHPVEENDAATYYCQQSYKDPLTFGQGTKLEIK CDR1 of Heavy Chain of murine antibody B4
SEQ ID NO. 100
DYVIH CDR2 of Heavy Chain of murine antibody B4
SEQ ID NO. 101
EIYPGSGSAYSNAKFKD CDR3 of Heavy Chain of murine antibody B4
SEQ ID NO. 102
RGNGTGFAY -continued CDR1 of Light Chain of murine antibody B4
SEQ ID NO. 103
KAGQSVDYDGDSYMN CDR2 of Light Chain of murine antibody B4
SEQ ID NO. 104
VASNLES CDR3 of Light Chain of murine antibody B4
SEQ ID NO. 105
QQSYKDPLT

| SEQ ID NO: | Name | Orientation | Amino Acid Sequence |
|---|---|---|---|
| 92 | HexaNAb1.0 Reverse ScFv | (dB4C7/UB-421)-5X-PGDM1400-5X-PGT121-5X-N6-5X-35022-5X-10E8v4 V5R S100cF-His | MGWSCIILFLVATATGVHSDIVLTQSPASLAV SLGQRATITCKAGQSVDYDGDSYMNWYQQKPG QPPKLLIYVASNLESGIPARFSGSGSGTDFTL NIHPVEENDAATYYCQQSYKDPLTFGQGTKLE IKGGGGSGGGGSGGGGSQVQLVQSGPELKKPG ASVKVSCKASGYTFTDYVIHWVKQATGQGLEW IGEIYPGSGSAYSNAKFKDRVTMTADKSSNTA YMELSSLTSDDTAVYFCARRGNGTGFAYWGQG TLVTVSSGGGGSGGGGSGGGGSGGGGSGGGGS QAQLVQSGPEVRKPGTSVKVSCKAPGNTLKTY DLHWVRSVPGQGLQWMGWISHEGDKKVIVERF KAKVTIDWDRSTNTAYLQLSGLTSGDTAVYYC AKGSKHRLRDYALYDDDGALNWAVDVDYLSNL EFWGQGTAVTVSSGGGGSGGGGSGGGGSDFVL TQSPHSLSVTPGESASISCKSSHSLIHGDRNN YLAWYVQKPGRSPQLLIYLASSRASGVPDRFS GSGSDKDFTLKISRVETEDVGTYYCMQGRESP WTFGQGTKVDIKGGGGSGGGGSGGGGSGGGGS GGGGSQMQLQESGPGLVKPSETLSLTCSVSGA SISDSYWSWIRRSPGKGLEWIGYVHKSGDTNY SPSLKSRVNLSLDTSKNQVSLSLVAATAADSG KYYCARTLHGRRIYGIVAFNEWFTYFYMDVWG NGTQVTVSSGGGGSGGGGSGGGGSSDISVAPG ETARISCGEKSLGSRAVQWYQHRAGQAPSLII YNNQDRPSGIPERFSGSPDSPFGTTATLTITS |

-continued

| SEQ ID NO: | Name | Orientation | Amino Acid Sequence |
|---|---|---|---|
| | | | VEAGDEADYYCHIWDSRVPTKWVFGGGTTLTV LGGGGSGGGGSGGGGSGGGGSGGGGSRAHLVQ SGTAMKKPGASVRVSCQTSGYTFTAHILFWFR QAPGRGLEWVGWIKPQYGAVNFGGGFRDRVTL TRDVYREIAYMDIRGLKPDDTAVYYCARDRSY GDSSWALDAWGQGTTVVVSAGGGGSGGGGSGG GGSYIHVTQSPSSLSVSIGDRVTINCQTSQGV GSDLHWYQHKPGRAPKLLIHHTSSVEDGVPSR FSGSGFHTSFNLTISDLQADDIATYYCQVLQF FGRGSRLHIKGGGGSGGGGSGGGGSGGGGSGG GGSQGQLVQSGAELKKPGASVKISCKTSGYRF NFYHINWIRQTAGRGPEWMGWISPYSGDKNLA PAFQDRVIMTTDTEVPVTSFTSTGAAYMEIRN LKFDDTGTYFCAKGLLRDGSSTWLPYLWGQGT LLTVSSGGGGSGGGGSGGGGSQSVLTQSASVS GSLGQSVTISCTGPNSVCCSHKSISWYQWPPG RAPTLIIYEDNERAPGISPRFSGYKSYWSAYL TISDLRPEDETTYYCCSYTHNSGCVFGTGTKV SVLGGGGSGGGGSGGGGSGGGGSGGGGSEVRL RESGGGLVKPGGSLRLSCSASGFDFDNAWMTW VRQPPGKGLEWVGRITGPGEGWSVDYAESVKG RFTISRDNTKNTLYLEMNNVRTEDTGYYFCAR TGKYYDFWFGYPPGEEYFQDWGQGTLVIVSSG GGGSGGGGSGGGGSSELTQDPAVSVALKQTVT ITCRGDSLRSHYASWYQKKPGQAPVLLFYGKN NRPSGIPDRFSGSASGNRASLTITGAQAEDEA DYYCSSRDKSGSRLSVFGGGTKLTVLGSGHHH HHH |
| 94 | PentaNAb4.0 Stem HC LS_v2 (heavy chain) | PGDM1400-5X-PGT121-5X-N6 HC | MGWSCIILFLVATATGVHSQAQLVQSGPEVRK PGTSVKVSCKAPGNTLKTYDLHWVRSVPGQGL QWMGWISHEGDKKVIVERFKAKVTIDWDRSTN TAYLQLSGLTSGDTAVYYCAKGSKHRLRDYAL YDDDGALNWAVDVDYLSNLEFWGQGTAVTVSS GGGGSGGGGSGGGGSDFVLTQSPHSLSVTPGE SASISCKSSHSLIHGDRNNYLAWYVQKPGRSP QLLIYLASSRASGVPDRFSGSGSDKDFTLKIS RVETEDVGTYYCMQGRESPWTFGQGTKVDIKG GGGSGGGGSGGGGSGGGGSGGGGSQMQLQESG PGLVKPSETLSLTCSVSGASISDSYWSWIRRS PGKGLEWIGYVHKSGDTNYSPSLKSRVNLSLD TSKNQVSLSLVAATAADSGKYYCARTLHGRRI YGIVAFNEWFTYFYMDVWGNGTQVTVSSGGGG SGGGGSGGGGSSDISVAPGETARISCGEKSLG SRAVQWYQHRAGQAPSLIIYNNQDRPSGIPER FSGSPDSPFGTTATLTITSVEAGDEADYYCHI WDSRVPTKWVFGGGTTLTVLGGGGSGGGGSGG GGSGGGGSGGGGSRAHLVQSGTAMKKPGASVR VSCQTSGYTFTAHILFWFRQAPGRGLEWVGWI KPQYGAVNFGGGFRDRVTLTRDVYREIAYMDI RGLKPDDTAVYYCARDRSYGDSSWALDAWGQG TTVVVSAASTKGPSVFPLAPSSKSTSGGTAAL GCLVKDYFPEPVTVSWNSGALTSGVHTFPAVL QSSGLYSLSSVVTVPSSSLGTQTYICNVNHKP SNTKVDKKVEPKSCDKTHTCPPCPAPELLGGP SVFLFPPKPKDTLMISRTPEVTCVVVDVSHED PEVKFNWYVDGVEVHNAKTKPREEQYNSTYRV VSVLTVLHQDWLNGKEYKCKVSNKALPAPIEK TISKAKGQPREPQVYTLPPSREEMTKNQVSLT CLVKGFYPSDIAVEWESNGQPENNYKTTPPVL DSDGSFFLYSKLTVDKSRWQQGNVFSCSVLHE ALHSHYTQKSLSLSPGK |
| 96 | PentaNAb4.0 Stem HC LS_v2 (light chain) | N6 KC-CK-35O22-5X-10E8v4 S100cF | MGWSCIILFLVATATGVHSYIHVTQSPSSLSV SIGDRVTINCQTSQGVGSDLHWYQHKPGRAPK LLIHHTSSVEDGVPSRFSGSGFHTSFNLTISD LQADDIATYYCQVLQFFGRGSRLHIKRTVAAP SVFIFPPSDEQLKSGTASVVCLLNNFYPREAK VQWKVDNALQSGNSQESVTEQDSKDSTYSLSS TLTLSKADYEKHKVYACEVTHQGLSSPVTKSF NRGECGGGGSGGGGSGGGGSGGGGSGGGGSQG QLVQSGAELKKPGASVKISCKTSGYRFNFYHI NWIRQTAGRGPEWMGWISPYSGDKNLAPAFQD RVIMTTDTEVPVTSFTSTGAAYMEIRNLKFDD TGTYFCAKGLLRDGSSTWLPYLWGQGTLLTVS SGGGGSGGGGSGGGGSQSVLTQSASVSGSLGQ |

-continued

| SEQ ID NO: | Name | Orientation | Amino Acid Sequence |
|---|---|---|---|
| | | | SVTISCTGPNSVCCSHKSISWYQWPPGRAPTL IIYEDNERAPGISPRFSGYKSYWSAYLTISDL RPEDETTYYCCSYTHNSGCVFGTGTKVSVLGG GGSGGGGSGGGGSGGGGSGGGGSEVRLVESGG GLVKPGGSLRLSCSASGFDFDNAWMTWVRQPP GKGLEWVGRITGPGEGWSVDYAESVKGRFTIS RDNTKNTLYLEMNNVRTEDTGYYFCARTGKYY DFWFGYPPGEEYFQDWGQGTLVIVSSGGGGSG GGGSGGGGSSELTQDPAVSVALKQTVTITCRG DSLRSHYASWYQKKPGQAPVLLFYGKNNRPSG IPDRFSGSASGNRASLTITGAQAEDEADYYCS SRDKSGSRLSVFGGGTKLTVL |

PentaNAb2.0:10E8v4_S100cF-5X-35O22-5X-N6-5X-PGT121-5X-VRC26.25-IgG3C hinge-IgG1 LS (SEQ ID NO. 106)

ATGGGATGGAGCTGTATTATTCTGTTTCTGGTCGCTACCGCTACCGGAGTGCATTCTTCTGAACTGACCCAG

GACCCCGCCGTGAGCGTGGCCCTGAAGCAGACCGTGACAATCACCTGCAGGGGCGACAGCCTGCGCTCCCAC

TACGCCAGCTGGTATCAGAAGAAGCCTGGCCAGGCCCCAGTGCTGCTGTTCTACGGCAAGAACAATAGGCCC

TCCGGCATCCCTGATCGCTTTTCCGGCTCTGCCAGCGGAAACAGGGCCAGCCTGACAATCACCGGAGCACAG

GCAGAGGACGAGGCAGATTACTATTGCAGCTCCCGGGACAAGTCCGGCTCTAGACTGAGCGTGTTCGGCGGC

GGCACCAAGCTGACAGTGCTGGGAGGAGGAGGCAGCGGCGGAGGAGGCTCCGGAGGCGGCGGCTCTGAGGTG

CGGCTGGTGGAGTCTGGAGGAGGCCTGGTGAAGCCAGGAGGCAGCCTGAGACTGAGCTGTTCCGCCTCTGGC

TTCGACTTTGATAATGCCTGGATGACATGGGTGCGGCAGCCACCTGGCAAGGGCCTGGAGTGGGTGGGAAGA

ATCACCGGACCAGGAGAGGGATGGTCTGTGGACTACGCCGAGAGCGTGAAGGGCCGGTTCACCATCTCCAGA

GATAACACCAAGAATACACTGTATCTGGAGATGAACAATGTGCGGACCGAGGACACAGGCTACTATTTCTGC

GCCAGAACCGGCAAGTACTATGATTTTTGGTTTGGCTACCCACCCGGCGAGGAGTATTTTCAGGACTGGGGC

CAGGGCACCCTGGTCATCGTGAGCAGCGGCGGCGGCGGCAGCGGCGGCGGCGGCTCCGGAGGAGGCGGCTCT

GGAGGAGGAGGCAGCGGGGGAGGGGGCAGCCAGTCCGTGCTGACCCAGTCTGCCAGCGTGTCCGGCTCTCTG

GGACAGAGCGTGACCATCTCCTGTACAGGCCCCAACAGCGTGTGCTGTAGCCACAAGAGCATCTCCTGGTAC

CAGTGGCCTCCAGGAAGGGCACCTACCCTGATCATCTATGAGGACAATGAGCGGGCCCCAGGCATCTCCCCC

AGATTCTCTGGCTACAAGTCTTATTGGAGCGCCTACCTGACAATCAGCGACCTGCGCCCCGAGGATGAGACA

ACATACTATTGCTGTTCCTATACCCACAACTCTGGCTGCGTGTTTGGCACAGGCACCAAGGTGTCCGTGCTG

GGCGGCGGCGGCAGCGGGGGCGGGGGCTCCGGAGGGGGCGGCTCTCAGGGCCAGCTGGTGCAGAGCGGAGCA

GAGCTGAAGAAGCCTGGAGCCAGCGTGAAGATCTCCTGTAAGACATCTGGCTACCGGTTCAACTTTTATCAC

ATCAATTGGATCAGGCAGACCGCAGGAAGGGGACCAGAGTGGATGGGCTGGATCTCCCCCTACTCTGGCGAT

AAGAACCTGGCCCCAGCCTTCCAGGACAGAGTGATCATGACCACAGATACCGAGGTGCCAGTGACCAGCTTC

ACCTCCACCGGAGCCGCCTACATGGAGATCAGGAATCTGAAGTTCGACGATACAGGCACCTATTTTTGCGCA

AAGGGCCTGCTGAGGGACGGCTCCTCTACCTGGCTGCCTTACCTGTGGGGACAGGGCACCCTGCTGACAGTG

AGCTCCGGCGGCGGGGGCAGCGGCGGCGGGGGCTCCGGAGGAGGAGGCTCTGGAGGAGGGGGCAGCGGAGGA

GGCGGCTCCTACATCCACGTGACCCAGTCCCCATCTAGCCTGTCTGTGAGCATCGGCGATCGGGTGACCATC

AACTGTCAGACATCTCAGGGCGTGGGCAGCGACCTGCACTGGTATCAGCACAAGCCTGGCAGGGCCCCAAAG

CTGCTGATCCACCACACATCCTCTGTGGAGGATGGAGTGCCAAGCCGCTTCTCCGGCTCTGGATTCCACACC

TCCTTTAATCTGACAATCTCTGACCTGCAGGCCGACGATATCGCCACCTACTATTGCCAGGTGCTGCAGTTC

TTTGGCCGGGGCTCCAGACTGCACATCAAGGGAGGAGGAGGCTCCGGGGGCGGAGGCTCTGGCGGCGGCGGC

-continued

AGCCGGGCCCACCTGGTGCAGAGCGGCACCGCCATGAAGAAGCCTGGCGCCAGCGTGAGAGTGTCCTGTCAG

ACATCTGGCTACACCTTCACCGCCCACATCCTGTTCTGGTTTAGGCAGGCACCAGGAAGAGGCCTGGAGTGG

GTGGGCTGGATCAAGCCCCAGTATGGAGCAGTGAACTTCGGAGGAGGCTTTCGGGACAGAGTGACACTGACC

CGGGACGTGTACAGAGAGATCGCCTATATGGATATCAGGGGCCTGAAGCCAGACGATACCGCCGTGTACTAT

TGCGCCAGGGACCGCTCCTACGGCGATAGCTCCTGGGCACTGGACGCATGGGGACAGGGCACCACAGTGGTG

GTGAGCGCCGGCGGCGGAGGCTCCGGCGGCGGGGGCTCTGGAGGAGGCGGCAGCGGAGGGGGAGGCTCCGGA

GGGGGAGGCTCTAGCGACATCTCCGTGGCCCCTGGCGAGACAGCCAGAATCTCTTGTGGCGAGAAGTCTCTG

GGCAGCAGGGCCGTGCAGTGGTACCAGCACAGGGCAGGACAGGCACCATCTCTGATCATCTATAACAATCAG

GATAGGCCAAGCGGCATCCCTGAGCGGTTCAGCGGCTCCCCCGACAGCCCTTTTGGCACCACAGCCACACTG

ACCATCACATCCGTGGAGGCAGGCGACGAAGCCGATTACTATTGCCACATCTGGGATTCCAGAGTGCCAACC

AAGTGGGTGTTCGGAGGAGGAACCACACTGACAGTGCTGGGAGGGGGGGGCTCTGGCGGCGGGGGCAGCGGG

GGAGGAGGCTCCCAGATGCAGCTGCAGGAGAGCGGACCAGGCCTGGTGAAGCCTAGCGAGACACTGAGCCTG

ACATGTTCTGTGAGCGGCGCCTCCATCTCTGACAGCTACTGGTCTTGGATCAGACGGAGCCCCGGCAAGGGC

CTGGAATGGATCGGCTACGTGCACAAGTCCGGCGATACAAACTATTCCCCATCTCTGAAGTCTCGGGTGAAC

CTGTCTCTGGACACCAGCAAGAATCAGGTGAGCCTGTCCCTGGTGGCAGCAACCGCAGCAGATAGCGGCAAG

TACTATTGCGCCAGAACACTGCACGGCAGGCGCATCTACGGCATCGTGGCCTTTAACGAGTGGTTCACCTAC

TTTTATATGGACGTGTGGGGCAATGGCACCCAGGTGACAGTGTCCTCTGGCGGGGGCGGCTCCGGAGGCGGA

GGCTCTGGCGGGGGCGGCAGCGGCGGGGGCGGCTCCGGGGGAGGCGGCTCTCAGAGCGTGCTGACCCAGCCA

CCTTCCGTGTCTGCCGCACCAGGACAGAAGGTGACCATCAGCTGTTCCGGCAACACATCCAATATCGGCAAC

AATTTCGTGTCTTGGTACCAGCAGAGGCCAGGAAGGGCACCACAGCTGCTGATCTATGAGACAGACAAGCGG

CCTTCCGGCATCCCAGATAGATTTTCTGCCAGCAAGTCCGGCACCAGCGGCACACTGGCAATCACCGGCCTG

CAGACAGGCGACGAAGCTGATTACTATTGCGCAACCTGGGCAGCCTCCCTGAGCTCCGCCAGGGTGTTCGGA

ACCGGAACAAAAGTGATCGTGCTGGTGGGCGGCGGAGGCTCTGGCGGAGGCGGCAGCGGCGGGGGGGGCTCC

CAGGTGCAGCTGGTGGAGAGCGGCGGCGGCGTGGTGCAGCCAGGCACCTCCCTGAGGCTGTCTTGTGCAGCA

AGCCAGTTCAGATTTGATGGCTACGGCATGCACTGGGTGCGCCAGGCACCAGGCAAGGGCCTGGAGTGGGTA

GCCTCTATCAGCCACGACGGCATCAAGAAGTACCACGCCGAGAAAGTGTGGGGCAGGTTCACCATCTCCCGC

GATAACTCTAAAAACACACTGTATCTGCAGATGAACTCCCTGAGGCCCGAGGACACCGCCCTGTACTATTGC

GCCAAGGACCTGCGCGAGGATGAGTGTGAGGAGTGGTGGTCCGACTACTATGATTTTGGCAAGCAGCTGCCT

TGCGCAAAGAGCAGGGGAGGCCTGGTGGGAATCGCCGATAATTGGGGCCAGGGCACCATGGTGACAGTGTCT

AGCGGATCCGGAGAGCTGAAGACCCCTCTGGGCGATACCACACACACATCCCCACGGAGCCCCGAGCCAAAG

TCCTCTGACACCCCACCCCCTAGCCCTAGATCCCCTGAGCCAAAGAGCTCCGATACACCACCCCCTTCTCCA

AGGAGCCCCGAGCCTAAGTCTAGCGACACCCCACCCCCTTGCCCCCGCTGTCCAGCACCAGAGCTGCTGGGA

GGACCAAGCGTGTTCCTGTTTCCACCCAAGCCTAAGGATACACTGATGATCTCTCGCACCCCCGAGGTGACA

TGCGTGGTGGTGGACGTGAGCCACGAGGACCCCGAGGTGAAGTTCAACTGGTACGTGGACGGCGTGGAGGTG

CACAATGCCAAGACCAAGCCCAGGGAGGAGCAGTACAACAGCACCTATCGCGTGGTGTCCGTGCTGACAGTG

CTGCACCAGGACTGGCTGAACGGCAAGGAGTACAAGTGCAAGGTGTCCAATAAGGCCCTGCCTGCCCCAATC

GAGAAGACAATCAGCAAGGCAAAGGGACAGCCAAGGGAGCCACAGGTGTACACCCTGCCTCCAAGCCGCGAG

GAGATGACCAAGAACCAGGTGTCCCTGACATGTCTGGTGAAGGGCTTCTATCCTAGCGATATCGCCGTGGAG

TGGGAGTCCAATGGCCAGCCAGAGAACAATTACAAGACCACACCCCCTGTGCTGGACTCCGATGGCTCTTTC

TTTCTGTATTCTAAGCTGACCGTGGACAAGAGCCGGTGGCAGCAGGGCAACGTGTTCAGCTGCTCTGTGCTG

-continued

```
CACGAAGCCCTGCACAGCCATTACACCCAGAAGAGCCTGAGCCTGAGCCCCGGAAAA
```

Amino acid:

(SEQ ID NO. 107)

```
MGWSCIILFLVATATGVHSSELTQDPAVSVALKQTVTITCRGDSLRSHYASWYQKKPGQAPVLLFYGKNNRP

SGIPDRFSGSASGNRASLTITGAQAEDEADYYCSSRDKSGSRLSVEGGGTKLTVLGGGGSGGGGSGGGGSEV

RLVESGGGLVKPGGSLRLSCSASGFDFDNAWMTWVRQPPGKGLEWVGRITGPGEGWSVDYAESVKGRFTISR

DNTKNTLYLEMNNVRTEDTGYYFCARTGKYYDFWEGYPPGEEYFQDWGQGTLVIVSSGGGGSGGGGSGGGGS

GGGGSGGGGSQSVLTQSASVSGSLGQSVTISCTGPNSVCCSHKSISWYQWPPGRAPTLIIYEDNERAPGISP

RFSGYKSYWSAYLTISDLRPEDETTYYCCSYTHNSGCVFGTGTKVSVLGGGGSGGGGSGGGGSQGQLVQSGA

ELKKPGASVKISCKTSGYRFNFYHINWIRQTAGRGPEWMGWISPYSGDKNLAPAFQDRVIMTTDTEVPVTSF

TSTGAAYMEIRNLKFDDTGTYFCAKGLLRDGSSTWLPYLWGQGTLLTVSSGGGGSGGGGSGGGGSGGGGSGG

GGSYIHVTQSPSSLSVSIGDRVTINCQTSQGVGSDLHWYQHKPGRAPKLLIHHTSSVEDGVPSRFSGSGFHT

SENLTISDLQADDIATYYCQVLQFFGRGSRLHIKGGGGSGGGGSGGGGSRAHLVQSGTAMKKPGASVRVSCQ

TSGYTFTAHILFWFRQAPGRGLEWVGWIKPQYGAVNFGGGFRDRVTLTRDVYREIAYMDIRGLKPDDTAVYY

CARDRSYGDSSWALDAWGQGTTVVVSAGGGGSGGGGSGGGGSGGGGSGGGGSSDISVAPGETARISCGEKSL

GSRAVQWYQHRAGQAPSLITYNNQDRPSGIPERFSGSPDSPEGTTATLTITSVEAGDEADYYCHIWDSRVPT

KWVFGGGTTLTVLGGGGSGGGGSGGGGSQMQLQESGPGLVKPSETLSLTCSVSGASISDSYWSWIRRSPGKG

LEWIGYVHKSGDTNYSPSLKSRVNLSLDTSKNQVSLSLVAATAADSGKYYCARTLHGRRIYGIVAFNEWFTY

FYMDVWGNGTQVTVSSGGGGSGGGGSGGGGSGGGGSGGGGSQSVLTQPPSVSAAPGQKVTISCSGNTSNIGN

NEVSWYQQRPGRAPQLLIYETDKRPSGIPDRFSASKSGTSGTLAITGLQTGDEADYYCATWAASLSSARVEG

TGTKVIVLVGGGGSGGGGSGGGGSQVQLVESGGGVVQPGTSLRLSCAASQFRFDGYGMHWVRQAPGKGLEWV

ASISHDGIKKYHAEKVWGRFTISRDNSKNTLYLQMNSLRPEDTALYYCAKDLREDECEEWWSDYYDFGKQLP

CAKSRGGLVGIADNWGQGTMVTVSSGSGELKTPLGDTTHTSPRSPEPKSSDTPPPSPRSPEPKSSDTPPPSP

RSPEPKSSDTPPPCPRCPAPELLGGPSVFLFPPKPKDTLMISRTPEVTCVVVDVSHEDPEVKFNWYVDGVEV

HNAKTKPREEQYNSTYRVVSVLTVLHQDWLNGKEYKCKVSNKALPAPIEKTISKAKGQPREPQVYTLPPSRE

EMTKNQVSLTCLVKGFYPSDIAVEWESNGQPENNYKTTPPVLDSDGSFFLYSKLTVDKSRWQQGNVFSCSVL

HEALHSHYTQKSLSLSPGK
```

The studies presented above, using prototypic HIV bNAbs to create multispecific Env binding functional moieties with enhanced breadth and/or potency through structure-based rational design and iterative optimization, as well as combinations of the optimized bispecific Abs to form multi-specific Abs will serve as a methodological foundation for the eventual expansion of this line of investigation in regard to the more imaginative anti-viral agents described in this disclosure.

Throughout this disclosure, various publications, patents and published patent specifications are referenced by an identifying citation. The disclosures of these publications, patents and published patent specifications are hereby incorporated by reference into the present disclosure to more fully describe the state of the art to which this invention pertains.

While the present teachings are described in conjunction with various embodiments, it is not intended that the present teachings be limited to such embodiments. On the contrary, the present teachings encompass various alternatives, modifications, and equivalents, as will be appreciated by those of skill in the art.

What is claimed is:

1. A multispecific anti-HIV antibody that binds to multiple epitopes on HIV envelope protein, wherein the antibody comprises
   i. amino acid sequences that bind to a V1/V2 apex glycan epitope selected from the group consisting of:
      (a) an amino acid sequence comprising a CDR H1, CDR H2 and CDR H3, wherein CDR H1 comprises QFRFDGYG (SEQ ID NO: 2), CDR H2 comprises ISHDGIKK (SEQ ID NO: 3) and CDR H3 comprises AKDLREDECEEWWSDDFGKQLP-CAKSRGGLVGIADN (SEQ ID NO: 4); and an amino acid sequence comprising a CDR L1, CDR L2 and CDR L3, wherein CDR LI comprises TSNIGNNF (SEQ ID NO: 6), CDR L2 comprises ETD (SEQ ID NO:7) and CDR L3 comprises ATWAASLSSARV (SEQ ID NO: 8); and
      (b) an amino acid sequence comprising a CDR H1, CDR H2 and CDR H3, wherein CDR H1 comprises GNTLKTYD SEQ ID NO: 10), CDR H2 comprises ISHEGDKK (SEQ ID NO: 11) and CDR H3 comprises AKGSKHRLRDYALDDDGALNWAV-DVDYLSNLEF (SEQ ID NO: 12); and
      an amino acid sequence comprising a CDR LI, CDR L2 and CDR L3, wherein CDR LI comprises HSLIHGDRNNY (SEQ ID NO: 14), CDR L2 comprises LAS (SEQ ID NO: 15) and CDR L3 comprises MQGRESPWT (SEQ ID NO: 16);
   ii. an amino acid sequence that binds to a V3-base glycan region epitope, wherein the amino acid comprises a CDR H1, CDR H2 and CDR H3, wherein CDR H1 comprises GASISDSY (SEQ ID NO: 18), CDR H2 comprises VHKSGDT (SEQ ID NO:19) and CDR H3 comprises ARTLHGRRIYGIVAFNEWFTYFYMDV (SEQ ID NO: 20); and an amino acid sequence comprising a CDR L1, CDR L2 and CDR L3, wherein CDR L1 comprises SLGSRA (SEQ ID NO: 22), CDR L2 comprises NNQ (SEQ ID NO: 23) and CDR L3 comprises HIWDSRVPTKWV (SEQ ID NO: 24);
   iii. an amino acid sequence that binds to a CD4 binding site (CD4bs) epitope wherein the amino acid comprises a CDR H1, CDR H2 and CDR H3, wherein CDR H1 comprises GYTFTAHI (SEQ ID NO: 26), CDR H2 comprises IKPQYGAV (SEQ ID NO: 27) and CDR H3 comprises AR (SEQ ID NO: 28); and an amino acid sequence comprising a CDR LI, CDR L2 and CDR L3, wherein CDR LI comprises QGVGSD (SEQ ID NO: 30), CDR L2 comprises HTS (SEQ ID NO: 31) and CDR L3 comprises QVLQF (SEQ ID NO: 32);
   iv. an amino acid sequence that binds to a gp120/gp41 interface epitope wherein the amino acid sequence comprises a CDR H1, CDR H2 and CDR H3, wherein CDR H1 comprises GYRFNFYH (SEQ ID NO: 34), CDR H2 comprises ISPYSGDK (SEQ ID NO: 35) and CDR H3 comprises DDTGTYFCAKGLLRDGSSTWLPYL (SEQ ID NO: 36); and an amino acid sequence comprising a CDR L1, CDR L2 and CDR L3, wherein CDR L1 comprises NSVCCSHKS (SEQ ID NO: 38), CDR L2 comprises EDN (SEQ ID NO: 39) and CDR L3 comprises CSYTHNSGCV (SEQ ID NO: 40); and
   v. an amino acid sequence that binds to a membrane proximal external region (MPER) epitope wherein the amino acid sequence comprises a CDR H1, CDR H2 and CDR H3, wherein CDR H1 comprises GFDFD-NAW (SEQ ID NO: 42), CDR H2 comprises ITGPGEGWSV (SEQ ID NO: 43) and CDR H3 comprises TGYYFCARTGKYYDFWSGYPPGEEYFQD (SEQ ID NO: 44); and an amino acid sequence comprising a CDR L1, CDR L2 and CDR L3, wherein CDR L1 comprises RGDSLRSHYAS (SEQ ID NO: 46), CDR L2 comprises GKNNRPS (SEQ ID NO: 47) and CDR L3 comprises SSRDKSGSRLSV (SEQ ID NO: 48).

2. The multispecific anti-HIV antibody of claim 1, wherein the antibody simultaneously binds the multiple epitopes.

3. The multispecific anti-HIV antibody of claim 1, wherein the amino acid sequences of i-v) are present on a single polypeptide chain.

4. The multispecific anti-HIV antibody of claim 1, wherein the antibody is capable of neutralizing at least 99% of the HIV viruses or HIV pseudoviruses listed in Table 1 with an IC50 value of less than 50 μg/mL.

5. The multispecific anti-HIV antibody of claim 4, wherein the antibody has an IC50 geomean of between less than or equal to 0.10 μg/ml and less than or equal to 0.006 μg/ml.

6. The multispecific anti-HIV antibody of claim 1, wherein the amino acid sequences of parts i-v) comprise amino acid sequences of single chain fragment variable (ScFv) moieties, wherein each ScFv moiety comprises an amino acid sequence from a light chain variable region (VL) and an amino acid sequence from a heavy chain variable region (VH) of an antibody.

7. The multispecific anti-HIV antibody of claim 6, wherein:

(i) one or more of the ScFv moieties is organized such that the VL is at the amino terminal end of the ScFv moiety and the VH is at the carboxy terminal end of the ScFv moiety;

(ii) one or more of the ScFv moieties is organized such that the VH is at the amino terminal end of the ScFv moiety and the VL is at the carboxy terminal end of thevScFv moiety; or (iii) each ScFv moiety is organized such that the VL is at the amino terminal end of the ScFv moiety and the VH is at the carboxy terminal end of the ScFv moiety.

8. The multispecific anti-HIV antibody of claim 6, wherein the VL and VH sequences are separated by one or more linking amino acids.

9. The multispecific anti-HIV antibody of claim 1, wherein the antibody further comprises an Fc region of an immunoglobulin or a variant thereof.

10. The multispecific anti-HIV antibody of claim 1, wherein the antibody comprises a first and second polypeptide chain, wherein the first and second polypeptide chains each comprise a. five ScFv moieties, wherein each ScFv moiety on a single chain recognizes an individual epitope, wherein each ScFv moiety comprises an amino acid sequence from a light chain variable region (VL) and an amino acid sequence from a heavy chain variable region (VH) of an antibody; and b. an Fc region of an immunoglobulin or a variant thereof.

11. The multispecific anti-HIV antibody of claim 6, wherein the ScFv moieties are separated on the polypeptide chain by one or more linking amino acids.

12. The multispecific anti-HIV antibody of claim 1, wherein the amino acid sequences of parts i-v) of claim 1 are organized on a single polypeptide chain in the following order, from its N-terminus to its C-terminus:

i. an amino acid sequence that binds to the V1/V2 apex glycan epitope;

ii. an amino acid sequence that binds to the V3-base glycan region epitope;

iii. an amino acid sequence that binds to the CD4 binding site (CD4bs) epitope;

iv. an amino acid sequence that binds to the gp120/gp41 interface epitope; and v. an amino acid sequence that binds to the membrane proximal external region (MPER) epitope.

13. The multispecific anti-HIV antibody of claim 1, wherein the amino acid sequences of parts i-v) of claim 1 are organized on a single polypeptide chain in the following order, from its N-terminus to its C-terminus:

i. an amino acid sequence that binds to the membrane proximal external region (MPER) epitope;

ii. an amino acid sequence that binds to the gp120/gp41 interface epitope;

iii. an amino acid sequence that binds to the CD4 binding site (CD4bs) epitope;

iv. an amino acid sequence that binds to the V3-base glycan region epitope; and v. an amino acid sequence that binds to the V1/V2 apex glycan epitope.

14. The multispecific anti-HIV antibody of claim 1, wherein the antibody comprises a first and second polypeptide chain, wherein the amino acid sequences of parts i-v) of claim 1 are organized in the following order, from its N-terminus to its C-terminus:

i. an amino acid sequence that binds to the membrane proximal external region (MPER) epitope;

ii. an amino acid sequence that binds to the gp120/gp41 interface epitope;

iii. an amino acid sequence that binds to the CD4 binding site (CD4bs) epitope;

iv. an amino acid sequence that binds to the V3-base glycan region epitope;

v. an amino acid sequence that binds to the V1/V2 apex glycan epitope; and vi. an Fc region of an immunoglobulin or a variant thereof.

15. The multispecific anti-HIV antibody of claim 1, wherein the antibody comprises a first and second polypeptide chain, wherein the amino acid sequences of parts i-v) of claim 1 are organized in the following order, from its N-terminus to its C-terminus:

i. an amino acid sequence that binds to the V1/V2 apex glycan epitope;

ii. an amino acid sequence that binds to the V3-base glycan region epitope;

iii. an amino acid sequence that binds to the CD4 binding site (CD4bs) epitope;

iv. an amino acid sequence that binds to the gp120/gp41 interface epitope;

v. an amino acid sequence that binds to the membrane proximal external region (MPER) epitope; and vi. an Fc region of an immunoglobulin or a variant thereof.

16. The multispecific anti-HIV antibody of claim 1, wherein the antibody comprises 1) A first polypeptide chain, wherein the amino acid sequences of parts i-v) of claim 1 are organized in the following order, from its N-terminus to its C-terminus:

i. an amino acid sequence that binds to the membrane proximal external region (MPER) epitope;

ii. an amino acid sequence that binds to the gp120/gp41 interface epitope;

iii. an amino acid sequence that binds to the CD4 binding site (CD4bs) epitope;

iv. an amino acid sequence that binds to the V3-base glycan region epitope;

v. an amino acid sequence that binds to the V1/V2 apex glycan epitope; and vi. an Fc region of an immunoglobulin or a variant thereof; and 2) A second polypeptide chain, wherein the amino acid sequences of parts i-v) of claim 1 are organized in the following order, from its N-terminus to its C-terminus:

i. an amino acid sequence that binds to the V1/V2 apex glycan epitope;

ii. an amino acid sequence that binds to the V3-base glycan region epitope;

iii. an amino acid sequence that binds to the CD4 binding site (CD4bs) epitope;

iv. an amino acid sequence that binds to the gp120/gp41 interface epitope;

v. an amino acid sequence that binds to the membrane proximal external region (MPER) epitope; and vi. an Fc region of an immunoglobulin or a variant thereof.

17. The multispecific anti-HIV antibody of claim 1, wherein:

i. the amino acid sequence that binds to the epitope of the V1/V2-glycan region comprises an amino acid sequence from an antibody selected from the group consisting of VRC26.25 and PGDM1400;

ii. the amino acid sequence that binds to the epitope of the V3-glycan region comprises an amino acid sequence from antibody PGT121;

iii. the amino acid sequence that binds to the epitope of the CD4-binding site (CD4bs) comprises an amino acid sequence from antibody N6;

iv. the amino acid sequence that binds to the epitope of the gp120/gp41 interface comprises an amino acid sequence from antibody 35022; and v. the amino acid sequence that binds to the epitope of the membrane proximal external region (MPER) comprises an amino acid sequence from an antibody selected from the group consisting of 10E8v4, 10E8v4_S100cF, and 10E8v4_V5R S100cF.

18. The multispecific anti-HIV antibody of claim 17, wherein i. the amino acid sequence from the antibody VRC26.25 comprises the VH region or a variant thereof comprising 1, 2, 3, or 4 conservative amino acid substitutions, wherein the VH region comprises SEQ ID NO:1; and the VL region or a variant thereof comprising 1, 2, 3, or 4 conservative amino acid substitutions, wherein the VL region comprises amino acids SEQ ID NO:5;

ii. the amino acid sequence from the antibody PGDM1400 comprises the VH region or a variant thereof comprising 1, 2, 3, or 4 conservative amino acid substitutions, wherein the VH region comprises SEQ ID NO:9; and the VL region or a variant thereof comprising 1, 2, 3, or 4 conservative amino acid substitutions, wherein the VL region comprises amino acids SEQ ID NO:13;

iii. the amino acid sequence from the antibody PGT121 comprises the VH region or a variant thereof comprising 1, 2, 3, or 4 conservative amino acid substitutions, wherein the VH region comprises SEQ ID NO:17; and the VL region or a variant thereof comprising 1, 2, 3, or 4 conservative amino acid substitutions, wherein the VL region comprises amino acids SEQ ID NO:21;

iv. the amino acid sequence from the antibody N6 comprises the VH region or a variant thereof comprising 1, 2, 3, or 4 conservative amino acid substitutions, wherein the VH region comprises SEQ ID NO:25; and the VL region or a variant thereof comprising 1, 2, 3, or 4 conservative amino acid substitutions, wherein the VL region comprises amino acids SEQ ID NO: 29;

v. the amino acid sequence from the antibody 35022 comprises the VH region or a variant thereof comprising 1, 2, 3, or 4 conservative amino acid substitutions, wherein the VH region comprises SEQ ID NO:33; and the VL region or a variant thereof comprising 1, 2, 3, or 4 conservative amino acid substitutions, wherein the VL region comprises amino acids SEQ ID NO: 37;

vi. the amino acid sequence from the antibody 10E8v4 comprises the VH region or a variant thereof comprising 1, 2, 3, or 4 conservative amino acid substitutions, wherein the VH region comprises SEQ ID NO:41; and VL region or a variant thereof comprising 1, 2, 3, or 4 conservative amino acid substitutions, wherein the VL region comprises amino acids SEQ ID NO: 45;

vii. the amino acid sequence from the antibody 10E8v4_S100cF comprises the VH region or a variant thereof comprising 1, 2, 3, or 4 conservative amino acid substitutions, wherein the VH region comprises SEQ ID NO:49; and the VL region or a variant thereof comprising 1, 2, 3, or 4 conservative amino acid substitutions, wherein the VL region comprises amino acids SEQ ID NO:45; and viii. the amino acid sequence from the antibody 10E8v4_V5R_S100cF comprises the VH region or a variant thereof comprising 1, 2, 3, or 4 conservative amino acid substitutions, wherein the VH region comprises SEQ ID NO:51; and the VL region or a variant thereof comprising 1, 2, 3, or 4 conservative amino acid substitutions, wherein the VL region comprises amino acids SEQ ID NO:45.

19. The multispecific anti-HIV antibody of claim 1, wherein the antibody comprises an IgG1 Fc region variant comprising mutations corresponding to M428L and N434S.

20. The multispecific anti-HIV antibody of claim 1, wherein the antibody comprises an immunoglobulin Fc region that has been modified to facilitate heterodimerization.

21. The multispecific anti-HIV antibody of claim 1, wherein the antibody further comprises a sequence tag that facilitates purification of the antibody.

22. The multispecific anti-HIV antibody of claim 1, wherein the antibody comprises any of SEQ ID NOS: 72-80.

23. A pharmaceutical composition comprising an antibody of claim 1 and a pharmaceutically acceptable carrier.

24. A method for treating or preventing HIV infection in a subject, comprising administering to the subject an effective amount of the composition of claim 23.

25. The method of claim 24, wherein the composition is administered in combination with another therapy.

26. The method of claim 25, wherein the therapy is an anti-retroviral therapy.

27. The multispecific anti-HIV antibody of claim 1, wherein the amino acid sequences of parts i-v) of claim 1 are organized on a single polypeptide chain in the following order, from its N-terminus to its C-terminus:

i. an amino acid sequence that binds to a CD4 epitope;

ii. an amino acid sequence that binds to a V1/V2 apex glycan epitope;

iii. an amino acid sequence that binds to the V3-base glycan region epitope;

iv. an amino acid sequence that binds to the CD4 binding site (CD4bs) epitope;

v. an amino acid sequence that binds to the gp120/gp41 interface epitope; and vi. an amino acid sequence that binds to the membrane proximal external region (MPER) epitope.

28. The multispecific anti-HIV antibody of claim 27, wherein the amino acid sequence of (i) is derived from the variable domains of the anti-CD4 antibody dB4C7/UB-421.

29. The multispecific anti-HIV antibody of claim 1, wherein the antibody comprises a first and second polypeptide chain, wherein the first polypeptide chain comprises a heavy chain variable region wherein the heavy chain variable region comprises;

i. an amino acid sequence that binds to a V1/V2 apex glycan epitope;

ii. an amino acid sequence that binds to a V3-base glycan region epitope; and iii. an amino acid sequence that binds to a CD4 binding site (CD4bs) epitope;

and wherein the second polypeptide chain comprises a light chain variable region wherein the light chain variable region comprises:

i. an amino acid sequence that binds to a CD4 binding site (CD4bs) epitope;

ii. an amino acid sequence that binds to a gp120/gp41 interface epitope; and iii. an amino acid sequence that binds to a membrane proximal external region (MPER) epitope.

30. The multi-specific anti-HIV antibody of claim 29, wherein the Fc domain comprises a M428L/N434S (LS) mutation.

* * * * *